US012797386B2

(12) United States Patent
Machajewski et al.

(10) Patent No.: US 12,797,386 B2
(45) Date of Patent: Nov. 17, 2026

(54) ALPHA-V-BETA-8 INTEGRIN INHIBITORS AND USES THEREOF

(71) Applicant: Pliant Therapeutics, Inc., South San Francisco, CA (US)

(72) Inventors: Timothy D. Machajewski, Martinez, CA (US); Darren Finkelstein, Los Gatos, CA (US); Timothy F. Hom, Sunnyvale, CA (US); Dennis Monteleone, San Francisco, CA (US); Manuel Angel Munoz, Vallejo, CA (US); Katerina Leftheris, San Mateo, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 354 days.

(21) Appl. No.: 18/395,241

(22) Filed: Dec. 22, 2023

(65) Prior Publication Data

US 2024/0245682 A1 Jul. 25, 2024

Related U.S. Application Data

(60) Provisional application No. 63/593,454, filed on Oct. 26, 2023, provisional application No. 63/585,565,
(Continued)

(51) Int. Cl.
*A61K 31/501* (2006.01)
*A61K 31/337* (2006.01)
(Continued)

(52) U.S. Cl.
CPC .......... *A61K 31/501* (2013.01); *A61K 31/337* (2013.01); *A61K 31/4375* (2013.01);
(Continued)

(58) Field of Classification Search
CPC ............ A61K 31/4375; A61K 31/4745; A61K 31/497; A61K 31/501; A61K 31/506;
(Continued)

(56) References Cited

U.S. PATENT DOCUMENTS

| | | | |
|---|---|---|---|
| 6,048,861 | A | 4/2000 | Askew, Jr. et al. |
| 8,354,509 | B2 | 1/2013 | Carven |

(Continued)

FOREIGN PATENT DOCUMENTS

| | | | |
|---|---|---|---|
| WO | 2008157162 | A1 | 12/2008 |
| WO | 2014/154725 | A1 | 10/2014 |

(Continued)

OTHER PUBLICATIONS

AlphaScreen® (2009). "Exclusive AlphaScreen and AlphaLISA Assay Technology," Perkin Elmer, Waltham, MA., 68 pages.

(Continued)

*Primary Examiner* — Sarah Pihonak
*Assistant Examiner* — Padmaja S Rao
(74) *Attorney, Agent, or Firm* — Morrison & Foerster LLP; Kraig Anderson; Johannes Hull

(57) ABSTRACT

The disclosure relates to compounds of formula (A) and formula (I), e.g.:

(I)

(Continued)

or a pharmaceutically acceptable salt thereof, wherein $R^1$, $R^2$, $R^3$, $R^4$, $L^1$, $L^2$, $L^3$, Y, and Q are as described herein. Compounds of formula (A) and formula (I) and pharmaceutical compositions thereof are inhibitors of at least one or more of $\alpha_v\beta_8$, $\alpha_v\beta_1$, and $\alpha_v\beta_6$ integrins. Also disclosed are methods for treating fibrosis such as nonalcoholic steatohepatitis (NASH), idiopathic pulmonary fibrosis (IPF) and nonspecific interstitial pneumonia (NSIP), and cancer comprising administration of the compounds and pharmaceutical compositions thereof.

42 Claims, 180 Drawing Sheets

Related U.S. Application Data filed on Sep. 26, 2023, provisional application No. 63/435,496, filed on Dec. 27, 2022.

(51) Int. Cl.

| | |
|---|---|
| ***A61K 31/4375*** | (2006.01) |
| ***A61K 31/4745*** | (2006.01) |
| ***A61K 31/497*** | (2006.01) |
| ***A61K 31/506*** | (2006.01) |
| ***A61K 31/513*** | (2006.01) |
| ***A61K 31/555*** | (2006.01) |
| ***A61K 31/7068*** | (2006.01) |
| ***A61P 35/00*** | (2006.01) |
| ***C07D 471/04*** | (2006.01) |
| ***G01N 33/50*** | (2006.01) |

(52) U.S. Cl.

CPC ........ *A61K 31/4745* (2013.01); *A61K 31/497* (2013.01); *A61K 31/506* (2013.01); *A61K 31/513* (2013.01); *A61K 31/555* (2013.01); *A61K 31/7068* (2013.01); *A61P 35/00* (2018.01); *C07D 471/04* (2013.01); *G01N 33/5011* (2013.01); *G01N 2333/57* (2013.01); *G01N 2333/96436* (2013.01)

(58) Field of Classification Search

CPC ... C07D 471/04; A61P 35/00; G01N 2333/57; G01N 2333/96436; G01N 33/5011

See application file for complete search history.

(56) References Cited

U.S. PATENT DOCUMENTS

| | | | |
|---|---|---|---|
| 8,900,587 | B2 | 12/2014 | Carven |
| 10,131,658 | B2 | 11/2018 | Degrado |
| 10,214,522 | B2 | 2/2019 | Degrado |
| 10,604,520 | B2 | 3/2020 | Jiang |
| 10,696,672 | B2 | 6/2020 | Morgans, Jr. |
| 10,793,564 | B2 | 10/2020 | Cha |
| 11,180,494 | B2 | 11/2021 | Cha et al. |
| 11,396,506 | B2 | 7/2022 | Leftheris et al. |
| 11,419,869 | B2 | 8/2022 | Decaris et al. |
| 11,560,376 | B2 | 1/2023 | Cha et al. |
| 11,634,418 | B2 | 4/2023 | Morgans, Jr. et al. |
| 11,673,887 | B2 | 6/2023 | Jiang |
| 11,858,931 | B2 | 1/2024 | Leftheris |
| 11,952,376 | B2 | 4/2024 | Cha |
| 2002/0010176 | A1 | 1/2002 | Askew |
| 2012/0289481 | A1 | 11/2012 | O'neil |
| 2014/0349968 | A1 | 11/2014 | O'neil |
| 2016/0264566 | A1 | 9/2016 | Degrado |
| 2016/0376266 | A1 | 12/2016 | Degrado |
| 2018/0008583 | A1 | 1/2018 | Fukunaga |
| 2018/0093984 | A1 | 4/2018 | Jiang |
| 2019/0276449 | A1 | 9/2019 | Cha |
| 2019/0322663 | A1 | 10/2019 | Morgans, Jr. |
| 2019/0345155 | A1 | 11/2019 | Ruminski et al. |
| 2020/0109141 | A1 | 4/2020 | Cha |
| 2020/0123151 | A1 | 4/2020 | Leftheris et al. |
| 2020/0352942 | A1 | 11/2020 | Cha et al. |
| 2021/0017171 | A1 | 1/2021 | Cha et al. |
| 2021/0024516 | A1 | 1/2021 | Jiang |
| 2021/0122747 | A1 | 4/2021 | Morgans, Jr. et al. |
| 2021/0147526 | A1 | 5/2021 | Andre et al. |
| 2022/0144829 | A1 | 5/2022 | Cha et al. |
| 2022/0177468 | A1 | 6/2022 | Cha et al. |
| 2022/0289743 | A1 | 9/2022 | Leftheris et al. |
| 2023/0028658 | A1 | 1/2023 | Turner et al. |
| 2023/0117605 | A1 | 4/2023 | Decaris et al. |
| 2023/0181546 | A1 | 6/2023 | Lefebvre et al. |
| 2023/0271960 | A1 | 8/2023 | Cha et al. |
| 2023/0293519 | A1 | 9/2023 | Lefebvre et al. |
| 2023/0365556 | A1 | 11/2023 | Jiang et al. |
| 2024/0043421 | A1 | 2/2024 | Morgans, Jr. |
| 2024/0122930 | A1 | 4/2024 | Lefebvre |
| 2024/0270742 | A1 | 8/2024 | Cha et al. |

FOREIGN PATENT DOCUMENTS

| | | | |
|---|---|---|---|
| WO | 2015048819 | A1 | 4/2015 |
| WO | 2016046226 | A1 | 3/2016 |
| WO | 2016145258 | A1 | 9/2016 |
| WO | 2016153054 | A1 | 9/2016 |
| WO | 2018009501 | A1 | 1/2018 |
| WO | 2018049068 | A1 | 3/2018 |
| WO | 2018089355 | A1 | 5/2018 |
| WO | 2018119087 | A1 | 6/2018 |
| WO | 2018160521 | A2 | 9/2018 |
| WO | 2018160522 | A1 | 9/2018 |
| WO | 2018160521 | A3 | 10/2018 |
| WO | 2019173653 | A1 | 9/2019 |
| WO | 2019175776 | A1 | 9/2019 |
| WO | 2020006315 | A1 | 1/2020 |
| WO | 2020047207 | A1 | 3/2020 |
| WO | 2020047208 | A1 | 3/2020 |
| WO | 2020047239 | A1 | 3/2020 |
| WO | 2020076862 | A1 | 4/2020 |
| WO | 2020210404 | A1 | 10/2020 |
| WO | 2021097338 | A1 | 5/2021 |
| WO | 2021225912 | A1 | 11/2021 |
| WO | 2022109598 | A1 | 5/2022 |
| WO | 2022232838 | A1 | 11/2022 |
| WO | 2023035000 | A1 | 3/2023 |
| WO | 2023064943 | A1 | 4/2023 |
| WO | 2023225119 | A1 | 11/2023 |
| WO | 2024015717 | A2 | 1/2024 |
| WO | 2024/145245 | A2 | 7/2024 |

OTHER PUBLICATIONS

Ayers, M. et al. (Aug. 2017). "IFN-γ-Related mRNA Profile Predicts Clinical Response to PD-1 Blockade," The Journal of Clinical Investigation 127(8):2930-2940.

Biffi, G. et al. (Feb. 2019). "IL1-Induced JAK/STAT Signaling Is Antagonized by TGFβ to Shape CAF Heterogeneity in Pancreatic Ductal Adenocarcinoma," Cancer Discovery 9(2):282-301.

Call, M.K. et al. (2004). "Lens Regeneration in Mice: Implications in Cataracts," Experimental Eye Research 78 (2):297-299.

Desai, V.D. et al. (Feb. 2010). "CD44 Expression Is Developmentally Regulated in the Mouse Lens and Increases in the Lens Epithelium After Injury," Differentiation 79(2):111-119, 19 pages.

Dodagatta-Marri, E. et al. (Jul. 6, 2021). "Integrin αvβ8 on T Cells Suppresses Anti-Tumor Immunity in Multiple Models and Is a Promising Target for Tumor Immunotherapy," Cell Reports 36(109309): 18 pages.

Dörwald, F.Z. (2005). "Side Reactions in Organic Synthesis: A Guide to Successful Synthesis Design," Weinheim: WILEY-VCH, 6 pages. (Preface).

Fajardo, D.C. et al. (2023). "1467 Selective Targeting of Integrins αVβ8 and αVβ1 Within The Dynamic Ecosystem of Pancreatic Cancer to Improve the Overall Anti-Tumor Response," J Immunother Cancer 11(Suppl 1):A1631.

(56) References Cited

OTHER PUBLICATIONS

Fu, C. (Aug. 31, 2017). Research and Development of New Traditional Chinese Medicines, China Traditional Chinese Medicine Press: Beijing, pp. 93-94, 8 pages. [English Machine Translation of Abstract].
Greszler, S.N. et al. (May 19, 2017, e-pub. May 1, 2017). "Synthesis of Substituted Cyclopropanecarboxylates via Room Temperature Palladium-Catalyzed α-Arylation of Reformatsky Reagents," Organic Letters 19(10):2490-2493, 1 page [Abstract].
International Preliminary Report on Patentability, issued Apr. 8, 2021, for PCT Application No. PCT/US2019/55252, filed Oct. 8, 2019, 9 pages.
International Search Report and Written Opinion, dated Jan. 23, 2020, for PCT Application No. PCT/US2019/55252, filed Oct. 8, 2019, 16 pages.
Jordan, V.C. (Mar. 2003). "Tamoxifen: A most Unlikely Pioneering Medicine," Nature Reviews 2:205-213.
Kim, D.S. et al. (2006). "Classification and Natural History of the Idiopathic Interstitial Pneumonias," Proc. Am. Thorac. Soc. 3:285-292.
Kinder, B.W. et al. (Jun. 2007). "Idiopathic Nonspecific Interstitial Pneumonia. Lung Manifestation of Undifferentiated Connective Tissue Disease?," Am. J. Respir. Crit. Care Med. 176:691-697.
Krishnamurty, A.T. et al. (Nov. 3, 2022, e-pub. Sep. 28, 2022). "LRRC15+ Myofibroblasts Dictate the Stromal Setpoint to Suppress Tumour Immunity," Nature 611:148-154, 21 pages.
Lainé, A. et al. (2021, e-pub. Oct. 28, 2021). "Regulatory T Cells Promote Cancer Immune-Escape Through Integrin αvβ8-Mediated TGF-β Activation," Nature Communications 12(6228):1-14.
Larrick, J. et al. (Jul. 1, 2022). "Blockade of αvβ8 integrin Synergizes With Checkpoint Inhibition to Enhance Anti-Tumor Immunity Through Cxcl9-Dependent Augmentation of CD8+ T Cell Cytotoxicity," Research Square, 28 pages.
Lynch, D. (2001, e-pub. Dec. 1, 2001). "Nonspecific Interstitial Pneumonia: Evolving Concepts," Radiology 221 (3):583-584.
Mamuya, F.A. et al. (2014). "The Roles of αV Integrins in Lens EMT And Posterior Capsular Opacification," Journal of Cellular and Molecular Medicine 18(4):656-670.
Mariathasan, S. et al. (Feb. 22, 2018). "TGFβ Attenuates Tumour Response to PD-L1 Blockade by Contributing to Exclusion of T Cells," Nature 554(7693):544-548, 28 pages.
Mohanty, S.K. et al. (2020). "Rotavirus Reassortant-Induced Murine Model of Liver Fibrosis Parallels Human Biliary Atresia," Hepatology 71(4):1316-1330.
Remington: The Science and Practice of Pharmacy, Lippincott Williams & Wilkins, Philadelphia, PA, 21st ed. (2006) TOC, 4 pages.
Rowe, R.C. et al. (2008). "Handbook of Pharmaceutical Excipients," 6th Edition, Pharmaceutical Press, TOC, 9 pages.
Stahl, P.H. et al. (2002). "Handbook of Pharmaceutical Salts: Properties, Selection and Use," Weinheim/Zurich, Wiley-VCH/VHCA, 2 pages, Abstract Only.
Takasaka, N. et al. (Oct. 18, 2018). "Integrin αvβ8-Expressing Tumor Cells Evade Host Immunity by Regulating TGF-β Activation in Immune Cells," JCI Insight 3(20):1-17.
Thomas, D.A. et al. (Nov. 2005). "TGF-β Directly Targets Cytotoxic T Cell Functions During Tumor Evasion of Immune Surveillance," Cancer Cell 8(5):369-380.
Ullman, E.F. et al. (Jun. 7, 1994). "Luminescent Oxygen Channeling Immunoassay: Measurement of Particle Binding Kinetics by Chemiluminescence," Proc. Natl. Acad. Sci. USA 91(12):5426-5430.
Wuts, P.G.M. et al. (2006). Greene's Protective Groups in Organic Synthesis 4th edition, Wiley-Interscience, New York, TOC, 6 pages.
Yang, Z.-Z. et al. (Sep. 2014). "TGF-β Upregulates CD70 Expression and Induces Exhaustion of Effector Memory T Cells in B-Cell Non-Hodgkin's Lymphoma," Leukemia 28(9):1872-1884, 23 pages.
International Preliminary Report on Patentability received for PCT Patent Application No. PCT/US2023/085812, mailed on Jul. 10, 2025, 10 pages.
International Search Report and Written Opinion, mailed May 24, 2024, for PCT Application No. PCT/US2023/085812, filed Dec. 22, 2023, 18 pages.
Invitation to Pay Additional Fees mailed on Mar. 18, 2024, for PCT Patent Application No. PCT/US2023/085812, filed Dec. 22, 2023, 2 pages.
Remington: The Science and Practice of Pharmacy, 21st Edition, Journal of Pharmacy Technology, Mar.-Apr. 2006, 22:133-135.

| Group | Antibody (IP RoA) | Compound (BID Oral) |
|---|---|---|
| 1 | Rat IgG Control | Vehicle |
| 2 | Anti-PD1(RMP1-14, 10mg/kg) | Vehicle |
| 3 | Anti-PD1(RMP1-14, 10mg/kg) | avb8 mAb |
| 4 | Anti-PD1(RMP1-14, 10mg/kg) | Test Compound (high dose) |
| 5 | | Test Compound (high dose) |
| 6 | Anti-PD1(RMP1-14, 10mg/kg) | Test Compound (med. dose) |
| 7 | Anti-PD1(RMP1-14, 10mg/kg) | Test Compound (low dose) |
| 8 | Anti-PD1(RMP1-14, 10mg/kg) | Alk5 inhibitor (1mg/kg) |

FIG. 12B

| | Vehicle | anti-PD-1 | Compound 39 | Compound 39 + anti-PD-1 |
|---|---|---|---|---|
| Median survival | 29.5 | 33 | 45 | 51 |

| | Vehicle | IgG2a control | anti-PD-1 | ADWA-11 | ADWA-11 + anti-PD-1 |
|---|---|---|---|---|---|
| Median survival | 29.5 | 31 | 33 | 34 | 41.5 |

Compound 39

Compound 39 + G/A 0 hours PCS

WT (Control for Reference Compound A)

WT (3 mg/mL)

WT (30 mg/mL)

WT (300 mg/mL)

WT (Control for Reference Compound C)

WT (Compound C)

Compound D 0 hours PCS

WT (Control for Reference Compound A)

WT (3 mg/mL)

WT (30 mg/mL)

WT (300 mg/mL)

WT (Control for Reference Compound C)

WT (Compound C)

Compound D

CD8⁺ T Cells

CD8+ T Cells

Reduction in Treg CD4 T cells

Pancreatic Adenocarcinoma

ALPHA-V-BETA-8 INTEGRIN INHIBITORS AND USES THEREOF

CROSS-REFERENCE TO RELATED APPLICATIONS

This application claims the benefit of U.S. Provisional Patent Appl. No. 63/435,496 filed Dec. 27, 2022, of U.S. Provisional Patent Appl. No. 63/585,565 filed Sep. 26, 2023, and of U.S. Provisional Patent Appl. No. 63/593,454 filed Oct. 26, 2023. The contents of those applications are hereby incorporated by reference herein in their entirety.

FIELD OF THE INVENTION

This disclosure relates generally to therapeutic agents that may be useful as $\alpha_V\beta_8$ integrin inhibitors. The therapeutic agents may be used in the treatment or prophylactic treatment of fibrosis such as idiopathic pulmonary fibrosis (IPF) and nonspecific interstitial pneumonia (NSIP). The therapeutic agents may also be used in the treatment of cancer.

BACKGROUND

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Primary biliary cholangitis (PBC), also known as primary biliary cirrhosis, is a chronic disease of the liver that causes damage and fibrosis in the liver. It results from a slow, progressive destruction of the small bile ducts of the liver, causing bile and other toxins to build up in the liver, a condition called cholestasis. Over time, this leads to scarring and fibrosis in both the liver and biliary tract.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. (Kim et al., Proc. Am. Thorac. Soc. (2006) 3:285-292; Lynch, D., Radiology (2001) 221:583-584; Kinder et al., Am. J. Respir. Crit. Care Med. (2007) 176: 691-697)

Biliary atresia (BA) is a fibro-obliterative cholangiopathy that affects approximately 1:5,000 to 1:18,000 infants, causing inflammation leading to end-stage liver disease. Patients generally die by two years of age without surgical intervention. Portoenterostomy can be performed in order to restore biliary drainage. However, even with restoration of biliary drainage, almost all patients will develop hepatic fibrosis and will need a liver transplant in order to survive (see Mohanty et al., "Rotavirus Reassortant-Induced Murine Model of Liver Fibrosis Parallels Human Biliary Atresia," Hepatology 71:1316 (2020)).

Ocular fibrosis encompasses numerous disorders of the eye. For example, TGFβ signaling in epithelial cells has been shown to cause an epithelial-mesenchymal transition (EMT) leading to fibrosis with similarities to cataract formation. Examples include anterior subcapsular cataracts (ASC) and posterior capsule opacification (PCO), which can occur after cataract surgery. Studies have shown that TGFβ-induced EMT is included in lens epithelial cell wound healing response and can induce expression of various extracellular matrix proteins associated with fibrosis and integrins, leading to vision-impairing production of myofibroblasts expressing α-smooth muscle actin (α-SMA) and lens fiber cells.

Available courses of treatment are scarce, as there are currently no options on the market proven to have an effect on long-term patient survival or symptomatology. There remains a need for treatment of fibrotic diseases.

The $\alpha_V\beta_8$ integrin is expressed in epithelial cells, and binds to the latency-associated peptide of transforming growth factor-β1 (TGFβ1) and mediates TGFβ1 activation. Its expression level is significantly increased after injury to lung and cholangiocytes, and plays a critical in vivo role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of $\alpha_V\beta_6$ is elevated in liver and bile duct of PSC patients.

SUMMARY

Disclosed are amino acid compounds that are $\alpha_V\beta_8$ integrin inhibitors, compositions containing these compounds and methods for treating diseases mediated by $\alpha_V\beta_8$ integrin such as a fibrotic disease or cancer.

In one aspect, provided is a compound of formula (A), or any variation thereof, or a salt thereof (e.g., a pharmaceutically acceptable salt thereof), as detailed herein.

In one aspect, provided is a compound of formula (I), or any variation thereof, or a salt thereof (e.g., a pharmaceutically acceptable salt thereof), as detailed herein.

Further provided is a pharmaceutical composition comprising a compound of formula (A), or any variation thereof detailed herein, or a salt thereof (e.g., a pharmaceutically acceptable salt thereof), and a pharmaceutically acceptable carrier or excipient.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

Also provided is a pharmaceutical composition comprising a compound of formula (A), or any variation thereof detailed herein, or a salt thereof (e.g., a pharmaceutically acceptable salt thereof), a checkpoint inhibitor, and a pharmaceutically acceptable carrier or excipient.

Also provided is a pharmaceutical composition comprising a compound of formula (I), or any variation thereof detailed herein, or a salt thereof (e.g., a pharmaceutically acceptable salt thereof), a checkpoint inhibitor, and a pharmaceutically acceptable carrier or excipient.

In another aspect, provided is a method of treating a fibrotic disease or condition in an individual (such as a human) in need thereof comprising administering to the individual a therapeutically effective amount of a compound of formula (A), or any variation thereof detailed herein, or a pharmaceutically acceptable salt thereof. In another aspect, provided is a method of treating a fibrotic disease or condition in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease or condition is pulmonary, liver, renal, cardiac, dermal, or gastrointestinal fibrosis. In other embodiments the fibrotic disease or condition is idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primarily biliary cholangitis (also known as primary biliary cirrhosis), systemic sclerosis associated interstitial lung disease, scleroderma (also known as systemic sclerosis), diabetic nephropathy, diabetic kidney disease, focal segmental glomerulosclerosis, chronic kidney disease, biliary atresia, and Crohn's Disease.

In another aspect, provided is a method of delaying the onset and/or development of a fibrotic disease or condition in an individual (such as a human) who is at risk for developing a fibrotic disease or condition comprising administering to the individual a therapeutically effective amount of a compound of formula (A), or any variation thereof detailed herein, or a pharmaceutically acceptable salt thereof. In another aspect, provided is a method of delaying the onset and/or development of a fibrotic disease or condition in an individual (such as a human) who is at risk for developing a fibrotic disease or condition comprising administering to the individual a therapeutically effective amount of a compound of formula (I), or any variation thereof detailed herein, or a pharmaceutically acceptable salt thereof. In some embodiments, the disease or condition is pulmonary, liver, renal, cardiac, dermal, or gastrointestinal fibrosis. In other embodiments the fibrotic disease or condition is idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primarily biliary cholangitis (also known as primary biliary cirrhosis), systemic sclerosis associated interstitial lung disease, scleroderma (also known as systemic sclerosis), diabetic nephropathy, diabetic kidney disease, focal segmental glomerulosclerosis, chronic kidney disease, biliary atresia, and Crohn's Disease.

Also provided is a compound of formula (A), or any variation thereof detailed herein, or a pharmaceutical composition thereof, for the treatment of a fibrotic disease.

Also provided is a compound of formula (I), or any variation thereof detailed herein, or a pharmaceutical composition thereof, for the treatment of a fibrotic disease.

Also provided is use of a compound of formula (A), or any variation thereof detailed herein, or a pharmaceutically acceptable salt thereof, in the manufacture of a medicament for the treatment of a fibrotic disease.

Also provided is use of a compound of formula (I), or any variation thereof detailed herein, or a pharmaceutically acceptable salt thereof, in the manufacture of a medicament for the treatment of a fibrotic disease.

Further provided is use of a compound of formula (A), or any variation thereof detailed herein, or a pharmaceutically acceptable salt thereof, or a pharmaceutical composition thereof, for the treatment of a disease mediated by cells that express $\alpha_V\beta_1$ and/or $\alpha_V\beta_8$. Further provided is use of a compound of formula (I), or any variation thereof detailed herein, or a pharmaceutically acceptable salt thereof, or a pharmaceutical composition thereof, for the treatment of a disease mediated by cells that express $\alpha_V\beta_1$ and/or $\alpha_V\beta_8$. In some embodiments, the cells are associated with the intrahepatic biliary system. In some embodiments, the cells are associated with the extrahepatic biliary system. In some embodiments, the cells are associated with the intrahepatic biliary system and the extrahepatic biliary system.

Further provided is a kit comprising a compound of formula (A), or any variation thereof detailed herein, or a pharmaceutically acceptable salt thereof. Further provided is a kit comprising a compound of formula (I), or any variation thereof detailed herein, or a pharmaceutically acceptable salt thereof. In some embodiments, the kit comprises instructions for use according to a method described herein, such as a method of treating a fibrotic disease in an individual. In some embodiments, the kit comprises instructions for use according to a method described herein, such as a method of treating a cancer in an individual.

Also provided is a kit comprising a compound of formula (A), or any variation thereof detailed herein, or a pharmaceutically acceptable salt thereof, and a checkpoint inhibitor.

Also provided is a kit comprising a compound of formula (I), or any variation thereof detailed herein, or a pharmaceutically acceptable salt thereof, and a checkpoint inhibitor. In some embodiments, the kit comprises instructions for use according to a method described herein, such as a method of treating a fibrotic disease in an individual. In some embodiments, the kit comprises instructions for use according to a method described herein, such as a method of treating a cancer in an individual.

Further provided is a method of inhibiting $\alpha_V\beta_8$ integrin in an individual comprising administering a compound of formula (A), or any variation thereof detailed herein, or a pharmaceutically acceptable salt thereof.

Further provided is a method of inhibiting $\alpha_V\beta_8$ integrin in an individual comprising administering a compound of formula (I), or any variation thereof detailed herein, or a pharmaceutically acceptable salt thereof.

Also provided is a method of inhibiting one or more of $\alpha_V\beta_1$, $\alpha_V\beta_6$, or $\alpha_V\beta_8$ integrin in an individual in need thereof, comprising administering to the individual a compound of formula (A), or any variation thereof detailed herein, or a pharmaceutically acceptable salt thereof, or a pharmaceutical composition thereof.

Also provided is a method of inhibiting one or more of $\alpha_V\beta_1$, $\alpha_V\beta_6$, or $\alpha_V\beta_8$ integrin in an individual in need thereof, comprising administering to the individual a compound of formula (I), or any variation thereof detailed herein, or a pharmaceutically acceptable salt thereof, or a pharmaceutical composition thereof.

Further provided is a method of inhibiting TGFβ activation in a cell comprising administering to the cell a compound of formula (A), or any variation thereof detailed herein, or a pharmaceutically acceptable salt thereof, or a pharmaceutical composition thereof.

Further provided is a method of inhibiting TGFβ activation in a cell comprising administering to the cell a compound of formula (I), or any variation thereof detailed herein, or a pharmaceutically acceptable salt thereof, or a pharmaceutical composition thereof.

Also provided is the use of a compound of formula (A), or any variation thereof detailed herein, or a pharmaceutically acceptable salt thereof, in the manufacture of a medicament for the treatment of a fibrotic disease.

Also provided is the use of a compound of formula (I), or any variation thereof detailed herein, or a pharmaceutically acceptable salt thereof, in the manufacture of a medicament for the treatment of a fibrotic disease.

Also provided is the use of a compound of formula (A), or any variation thereof detailed herein, or a pharmaceutically acceptable salt thereof, or a pharmaceutical composition thereof, in the manufacture of a medicament for the treatment of a disease mediated by cells that express one or more of: $\alpha_V\beta_1$; $\alpha_V\beta_6$; and $\alpha_V\beta_8$. Also provided is the use of a compound of formula (I), or any variation thereof detailed herein, or a pharmaceutically acceptable salt thereof, or a pharmaceutical composition thereof, in the manufacture of a medicament for the treatment of a disease mediated by cells that express one or more of: $\alpha_V\beta_1$; $\alpha_V\beta_6$; and $\alpha_V\beta_8$. For example, in some embodiments the disease is mediated by cells that express $\alpha_V\beta_1$. In some embodiments, the disease is mediated by cells that express $\alpha_V\beta_6$. In some embodiments, the disease is mediated by cells that express $\alpha_V\beta_8$. In some embodiments, the disease is mediated by cells that express $\alpha_V\beta_1$ and $\alpha_V\beta_6$. In some embodiments, the disease is mediated by cells that express $\alpha_V\beta_1$ and $\alpha_V\beta_8$. In some embodiments, the fibrotic disease is mediated by cells that express $\alpha_V\beta_6$ and $\alpha_V\beta_8$. In some embodiments, the fibrotic disease is mediated by cells that express $\alpha_V\beta_1$, $\alpha_V\beta_6$, and $\alpha_V\beta_8$.

In another aspect provided is a method of treating cancer in an individual in need thereof, comprising administering to the individual a compound of formula (A), or any variation thereof detailed herein, or a pharmaceutically acceptable salt thereof, or a pharmaceutical composition thereof. In some embodiments, the method further comprises administering to the individual a checkpoint inhibitor.

In another aspect provided is a method of treating cancer in an individual in need thereof, comprising administering to the individual a compound of formula (I), or any variation thereof detailed herein, or a pharmaceutically acceptable salt thereof, or a pharmaceutical composition thereof. In some embodiments, the method further comprises administering to the individual a checkpoint inhibitor.

Also provided is the use of a compound of formula (A), or any variation thereof detailed herein, or a pharmaceutically acceptable salt thereof, or a pharmaceutical composition thereof, in the manufacture of a medicament for the treatment of a cancer.

Also provided is the use of a compound of formula (I), or any variation thereof detailed herein, or a pharmaceutically acceptable salt thereof, or a pharmaceutical composition thereof, in the manufacture of a medicament for the treatment of a cancer.

Also provided is the use of a compound of formula (A), or any variation thereof detailed herein, or a pharmaceutically acceptable salt thereof, or a pharmaceutical composition thereof, and a checkpoint inhibitor, together in the manufacture of a medicament for the treatment of a disease mediated by cells that express one or more of: $\alpha_V\beta_1$; $\alpha_V\beta_6$; and $\alpha_V\beta_8$. Also provided is the use of a compound of formula (A), or any variation thereof detailed herein, or a pharmaceutically acceptable salt thereof, or a pharmaceutical composition thereof, and a checkpoint inhibitor, together in the manufacture of a medicament for the treatment of cancer.

Also provided is the use of a compound of formula (I), or any variation thereof detailed herein, or a pharmaceutically acceptable salt thereof, or a pharmaceutical composition thereof, and a checkpoint inhibitor, together in the manufacture of a medicament for the treatment of a disease mediated by cells that express one or more of: $\alpha_V\beta_1$; $\alpha_V\beta_6$; and $\alpha_V\beta_8$. Also provided is the use of a compound of formula (I), or any variation thereof detailed herein, or a pharmaceutically acceptable salt thereof, or a pharmaceutical composition thereof, and a checkpoint inhibitor, together in the manufacture of a medicament for the treatment of cancer.

Further provided is a method of treating a subject in need thereof. In some embodiments, the method includes providing the subject. In some embodiments, the subject includes at least one tissue in need of therapy. In some embodiments, the at least one tissue is characterized by at least one value that is elevated compared to a healthy value in a healthy state of the tissue. In some embodiments, the tissue includes an elevated value of $\alpha_V\beta_1$ integrin activity and/or expression. In some embodiments, the tissue includes an elevated value of $\alpha_V\beta_6$ integrin activity and/or expression. In some embodiments, the tissue includes an elevated value of $\alpha_V\beta_8$ integrin activity and/or expression. In some embodiments, the tissue includes an elevated value of a pSMAD/SMAD ratio. In some embodiments, the tissue includes an elevated value of new collagen formation or accumulation. In some embodiments, the tissue includes an elevated value of total collagen. In some embodiments, the tissue includes an elevated value of Type I Collagen gene Col1a1 expression. In some embodiments, the tissue includes an elevated value of perforin. In some embodiments, the tissue includes an elevated value of Granzyme B. In some embodiments, the tissue includes an elevated value of interferon γ. In some embodiments, the method includes administering to the subject a therapeutically effective amount of a compound of formula (A), or any variation thereof detailed herein, or a pharmaceutically acceptable salt thereof, or a pharmaceutical composition thereof. In some embodiments, the method includes administering to the subject a therapeutically effective amount of a compound of formula (I), or any variation thereof detailed herein, or a pharmaceutically acceptable salt thereof, or a pharmaceutical composition thereof.

Also provided is a method of characterizing anticancer activity of a small molecule inhibitor in a subject. In some embodiments, the method includes providing a first live cell sample from the subject. In some embodiments, the first live cell sample is characterized by the presence of at least one integrin capable of activating transforming growth factor β (TGF-β) from latency associated peptide-TGF-β. In some embodiments, the method includes determining a first value in the first live cell sample. In some embodiments, the first value is a pSMAD2/SMAD2 ratio. In some embodiments, the first value is a pSMAD3/SMAD3 ratio. In some embodiments, the first value is a perforin level. In some embodiments, the first value is a granzyme B level. In some embodiments, the first value is an interferon γ level. In some embodiments, the method includes administering the small molecule to the subject. In some embodiments, the method includes providing a second live cell sample from the subject. In some embodiments, the second live cell sample is drawn from the same tissue in the subject as the first live cell sample. In some embodiments, the method includes determining a second value in the second live cell sample. In some embodiments, the second value corresponds to the pSMAD2/SMAD2 ratio, pSMAD3/SMAD3 ratio, perforin level, granzyme B level, or interferon γ level of the first value. In some embodiments, the method includes characterizing the anticancer activity of the small molecule in the subject by comparing the second value to the first value.

In another aspect, provided is a method of making a compound of formula (A) or any variation thereof. Also provided are compound intermediates useful in synthesis of a compound of formula (A), or any variation thereof.

In another aspect, provided is a method of making a compound of formula (I) or any variation thereof. Also provided are compound intermediates useful in synthesis of a compound of formula (I), or any variation thereof.

In another aspect, provided is a compound of formula (A) or any variation thereof produced by a process disclosed herein.

In another aspect, provided is a compound of formula (I) or any variation thereof produced by a process disclosed herein.

It is understood that aspects and variations described herein also include "consisting of" and/or "consisting essentially of" aspects and variations.

BRIEF DESCRIPTION OF THE FIGURES

FIG. 12B is a table showing the compounds and dosages used for each group.

FIG. 35 depicts a survival curve displaying the survival probability over a time period of 30 days for vehicle, vehicle+anti-mPD-1, and Compound 39+anti-mPD-1.

FIG. 36 depicts a graph for an EMT-6 syngeneic model showing tumor volume over a thirty day period for vehicle, anti-PD1+vehicle, Compound 39, and anti-PD1+$\alpha_V\beta_8$ SMI.

FIG. 37 depicts a graph showing $CD8^+$ T cells/$mm^2$ of tumor for vehicle, anti-mPD-1, $\alpha_V\beta_8$ small molecule inhibitor (SMI), and anti-mPD-1+$\alpha_V\beta_8$ SMI. p<0.01 by one way ANOVA and **p<0.0001 by one way ANOVA.

FIG. 38 depicts an I-O for various enzymes for vehicle, anti-mPD-1+vehicle, $\alpha_V\beta_8$ small molecule inhibitor (SMI), and anti-mPD-1+$\alpha_V\beta_8$ SMI.

FIG. 39 depicts a graph showing tumor volume in EMT6 tumors for vehicle and Compound 39 over a 15 day time period.

FIG. 40A depicts a graph showing plasma biomarker response for CXCL9 after 14 days of monotherapy with Compound 39.

FIG. 40B depicts a graph showing plasma biomarker response for VEGFα after 14 days of monotherapy with Compound 39.

FIG. 41 depicts a graph showing tumor growth inhibition in Pan02 tumors for Rat IgG2a+vehicle, anti-mPD-1+vehicle, and anti-mPD-1+Compound 39 over a 30 day time period.

FIG. 42 depicts a graph comparing pSMAD3/SMAD3 between vehicle+Rat IgG2a, anti-mPD-1+vehicle, and anti-mPD-1+Compound 39.

FIG. 43 depicts a graph comparing size of $CD8^+$ T cells/$mm^2$ of tumor between vehicle, anti-mPD-1, and anti-mPD-1+Compound 39.

FIG. 44 depicts a graph showing tumor volume in an EMT6 syngeneic model for IgG+vehicle, anti-mPD-1+vehicle, and Compound 39+anti-mPD-1 up to 15 days post-treatment.

FIG. 45A depicts a percent of total non-granulocytes associated with a healthy group, a vehicle+IgG group, a vehicle+α-mPD-1 group, and an α-mPD-1+Compound 39 group.

Figures 45A, 45B, 45C:
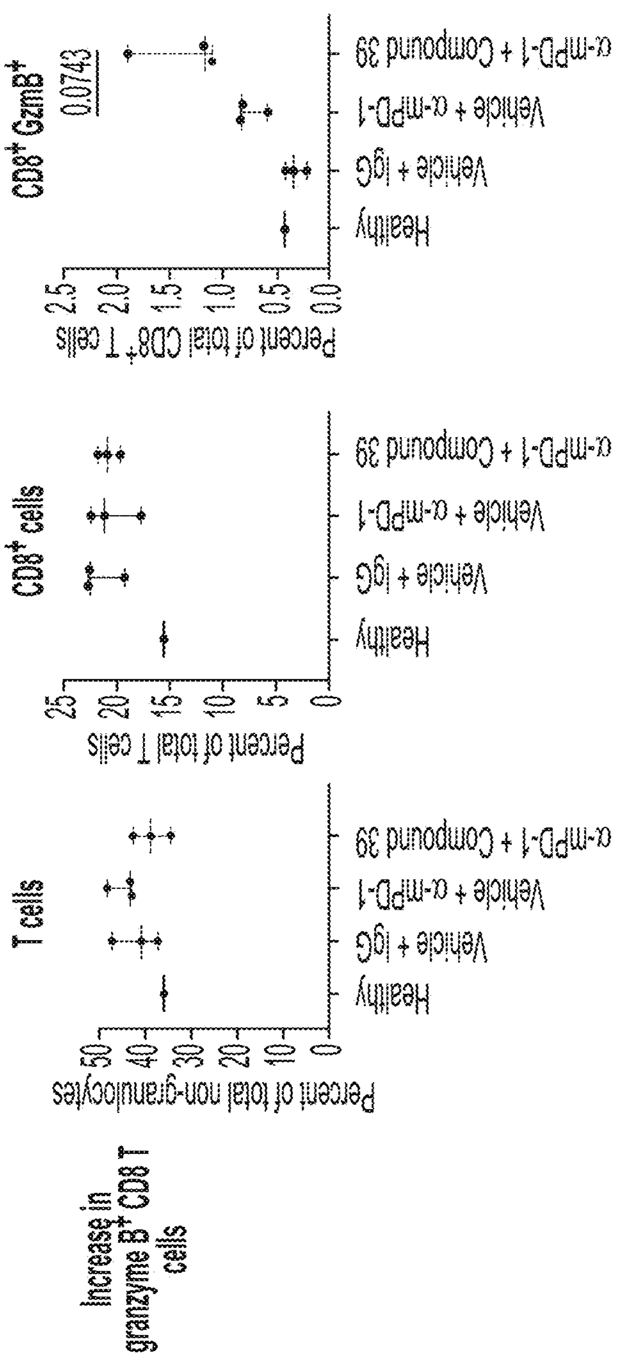

FIG. 45B depicts a percent of total T cells associated with a healthy group, a vehicle+IgG group, a vehicle+α-mPD-1 group, and an α-mPD-1+Compound 39 group.

FIG. 45C depicts a percent of total $CD8^+$ T cells associated with a healthy group, a vehicle+IgG group, a vehicle+α-mPD-1 group, and an α-mPD-1+Compound 39 group.

Figure 45D:
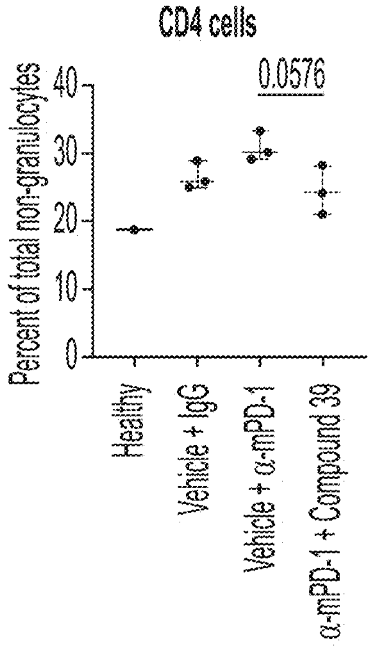

FIG. 45D depicts a percent of non-granulocytes associated with a healthy group, a vehicle+IgG group, a vehicle+α-mPD-1 group, and an α-mPD-1+Compound 39 group.

Figure 45E:
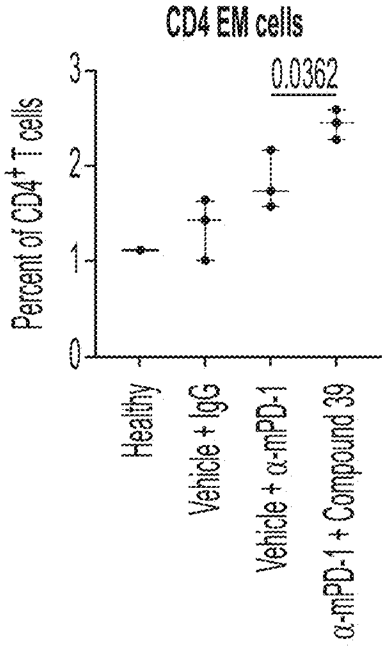

FIG. 45E depicts a percent of $CD4^+$ T cells associated with a healthy group, a vehicle+IgG group, a vehicle+α-mPD-1 group, and an α-mPD-1+Compound 39 group.

Figure 45F:
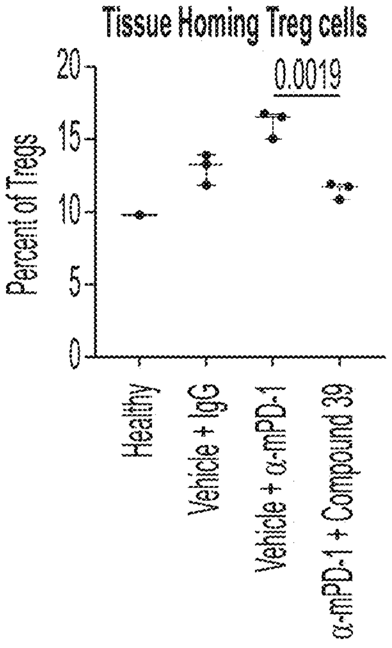

FIG. 45F depicts a percent of tissue homing Treg cells associated with a healthy group, a vehicle+IgG group, a vehicle+α-mPD-1 group, and an α-mPD-1+Compound 39 group.

Figure 46:
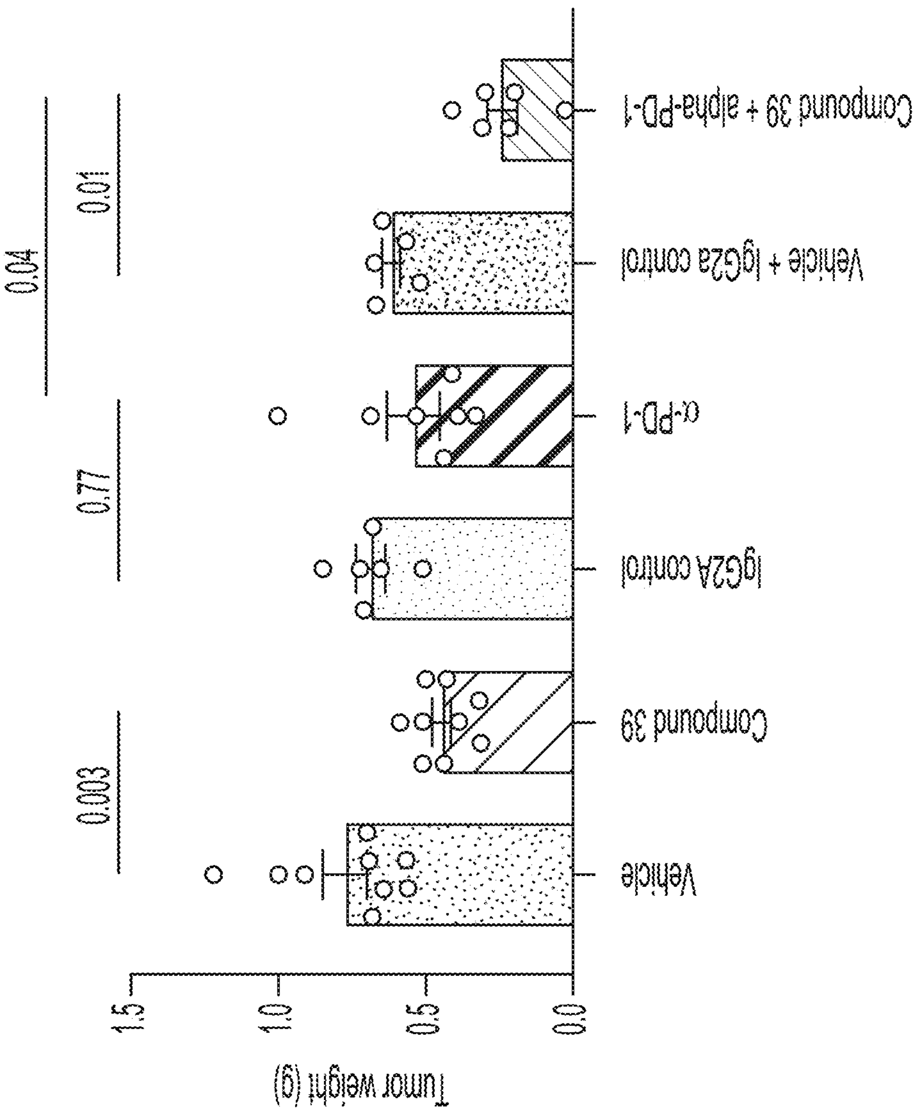

FIG. 46 depicts a graph associated with tumor weight in an immunocompetent KPC model for various groups. Statistical assessment by one-way ANOVA.

Figure 47:
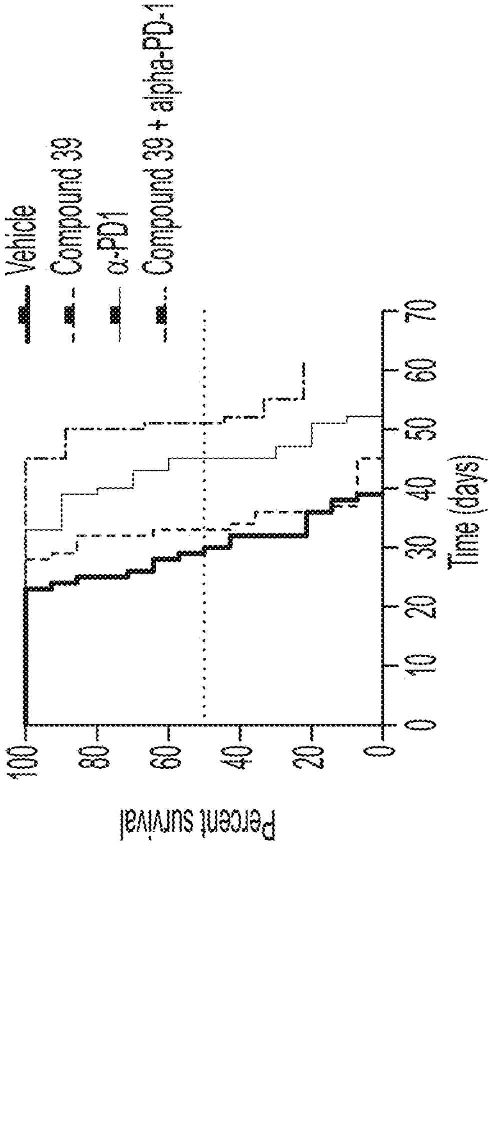

FIG. 47 depicts a survival curve in in an immunocompetent KPC model for various groups over 70 days. p<0.01 by one-way ANOVA with Tukey and **p<0.0001 by one-way ANOVA with Tukey.

Figure 48:
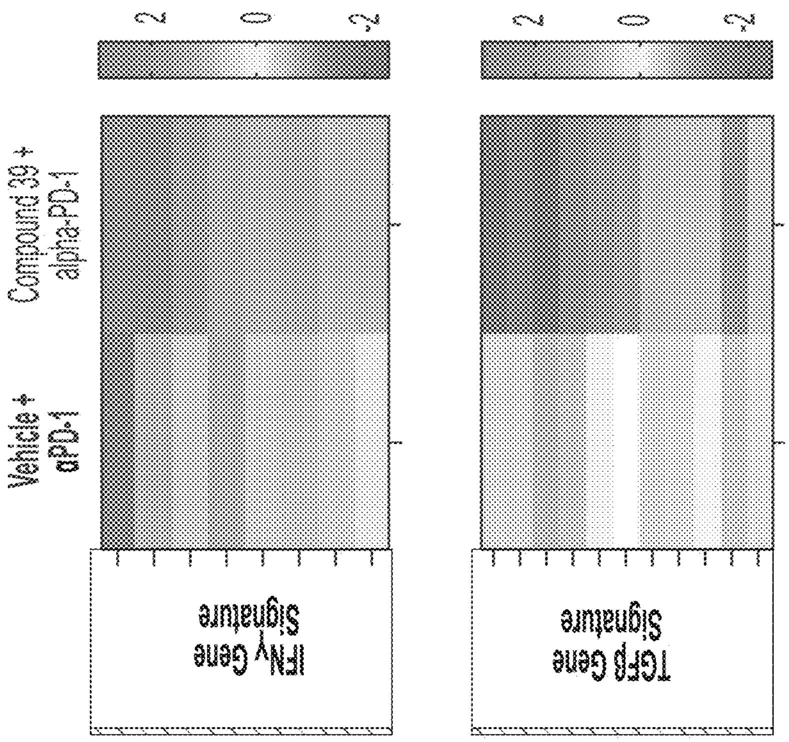

FIG. 48 depicts an IFN-γ gene signature (top) and a TGFβ gene signature (bottom) for vehicle+αPD1 and Compound 39+α-PD1.

Figure 49:
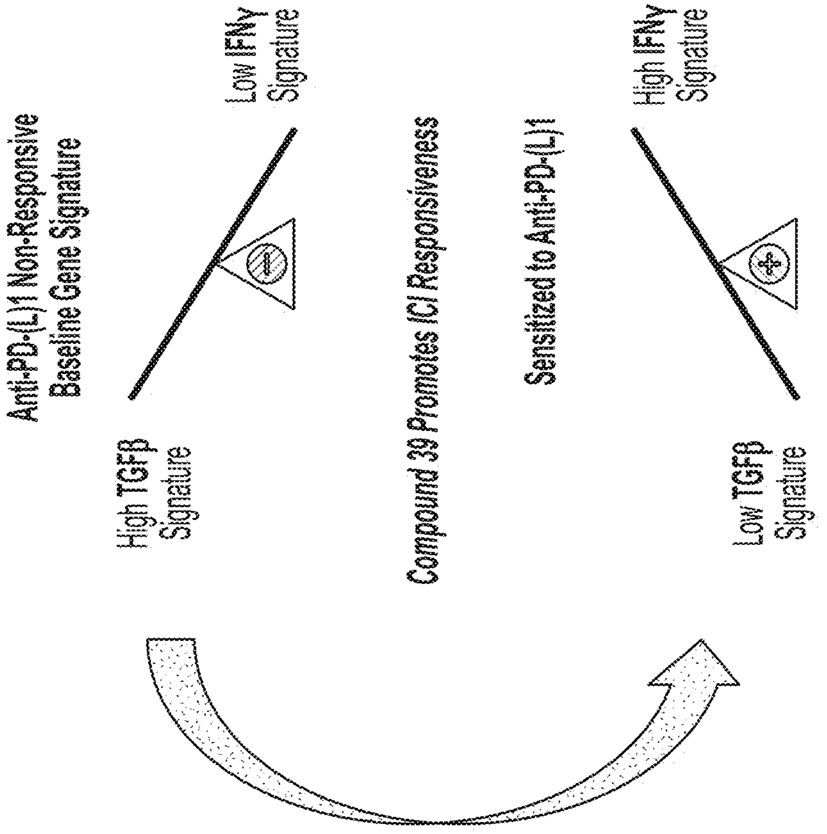

FIG. 49 depicts a schematic diagram associated with Compound 39 promoting ICI responsiveness.

Figure 50A:
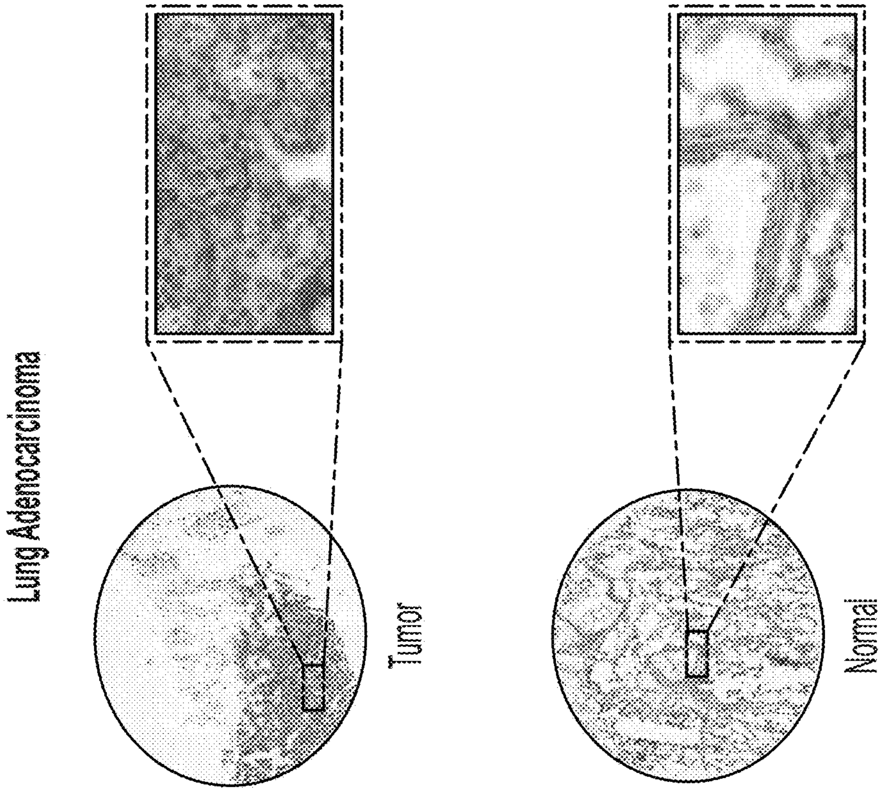

FIG. 50A depicts images associated with IHC detection of $\alpha_V\beta_1$ in lung adenocarcinoma.

Figure 50B:
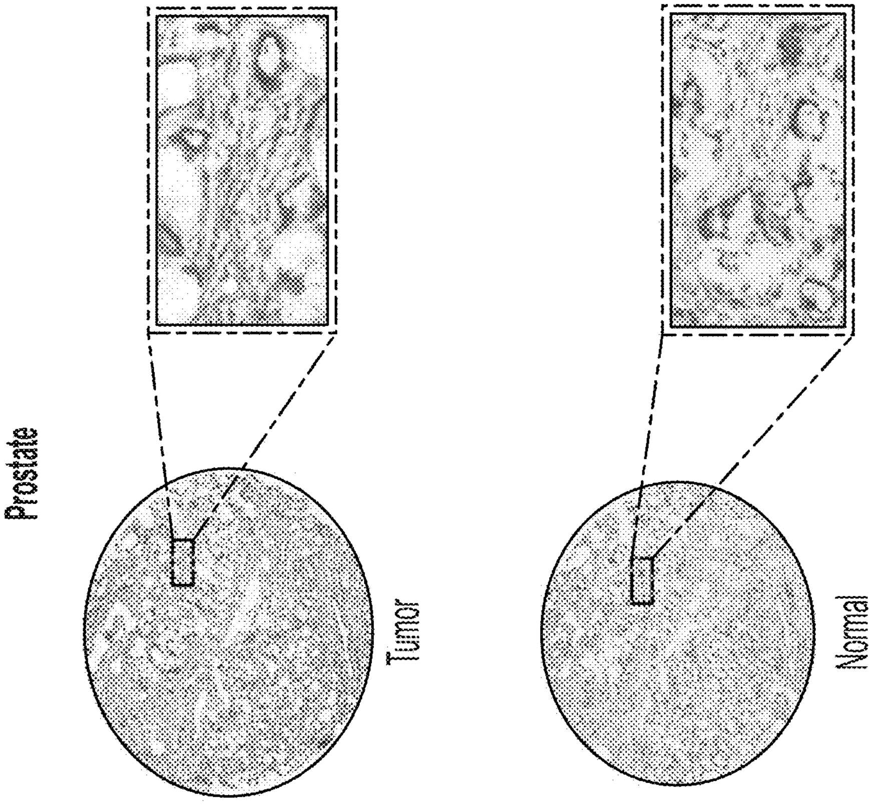

FIG. 50B depicts images associated with IHC detection of $\alpha_V\beta_1$ in prostate cancer.

Figure 50C:
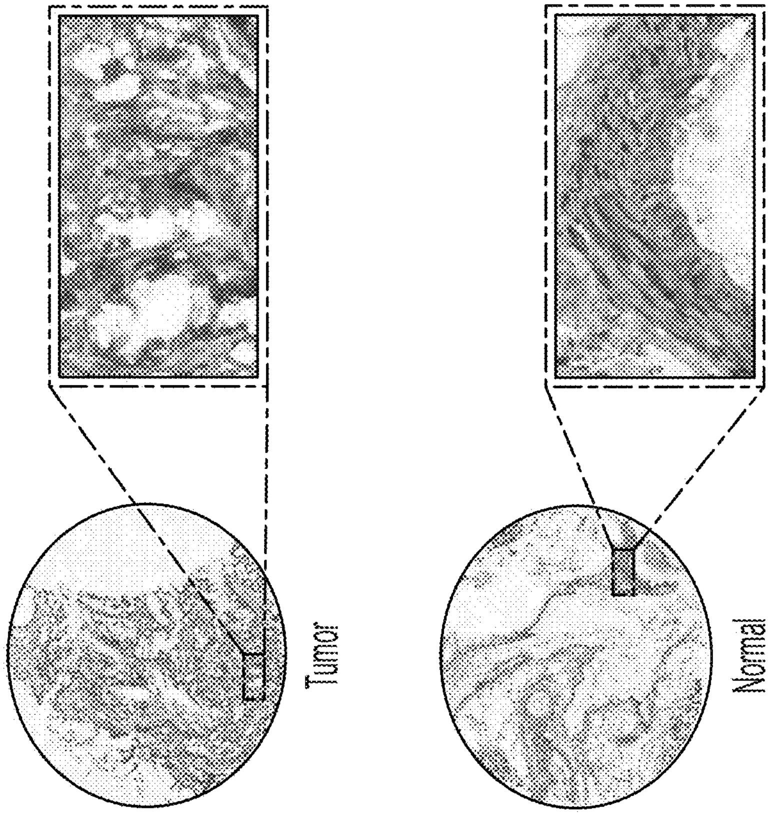

FIG. 50C depicts images associated with IHC detection of $\alpha_V\beta_1$ in pancreatic adenocarcinoma.

Figure 51:
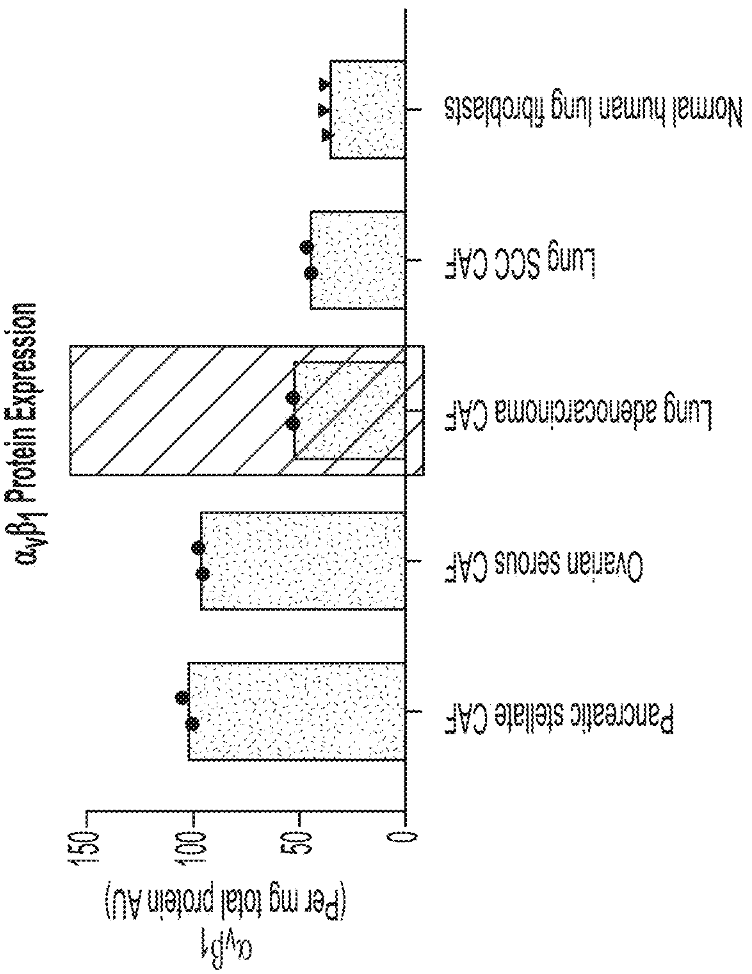

FIG. 51 depicts a chart associated with $\alpha_V\beta_1$ protein expression in various cancer-associated fibroblasts (CAF).

Figure 52:
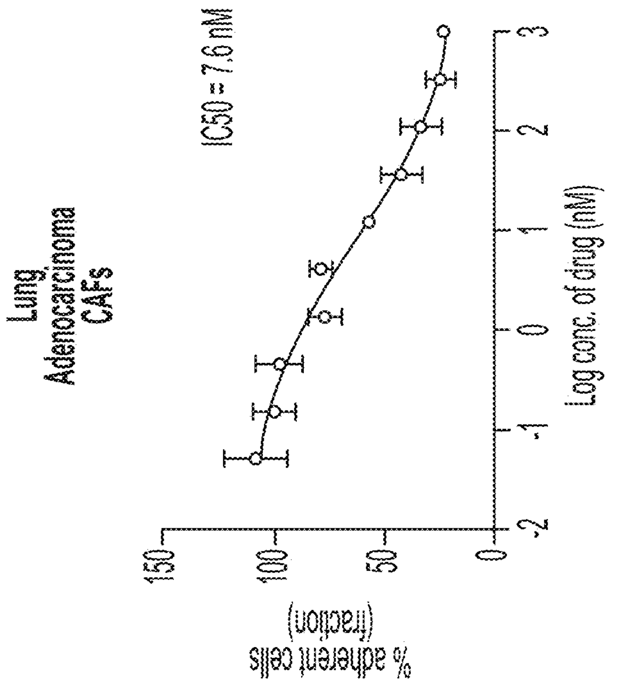

FIG. 52 depicts a graph associated with percent adherent cells (fraction) for Compound 39 in lung adenocarcinoma cancer-associated fibroblasts (CAF) from FIG. 51.

Figure 53B:
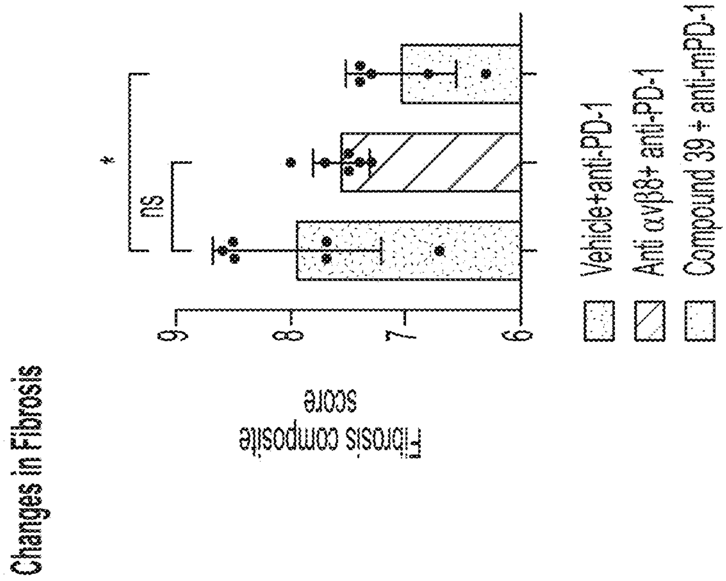
Figure 53A:
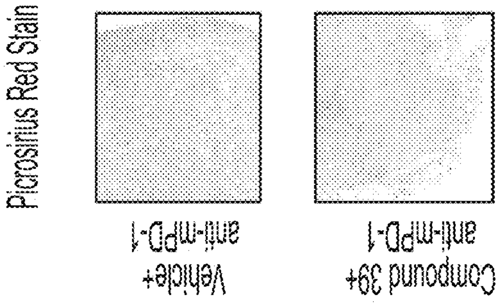

FIG. 53A depicts two picrosirius red stains for vehicle+anti-mPD-1 (top) and Compound 39+anti-mPD-1 (bottom).

FIG. 53B depicts a graph showing the fibrosis composite score for vehicle+anti-PD-1, anti-$\alpha_V\beta_8$+anti-PD-1, and Compound 39+anti-mPD-1.

Figures 54A, 54B:
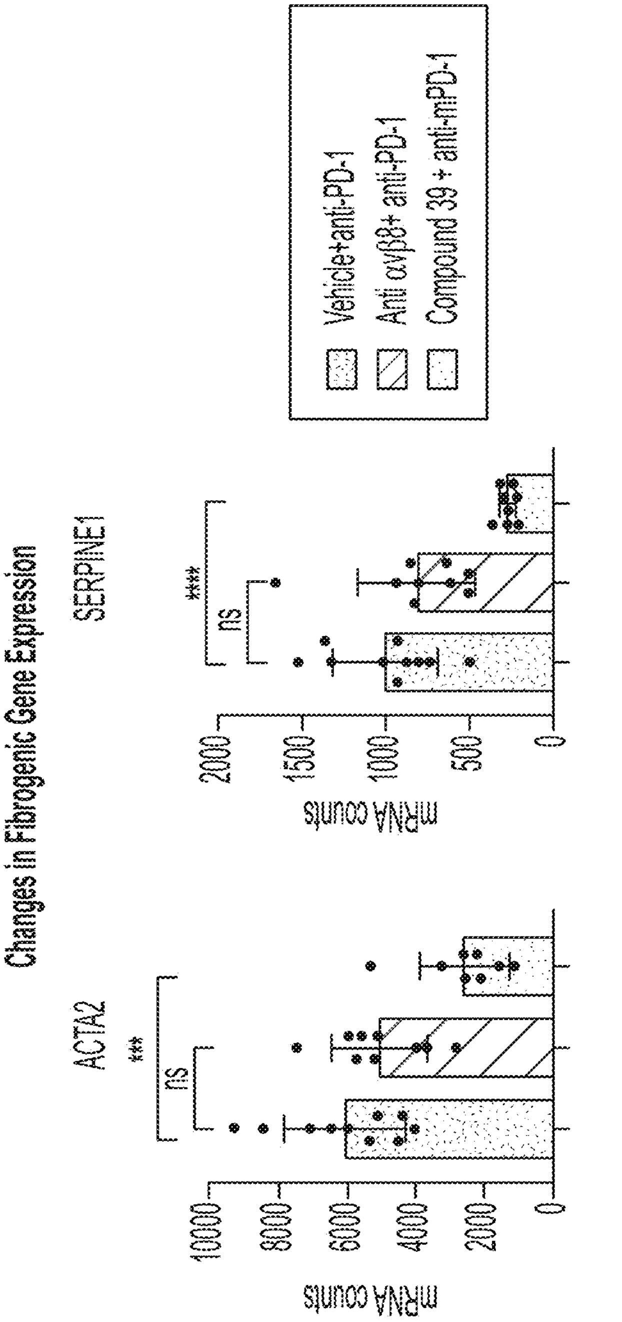

FIG. 54A depicts a graph associated with changes in ACTA2 for vehicle+anti-PD-1, anti-$\alpha_V\beta_8$+anti-PD-1, and Compound 39+anti-mPD-1.

FIG. 54B depicts a graph associated with changes in SERPINE1 for vehicle+anti-PD-1, anti-$\alpha_V\beta_8$+anti-PD-1, and Compound 39+anti-mPD-1.

Figures 54C, 54D:
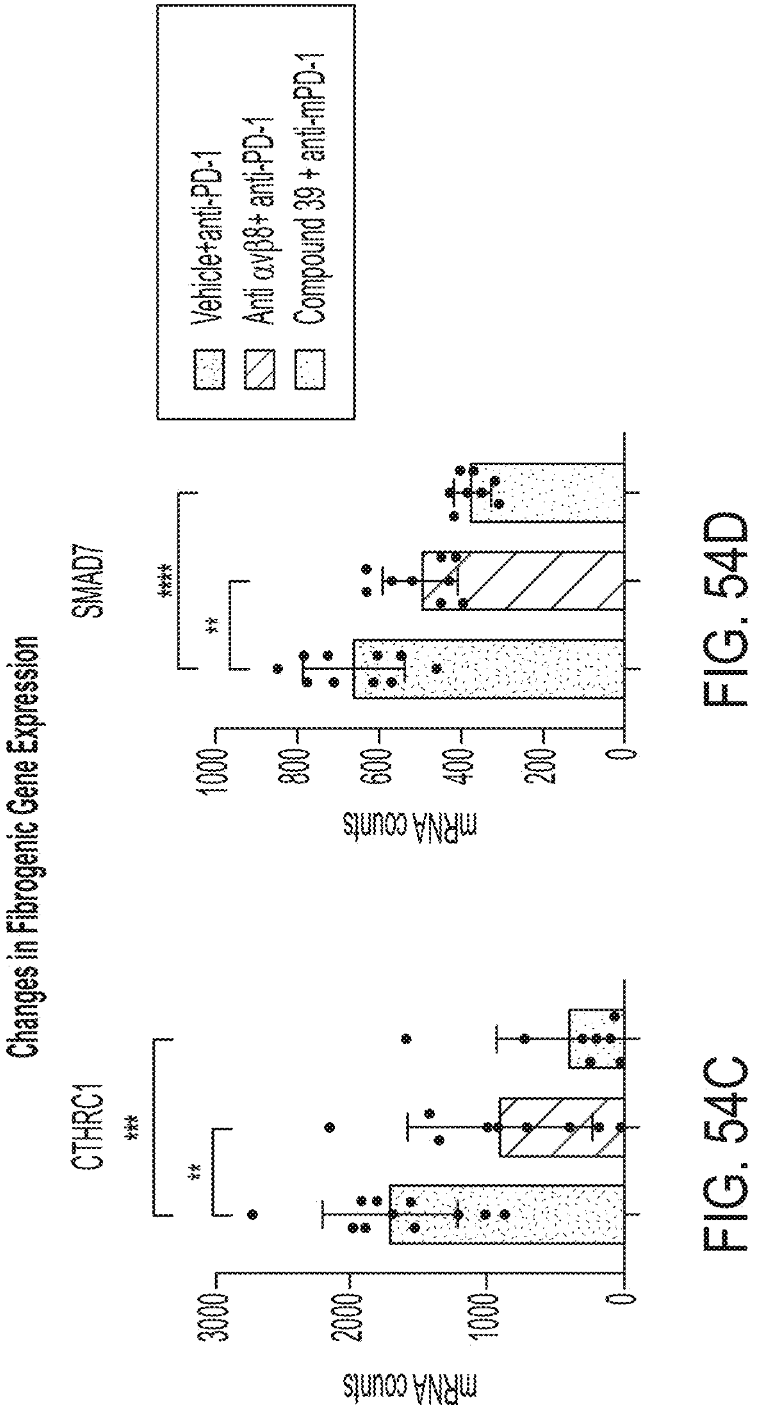

FIG. 54C depicts a graph associated with changes in CTHRC1 for vehicle+anti-PD-1, anti-$\alpha_V\beta_8$+anti-PD-1, and Compound 39+anti-mPD-1.

FIG. 54D depicts a graph associated with changes in SMAD7 for vehicle+anti-PD-1, anti-$\alpha_V\beta_8$+anti-PD-1, and Compound 39+anti-mPD-1.

Figure 55A:
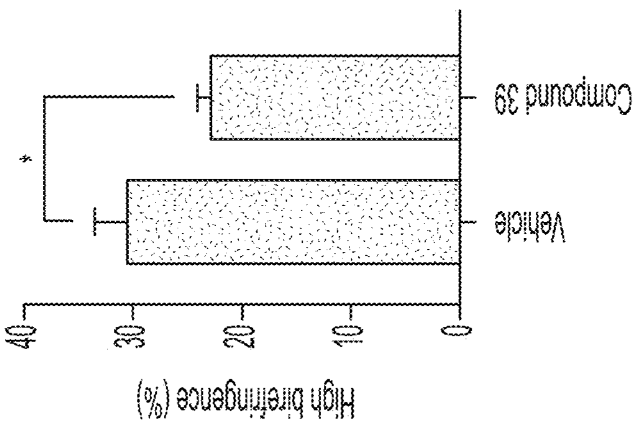

FIG. 55A depicts a graph associated with high birefringence (percentage) for vehicle and Compound 39. Statistical assessment by one-way ANOVA with Tukey.

Figure 55B:
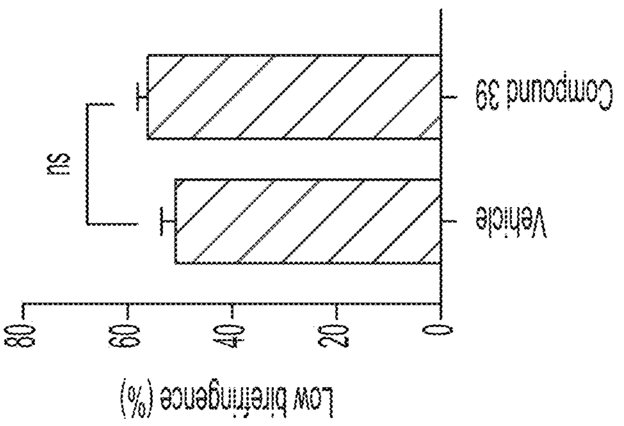

FIG. 55B depicts a graph associated with low birefringence (percentage) for vehicle and Compound 39. Statistical assessment by one-way ANOVA with Tukey.

Figure 55C:
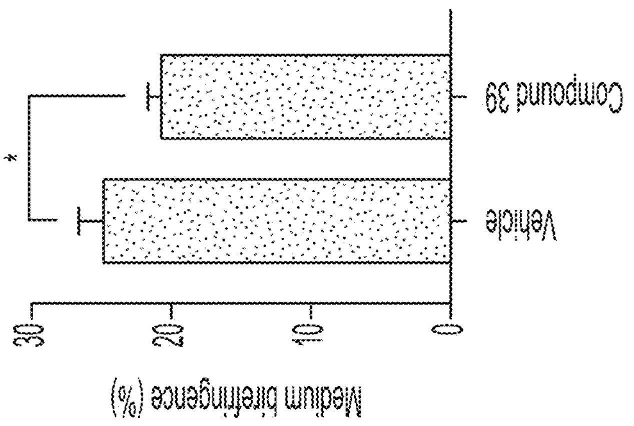

FIG. 55C depicts a graph associated with medium birefringence (percentage) for vehicle and Compound 39. Statistical assessment by one-way ANOVA with Tukey.

Figure 56:
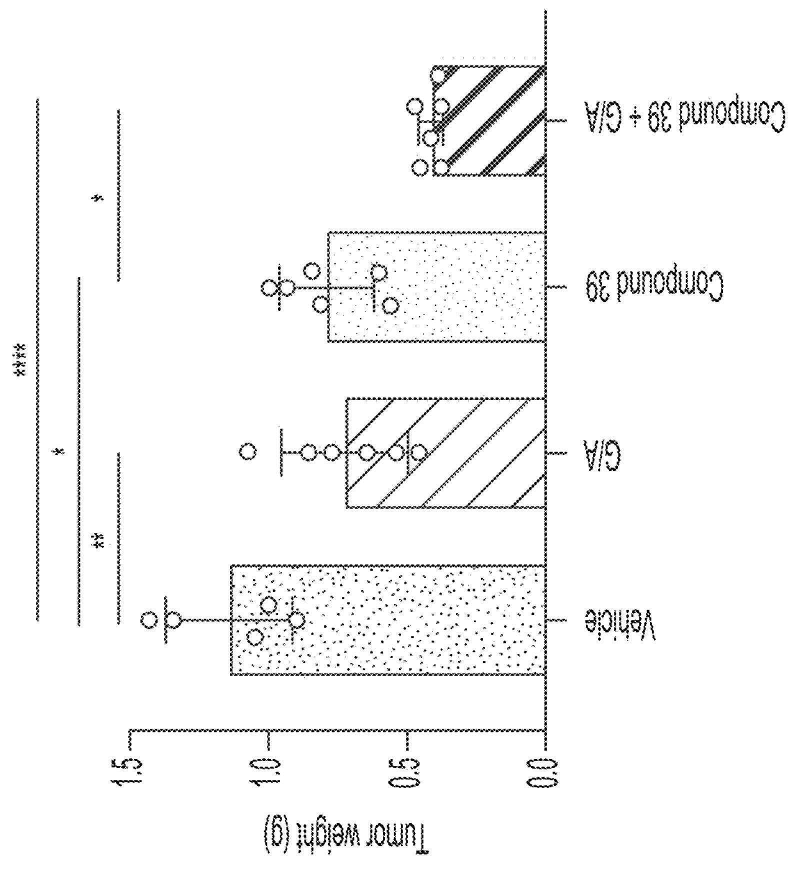

FIG. 56 depicts a graph associated with tumor weight in an orthotopic immunodeficient PDX-10 model for vehicle, Gemcitabine/Abraxane (G/A), Compound 39, and Compound 39+G/A, where *p<0.05 by one-way ANOVA with Tukey, p<0.01 by one-way ANOVA with Tukey, and **p<0.0001 by one-way ANOVA with Tukey.

Figure 57:
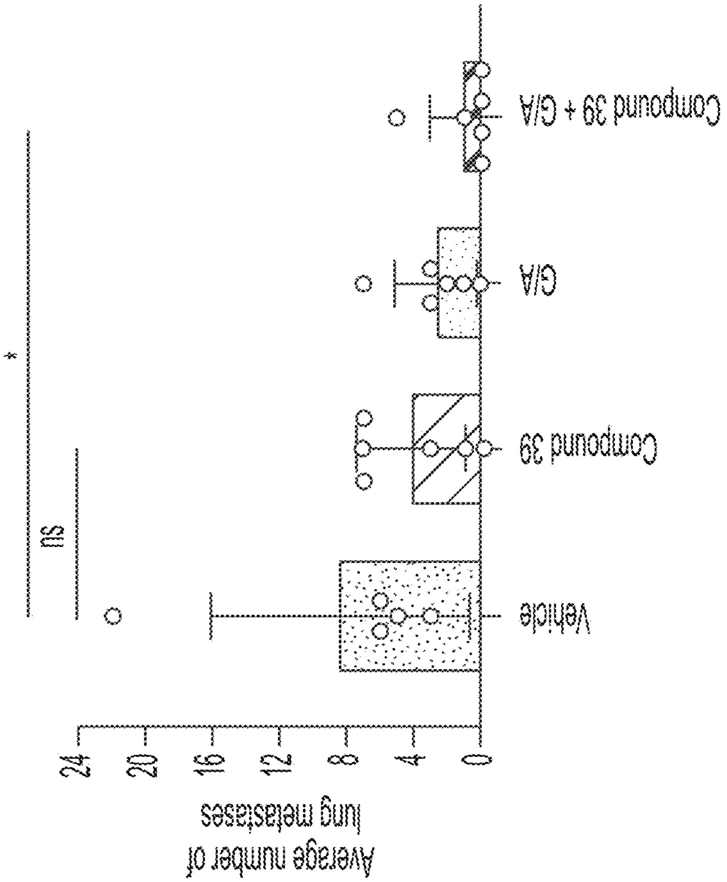

FIG. 57 depicts a graph associated with the average number of lung metastases in an orthotopic immunodeficient PDX-10 model for vehicle, Gemcitabine/Abraxane (G/A), Compound 39, and Compound 39+G/A, where *p<0.05 by one-way ANOVA with Tukey.

Figure 58:
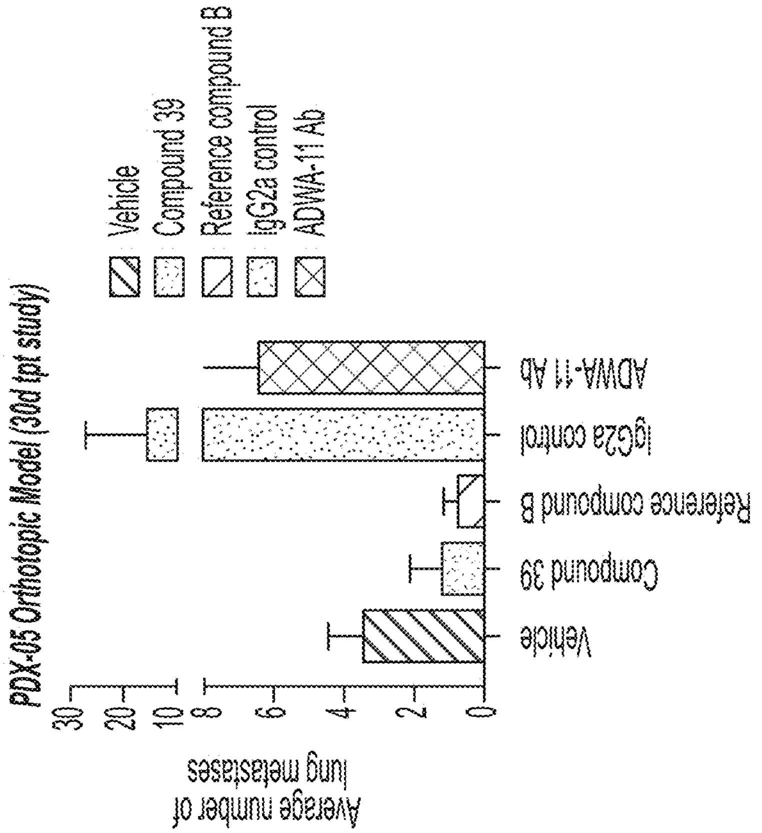

FIG. 58 depicts a graph associated with an average number of lung metastases in an PDX-05 orthotopic model for various groups in a 30 day study.

Figure 59:
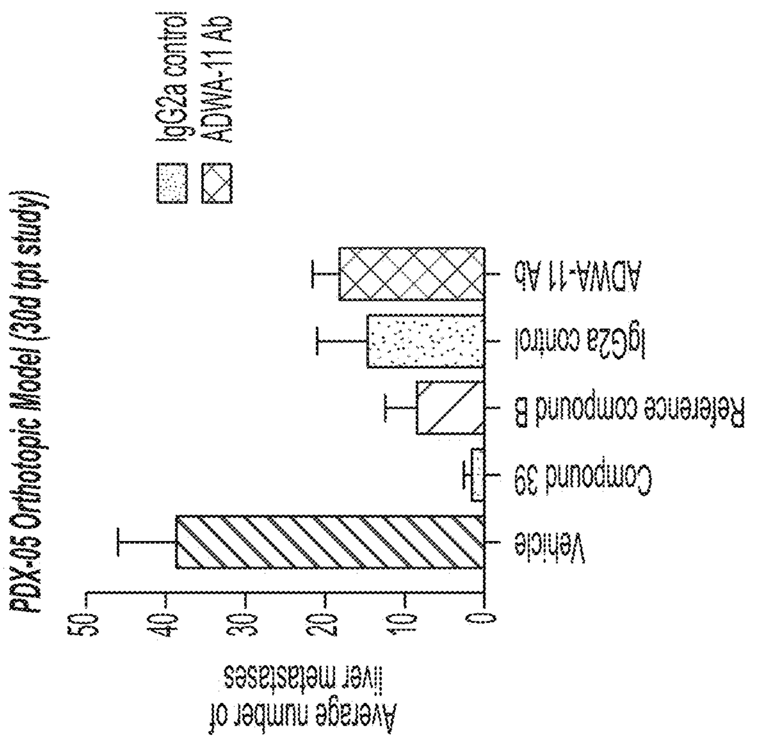

FIG. 59 depicts a graph associated with an average number of liver metastases in an PDX-05 orthotopic model for various groups in a 30 day study.

Figure 60:
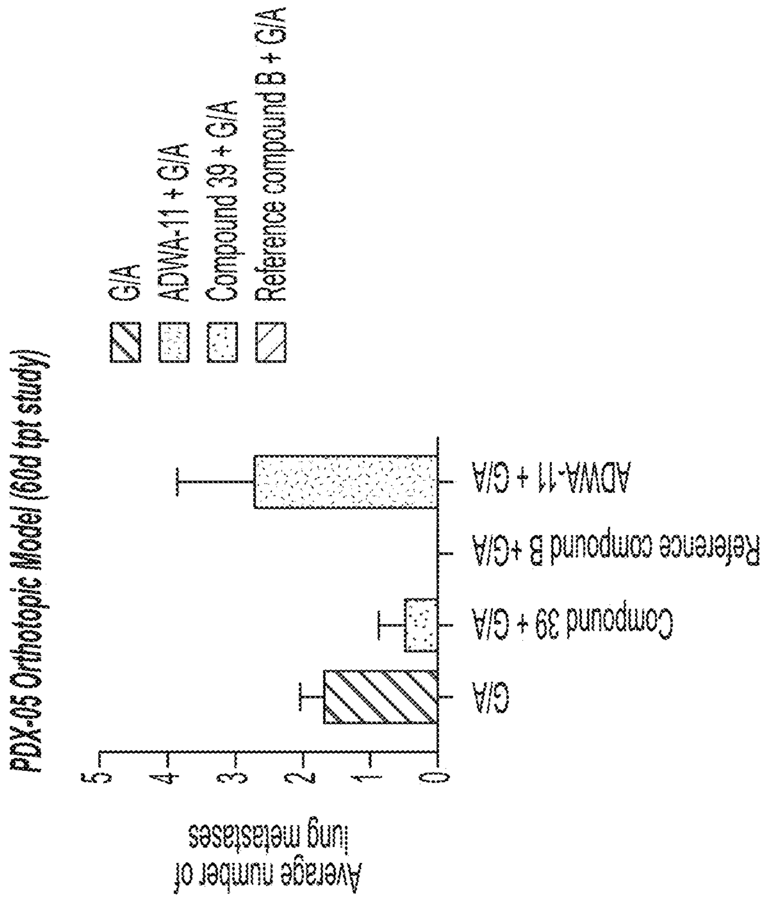

FIG. 60 depicts a graph associated with an average number of lung metastases in an PDX-05 orthotopic model for various groups in a 60 day study.

Figure 61:
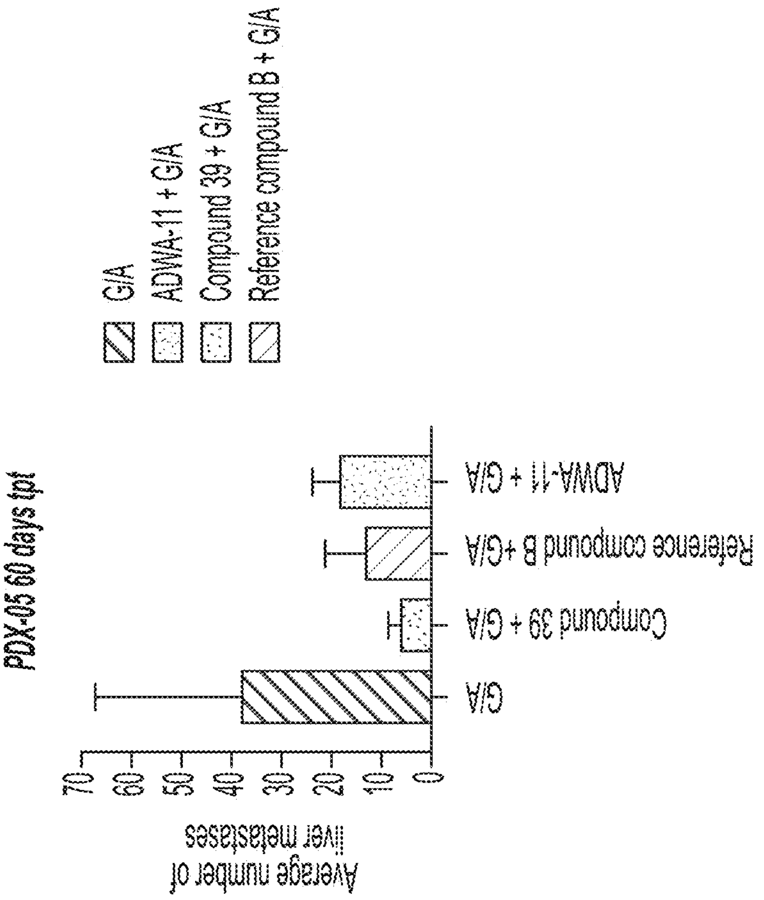

FIG. 61 depicts a graph associated with an average number of liver metastases in an PDX-05 orthotopic model for various groups in a 60 day study.

Figure 62:
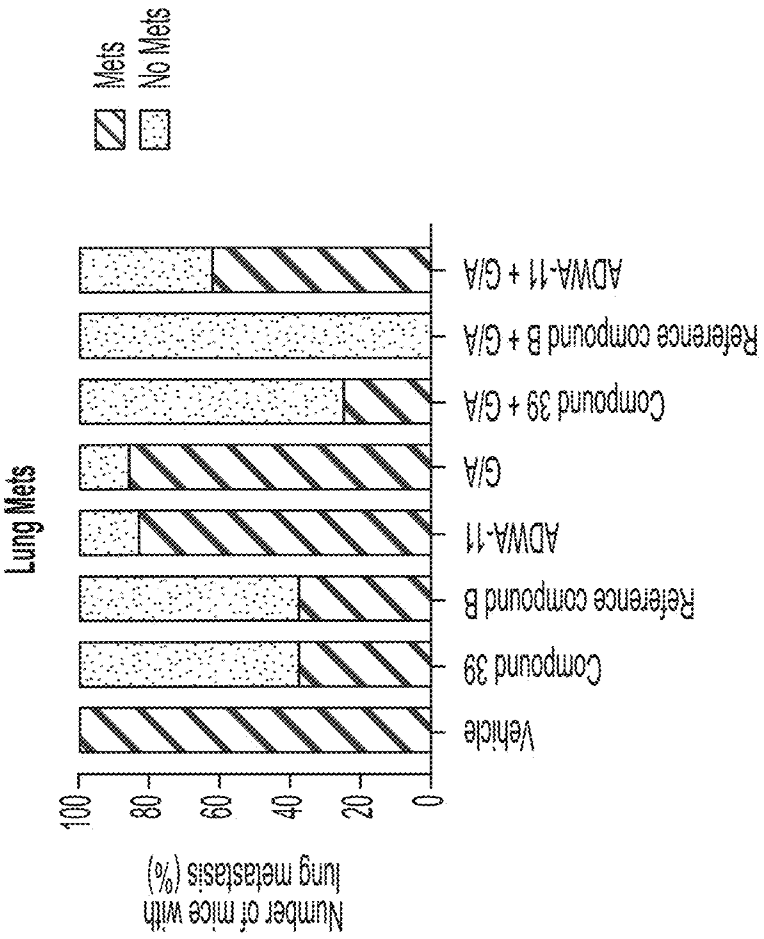

FIG. 62 depicts a graph associated with the number of mice having lung metastasis for various groups.

Figure 63:
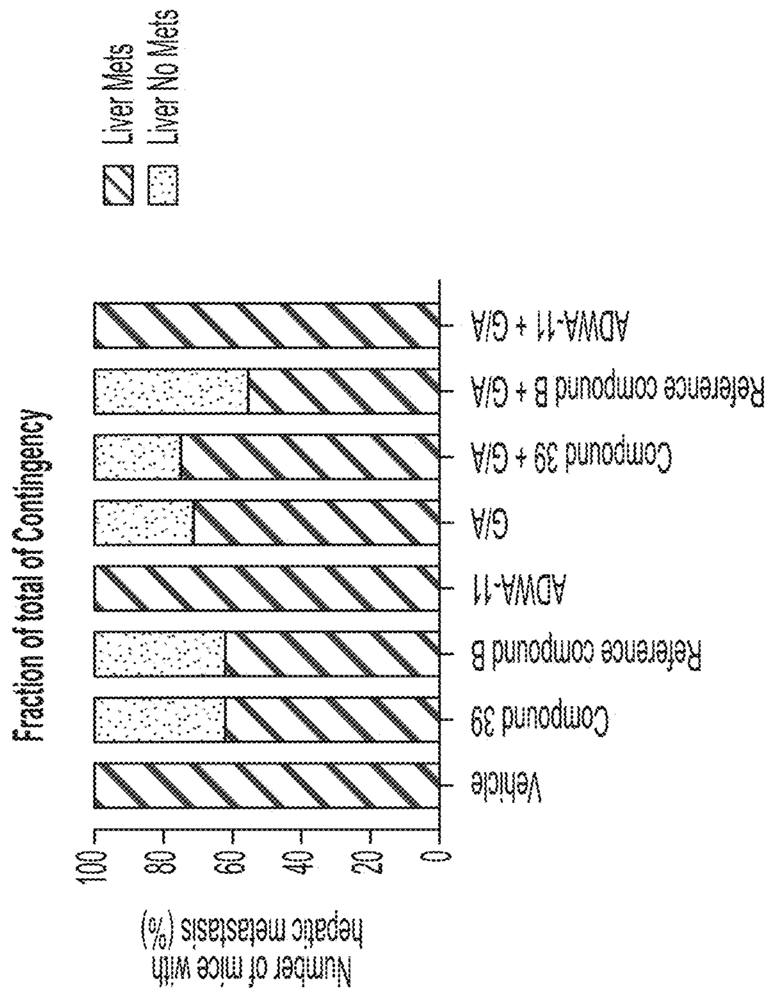

FIG. 63 depicts a graph associated with the number of mice having hepatic metastasis for various groups.

Figure 64:
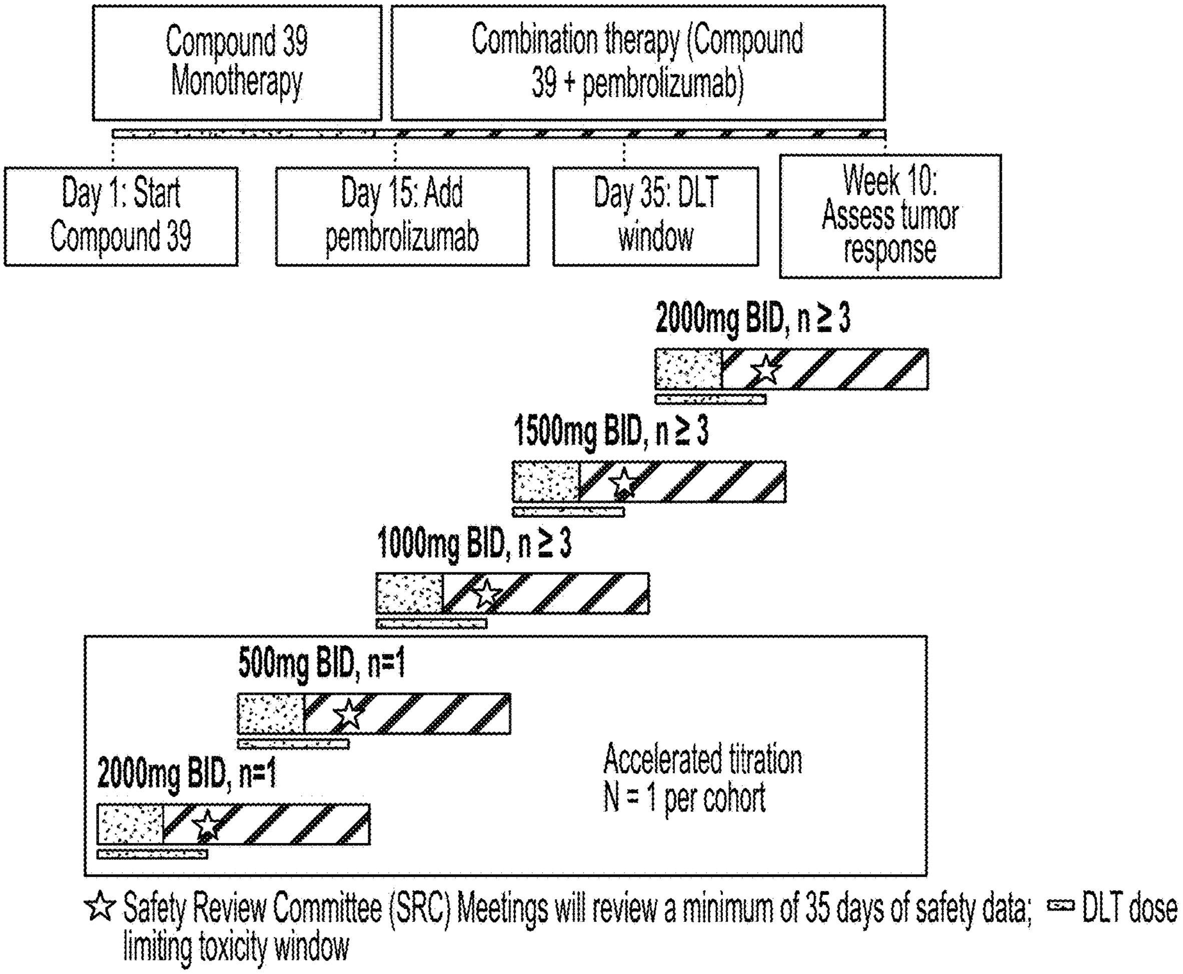

FIG. 64 depicts a schematic diagram of the Phase 1 clinical overview: two-part study to assess safety, tolerability, pharmacokinetics and preliminary evidence of antitumor activity.

Figure 65:
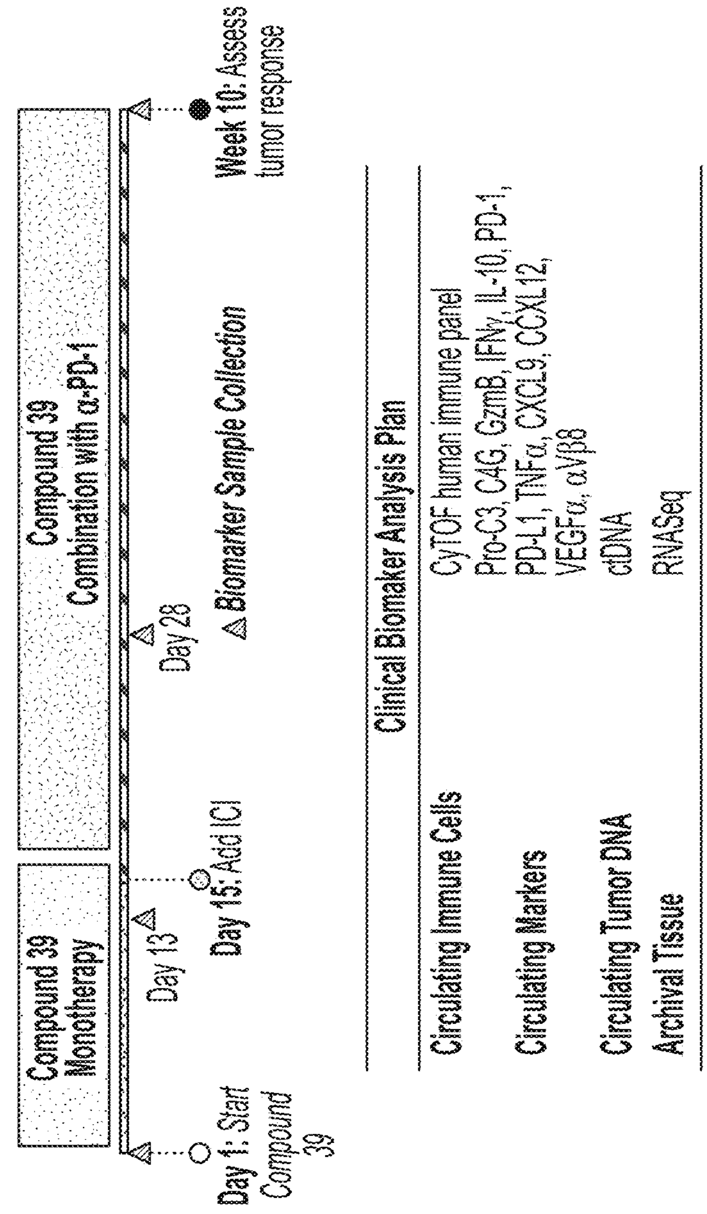

FIG. 65 depicts a schematic diagram of the clinical biomarker plan.

Figure 66:
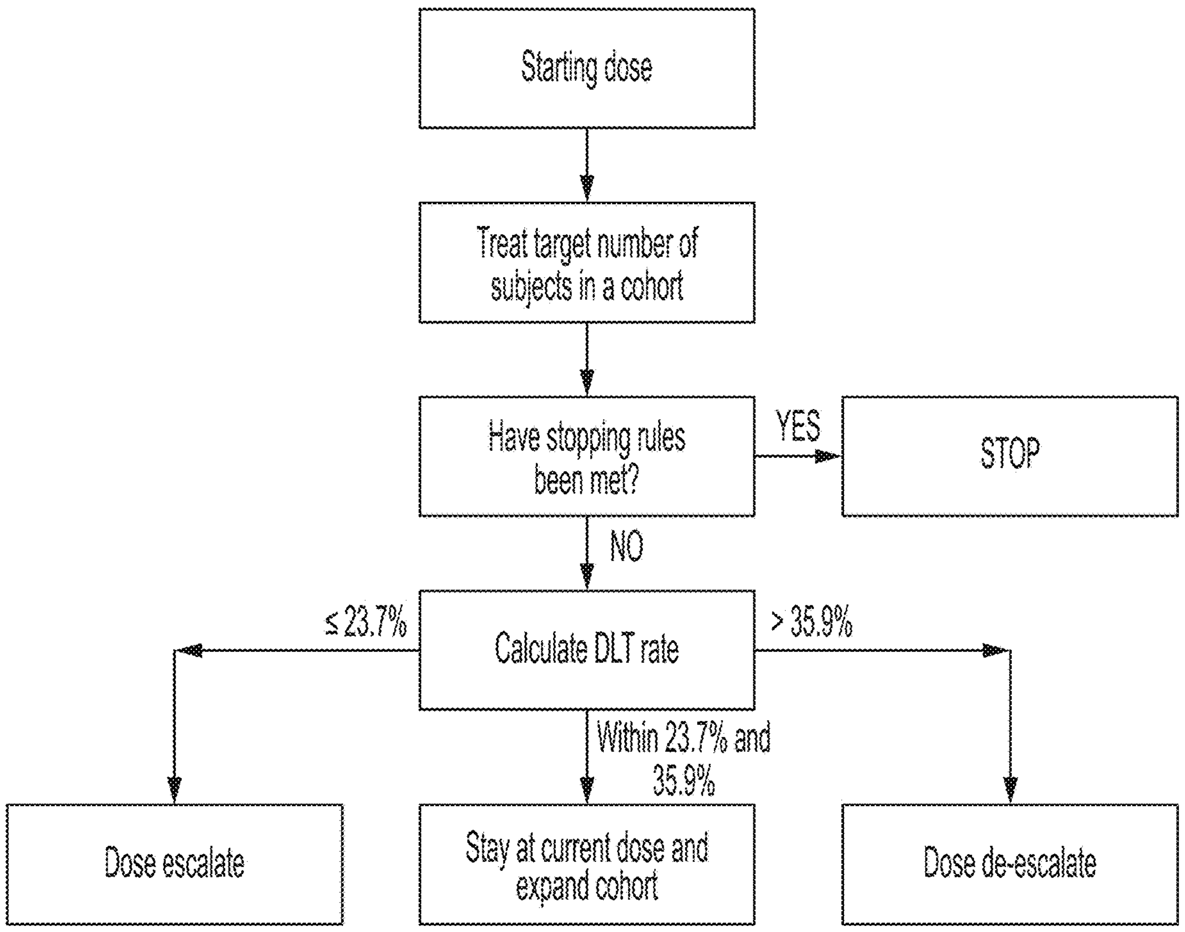

FIG. 66 depicts a schematic diagram of Bayesian optimal interval (BOIN) dose escalation and decision criteria for Example B10.

Figure 67:
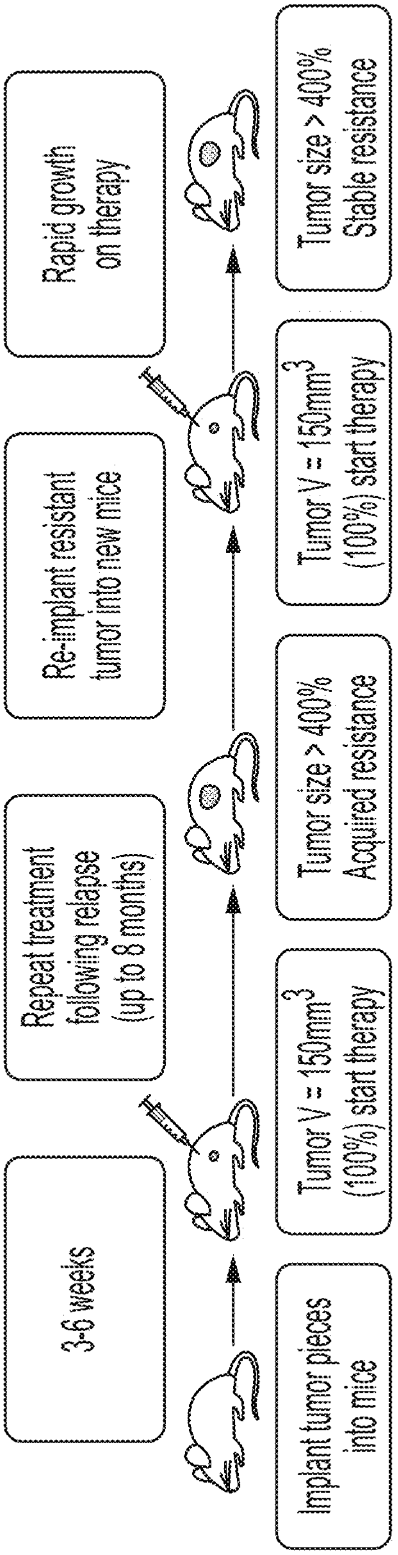

FIG. 67 depicts a schematic diagram of a PDA model of FOLFIRINOX resistance.

Figure 68B:
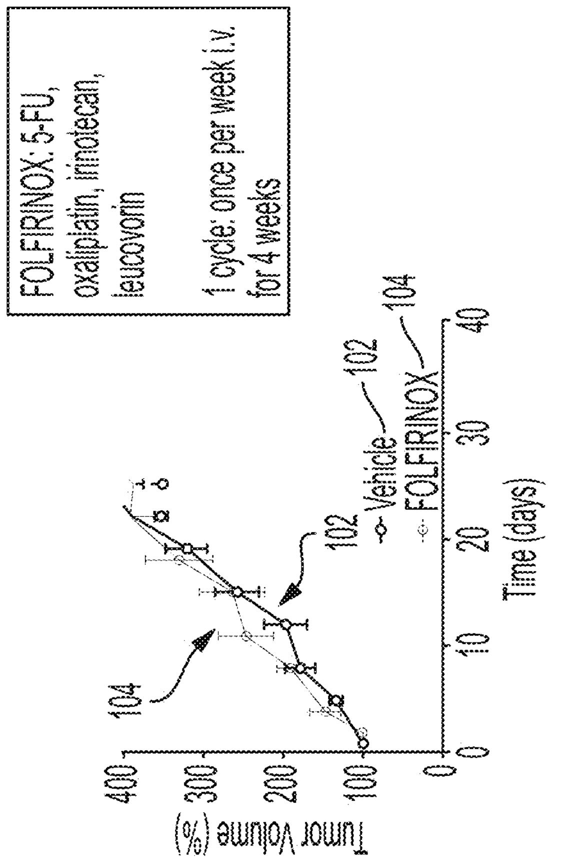
Figure 68A:
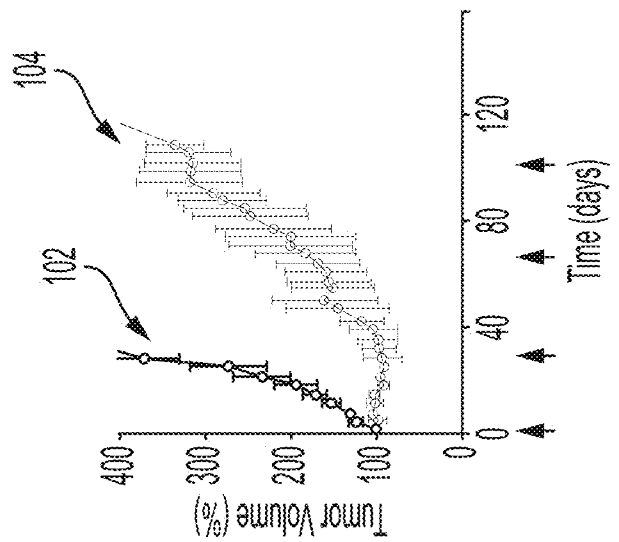

FIG. 68A depicts a graph showing tumor volume (percentage) for a vehicle 102 and for FOLFIRINOX 104 over a time period of 120 days for the PDA model.

FIG. 68B depicts a graph showing tumor volume (percentage) for a vehicle 102 and for FOLFIRINOX 104 over a time period of 40 days for the PDA model.

Figure 69B:
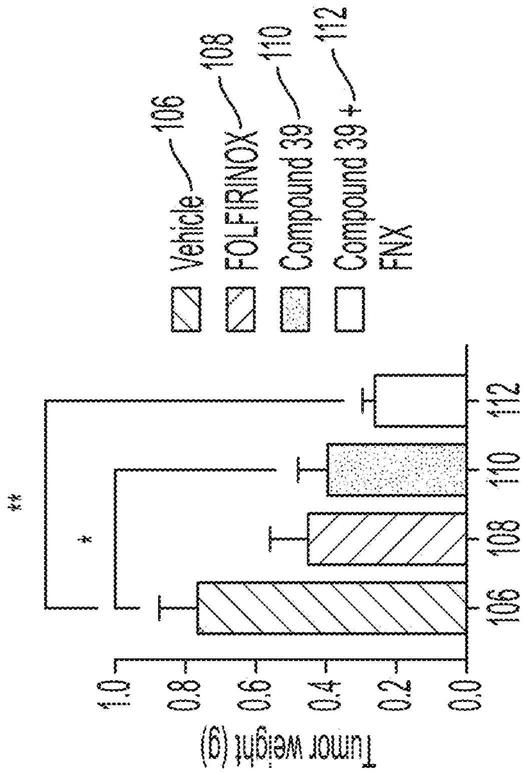
Figure 69A:
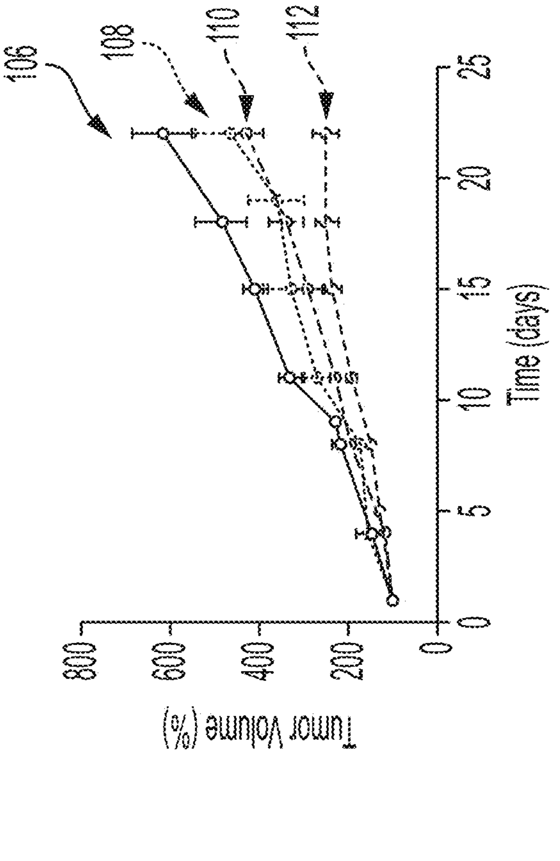

FIG. 69A depicts a graph showing tumor volume (percentage) for a vehicle 106, FOLFIRINOX (FNX) 108, Compound 39 110, and Compound 39+FX 112 over a time period of 25 days for the PDA model.

FIG. 69B depicts a chart showing the tumor volume (grams) for a vehicle 106, FOLFIRINOX (FNX) 108, Compound 39 110, and Compound 39+FX 112 associated with FIG. 69A.

Figure 70:
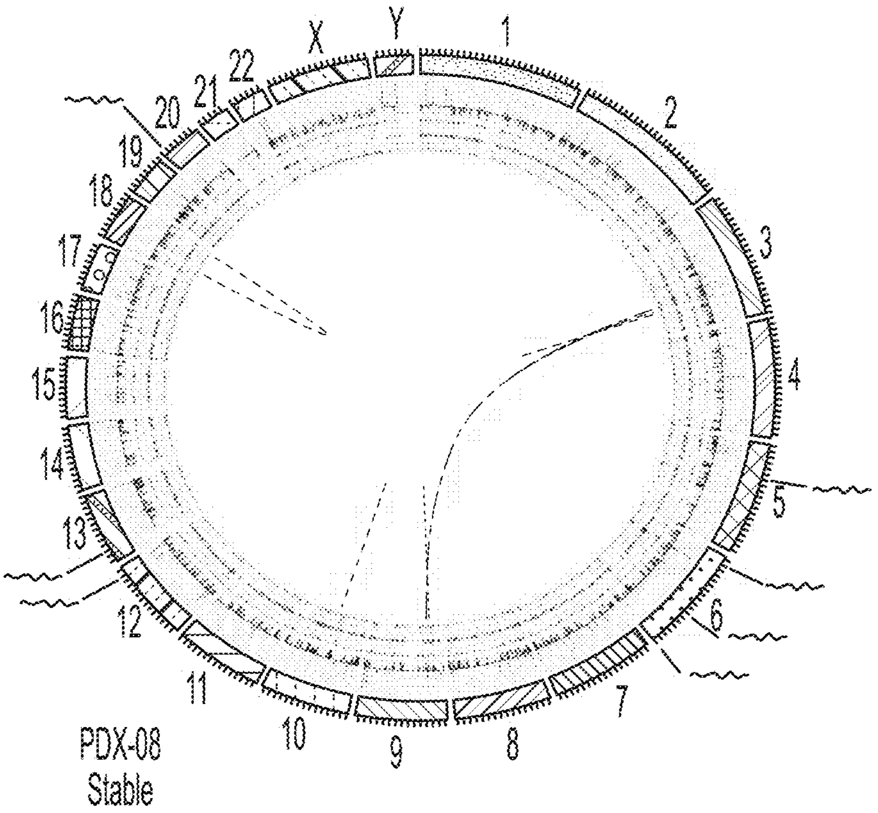

FIG. 70 depicts a schematic diagram of a generic epithelial-mesenchymal transition (EMT) signature of PDX-08.

Figure 71:
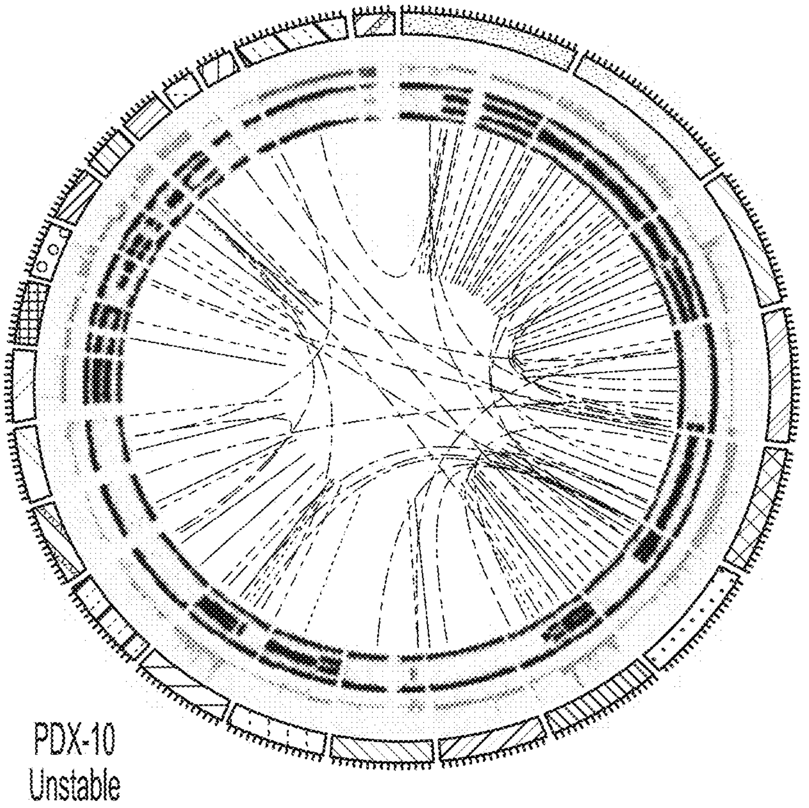

FIG. 71 depicts a schematic diagram of a generic epithelial-mesenchymal transition (EMT) signature of PDX-10.

Figure 72:
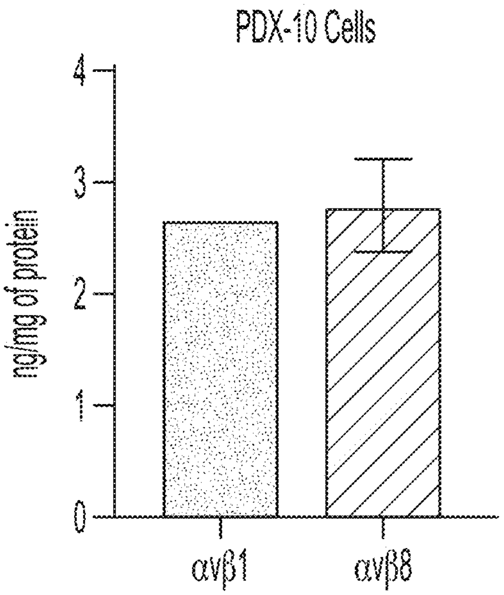

FIG. 72 depicts a chart showing an amount of protein (ng/mg) for $\alpha_v\beta_1$ and $\alpha_v\beta_8$ in a PDX-10 orthotopic model.

Figure 73:
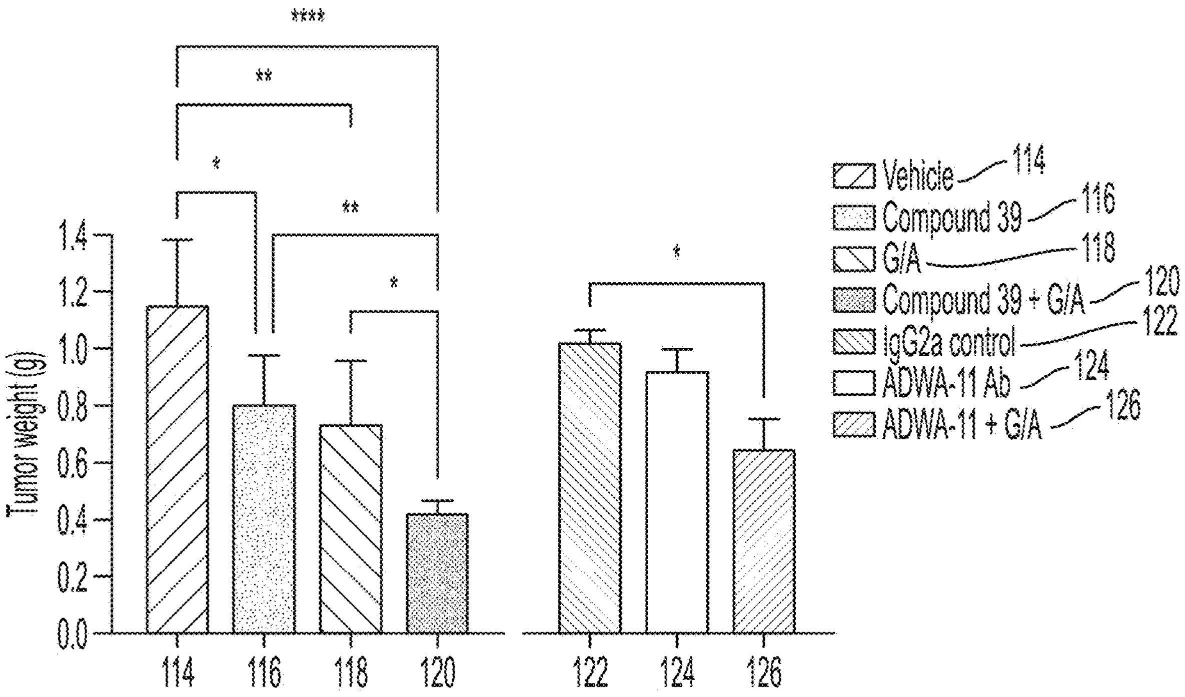

FIG. 73 depicts a chart showing a tumor weight (g) for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Figure 74:
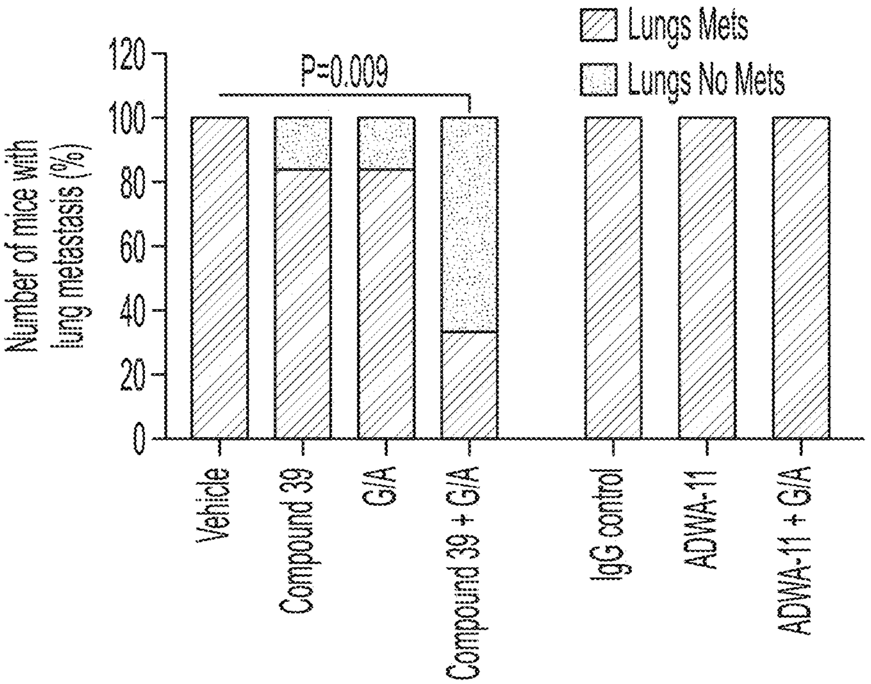

FIG. 74 depicts a chart showing a number of mice with lung metastasis (percentage) for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Figure 75:
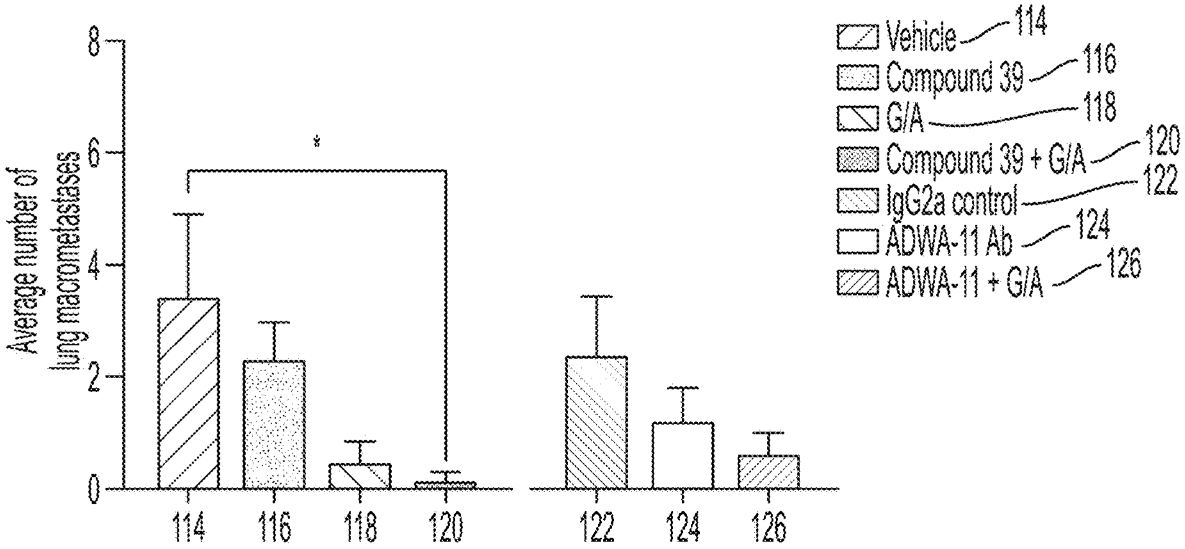

FIG. 75 depicts a chart showing an average number of lung macro-metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Figure 76:
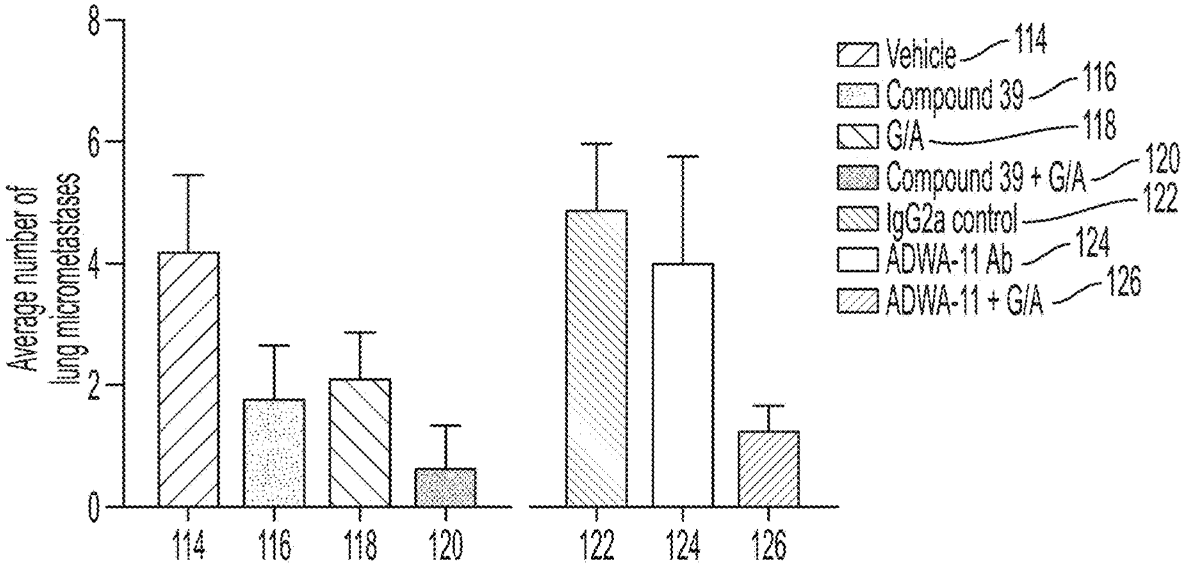

FIG. 76 depicts a chart showing an average number of lung micro-metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Figure 77:
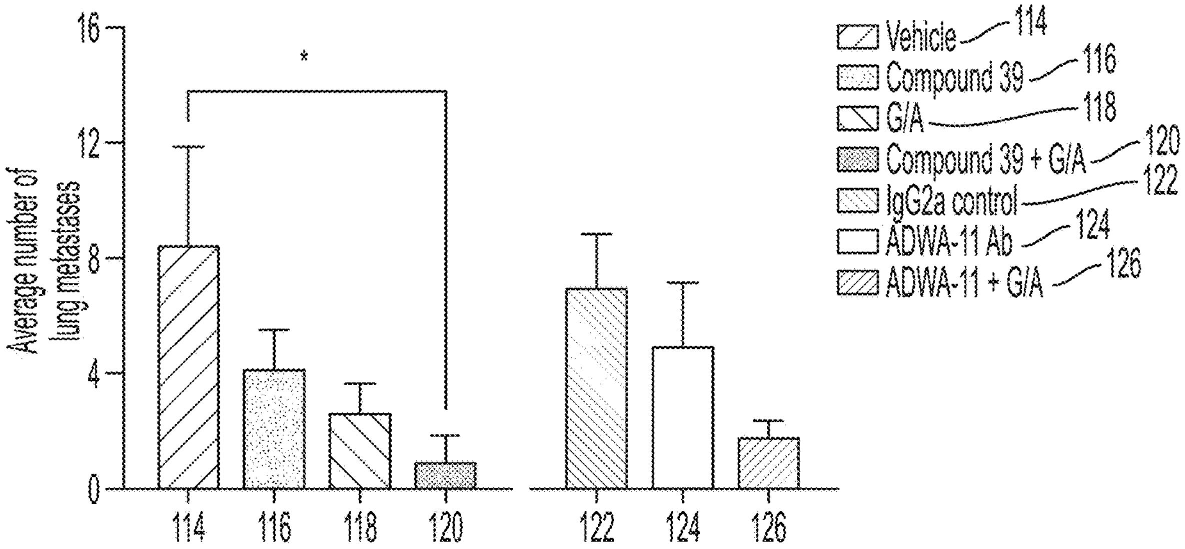

FIG. 77 depicts a chart showing an average number of lung metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Figure 78B:
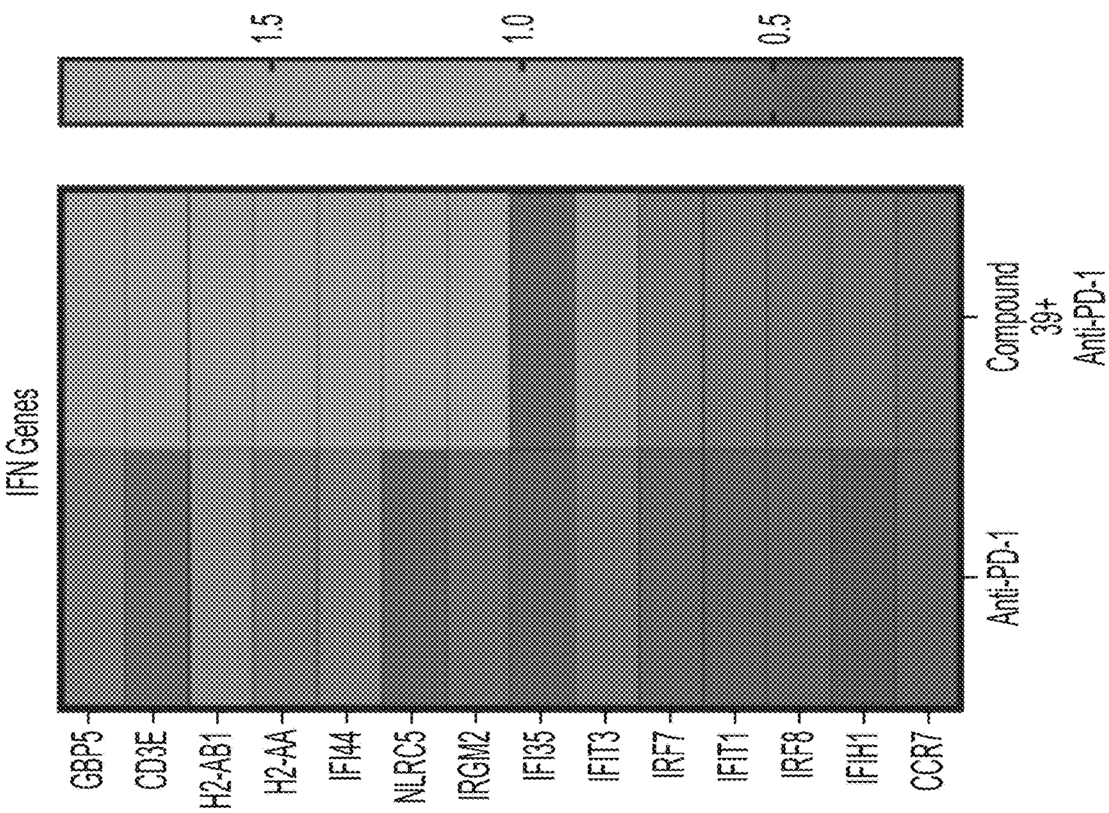
Figure 78A:
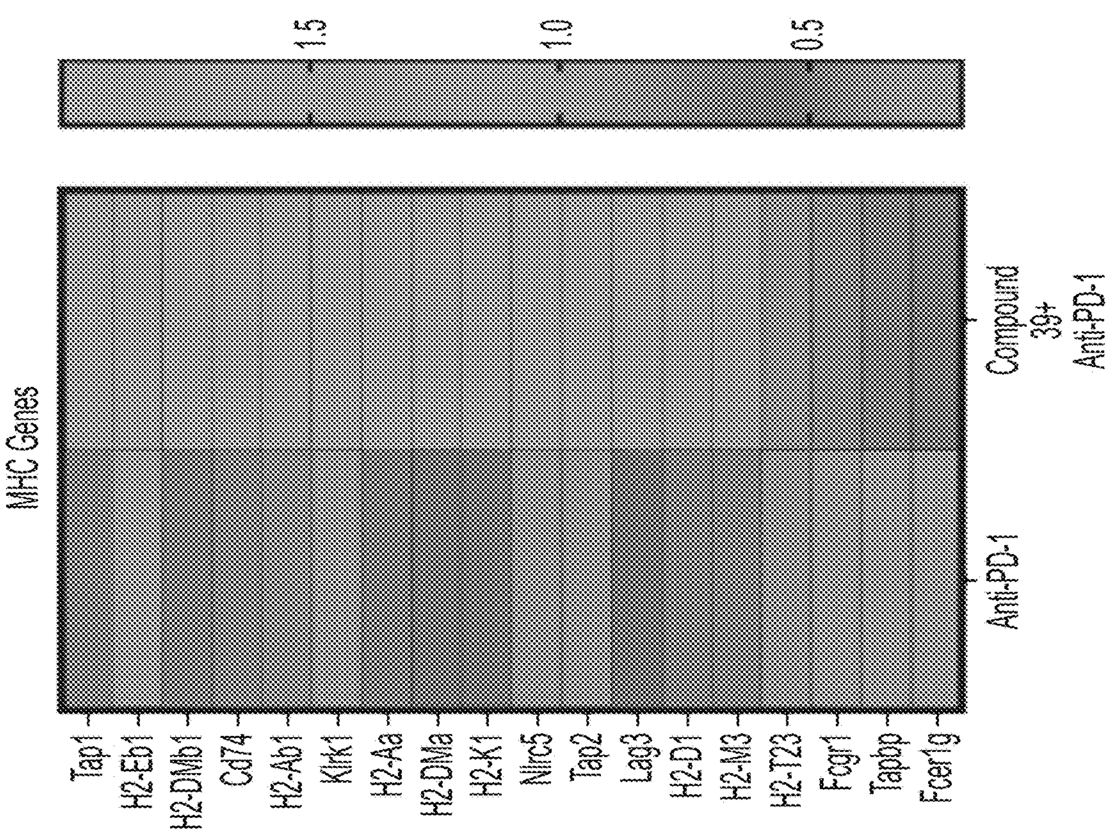

FIG. 78A depicts a schematic diagram showing various major histocompatibility complex (MHC) gene expression associated with anti-PD1 and Compound 39+anti-PD1 in a syngeneic model of PDA (Pan02).

FIG. 78B depicts a schematic diagram showing various type-I interferon (IFN) gene expression associated with anti-PD1 and Compound 39+anti-PD1 in a syngeneic model of PDA (Pan02).

Figure 79:
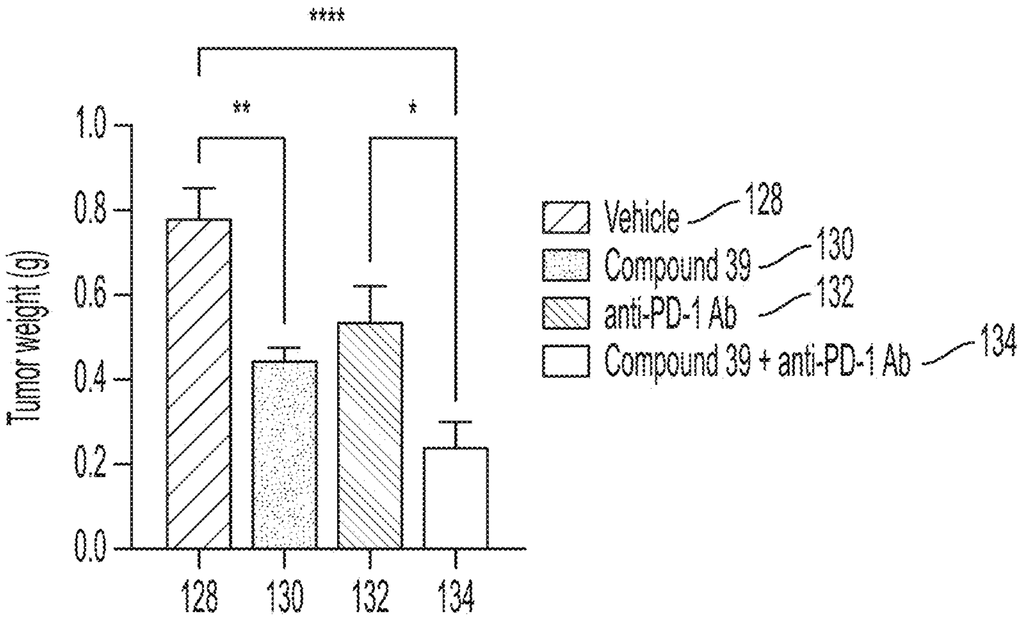

FIG. 79 depicts a chart showing tumor weight (g) for a vehicle 128, Compound 39 130, anti-PD-1 Ab 132, and Compound 39+anti-PD-1 Ab 134.

Figure 80:
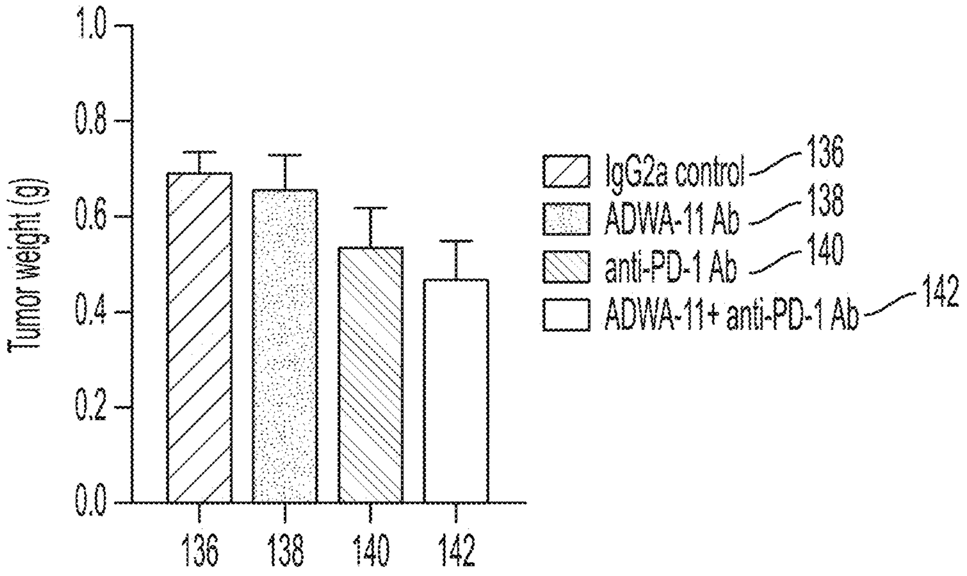

FIG. 80 depicts a chart showing tumor weight (g) for an IgG2a control 136, ADWA-11 Ab 138, anti-PD-1 Ab 140, and ADWA-11+anti-PD-1 Ab 142.

Figure 81:
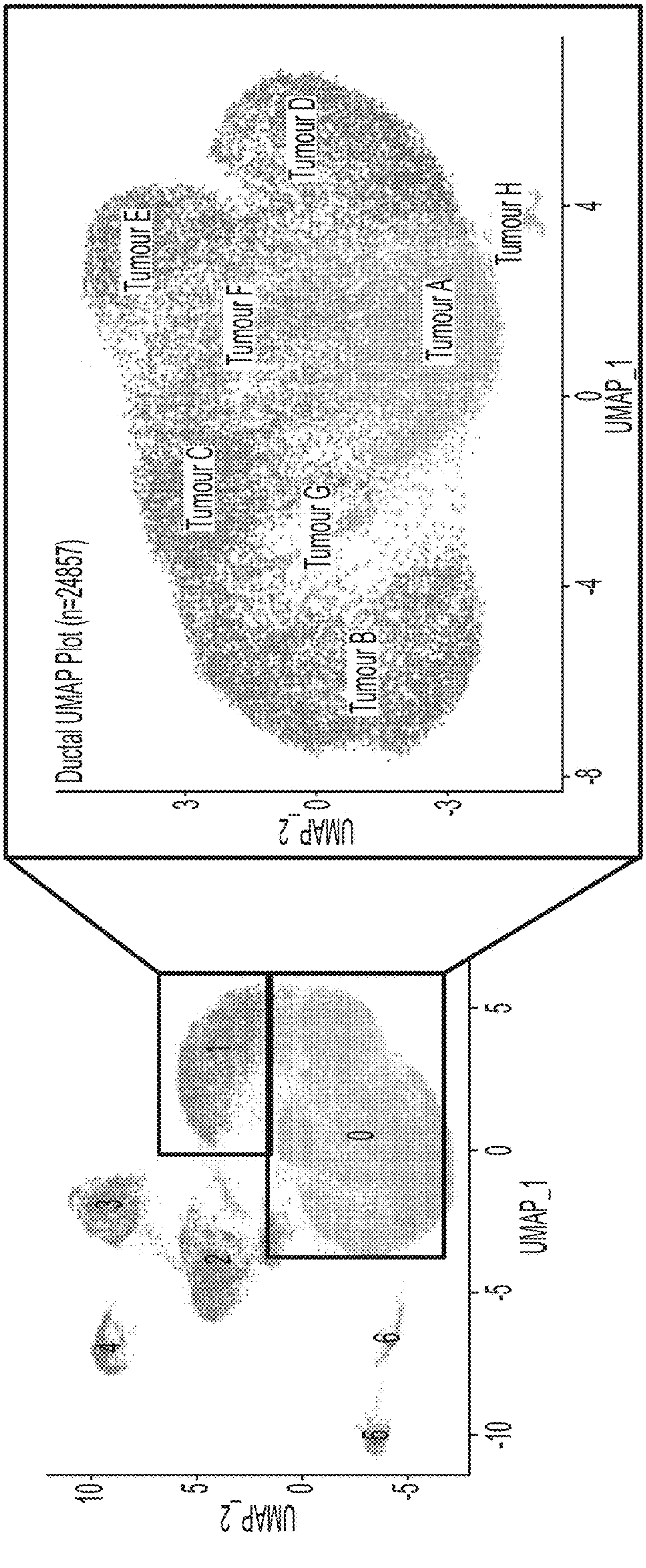

FIG. 81 depicts a ductal Uniform Manifold Approximation and Projection (UMAP) plot showing various tumors.

Figure 82:
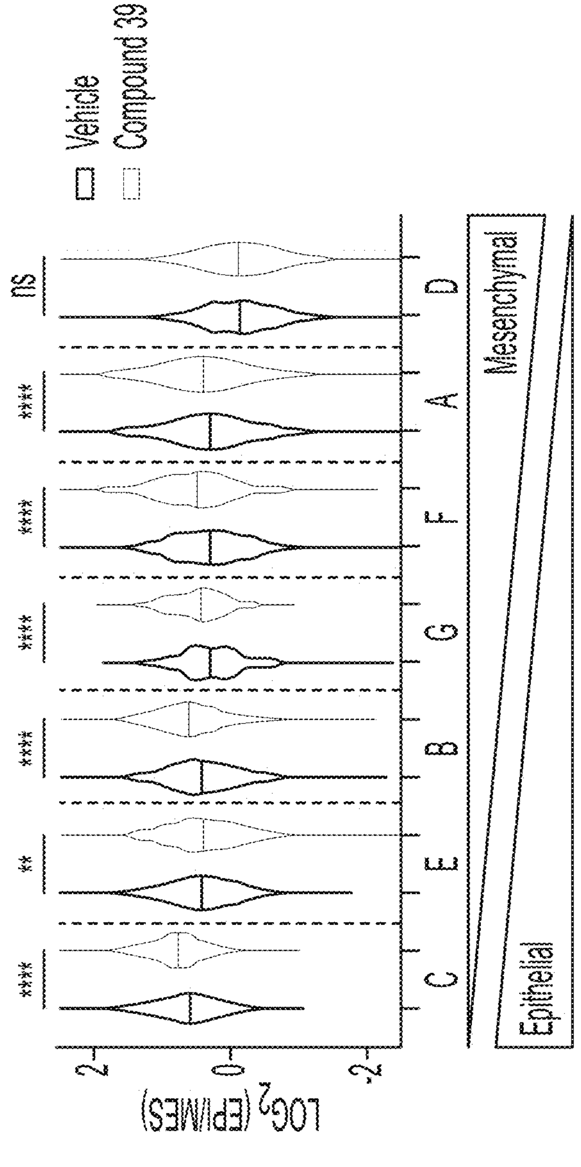

FIG. 82 depicts a graph showing a generic epithelial-mesenchymal transition (EMT) signature for various tumors (Tumor A, Tumor C, Tumor E, Tumor B, Tumor G, Tumor F, and Tumor D) subjected to a vehicle and to Compound 39.

Figure 83:
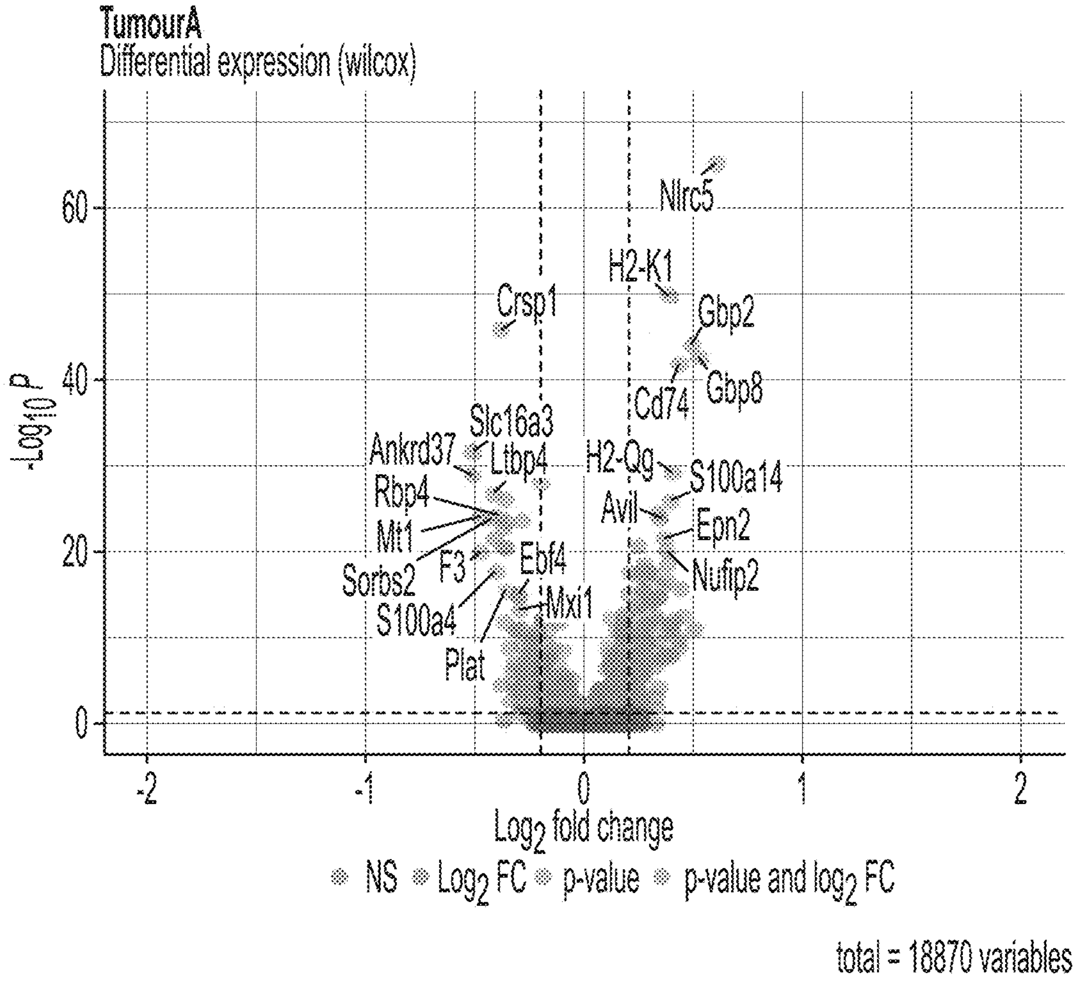

FIG. 83 depicts a graph showing a differential expression for Tumor A.

Figure 84:
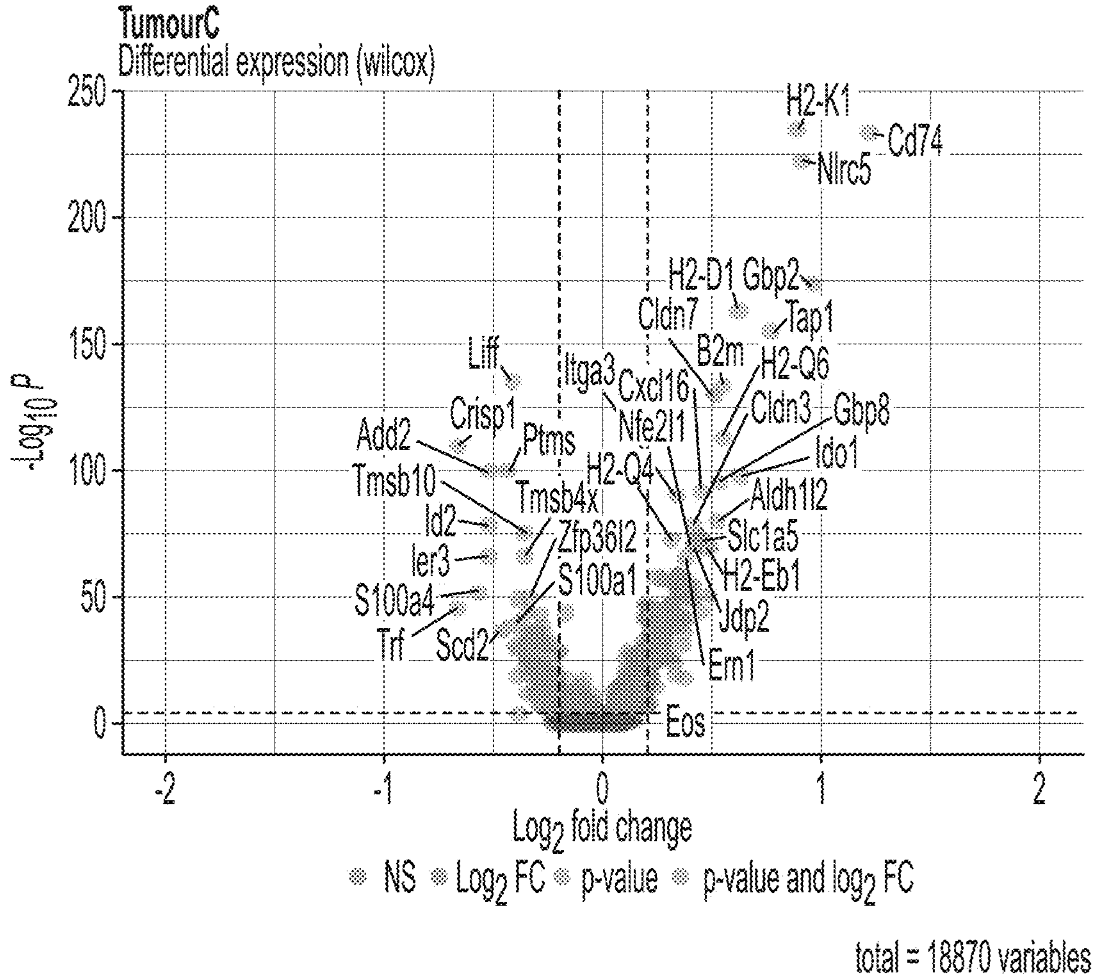

FIG. 84 depicts a graph showing a differential expression for Tumor C.

Figure 85:
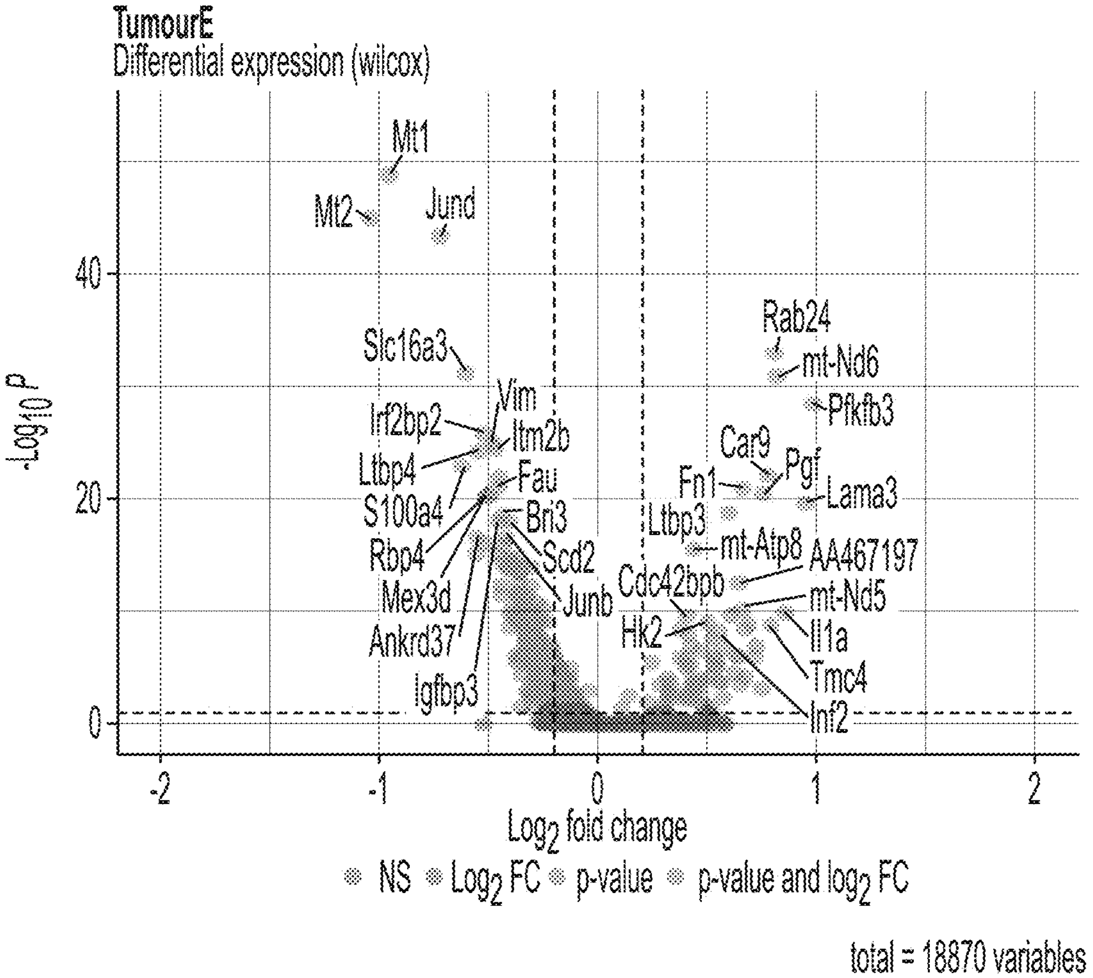

FIG. 85 depicts a graph showing a differential expression for Tumor E.

Figure 86:
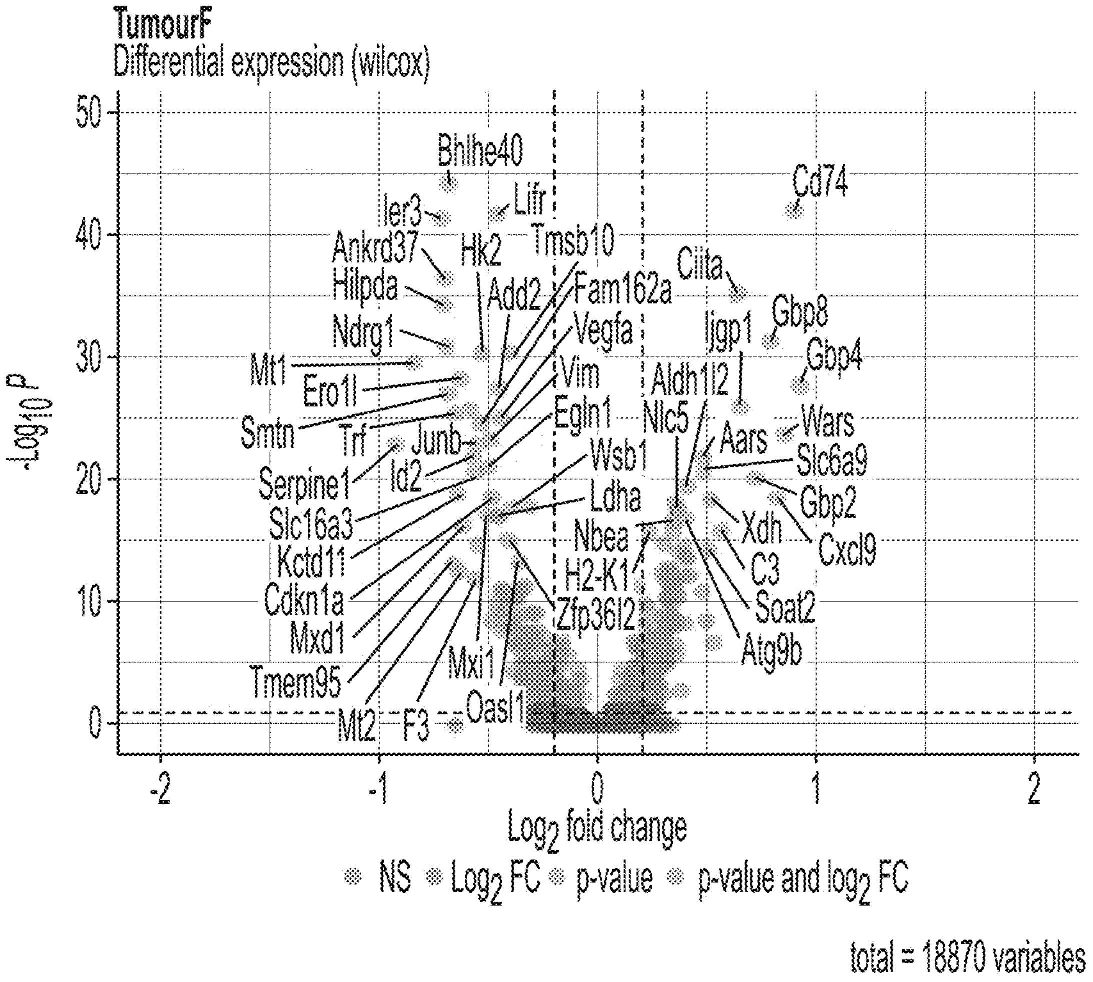

FIG. 86 depicts a graph showing a differential expression for Tumor F.

Figure 87:
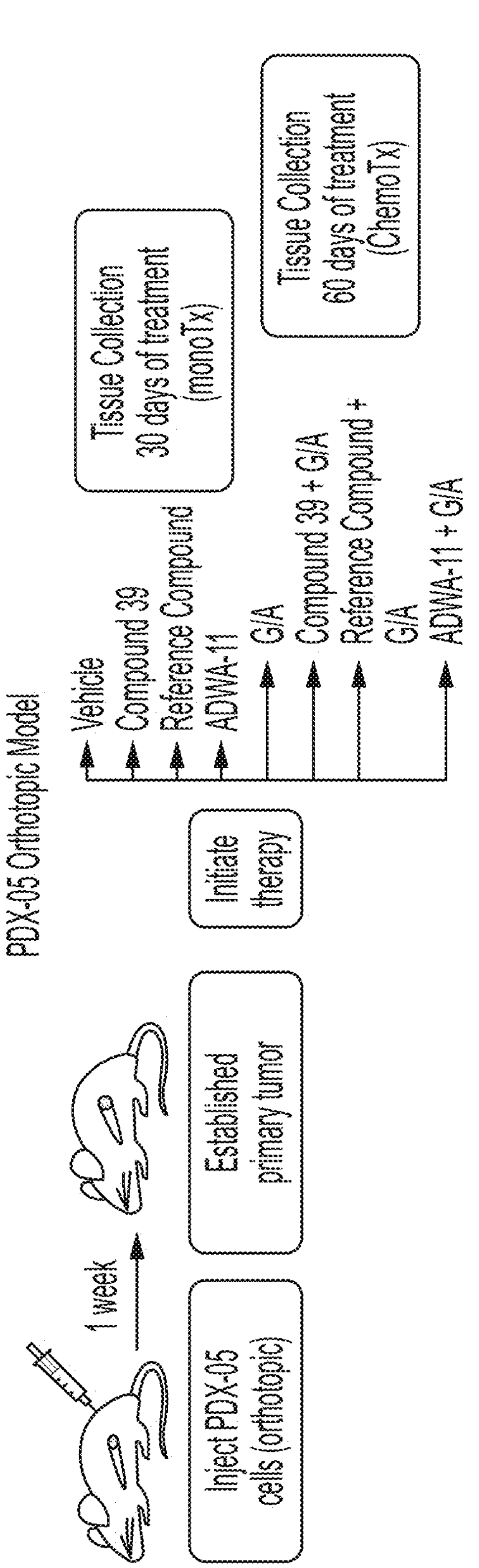

FIG. 87 depicts a schematic diagram associated with a PDX-05 orthotopic model.

Figure 88:
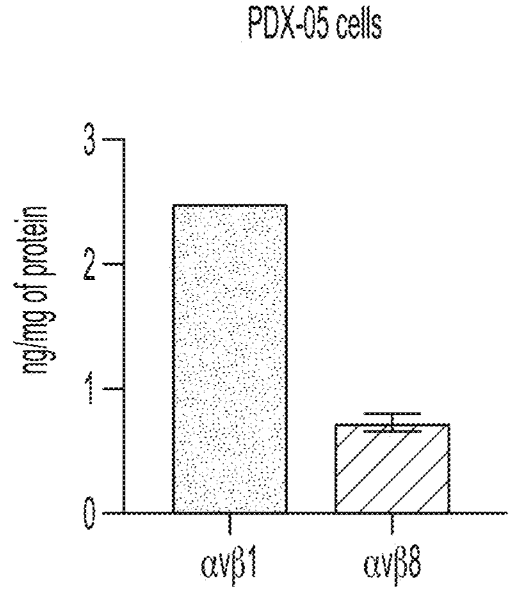

FIG. 88 depicts a chart showing an amount of protein (ng/mg) for $\alpha_v\beta_1$ and $\alpha_v\beta_8$ in a PDX-05 orthotopic model.

Figure 89:
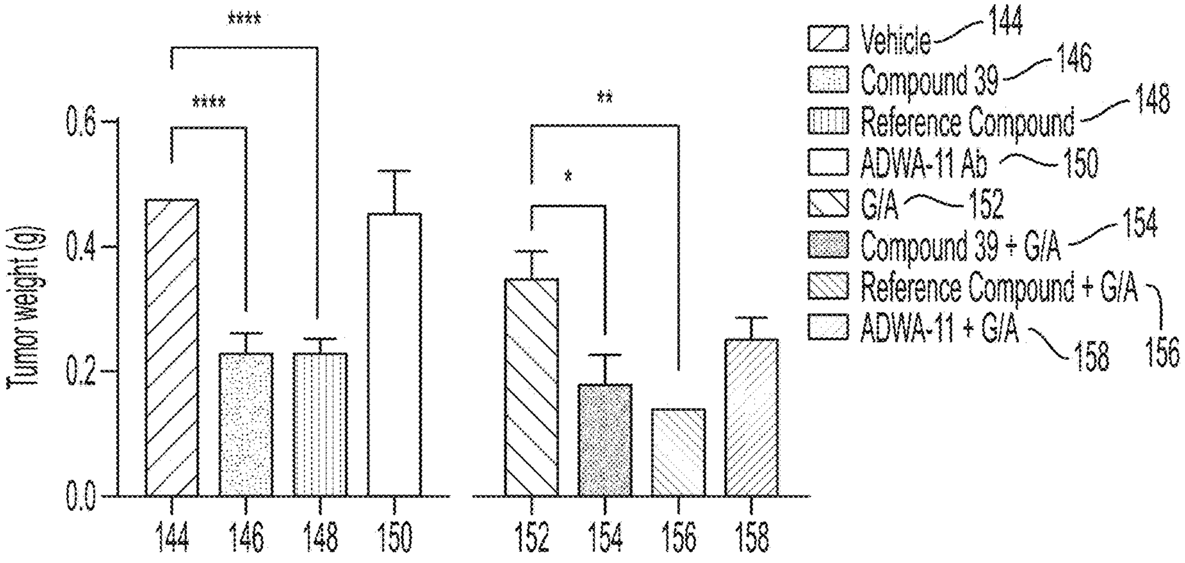

FIG. 89 depicts a chart showing tumor weight (g) for a vehicle 144, Compound 39 146, a Reference Compound 148, ADWA-11 Ab 150, Gemcitabine/Abraxane (G/A) 152, Compound 39+G/A 154, a Reference Compound+G/A 156, and ADWA-11+G/A 158 in a PDX-05 orthotopic model.

Figure 90:
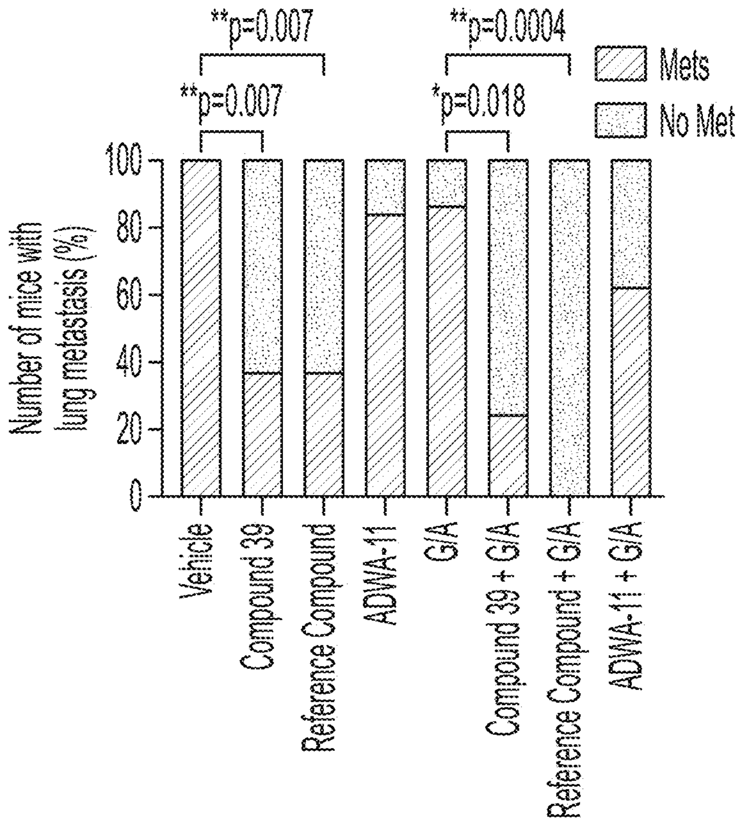

FIG. 90 depicts a chart showing a number of mice with lung metastasis (percentage) for a vehicle 144, Compound 39 146, a Reference Compound 148, ADWA-11 Ab 150, Gemcitabine/Abraxane (G/A) 152, Compound 39+G/A 154, a Reference Compound+G/A 156, and ADWA-11+G/A 158 in a PDX-05 orthotopic model.

Figure 91:
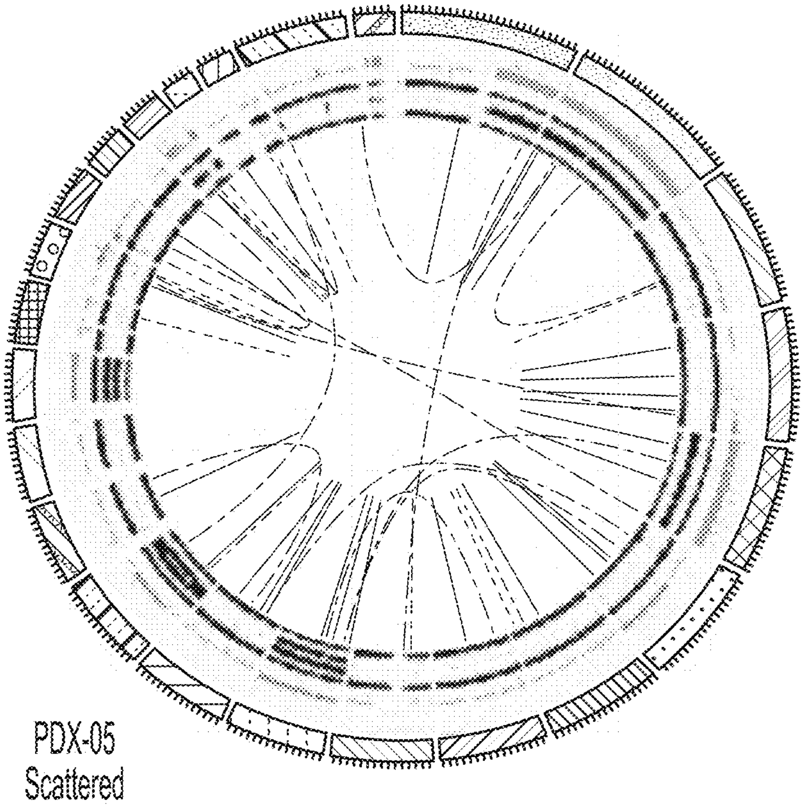

FIG. 91 depicts a schematic diagram of a generic epithelial-mesenchymal transition (EMT) signature of PDX-05.

Figure 92:
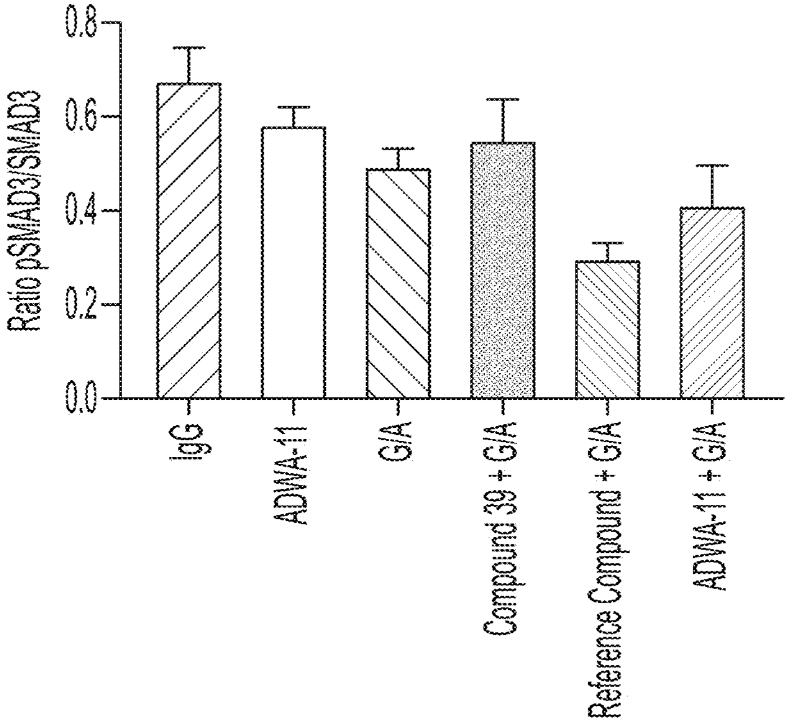

FIG. 92 depicts a chart showing a ratio of pSMDA3/SMAD3 for IgG, ADWA-11, Gemcitabine/Abraxane (G/A), Compound 39+G/A, a Reference Compound+G/A, and ADWA-11+G/A in a PDX-05 orthotopic model.

Figure 93:
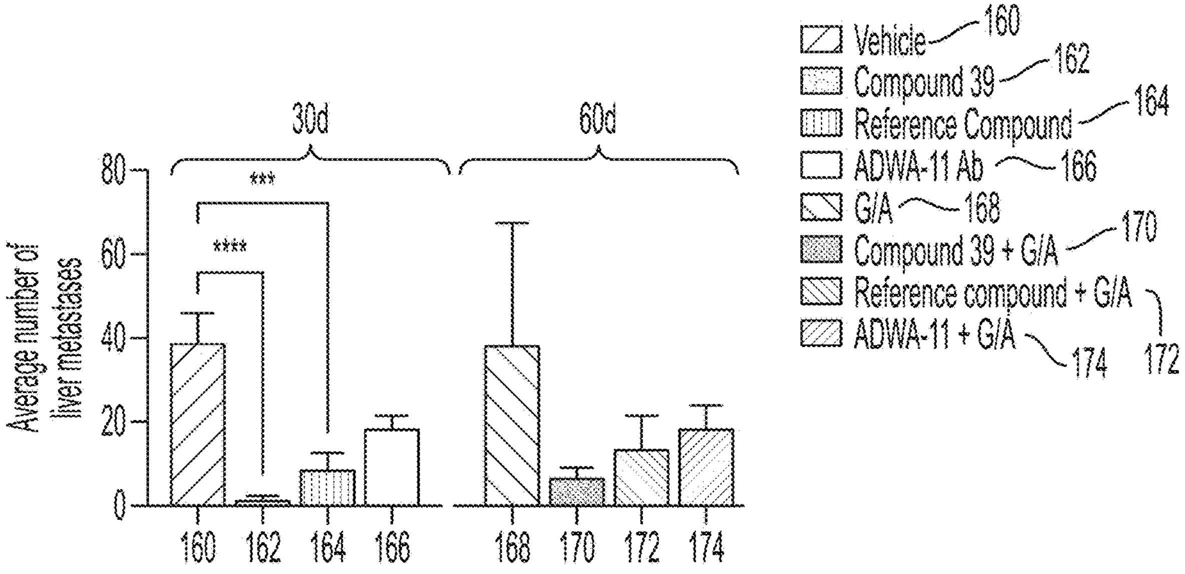

FIG. 93 depicts a chart showing an average number of liver metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model.

Figure 94:
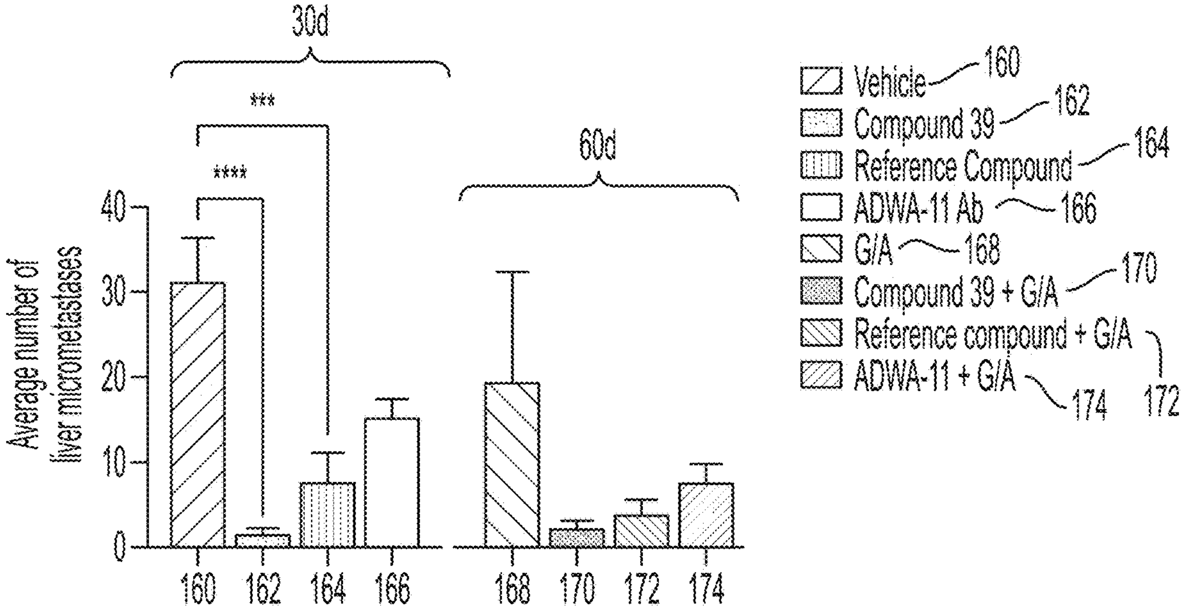

FIG. 94 depicts a chart showing an average number of liver micro-metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model.

Figure 95:
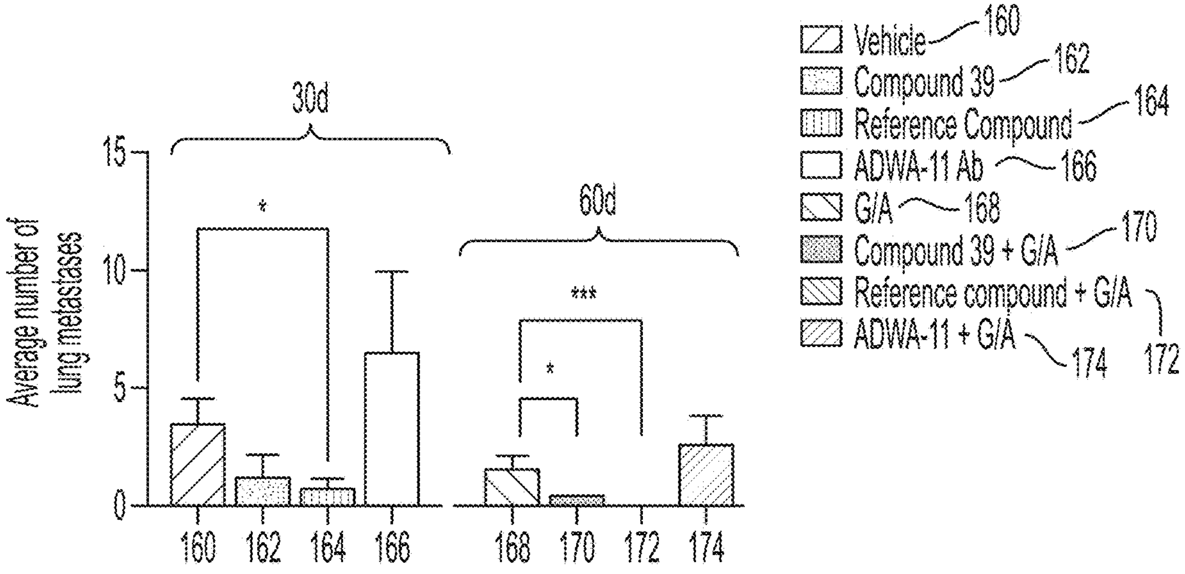

FIG. 95 depicts a chart showing an average number of lung metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model.

Figure 96:
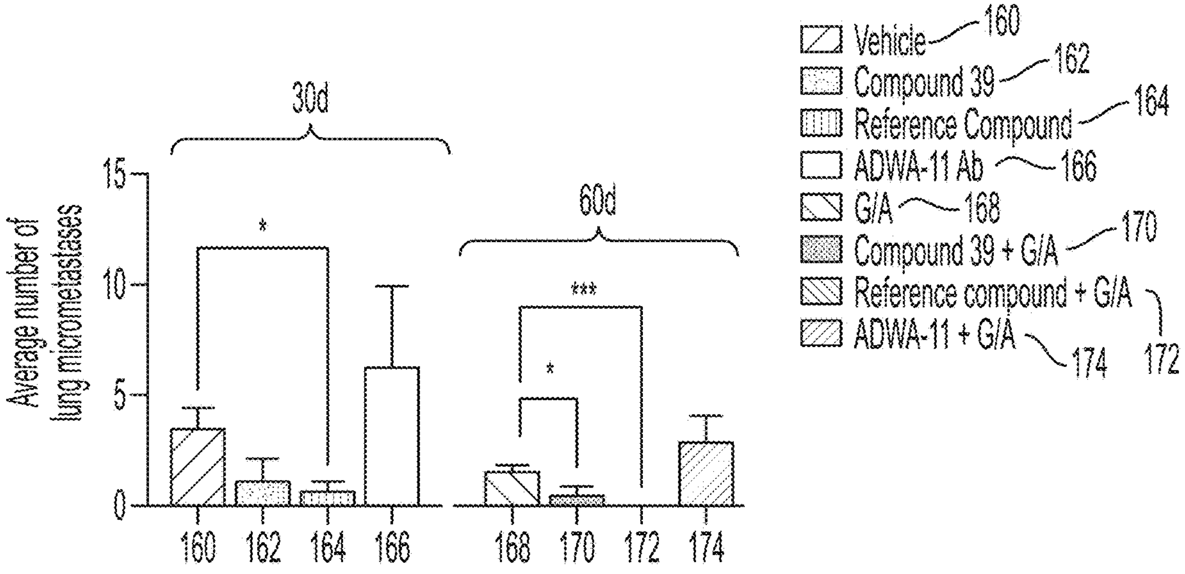

FIG. 96 depicts a chart showing an average number of lung micro-metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model.

Figure 97:
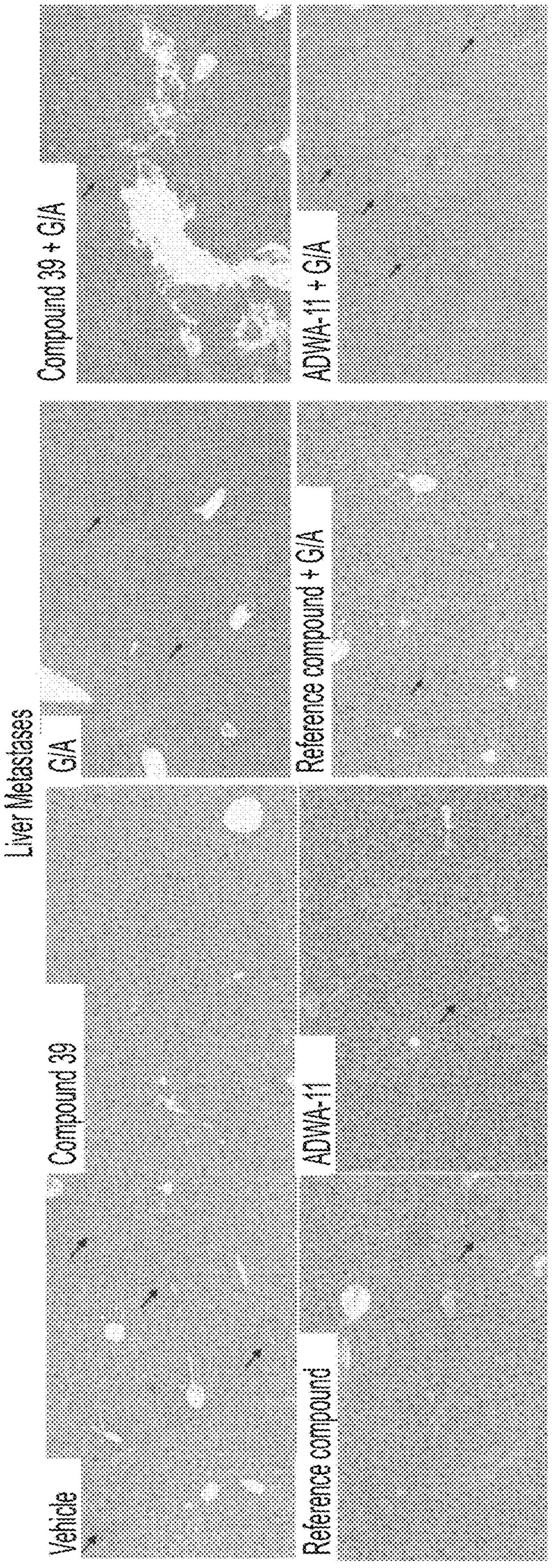

FIG. 97 depicts various images of Pico Sirius Red (PSR) stained liver metastases for a vehicle, Compound 39, Gemcitabine/Abraxane (G/A), Compound 39+G/A, a Reference compound, ADWA-11, a Reference compound+G/A and ADWA-11+G/A in an PDX-05 orthotopic model.

Figure 98:
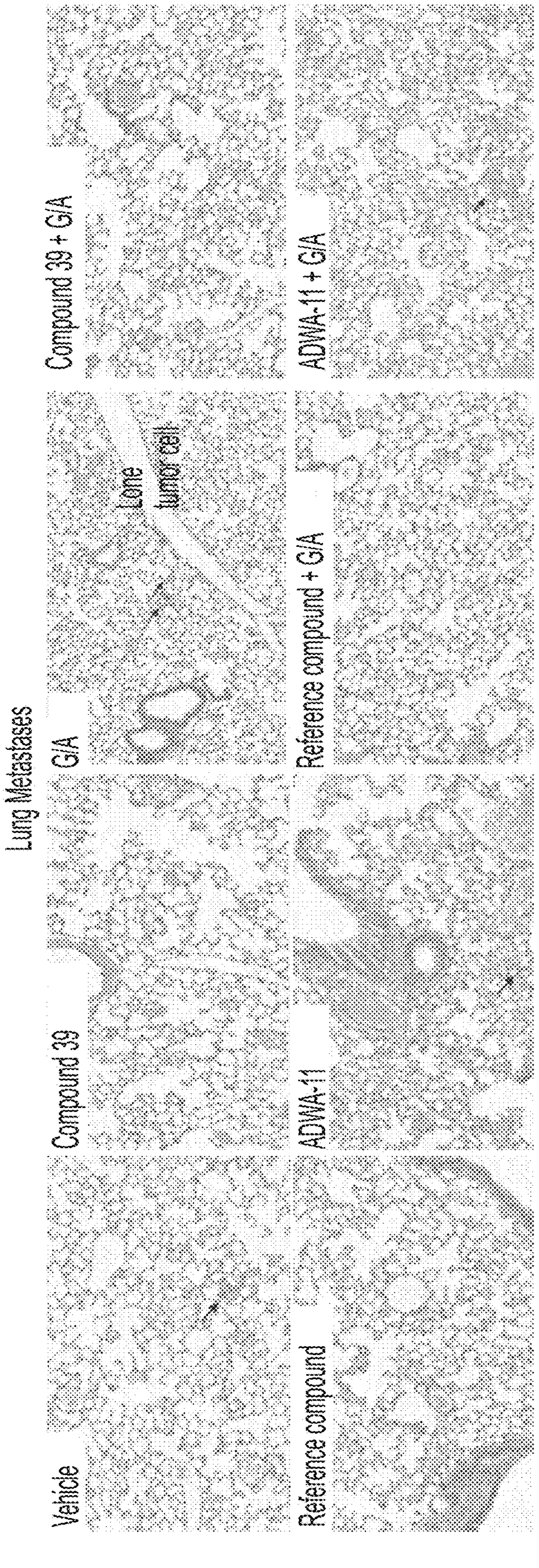

FIG. 98 depicts various images of Pico Sirius Red (PSR) stained lung metastases for a vehicle, Compound 39, Gemcitabine/Abraxane (G/A), Compound 39+G/A, a Reference compound, ADWA-11, a Reference compound+G/A and ADWA-11+G/A in an PDX-05 orthotopic model.

Figure 99:
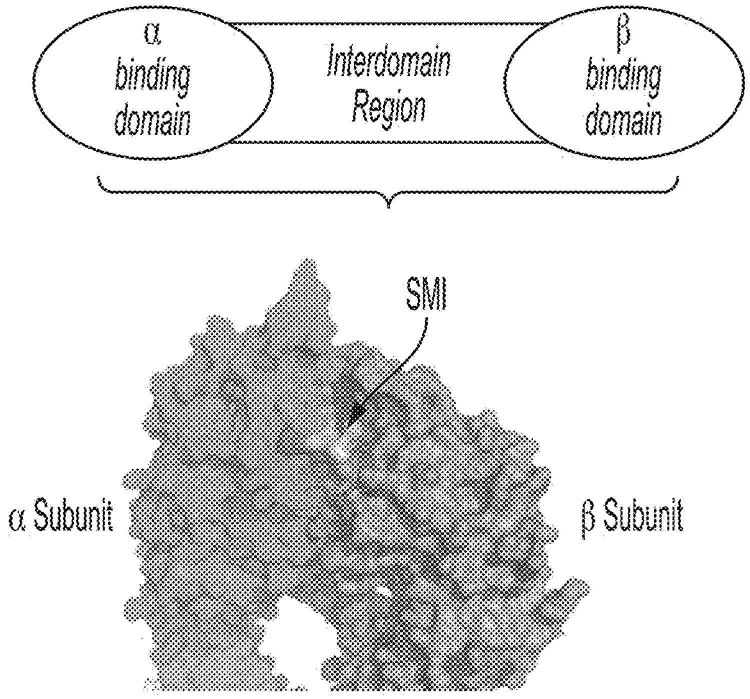

FIG. 99 depicts a schematic diagram of Compound 39 (top) and a molecular rendering bound to $\alpha_V\beta_8$ (bottom).

Figure 100:
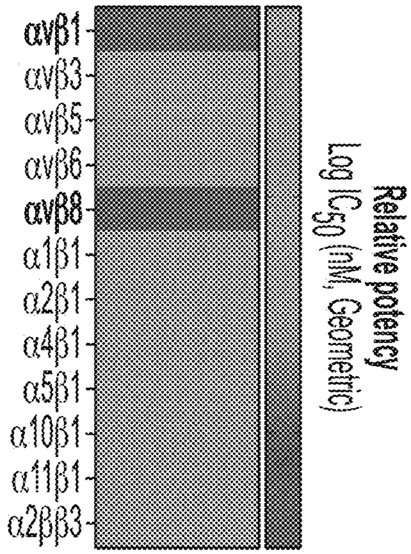

FIG. 100 depicts a heatmap showing the relative $IC_{50}$ potencies of Compound 39 compared to indicated integrin indications.

Figure 101:
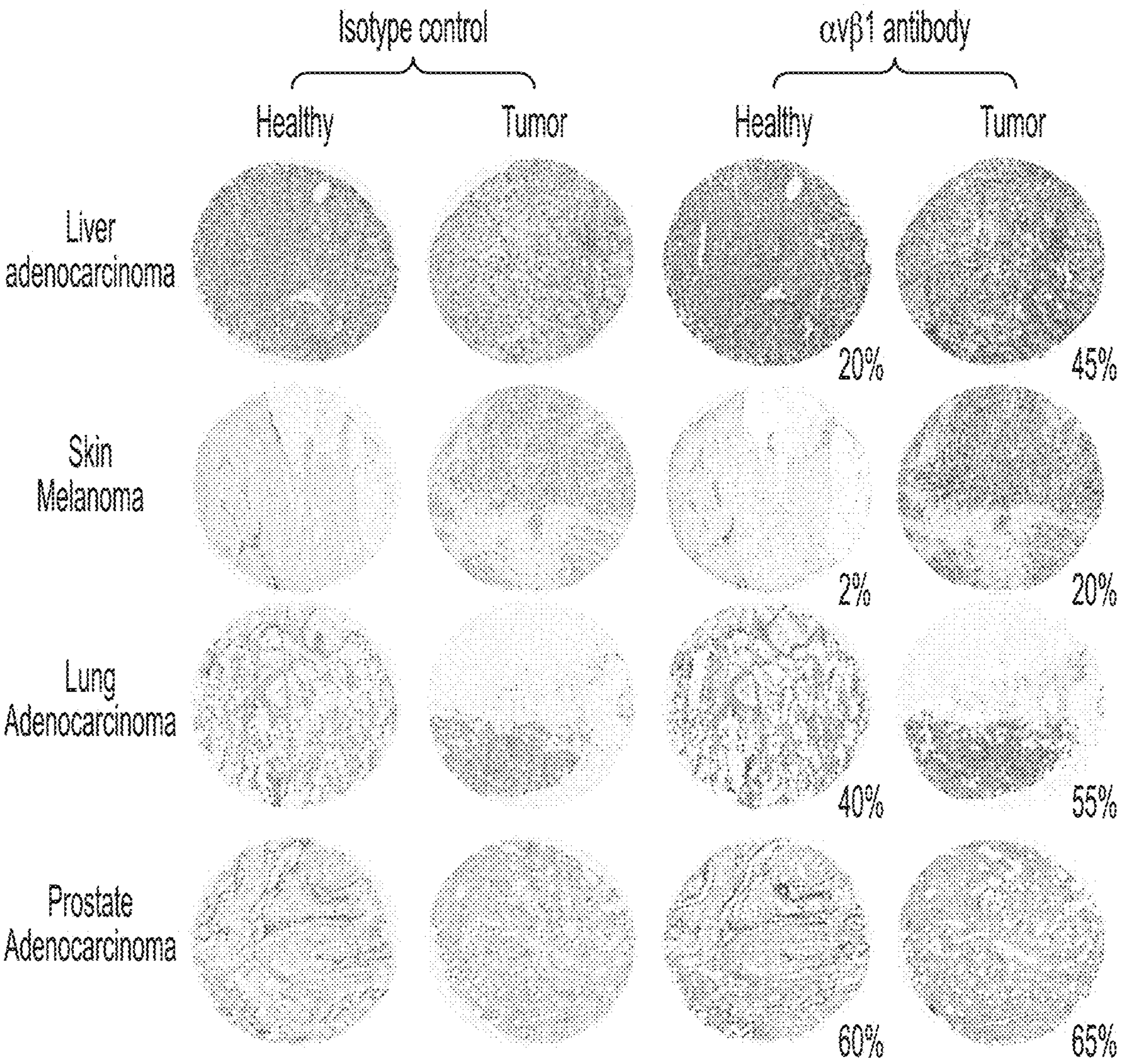

FIG. 101 depicts images of OCT-embedded human tissue cores showing the expression of $\alpha_V\beta_1$ by IHC.

Figure 102:
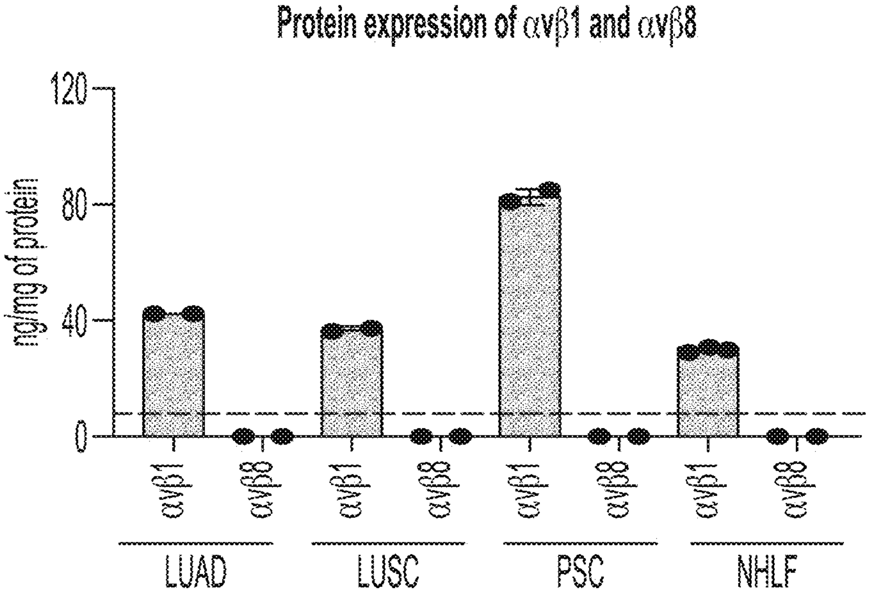

FIG. 102 depicts a chart showing protein expression of $\alpha_V\beta_1$ on CAFs isolated from indicated carcinomas compared to normal human lung fibroblasts (NHLF) determined by electroluminescence meso scale discovery assay.

Figure 103:
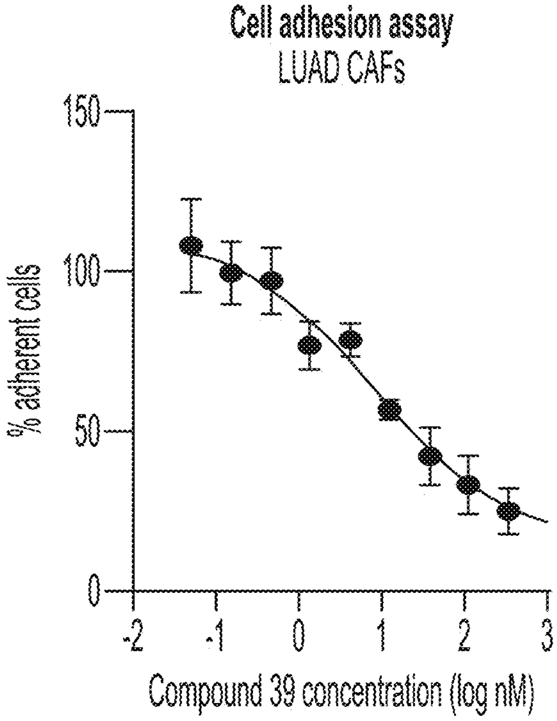

FIG. 103 depicts a graph associated with a cell adhesion assay depicting a percentage of adherent cells associated with lung adenocarcinoma (LUAD) cancer associated fibroblasts (CAFs) for various concentrations of Compound 39 (log nM).

Figure 104A:
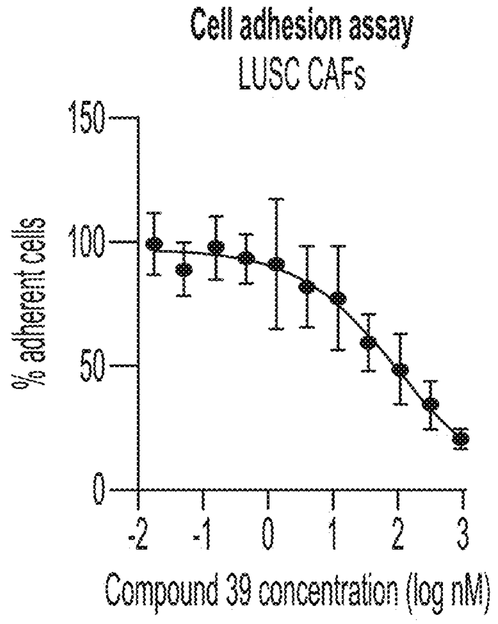

FIG. 104A depicts a graph associated with a cell adhesion assay depicting a percentage of adherent cells associated with lung squamous cell carcinoma (LUSC) cancer associated fibroblasts (CAFs) for various concentrations of Compound 39 (log nM).

Figure 104B:
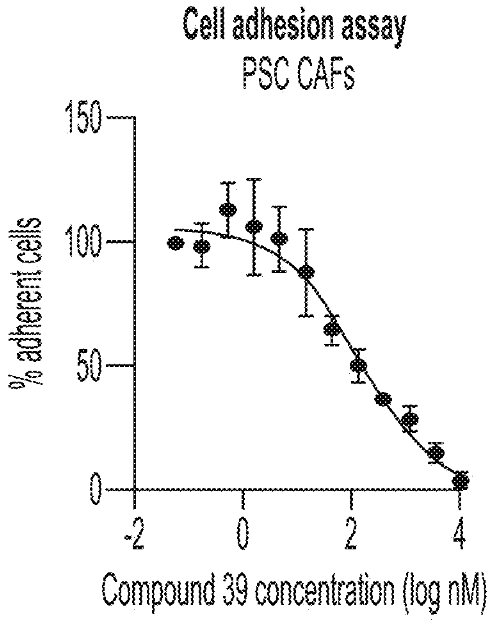

FIG. 104B depicts a graph associated with a cell adhesion assay depicting a percentage of adherent cells associated with pancreatic stellate cancer associated fibroblasts (CAFs) for various concentrations of Compound 39 (log nM).

Figure 105:
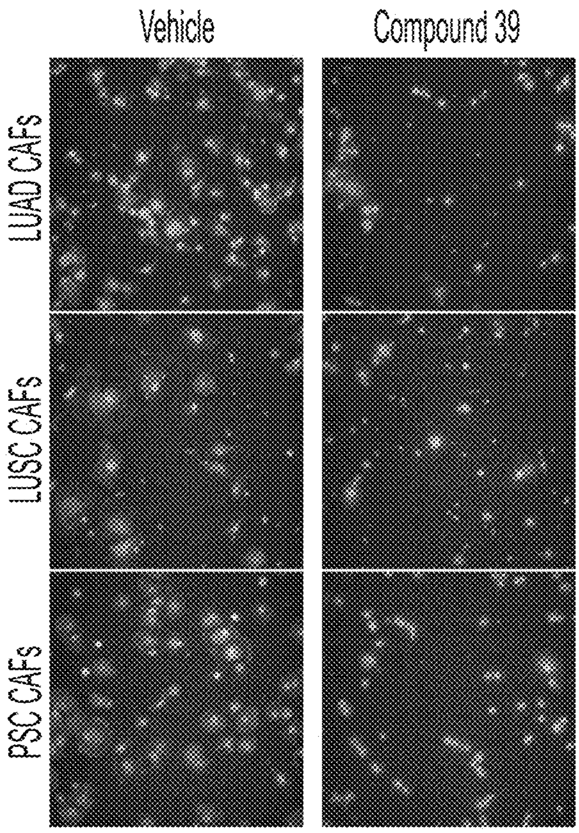

FIG. 105 depicts images showing the adhesion of cancer associated fibroblasts (CAFs) on LAP-coated plates in the presence or absence of Compound 39.

Figure 106:
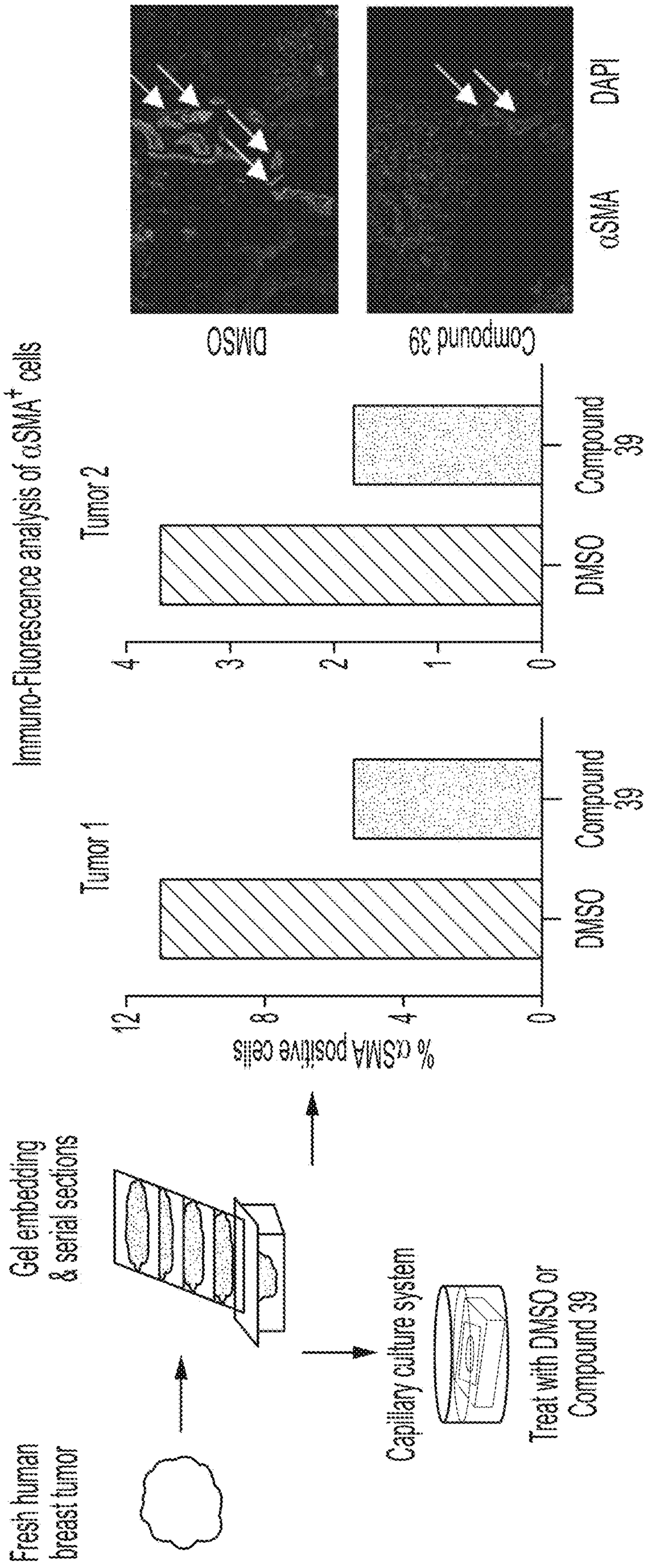

FIG. 106 depicts a schematic diagram of a process (left) associated with freshly collected human breast tumor tissue being treated with Compound 39 ex vivo for a time period, a graph showing an immune-fluorescence analysis of $\alpha SMA^+$ cells (middle), and representative images of αSMA and DAPI-stained tissues (right).

Figure 107:
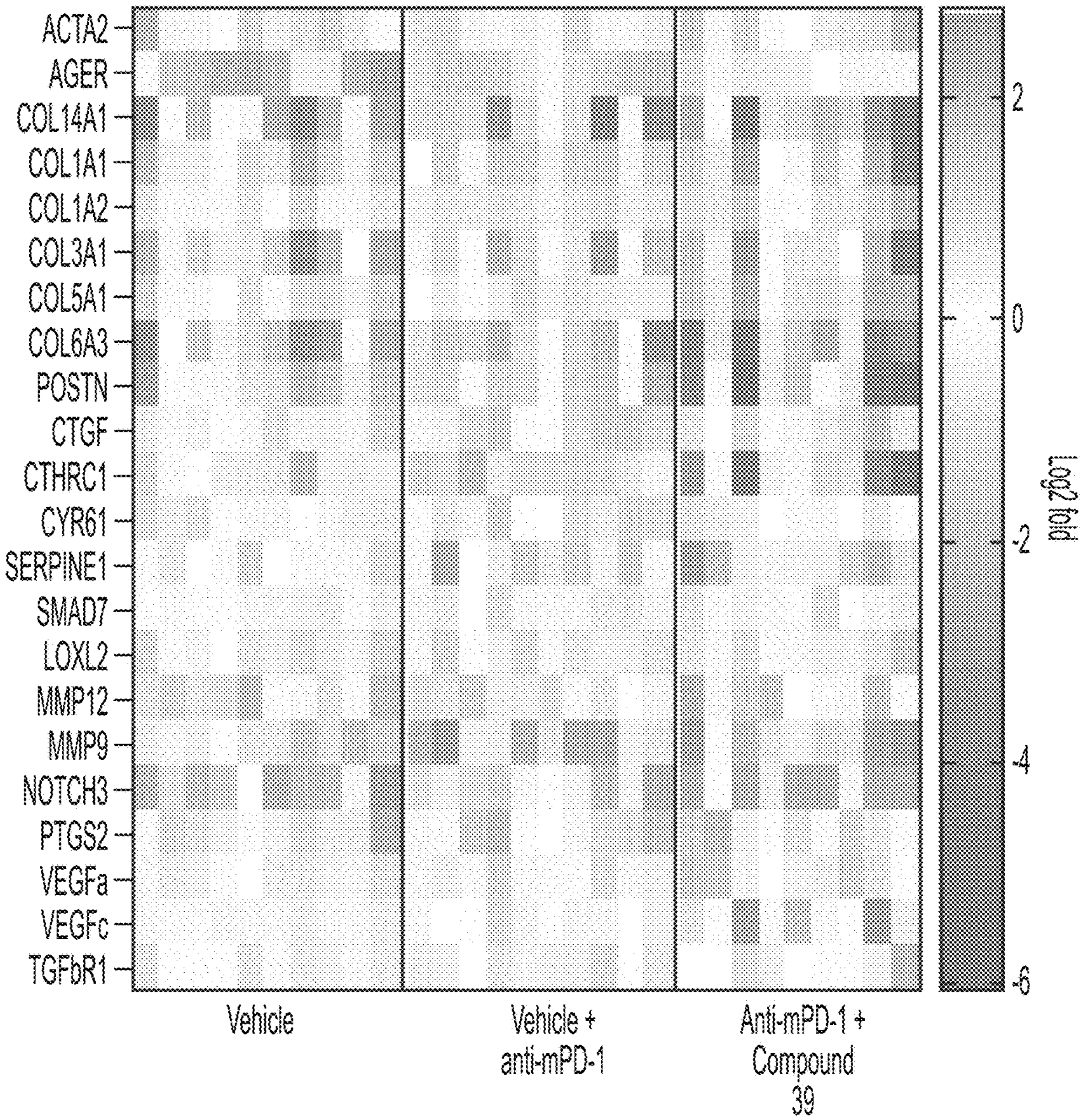

FIG. 107 depicts Compound 39 in combination with anti-mPD-1 reducing the expression of fibrotic markers in EMT6 tumors.

Figure 108:
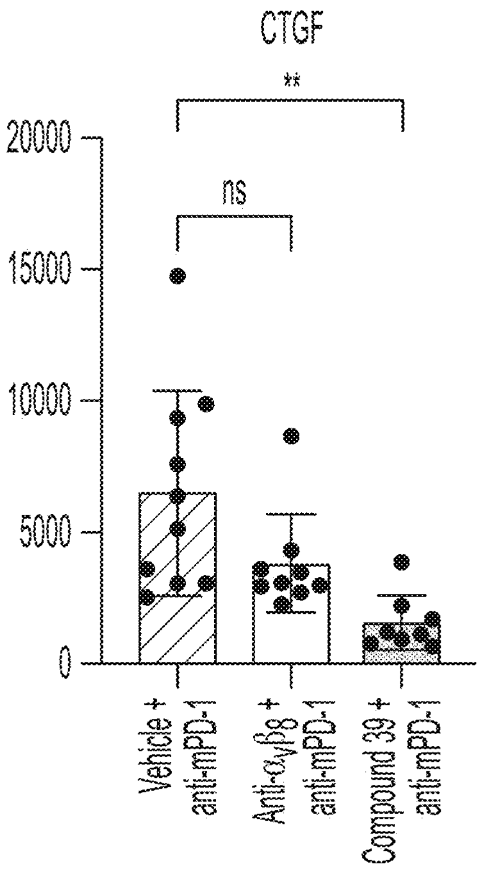

FIG. 108 depicts a graph showing the expression of connective tissue growth factor (CTGF) for vehicle+anti-mPD-1, anti-$\alpha_V\beta_8$+anti-mPD-1, and Compound 39+anti-mPD-1. Error bars show ±S.D. *p=0.05, p=0.01, *p=0.001, and ****p=0.0001 calculated by one-way Anova.

Figure 109:
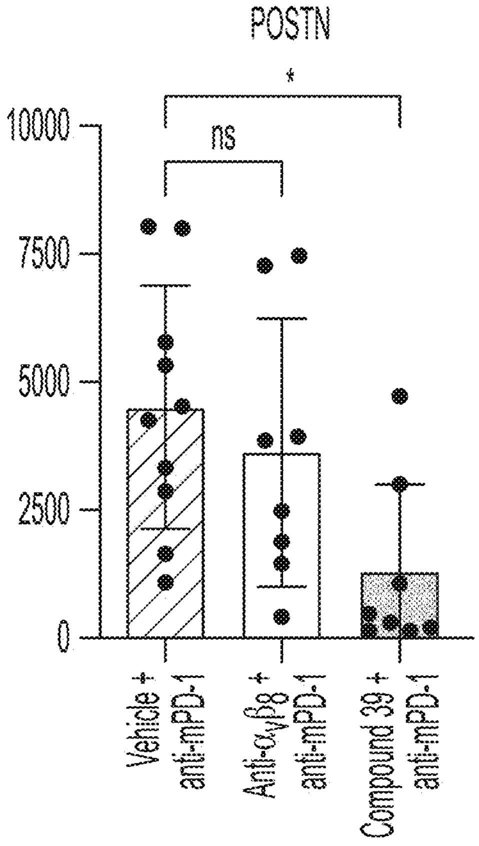

FIG. 109 depicts a graph showing the expression of periostin (POSTN) for vehicle+anti-mPD-1, anti-$\alpha_V\beta_8$+anti-mPD-1, and Compound 39+anti-mPD-1. Error bars show S.D. *p=0.05, p=0.01, *p=0.001, and ****p=0.0001 calculated by one-way Anova.

Figure 110:
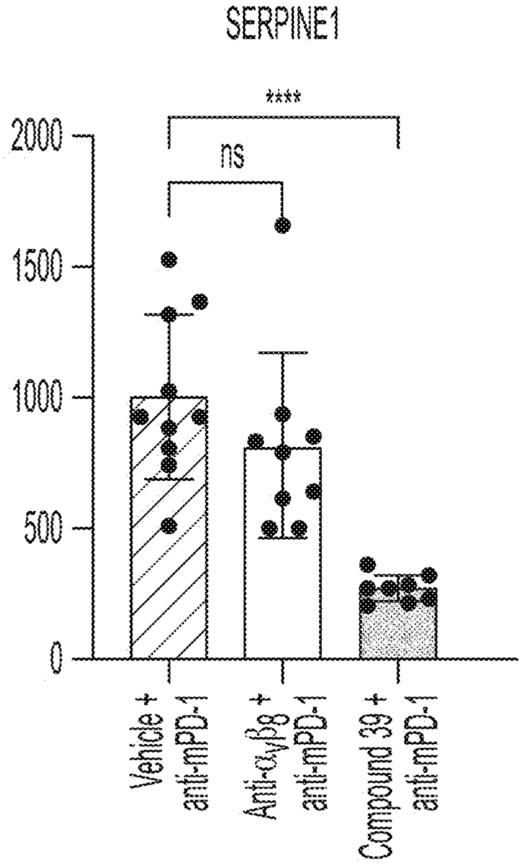

FIG. 110 depicts a graph showing the expression of plasminogen activator inhibitor-1 (SERPINE1) gene for vehicle+anti-mPD-1, anti-$\alpha_V\beta_8$+anti-mPD-1, and Compound 39+anti-mPD-1. Error bars show ±S.D. *p=0.05, p=0.01, *p=0.001, and ****p=0.0001 calculated by one-way Anova.

Figure 111:
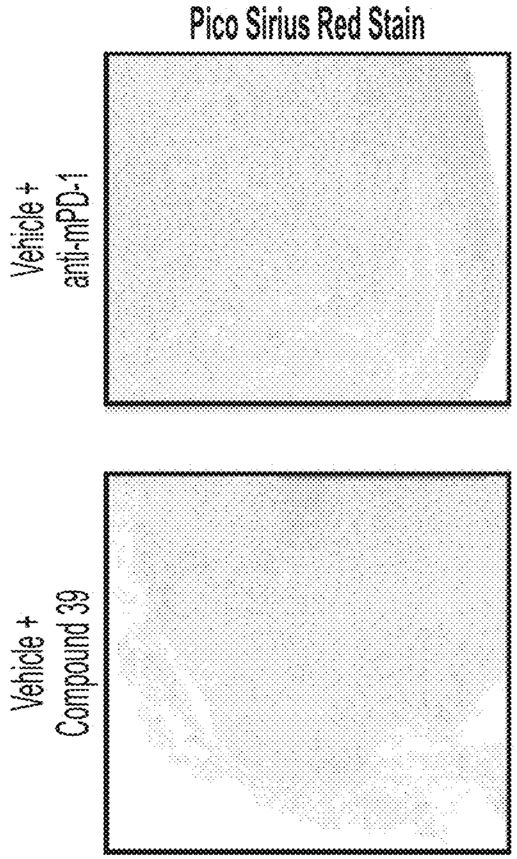

FIG. 111 depicts images associated with a Pico Sirius red stain for Vehicle+anti-mPD-1 (top) and vehicle+Compound 39 (bottom).

Figure 112:
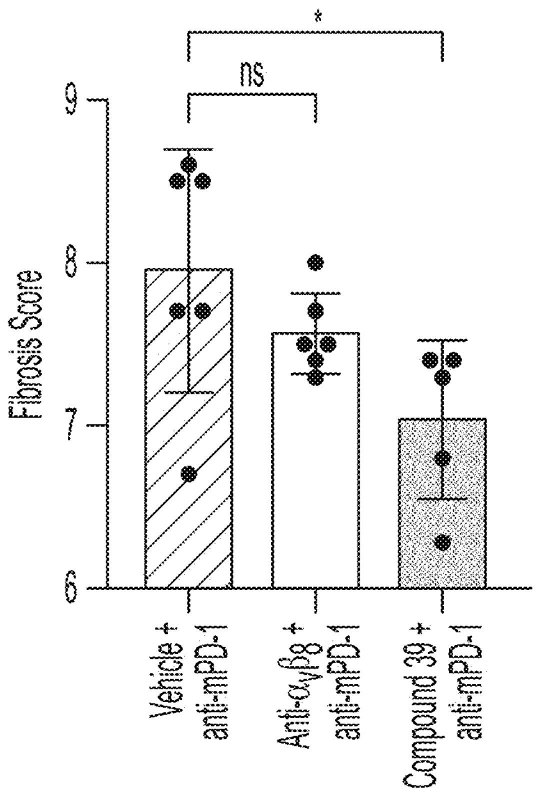

FIG. 112 depicts a graph associated with a fibrosis score for vehicle+anti-mPD-1, anti-$\alpha_V\beta_8$+anti-mPD-1, and Compound 39+anti-mPD-1. Error bars show ±S.D. *p=0.05, p=0.01, *p=0.001, and ****p=0.0001 calculated by one-way Anova.

DETAILED DESCRIPTION

Provided herein are, inter alia, compounds of formula (A), and variations thereof, pharmaceutical compositions comprising compounds of formula (A), and methods of using such compounds and compositions in treating fibrotic diseases. Compounds and pharmaceutical compositions comprising salts of compounds of formula (A) are provided as well.

Also provided herein are, inter alia, compounds of formula (I), and variations thereof, pharmaceutical compositions comprising compounds of formula (I), and methods of using such compounds and compositions in treating fibrotic diseases. Compounds and pharmaceutical compositions comprising salts of compounds of formula (I) are provided as well.

Unless specifically defined otherwise, all technical and scientific terms used herein shall be taken to have the same meaning as commonly understood by one of ordinary skill in the art.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X". Likewise, reference to a value "X" also includes description of "about X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene ($-CH_2-$), ethylene ($-CH_2CH_2-$), propylene ($-CH_2CH_2CH_2-$), isopropylene ($-CH_2CH(CH_3)-$), butylene ($-CH_2(CH_2)_2CH_2-$), isobutylene ($-CH_2CH(CH_3)CH_2-$), pentylene ($-CH_2(CH_2)_3CH_2-$), hexylene ($-CH_2(CH_2)_4CH_2-$), heptylene ($-CH_2(CH_2)_5CH_2-$), octylene ($-CH_2(CH_2)_6CH_2-$), and the like. It is understood that when alkylene is substituted (for example with a cycloalkyl group), the substituent is not one of the sites of bivalency. For example, propylene substitution with cyclopropyl may provide

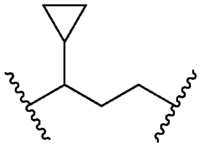 [SMILES: *CCC(*)C1CC1]

but does not provide

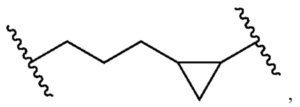 [SMILES: *CCCC1CC1*]

wherein the wavy line denotes a site of bivalency.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C═C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) ($—CH═CH—$), propenylene ($—CH═CHCH_2—$), 1,4-but-1-enylene ($—CH═CH—CH_2CH_2—$), 1,4-but-2-enylene ($—CH_2CH═CHCH_2—$), 1,6-hex-1-enylene ($—CH═CH—(CH_2)_3CH_2—$), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) ($—C≡C—$), propynylene ($—C≡CCH_2—$), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 annular carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom (e.g., 1,1-cyclopropylene) or different ring carbon atoms (e.g., 1,2-cyclopropylene). When a cycloalkylene attaches to the remaining structures via two different ring carbon atoms, the connecting bonds may be cis or trans to each other (e.g., cis-1,2-cyclopropylene or trans-1,2-cyclopropylene). If points of attachment are not specified, the moiety can include any chemically possible attachments. For example, cyclopropylene can indicate 1,1-cyclopropylene or 1,2-cyclopropylene (e.g., cis-1,2-cyclopropylene, trans-1,2-cyclopropylene, or a mixture thereof), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C═C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings are carbocyclic and may or may not be aromatic, provided at least one ring in the multiple condensed ring structure is aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may be carbocyclic or may contain one or more annular heteroatom and which may or may not be aromatic, provided at least one ring in the multiple condensed ring structure is both aromatic and contains at least one annular heteroatom. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having from 1 to 14 annular carbon atoms and from 1 to 6 annular heteroatoms, such as nitrogen, sulfur or oxygen, and the like. A heterocyclic group may have a single ring (e.g., pyrrolidinyl) or multiple condensed rings (e.g., decahydroisoquinolin-1-yl), which condensed rings may or may not be aromatic and which may be carbocylic or contain one or more annular heteroatoms, but which excludes heteroaryl rings. A heterocycle comprising more than one ring may be fused, bridged or spiro, or any combination thereof. In fused ring systems, one or more of the fused rings can be cycloalkyl or aryl, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with one or more halogens, it may be referred to by using the prefix "halo," e.g., haloaryl, haloalkyl, etc. refer to aryl and alkyl substituted with one or more halo groups, which in the case of two or more halo groups may be, but are not necessarily the same halogen. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred haloalkyl, e.g., perhaloalkyl group is trifluoromethyl ($—CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($—OCF_3$).

"Carbonyl" refers to the group C=O.

"Thiocarbonyl" refers to the group C=S.

"Oxo" refers to the moiety =O.

"D" refers to deuterium ($^2H$).

"Boc" refers to tert-butyloxycarbonyl.

"Cbz" refers to carboxybenzyl.

"HATU" refers to 1-[bis(dimethylamino)methylene]-1H-1,2,3-triazolo[4,5-b]pyridinium 3-oxide hexafluorophosphate.

"BOP" refers to benzotriazol-1-yloxytris(dimethylamino) phosphonium hexafluorophosphate.

"PyBOP" refers to benzotriazol-1-yl-oxytripyrrolidino-phosphonium hexafluorophosphate.

"Optionally substituted" unless otherwise specified means that a group may be unsubstituted or substituted by one or more (e.g., 1, 2, 3, 4 or 5) of the substituents listed for that group in which the substituents may be the same of different. In some embodiments, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In some embodiments, an optionally substituted group is unsubstituted.

Unless clearly indicated otherwise, "an individual" or "a subject" as used herein intends a mammal, including but not limited to a primate, human, bovine, horse, feline, canine, or rodent. In one variation, the individual or subject is a human.

As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods herein contemplate any one or more of these aspects of treatment.

As used herein, the term "effective amount" intends such amount of a compound herein which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, the term "composition" or "pharmaceutical composition" refers to the combination of an active agent with an excipient or a carrier, inert or active, making the composition especially suitable for diagnostic or therapeutic use in vivo or ex vivo. Pharmaceutical compositions may be prepared by known pharmaceutical methods. Suitable compositions, excipients, or carriers can be found, e.g., in *Remington: The Science and Practice of Pharmacy*, Lippincott Williams & Wilkins, $21^{st}$ ed. (2005), which is incorporated herein by reference in its entirety.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

"Pharmaceutically acceptable salts" are those salts which retain at least some of the biological activity of the free (non-salt) compound and which can be administered as drugs or pharmaceuticals to an individual. See, e.g., *Handbook of Pharmaceutical Salts Properties, Selection, and Use*, International Union of Pure and Applied Chemistry, John Wiley & Sons (2008), hereby incorporated by reference in its entirety. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases which can be used to prepared salts include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound as an active ingredient. See, e.g., *Handbook of Pharmaceutical Excipients*. $6^{th}$ Edition, Pharmaceutical Press (2008), hereby incorporated by reference in its entirety. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless otherwise stated, "substantially pure" intends a composition that contains no more than 10% impurity, such as a composition comprising less than about 9%, 7%, 5%, 3%, 1%, 0.5% impurity.

The term "comprise" or variations such as "comprises" or "comprising," will be understood to imply the inclusion of a stated element, integer or step, or group of elements, integers or steps, but not the exclusion of any other element, integer or step, or group of elements, integers or steps. It is understood that aspects and embodiments described herein as "comprising" include "consisting of" and "consisting essentially of" embodiments.

When a composition is described as "consisting essentially of" the listed components, the composition contains the components expressly listed, and may contain other components which do not substantially affect the disease or condition being treated such as trace impurities. However, the composition either does not contain any other components which do substantially affect the disease or condition being treated other than those components expressly listed; or, if the composition does contain extra components other than those listed which substantially affect the disease or condition being treated, the composition does not contain a sufficient concentration or amount of those extra components to substantially affect the disease or condition being treated. When a method is described as "consisting essentially of" the listed steps, the method contains the steps listed, and may contain other steps that do not substantially affect the disease or condition being treated, but the method does not contain any other steps which substantially affect the disease or condition being treated other than those steps expressly listed.

As used herein, where enantiomeric and/or diastereomeric forms exist of a given structure, "flat bonds" indicate that all stereoisomeric forms of the depicted structure may be present, e.g., Compound 1 in Table 1, as shown below.

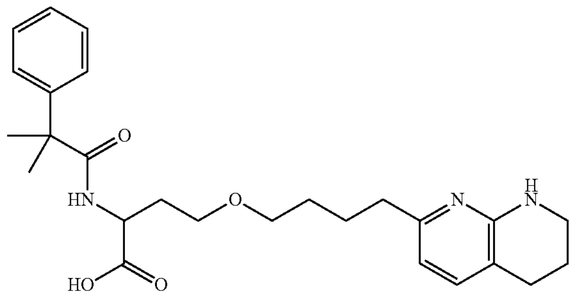 [SMILES: CC(C)(C(=O)NC(CCOCCCCc1ccc2c(n1)NCCC2)C(=O)O)c1ccccc1]

Compounds

In one aspect, provided is a compound of formula (A):

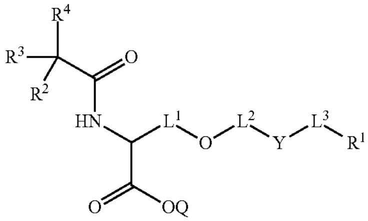

(A)

or a pharmaceutically acceptable salt thereof, wherein:

$R^1$ is 5,6,7,8-tetrahydro-1,8-naphthyridin-2-yl optionally substituted by one or more $R^{1a}$, 1,2,3,4-tetrahydro-1,8-naphthyridin-2-yl optionally substituted by one or more $R^{1b}$, 6-aminopyridin-2-yl optionally substituted by one or more $R^{1c}$, or (pyridin-2-yl)amino optionally substituted by one or more $R^{1d}$;

$R^2$ is H or $C_1$-$C_6$ alkyl;

$R^3$ is H or $C_1$-$C_6$ alkyl;

or $R^2$ and $R^3$ are taken together with the carbon atom to which they are attached to form a $C_3$-$C_6$ cycloalkyl or a 3-to-6-membered heterocyclyl optionally substituted by $R^{2a}$;

$R^4$ is phenyl, 5-to-6-membered heteroaryl, 6-membered heterocyclyl, or $C_1$-$C_6$ haloalkyl;

wherein the 5-to-6-membered heteroaryl contains at least one nitrogen atom and is optionally fused to a phenyl group;

wherein the 6-membered heterocyclyl contains at least one nitrogen atom and is optionally fused to a phenyl group;

wherein the phenyl and 5-to-6-membered heteroaryl are optionally substituted by one or more $R^{4a}$; and wherein the 6-membered heterocyclyl is optionally substituted by one or more groups selected from the group consisting of: $R^{4a}$ and oxo;

or $R^2$, $R^3$, and $R^4$ are taken together to form a 5-membered heteroaryl containing two nitrogen atoms and substituted with phenyl, wherein the phenyl group is optionally substituted by one or more $R^{4a}$;

each $R^{4a}$ is independently halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(═O)—$NH_2$;

or $R^{4a}$ and $R^2$ are taken together with the atoms to which they are attached to form a 6-membered heterocyclyl, wherein the heterocyclyl contains one oxygen atom;

Q is H or $C_1$-$C_8$ alkyl;

$L^1$ is $C_2$-$C_4$ alkylene optionally substituted by one or more Lia;

$L^2$ is a bond or $C_1$-$C_3$ alkylene optionally substituted by one or more $L^{2a}$;

$L^3$ is $C_2$-$C_4$ alkylene optionally substituted by one or more $L^{3a}$;

Y is a bond;

$R^{1a}$, $R^{1b}$, $R^{1c}$, $R^{1d}$, $R^{2a}$, $L^{1a}$, $L^{2a}$, and $L^{3a}$ are each independently selected from $R^4$;

two $R^{1a}$ groups on the same carbon atom are optionally taken together with the carbon atom to which they are attached to form a $C_3$-$C_6$ cycloalkyl;

two $R^{1b}$ groups on the same carbon atom are optionally taken together with the carbon atom to which they are attached to form a $C_3$-$C_6$ cycloalkyl;

each $R^A$ is independently deuterium, halogen, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, 5- to 10-membered heteroaryl, —CN, —$OR^5$, —$SR^5$, —$NR^6R^7$, —$NO_2$, —C═NH($OR^5$), —C(O)$R^5$, —OC(O)$R^5$, —C(O)$OR^5$, —C(O)$NR^6R^7$, —$NR^5$C(O)$R^6$, —$NR^5$C(O)$OR^6$, —$NR^5$C(O)$NR^6R^7$, —S(O)$R^5$, —$S(O)_2R^5$, —$NR^5$S(O)$R^6$, —$NR^5S(O)_2R^6$, —S(O)$NR^6R^7$, —$S(O)_2NR^6R^7$, or —P(O)($OR^5$)($OR^6$), wherein the $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, and 5- to 10-membered heteroaryl of $R^A$ are independently optionally substituted by one or more $R^{Aa}$; each $R^{Aa}$ is independently deuterium, halogen, oxo, —$OR^8$, —$NR^8R^9$, —C(O)$R^8$, —C(O)$OR^8$, —$NR^8$C(O)$OR^{10}$, —CN, —S(O)$R^8$, —$S(O)_2R^8$, —P(O)($OR^8$)($OR^9$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl, wherein the 3- to 12-membered heterocyclyl, 5- to 10-membered heteroaryl, $C_6$-$C_{14}$ aryl, and $C_1$-$C_6$ alkyl of $R^{Aa}$ are independently optionally substituted by one or more $R^{Ab}$;

each $R^{Ab}$ is independently deuterium, oxo, —OH, —O($^2$H), halogen, or $C_1$-$C_6$ alkyl optionally substituted by one or more of deuterium, halogen, —OH, —O($^2$H), or oxo;

each $R^5$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 10-membered heterocyclyl of $R^5$ are each independently optionally substituted by one or more $R^{5a}$;

each $R^{5a}$ is independently halogen, deuterium, oxo, —CN, —$OR^{10}$, —$NR^{11}R^{12}$, —P(O)($OR^{11}$)($OR^{12}$), 3- to 12-membered heterocyclyl, or $C_1$-$C_6$ alkyl optionally substituted by one or more of deuterium, halogen, —OH, —O($^2$H), or oxo;

each $R^6$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^6$ are independently optionally substituted by one or more of deuterium, halogen, oxo, —CN, —$OR^{10}$, —$NR^{11}R^{12}$, or $C_1$-$C_6$ alkyl optionally substituted by one or more of deuterium, halogen, —OH, —O($^2$H), or oxo; each $R^7$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^7$ are independently optionally substituted by one or more of deuterium, halogen, oxo, —CN, —$OR^{10}$, —$NR^{11}R^{12}$, or $C_1$-$C_6$ alkyl optionally substituted by one or more of deuterium, halogen, —OH, —O($^2$H), or oxo;

or $R^6$ and $R^7$ are taken together with the atom to which they are attached to form a 3- to 10-membered heterocyclyl optionally substituted by one or more of deuterium, halogen, oxo, —$OR^{10}$, —$NR^{11}R^{12}$, or $C_1$-$C_6$ alkyl optionally substituted by one or more of deuterium, halogen, oxo, —OH, or —O($^2$H);

each $R^8$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^9$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^{10}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^{11}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo; and each $R^{12}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

or $R^{11}$ and $R^{12}$ are taken together with the atom to which they are attached to form a 3-6 membered heterocyclyl optionally substituted by one or more of deuterium, halogen, oxo or $C_1$-$C_6$ alkyl optionally substituted by one or more of deuterium, oxo, or halogen.

In one aspect, provided is a compound of formula (I):

(I)

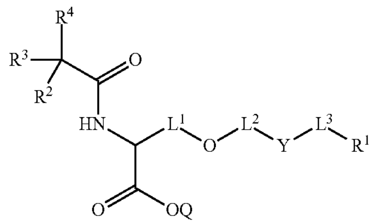

or a pharmaceutically acceptable salt thereof, wherein:

$R^1$ is 5,6,7,8-tetrahydro-1,8-naphthyridin-2-yl optionally substituted by one or more $R^{1a}$, 1,2,3,4-tetrahydro-1,8-naphthyridin-2-yl optionally substituted by one or more $R^{1b}$, 6-aminopyridin-2-yl optionally substituted by $R^{1c}$, or (pyridin-2-yl)amino optionally substituted by one or more $R^{1d}$;

$R^2$ is H or $C_1$-$C_6$ alkyl;

$R^3$ is H or $C_1$-$C_6$ alkyl;

or $R^2$ and $R^3$ are taken together with the carbon atom to which they are attached to form a $C_3$-$C_6$ cycloalkyl or a 3-to-6-membered heterocyclyl;

$R^4$ is phenyl, 5-to-6-membered heteroaryl, or 6-membered heterocyclyl, wherein the 5-to-6-membered heteroaryl contains at least one nitrogen atom and is optionally fused to a phenyl group;

wherein the 6-membered heterocyclyl contains at least one nitrogen atom and is optionally fused to a phenyl group;

wherein the phenyl and 5-to-6-membered heteroaryl are optionally substituted by one or more $R^{4a}$; and wherein the 6-membered heterocyclyl is optionally substituted by one or more groups selected from the group consisting of: $R^{4a}$ and oxo;

each $R^{4a}$ is independently halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), —O—($C_1$-$C_6$ haloalkyl), or —$S(O)_2$($C_1$-$C_6$ alkyl);

or $R^{4a}$ and $R^2$ are taken together with the atoms to which they are attached to form a 6-membered heterocyclyl, wherein the heterocyclyl contains one oxygen atom;

Q is H or $C_1$-$C_8$ alkyl;

$L^1$ is $C_2$-$C_4$ alkylene optionally substituted by one or more $L^{1a}$;

$L^2$ is a bond or $C_1$-$C_3$ alkylene optionally substituted by one or more $L^{2a}$;

$L^3$ is $C_2$-$C_4$ alkylene optionally substituted by one or more $L^{3a}$;

Y is a bond;

$R^{1a}$, $R^{1b}$, $R^{1c}$, $R^{1d}$, $L^{1a}$, $L^{2a}$, and $L^{3a}$ are each independently selected from $R^A$;

two $R^{1a}$ groups on the same carbon atom are optionally taken together with the carbon atom to which they are attached to form a $C_3$-$C_6$ cycloalkyl;

two $R^{1b}$ groups on the same carbon atom are optionally taken together with the carbon atom to which they are attached to form a $C_3$-$C_6$ cycloalkyl;

each $R^A$ is independently deuterium, halogen, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, 5- to 10-membered heteroaryl, —CN, —$OR^5$, —$SR^5$, —$NR^6R^7$, —$NO_2$, —C═NH($OR^5$), —C(O)$R^5$, —OC(O)$R^5$, —C(O)$OR^5$, —C(O)$NR^6R^7$, —$NR^5$C(O)$R^6$, —$NR^5$C(O)$OR^6$, —$NR^5$C(O)$NR^6R^7$, —S(O)$R^5$, —$S(O)_2R^5$, —$NR^5$S(O)$R^6$, —$NR^5S(O)_2R^6$, —S(O)$NR^6R^7$, —$S(O)_2NR^6R^7$, or —P(O)($OR^5$)($OR^6$), wherein the $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, and 5- to 10-membered heteroaryl of $R^A$ are independently optionally substituted by one or more $R^{Aa}$;

each $R^{Aa}$ is independently deuterium, halogen, oxo, —$OR^8$, —$NR^8R^9$, —C(O)$R^8$, —C(O)$OR^8$, —$NR^8$C(O)$OR^{10}$, —CN, —S(O)$R^8$, —$S(O)_2R^8$, —P(O)($OR^8$)($OR^9$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl, wherein the 3- to 12-membered heterocyclyl, 5- to 10-membered heteroaryl, $C_6$-$C_{14}$ aryl, and $C_1$-$C_6$ alkyl of $R^{Aa}$ are independently optionally substituted by one or more $R^{Ab}$;

each $R^{Ab}$ is independently deuterium, oxo, —OH, —O($^2$H), halogen, or $C_1$-$C_6$ alkyl optionally substituted by one or more of deuterium, halogen, —OH, —O($^2$H), or oxo;

each $R^5$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 10-membered heterocyclyl of $R^5$ are each independently optionally substituted by one or more $R^{5a}$;

each $R^{5a}$ is independently halogen, deuterium, oxo, —CN, —$OR^{10}$, —$NR^{11}R^{12}$, —P(O)($OR^{11}$)($OR^{12}$), 3- to 12-membered heterocyclyl, or $C_1$-$C_6$ alkyl optionally substituted by one or more of deuterium, halogen, —OH, —O($^2$H), or oxo;

each $R^6$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^6$ are independently optionally substituted by one or more of deuterium, halogen, oxo, —CN, —$OR^{10}$, —$NR^{11}R^{12}$, or $C_1$-$C_6$ alkyl optionally substituted by one or more of deuterium, halogen, —OH, —O($^2$H), or oxo;

each $R^7$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^7$ are independently optionally substituted by one or more of deuterium, halogen, oxo, —CN, —$OR^{10}$, —$NR^{11}R^{12}$, or $C_1$-$C_6$ alkyl optionally substituted by one or more of deuterium, halogen, —OH, —O($^2$H), or oxo;

or $R^6$ and $R^7$ are taken together with the atom to which they are attached to form a 3- to 10-membered heterocyclyl optionally substituted by one or more of deuterium, halogen, oxo, —$OR^{10}$, —$NR^{11}R^{12}$, or $C_1$-$C_6$ alkyl optionally substituted by one or more of deuterium, halogen, oxo, —OH, or —O($^2$H);

each $R^8$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^9$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^{10}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

each $R^{11}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo; and each $R^{12}$ is independently hydrogen, deuterium, $C_1$-$C_6$ alkyl optionally substituted by one or more of deuterium, halogen, or oxo, $C_2$-$C_6$ alkenyl optionally substituted by one or more of deuterium, halogen, or oxo, or $C_2$-$C_6$ alkynyl optionally substituted by one or more of deuterium, halogen, or oxo;

or $R^{11}$ and $R^{12}$ are taken together with the atom to which they are attached to form a 3-6 membered heterocyclyl optionally substituted by one or more of deuterium, halogen, oxo or $C_1$-$C_6$ alkyl optionally substituted by one or more of deuterium, oxo, or halogen.

In one variation is provided a compound of the formula (I), or a pharmaceutically acceptable salt thereof, wherein the carbon bearing the $CO_2Q$ and $N(H)C(O)C(R^2)(R^3)R^4$ moieties is in the "S" configuration. In another variation is provided a compound of the formula (I), or a pharmaceutically acceptable salt thereof, wherein the carbon bearing the $CO_2Q$ and $N(H)C(O)C(R^2)(R^3)R^4$ moieties is in the "R" configuration. Mixtures of a compound of the formula (I) are also embraced, including racemic or non-racemic mixtures of a given compound, and mixtures of two or more compounds of different chemical formulae.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^4$ of formula (I) or formula (A) may be combined with every description, variation, embodiment or aspect of $R^1$, $R^2$, $R^3$, $L^1$, $L^2$, $L^3$, Y, and/or Q the same as if each and every combination were specifically and individually listed. It is also understood that all descriptions, variations, embodiments or aspects of formula (I) or formula (A), where applicable, apply equally to other formulae detailed herein, and are equally described, the same as if each and every description, variation, embodiment or aspect were separately and individually listed for all formulae. For example, all descriptions, variations, embodiments or aspects of formula (I) or formula (A), where applicable, apply equally to any of formulae (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), and (IV) detailed herein, and are equally described, the same as if each and every description, variation, embodiment or aspect were separately and individually listed for all formulae.

In some embodiments of the compound of formula (I), or a pharmaceutically acceptable salt thereof, $L^1$ is unsubstituted $C_2$-$C_4$ alkylene. In a particular variation, $L^1$ is $-CH_2-CH_2-$, $-CH_2-CH_2-CH_2-$, or $-CH_2-CH_2-CH_2-CH_2-$. In a particular variation, $L^1$ is $-CH_2CH_2-$.

In some embodiments of the compound of formula (I), or a pharmaceutically acceptable salt thereof, $L^2$ is a bond.

In some embodiments of the compound of formula (I), or a pharmaceutically acceptable salt thereof, $L^2$ is unsubstituted $C_1$-$C_3$ alkylene. In a particular variation, $L^2$ is $-CH_2CH_2-$ In some embodiments of the compound of formula (I), or a pharmaceutically acceptable salt thereof, $L^3$ is unsubstituted $C_2$-$C_4$ alkylene. In a particular variation, $L^3$ is $-CH_2CH_2-$. In a particular variation, $L^3$ is $-CH_2CH_2CH_2CH_2-$.

In some embodiments of the compound of formula (I), or a pharmaceutically acceptable salt thereof, $-L^1$-O-$L^2$-Y-$L^3$- are taken together to form

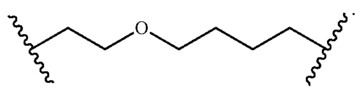 [SMILES: *CCCCOCC*]

In some embodiments of the compound of formula (I), or a pharmaceutically acceptable salt thereof, at least one of $R^4$, $R^{4a}$, $R^{4b}$, $R^5$, $R^{5a}$, $R^6$, $R^7$, $R^8$, $R^9$, $R^{10}$, $R^{11}$, or $R^{12}$ is deuterium.

In some embodiments, the compound of formula (I) is of the formula (II-a):

(II-a)

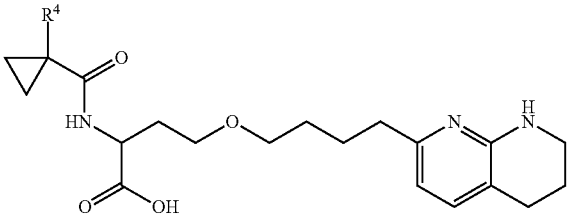

or a pharmaceutically acceptable salt thereof, wherein $R^4$ is as defined for formula (I). In some embodiments of the compound of formula (II-a), $R^4$ is phenyl optionally substituted by one or more $R^{4a}$. In some embodiments of the compound of formula (II-a), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-a), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-a), $R^4$ is pyridyl or pyrimidinyl, wherein the pyridyl or pyrimidinyl is optionally substituted by one or more $R^{4a}$. In some embodiments of the compound of formula (II-a), $R^4$ is pyridyl is optionally substituted by one or more $R^{4a}$. In some embodiments of the compound of formula (II-a), $R^4$ is pyrimidinyl is optionally substituted by one or more $R^{4a}$. In some embodiments of the compound of formula (II-a), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-b):

(II-b)

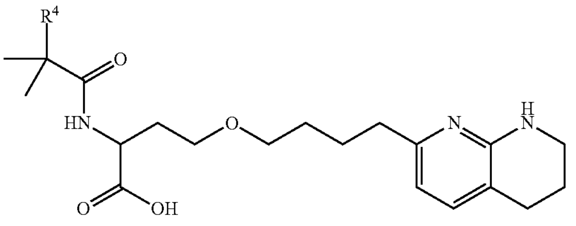

or a pharmaceutically acceptable salt thereof, wherein $R^4$ is as defined for formula (I). In some embodiments of the compound of formula (II-b), $R^4$ is phenyl optionally substituted by one or more $R^{4a}$. In some embodiments of the compound of formula (II-b), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-b), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-b), $R^4$ is pyridyl or pyrimidinyl, wherein the pyridyl or pyrimidinyl is optionally substituted by one or more $R^{4a}$. In some embodiments of the compound of formula (II-b), $R^4$ is pyridyl is optionally substituted by one or more $R^{4a}$. In some embodiments of the compound of formula (II-b), $R^4$ is pyrimidinyl is optionally substituted by one or more $R^{4a}$. In some embodiments of the compound of formula (II-b), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-c):

(II-c)

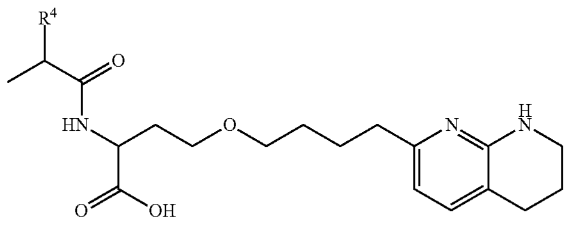

or a pharmaceutically acceptable salt thereof, wherein $R^4$ is as defined for formula (I). In some embodiments of the compound of formula (II-c), $R^4$ is phenyl optionally substituted by one or more $R^{4a}$. In some embodiments of the compound of formula (II-c), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-c), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-c), $R^4$ is pyridyl or pyrimidinyl, wherein the pyridyl or pyrimidinyl is optionally substituted by one or more $R^{4a}$. In some embodiments of the compound of formula (II-c), $R^4$ is pyridyl is optionally substituted by one or more $R^{4a}$. In some embodiments of the compound of formula (II-c), $R^4$ is pyrimidinyl is optionally substituted by one or more $R^{4a}$. In some embodiments of the compound of formula (II-c), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-d):

(II-d)

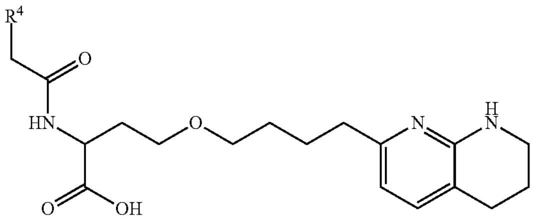

or a pharmaceutically acceptable salt thereof, wherein $R^4$ is as defined for formula (I). In some embodiments of the compound of formula (II-d), $R^4$ is phenyl optionally substituted by one or more $R^{4a}$. In some embodiments of the compound of formula (II-d), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-d), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-d), $R^4$ is pyridyl or pyrimidinyl, wherein the pyridyl or pyrimidinyl is optionally substituted by one or more $R^{4a}$. In some embodiments of the compound of formula (II-d), $R^4$ is pyridyl is optionally substituted by one or more $R^{4a}$. In some embodiments of the compound of formula (II-d), $R^4$ is pyrimidinyl is optionally substituted by one or more $R^{4a}$. In some embodiments of the compound of formula (II-d), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-e):

(II-e)

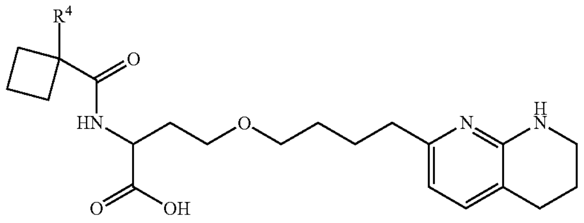

or a pharmaceutically acceptable salt thereof, wherein $R^4$ is as defined for formula (I). In some embodiments of the compound of formula (II-e), $R^4$ is phenyl optionally substituted by one or more $R^{4a}$. In some embodiments of the compound of formula (II-e), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-e), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-e), $R^4$ is pyridyl or pyrimidinyl, wherein the pyridyl or pyrimidinyl is optionally substituted by one or more $R^{4a}$. In some embodiments of the compound of formula (II-e), $R^4$ is pyridyl is optionally substituted by one or more $R^{4a}$. In some embodiments of the compound of formula (II-e), $R^4$ is pyrimidinyl is optionally substituted by one or more $R^{4a}$. In some embodiments of the compound of formula (II-e), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-f):

(II-f)

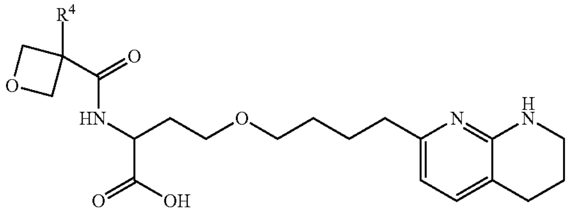

or a pharmaceutically acceptable salt thereof, wherein $R^4$ is as defined for formula (I). In some embodiments of the compound of formula (II-f), $R^4$ is phenyl optionally substituted by one or more $R^{4a}$. In some embodiments of the compound of formula (II-f), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-f), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-f), $R^4$ is pyridyl or pyrimidinyl, wherein the pyridyl or pyrimidinyl is optionally substituted by one or more $R^{4a}$. In some embodiments of the compound of formula (II-f), $R^4$ is pyridyl is optionally substituted by one or more $R^{4a}$. In some embodiments of the compound of formula (II-f), $R^4$ is pyrimidinyl is optionally substituted by one or more $R^{4a}$. In some embodiments of the compound of formula (II-f), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (II-g):

(II-g)

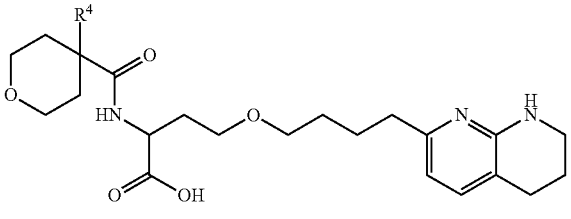

or a pharmaceutically acceptable salt thereof, wherein $R^4$ is as defined for formula (I). In some embodiments of the compound of formula (II-g), $R^4$ is phenyl optionally substituted by one or more $R^{4a}$. In some embodiments of the compound of formula (II-g), $R^4$ is 5-to-6-membered heteroaryl containing at least one nitrogen atom and is optionally fused to a phenyl group, wherein the 5-to-6-membered heteroaryl is optionally substituted by one or more $R^{4a}$. In some embodiments of the compound of formula (II-g), $R^4$ is 5-to-6-membered heteroaryl containing at least one nitrogen atom, wherein the 5-to-6-membered heteroaryl is optionally substituted by one or more $R^{4a}$. In some embodiments of the compound of formula (II-g), $R^4$ is pyridyl or pyrimidinyl, wherein the pyridyl or pyrimidinyl is optionally substituted by one or more $R^{4a}$. In some embodiments of the compound of formula (II-g), $R^4$ is pyridyl is optionally substituted by one or more $R^{4a}$. In some embodiments of the compound of formula (II-g), $R^4$ is pyrimidinyl is optionally substituted by one or more $R^{4a}$. In some embodiments of the compound of formula (II-g), $R^4$ is 6-membered heterocyclyl containing at least one nitrogen atom and is optionally fused to a phenyl group, wherein the 6-membered heterocyclyl is optionally substituted by one or more groups selected from the group consisting of $R^{4a}$ and oxo.

In some embodiments, the compound of formula (I) is of the formula (III-a):

(III-a)

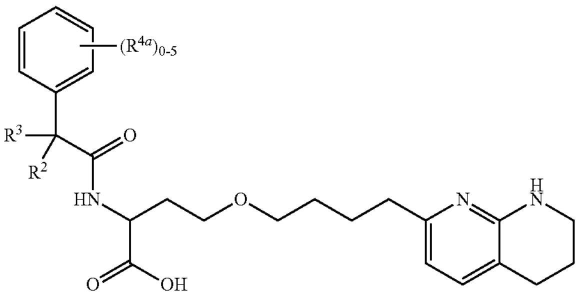

or a pharmaceutically acceptable salt thereof, wherein $R^2$, $R^3$, and $R^{4a}$ are as defined for formula (I). In some embodiments of the compound of formula (III-a), $R^2$ and $R^3$ are taken together with the carbon atom to which they are attached to form a $C_3$-$C_6$ cycloalkyl or a 3-to-6-membered heterocyclyl. In some embodiments of the compound of formula (III-a), $R^2$ and $R^3$ are taken together with the carbon atom to which they are attached to form a $C_3$-$C_6$ cycloalkyl. In some embodiments of the compound of formula (III-a), $R^2$ and $R^3$ are taken together with the carbon atom to which they are attached to form cyclopropyl or cyclobutyl. In some embodiments of the compound of formula (III-a), $R^2$ and $R^3$ are taken together with the carbon atom to which they are attached to form cyclobutyl. In some embodiments of the compound of formula (III-a), $R^2$ and $R^3$ are taken together with the carbon atom to which they are attached to form cyclopropyl. In some embodiments of the compound of formula (III-a), $R^2$ and $R^3$ are taken together with the carbon atom to which they are attached to form a 3-to-6-membered heterocyclyl. In some embodiments of the compound of formula (III-a), $R^2$ and $R^3$ are taken together with the carbon atom to which they are attached to form a 4-to-6-membered heterocyclyl. In some embodiments of the compound of formula (III-a), $R^2$ and $R^3$ are taken together with the carbon atom to which they are attached to form an oxetane or pyran. In some embodiments of the compound of formula (III-a), $R^2$ and $R^3$ are taken together with the carbon atom to which they are attached to form an oxetane or pyran. In some embodiments of the compound of formula (III-a), $R^2$ and $R^3$ are taken together with the carbon atom to which they are attached to form

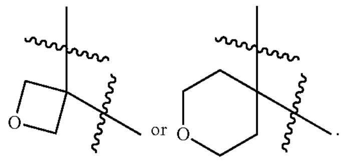 [SMILES: *C1(*)COC1 ; *C1(*)CCOCC1]

In some embodiments of the compound of formula (III-a), $R^2$ and $R^3$ are taken together with the carbon atom to which they are attached to form

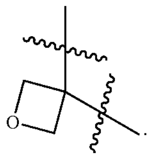 [SMILES: *C1(*)COC1]

In some embodiments of the compound of formula (III-a), $R^2$ and $R^3$ are taken together with the carbon atom to which they are attached to form.

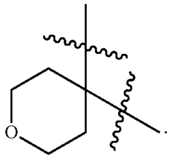 [SMILES: *C1(*)CCOCC1]

In some embodiments, the compound of formula (I) is of the formula (III-b-1):

(III-b-1)

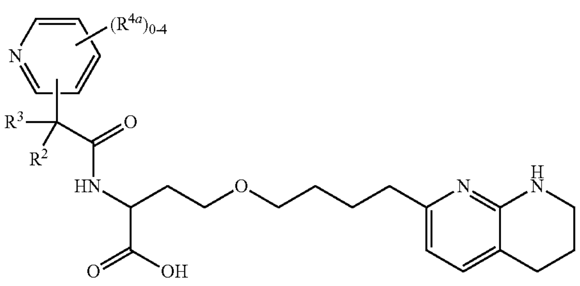

or a pharmaceutically acceptable salt thereof, wherein $R^2$, $R^3$, and $R^{4a}$ are as defined for formula (I). In some embodiments of the compound of formula (III-b-1), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-1), $R^2$ and $R^3$ are taken together with the carbon atom to which they are attached to form a $C_3$-$C_6$ cycloalkyl. In some embodiments of the compound of formula (III-b-1), $R^2$ and $R^3$ are taken together with the carbon atom to which they are attached to form cyclopropyl or cyclobutyl. In some embodiments of the compound of formula (III-b-1), $R^2$ and $R^3$ are taken together with the carbon atom to which they are attached to form cyclobutyl. In some embodiments of the compound of formula (III-b-1), $R^2$ and $R^3$ are taken together with the carbon atom to which they are attached to form cyclopropyl. In some embodiments of the compound of formula (III-b-1), $R^2$ and $R^3$ are taken together with the carbon atom to which they are attached to form a 3-to-6-membered heterocyclyl. In some embodiments of the compound of formula (III-b-1), $R^2$ and $R^3$ are taken together with the carbon atom to which they are attached to form a 4-to-6-membered heterocyclyl. In some embodiments of the compound of formula (III-b-1), $R^2$ and $R^3$ are taken together with the carbon atom to which they are attached to form an oxetane or pyran. In some embodiments of the compound of formula (III-b-1), $R^2$ and $R^3$ are taken together with the carbon atom to which they are attached to form an oxetane or pyran. In some embodiments of the compound of formula (III-b-1), $R^2$ and $R^3$ are taken together with the carbon atom to which they are attached to form

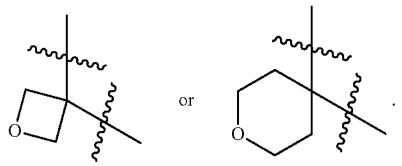 [SMILES: *C1(*)COC1 ; *C1(*)CCOCC1]

In some embodiments of the compound of formula (III-b-1), $R^2$ and $R^3$ are taken together with the carbon atom to which they are attached to form

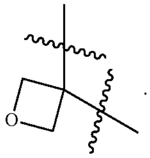 [SMILES: *C1(*)COC1]

In some embodiments of the compound of formula (III-b-1), $R^2$ and $R^3$ are taken together with the carbon atom to which they are attached to form

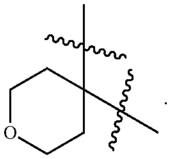 [SMILES: *C1(*)CCOCC1]

In some embodiments, the compound of formula (I) is of the formula (III-b-2):

(III-b-2)

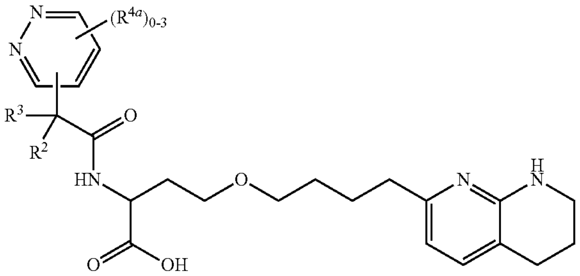

or a pharmaceutically acceptable salt thereof, wherein $R^2$, $R^3$, and $R^{4a}$ are as defined for formula (I). In some embodiments of the compound of formula (III-b-2), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-2), $R^2$ and $R^3$ are taken together with the carbon atom to which they are attached to form a $C_3$-$C_6$ cycloalkyl. In some embodiments of the compound of formula (III-b-2), $R^2$ and $R^3$ are taken together with the carbon atom to which they are attached to form cyclopropyl or cyclobutyl. In some embodiments of the compound of formula (III-b-2), $R^2$ and $R^3$ are taken together with the carbon atom to which they are attached to form cyclobutyl. In some embodiments of the compound of formula (III-b-2), $R^2$ and $R^3$ are taken together with the carbon atom to which they are attached to form cyclopropyl. In some embodiments of the compound of formula (III-b-2), $R^2$ and $R^3$ are taken together with the carbon atom to which they are attached to form a 3-to-6-membered heterocyclyl. In some embodiments of the compound of formula (III-b-2), $R^2$ and $R^3$ are taken together with the carbon atom to which they are attached to form a 4-to-6-membered heterocyclyl. In some embodiments of the compound of formula (III-b-2), $R^2$ and $R^3$ are taken together with the carbon atom to which they are attached to form an oxetane or pyran. In some embodiments of the compound of formula (III-b-2), $R^2$ and $R^3$ are taken together with the carbon atom to which they are attached to form an oxetane or pyran. In some embodiments of the compound of formula (III-b-2), $R^2$ and $R^3$ are taken together with the carbon atom to which they are attached to form

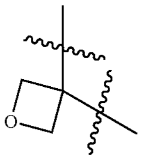

or

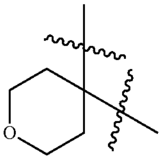

.

In some embodiments of the compound of formula (III-b-2), $R^2$ and $R^3$ are taken together with the carbon atom to which they are attached to form

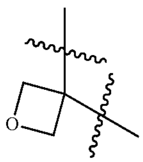

.

In some embodiments of the compound of formula (III-b-2), $R^2$ and $R^3$ are taken together with the carbon atom to which they are attached to form

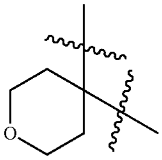

.

In some embodiments, the compound of formula (I) is of the formula (III-b-3):

(III-b-3)

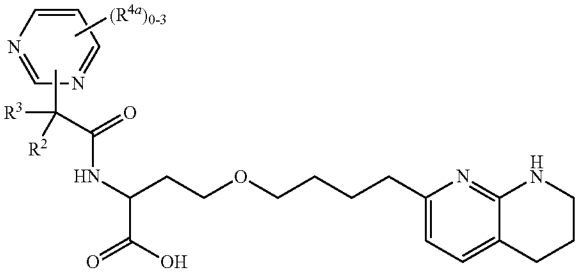

or a pharmaceutically acceptable salt thereof, wherein $R^2$, $R^3$, and $R^{4a}$ are as defined for formula (I). In some embodiments of the compound of formula (III-b-3), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-3), $R^2$ and $R^3$ are taken together with the carbon atom to which they are attached to form a $C_3$-$C_6$ cycloalkyl. In some embodiments of the compound of formula (III-b-3), $R^2$ and $R^3$ are taken together with the carbon atom to which they are attached to form cyclopropyl or cyclobutyl. In some embodiments of the compound of formula (III-b-3), $R^2$ and $R^3$ are taken together with the carbon atom to which they are attached to form cyclobutyl. In some embodiments of the compound of formula (III-b-3), $R^2$ and $R^3$ are taken together with the carbon atom to which they are attached to form cyclopropyl. In some embodiments of the compound of formula (III-b-3), $R^2$ and $R^3$ are taken together with the carbon atom to which they are attached to form a 3-to-6-membered heterocyclyl. In some embodiments of the compound of formula (III-b-3), $R^2$ and $R^3$ are taken together with the carbon atom to which they are attached to form a 4-to-6-membered heterocyclyl. In some embodiments of the compound of formula (III-b-3), $R^2$ and $R^3$ are taken together with the carbon atom to which they are attached to form an oxetane or pyran. In some embodiments of the compound of formula (III-b-3), $R^2$ and $R^3$ are taken together with the carbon atom to which they are attached to form an oxetane or pyran. In some embodiments of the compound of formula (III-b-3), $R^2$ and $R^3$ are taken together with the carbon atom to which they are attached to form

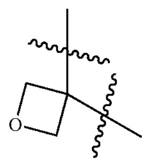
or
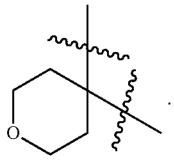 [SMILES: *C1(*)CCOCC1]
.

In some embodiments of the compound of formula (III-b-3), $R^2$ and $R^3$ are taken together with the carbon atom to which they are attached to form

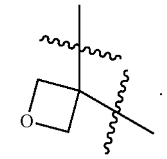 [SMILES: *C1(*)COC1]
.

In some embodiments of the compound of formula (III-b-3), $R^2$ and $R^3$ are taken together with the carbon atom to which they are attached to form

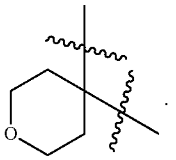 [SMILES: *C1(*)CCOCC1]
.

In some embodiments, the compound of formula (I) is of the formula (III-b-4):

(III-b-4)

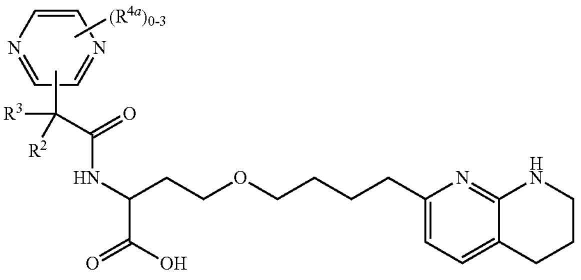

or a pharmaceutically acceptable salt thereof, wherein $R^2$, $R^3$, and $R^{4a}$ are as defined for formula (I). In some embodiments of the compound of formula (III-b-4), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-4), $R^2$ and $R^3$ are taken together with the carbon atom to which they are attached to form a $C_3$-$C_6$ cycloalkyl. In some embodiments of the compound of formula (III-b-4), $R^2$ and $R^3$ are taken together with the carbon atom to which they are attached to form cyclopropyl or cyclobutyl. In some embodiments of the compound of formula (III-b-4), $R^2$ and $R^3$ are taken together with the carbon atom to which they are attached to form cyclobutyl. In some embodiments of the compound of formula (III-b-4), $R^2$ and $R^3$ are taken together with the carbon atom to which they are attached to form cyclopropyl. In some embodiments of the compound of formula (III-b-4), $R^2$ and $R^3$ are taken together with the carbon atom to which they are attached to form a 3-to-6-membered heterocyclyl. In some embodiments of the compound of formula (III-b-4), $R^2$ and $R^3$ are taken together with the carbon atom to which they are attached to form a 4-to-6-membered heterocyclyl. In some embodiments of the compound of formula (III-b-4), $R^2$ and $R^3$ are taken together with the carbon atom to which they are attached to form an oxetane or pyran. In some embodiments of the compound of formula (III-b-4), $R^2$ and $R^3$ are taken together with the carbon atom to which they are attached to form an oxetane or pyran. In some embodiments of the compound of formula (III-b-4), $R^2$ and $R^3$ are taken together with the carbon atom to which they are attached to form

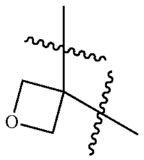
or
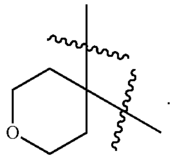
.

In some embodiments of the compound of formula (III-b-4), $R^2$ and $R^3$ are taken together with the carbon atom to which they are attached to form

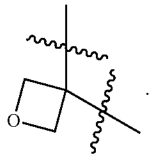 [SMILES: *C1(*)COC1]
.

In some embodiments of the compound of formula (III-b-4), $R^2$ and $R^3$ are taken together with the carbon atom to which they are attached to form

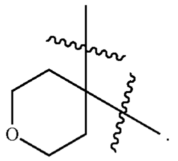 [SMILES: *C1(*)CCOCC1]
.

In some embodiments, the compound of formula (I) is of the formula (III-b-5):

(III-b-5)

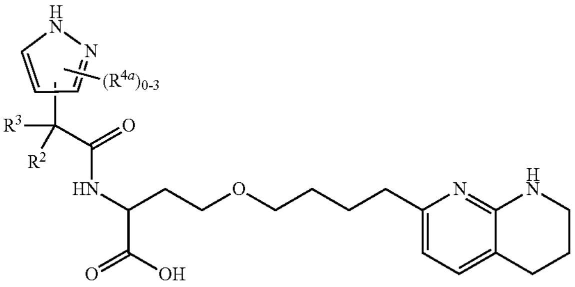

or a pharmaceutically acceptable salt thereof, wherein $R^2$, $R^3$, and $R^{4a}$ are as defined for formula (I). In some embodiments of the compound of formula (III-b-5), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-5), $R^2$ and $R^3$ are taken together with the carbon atom to which they are attached to form a $C_3$-$C_6$ cycloalkyl. In some embodiments of the compound of formula (III-b-5), $R^2$ and $R^3$ are taken together with the carbon atom to which they are attached to form cyclopropyl or cyclobutyl. In some embodiments of the compound of formula (III-b-5), $R^2$ and $R^3$ are taken together with the carbon atom to which they are attached to form cyclobutyl. In some embodiments of the compound of formula (III-b-5), $R^2$ and $R^3$ are taken together with the carbon atom to which they are attached to form cyclopropyl. In some embodiments of the compound of formula (III-b-5), $R^2$ and $R^3$ are taken together with the carbon atom to which they are attached to form a 3-to-6-membered heterocyclyl. In some embodiments of the compound of formula (III-b-5), $R^2$ and $R^3$ are taken together with the carbon atom to which they are attached to form a 4-to-6-membered heterocyclyl. In some embodiments of the compound of formula (III-b-5), $R^2$ and $R^3$ are taken together with the carbon atom to which they are attached to form an oxetane or pyran. In some embodiments of the compound of formula (III-b-5), $R^2$ and $R^3$ are taken together with the carbon atom to which they are attached to form an oxetane or pyran. In some embodiments of the compound of formula (III-b-5), $R^2$ and $R^3$ are taken together with the carbon atom to which they are attached to form

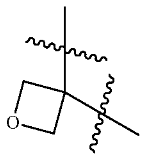

or

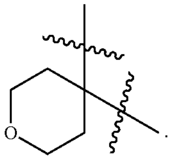

In some embodiments of the compound of formula (III-b-5), $R^2$ and $R^3$ are taken together with the carbon atom to which they are attached to form

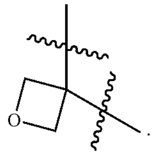

In some embodiments of the compound of formula (III-b-5), $R^2$ and $R^3$ are taken together with the carbon atom to which they are attached to form

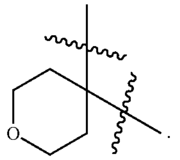

In some embodiments, the compound of formula (I) is of the formula (III-b-6):

(III-b-6)

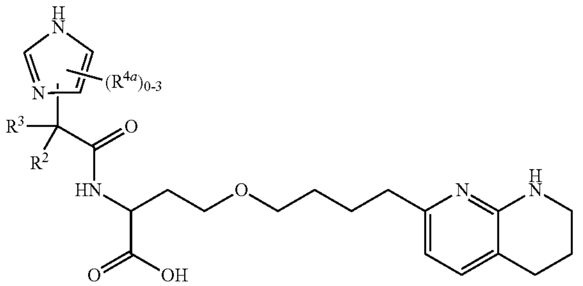

or a pharmaceutically acceptable salt thereof, wherein $R^2$, $R^3$, and $R^{4a}$ are as defined for formula (I). In some embodiments of the compound of formula (III-b-6), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-6), $R^2$ and $R^3$ are taken together with the carbon atom to which they are attached to form a $C_3$-$C_6$ cycloalkyl. In some embodiments of the compound of formula (III-b-6), $R^2$ and $R^3$ are taken together with the carbon atom to which they are attached to form cyclopropyl or cyclobutyl. In some embodiments of the compound of formula (III-b-6), $R^2$ and $R^3$ are taken together with the carbon atom to which they are attached to form cyclobutyl. In some embodiments of the compound of formula (III-b-6), $R^2$ and $R^3$ are taken together with the carbon atom to which they are attached to form cyclopropyl. In some embodiments of the compound of formula (III-b-6), $R^2$ and $R^3$ are taken together with the carbon atom to which they are attached to form a 3-to-6-membered heterocyclyl. In some embodiments of the compound of formula (III-b-6), $R^2$ and $R^3$ are taken together with the carbon atom to which they are attached to form a 4-to-6-membered heterocyclyl. In some embodiments of the compound of formula (III-b-6), $R^2$ and $R^3$ are taken together with the carbon atom to which they are attached to form an oxetane or pyran. In some embodiments of the compound of formula (III-b-6), $R^2$ and $R^3$ are taken together with the carbon atom to which they are attached to form an oxetane or pyran. In some embodiments of the compound of formula (III-b-6), $R^2$ and $R^3$ are taken together with the carbon atom to which they are attached to form

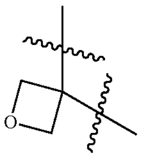

or

-continued

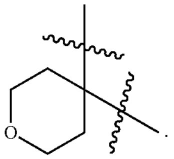 [SMILES: *C1(*)CCOCC1]

In some embodiments of the compound of formula (III-b-6), $R^2$ and $R^3$ are taken together with the carbon atom to which they are attached to form

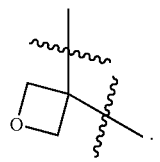 [SMILES: *C1(*)COC1]

In some embodiments of the compound of formula (III-b-6), $R^2$ and $R^3$ are taken together with the carbon atom to which they are attached to form

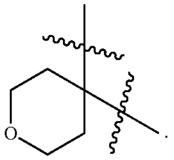

In some embodiments, the compound of formula (I) is of the formula (III-b-7):

(III-b-7)

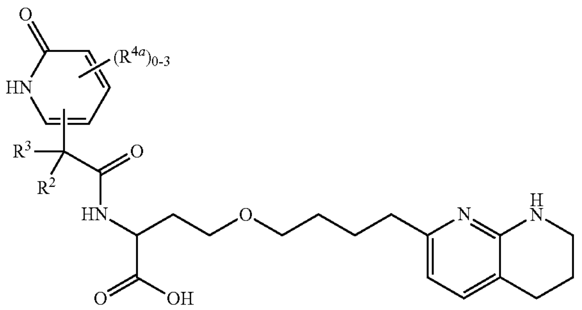

or a pharmaceutically acceptable salt thereof, wherein $R^2$, $R^3$, and $R^{4a}$ are as defined for formula (I). In some embodiments of the compound of formula (III-b-7), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-7), $R^2$ and $R^3$ are taken together with the carbon atom to which they are attached to form a $C_3$-$C_6$ cycloalkyl. In some embodiments of the compound of formula (III-b-7), $R^2$ and $R^3$ are taken together with the carbon atom to which they are attached to form cyclopropyl or cyclobutyl. In some embodiments of the compound of formula (III-b-7), $R^2$ and $R^3$ are taken together with the carbon atom to which they are attached to form cyclobutyl. In some embodiments of the compound of formula (III-b-7), $R^2$ and $R^3$ are taken together with the carbon atom to which they are attached to form cyclopropyl. In some embodiments of the compound of formula (III-b-7), $R^2$ and $R^3$ are taken together with the carbon atom to which they are attached to form a 3-to-6-membered heterocyclyl. In some embodiments of the compound of formula (III-b-7), $R^2$ and $R^3$ are taken together with the carbon atom to which they are attached to form a 4-to-6-membered heterocyclyl. In some embodiments of the compound of formula (III-b-7), $R^2$ and $R^3$ are taken together with the carbon atom to which they are attached to form an oxetane or pyran. In some embodiments of the compound of formula (III-b-7), $R^2$ and $R^3$ are taken together with the carbon atom to which they are attached to form an oxetane or pyran. In some embodiments of the compound of formula (III-b-7), $R^2$ and $R^3$ are taken together with the carbon atom to which they are attached to form

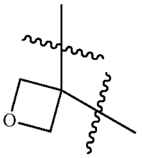

or

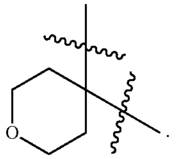

In some embodiments of the compound of formula (III-b-7), $R^2$ and $R^3$ are taken together with the carbon atom to which they are attached to form

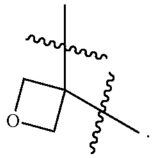

In some embodiments of the compound of formula (III-b-7), $R^2$ and $R^3$ are taken together with the carbon atom to which they are attached to form

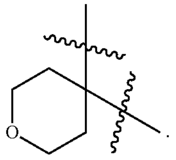 [SMILES: *C1(*)CCOCC1]

In some embodiments, the compound of formula (I) is of the formula (III-b-8):

(III-b-8)

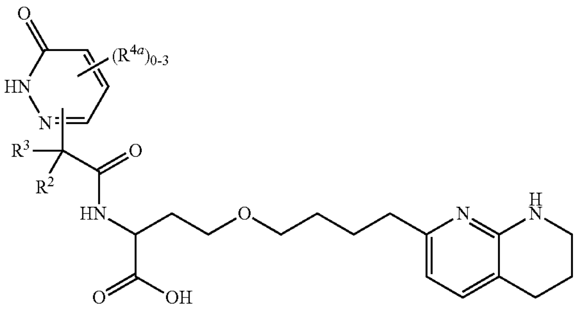

or a pharmaceutically acceptable salt thereof, wherein $R^2$, $R^3$, and $R^{4a}$ are as defined for formula (I). In some embodiments of the compound of formula (III-b-8), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-8), $R^2$ and $R^3$ are taken together with the carbon atom to which they are attached to form a $C_3$-$C_6$ cycloalkyl. In some embodiments of the compound of formula (III-b-8), $R^2$ and $R^3$ are taken together with the carbon atom to which they are attached to form cyclopropyl or cyclobutyl. In some embodiments of the compound of formula (III-b-8), $R^2$ and $R^3$ are taken together with the carbon atom to which they are attached to form cyclobutyl. In some embodiments of the compound of formula (III-b-8), $R^2$ and $R^3$ are taken together with the carbon atom to which they are attached to form cyclopropyl. In some embodiments of the compound of formula (III-b-8), $R^2$ and $R^3$ are taken together with the carbon atom to which they are attached to form a 3-to-6-membered heterocyclyl. In some embodiments of the compound of formula (III-b-8), $R^2$ and $R^3$ are taken together with the carbon atom to which they are attached to form a 4-to-6-membered heterocyclyl. In some embodiments of the compound of formula (III-b-8), $R^2$ and $R^3$ are taken together with the carbon atom to which they are attached to form an oxetane or pyran. In some embodiments of the compound of formula (III-b-8), $R^2$ and $R^3$ are taken together with the carbon atom to which they are attached to form an oxetane or pyran. In some embodiments of the compound of formula (III-b-8), $R^2$ and $R^3$ are taken together with the carbon atom to which they are attached to form

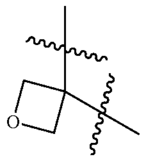

or

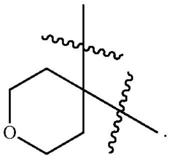 [SMILES: *C1(*)CCOCC1]

In some embodiments of the compound of formula (III-b-8), $R^2$ and $R^3$ are taken together with the carbon atom to which they are attached to form

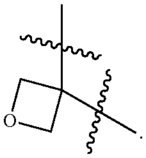 [SMILES: *C1(*)COC1]

In some embodiments of the compound of formula (III-b-8), $R^2$ and $R^3$ are taken together with the carbon atom to which they are attached to form

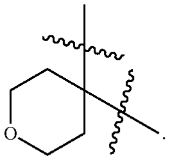 [SMILES: *C1(*)CCOCC1]

In some embodiments, the compound of formula (I) is of the formula (III-b-9):

(III-b-9)

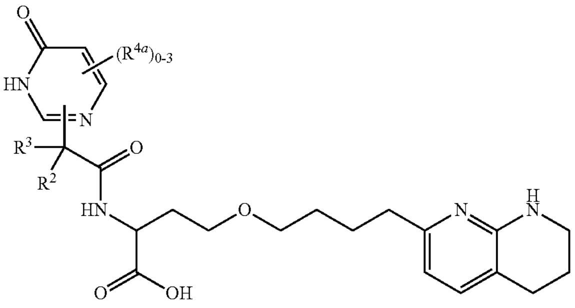

or a pharmaceutically acceptable salt thereof, wherein $R^2$, $R^3$, and $R^{4a}$ are as defined for formula (I). In some embodiments of the compound of formula (III-b-9), $R^2$ and $R^3$ are taken together with the carbon atom to which they are attached to form a $C_3$-$C_6$ cycloalkyl or a 3-to-6-membered heterocyclyl. In some embodiments of the compound of formula (III-b-9), $R^2$ and $R^3$ are taken together with the carbon atom to which they are attached to form a $C_3$-$C_6$ cycloalkyl. In some embodiments of the compound of formula (III-b-9), $R^2$ and $R^3$ are taken together with the carbon atom to which they are attached to form cyclopropyl or cyclobutyl. In some embodiments of the compound of formula (III-b-9), $R^2$ and $R^3$ are taken together with the carbon atom to which they are attached to form cyclobutyl. In some embodiments of the compound of formula (III-b-9), $R^2$ and $R^3$ are taken together with the carbon atom to which they are attached to form cyclopropyl. In some embodiments of the compound of formula (III-b-9), $R^2$ and $R^3$ are taken together with the carbon atom to which they are attached to form a 3-to-6-membered heterocyclyl. In some embodiments of the compound of formula (III-b-9), $R^2$ and $R^3$ are taken together with the carbon atom to which they are attached to form a 4-to-6-membered heterocyclyl. In some embodiments of the compound of formula (III-b-9), $R^2$ and $R^3$ are taken together with the carbon atom to which they are attached to form an oxetane or pyran. In some embodiments of the compound of formula (III-b-9), $R^2$ and $R^3$ are taken together with the carbon atom to which they are attached to form an oxetane or pyran. In some embodiments of the compound of formula (III-b-9), $R^2$ and $R^3$ are taken together with the carbon atom to which they are attached to form

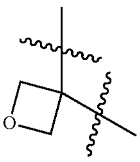

or

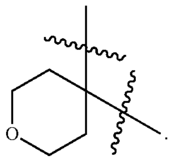

In some embodiments of the compound of formula (III-b-9), $R^2$ and $R^3$ are taken together with the carbon atom to which they are attached to form

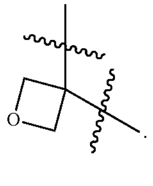

In some embodiments of the compound of formula (III-b-9), $R^2$ and $R^3$ are taken together with the carbon atom to which they are attached to form

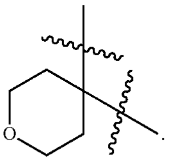 [SMILES: *C1(*)CCOCC1]

In some embodiments, the compound of formula (I) is of the formula (IV):

(IV)

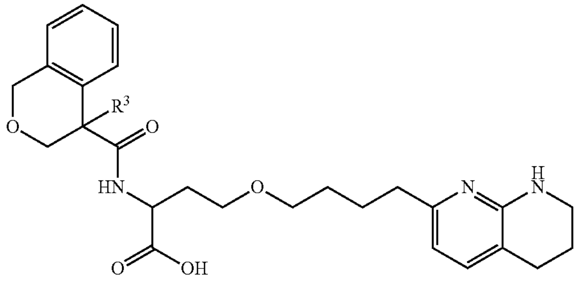

or a pharmaceutically acceptable salt thereof, wherein $R^3$ is as defined for formula (I).

In some embodiments, the compound of Formula (I) is

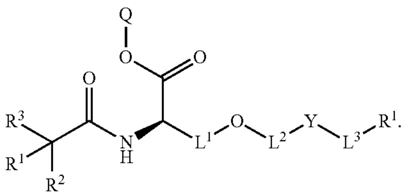

Also provided in another embodiment is a compound of formula (I), or a pharmaceutically acceptable salt thereof, wherein $R^1$ is 5,6,7,8-tetrahydro-1,8-naphthyridin-2-yl optionally substituted by one or more $R^{1a}$, 1,2,3,4-tetrahydro-1,8-naphthyridin-2-yl optionally substituted by one or more $R^{1b}$, 6-aminopyridin-2-yl optionally substituted by one or more $R^{1c}$, or (pyridin-2-yl)amino optionally substituted by one or more $R^{1d}$. In one aspect of the foregoing embodiment, $R^1$ is 5,6,7,8-tetrahydro-1,8-naphthyridin-2-yl optionally substituted by one or more $R^{1a}$. In one aspect of the foregoing embodiment, $R^1$ is unsubstituted 5,6,7,8-tetrahydro-1,8-naphthyridin-2-yl. In one aspect of the foregoing embodiment, $R^1$ is 5,6,7,8-tetrahydro-1,8-naphthyridin-2-yl substituted by two $R^{1a}$ groups on the same carbon atom, wherein the two $R^{1a}$ groups are taken together with the carbon atom to which they are attached to form a $C_3$-$C_6$ cycloalkyl (e.g., cyclopropyl). In one aspect of the foregoing embodiment, $R^1$ is 1,2,3,4-tetrahydro-1,8-naphthyridin-2-yl optionally substituted by one or more $R^{1b}$. In one aspect of the foregoing embodiment, $R^1$ is unsubstituted 1,2,3,4-tetrahydro-1,8-naphthyridin-2-yl. In one aspect of the foregoing embodiment, $R^1$ is 1,2,3,4-tetrahydro-1,8-naphthyridin-2-yl substituted by two $R^{1b}$ groups on the same carbon atom, wherein the two $R^{1b}$ groups are taken together with the carbon atom to which they are attached to form a $C_3$-$C_6$ cycloalkyl (e.g., cyclopropyl).

Also provided in another embodiment is a compound of formula (I), or a pharmaceutically acceptable salt thereof, wherein $R^2$ and $R^3$ are independently H or $C_1$-$C_6$ alkyl. In one aspect of the foregoing embodiment, $R^2$ and $R^3$ are the same. In one aspect of the foregoing embodiment, $R^2$ and $R^3$ are different. In one aspect of the foregoing embodiment, $R^2$ and $R^3$ are both H. In one aspect of the foregoing embodiment, $R^2$ is H and $R^3$ is $C_1$-$C_6$ alkyl. In one aspect of the foregoing embodiment, $R^2$ is H and $R^3$ is $C_1$-$C_3$ alkyl. In one aspect of the foregoing embodiment, $R^2$ is H and $R^3$ is $-CH_3$. In one aspect of the foregoing embodiment, $R^2$ and $R^3$ are independently $C_1$-$C_6$ alkyl. In one aspect of the foregoing embodiment, $R^2$ and $R^3$ are independently $C_1$-$C_3$ alkyl. In one aspect of the foregoing embodiment, $R^2$ and $R^3$ are independently methyl, ethyl, n-propyl, or isopropyl. In one aspect of the foregoing embodiment, $R^2$ and $R^3$ are both $-CH_3$.

Also provided in another embodiment is a compound of formula (I), or a pharmaceutically acceptable salt thereof, wherein $R^2$ and $R^3$ are taken together with the carbon atom to which they are attached to form $C_3$-$C_6$ cycloalkyl. In one aspect of the foregoing embodiment, $R^2$ and $R^3$ are taken together with the carbon atom to which they are attached to form $C_3$-$C_4$ cycloalkyl. In one aspect of the foregoing embodiment, $R^2$ and $R^3$ are taken together with the carbon atom to which they are attached to form cyclopropyl. In one aspect of the foregoing embodiment, $R^2$ and $R^3$ are taken together with the carbon atom to which they are attached to form cyclobutyl.

Also provided in another embodiment is a compound of formula (I), or a pharmaceutically acceptable salt thereof, wherein $R^2$ and $R^3$ are taken together with the carbon atom to which they are attached to form a 3-to-6-membered heterocyclyl. In one aspect of the foregoing embodiment, $R^2$ and $R^3$ are taken together with the carbon atom to which they are attached to form a 3-to-6-membered heterocyclyl, wherein the heterocyclyl contains at least one oxygen atom. In one aspect of the foregoing embodiment, $R^2$ and $R^3$ are taken together with the carbon atom to which they are attached to form a 4-to-6-membered heterocyclyl. In one aspect of the foregoing embodiment, $R^2$ and $R^3$ are taken together with the carbon atom to which they are attached to form a 4-to-6-membered heterocyclyl, wherein the heterocyclyl contains at least one oxygen atom. In one aspect of the foregoing embodiment, $R^2$ and $R^3$ are taken together with the carbon atom to which they are attached to form oxetanyl. In one aspect of the foregoing embodiment, $R^2$ and $R^3$ are taken together with the carbon atom to which they are attached to form tetrahydropyranyl. In one aspect of the foregoing embodiment, $R^2$ and $R^3$ are taken together with the carbon atom to which they are attached to form

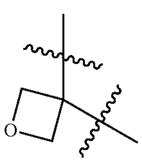
or
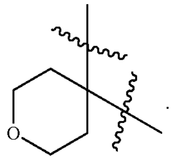
.

In one aspect of the foregoing embodiment, $R^2$ and $R^3$ are taken together with the carbon atom to which they are attached to form

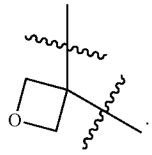 [SMILES: *C1(*)COC1]
.

In one aspect of the foregoing embodiment, $R^2$ and $R^3$ are taken together with the carbon atom to which they are attached to form

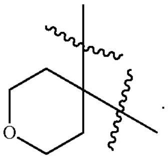
.

Also provided in another embodiment is a compound of formula (A), or a pharmaceutically acceptable salt thereof, wherein $R^2$ and $R^3$ are taken together with the carbon atom to which they are attached to form a $C_3$-$C_6$ cycloalkyl substituted by $R^{2a}$. In one aspect of the foregoing embodiment, $R^2$ and $R^3$ are taken together with the carbon atom to which they are attached to form a $C_3$-$C_6$ cycloalkyl substituted by deuterium or $C_1$-$C_6$ alkyl optionally substituted by halogen. In one aspect of the foregoing embodiment, $R^2$ and $R^3$ are taken together with the carbon atom to which they are attached to form cyclopropyl substituted by $R^{2a}$. In one aspect of the foregoing embodiment, $R^2$ and $R^3$ are taken together with the carbon atom to which they are attached to form

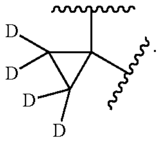 [SMILES: *C1(*)C([2H])([2H])C1([2H])[2H]]
.

Also provided in another embodiment is a compound of formula (A), or a pharmaceutically acceptable salt thereof, wherein $R^2$ and $R^3$ are taken together with the carbon atom to which they are attached to form a 3-to-6-membered heterocyclyl substituted by $R^{2a}$. In one aspect of the foregoing embodiment, $R^2$ and $R^3$ are taken together with the carbon atom to which they are attached to form a 3-to-6-membered heterocyclyl substituted by deuterium or $C_1$-$C_6$ alkyl optionally substituted by halogen. In one aspect of the foregoing embodiment, $R^2$ and $R^3$ are taken together with the carbon atom to which they are attached to form piperdine substituted by $R^{2a}$. In one aspect of the foregoing embodiment, $R^2$ and $R^3$ are taken together with the carbon atom to which they are attached to form

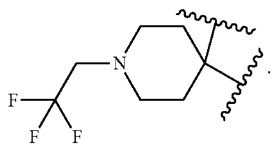 [SMILES: *C1(*)CCN(CC(F)(F)F)CC1]
.

Also provided in another embodiment is a compound of formula (A), or a pharmaceutically acceptable salt thereof, wherein $R^4$ is phenyl optionally substituted by one or more $R^{4a}$. In one aspect of the foregoing embodiment, $R^4$ is unsubstituted phenyl. In one aspect of the foregoing embodiment, $R^4$ is phenyl substituted by 1-5 $R^{4a}$ groups, wherein each $R^{4a}$ is independently selected from halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(=O)—$NH_2$.

Also provided in another embodiment is a compound of formula (I), or a pharmaceutically acceptable salt thereof, wherein $R^4$ is phenyl optionally substituted by one or more $R^{4a}$. In one aspect of the foregoing embodiment, $R^4$ is unsubstituted phenyl. In one aspect of the foregoing embodiment, $R^4$ is phenyl substituted by 1-5 $R^{4a}$ groups, wherein each $R^{4a}$ is independently selected from halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), —O—($C_1$-$C_6$ haloalkyl), and —$S(O)_2$($C_1$-$C_6$ alkyl). In one aspect of the foregoing embodiment, $R^4$ is phenyl substituted by 1-5 $R^{4a}$ groups, wherein each $R^{4a}$ is independently selected from F, Cl, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl), and —$S(O)_2$($C_1$-$C_3$ alkyl). In one aspect of the foregoing embodiment, $R^4$ is phenyl substituted by 1-5 $R^{4a}$ groups, wherein at least one $R^{4a}$ group is halo (e.g., F or Cl). In one aspect of the foregoing embodiment, $R^4$ is phenyl substituted by 1-5 $R^{4a}$ groups, wherein at least one $R^{4a}$ group is CN. In one aspect of the foregoing embodiment, $R^4$ is phenyl substituted by 1-5 $R^{4a}$ groups, wherein at least one $R^{4a}$ group is $C_1$-$C_3$ alkyl (e.g., —$CH_3$). In one aspect of the foregoing embodiment, $R^4$ is phenyl substituted by 1-5 $R^{4a}$ groups, wherein at least one $R^{4a}$ group is —O—($C_1$-$C_3$ alkyl) (e.g., —O—$CH_3$). In one aspect of the foregoing embodiment, $R^4$ is phenyl substituted by 1-5 $R^{4a}$ groups, wherein at least one $R^{4a}$ group is —O—($C_1$-$C_3$ haloalkyl) (e.g., —O—$CHF_2$). In one aspect of the foregoing embodiment, $R^4$ is phenyl substituted by 1-5 $R^{4a}$ groups, wherein at least one $R^{4a}$ group is —$S(O)_2$($C_1$-$C_3$ alkyl). In another aspect of the foregoing embodiment, $R^4$ is phenyl substituted by 2-5 $R^{4a}$ groups, wherein each $R^{4a}$ is independently selected from halo, CN, —O—($C_1$-$C_6$ alkyl), and —O—($C_1$-$C_6$ haloalkyl). In another aspect of the foregoing embodiment, $R^4$ is phenyl substituted by 2-5 $R^{4a}$ groups, wherein at least two of the $R^{4a}$ groups are halo (e.g., fluoro or chloro). In another aspect of the foregoing embodiment, $R^4$ is phenyl substituted by 2-5 $R^{4a}$ groups, wherein at least one of the $R^{4a}$ groups is halo (e.g., fluoro or chloro) and at least one of the $R^{4a}$ groups is CN. In another aspect of the foregoing embodiment, $R^4$ is phenyl substituted by 2-5 $R^{4a}$ groups, wherein at least one of the $R^{4a}$ groups is halo (e.g., fluoro or chloro) and at least one of the $R^{4a}$ groups is —O—($C_1$-$C_3$ alkyl) (e.g., —O—$CH_3$). In another aspect of the foregoing embodiment, $R^4$ is phenyl substituted by 2-5 $R^{4a}$ groups, wherein at least one of the $R^{4a}$ groups is halo (e.g., fluoro or chloro) and at least one of the $R^{4a}$ groups is —O—($C_1$-$C_3$ haloalkyl) (e.g., —O—$CHF_2$). In another aspect of the foregoing embodiment, $R^4$ is phenyl substituted by 2-5 $R^{4a}$ groups, wherein at least one of the $R^{4a}$ groups is CN and at least one of the $R^{4a}$ groups is —O—($C_1$-$C_3$ alkyl) (e.g., —O—$CH_3$).

Also provided in another embodiment is a compound of formula (A), or a pharmaceutically acceptable salt thereof, wherein $R^4$ is 5-to-6-membered heteroaryl containing at least one nitrogen atom, wherein the 5-to-6-membered heteroaryl is optionally fused to a phenyl group and wherein the 5-to-6-membered heteroaryl is optionally substituted by one or more $R^{4a}$. In another aspect of the foregoing embodiment, $R^4$ is 5-to-6-membered heteroaryl, wherein the 5-to-6-membered heteroaryl contains at least one nitrogen atom and is optionally substituted by one or more $R^{4a}$. In another aspect of the foregoing embodiment, $R^4$ is 5-membered heteroaryl, wherein the 5-membered heteroaryl contains two nitrogen atoms (e.g., $R^4$ is pyrazolyl, imidazolyl, or thiazolyl) and is optionally substituted by one or more $R^{4a}$. In another aspect of the foregoing embodiment, $R^4$ is 6-membered heteroaryl, wherein the 6-membered heteroaryl contains one nitrogen atom and is optionally substituted by one or more $R^{4a}$. In another aspect of the foregoing embodiment, $R^4$ is pyridinyl optionally substituted by one or more $R^{4a}$. In another aspect of the foregoing embodiment, $R^4$ is 6-membered heteroaryl, wherein the 6-membered heteroaryl contains two nitrogen atoms (e.g., $R^4$ is pyrimidinyl or pyrazinyl) and is optionally substituted by one or more $R^{4a}$. In another aspect of the foregoing embodiment, $R^4$ is pyrazolyl, imidazolyl, thiazolyl, pyridinyl, pyrimidinyl, or pyrazinyl, each of which is substituted by 1-4 $R^{4a}$ groups, wherein the $R^{4a}$ groups are independently selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(═O)—$NH_2$.

Also provided in another embodiment is a compound of formula (A), or a pharmaceutically acceptable salt thereof, wherein $R^4$ is 6-membered heterocyclyl containing at least one nitrogen atom, wherein the 6-membered heterocyclyl is optionally fused to a phenyl group and wherein the 6-membered heterocyclyl is optionally substituted by one or more $R^{4a}$ or oxo. In another aspect of the foregoing embodiment, $R^4$ is 6-membered heterocyclyl, wherein the 6-membered heterocyclyl contains one nitrogen atom and is optionally substituted by one or more $R^{4a}$ or oxo. In another aspect of the foregoing embodiment, $R^4$ is 6-membered heterocyclyl, wherein the 6-membered heterocyclyl contains two nitrogen atoms and is optionally substituted by one or more $R^{4a}$ or oxo. In another aspect of the foregoing embodiment, $R^4$ is 6-membered heterocyclyl optionally fused to a phenyl group, wherein the 6-membered heterocyclyl contains one nitrogen atom, is substituted by one oxo group, and is optionally substituted by one or more $R^{4a}$. In another aspect of the foregoing embodiment, $R^4$ is substituted by 1-4 $R^{4a}$ or oxo groups, wherein the $R^{4a}$ groups are independently selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(═O)—$NH_2$. In another aspect of the foregoing embodiment, $R^4$ is

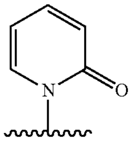 [SMILES: *n1ccccc1=O]

optionally fused to a phenyl group and optionally substituted by one or more $R^{4a}$. In another aspect of the foregoing embodiment, $R^4$ is

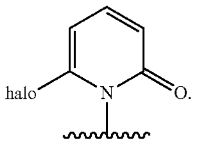

In another aspect of the foregoing embodiment, $R^4$ is

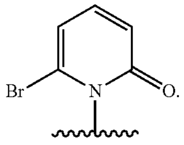

In another aspect of the foregoing embodiment, $R^4$ is

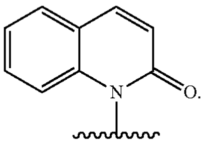 [SMILES: *n1c(=O)ccc2ccccc21]

Also provided in another embodiment is a compound of formula (I), or a pharmaceutically acceptable salt thereof, wherein $R^4$ is 5-to-6-membered heteroaryl containing at least one nitrogen atom, wherein the 5-to-6-membered heteroaryl is optionally fused to a phenyl group and wherein the 5-to-6-membered heteroaryl is optionally substituted by one or more $R^{4a}$. In another aspect of the foregoing embodiment, $R^4$ is 6-membered heteroaryl (e.g., pyrimidinyl) fused to phenyl. In another aspect of the foregoing embodiment, $R^4$ is 5-to-6-membered heteroaryl, wherein the 5-to-6-membered heteroaryl contains at least one nitrogen atom and is optionally substituted by one or more $R^{4a}$. In another aspect of the foregoing embodiment, $R^4$ is 5-membered heteroaryl, wherein the 5-membered heteroaryl contains two nitrogen atoms (e.g., $R^4$ is pyrazolyl, imidazolyl, or thiazolyl) and is optionally substituted by one or more $R^{4a}$. In another aspect of the foregoing embodiment, $R^4$ is 6-membered heteroaryl, wherein the 6-membered heteroaryl contains one nitrogen atom and is optionally substituted by one or more $R^{4a}$. In another aspect of the foregoing embodiment, $R^4$ is pyridinyl optionally substituted by one or more $R^{4a}$. In another aspect of the foregoing embodiment, $R^4$ is 6-membered heteroaryl, wherein the 6-membered heteroaryl contains two nitrogen atoms (e.g., $R^4$ is pyrimidinyl or pyrazinyl) and is optionally substituted by one or more $R^{4a}$. In another aspect of the foregoing embodiment, $R^4$ is pyrazolyl, imidazolyl, thiazolyl, pyridinyl, pyrimidinyl, or pyrazinyl, each of which is unsubstituted. In another aspect of the foregoing embodiment, $R^4$ is pyrazolyl, imidazolyl, thiazolyl, pyridinyl, pyrimidinyl, or pyrazinyl, each of which is substituted by 1-4 $R^{4a}$ groups, wherein the $R^{4a}$ groups are independently selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), and —O—($C_1$-$C_6$ haloalkyl). In another aspect of the foregoing embodiment, $R^4$ is pyrazolyl, imidazolyl, thiazolyl, pyridinyl, pyrimidinyl, or pyrazinyl, each of which is substituted by 1-4 $R^{4a}$ groups, wherein the $R^{4a}$ groups are independently selected from the group consisting of halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), and —O—($C_1$-$C_3$ haloalkyl). In another aspect of the foregoing embodiment, $R^4$ is pyrazolyl, imidazolyl, thiazolyl, pyridinyl, pyrimidinyl, or pyrazinyl, each of which is substituted by 1-4 $R^{4a}$ groups, wherein the $R^{4a}$ groups are independently selected from the group consisting of F, Cl, CN, —$CH_3$, —$CF_3$, —$CHF_2$, —$CH_2F$, —$CH_2$—O—$CH_3$, cyclopropyl, —O—$CH_3$, and —O—$CHF_2$. In one aspect of the foregoing embodiment, $R^4$ is substituted by 1-4 $R^{4a}$ groups, wherein at least one $R^{4a}$ group is F or Cl. In one aspect of the foregoing embodiment, $R^4$ is substituted by 1-4 $R^{4a}$ groups, wherein at least one $R^{4a}$ group is CN. In one aspect of the foregoing embodiment, $R^4$ is substituted by 1-4 $R^{4a}$ groups, wherein at least one $R^{4a}$ group is $C_1$-$C_3$ alkyl. In one aspect of the foregoing embodiment, $R^4$ is substituted by 1-4 $R^{4a}$ groups, wherein at least one $R^{4a}$ group is $C_1$-$C_3$ haloalkyl. In one aspect of the foregoing embodiment, $R^4$ is substituted by 1-4 $R^{4a}$ groups, wherein at least one $R^{4a}$ group is —($C_1$-$C_3$ alkylene)-O—($C_1$-$C_3$ alkyl). In one aspect of the foregoing embodiment, $R^4$ is substituted by 1-4 $R^{4a}$ groups, wherein at least one $R^{4a}$ group is cyclopropyl. In one aspect of the foregoing embodiment, $R^4$ is substituted by 1-4 $R^{4a}$ groups, wherein at least one $R^{4a}$ group is —O—($C_1$-$C_3$ alkyl). In one aspect of the foregoing embodiment, $R^4$ is substituted by 1-4 $R^{4a}$ groups, wherein at least one $R^{4a}$ group is —O—($C_1$-$C_3$ haloalkyl). In one aspect of the foregoing embodiment, $R^4$ is substituted by 2-4 $R^{4a}$ groups, wherein at least one $R^{4a}$ group is F, and wherein at least one $R^{4a}$ group is Cl. In one aspect of the foregoing embodiment, $R^4$ is substituted by 2-4 $R^{4a}$ groups, wherein at least one $R^{4a}$ group is F, and wherein at least one $R^{4a}$ group is $C_1$-$C_3$ alkyl. In one aspect of the foregoing embodiment, $R^4$ is substituted by 2-4 $R^{4a}$ groups, wherein at least one $R^{4a}$ group is Cl, and wherein at least one $R^{4a}$ group is $C_1$-$C_3$ alkyl. In one aspect of the foregoing embodiment, $R^4$ is substituted by 2-4 $R^{4a}$ groups, wherein at least one $R^{4a}$ group is Cl, and wherein at least one $R^{4a}$ group is —O—($C_1$-$C_3$ alkyl). In one aspect of the foregoing embodiment, $R^4$ is substituted by 2-4 $R^{4a}$ groups, wherein at least two $R^{4a}$ groups are Cl.

Also provided in another embodiment is a compound of formula (A), or a pharmaceutically acceptable salt thereof, wherein $R^4$ is pyridinyl substituted by 1-4 $R^{4a}$ groups, wherein the $R^{4a}$ groups are selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(═O)—$NH_2$.

Also provided in another embodiment is a compound of formula (I), or a pharmaceutically acceptable salt thereof, wherein $R^4$ is pyridinyl substituted by 1-4 $R^{4a}$ groups, wherein the $R^{4a}$ groups are selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), —O—($C_1$-$C_6$ haloalkyl). In one aspect of the foregoing embodiment, $R^4$ is pyridinyl substituted by 1-4 $R^{4a}$ groups, wherein the $R^{4a}$ groups are independently selected from the group consisting of halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl). In one aspect of the foregoing embodiment, $R^4$ is pyridinyl substituted by 1-4 $R^{4a}$ groups, wherein the $R^{4a}$ groups are independently selected from the group consisting of F, Cl, CN, —$CH_3$, —$CF_3$, —$CHF_2$, —$CH_2F$, —$CH_2$—O—$CH_3$, cyclopropyl, —O—$CH_3$, and —O—$CHF_2$. In one aspect of the foregoing embodiment, $R^4$ is pyridinyl substituted by 2-4 $R^{4a}$ groups, wherein the $R^{4a}$ groups are independently selected from the group consisting of halo (e.g., F or Cl), $C_1$-$C_3$ alkyl (e.g., —$CH_3$), and —O—($C_1$-$C_3$ alkyl) (e.g., —O—$CH_3$). In one aspect of the foregoing embodiment, $R^4$ is pyridinyl substituted by 2-4 $R^{4a}$ groups, wherein at least two of the $R^{4a}$ groups are halo (e.g., fluoro or chloro). In one aspect of the foregoing embodiment, $R^4$ is pyridinyl substituted by 2-4 $R^{4a}$ groups, wherein at least one of the $R^{4a}$ groups is halo (e.g., fluoro or chloro), and at least one of the $R^{4a}$ groups is $C_1$-$C_3$ alkyl (e.g., —$CH_3$). In one aspect of the foregoing embodiment, $R^4$ is pyridinyl substituted by 2-4 $R^{4a}$ groups, wherein at least one of the $R^{4a}$ groups is halo (e.g., fluoro or chloro), and at least one of the $R^{4a}$ groups is —O—($C_1$-$C_3$ alkyl) (e.g., —O—$CH_3$).

Also provided in another embodiment is a compound of formula (I), or a pharmaceutically acceptable salt thereof, wherein $R^4$ is a 5-membered heteroaryl, wherein the 5-membered heteroaryl contains at least one nitrogen atom and is optionally substituted by one or more $R^{4a}$. In one aspect of the foregoing embodiment, $R^4$ is a 5-membered heteroaryl containing at least one nitrogen atom and at least one additional heteroatom selected from oxygen and sulfur (e.g., $R^4$ is thiazolyl) and is optionally substituted by one or more $R^{4a}$. In one aspect of the foregoing embodiment, $R^4$ is a 5-membered heteroaryl, wherein the 5-membered heteroaryl contains one nitrogen atom and is optionally substituted by one or more $R^{4a}$. In one aspect of the foregoing embodiment, $R^4$ is a 5-membered heteroaryl, wherein the 5-membered heteroaryl contains two nitrogen atoms (e.g., $R^4$ is pyrazolyl or imidazolyl) and is optionally substituted by one or more $R^{4a}$. In one aspect of the foregoing embodiment, $R^4$ is unsubstituted 5-membered heteroaryl (e.g., pyrazolyl or imidazolyl). In one aspect of the foregoing embodiment, $R^4$ is a 5-membered heteroaryl (e.g., pyrazolyl or imidazolyl) substituted by 1-3 $R^{4a}$ groups, wherein the $R^{4a}$ groups are independently selected from the group consisting of halo, CN, $C_1$-$C_6$ alkyl, and $C_1$-$C_6$ haloalkyl. In one aspect of the foregoing embodiment, $R^4$ is a 5-membered heteroaryl (e.g., pyrazolyl or imidazolyl) substituted 1-3 $R^{4a}$ groups, wherein the $R^{4a}$ groups are independently selected from the group consisting of F, Cl, CN, $C_1$-$C_3$ alkyl (e.g., —$CH_3$), and $C_1$-$C_3$ haloalkyl (e.g., —$CF_3$). In one aspect of the foregoing embodiment, $R^4$ is a 5-membered heteroaryl (e.g., pyrazolyl or imidazolyl) substituted by 2-3 $R^{4a}$ groups, wherein the $R^{4a}$ groups are independently selected from the group consisting of halo (e.g., F or Cl), CN, $C_1$-$C_3$ alkyl (e.g., —$CH_3$), and $C_1$-$C_3$ haloalkyl (e.g., —$CF_3$). In one aspect of the foregoing embodiment, $R^4$ is a 5-membered heteroaryl (e.g., pyrazolyl or imidazolyl) substituted by 2-3 $R^{4a}$ groups, wherein at least two of the $R^{4a}$ groups are halo (e.g., chloro). In one aspect of the foregoing embodiment, $R^4$ is a 5-membered heteroaryl (e.g., pyrazolyl or imidazolyl) substituted by 2-3 $R^{4a}$ groups, wherein at least one of the $R^{4a}$ groups is halo (e.g., chloro) and at least one of the $R^{4a}$ groups is $C_1$-$C_3$ alkyl (e.g., —$CH_3$). In one aspect of the foregoing embodiment, $R^4$ is a 5-membered heteroaryl (e.g., pyrazolyl or imidazolyl) substituted by 2-3 $R^{4a}$ groups, wherein at least one of the $R^{4a}$ groups is CN and at least one of the $R^{4a}$ groups is $C_1$-$C_3$ alkyl (e.g., —$CH_3$). In one aspect of the foregoing embodiment, $R^4$ is a 5-membered heteroaryl (e.g., pyrazolyl or imidazolyl) substituted by 2-3 $R^{4a}$ groups, wherein at least one of the $R^{4a}$ groups is $C_1$-$C_3$ alkyl (e.g., —$CH_3$) and at least one of the $R^{4a}$ groups is $C_1$-$C_3$ haloalkyl (e.g., —$CF_3$).

Also provided in another embodiment is a compound of formula (I), or a pharmaceutically acceptable salt thereof, wherein $R^4$ is a 6-membered heteroaryl, wherein the 6-membered heteroaryl contains two nitrogen atoms (e.g., $R^4$ is pyrimidinyl or pyrazinyl) and is optionally substituted by one or more $R^{4a}$. In one aspect of the foregoing embodiment, $R^4$ is unsubstituted 6-membered heteroaryl containing two nitrogen atoms (e.g., pyrimidinyl or pyrazinyl). In one aspect of the foregoing embodiment, $R^4$ is a 6-membered heteroaryl containing two nitrogen atoms (e.g., pyrimidinyl or pyrazinyl) substituted by 1-3 $R^{4a}$ groups, wherein the $R^{4a}$ groups are independently selected from the group consisting of halo, $C_1$-$C_6$ alkyl, $C_1$-$C_6$ haloalkyl, and —O—($C_1$-$C_6$ alkyl). In one aspect of the foregoing embodiment, $R^4$ is a 6-membered heteroaryl containing two nitrogen atoms (e.g., pyrimidinyl or pyrazinyl) substituted by 1-3 $R^{4a}$ groups, wherein the $R^{4a}$ groups are independently selected from the group consisting of halo, Ci-C alkyl, $C_1$-$C_3$ haloalkyl, and —O—($C_1$-$C_3$ alkyl). In one aspect of the foregoing embodiment, $R^4$ is a 6-membered heteroaryl containing two nitrogen atoms (e.g., pyrimidinyl or pyrazinyl) substituted by 1-3 $R^{4a}$ groups, wherein the $R^{4a}$ groups are independently selected from the group consisting of Cl, $CH_3$, —$CF_3$, —$CHF_2$, and —O—$CH_3$. In one aspect of the foregoing embodiment, $R^4$ is a 6-membered heteroaryl containing two nitrogen atoms (e.g., pyrimidinyl or pyrazinyl) substituted by 2-3 $R^{4a}$ groups, wherein the $R^{4a}$ groups are independently selected from the group consisting of halo (e.g., Cl), $C_1$-$C_6$ alkyl (e.g., —$CH_3$), and —O—($C_1$-$C_6$ alkyl) (e.g., —O—$CH_3$). In one aspect of the foregoing embodiment, $R^4$ is a 6-membered heteroaryl containing two nitrogen atoms (e.g., pyrimidinyl or pyrazinyl) substituted by 2-3 $R^{4a}$ groups, wherein at least one of the $R^{4a}$ groups is halo (e.g., chloro) and at least one of the $R^{4a}$ groups is $C_1$-$C_3$ alkyl (e.g., —$CH_3$). In one aspect of the foregoing embodiment, $R^4$ is a 6-membered heteroaryl containing two nitrogen atoms (e.g., pyrimidinyl or pyrazinyl) substituted by 2-3 $R^{4a}$ groups, wherein at least one of the $R^{4a}$ groups is halo (e.g., chloro) and at least one of the $R^{4a}$ groups is —O—($C_1$-$C_3$ alkyl) (e.g., —O—$CH_3$). In one aspect of the foregoing embodiment, $R^4$ is a 6-membered heteroaryl containing two nitrogen atoms (e.g., pyrimidinyl or pyrazinyl) substituted by 2-3 $R^{4a}$ groups, wherein at least two of the $R^{4a}$ groups are $C_1$-$C_3$ alkyl (e.g., —$CH_3$). In one aspect of the foregoing embodiment, $R^4$ is a 6-membered heteroaryl containing two nitrogen atoms (e.g., pyrimidinyl or pyrazinyl) substituted by 2-3 $R^{4a}$ groups, wherein at least one of the $R^{4a}$ groups is $C_1$-$C_3$ alkyl (e.g., —$CH_3$) and at least one of the $R^{4a}$ groups is —O—($C_1$-$C_3$ alkyl) (e.g., —O—$CH_3$).

Also provided in another embodiment is a compound of formula (I), or a pharmaceutically acceptable salt thereof, wherein $R^4$ is a 6-membered heterocyclyl, wherein the 6-membered heterocyclyl contains at least one nitrogen atom, is optionally fused to a phenyl group, and is optionally substituted by one or more groups selected from the group consisting of $R^{4a}$ (e.g., Cl) and oxo. In one aspect of the foregoing embodiment, $R^4$ is a 6-membered heterocyclyl containing one nitrogen atom, wherein the 6-membered heterocyclyl is fused to a phenyl group and is substituted by oxo. In one aspect of the foregoing embodiment, $R^4$ is a 6-membered heterocyclyl, wherein the 6-membered heterocyclyl contains one nitrogen atom and is optionally substituted by one or more groups selected from the group consisting of $R^{4a}$ (e.g., Cl) and oxo. In one aspect of the foregoing embodiment, $R^4$ is 6-membered heterocyclyl, wherein the 6-membered heterocyclyl contains two nitrogen atoms and is optionally substituted by one or more groups selected from the group consisting of $R^{4a}$ (e.g., Cl) and oxo. In one aspect of the foregoing embodiment, $R^4$ is substituted by Cl and oxo. In one aspect of the foregoing embodiment, $R^4$ is a 6-membered heterocyclyl, wherein the 6-membered heterocyclyl contains one nitrogen atom and is substituted by Cl and oxo. In one aspect of the foregoing embodiment, $R^4$ is a 6-membered heterocyclyl, wherein the 6-membered heterocyclyl contains two nitrogen atoms and is substituted by Cl and oxo.

Also provided in another embodiment is a compound of formula (A), or a pharmaceutically acceptable salt thereof, wherein $R^4$ is $C_1$-$C_6$ haloalkyl. In one aspect of the foregoing embodiment, $R^4$ is $C_1$-$C_6$ fluoroalkyl. In one aspect of the foregoing, $R^4$ is Cl haloalkyl. In one aspect of the foregoing, $R^4$ is $C_1$-$C_6$ fluoroalkyl. In one aspect of the foregoing embodiment, $R^4$ is

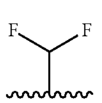 or 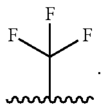.

Also provided in another embodiment is a compound of formula (A), or a pharmaceutically acceptable salt thereof, wherein $R^2$, $R^3$, and $R^4$ are taken together to form a 5-membered heteroaryl containing two nitrogen atoms and substituted with phenyl, wherein the phenyl group is optionally substituted by one or more $R^{4a}$. In one aspect of the foregoing embodiment, $R^2$, $R^3$, and $R^4$ are taken together to form

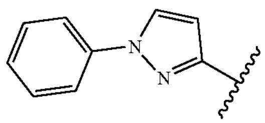,

-continued

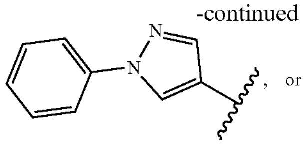 , or 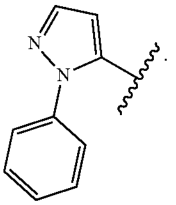 .

Also provided in another embodiment is a compound of formula (A), or a pharmaceutically acceptable salt thereof, wherein each $R^{4a}$ is independently selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —OH, —O—($C_1$-$C_6$ alkyl), —O—($C_1$-$C_6$ haloalkyl), —$S(O)_2$($C_1$-$C_6$ alkyl), or —C(═O)—$NH_2$.

Also provided in another embodiment is a compound of formula (I), or a pharmaceutically acceptable salt thereof, wherein each $R^{4a}$ is independently selected from the group consisting of halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), —O—($C_1$-$C_6$ haloalkyl), and —$S(O)_2$($C_1$-$C_6$ alkyl). In one aspect of the foregoing embodiment, each $R^{4a}$ is independently selected from the group consisting of halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl), and —$S(O)_2$($C_1$-$C_3$ alkyl). In one aspect of the foregoing embodiment, each $R^{4a}$ is independently selected from the group consisting of F, Cl, CN, —$CH_3$, —$CH_2F$, —$CHF_2$, —$CF_3$, —$CH_2$—O—$CH_3$, cyclopropyl, —$OCH_3$, —$OCHF_2$, and —$S(O)_2CH_3$.

In some embodiments, $R^{4a}$ is halo. In some embodiments, $R^{4a}$ is F or Cl. In some embodiments, $R^{4a}$ is F. In some embodiments, $R^{4a}$ is Cl.

In some embodiments, $R^{4a}$ is CN.

In some embodiments, $R^{4a}$ is $C_1$-$C_6$ alkyl. In some embodiments, $R^{4a}$ is $C_1$-$C_3$ alkyl. In some embodiments, $R^{4a}$ is methyl, ethyl, n-propyl, or isopropyl. In some embodiments, $R^{4a}$ is methyl, ethyl, or isopropyl. In some embodiments, $R^{4a}$ is —$CH_3$.

In some embodiments, $R^{4a}$ is $C_1$-$C_6$ haloalkyl. In some embodiments, $R^{4a}$ is $C_1$-$C_3$ haloalkyl. In some embodiments, the halogen atoms are all fluoro atoms. In some embodiments, the halogen atoms are all chloro atoms. In some embodiments, the halogen atoms are a combination of fluoro and chloro atoms. In some embodiments, $R^{4a}$ is —$CF_3$, —$CCl_3$, —$CF_2Cl$, —$CFCl_2$, —$CHF_2$, —$CH_2F$, —$CHCl_2$, —$CH_2Cl$, or —CHFCl. In some embodiments, $R^{4a}$ is —$CF_3$, —$CHF_2$, —$CH_2F$. In some embodiments, $R^{4a}$ is —$CF_3$. In some embodiments, $R^{4a}$ is —$CHF_2$. In some embodiments, $R^{4a}$ is —$CH_2F$.

In some embodiments, $R^{4a}$ is —($C_1$-$C_6$ alkylene)-O—($C_1$-$C_6$ alkyl). In some embodiments, $R^{4a}$ is —($C_1$-$C_3$ alkylene)-O—($C_1$-$C_3$ alkyl). In some embodiments, $R^{4a}$ is —$CH_2$—O—$CH_3$, —$CH_2$—O—$CH_2CH_3$, —$CH_2$—O—$CH_2CH_2CH_3$, or —$CH_2O$—$CH(CH_3)_2$. In some embodiments, $R^{4a}$ is —$CH_2CH_2$—O—$CH_3$, —$CH_2CH_2$—O—$CH_2CH_3$, —$CH_2CH_2$—O—$CH_2CH_2CH_3$, or —$CH_2CH_2O$—$CH(CH_3)_2$. In some embodiments, $R^{4a}$ is —$CH_2CH_2CH_2$—O—$CH_3$, —$CH_2CH_2CH_2$—O—$CH_2CH_3$, —$CH_2CH_2CH_2$—O—$CH_2CH_2CH_3$, or —$CH_2CH_2CH_2O$—$CH(CH_3)_2$. In some embodiments, $R^{4a}$ is —$CH_2$—O—$CH_3$.

In some embodiments, $R^{4a}$ is $C_3$-$C_6$ cycloalkyl. In some embodiments, $R^{4a}$ is cyclopropyl, cyclobutyl, cyclopentyl, or cyclohexyl. In some embodiments, $R^{4a}$ is cyclopropyl.

In some embodiments, $R^{4a}$ is —O—($C_1$-$C_6$ alkyl). In some embodiments, $R^{4a}$ is —O—($C_1$-$C_3$ alkyl). In some embodiments, $R^{4a}$ is —O—$CH_3$, —O—$CH_2CH_3$, —O—$CH_2CH_2CH_3$, or —O—$CH(CH_3)_2$. In some embodiments, $R^{4a}$ is —O—$CH_3$.

In some embodiments, $R^{4a}$ is —O—($C_1$-$C_6$ haloalkyl). In some embodiments, $R^{4a}$ is —O—($C_1$-$C_3$ haloalkyl). In some embodiments, the halogen atoms are all fluoro atoms. In some embodiments, the halogen atoms are all chloro atoms. In some embodiments, the halogen atoms are a combination of fluoro and chloro atoms. In some embodiments, $R^{4a}$ is —O—$CF_3$, —O—$CCl_3$, —O—$CF_2Cl$, —O—$CFCl_2$, —O—$CHF_2$, —O—$CH_2F$, —O—$CHCl_2$, —O—$CH_2Cl$, or —O—CHFCl. In some embodiments, $R^{4a}$ is —O—$CHF_2$.

In some embodiments, $R^{4a}$ is —$S(O)_2$($C_1$-$C_6$ alkyl). In some embodiments, $R^{4a}$ is —$S(O)_2$($C_1$-$C_4$ alkyl). In some embodiments, $R^{4a}$ is —$S(O)_2CH_3$.

In some embodiments $R^{4a}$ is —OH. In some embodiments $R^{4a}$ is —C(═O)—$NH_2$.

Also provided in another embodiment is a compound of formula (I), or a pharmaceutically acceptable salt thereof, wherein $R^{4a}$ and $R^2$ are taken together with the atoms to which they are attached to form a 6-membered heterocyclyl. In some embodiments, $R^{4a}$ and $R^2$ are taken together with the atoms to which they are attached to form a 6-membered heterocyclyl, wherein the heterocyclyl contains one oxygen atom. In some embodiments, $R^4$ is phenyl, $R^{4a}$ and $R^2$ are taken together with the atoms to which they are attached to form a 6-membered heterocyclyl, wherein the heterocyclyl contains one oxygen atom. In some embodiments, $R^2$, $R^3$, and $R^4$ are taken together with the carbon atom to which they are attached to form

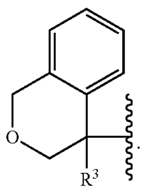

In some embodiments, $R^2$, $R^3$, and $R^4$ are taken together with the carbon atom to which they are attached to form

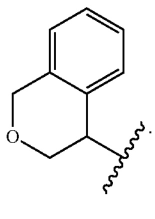

In some embodiments, $R^2$, $R^3$, and $R^4$ are taken together with the carbon atom to which they are attached to form

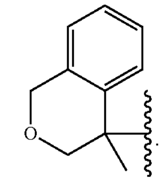 [SMILES: *C1(C)COCc2ccccc21]
Also provided is a compound of formula (I), or a pharmaceutically acceptable salt thereof, wherein $R^4$ is selected from the group consisting of:
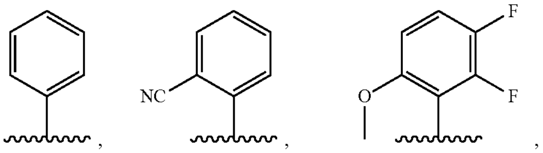
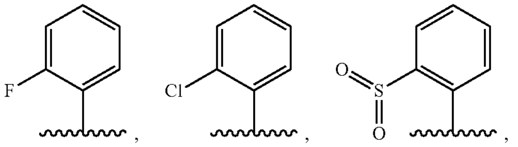
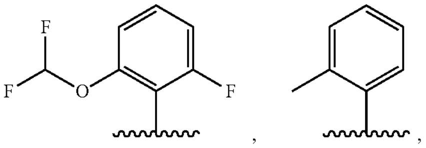
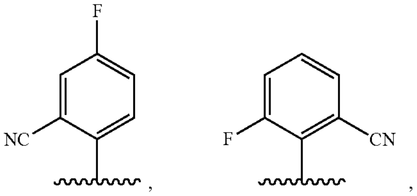
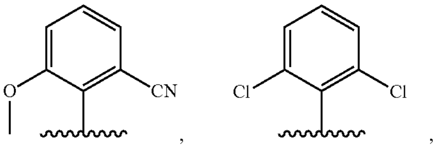
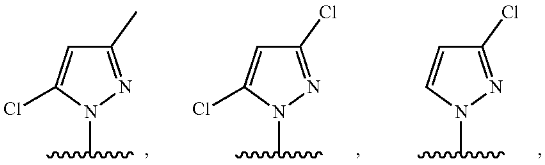
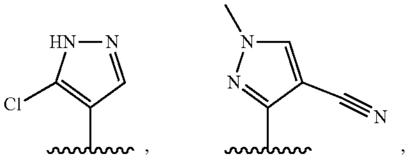
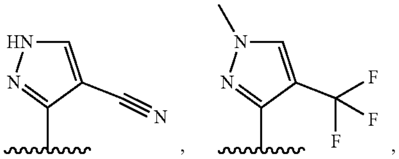
-continued
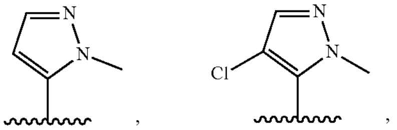
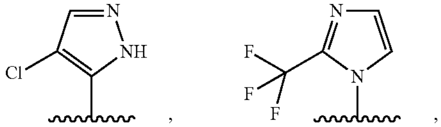
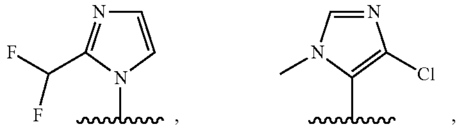
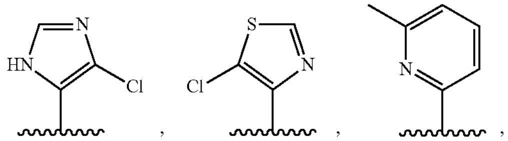
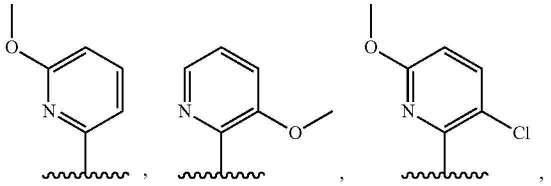
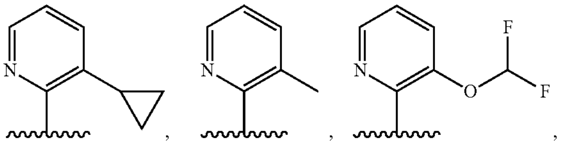
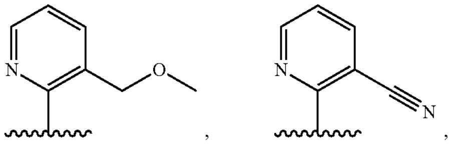
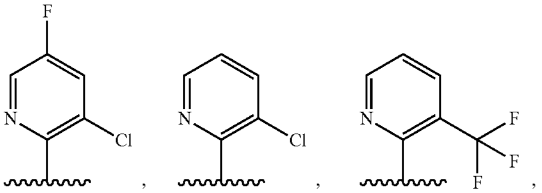
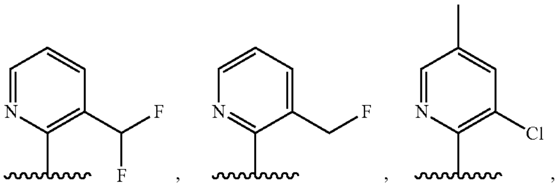
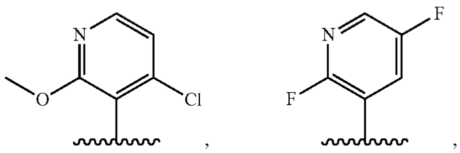
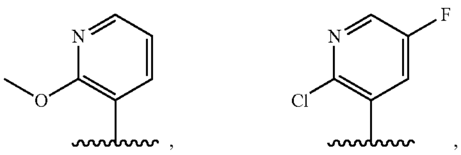

-continued
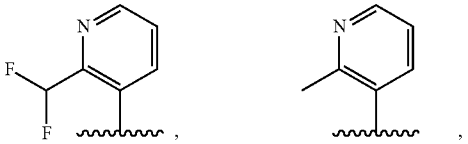
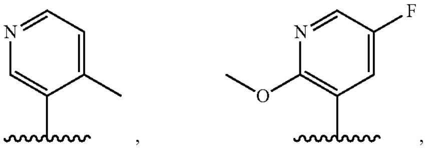
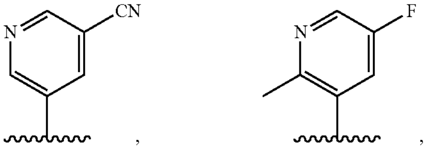
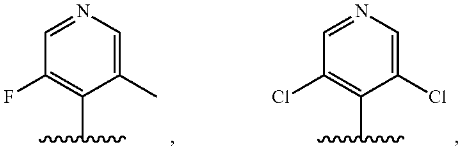
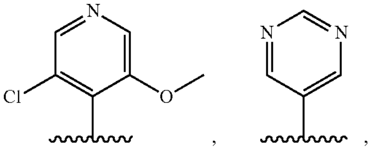
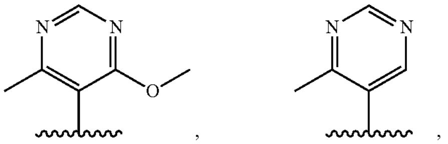
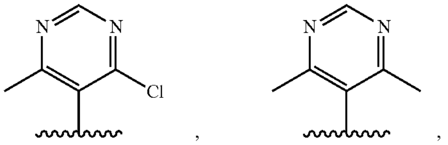
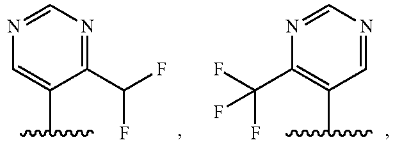
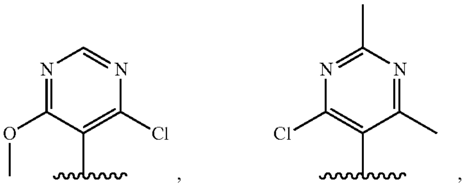
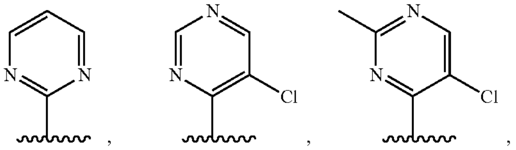
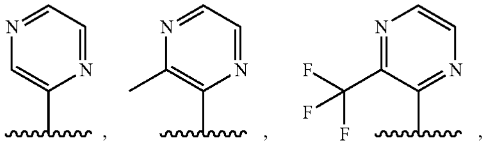
-continued
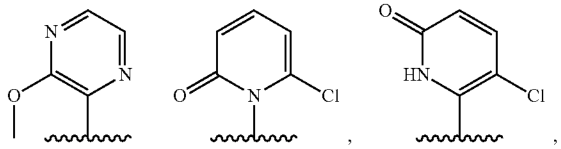
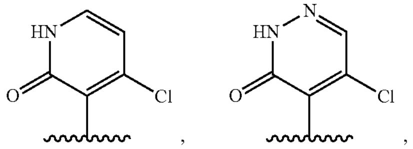
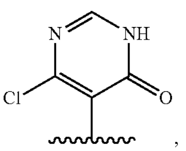
and
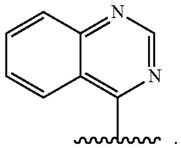
Also provided is a compound of formula (I), or a pharmaceutically acceptable salt thereof, wherein $R^4$ is selected from the group consisting of:
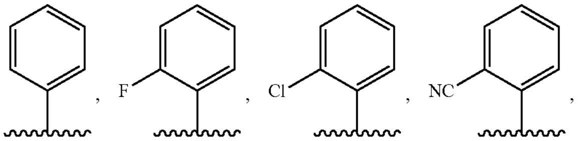
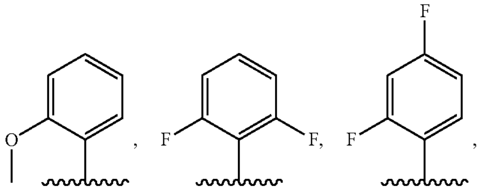
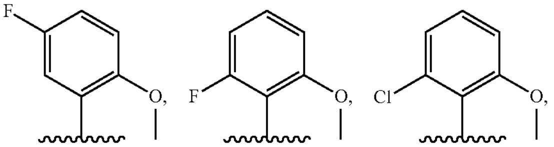
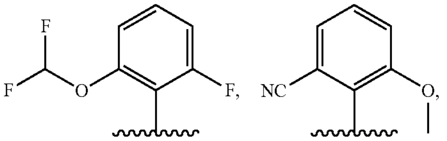
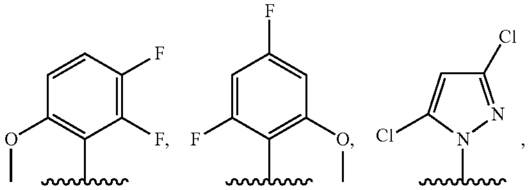
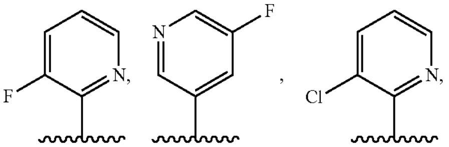
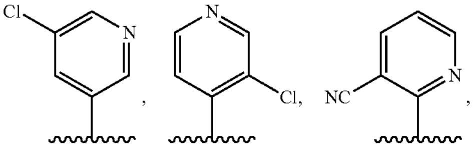

-continued

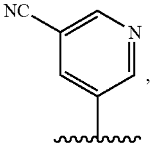, 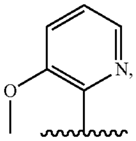 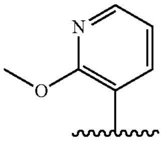,

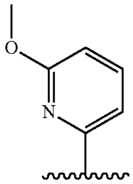, 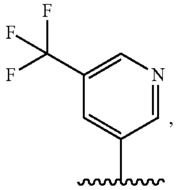, 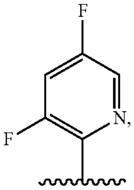

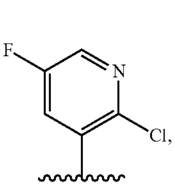 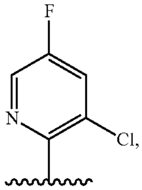 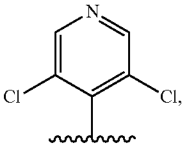

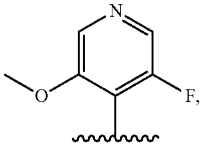 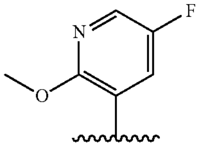,

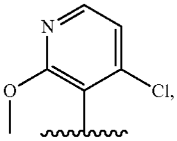 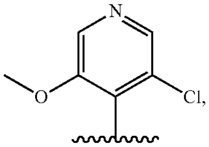 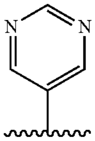

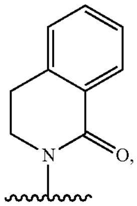 and 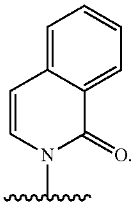

Also provided is a compound of formula (A), or a pharmaceutically acceptable salt thereof, wherein $R^4$ is selected from the group consisting of

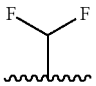 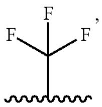 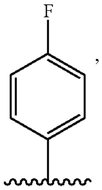, 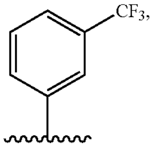

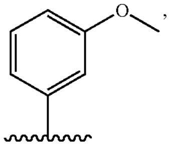, 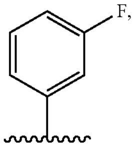 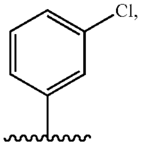

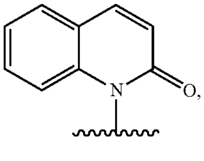 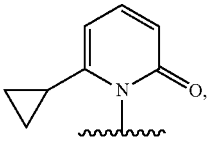

-continued

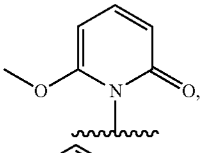 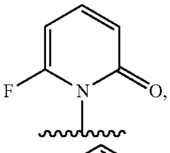

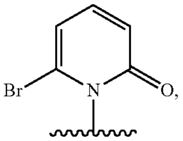 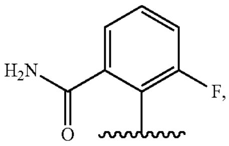

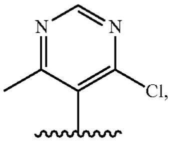 or 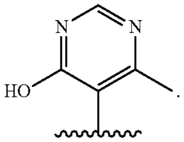

Also provided in another embodiment is a compound of formula (I), or a pharmaceutically acceptable salt thereof, wherein Q is H or $C_1$-$C_8$ alkyl. In one aspect of the foregoing embodiment, Q is H. In one aspect of the foregoing embodiment, Q is $C_1$-$C_6$ alkyl. In one aspect of the foregoing embodiment, Q is methyl, ethyl, n-propyl, or isopropyl, n-butyl, t-butyl, isobutyl, or sec-butyl. In one aspect of the foregoing embodiment, Q is methyl.

In one aspect, provided is a compound of formula (I) or a pharmaceutically acceptable salt thereof, wherein the compound has any one or more of the following features:

(I) $R^1$ is

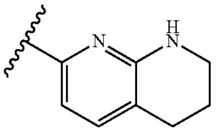 or 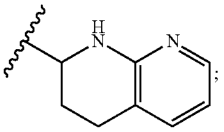;

(II) -$L^1$-O-$L^2$-Y-$L^3$- are taken together to form

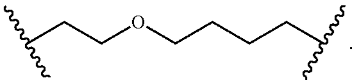 [SMILES: *CCCCOCC*].

(III) Q is H or $C_1$-$C_6$ alkyl (e.g., —$CH_3$ or —$CH_2CH_3$);

(IV) $R^2$ and $R^3$ are:

(i) both H;

(ii) both —$CH_3$; or (iii) taken together with the carbon atom to which they are attached to form a cyclopropyl; and (V) $R^4$ is:

(i) phenyl substituted by 0-5 $R^{4a}$ groups;

(ii) 5-membered heteroaryl containing at least one nitrogen atom (e.g., pyrazolyl or imidazolyl) and substituted by 0-4 $R^{4a}$ groups;

(iii) 6-membered heteroaryl containing at least one nitrogen atom (e.g., pyridinyl, pyrimidinyl or pyrazinyl) and substituted by 0-4 $R^{4a}$ groups; or (iv) 6-membered heterocyclyl containing at least one nitrogen atom (e.g.) and substituted by 0-4 groups selected from the group consisting of $R^{4a}$ and oxo.

In one aspect of this variation, (I), (II), (III), and (IV)(i) apply. In another variation, (I), (II), (III), and (IV)(ii) apply. In another variation, (I), (II), (III), and (IV)(iii) apply.

In the variations in the preceding paragraph, it is understood that each combination of variables is described. For example, it is understood that each variation of feature (IV) may be combined with each variation of feature (V) the same as if each and every variation of features (IV) and (V) were specifically and individually listed. Thus, it is understood that the following combinations are described: (IV)(i)+(V)(i); (IV)(i)+(V)(ii); (IV)(i)+(V)(iii); (IV)(i)+(V)(iv); (IV)(ii)+(V)(i); (IV)(ii)+(V)(ii); (IV)(ii)+(V)(iii); (IV)(ii)+(V)(iv); (IV)(iii)+(V)(i); (IV)(iii)+(V)(ii); (IV)(iii)+(V)(iii); and (IV)(iii)+(V)(iv).

In some embodiments, $R^1$ is

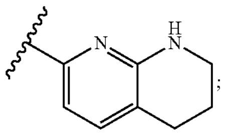 [SMILES: *c1ccc2c(n1)NCCC2]

$R^2$ and $R^3$ are independently H or methyl, or $R^2$ and $R^3$ are taken together with the carbon atom to which they are attached to form cyclopropyl; $R^4$ is phenyl, pyrazolyl, imidazolyl, thiazolyl, pyridinyl, 2-oxopyridinyl, pyridazinyl, pyrimidinyl, pyrazinyl, dihydropyridinyl, dihydropyrimidinyl, dihydropyridazinyl, or quinazolinyl; wherein the phenyl, pyrazolyl, imidazolyl, thiazolyl, pyridinyl, 2-oxopyridinyl, pyridazinyl, pyrimidinyl, pyrazinyl, or quinazolinyl are optionally substituted by one or more $R^{4a}$ groups; and wherein the dihydropyridinyl, dihydropyrimidinyl, or dihydropyridazinyl are optionally substituted by one or more groups selected from the group consisting of $R^{4a}$ and oxo; each $R^{4a}$ is independently halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl), or —$S(O)_2$($C_1$-$C_3$ alkyl); Q is H; and -$L^1$-O-$L^2$-Y-$L^3$- are taken together to form

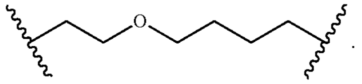 [SMILES: *CCCCOCC*]

In some embodiments, $R^1$ is

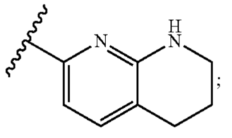 [SMILES: *c1ccc2c(n1)NCCC2]

$R^2$ and $R^3$ are taken together with the carbon atom to which they are attached to form cyclopropyl; $R^4$ is phenyl, pyrazolyl, imidazolyl, thiazolyl, pyridinyl, 2-oxopyridinyl, pyridazinyl, pyrimidinyl, pyrazinyl, dihydropyridinyl, dihydropyrimidinyl, dihydropyridazinyl, or quinazolinyl; wherein the phenyl, pyrazolyl, imidazolyl, thiazolyl, pyridinyl, 2-oxopyridinyl, pyridazinyl, pyrimidinyl, pyrazinyl, or quinazolinyl are optionally substituted by one or more $R^{4a}$ groups; and wherein the dihydropyridinyl, dihydropyrimidinyl, or dihydropyridazinyl are optionally substituted by one or more groups selected from the group consisting of $R^{4a}$ and oxo; each $R^{4a}$ is independently halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl), or —$S(O)_2$($C_1$-$C_3$ alkyl); Q is H; and -$L^1$-O-$L^2$-Y-$L^3$- are taken together to form

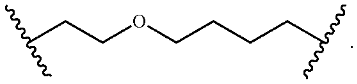 [SMILES: *CCCCOCC*]

In some embodiments, $R^1$ is

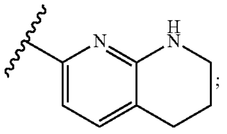 [SMILES: *c1ccc2c(n1)NCCC2]

$R^2$ and $R^3$ are taken together with the carbon atom to which they are attached to form cyclopropyl; $R^4$ is pyrazolyl, imidazolyl, thiazolyl, pyridinyl, 2-oxopyridinyl, pyridazinyl, pyrimidinyl, pyrazinyl, dihydropyridinyl, dihydropyrimidinyl, dihydropyridazinyl, or quinazolinyl; wherein the pyrazolyl, imidazolyl, thiazolyl, pyridinyl, 2-oxopyridinyl, pyridazinyl, pyrimidinyl, pyrazinyl, or quinazolinyl are optionally substituted by one or more $R^{4a}$ groups; and wherein the dihydropyridinyl, dihydropyrimidinyl, or dihydropyridazinyl are optionally substituted by one or more groups selected from the group consisting of $R^{4a}$ and oxo; each $R^{4a}$ is independently halo, CN, $C_1$-$C_3$ alkyl, $C_1$-$C_3$ haloalkyl, —($C_1$-$C_3$ alkylene)-O—($C_1$-$C_3$ alkyl), $C_3$-$C_6$ cycloalkyl, —O—($C_1$-$C_3$ alkyl), —O—($C_1$-$C_3$ haloalkyl), or —$S(O)_2$($C_1$-$C_3$ alkyl); Q is H; and -$L^1$-O-$L^2$-Y-$L^3$- are taken together to form

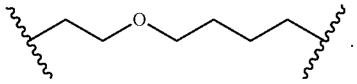 [SMILES: *CCCCOCC*]

When a moiety is contemplated, it is understood that the moiety can be attached to the rest of the structure at any available position. For example, 3-chloro-6-methoxypyridinyl may be attached to the rest of the structure at the 2-, 4-, or 5-position (such as in 3-chloro-6-methoxypyridin-2-yl, 3-chloro-6-methoxypyridin-4-yl, or 3-chloro-6-methoxypyridin-5-yl, respectively). The $R^4$ groups described herein are shown as attached at specific positions (e.g., pyridin-2-yl or pyrimidin-5-yl) but they can also be attached via any other available valence (e.g., pyridin-3-yl or pyrimidin-4-yl respectively).

Any embodiments provided herein of a compound of formula (I), or stereoisomer or tautomer thereof, or a pharmaceutically acceptable salt of any of the foregoing, apply where applicable to any other formula detailed herein, the same as if each and every embodiment were specifically and individually listed. In particular, any embodiments provided herein of a compound of formula (I), or a stereoisomer or tautomer thereof, or a pharmaceutically acceptable salt of any of the foregoing, apply where applicable to compounds of formula (A), or a stereoisomer or tautomer thereof, or a pharmaceutically acceptable salt of any of the foregoing, the same as if each and every embodiment were specifically and individually listed for formula (A). Thus, it is understood and described that each embodiment provided herein of a compound of formula (I), or a stereoisomer or tautomer thereof, or a pharmaceutically acceptable salt of any of the foregoing, such as embodiments related to $R^1$, $R^2$, $R^3$, $R^4$, $R^5$, $R^6$, $R^7$, $R^8$, $R^9$, $R^{10}$, $R^{11}$, $R^{12}$, Q, $L^1$, $L^2$, $L^3$, Y, $R^{1a}$, $R^{1b}$, $R^{1c}$, $R^{1d}$, $R^{2a}$, $R^{4a}$, $R^{5a}$, $L^{1a}$, $L^{2a}$, $L^{3a}$, $R^A$, $R^{Aa}$, $R^{Ab}$, or a stereoisomer or tautomer thereof, or a pharmaceutically acceptable salt of any of the foregoing, the same as if each and every embodiment were specifically and individually listed. It also understood and described that all such embodiments may be used in any of the pharmaceutical compositions, methods, kits, uses, or other aspects detailed herein.

Representative compounds are listed in Table 1.

TABLE 1

| Compound # | Structure |
|---|---|
| 1 | 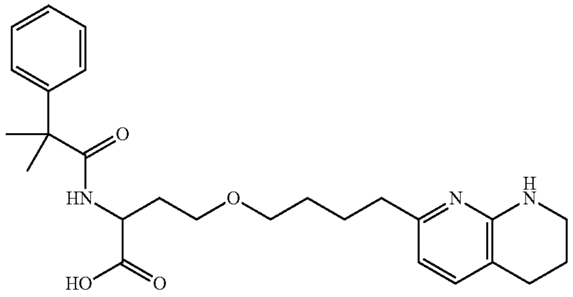 [SMILES: CC(C)(C(=O)NC(CCOCCCCc1ccc2c(n1)NCCC2)C(=O)O)c1ccccc1] |
| 2 | 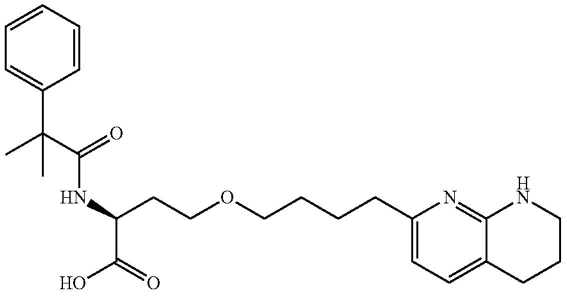 [SMILES: CC(C)(C(=O)N[C@@H](CCOCCCCc1ccc2c(n1)NCCC2)C(=O)O)c1ccccc1] |
| 3 | 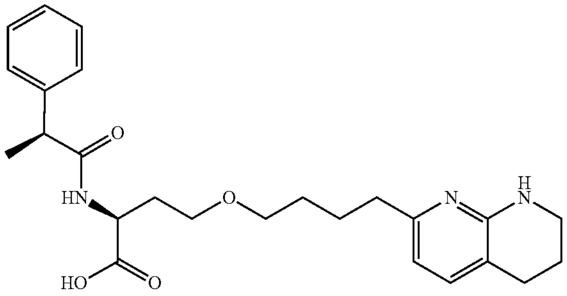 [SMILES: C[C@H](C(=O)N[C@@H](CCOCCCCc1ccc2c(n1)NCCC2)C(=O)O)c1ccccc1] |
| 4 | 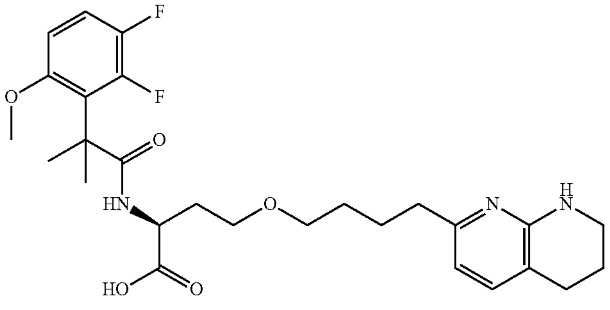 [SMILES: COc1ccc(F)c(F)c1C(C)(C)C(=O)N[C@@H](CCOCCCCc1ccc2c(n1)NCCC2)C(=O)O] |

TABLE 1-continued
| Compound # | Structure |
|---|---|
| 5 | 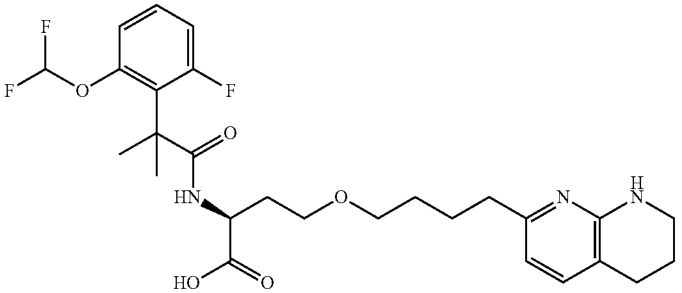 [SMILES: CC(C)(C(=O)N[C@@H](CCOCCCCc1ccc2c(n1)NCCC2)C(=O)O)c1c(F)cccc1OC(F)F] |
| 6 | 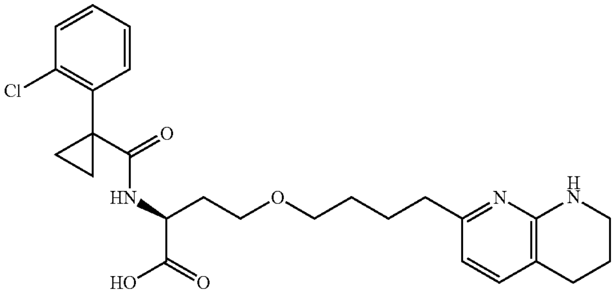 [SMILES: O=C(O)[C@H](CCOCCCCc1ccc2c(n1)NCCC2)NC(=O)C1(c2ccccc2Cl)CC1] |
| 7 | 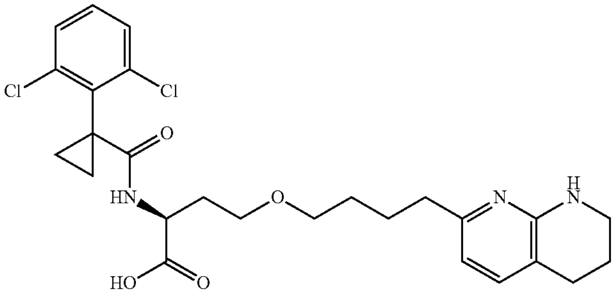 [SMILES: O=C(O)[C@H](CCOCCCCc1ccc2c(n1)NCCC2)NC(=O)C1(c2c(Cl)cccc2Cl)CC1] |
| 8 | 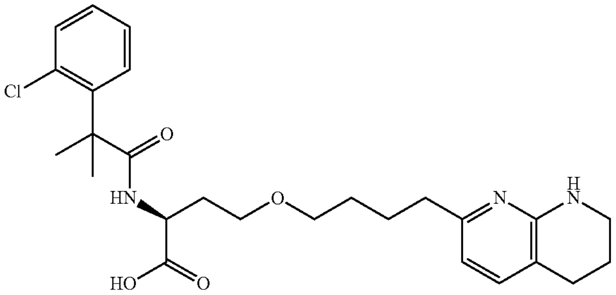 [SMILES: CC(C)(C(=O)N[C@@H](CCOCCCCc1ccc2c(n1)NCCC2)C(=O)O)c1ccccc1Cl] |
| 9 | 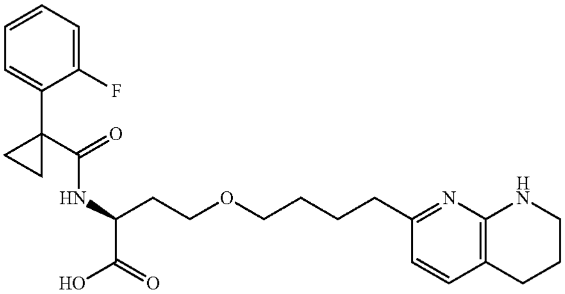 [SMILES: O=C(O)[C@H](CCOCCCCc1ccc2c(n1)NCCC2)NC(=O)C1(c2ccccc2F)CC1] |

TABLE 1-continued
| Compound # | Structure |
| --- | --- |
| 10 | 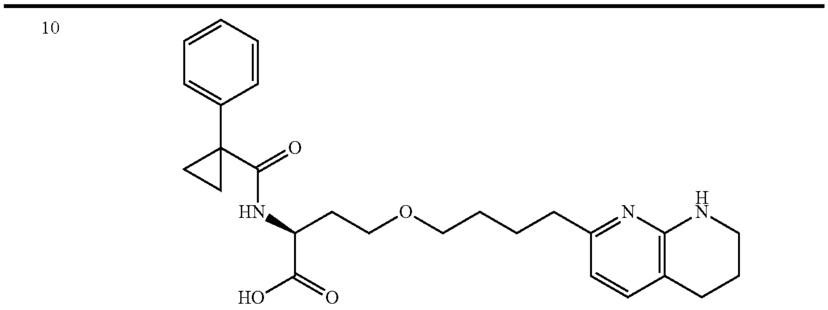 |
| 11 | 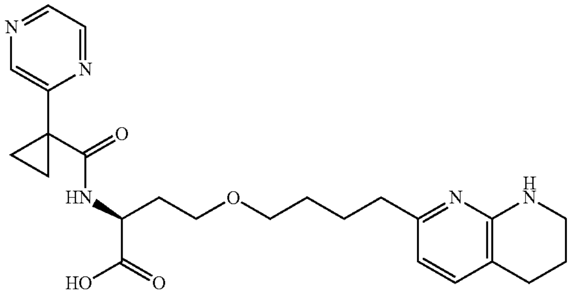 [SMILES: O=C(O)[C@H](CCOCCCCc1ccc2c(n1)NCCC2)NC(=O)C1(c2cnccn2)CC1] |
| 12 | 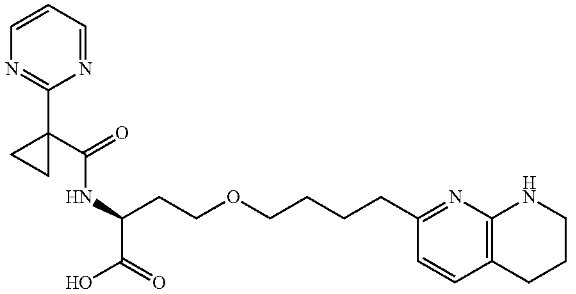 [SMILES: O=C(O)[C@H](CCOCCCCc1ccc2c(n1)NCCC2)NC(=O)C1(c2ncccn2)CC1] |
| 13 | 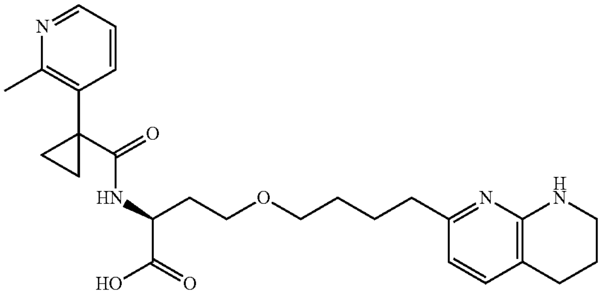 |
| 14 | 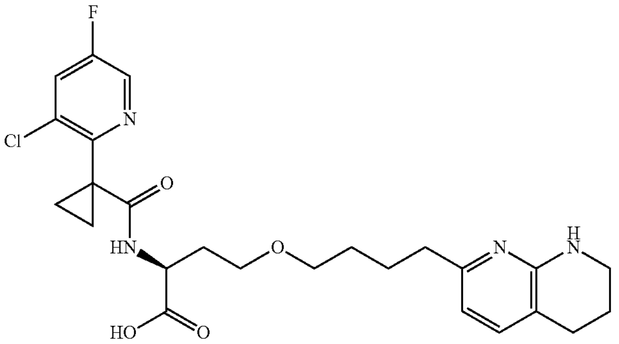 [SMILES: O=C(O)[C@H](CCOCCCCc1ccc2c(n1)NCCC2)NC(=O)C1(c2ncc(F)cc2Cl)CC1] |

TABLE 1-continued
| Compound # | Structure |
| --- | --- |
| 15 | 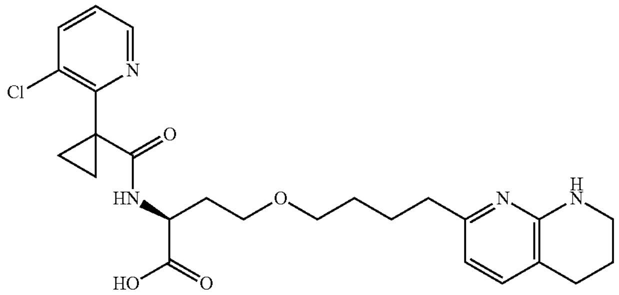 [SMILES: O=C(O)[C@H](CCOCCCCc1ccc2c(n1)NCCC2)NC(=O)C1(c2ncccc2Cl)CC1] |
| 16 | 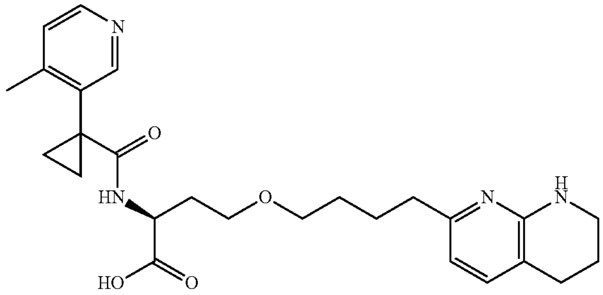 [SMILES: Cc1ccncc1C1(C(=O)N[C@@H](CCOCCCCc2ccc3c(n2)NCCC3)C(=O)O)CC1] |
| 17 | 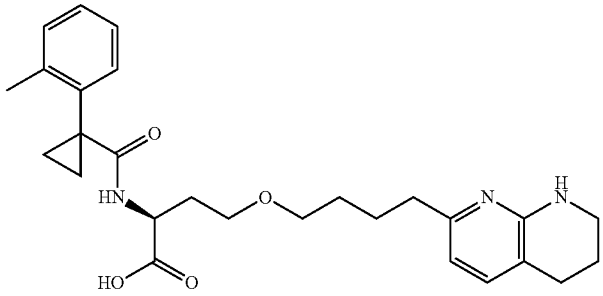 [SMILES: Cc1ccccc1C1(C(=O)N[C@@H](CCOCCCCc2ccc3c(n2)NCCC3)C(=O)O)CC1] |
| 18 | 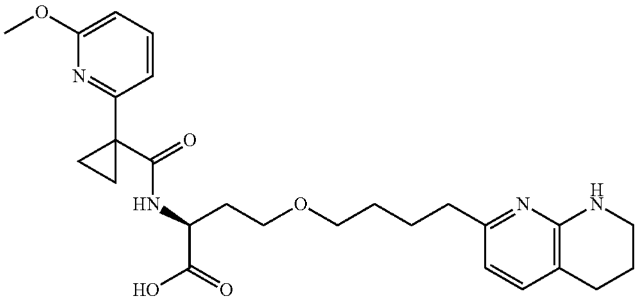 [SMILES: COc1cccc(C2(C(=O)N[C@@H](CCOCCCCc3ccc4c(n3)NCCC4)C(=O)O)CC2)n1] |
| 19 | 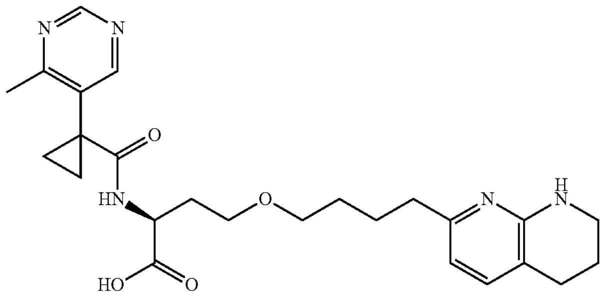 [SMILES: Cc1ncncc1C1(C(=O)N[C@@H](CCOCCCCc2ccc3c(n2)NCCC3)C(=O)O)CC1] |

TABLE 1-continued
| Compound # | Structure |
|---|---|
| 20 | 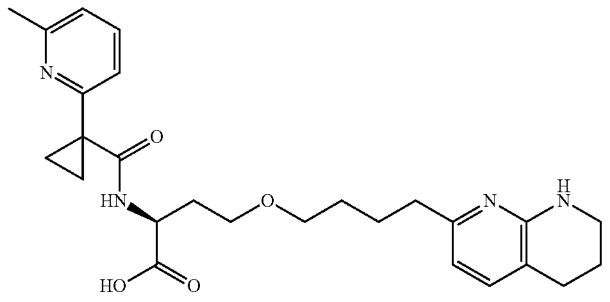 [SMILES: Cc1cccc(C2(C(=O)N[C@@H](CCOCCCCc3ccc4c(n3)NCCC4)C(=O)O)CC2)n1] |
| 21 | 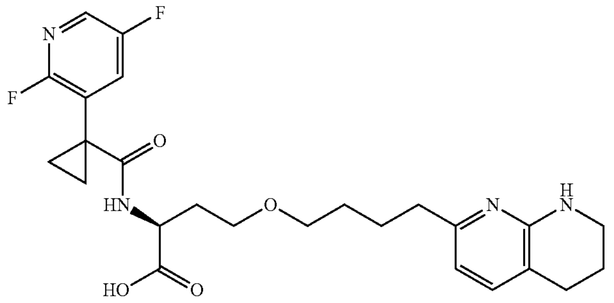 [SMILES: O=C(O)[C@H](CCOCCCCc1ccc2c(n1)NCCC2)NC(=O)C1(c2cc(F)cnc2F)CC1] |
| 22 | 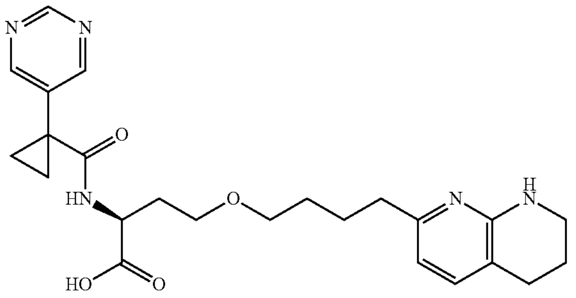 |
| 23 | 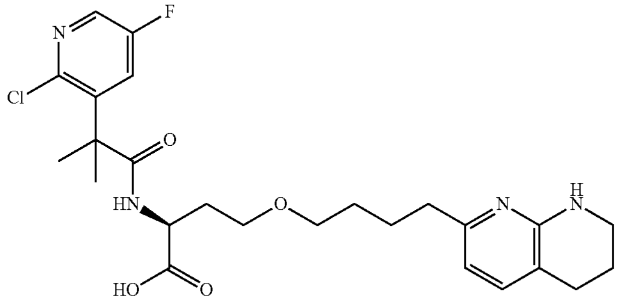 [SMILES: CC(C)(C(=O)N[C@@H](CCOCCCCc1ccc2c(n1)NCCC2)C(=O)O)c1cc(F)cnc1Cl] |
| 24 | 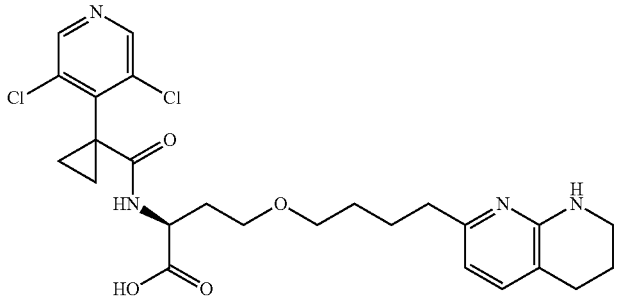 [SMILES: O=C(O)[C@H](CCOCCCCc1ccc2c(n1)NCCC2)NC(=O)C1(c2c(Cl)cncc2Cl)CC1] |

TABLE 1-continued
| Compound # | Structure |
|---|---|
| 25 | 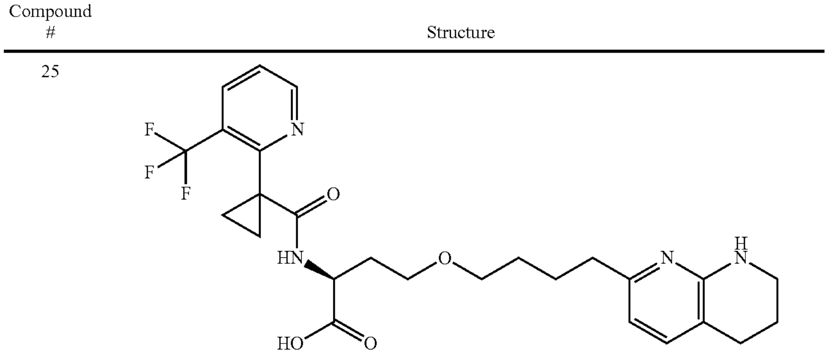 |
| 26 | 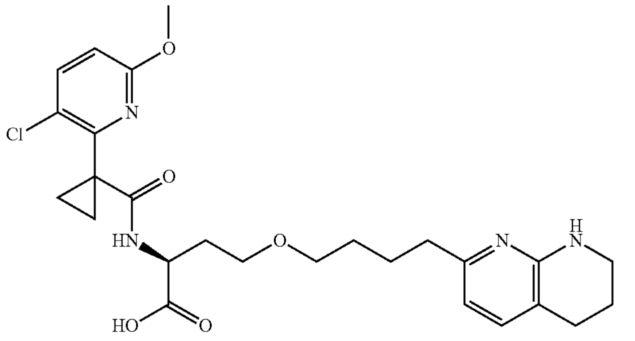 [SMILES: COc1ccc(Cl)c(C2(C(=O)N[C@@H](CCOCCCCc3ccc4c(n3)NCCC4)C(=O)O)CC2)n1] |
| 27 | 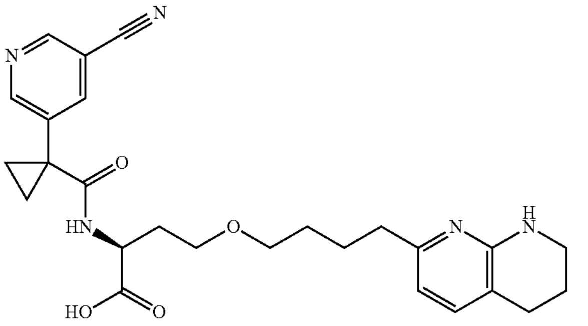 [SMILES: N#Cc1cncc(C2(C(=O)N[C@@H](CCOCCCCc3ccc4c(n3)NCCC4)C(=O)O)CC2)c1] |
| 28 | 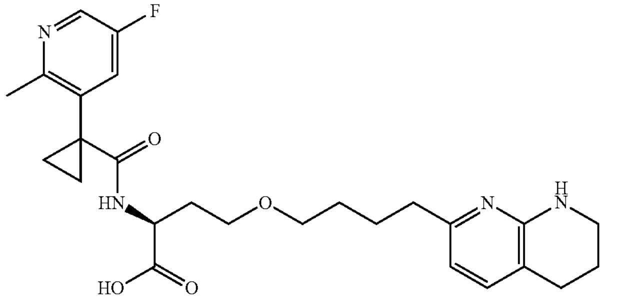 [SMILES: Cc1ncc(F)cc1C1(C(=O)N[C@@H](CCOCCCCc2ccc3c(n2)NCCC3)C(=O)O)CC1] |
| 29 | 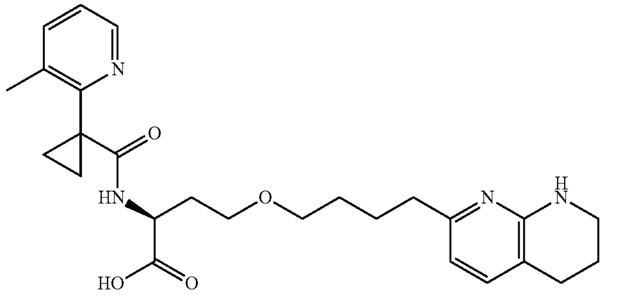 |

TABLE 1-continued
| Compound # | Structure |
|---|---|
| 30 | 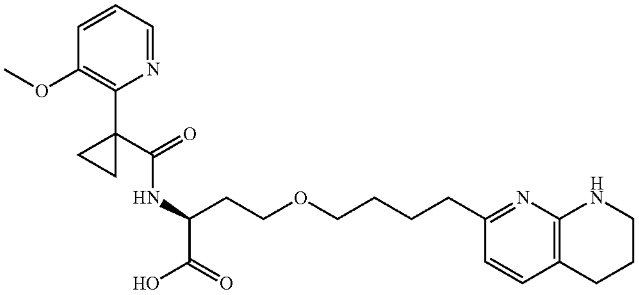 [SMILES: COc1cccnc1C1(C(=O)N[C@@H](CCOCCCCc2ccc3c(n2)NCCC3)C(=O)O)CC1] |
| 31 | 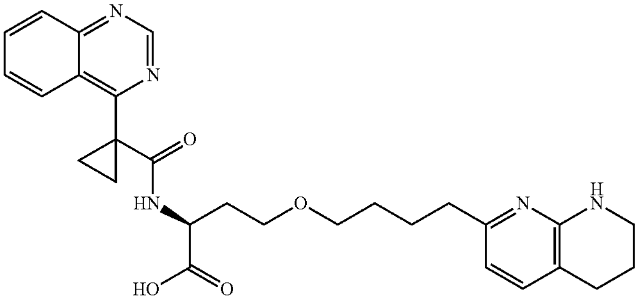 [SMILES: O=C(O)[C@H](CCOCCCCc1ccc2c(n1)NCCC2)NC(=O)C1(c2ncnc3ccccc23)CC1] |
| 32 | 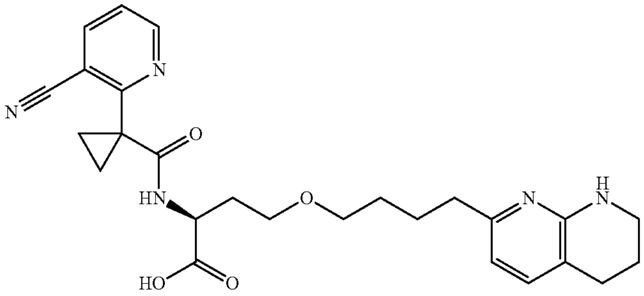 |
| 33 | 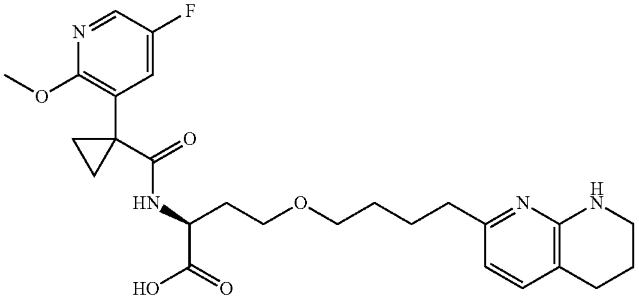 [SMILES: COc1ncc(F)cc1C1(C(=O)N[C@@H](CCOCCCCc2ccc3c(n2)NCCC3)C(=O)O)CC1] |
| 34 | 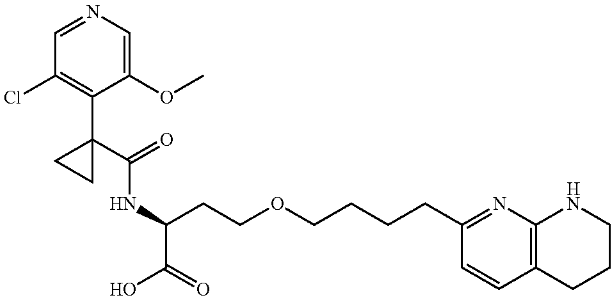 [SMILES: COc1cncc(Cl)c1C1(C(=O)N[C@@H](CCOCCCCc2ccc3c(n2)NCCC3)C(=O)O)CC1] |

TABLE 1-continued
| Compound # | Structure |
| --- | --- |
| 35 | 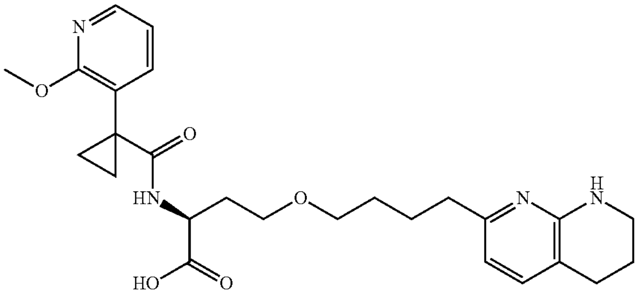 [SMILES: COc1ncccc1C1(C(=O)N[C@@H](CCOCCCCc2ccc3c(n2)NCCC3)C(=O)O)CC1] |
| 36 | 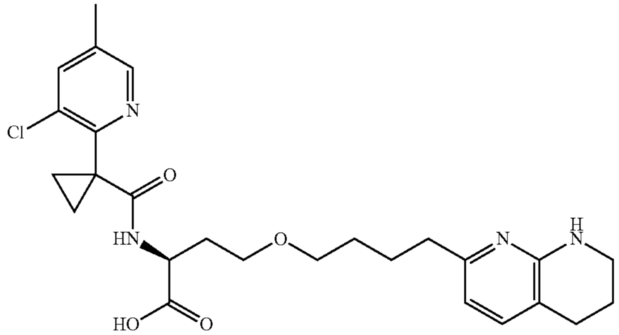 [SMILES: Cc1cnc(C2(C(=O)N[C@@H](CCOCCCCc3ccc4c(n3)NCCC4)C(=O)O)CC2)c(Cl)c1] |
| 37 | 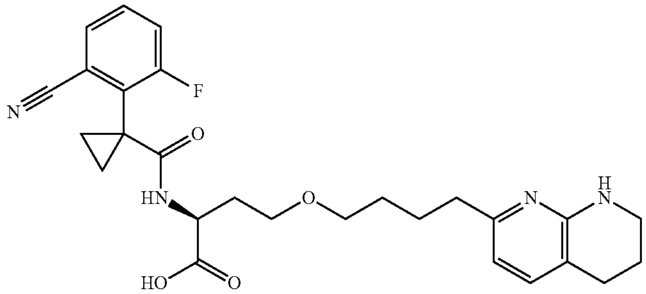 [SMILES: N#Cc1cccc(F)c1C1(C(=O)N[C@@H](CCOCCCCc2ccc3c(n2)NCCC3)C(=O)O)CC1] |
| 38 | 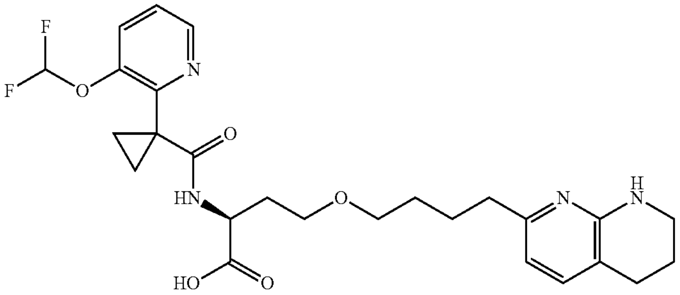 [SMILES: O=C(O)[C@H](CCOCCCCc1ccc2c(n1)NCCC2)NC(=O)C1(c2ncccc2OC(F)F)CC1] |
| 39 | 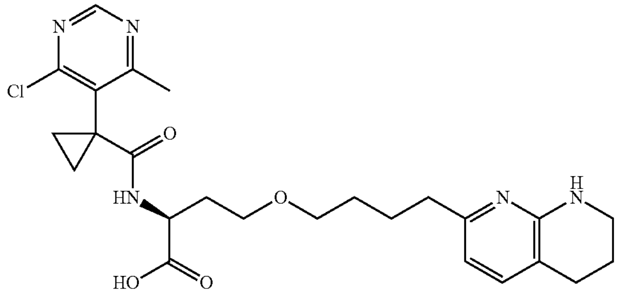 [SMILES: Cc1ncnc(Cl)c1C1(C(=O)N[C@@H](CCOCCCCc2ccc3c(n2)NCCC3)C(=O)O)CC1] |

TABLE 1-continued
| Compound # | Structure |
|---|---|
| 40 | 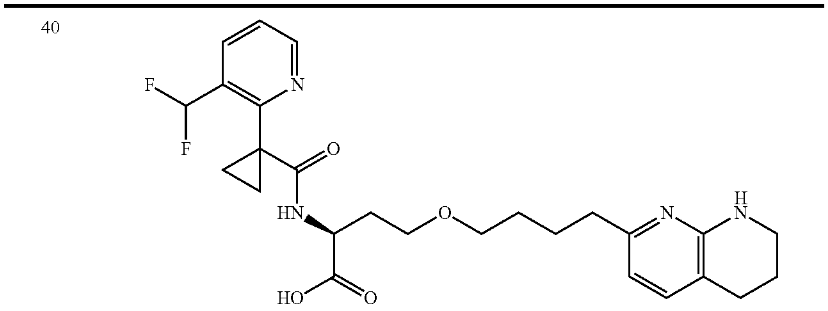 |
| 41 | 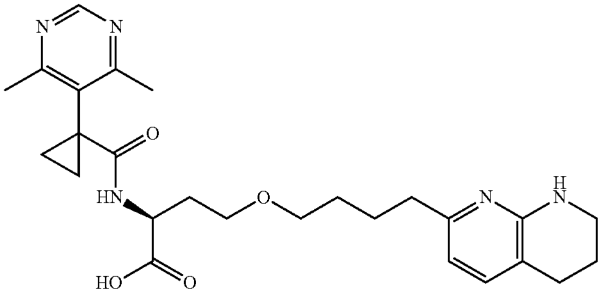 [SMILES: Cc1ncnc(C)c1C1(C(=O)N[C@@H](CCOCCCCc2ccc3c(n2)NCCC3)C(=O)O)CC1] |
| 42 | 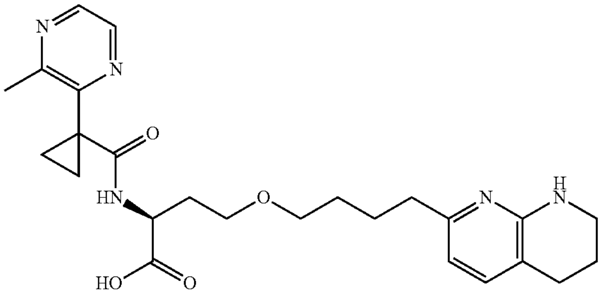 [SMILES: Cc1nccnc1C1(C(=O)N[C@@H](CCOCCCCc2ccc3c(n2)NCCC3)C(=O)O)CC1] |
| 43 | 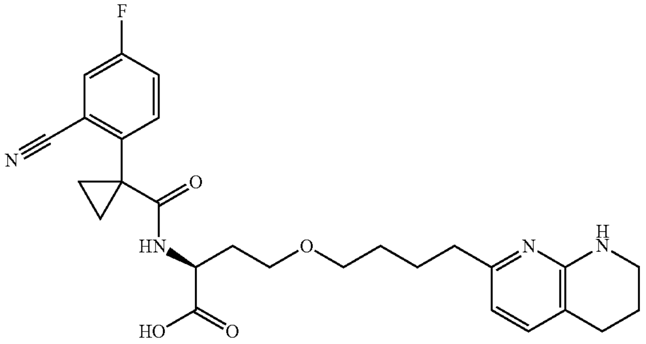 [SMILES: N#Cc1cc(F)ccc1C1(C(=O)N[C@@H](CCOCCCCc2ccc3c(n2)NCCC3)C(=O)O)CC1] |
| 44 | 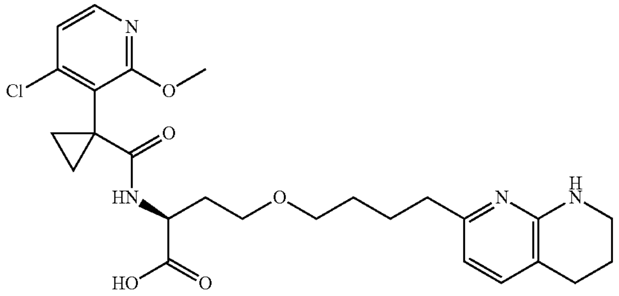 [SMILES: COc1nccc(Cl)c1C1(C(=O)N[C@@H](CCOCCCCc2ccc3c(n2)NCCC3)C(=O)O)CC1] |

TABLE 1-continued
| Compound # | Structure |
|---|---|
| 45 | 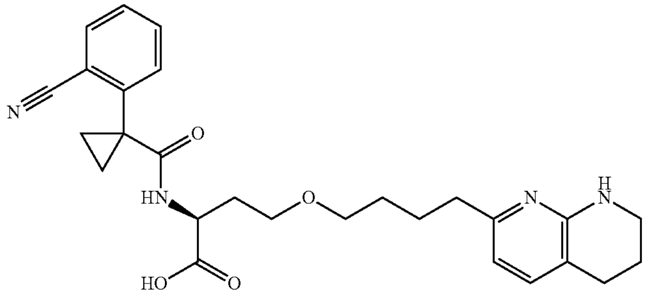 [SMILES: N#Cc1ccccc1C1(C(=O)N[C@@H](CCOCCCCc2ccc3c(n2)NCCC3)C(=O)O)CC1] |
| 46 | 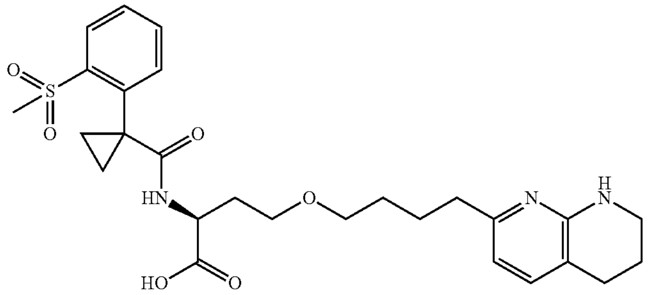 [SMILES: CS(=O)(=O)c1ccccc1C1(C(=O)N[C@@H](CCOCCCCc2ccc3c(n2)NCCC3)C(=O)O)CC1] |
| 47 | 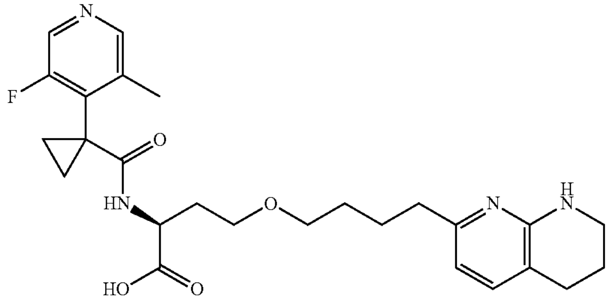 [SMILES: Cc1cncc(F)c1C1(C(=O)N[C@@H](CCOCCCCc2ccc3c(n2)NCCC3)C(=O)O)CC1] |
| 48 | 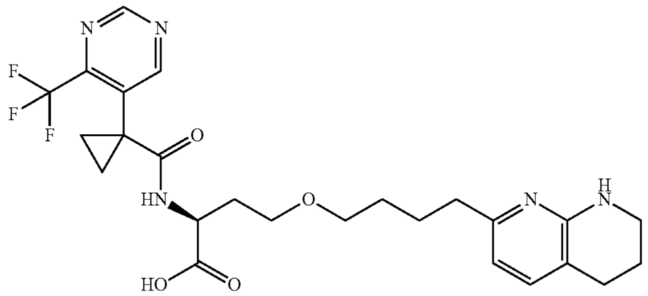 [SMILES: O=C(O)[C@H](CCOCCCCc1ccc2c(n1)NCCC2)NC(=O)C1(c2cncnc2C(F)(F)F)CC1] |
| 49 | 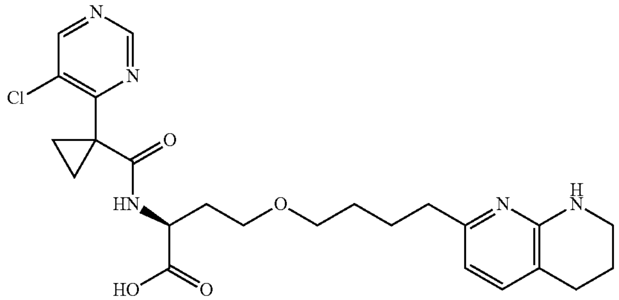 [SMILES: O=C(O)[C@H](CCOCCCCc1ccc2c(n1)NCCC2)NC(=O)C1(c2ncncc2Cl)CC1] |

TABLE 1-continued
| Compound # | Structure |
|---|---|
| 50 | 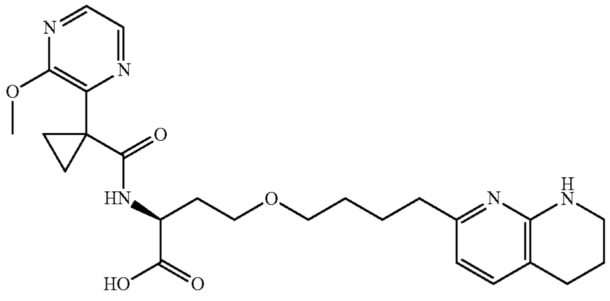 [SMILES: COc1nccnc1C1(C(=O)N[C@@H](CCOCCCCc2ccc3c(n2)NCCC3)C(=O)O)CC1] |
| 51 | 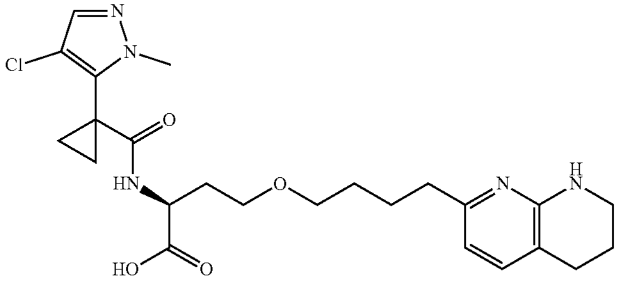 [SMILES: Cn1ncc(Cl)c1C1(C(=O)N[C@@H](CCOCCCCc2ccc3c(n2)NCCC3)C(=O)O)CC1] |
| 52 | 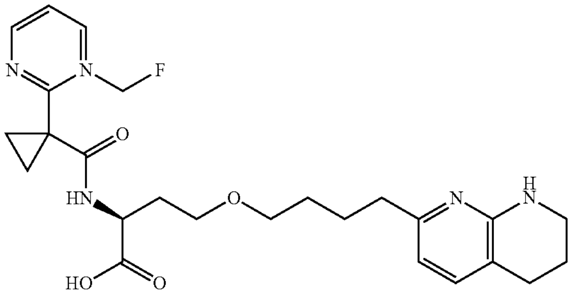 |
| 53 | 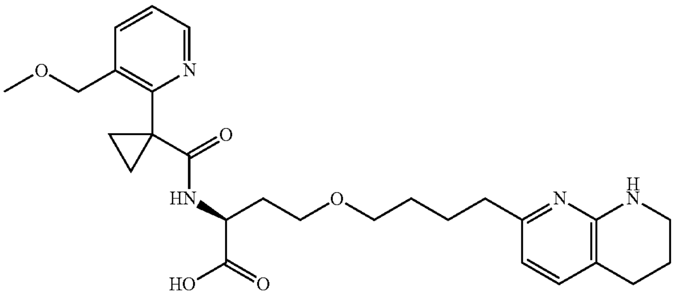 [SMILES: COCc1cccnc1C1(C(=O)N[C@@H](CCOCCCCc2ccc3c(n2)NCCC3)C(=O)O)CC1] |
| 54 | 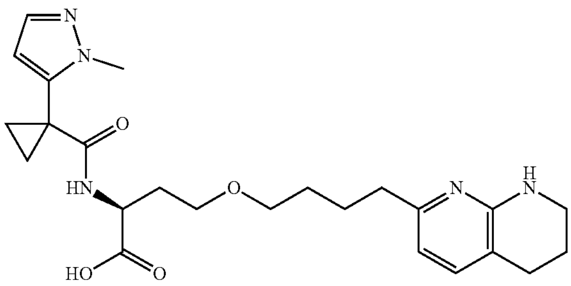 [SMILES: Cn1nccc1C1(C(=O)N[C@@H](CCOCCCCc2ccc3c(n2)NCCC3)C(=O)O)CC1] |

TABLE 1-continued
| Compound # | Structure |
| --- | --- |
| 55 | 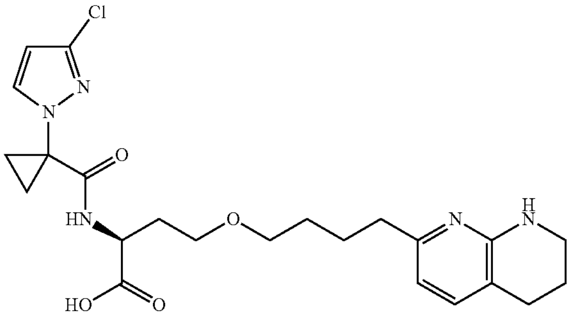 [SMILES: O=C(O)[C@H](CCOCCCCc1ccc2c(n1)NCCC2)NC(=O)C1(n2ccc(Cl)n2)CC1] |
| 56 | 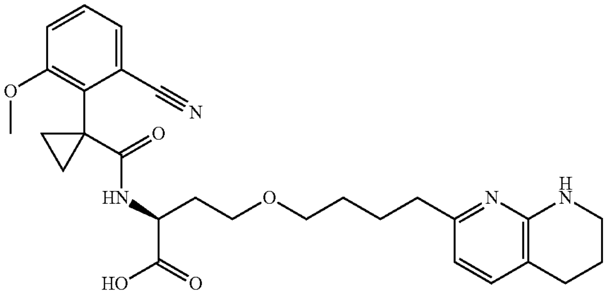 [SMILES: COc1cccc(C#N)c1C1(C(=O)N[C@@H](CCOCCCCc2ccc3c(n2)NCCC3)C(=O)O)CC1] |
| 57 | 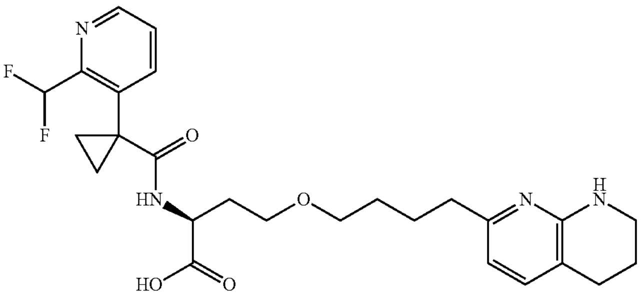 [SMILES: O=C(O)[C@H](CCOCCCCc1ccc2c(n1)NCCC2)NC(=O)C1(c2cccnc2C(F)F)CC1] |
| 58 | 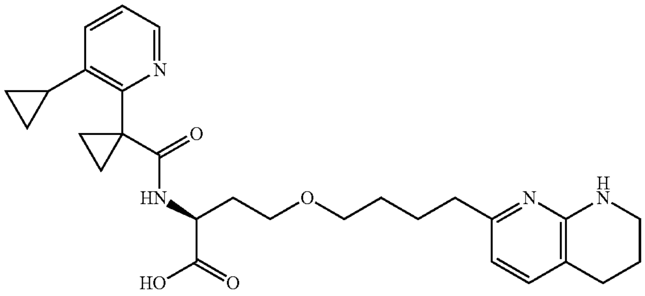 [SMILES: O=C(O)[C@H](CCOCCCCc1ccc2c(n1)NCCC2)NC(=O)C1(c2ncccc2C2CC2)CC1] |
| 59 | 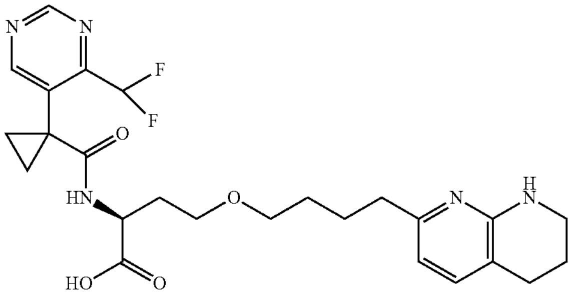 [SMILES: O=C(O)[C@H](CCOCCCCc1ccc2c(n1)NCCC2)NC(=O)C1(c2cncnc2C(F)F)CC1] |

TABLE 1-continued
| Compound # | Structure |
| --- | --- |
| 60 | 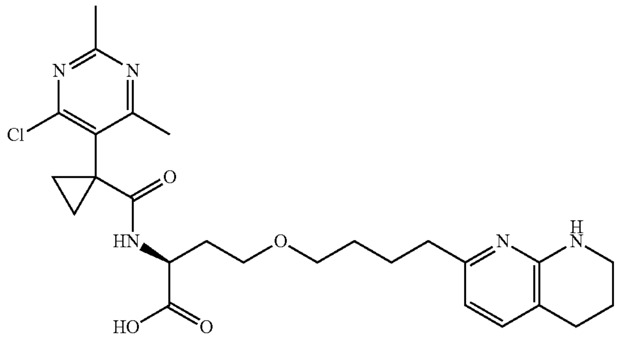 [SMILES: Cc1nc(C)c(C2(C(=O)N[C@@H](CCOCCCCc3ccc4c(n3)NCCC4)C(=O)O)CC2)c(Cl)n1] |
| 61 | 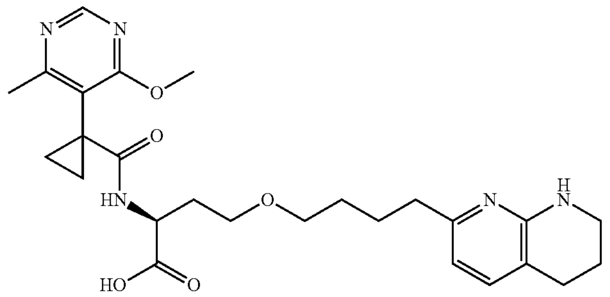 [SMILES: COc1ncnc(C)c1C1(C(=O)N[C@@H](CCOCCCCc2ccc3c(n2)NCCC3)C(=O)O)CC1] |
| 62 | 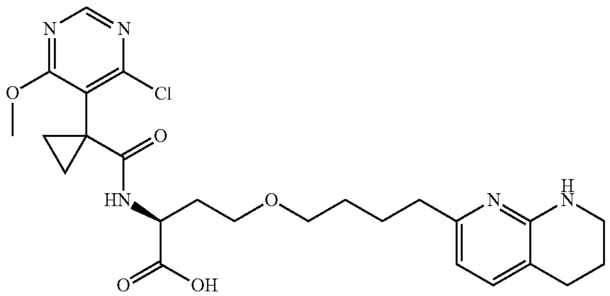 [SMILES: COc1ncnc(Cl)c1C1(C(=O)N[C@@H](CCOCCCCc2ccc3c(n2)NCCC3)C(=O)O)CC1] |
| 63 | 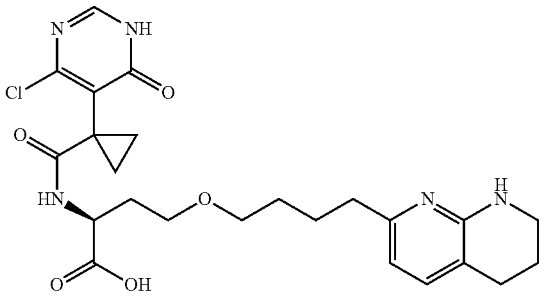 [SMILES: O=C(O)[C@H](CCOCCCCc1ccc2c(n1)NCCC2)NC(=O)C1(c2c(Cl)nc[nH]c2=O)CC1] |
| 64 | 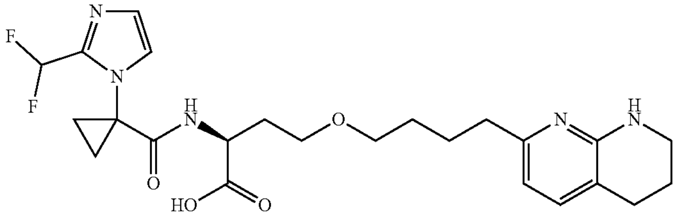 [SMILES: O=C(O)[C@H](CCOCCCCc1ccc2c(n1)NCCC2)NC(=O)C1(n2ccnc2C(F)F)CC1] |

TABLE 1-continued
| Compound # | Structure |
| --- | --- |
| 65 | 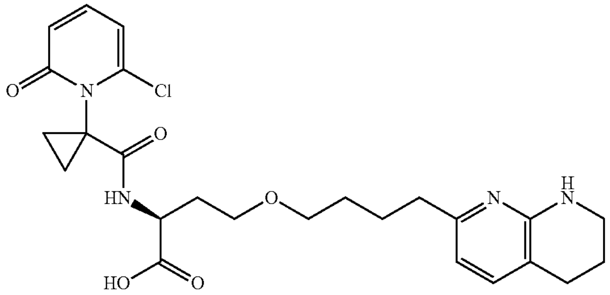 [SMILES: O=C(O)[C@H](CCOCCCCc1ccc2c(n1)NCCC2)NC(=O)C1(n2c(Cl)cccc2=O)CC1] |
| 66 | 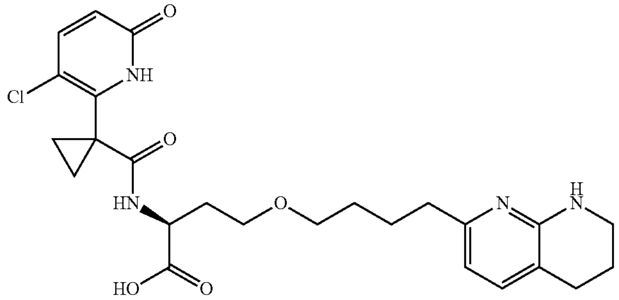 [SMILES: O=C(O)[C@H](CCOCCCCc1ccc2c(n1)NCCC2)NC(=O)C1(c2[nH]c(=O)ccc2Cl)CC1] |
| 67 | 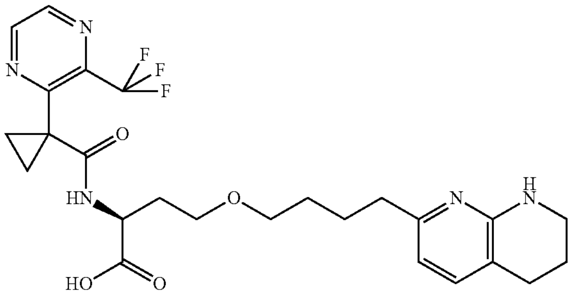 [SMILES: O=C(O)[C@H](CCOCCCCc1ccc2c(n1)NCCC2)NC(=O)C1(c2nccnc2C(F)(F)F)CC1] |
| 68 | 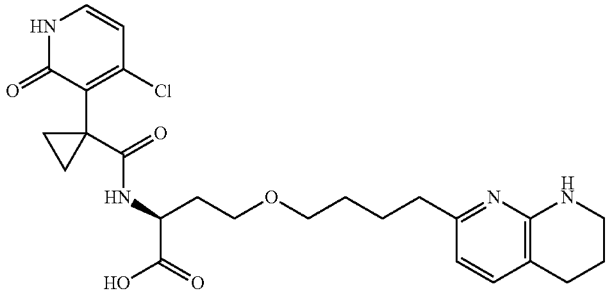 [SMILES: O=C(O)[C@H](CCOCCCCc1ccc2c(n1)NCCC2)NC(=O)C1(c2c(Cl)cc[nH]c2=O)CC1] |
| 69 | 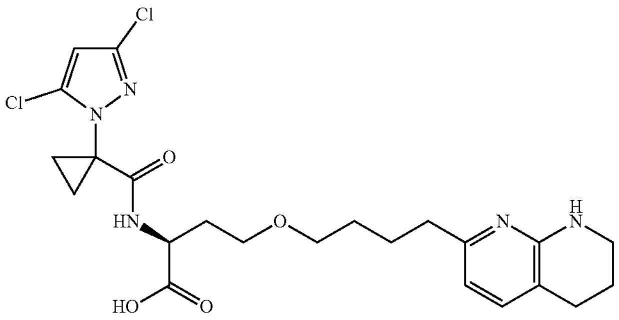 [SMILES: O=C(O)[C@H](CCOCCCCc1ccc2c(n1)NCCC2)NC(=O)C1(n2nc(Cl)cc2Cl)CC1] |

TABLE 1-continued
| Compound # | Structure |
|---|---|
| 70 | 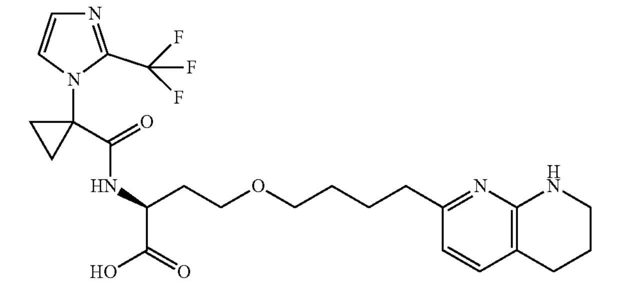 [SMILES: O=C(O)[C@H](CCOCCCCc1ccc2c(n1)NCCC2)NC(=O)C1(n2ccnc2C(F)(F)F)CC1] |
| 71 | 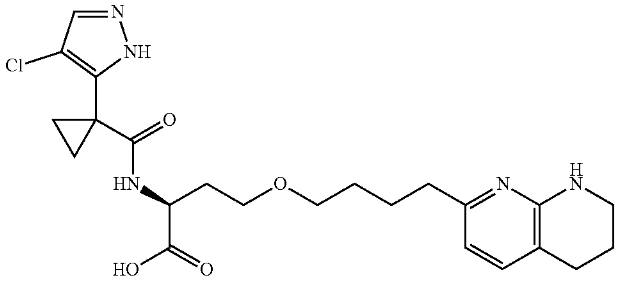 [SMILES: O=C(O)[C@H](CCOCCCCc1ccc2c(n1)NCCC2)NC(=O)C1(c2[nH]ncc2Cl)CC1] |
| 72 | 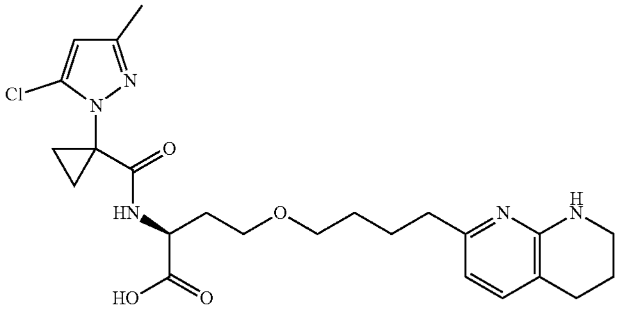 [SMILES: Cc1cc(Cl)n(C2(C(=O)N[C@@H](CCOCCCCc3ccc4c(n3)NCCC4)C(=O)O)CC2)n1] |
| 73 | 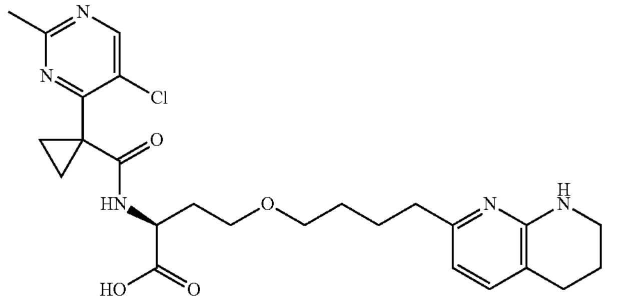 [SMILES: Cc1ncc(Cl)c(C2(C(=O)N[C@@H](CCOCCCCc3ccc4c(n3)NCCC4)C(=O)O)CC2)n1] |
| 74 | 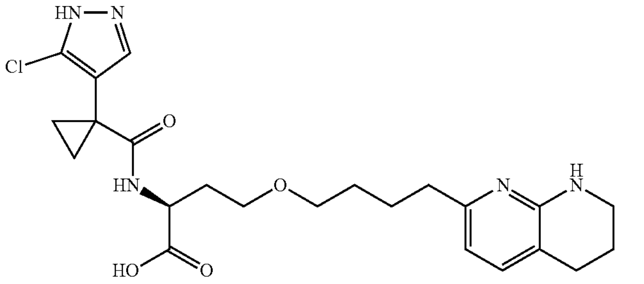 [SMILES: O=C(O)[C@H](CCOCCCCc1ccc2c(n1)NCCC2)NC(=O)C1(c2cn[nH]c2Cl)CC1] |

TABLE 1-continued
| Compound # | Structure |
| --- | --- |
| 75 | 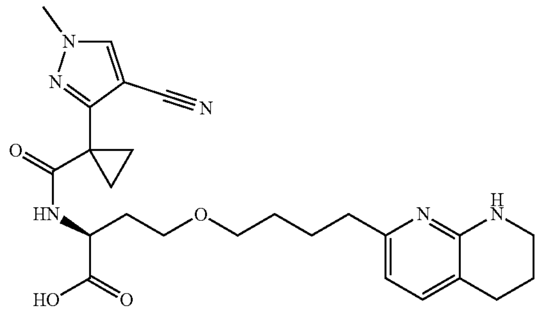 [SMILES: Cn1cc(C#N)c(C2(C(=O)N[C@@H](CCOCCCCc3ccc4c(n3)NCCC4)C(=O)O)CC2)n1] |
| 76 | 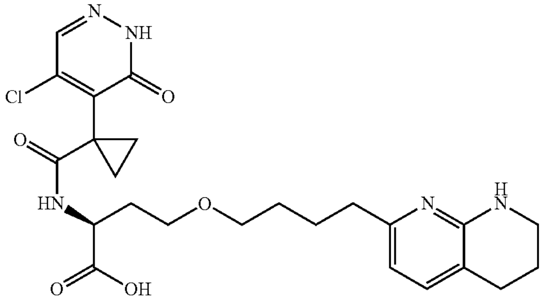 [SMILES: O=C(O)[C@H](CCOCCCCc1ccc2c(n1)NCCC2)NC(=O)C1(c2c(Cl)cn[nH]c2=O)CC1] |
| 77 | 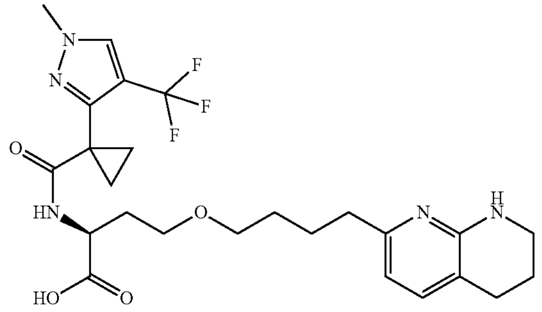 [SMILES: Cn1cc(C(F)(F)F)c(C2(C(=O)N[C@@H](CCOCCCCc3ccc4c(n3)NCCC4)C(=O)O)CC2)n1] |
| 78 | 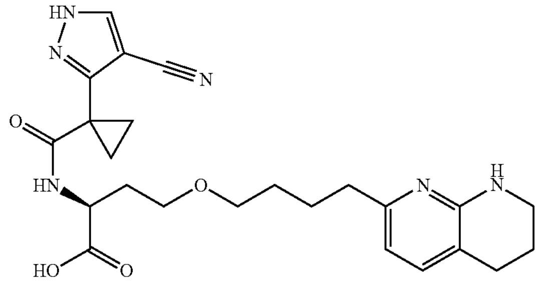 [SMILES: N#Cc1c[nH]nc1C1(C(=O)N[C@@H](CCOCCCCc2ccc3c(n2)NCCC3)C(=O)O)CC1] |
| 79 | 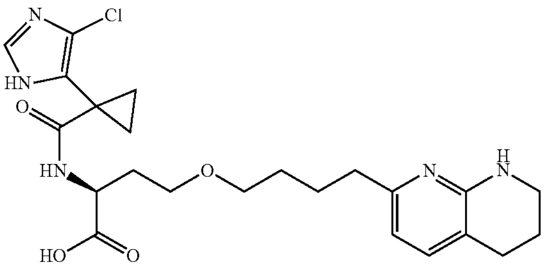 [SMILES: O=C(O)[C@H](CCOCCCCc1ccc2c(n1)NCCC2)NC(=O)C1(c2[nH]cnc2Cl)CC1] |

TABLE 1-continued
| Compound # | Structure |
|---|---|
| 80 | 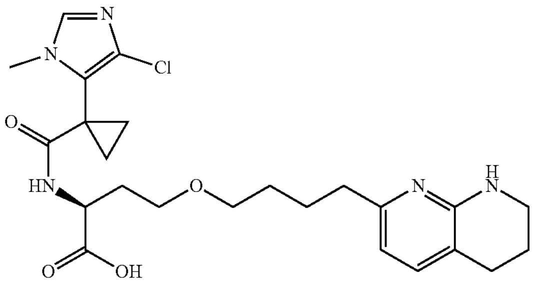 [SMILES: Cn1cnc(Cl)c1C1(C(=O)N[C@@H](CCOCCCCc2ccc3c(n2)NCCC3)C(=O)O)CC1] |
| 81 | 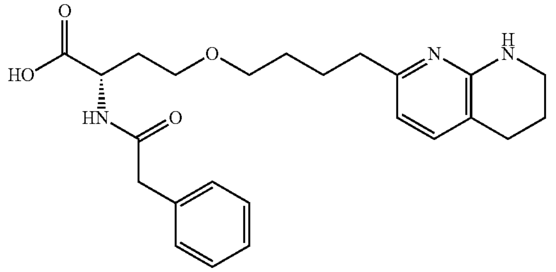 [SMILES: O=C(Cc1ccccc1)N[C@@H](CCOCCCCc1ccc2c(n1)NCCC2)C(=O)O] |
| 82 | 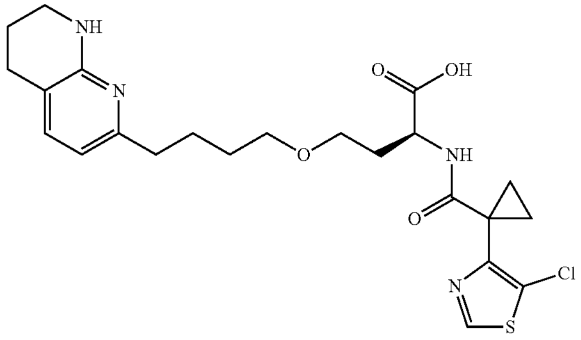 [SMILES: O=C(O)[C@H](CCOCCCCc1ccc2c(n1)NCCC2)NC(=O)C1(c2ncsc2Cl)CC1] |
| 83 | 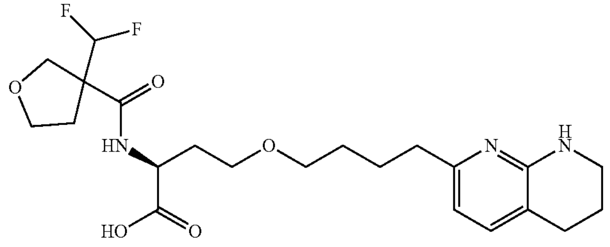 [SMILES: O=C(O)[C@H](CCOCCCCc1ccc2c(n1)NCCC2)NC(=O)C1(C(F)F)CCOC1] |
| 84 | 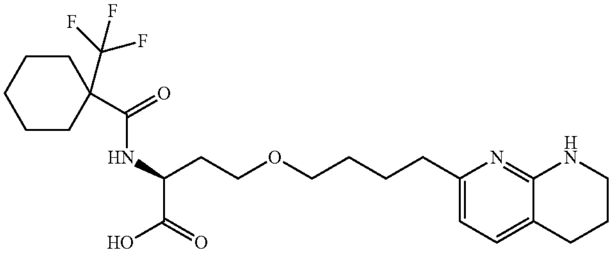 [SMILES: O=C(O)[C@H](CCOCCCCc1ccc2c(n1)NCCC2)NC(=O)C1(C(F)(F)F)CCCCC1] |

TABLE 1-continued
| Compound # | Structure |
| --- | --- |
| 85 | 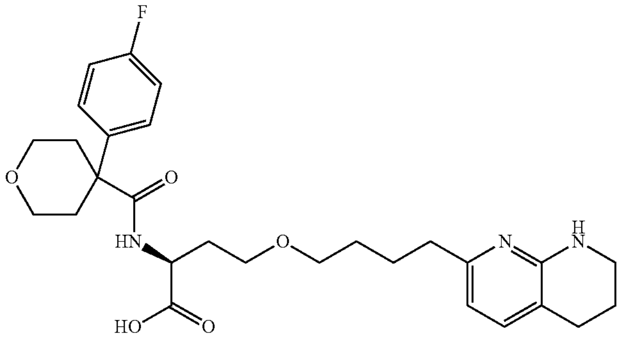 [SMILES: O=C(O)[C@H](CCOCCCCc1ccc2c(n1)NCCC2)NC(=O)C1(c2ccc(F)cc2)CCOCC1] |
| 86 | 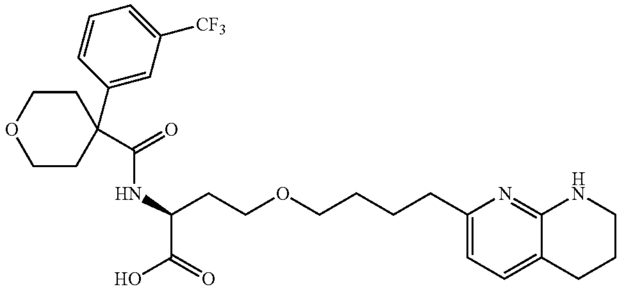 |
| 87 | 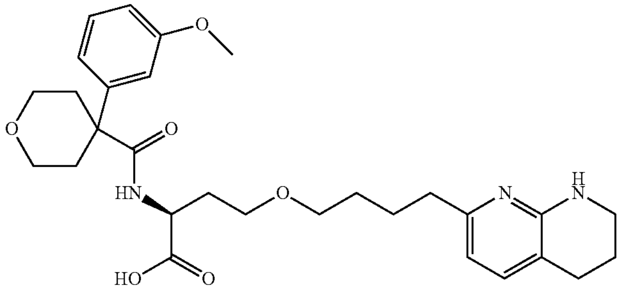 [SMILES: COc1cccc(C2(C(=O)N[C@@H](CCOCCCCc3ccc4c(n3)NCCC4)C(=O)O)CCOCC2)c1] |
| 88 | 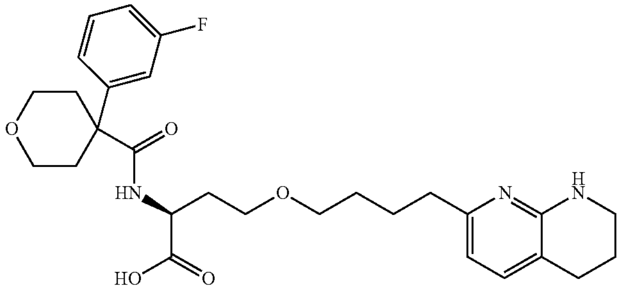 |
| 89 | 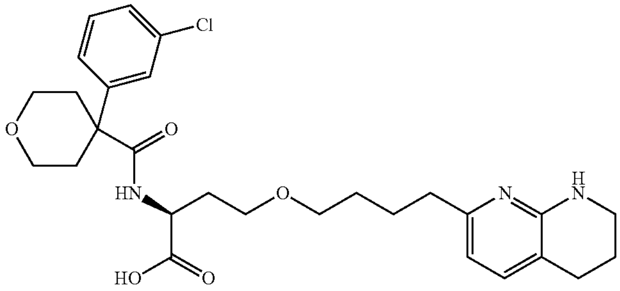 [SMILES: O=C(O)[C@H](CCOCCCCc1ccc2c(n1)NCCC2)NC(=O)C1(c2cccc(Cl)c2)CCOCC1] |

TABLE 1-continued
| Compound # | Structure |
|---|---|
| 90 | 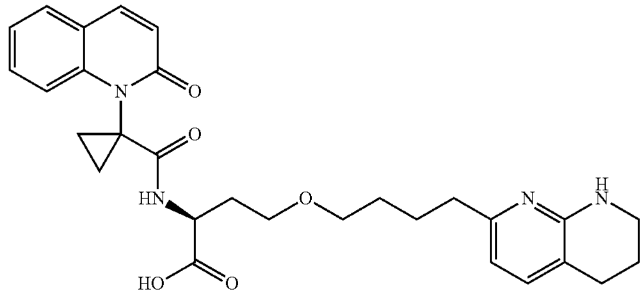 [SMILES: O=C(O)[C@H](CCOCCCCc1ccc2c(n1)NCCC2)NC(=O)C1(n2c(=O)ccc3ccccc32)CC1] |
| 91 | 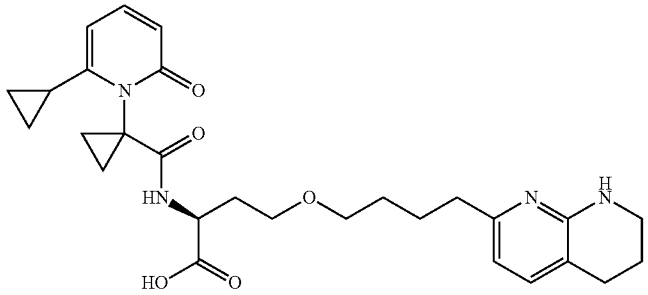 [SMILES: O=C(O)[C@H](CCOCCCCc1ccc2c(n1)NCCC2)NC(=O)C1(n2c(C3CC3)cccc2=O)CC1] |
| 92 | 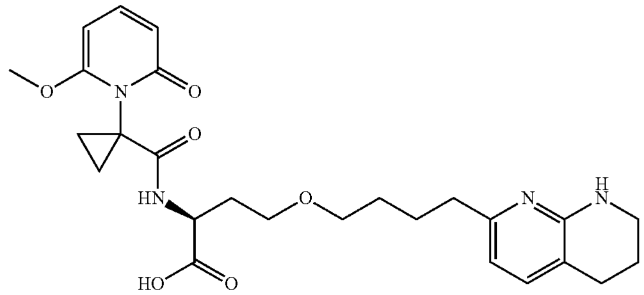 [SMILES: COc1cccc(=O)n1C1(C(=O)N[C@@H](CCOCCCCc2ccc3c(n2)NCCC3)C(=O)O)CC1] |
| 93 | 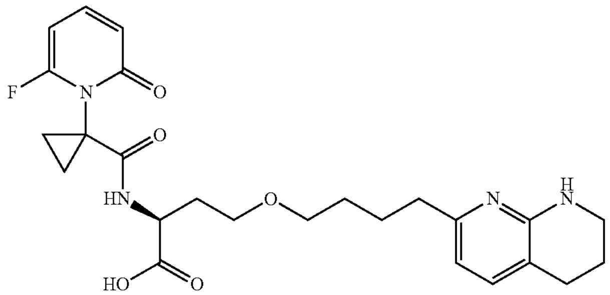 [SMILES: O=C(O)[C@H](CCOCCCCc1ccc2c(n1)NCCC2)NC(=O)C1(n2c(F)cccc2=O)CC1] |
| 94 | 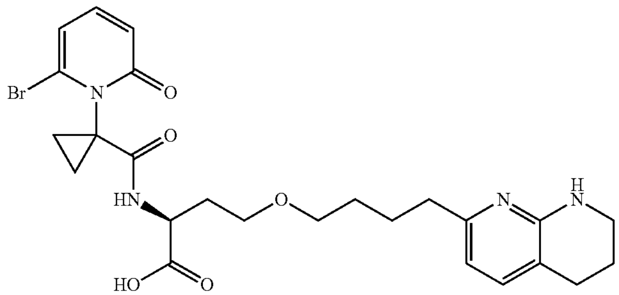 |

TABLE 1-continued
| Compound # | Structure |
| --- | --- |
| 95 | 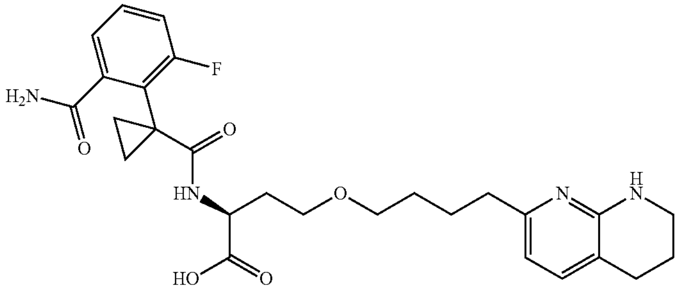 [SMILES: NC(=O)c1cccc(F)c1C1(C(=O)N[C@@H](CCOCCCCc2ccc3c(n2)NCCC3)C(=O)O)CC1] |
| 96 | 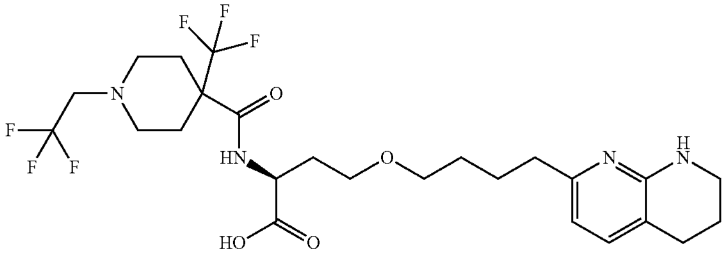 [SMILES: O=C(O)[C@H](CCOCCCCc1ccc2c(n1)NCCC2)NC(=O)C1(C(F)(F)F)CCN(CC(F)(F)F)CC1] |
| 97 | 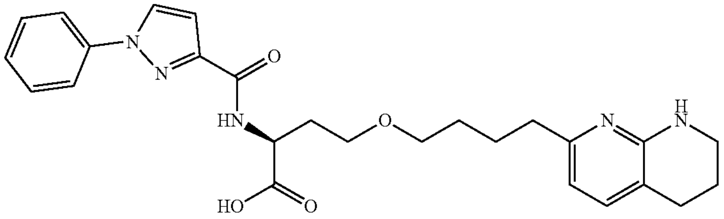 [SMILES: O=C(N[C@@H](CCOCCCCc1ccc2c(n1)NCCC2)C(=O)O)c1ccn(-c2ccccc2)n1] |
| 98 | 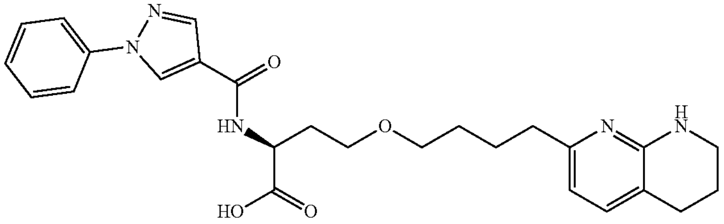 [SMILES: O=C(N[C@@H](CCOCCCCc1ccc2c(n1)NCCC2)C(=O)O)c1cnn(-c2ccccc2)c1] |
| 99 | 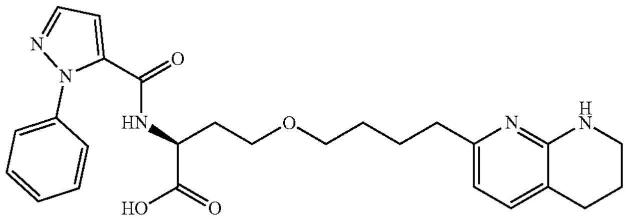 [SMILES: O=C(N[C@@H](CCOCCCCc1ccc2c(n1)NCCC2)C(=O)O)c1ccnn1-c1ccccc1] |
| 100 | 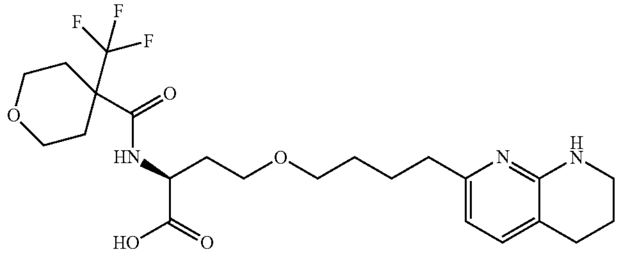 [SMILES: O=C(O)[C@H](CCOCCCCc1ccc2c(n1)NCCC2)NC(=O)C1(C(F)(F)F)CCOCC1] |

TABLE 1-continued

| Compound # | Structure |
|---|---|
| 101 | 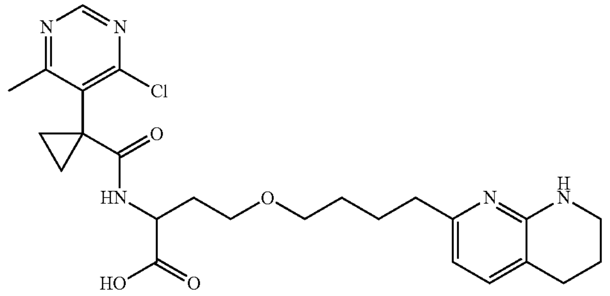 [SMILES: Cc1ncnc(Cl)c1C1(C(=O)NC(CCOCCCCc2ccc3c(n2)NCCC3)C(=O)O)CC1] |
| 102 | 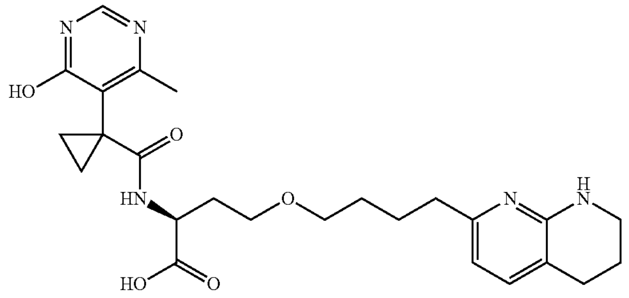 [SMILES: Cc1ncnc(O)c1C1(C(=O)N[C@@H](CCOCCCCc2ccc3c(n2)NCCC3)C(=O)O)CC1] |
| 103 | 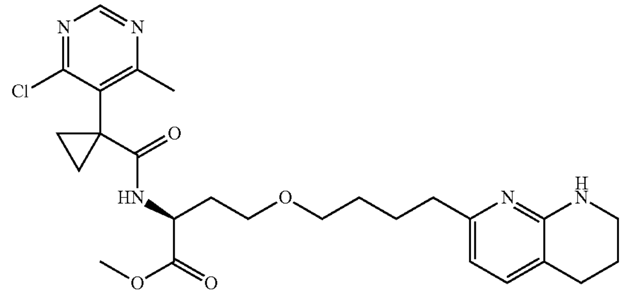 [SMILES: COC(=O)[C@H](CCOCCCCc1ccc2c(n1)NCCC2)NC(=O)C1(c2c(C)ncnc2Cl)CC1] |
| 104 | 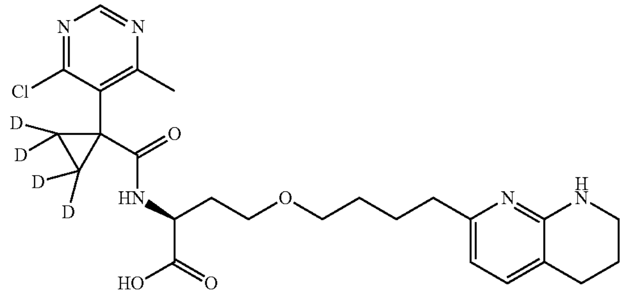 [SMILES: [2H]C1([2H])C([2H])([2H])C1(C(=O)N[C@@H](CCOCCCCc1ccc2c(n1)NCCC2)C(=O)O)c1c(C)ncnc1Cl] |

In some embodiments, provided is a compound selected from the compounds depicted in Table 1, or a stereoisomer thereof (including a mixture of two or more stereoisomers thereof), or a pharmaceutically acceptable salt thereof. In some embodiments, the compound is a salt of a compound selected from the compounds depicted in Table 1, or a stereoisomer thereof. The "flat" versions of all compounds depicted in Table 1 are also contemplated in this disclosure, including flat versions of any specific stereoisomeric forms in the Table.

In some embodiments, provided is a compound selected from compounds 1-82 depicted in Table 1, or a stereoisomer thereof (including a mixture of two or more stereoisomers thereof), or a pharmaceutically acceptable salt thereof. In some embodiments, the compound is a salt of a compound selected from compounds 1-82 depicted in Table 1, or a stereoisomer thereof. The "flat" versions of compounds 1-82 depicted in Table 1 are also contemplated in this disclosure, including flat versions of any specific stereoisomeric forms of compounds 1-82 in the Table.

In some embodiments, provided is a compound selected from compounds 83-104 depicted in Table 1, or a stereoisomer thereof (including a mixture of two or more stereoisomers thereof), or a pharmaceutically acceptable salt thereof. In some embodiments, the compound is a salt of a compound selected from compounds 83-104 depicted in Table 1, or a stereoisomer thereof. The "flat" versions of compounds 83-104 depicted in Table 1 are also contemplated in this disclosure, including flat versions of any specific stereoisomeric forms of compounds 83-104 in the Table.

In one variation, the compound detailed herein is selected from the group consisting of:

N-(2-methyl-2-phenylpropanoyl)-O-(4-(5,6,7,8-tetrahydro-1,8-naphthyridin-2-yl)butyl)homoserine;

N-(2-phenylpropanoyl)-O-(4-(5,6,7,8-tetrahydro-1,8-naphthyridin-2-yl)butyl)homoserine;

N-(2-(2,3-difluoro-6-methoxyphenyl)-2-methylpropanoyl)-O-(4-(5,6,7,8-tetrahydro-1,8-naphthyridin-2-yl)butyl)homoserine;

N-(2-(2-(difluoromethoxy)-6-fluorophenyl)-2-methylpropanoyl)-O-(4-(5,6,7,8-tetrahydro-1,8-naphthyridin-2-yl)butyl)homoserine;

N-(1-(2-chlorophenyl)cyclopropane-1-carbonyl)-O-(4-(5,6,7,8-tetrahydro-1,8-naphthyridin-2-yl)butyl)homoserine;

N-(1-(2,6-dichlorophenyl)cyclopropane-1-carbonyl)-O-(4-(5,6,7,8-tetrahydro-1,8-naphthyridin-2-yl)butyl)homoserine;

N-(2-(2-chlorophenyl)-2-methylpropanoyl)-O-(4-(5,6,7,8-tetrahydro-1,8-naphthyridin-2-yl)butyl)homoserine;

N-(1-(2-fluorophenyl)cyclopropane-1-carbonyl)-O-(4-(5,6,7,8-tetrahydro-1,8-naphthyridin-2-yl)butyl)homoserine;

N-(1-phenylcyclopropane-1-carbonyl)-O-(4-(5,6,7,8-tetrahydro-1,8-naphthyridin-2-yl)butyl)homoserine;

N-(1-(pyrazin-2-yl)cyclopropane-1-carbonyl)-O-(4-(5,6,7,8-tetrahydro-1,8-naphthyridin-2-yl)butyl)homoserine;

N-(1-(pyrimidin-2-yl)cyclopropane-1-carbonyl)-O-(4-(5,6,7,8-tetrahydro-1,8-naphthyridin-2-yl)butyl)homoserine;

N-(1-(2-methylpyridin-3-yl)cyclopropane-1-carbonyl)-O-(4-(5,6,7,8-tetrahydro-1,8-naphthyridin-2-yl)butyl)homoserine;

N-(1-(3-chloro-5-fluoropyridin-2-yl)cyclopropane-1-carbonyl)-O-(4-(5,6,7,8-tetrahydro-1,8-naphthyridin-2-yl)butyl)homoserine;

N-(1-(3-chloropyridin-2-yl)cyclopropane-1-carbonyl)-O-(4-(5,6,7,8-tetrahydro-1,8-naphthyridin-2-yl)butyl)homoserine;

N-(1-(4-methylpyridin-3-yl)cyclopropane-1-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1-(o-tolyl)cyclopropane-1-carbonyl)homoserine;

N-(1-(6-methoxypyridin-2-yl)cyclopropane-1-carbonyl)-O-(4-(5,6,7,8-tetrahydro-1,8-naphthyridin-2-yl)butyl)homoserine;

N-(1-(4-methylpyrimidin-5-yl)cyclopropane-1-carbonyl)-O-(4-(5,6,7,8-tetrahydro-1,8-naphthyridin-2-yl)butyl)homoserine;

N-(1-(6-methylpyridin-2-yl)cyclopropane-1-carbonyl)-O-(4-(5,6,7,8-tetrahydro-1,8-naphthyridin-2-yl)butyl)homoserine;

N-(1-(2,5-difluoropyridin-3-yl)cyclopropane-1-carbonyl)-O-(4-(5,6,7,8-tetrahydro-1,8-naphthyridin-2-yl)butyl)homoserine;

N-(1-(pyrimidin-5-yl)cyclopropane-1-carbonyl)-O-(4-(5,6,7,8-tetrahydro-1,8-naphthyridin-2-yl)butyl)homoserine;

N-(2-(2-chloro-5-fluoropyridin-3-yl)-2-methylpropanoyl)-O-(4-(5,6,7,8-tetrahydro-1,8-naphthyridin-2-yl)butyl)homoserine;

N-(1-(3,5-dichloropyridin-4-yl)cyclopropane-1-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1-(3-(trifluoromethyl)pyridin-2-yl)cyclopropane-1-carbonyl)homoserine;

N-(1-(3-chloro-6-methoxypyridin-2-yl)cyclopropane-1-carbonyl)-O-(4-(5,6,7,8-tetrahydro-1,8-naphthyridin-2-yl)butyl)homoserine;

N-(1-(5-cyanopyridin-3-yl)cyclopropane-1-carbonyl)-O-(4-(5,6,7,8-tetrahydro-1,8-naphthyridin-2-yl)butyl)homoserine;

N-(1-(5-fluoro-2-methylpyridin-3-yl)cyclopropane-1-carbonyl)-O-(4-(5,6,7,8-tetrahydro-1,8-naphthyridin-2-yl)butyl)homoserine;

N-(1-(3-methylpyridin-2-yl)cyclopropane-1-carbonyl)-O-(4-(5,6,7,8-tetrahydro-1,8-naphthyridin-2-yl)butyl)homoserine;

N-(1-(3-methoxypyridin-2-yl)cyclopropane-1-carbonyl)-O-(4-(5,6,7,8-tetrahydro-1,8-naphthyridin-2-yl)butyl)homoserine;

N-(1-(quinazolin-4-yl)cyclopropane-1-carbonyl)-O-(4-(5,6,7,8-tetrahydro-1,8-naphthyridin-2-yl)butyl)homoserine;

N-(1-(3-cyanopyridin-2-yl)cyclopropane-1-carbonyl)-O-(4-(5,6,7,8-tetrahydro-1,8-naphthyridin-2-yl)butyl)homoserine;

N-(1-(5-fluoro-2-methoxypyridin-3-yl)cyclopropane-1-carbonyl)-O-(4-(5,6,7,8-tetrahydro-1,8-naphthyridin-2-yl)butyl)homoserine;

N-(1-(3-chloro-5-methoxypyridin-4-yl)cyclopropane-1-carbonyl)-O-(4-(5,6,7,8-tetrahydro-1,8-naphthyridin-2-yl)butyl)homoserine;

N-(1-(2-methoxypyridin-3-yl)cyclopropane-1-carbonyl)-O-(4-(5,6,7,8-tetrahydro-1,8-naphthyridin-2-yl)butyl)homoserine;

N-(1-(3-chloro-5-methylpyridin-2-yl)cyclopropane-1-carbonyl)-O-(4-(5,6,7,8-tetrahydro-1,8-naphthyridin-2-yl)butyl)homoserine;

N-(1-(2-cyano-6-fluorophenyl)cyclopropane-1-carbonyl)-O-(4-(5,6,7,8-tetrahydro-1,8-naphthyridin-2-yl)butyl)homoserine;

N-(1-(3-(difluoromethoxy)pyridin-2-yl)cyclopropane-1-carbonyl)-O-(4-(5,6,7,8-tetrahydro-1,8-naphthyridin-2-yl)butyl)homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)homoserine;

N-(1-(3-(difluoromethyl)pyridin-2-yl)cyclopropane-1-carbonyl)-O-(4-(5,6,7,8-tetrahydro-1,8-naphthyridin-2-yl)butyl)homoserine;

N-(1-(4,6-dimethylpyrimidin-5-yl)cyclopropane-1-carbonyl)-O-(4-(5,6,7,8-tetrahydro-1,8-naphthyridin-2-yl)butyl)homoserine;

N-(1-(3-methylpyrazin-2-yl)cyclopropane-1-carbonyl)-O-(4-(5,6,7,8-tetrahydro-1,8-naphthyridin-2-yl)butyl)homoserine;

N-(1-(2-cyano-4-fluorophenyl)cyclopropane-1-carbonyl)-O-(4-(5,6,7,8-tetrahydro-1,8-naphthyridin-2-yl)butyl)homoserine;

N-(1-(4-chloro-2-methoxypyridin-3-yl)cyclopropane-1-carbonyl)-O-(4-(5,6,7,8-tetrahydro-1,8-naphthyridin-2-yl)butyl)homoserine;

N-(1-(2-cyanophenyl)cyclopropane-1-carbonyl)-O-(4-(5,6,7,8-tetrahydro-1,8-naphthyridin-2-yl)butyl)homoserine;

N-(1-(2-(methylsulfonyl)phenyl)cyclopropane-1-carbonyl)-O-(4-(5,6,7,8-tetrahydro-1,8-naphthyridin-2-yl)butyl)homoserine;

N-(1-(3-fluoro-5-methylpyridin-4-yl)cyclopropane-1-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1-(4-(trifluoromethyl)pyrimidin-5-yl)cyclopropane-1-carbonyl)homoserine;

N-(1-(5-chloropyrimidin-4-yl)cyclopropane-1-carbonyl)-O-(4-(5,6,7,8-tetrahydro-1,8-naphthyridin-2-yl)butyl)homoserine;

N-(1-(3-methoxypyrazin-2-yl)cyclopropane-1-carbonyl)-O-(4-(5,6,7,8-tetrahydro-1,8-naphthyridin-2-yl)butyl)homoserine;

N-(1-(4-chloro-1-methyl-1H-pyrazol-5-yl)cyclopropane-1-carbonyl)-O-(4-(5,6,7,8-tetrahydro-1,8-naphthyridin-2-yl)butyl)homoserine;

N-(1-(3-(fluoromethyl)pyridin-2-yl)cyclopropane-1-carbonyl)-O-(4-(5,6,7,8-tetrahydro-1,8-naphthyridin-2-yl)butyl)homoserine;

N-(1-(3-(methoxymethyl)pyridin-2-yl)cyclopropane-1-carbonyl)-O-(4-(5,6,7,8-tetrahydro-1,8-naphthyridin-2-yl)butyl)homoserine;

N-(1-(1-methyl-1H-pyrazol-5-yl)cyclopropane-1-carbonyl)-O-(4-(5,6,7,8-tetrahydro-1,8-naphthyridin-2-yl)butyl)homoserine;

N-(1-(3-chloro-1H-pyrazol-1-yl)cyclopropane-1-carbonyl)-O-(4-(5,6,7,8-tetrahydro-1,8-naphthyridin-2-yl)butyl)homoserine;

N-(1-(2-cyano-6-methoxyphenyl)cyclopropane-1-carbonyl)-O-(4-(5,6,7,8-tetrahydro-1,8-naphthyridin-2-yl)butyl)homoserine;

N-(1-(2-(difluoromethyl)pyridin-3-yl)cyclopropane-1-carbonyl)-O-(4-(5,6,7,8-tetrahydro-1,8-naphthyridin-2-yl)butyl)homoserine;

N-(1-(3-cyclopropylpyridin-2-yl)cyclopropane-1-carbonyl)-O-(4-(5,6,7,8-tetrahydro-1,8-naphthyridin-2-yl)butyl)homoserine;

N-(1-(4-(difluoromethyl)pyrimidin-5-yl)cyclopropane-1-carbonyl)-O-(4-(5,6,7,8-tetrahydro-1,8-naphthyridin-2-yl)butyl)homoserine;

N-(1-(4-chloro-2,6-dimethylpyrimidin-5-yl)cyclopropane-1-carbonyl)-O-(4-(5,6,7,8-tetrahydro-1,8-naphthyridin-2-yl)butyl)homoserine;

N-(1-(4-methoxy-6-methylpyrimidin-5-yl)cyclopropane-1-carbonyl)-O-(4-(5,6,7,8-tetrahydro-1,8-naphthyridin-2-yl)butyl)homoserine;

N-(1-(4-chloro-6-methoxypyrimidin-5-yl)cyclopropane-1-carbonyl)-O-(4-(5,6,7,8-tetrahydro-1,8-naphthyridin-2-yl)butyl)homoserine;

N-(1-(4-chloro-6-oxo-1,6-dihydropyrimidin-5-yl)cyclopropane-1-carbonyl)-O-(4-(5,6,7,8-tetrahydro-1,8-naphthyridin-2-yl)butyl)homoserine;

N-(1-(5-(difluoromethyl)-1H-imidazol-1-yl)cyclopropane-1-carbonyl)-O-(4-(5,6,7,8-tetrahydro-1,8-naphthyridin-2-yl)butyl)homoserine;

N-(1-(6-chloro-2-oxopyridin-1(2H)-yl)cyclopropane-1-carbonyl)-O-(4-(5,6,7,8-tetrahydro-1,8-naphthyridin-2-yl)butyl)homoserine;

N-(1-(3-chloro-6-oxo-1,6-dihydropyridin-2-yl)cyclopropane-1-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1-(3-(trifluoromethyl)pyrazin-2-yl)cyclopropane-1-carbonyl)homoserine;

N-(1-(4-chloro-2-oxo-1,2-dihydropyridin-3-yl)cyclopropane-1-carbonyl)-O-(4-(5,6,7,8-tetrahydro-1,8-naphthyridin-2-yl)butyl)homoserine;

N-(1-(3,5-dichloro-1H-pyrazol-1-yl)cyclopropane-1-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1-(2-(trifluoromethyl)-1H-imidazol-1-yl)cyclopropane-1-carbonyl)homoserine;

N-(1-(4-chloro-1H-pyrazol-5-yl)cyclopropane-1-carbonyl)-O-(4-(5,6,7,8-tetrahydro-1,8-naphthyridin-2-yl)butyl)homoserine;

N-(1-(5-chloro-3-methyl-1H-pyrazol-1-yl)cyclopropane-1-carbonyl)-O-(4-(5,6,7,8-tetrahydro-1,8-naphthyridin-2-yl)butyl)homoserine;

N-(1-(5-chloro-2-methylpyrimidin-4-yl)cyclopropane-1-carbonyl)-O-(4-(5,6,7,8-tetrahydro-1,8-naphthyridin-2-yl)butyl)homoserine;

N-(1-(5-chloro-1H-pyrazol-4-yl)cyclopropane-1-carbonyl)-O-(4-(5,6,7,8-tetrahydro-1,8-naphthyridin-2-yl)butyl)homoserine;

N-(1-(4-cyano-1-methyl-1H-pyrazol-3-yl)cyclopropane-1-carbonyl)-O-(4-(5,6,7,8-tetrahydro-1,8-naphthyridin-2-yl)butyl)homoserine;

N-(1-(5-chloro-3-oxo-2,3-dihydropyridazin-4-yl)cyclopropane-1-carbonyl)-O-(4-(5,6,7,8-tetrahydro-1,8-naphthyridin-2-yl)butyl)homoserine;

N-(1-(1-methyl-4-(trifluoromethyl)-1H-pyrazol-3-yl)cyclopropane-1-carbonyl)-O-(4-(5,6,7,8-tetrahydro-1,8-naphthyridin-2-yl)butyl)homoserine;

N-(1-(4-cyano-1H-pyrazol-3-yl)cyclopropane-1-carbonyl)-O-(4-(5,6,7,8-tetrahydro-1,8-naphthyridin-2-yl)butyl)homoserine;

N-(1-(4-chloro-1H-imidazol-5-yl)cyclopropane-1-carbonyl)-O-(4-(5,6,7,8-tetrahydro-1,8-naphthyridin-2-yl)butyl)homoserine;

N-(1-(4-chloro-1-methyl-1H-imidazol-5-yl)cyclopropane-1-carbonyl)-O-(4-(5,6,7,8-tetrahydro-1,8-naphthyridin-2-yl)butyl)homoserine;

N-(2-phenylacetyl)-O-(4-(5,6,7,8-tetrahydro-1,8-naphthyridin-2-yl)butyl)homoserine; and N-(1-(5-chlorothiazol-4-yl)cyclopropane-1-carbonyl)-O-(4-(5,6,7,8-tetrahydro-1,8-naphthyridin-2-yl)butyl)homoserine, or a pharmaceutically acceptable salt thereof.

In one variation, the compound detailed herein is selected from the group consisting of:

N-(3-(difluoromethyl)tetrahydrofuran-3-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(trifluoromethyl)cyclohexane-1-carbonyl)-L-homoserine;

N-(4-(4-fluorophenyl)tetrahydro-2H-pyran-4-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(3-(trifluoromethyl)phenyl)tetrahydro-2H-pyran-4-carbonyl)-L-homoserine;

N-(4-(3-methoxyphenyl)tetrahydro-2H-pyran-4-carbonyl)-O-(4-(5,6,7,8-tetrahydro-1,8-naphthyridin-2-yl)butyl)-L-homoserine;

N-(4-(3-fluorophenyl)tetrahydro-2H-pyran-4-carbonyl)-O-(4-(5,6,7,8-tetrahydro-1,8-naphthyridin-2-yl)butyl)-L-homoserine;

N-(4-(3-chlorophenyl)tetrahydro-2H-pyran-4-carbonyl)-O-(4-(5,6,7,8-tetrahydro-1,8-naphthyridin-2-yl)butyl)-L-homoserine;

N-(1-(2-oxoquinolin-1(2H)-yl)cyclopropane-1-carbonyl)-O-(4-(5,6,7,8-tetrahydro-1,8-naphthyridin-2-yl)butyl)-L-homoserine;

N-(1-(6-cyclopropyl-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-methoxy-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-fluoro-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-bromo-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(2-carbamoyl-6-fluorophenyl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(2,2,2-trifluoroethyl)-4-(trifluoromethyl)piperidine-4-carbonyl)-L-homoserine;

N-(1-phenyl-1H-pyrazole-3-carbonyl)-O-(4-(5,6,7,8-tetrahydro-1,8-naphthyridin-2-yl)butyl)-L-homoserine;

N-(1-phenyl-1H-pyrazole-4-carbonyl)-O-(4-(5,6,7,8-tetrahydro-1,8-naphthyridin-2-yl)butyl)-L-homoserine;

N-(1-phenyl-1H-pyrazole-5-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(trifluoromethyl)tetrahydro-2H-pyran-4-carbonyl)-L-homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)homoserine;

N-(1-(4-hydroxy-6-methylpyrimidin-5-yl)cyclopropane-1-carbonyl)-O-(4-(5,6,7,8-tetrahydro-1,8-naphthyridin-2-yl)butyl)-L-homoserine;

methyl N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserinate;

N-(1-(4-chloro-6-methylpyrimidin-5-yl)cyclopropane-1-carbonyl-2,2,3,3-d4)-O-(4-(5,6,7,8-tetrahydro-1,8-naphthyridin-2-yl)butyl)-L-homoserine;

or a pharmaceutically acceptable salt thereof.

In various embodiments, the compound selected from the group consisting of the compounds of the enumerated Examples, e.g., Compounds 1-82, or a pharmaceutically acceptable salt thereof. For example, the compound may be selected from the group consisting of:

N-(2-methyl-2-phenylpropanoyl)-O-(4-(5,6,7,8-tetrahydro-1,8-naphthyridin-2-yl)butyl)homoserine;

N-(2-methyl-2-phenylpropanoyl)-O-(4-(5,6,7,8-tetrahydro-1,8-naphthyridin-2-yl)butyl)-L-homoserine;

N-((S)-2-phenylpropanoyl)-O-(4-(5,6,7,8-tetrahydro-1,8-naphthyridin-2-yl)butyl)-L-homoserine;

N-(2-(2,3-difluoro-6-methoxyphenyl)-2-methylpropanoyl)-O-(4-(5,6,7,8-tetrahydro-1,8-naphthyridin-2-yl)butyl)-L-homoserine;

N-(2-(2-(difluoromethoxy)-6-fluorophenyl)-2-methylpropanoyl)-O-(4-(5,6,7,8-tetrahydro-1,8-naphthyridin-2-yl)butyl)-L-homoserine;

N-(1-(2-chlorophenyl)cyclopropane-1-carbonyl)-O-(4-(5,6,7,8-tetrahydro-1,8-naphthyridin-2-yl)butyl)-L-homoserine;

N-(1-(2,6-dichlorophenyl)cyclopropane-1-carbonyl)-O-(4-(5,6,7,8-tetrahydro-1,8-naphthyridin-2-yl)butyl)-L-homoserine;

N-(2-(2-chlorophenyl)-2-methylpropanoyl)-O-(4-(5,6,7,8-tetrahydro-1,8-naphthyridin-2-yl)butyl)-L-homoserine;

N-(1-(2-fluorophenyl)cyclopropane-1-carbonyl)-O-(4-(5,6,7,8-tetrahydro-1,8-naphthyridin-2-yl)butyl)-L-homoserine;

N-(1-phenylcyclopropane-1-carbonyl)-O-(4-(5,6,7,8-tetrahydro-1,8-naphthyridin-2-yl)butyl)-L-homoserine;

N-(1-(pyrazin-2-yl)cyclopropane-1-carbonyl)-O-(4-(5,6,7,8-tetrahydro-1,8-naphthyridin-2-yl)butyl)-L-homoserine;

N-(1-(pyrimidin-2-yl)cyclopropane-1-carbonyl)-O-(4-(5,6,7,8-tetrahydro-1,8-naphthyridin-2-yl)butyl)-L-homoserine;

N-(1-(2-methylpyridin-3-yl)cyclopropane-1-carbonyl)-O-(4-(5,6,7,8-tetrahydro-1,8-naphthyridin-2-yl)butyl)-L-homoserine;

N-(1-(3-chloro-5-fluoropyridin-2-yl)cyclopropane-1-carbonyl)-O-(4-(5,6,7,8-tetrahydro-1,8-naphthyridin-2-yl)butyl)-L-homoserine;

N-(1-(3-chloropyridin-2-yl)cyclopropane-1-carbonyl)-O-(4-(5,6,7,8-tetrahydro-1,8-naphthyridin-2-yl)butyl)-L-homoserine;

N-(1-(4-methylpyridin-3-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(o-tolyl)cyclopropane-1-carbonyl)-L-homoserine;

N-(1-(6-methoxypyridin-2-yl)cyclopropane-1-carbonyl)-O-(4-(5,6,7,8-tetrahydro-1,8-naphthyridin-2-yl)butyl)-L-homoserine;

N-(1-(4-methylpyrimidin-5-yl)cyclopropane-1-carbonyl)-O-(4-(5,6,7,8-tetrahydro-1,8-naphthyridin-2-yl)butyl)-L-homoserine;

N-(1-(6-methylpyridin-2-yl)cyclopropane-1-carbonyl)-O-(4-(5,6,7,8-tetrahydro-1,8-naphthyridin-2-yl)butyl)-L-homoserine;

N-(1-(2,5-difluoropyridin-3-yl)cyclopropane-1-carbonyl)-O-(4-(5,6,7,8-tetrahydro-1,8-naphthyridin-2-yl)butyl)-L-homoserine;

N-(1-(pyrimidin-5-yl)cyclopropane-1-carbonyl)-O-(4-(5,6,7,8-tetrahydro-1,8-naphthyridin-2-yl)butyl)-L-homoserine;

N-(2-(2-chloro-5-fluoropyridin-3-yl)-2-methylpropanoyl)-O-(4-(5,6,7,8-tetrahydro-1,8-naphthyridin-2-yl)butyl)-L-homoserine;

N-(1-(3,5-dichloropyridin-4-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(3-(trifluoromethyl)pyridin-2-yl)cyclopropane-1-carbonyl)-L-homoserine;

N-(1-(3-chloro-6-methoxypyridin-2-yl)cyclopropane-1-carbonyl)-O-(4-(5,6,7,8-tetrahydro-1,8-naphthyridin-2-yl)butyl)-L-homoserine;

N-(1-(5-cyanopyridin-3-yl)cyclopropane-1-carbonyl)-O-(4-(5,6,7,8-tetrahydro-1,8-naphthyridin-2-yl)butyl)-L-homoserine;

N-(1-(5-fluoro-2-methylpyridin-3-yl)cyclopropane-1-carbonyl)-O-(4-(5,6,7,8-tetrahydro-1,8-naphthyridin-2-yl)butyl)-L-homoserine;

N-(1-(3-methylpyridin-2-yl)cyclopropane-1-carbonyl)-O-(4-(5,6,7,8-tetrahydro-1,8-naphthyridin-2-yl)butyl)-L-homoserine;

N-(1-(3-methoxypyridin-2-yl)cyclopropane-1-carbonyl)-O-(4-(5,6,7,8-tetrahydro-1,8-naphthyridin-2-yl)butyl)-L-homoserine;

N-(1-(quinazolin-4-yl)cyclopropane-1-carbonyl)-O-(4-(5,6,7,8-tetrahydro-1,8-naphthyridin-2-yl)butyl)-L-homoserine;

N-(1-(3-cyanopyridin-2-yl)cyclopropane-1-carbonyl)-O-(4-(5,6,7,8-tetrahydro-1,8-naphthyridin-2-yl)butyl)-L-homoserine;

N-(1-(5-fluoro-2-methoxypyridin-3-yl)cyclopropane-1-carbonyl)-O-(4-(5,6,7,8-tetrahydro-1,8-naphthyridin-2-yl)butyl)-L-homoserine;

N-(1-(3-chloro-5-methoxypyridin-4-yl)cyclopropane-1-carbonyl)-O-(4-(5,6,7,8-tetrahydro-1,8-naphthyridin-2-yl)butyl)-L-homoserine;

N-(1-(2-methoxypyridin-3-yl)cyclopropane-1-carbonyl)-O-(4-(5,6,7,8-tetrahydro-1,8-naphthyridin-2-yl)butyl)-L-homoserine;

N-(1-(3-chloro-5-methylpyridin-2-yl)cyclopropane-1-carbonyl)-O-(4-(5,6,7,8-tetrahydro-1,8-naphthyridin-2-yl)butyl)-L-homoserine;

N-(1-(2-cyano-6-fluorophenyl)cyclopropane-1-carbonyl)-O-(4-(5,6,7,8-tetrahydro-1,8-naphthyridin-2-yl)butyl)-L-homoserine;

N-(1-(3-(difluoromethoxy)pyridin-2-yl)cyclopropane-1-carbonyl)-O-(4-(5,6,7,8-tetrahydro-1,8-naphthyridin-2-yl)butyl)-L-homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserine;

N-(1-(3-(difluoromethyl)pyridin-2-yl)cyclopropane-1-carbonyl)-O-(4-(5,6,7,8-tetrahydro-1,8-naphthyridin-2-yl)butyl)-L-homoserine;

N-(1-(4,6-dimethylpyrimidin-5-yl)cyclopropane-1-carbonyl)-O-(4-(5,6,7,8-tetrahydro-1,8-naphthyridin-2-yl)butyl)-L-homoserine;

N-(1-(3-methylpyrazin-2-yl)cyclopropane-1-carbonyl)-O-(4-(5,6,7,8-tetrahydro-1,8-naphthyridin-2-yl)butyl)-L-homoserine;

N-(1-(2-cyano-4-fluorophenyl)cyclopropane-1-carbonyl)-O-(4-(5,6,7,8-tetrahydro-1,8-naphthyridin-2-yl)butyl)-L-homoserine;

N-(1-(4-chloro-2-methoxypyridin-3-yl)cyclopropane-1-carbonyl)-O-(4-(5,6,7,8-tetrahydro-1,8-naphthyridin-2-yl)butyl)-L-homoserine;

N-(1-(2-cyanophenyl)cyclopropane-1-carbonyl)-O-(4-(5,6,7,8-tetrahydro-1,8-naphthyridin-2-yl)butyl)-L-homoserine;

N-(1-(2-(methylsulfonyl)phenyl)cyclopropane-1-carbonyl)-O-(4-(5,6,7,8-tetrahydro-1,8-naphthyridin-2-yl)butyl)-L-homoserine;

N-(1-(3-fluoro-5-methylpyridin-4-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(4-(trifluoromethyl)pyrimidin-5-yl)cyclopropane-1-carbonyl)-L-homoserine;

N-(1-(5-chloropyrimidin-4-yl)cyclopropane-1-carbonyl)-O-(4-(5,6,7,8-tetrahydro-1,8-naphthyridin-2-yl)butyl)-L-homoserine;

N-(1-(3-methoxypyrazin-2-yl)cyclopropane-1-carbonyl)-O-(4-(5,6,7,8-tetrahydro-1,8-naphthyridin-2-yl)butyl)-L-homoserine;

N-(1-(4-chloro-1-methyl-1H-pyrazol-5-yl)cyclopropane-1-carbonyl)-O-(4-(5,6,7,8-tetrahydro-1,8-naphthyridin-2-yl)butyl)-L-homoserine;

N-(1-(3-(fluoromethyl)pyridin-2-yl)cyclopropane-1-carbonyl)-O-(4-(5,6,7,8-tetrahydro-1,8-naphthyridin-2-yl)butyl)-L-homoserine;

N-(1-(3-(methoxymethyl)pyridin-2-yl)cyclopropane-1-carbonyl)-O-(4-(5,6,7,8-tetrahydro-1,8-naphthyridin-2-yl)butyl)-L-homoserine;

N-(1-(1-methyl-1H-pyrazol-5-yl)cyclopropane-1-carbonyl)-O-(4-(5,6,7,8-tetrahydro-1,8-naphthyridin-2-yl)butyl)-L-homoserine;

N-(1-(3-chloro-1H-pyrazol-1-yl)cyclopropane-1-carbonyl)-O-(4-(5,6,7,8-tetrahydro-1,8-naphthyridin-2-yl)butyl)-L-homoserine;

N-(1-(2-cyano-6-methoxyphenyl)cyclopropane-1-carbonyl)-O-(4-(5,6,7,8-tetrahydro-1,8-naphthyridin-2-yl)butyl)-L-homoserine;

N-(1-(2-(difluoromethyl)pyridin-3-yl)cyclopropane-1-carbonyl)-O-(4-(5,6,7,8-tetrahydro-1,8-naphthyridin-2-yl)butyl)-L-homoserine;

N-(1-(3-cyclopropylpyridin-2-yl)cyclopropane-1-carbonyl)-O-(4-(5,6,7,8-tetrahydro-1,8-naphthyridin-2-yl)butyl)-L-homoserine;

N-(1-(4-(difluoromethyl)pyrimidin-5-yl)cyclopropane-1-carbonyl)-O-(4-(5,6,7,8-tetrahydro-1,8-naphthyridin-2-yl)butyl)-L-homoserine;

N-(1-(4-chloro-2,6-dimethylpyrimidin-5-yl)cyclopropane-1-carbonyl)-O-(4-(5,6,7,8-tetrahydro-1,8-naphthyridin-2-yl)butyl)-L-homoserine;

N-(1-(4-methoxy-6-methylpyrimidin-5-yl)cyclopropane-1-carbonyl)-O-(4-(5,6,7,8-tetrahydro-1,8-naphthyridin-2-yl)butyl)-L-homoserine;

N-(1-(4-chloro-6-methoxypyrimidin-5-yl)cyclopropane-1-carbonyl)-O-(4-(5,6,7,8-tetrahydro-1,8-naphthyridin-2-yl)butyl)-L-homoserine;

N-(1-(4-chloro-6-oxo-1,6-dihydropyrimidin-5-yl)cyclopropane-1-carbonyl)-O-(4-(5,6,7,8-tetrahydro-1,8-naphthyridin-2-yl)butyl)-L-homoserine;

N-(1-(5-(difluoromethyl)-1H-imidazol-1-yl)cyclopropane-1-carbonyl)-O-(4-(5,6,7,8-tetrahydro-1,8-naphthyridin-2-yl)butyl)-L-homoserine;

N-(1-(6-chloro-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(3-chloro-6-oxo-1,6-dihydropyridin-2-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(3-(trifluoromethyl)pyrazin-2-yl)cyclopropane-1-carbonyl)-L-homoserine;

N-(1-(4-chloro-2-oxo-1,2-dihydropyridin-3-yl)cyclopropane-1-carbonyl)-O-(4-(5,6,7,8-tetrahydro-1,8-naphthyridin-2-yl)butyl)-L-homoserine;

N-(1-(3,5-dichloro-1H-pyrazol-1-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(2-(trifluoromethyl)-1H-imidazol-1-yl)cyclopropane-1-carbonyl)-L-homoserine;

N-(1-(4-chloro-1H-pyrazol-5-yl)cyclopropane-1-carbonyl)-O-(4-(5,6,7,8-tetrahydro-1,8-naphthyridin-2-yl)butyl)-L-homoserine;

N-(1-(5-chloro-3-methyl-1H-pyrazol-1-yl)cyclopropane-1-carbonyl)-O-(4-(5,6,7,8-tetrahydro-1,8-naphthyridin-2-yl)butyl)-L-homoserine;

N-(1-(5-chloro-2-methylpyrimidin-4-yl)cyclopropane-1-carbonyl)-O-(4-(5,6,7,8-tetrahydro-1,8-naphthyridin-2-yl)butyl)-L-homoserine;

N-(1-(5-chloro-1H-pyrazol-4-yl)cyclopropane-1-carbonyl)-O-(4-(5,6,7,8-tetrahydro-1,8-naphthyridin-2-yl)butyl)-L-homoserine;

N-(1-(4-cyano-1-methyl-1H-pyrazol-3-yl)cyclopropane-1-carbonyl)-O-(4-(5,6,7,8-tetrahydro-1,8-naphthyridin-2-yl)butyl)-L-homoserine;

N-(1-(5-chloro-3-oxo-2,3-dihydropyridazin-4-yl)cyclopropane-1-carbonyl)-O-(4-(5,6,7,8-tetrahydro-1,8-naphthyridin-2-yl)butyl)-L-homoserine;

N-(1-(1-methyl-4-(trifluoromethyl)-1H-pyrazol-3-yl)cyclopropane-1-carbonyl)-O-(4-(5,6,7,8-tetrahydro-1,8-naphthyridin-2-yl)butyl)-L-homoserine;

N-(1-(4-cyano-1H-pyrazol-3-yl)cyclopropane-1-carbonyl)-O-(4-(5,6,7,8-tetrahydro-1,8-naphthyridin-2-yl)butyl)-L-homoserine;

N-(1-(4-chloro-1H-imidazol-5-yl)cyclopropane-1-carbonyl)-O-(4-(5,6,7,8-tetrahydro-1,8-naphthyridin-2-yl)butyl)-L-homoserine;

N-(1-(4-chloro-1-methyl-1H-imidazol-5-yl)cyclopropane-1-carbonyl)-O-(4-(5,6,7,8-tetrahydro-1,8-naphthyridin-2-yl)butyl)-L-homoserine;

N-(2-phenylacetyl)-O-(4-(5,6,7,8-tetrahydro-1,8-naphthyridin-2-yl)butyl)-L-homoserine; and N-(1-(5-chlorothiazol-4-yl)cyclopropane-1-carbonyl)-O-(4-(5,6,7,8-tetrahydro-1,8-naphthyridin-2-yl)butyl)-L-homoserine, or a pharmaceutically acceptable salt thereof.

In various embodiments, the compound selected from the group consisting of the compounds of the enumerated Examples, e.g., Compounds 83-104, or a pharmaceutically acceptable salt thereof. For example, the compound may be selected from the group consisting of:

N-(3-(difluoromethyl)tetrahydrofuran-3-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(trifluoromethyl)cyclohexane-1-carbonyl)-L-homoserine;

N-(4-(4-fluorophenyl)tetrahydro-2H-pyran-4-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(3-(trifluoromethyl)phenyl)tetrahydro-2H-pyran-4-carbonyl)-L-homoserine;

N-(4-(3-methoxyphenyl)tetrahydro-2H-pyran-4-carbonyl)-O-(4-(5,6,7,8-tetrahydro-1,8-naphthyridin-2-yl)butyl)-L-homoserine;

N-(4-(3-fluorophenyl)tetrahydro-2H-pyran-4-carbonyl)-O-(4-(5,6,7,8-tetrahydro-1,8-naphthyridin-2-yl)butyl)-L-homoserine;

N-(4-(3-chlorophenyl)tetrahydro-2H-pyran-4-carbonyl)-O-(4-(5,6,7,8-tetrahydro-1,8-naphthyridin-2-yl)butyl)-L-homoserine;

N-(1-(2-oxoquinolin-1(2H)-yl)cyclopropane-1-carbonyl)-O-(4-(5,6,7,8-tetrahydro-1,8-naphthyridin-2-yl)butyl)-L-homoserine;

N-(1-(6-cyclopropyl-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-methoxy-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-fluoro-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-bromo-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(2-carbamoyl-6-fluorophenyl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(2,2,2-trifluoroethyl)-4-(trifluoromethyl)piperidine-4-carbonyl)-L-homoserine;

N-(1-phenyl-1H-pyrazole-3-carbonyl)-O-(4-(5,6,7,8-tetrahydro-1,8-naphthyridin-2-yl)butyl)-L-homoserine;

N-(1-phenyl-1H-pyrazole-4-carbonyl)-O-(4-(5,6,7,8-tetrahydro-1,8-naphthyridin-2-yl)butyl)-L-homoserine;

N-(1-phenyl-1H-pyrazole-5-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(trifluoromethyl)tetrahydro-2H-pyran-4-carbonyl)-L-homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)homoserine;

N-(1-(4-hydroxy-6-methylpyrimidin-5-yl)cyclopropane-1-carbonyl)-O-(4-(5,6,7,8-tetrahydro-1,8-naphthyridin-2-yl)butyl)-L-homoserine;

methyl N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserinate;

N-(1-(4-chloro-6-methylpyrimidin-5-yl)cyclopropane-1-carbonyl-2,2,3,3-d4)-O-(4-(5,6,7,8-tetrahydro-1,8-naphthyridin-2-yl)butyl)-L-homoserine;

or a pharmaceutically acceptable salt thereof.

In one variation, the compound detailed herein is selected from the group consisting of:

N-((S)-2-phenylpropanoyl)-O-(4-(5,6,7,8-tetrahydro-1,8-naphthyridin-2-yl)butyl)-L-homoserine;

N-(1-(2-chlorophenyl)cyclopropane-1-carbonyl)-O-(4-(5,6,7,8-tetrahydro-1,8-naphthyridin-2-yl)butyl)-L-homoserine;

N-(1-(2,6-dichlorophenyl)cyclopropane-1-carbonyl)-O-(4-(5,6,7,8-tetrahydro-1,8-naphthyridin-2-yl)butyl)-L-homoserine;

N-(1-(2-fluorophenyl)cyclopropane-1-carbonyl)-O-(4-(5,6,7,8-tetrahydro-1,8-naphthyridin-2-yl)butyl)-L-homoserine;

N-(1-(2-methylpyridin-3-yl)cyclopropane-1-carbonyl)-O-(4-(5,6,7,8-tetrahydro-1,8-naphthyridin-2-yl)butyl)-L-homoserine;

N-(1-(3-chloro-5-fluoropyridin-2-yl)cyclopropane-1-carbonyl)-O-(4-(5,6,7,8-tetrahydro-1,8-naphthyridin-2-yl)butyl)-L-homoserine;

N-(1-(3-chloropyridin-2-yl)cyclopropane-1-carbonyl)-O-(4-(5,6,7,8-tetrahydro-1,8-naphthyridin-2-yl)butyl)-L-homoserine;

N-(1-(4-methylpyridin-3-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(o-tolyl)cyclopropane-1-carbonyl)-L-homoserine;

N-(1-(6-methoxypyridin-2-yl)cyclopropane-1-carbonyl)-O-(4-(5,6,7,8-tetrahydro-1,8-naphthyridin-2-yl)butyl)-L-homoserine;

N-(1-(4-methylpyrimidin-5-yl)cyclopropane-1-carbonyl)-O-(4-(5,6,7,8-tetrahydro-1,8-naphthyridin-2-yl)butyl)-L-homoserine;

N-(1-(2,5-difluoropyridin-3-yl)cyclopropane-1-carbonyl)-O-(4-(5,6,7,8-tetrahydro-1,8-naphthyridin-2-yl)butyl)-L-homoserine;

N-(1-(3,5-dichloropyridin-4-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(3-(trifluoromethyl)pyridin-2-yl)cyclopropane-1-carbonyl)-L-homoserine;

N-(1-(3-chloro-6-methoxypyridin-2-yl)cyclopropane-1-carbonyl)-O-(4-(5,6,7,8-tetrahydro-1,8-naphthyridin-2-yl)butyl)-L-homoserine;

N-(1-(5-fluoro-2-methylpyridin-3-yl)cyclopropane-1-carbonyl)-O-(4-(5,6,7,8-tetrahydro-1,8-naphthyridin-2-yl)butyl)-L-homoserine;

N-(1-(3-methylpyridin-2-yl)cyclopropane-1-carbonyl)-O-(4-(5,6,7,8-tetrahydro-1,8-naphthyridin-2-yl)butyl)-L-homoserine;

N-(1-(quinazolin-4-yl)cyclopropane-1-carbonyl)-O-(4-(5,6,7,8-tetrahydro-1,8-naphthyridin-2-yl)butyl)-L-homoserine;

N-(1-(3-cyanopyridin-2-yl)cyclopropane-1-carbonyl)-O-(4-(5,6,7,8-tetrahydro-1,8-naphthyridin-2-yl)butyl)-L-homoserine;

N-(1-(5-fluoro-2-methoxypyridin-3-yl)cyclopropane-1-carbonyl)-O-(4-(5,6,7,8-tetrahydro-1,8-naphthyridin-2-yl)butyl)-L-homoserine;

N-(1-(3-chloro-5-methoxypyridin-4-yl)cyclopropane-1-carbonyl)-O-(4-(5,6,7,8-tetrahydro-1,8-naphthyridin-2-yl)butyl)-L-homoserine;

N-(1-(3-chloro-5-methylpyridin-2-yl)cyclopropane-1-carbonyl)-O-(4-(5,6,7,8-tetrahydro-1,8-naphthyridin-2-yl)butyl)-L-homoserine;

N-(1-(2-cyano-6-fluorophenyl)cyclopropane-1-carbonyl)-O-(4-(5,6,7,8-tetrahydro-1,8-naphthyridin-2-yl)butyl)-L-homoserine;

N-(1-(3-(difluoromethoxy)pyridin-2-yl)cyclopropane-1-carbonyl)-O-(4-(5,6,7,8-tetrahydro-1,8-naphthyridin-2-yl)butyl)-L-homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserine;

N-(1-(3-(difluoromethyl)pyridin-2-yl)cyclopropane-1-carbonyl)-O-(4-(5,6,7,8-tetrahydro-1,8-naphthyridin-2-yl)butyl)-L-homoserine;

N-(1-(3-methylpyrazin-2-yl)cyclopropane-1-carbonyl)-O-(4-(5,6,7,8-tetrahydro-1,8-naphthyridin-2-yl)butyl)-L-homoserine;

N-(1-(2-cyano-4-fluorophenyl)cyclopropane-1-carbonyl)-O-(4-(5,6,7,8-tetrahydro-1,8-naphthyridin-2-yl)butyl)-L-homoserine;

N-(1-(3-fluoro-5-methylpyridin-4-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(4-(trifluoromethyl)pyrimidin-5-yl)cyclopropane-1-carbonyl)-L-homoserine;

N-(1-(5-chloropyrimidin-4-yl)cyclopropane-1-carbonyl)-O-(4-(5,6,7,8-tetrahydro-1,8-naphthyridin-2-yl)butyl)-L-homoserine;

N-(1-(4-chloro-1-methyl-1H-pyrazol-5-yl)cyclopropane-1-carbonyl)-O-(4-(5,6,7,8-tetrahydro-1,8-naphthyridin-2-yl)butyl)-L-homoserine;

N-(1-(3-(fluoromethyl)pyridin-2-yl)cyclopropane-1-carbonyl)-O-(4-(5,6,7,8-tetrahydro-1,8-naphthyridin-2-yl)butyl)-L-homoserine;

N-(1-(2-cyano-6-methoxyphenyl)cyclopropane-1-carbonyl)-O-(4-(5,6,7,8-tetrahydro-1,8-naphthyridin-2-yl)butyl)-L-homoserine;

N-(1-(4-(difluoromethyl)pyrimidin-5-yl)cyclopropane-1-carbonyl)-O-(4-(5,6,7,8-tetrahydro-1,8-naphthyridin-2-yl)butyl)-L-homoserine;

N-(1-(4-chloro-2,6-dimethylpyrimidin-5-yl)cyclopropane-1-carbonyl)-O-(4-(5,6,7,8-tetrahydro-1,8-naphthyridin-2-yl)butyl)-L-homoserine;

N-(1-(4-methoxy-6-methylpyrimidin-5-yl)cyclopropane-1-carbonyl)-O-(4-(5,6,7,8-tetrahydro-1,8-naphthyridin-2-yl)butyl)-L-homoserine;

N-(1-(4-chloro-6-methoxypyrimidin-5-yl)cyclopropane-1-carbonyl)-O-(4-(5,6,7,8-tetrahydro-1,8-naphthyridin-2-yl)butyl)-L-homoserine;

N-(1-(6-chloro-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(3-chloro-6-oxo-1,6-dihydropyridin-2-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(3-(trifluoromethyl)pyrazin-2-yl)cyclopropane-1-carbonyl)-L-homoserine;

N-(1-(4-chloro-2-oxo-1,2-dihydropyridin-3-yl)cyclopropane-1-carbonyl)-O-(4-(5,6,7,8-tetrahydro-1,8-naphthyridin-2-yl)butyl)-L-homoserine;

N-(1-(3,5-dichloro-1H-pyrazol-1-yl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(2-(trifluoromethyl)-1H-imidazol-1-yl)cyclopropane-1-carbonyl)-L-homoserine;

N-(1-(4-chloro-1H-pyrazol-5-yl)cyclopropane-1-carbonyl)-O-(4-(5,6,7,8-tetrahydro-1,8-naphthyridin-2-yl)butyl)-L-homoserine;

N-(1-(5-chloro-3-methyl-1H-pyrazol-1-yl)cyclopropane-1-carbonyl)-O-(4-(5,6,7,8-tetrahydro-1,8-naphthyridin-2-yl)butyl)-L-homoserine;

N-(1-(5-chloro-2-methylpyrimidin-4-yl)cyclopropane-1-carbonyl)-O-(4-(5,6,7,8-tetrahydro-1,8-naphthyridin-2-yl)butyl)-L-homoserine;

N-(1-(5-chloro-1H-pyrazol-4-yl)cyclopropane-1-carbonyl)-O-(4-(5,6,7,8-tetrahydro-1,8-naphthyridin-2-yl)butyl)-L-homoserine;

N-(1-(4-cyano-1-methyl-1H-pyrazol-3-yl)cyclopropane-1-carbonyl)-O-(4-(5,6,7,8-tetrahydro-1,8-naphthyridin-2-yl)butyl)-L-homoserine;

N-(1-(5-chloro-3-oxo-2,3-dihydropyridazin-4-yl)cyclopropane-1-carbonyl)-O-(4-(5,6,7,8-tetrahydro-1,8-naphthyridin-2-yl)butyl)-L-homoserine;

N-(1-(1-methyl-4-(trifluoromethyl)-1H-pyrazol-3-yl)cyclopropane-1-carbonyl)-O-(4-(5,6,7,8-tetrahydro-1,8-naphthyridin-2-yl)butyl)-L-homoserine;

N-(1-(4-cyano-1H-pyrazol-3-yl)cyclopropane-1-carbonyl)-O-(4-(5,6,7,8-tetrahydro-1,8-naphthyridin-2-yl)butyl)-L-homoserine;

N-(1-(4-chloro-1H-imidazol-5-yl)cyclopropane-1-carbonyl)-O-(4-(5,6,7,8-tetrahydro-1,8-naphthyridin-2-yl)butyl)-L-homoserine;

N-(1-(4-chloro-1-methyl-1H-imidazol-5-yl)cyclopropane-1-carbonyl)-O-(4-(5,6,7,8-tetrahydro-1,8-naphthyridin-2-yl)butyl)-L-homoserine;

N-(1-(5-chlorothiazol-4-yl)cyclopropane-1-carbonyl)-O-(4-(5,6,7,8-tetrahydro-1,8-naphthyridin-2-yl)butyl)-L-homoserine; and or a pharmaceutically acceptable salt thereof.

In one variation, the compound detailed herein is selected from the group consisting of:

N-(2-methyl-2-phenylpropanoyl)-O-(4-(5,6,7,8-tetrahydro-1,8-naphthyridin-2-yl)butyl)-L-homoserine;

N-(2-(2,3-difluoro-6-methoxyphenyl)-2-methylpropanoyl)-O-(4-(5,6,7,8-tetrahydro-1,8-naphthyridin-2-yl)butyl)-L-homoserine;

N-(2-(2-(difluoromethoxy)-6-fluorophenyl)-2-methylpropanoyl)-O-(4-(5,6,7,8-tetrahydro-1,8-naphthyridin-2-yl)butyl)-L-homoserine;

N-(2-(2-chlorophenyl)-2-methylpropanoyl)-O-(4-(5,6,7,8-tetrahydro-1,8-naphthyridin-2-yl)butyl)-L-homoserine;

N-(1-phenylcyclopropane-1-carbonyl)-O-(4-(5,6,7,8-tetrahydro-1,8-naphthyridin-2-yl)butyl)-L-homoserine;

N-(1-(pyrazin-2-yl)cyclopropane-1-carbonyl)-O-(4-(5,6,7,8-tetrahydro-1,8-naphthyridin-2-yl)butyl)-L-homoserine;

N-(1-(pyrimidin-2-yl)cyclopropane-1-carbonyl)-O-(4-(5,6,7,8-tetrahydro-1,8-naphthyridin-2-yl)butyl)-L-homoserine;

N-(1-(6-methylpyridin-2-yl)cyclopropane-1-carbonyl)-O-(4-(5,6,7,8-tetrahydro-1,8-naphthyridin-2-yl)butyl)-L-homoserine;

N-(1-(pyrimidin-5-yl)cyclopropane-1-carbonyl)-O-(4-(5,6,7,8-tetrahydro-1,8-naphthyridin-2-yl)butyl)-L-homoserine;

N-(2-(2-chloro-5-fluoropyridin-3-yl)-2-methylpropanoyl)-O-(4-(5,6,7,8-tetrahydro-1,8-naphthyridin-2-yl)butyl)-L-homoserine;

N-(1-(5-cyanopyridin-3-yl)cyclopropane-1-carbonyl)-O-(4-(5,6,7,8-tetrahydro-1,8-naphthyridin-2-yl)butyl)-L-homoserine;

N-(1-(3-methoxypyridin-2-yl)cyclopropane-1-carbonyl)-O-(4-(5,6,7,8-tetrahydro-1,8-naphthyridin-2-yl)butyl)-L-homoserine;

N-(1-(2-methoxypyridin-3-yl)cyclopropane-1-carbonyl)-O-(4-(5,6,7,8-tetrahydro-1,8-naphthyridin-2-yl)butyl)-L-homoserine;

N-(1-(4,6-dimethylpyrimidin-5-yl)cyclopropane-1-carbonyl)-O-(4-(5,6,7,8-tetrahydro-1,8-naphthyridin-2-yl)butyl)-L-homoserine;

N-(1-(4-chloro-2-methoxypyridin-3-yl)cyclopropane-1-carbonyl)-O-(4-(5,6,7,8-tetrahydro-1,8-naphthyridin-2-yl)butyl)-L-homoserine;

N-(1-(2-cyanophenyl)cyclopropane-1-carbonyl)-O-(4-(5,6,7,8-tetrahydro-1,8-naphthyridin-2-yl)butyl)-L-homoserine;

N-(1-(2-(methylsulfonyl)phenyl)cyclopropane-1-carbonyl)-O-(4-(5,6,7,8-tetrahydro-1,8-naphthyridin-2-yl)butyl)-L-homoserine;

N-(1-(3-methoxypyrazin-2-yl)cyclopropane-1-carbonyl)-O-(4-(5,6,7,8-tetrahydro-1,8-naphthyridin-2-yl)butyl)-L-homoserine;

N-(1-(3-(methoxymethyl)pyridin-2-yl)cyclopropane-1-carbonyl)-O-(4-(5,6,7,8-tetrahydro-1,8-naphthyridin-2-yl)butyl)-L-homoserine;

N-(1-(1-methyl-1H-pyrazol-5-yl)cyclopropane-1-carbonyl)-O-(4-(5,6,7,8-tetrahydro-1,8-naphthyridin-2-yl)butyl)-L-homoserine;

N-(1-(3-chloro-1H-pyrazol-1-yl)cyclopropane-1-carbonyl)-O-(4-(5,6,7,8-tetrahydro-1,8-naphthyridin-2-yl)butyl)-L-homoserine;

N-(1-(2-(difluoromethyl)pyridin-3-yl)cyclopropane-1-carbonyl)-O-(4-(5,6,7,8-tetrahydro-1,8-naphthyridin-2-yl)butyl)-L-homoserine;

N-(1-(3-cyclopropylpyridin-2-yl)cyclopropane-1-carbonyl)-O-(4-(5,6,7,8-tetrahydro-1,8-naphthyridin-2-yl)butyl)-L-homoserine;

N-(1-(4-chloro-6-oxo-1,6-dihydropyrimidin-5-yl)cyclopropane-1-carbonyl)-O-(4-(5,6,7,8-tetrahydro-1,8-naphthyridin-2-yl)butyl)-L-homoserine;

N-(1-(5-(difluoromethyl)-1H-imidazol-1-yl)cyclopropane-1-carbonyl)-O-(4-(5,6,7,8-tetrahydro-1,8-naphthyridin-2-yl)butyl)-L-homoserine; and N-(2-phenylacetyl)-O-(4-(5,6,7,8-tetrahydro-1,8-naphthyridin-2-yl)butyl)-L-homoserine;

or a pharmaceutically acceptable salt thereof.

In one variation, the compound detailed herein is selected from the group consisting of:

N-(3-(difluoromethyl)tetrahydrofuran-3-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(trifluoromethyl)cyclohexane-1-carbonyl)-L-homoserine;

N-(4-(4-fluorophenyl)tetrahydro-2H-pyran-4-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(3-(trifluoromethyl)phenyl)tetrahydro-2H-pyran-4-carbonyl)-L-homoserine;

N-(4-(3-methoxyphenyl)tetrahydro-2H-pyran-4-carbonyl)-O-(4-(5,6,7,8-tetrahydro-1,8-naphthyridin-2-yl)butyl)-L-homoserine;

N-(4-(3-fluorophenyl)tetrahydro-2H-pyran-4-carbonyl)-O-(4-(5,6,7,8-tetrahydro-1,8-naphthyridin-2-yl)butyl)-L-homoserine;

N-(4-(3-chlorophenyl)tetrahydro-2H-pyran-4-carbonyl)-O-(4-(5,6,7,8-tetrahydro-1,8-naphthyridin-2-yl)butyl)-L-homoserine;

N-(1-(2-oxoquinolin-1(2H)-yl)cyclopropane-1-carbonyl)-O-(4-(5,6,7,8-tetrahydro-1,8-naphthyridin-2-yl)butyl)-L-homoserine;

N-(1-(6-cyclopropyl-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-methoxy-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-fluoro-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(6-bromo-2-oxopyridin-1(2H)-yl)cyclopropane-1-carbonyl)-O-(4-(5,6,7,8-tetrahydro-1,8-naphthyridin-2-yl)butyl)-L-homoserine;

N-(1-(2-carbamoyl-6-fluorophenyl)cyclopropane-1-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(1-(2,2,2-trifluoroethyl)-4-(trifluoromethyl)piperidine-4-carbonyl)-L-homoserine;

N-(1-phenyl-1H-pyrazole-3-carbonyl)-O-(4-(5,6,7,8-tetrahydro-1,8-naphthyridin-2-yl)butyl)-L-homoserine;

N-(1-phenyl-1H-pyrazole-4-carbonyl)-O-(4-(5,6,7,8-tetrahydro-1,8-naphthyridin-2-yl)butyl)-L-homoserine;

N-(1-phenyl-1H-pyrazole-5-carbonyl)-O-(4-(5,6,7,8-tetrahydro-1,8-naphthyridin-2-yl)butyl)-L-homoserine;

O-(4-(5,6,7,8-tetrahydro-1,8-naphthyridin-2-yl)butyl)-N-(4-(trifluoromethyl)tetrahydro-2H-pyran-4-carbonyl)-L-homoserine;

N-(1-(4-chloro-6-methylpyrimidin-5-yl)cyclopropane-1-carbonyl)-O-(4-(5,6,7,8-tetrahydro-1,8-naphthyridin-2-yl)butyl)homoserine;

N-(1-(4-hydroxy-6-methylpyrimidin-5-yl)cyclopropane-1-carbonyl)-O-(4-(5,6,7,8-tetrahydro-1,8-naphthyridin-2-yl)butyl)-L-homoserine;

methyl N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserinate;

N-(1-(4-chloro-6-methylpyrimidin-5-yl)cyclopropane-1-carbonyl-2,2,3,3-d4)-O-(4-(5,6,7,8-tetrahydro-1,8-naphthyridin-2-yl)butyl)-L-homoserine;

or a pharmaceutically acceptable salt thereof.

In some embodiments of the species recited herein, the alkyl esters of the free acid species are also encompassed, such as $C_1$-$C_8$ alkyl esters or $C_1$-$C_4$ alkyl esters. In such embodiments, embraced are the alkyl esters (e.g., homoserinate esters) of the free acid, for example, the methyl ester, ethyl ester, n-propyl ester, isopropyl ester, n-butyl ester, sec-butyl ester, isobutyl ester, and tert-butyl ester, as well as the various constitutional isomers of higher alkyl groups, such as $C_5$-$C_8$ alkyl esters.

In some embodiments, a composition, such as a pharmaceutical composition, is provided wherein the composition comprises a compound selected from the group consisting of one or more of the compounds depicted in Table 1, or a stereoisomer thereof (including a mixture of two or more stereoisomers thereof), or a pharmaceutically acceptable salt thereof. In some embodiments, the composition comprises a compound selected from the group consisting of a salt of one or more of the compounds depicted in Table 1. In one aspect, the composition is a pharmaceutical composition that further comprises a pharmaceutically acceptable carrier.

In some embodiments, all salts of compounds referred to herein, such as pharmaceutically acceptable salts, are embraced. In some embodiments, any or all of the stereochemical forms, including any enantiomeric or diastereomeric forms, and any tautomers or other forms of the compounds are embraced. Unless stereochemistry is explicitly indicated in a chemical structure or name, the structure or name is intended to embrace all possible stereoisomers of a compound depicted. In some embodiments, all forms of the compounds, such as crystalline or non-crystalline forms, are included. In some embodiments, prodrugs, solvates and metabolites of the compounds are embraced. Compositions comprising a compound of formula (A) or formula (I) are also intended, such as a composition of substantially pure compound, including a specific stereochemical form thereof. In some embodiments, compositions comprising a mixture of compounds of formula (A) or formula (I) in any ratio are also embraced, including mixtures of two or more stereochemical forms of a compound of formula (A) or formula (I) in any ratio, such that racemic, non-racemic, enantioenriched and scalemic mixtures of a compound. In some embodiments, where one or more tertiary amine moiety is present in the compound, the N-oxides are also provided and described.

Further provided is a pharmaceutical composition comprising a compound of formula (A), or any variation thereof detailed herein, or a salt thereof (e.g., a pharmaceutically acceptable salt thereof), and a pharmaceutically acceptable carrier or excipient.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

Also provided is a pharmaceutical composition comprising a compound of formula (A), or any variation thereof detailed herein, or a salt thereof (e.g., a pharmaceutically acceptable salt thereof), a checkpoint inhibitor, and a pharmaceutically acceptable carrier or excipient.

Also provided is a pharmaceutical composition comprising a compound of formula (I), or any variation thereof detailed herein, or a salt thereof (e.g., a pharmaceutically acceptable salt thereof), a checkpoint inhibitor, and a pharmaceutically acceptable carrier or excipient.

In various embodiments, the checkpoint inhibitor inhibits one of, or one or more of: PD-1, PD-L1, and CTLA-4. For example, in some embodiments, the checkpoint inhibitor inhibits PD-1. In some embodiments, the checkpoint inhibitor inhibits PD-L1. In some embodiments, the checkpoint inhibitor inhibits CTLA-4.

As used herein, "PD-1" checkpoint inhibitors may include, for example: pembrolizumab (also known as MK-3475, lambrolizumab, or Keytruda), which has been targeted at, e.g., melanoma, non-small cell lung cancer, head and neck squamous cell carcinoma; nivolumab, which has been targeted at, e.g., melanoma, squamous cell lung cancer, renal cell carcinoma, and Hodgkin's lymphoma; cemiplimab, which has been targeted at, e.g., cutaneous squamous cell carcinoma (CSCC); spartalizumab, which has been targeted at, e.g., solid tumors and lymphomas; camrelizumab, which has been targeted at, e.g., Hodgkin's lymphoma; sintilimab, which has been targeted at, e.g., non-small cell lung cancer; tislelizumab, which has been targeted at, e.g., solid tumors and hematologic cancers; toripalimab; dostarlimab; INCMGA00012 (MGA012); AMP-224; and AMP-514.

As used herein, "PD-L1" checkpoint inhibitors may include, for example: atezolizumab (Tecentriq), which has been targeted at, e.g., urothelial carcinoma and non-small cell lung cancer; avelumab (Bavencio), which has been targeted at, e.g., metastatic Merkel cell carcinoma and gastric cancer; durvalumab (Imfinzi), which has been targeted at, e.g., urothelial carcinoma and non-small cell lung cancer, e.g., unresectable non-small cell lung cancer after chemoradiation; KN035; CK-301; and BMS-986189.

As used herein, "CTLA4" checkpoint inhibitors may include, for example: ipilimumab, which has been targeted at, e.g., melanoma, lung cancer, and pancreatic cancer; and tremelimumab, which has been targeted at, e.g., melanoma, mesothelioma, and non-small cell lung cancer.

Other checkpoint inhibitors may include dual action compounds, for example: AUNP12, a dual PD-1/PD-L1 inhibitor; and CA-170, a PD-L1 and VISTA antagonist.

Accordingly, in various embodiments, the checkpoint inhibitor includes at least one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab.

Further provided is the use of a compound of formula (A) or formula (I), or any variation thereof detailed herein, or a pharmaceutically acceptable salt thereof, or a pharmaceutical composition thereof, for the treatment of a disease mediated by cells that express one or more of: $\alpha_V\beta_1$; $\alpha_V\beta_6$; and $\alpha_V\beta_8$.

In various embodiments, the use of the compound of formula (A) or formula (I), or any variation thereof detailed herein, or a pharmaceutically acceptable salt thereof, or a pharmaceutical composition thereof, for the treatment of a disease mediated by cells that express one or more of: $\alpha_V\beta_1$; $\alpha_V\beta_6$; and $\alpha_V\beta_8$, is further provided in combination with a checkpoint inhibitor. In some embodiments, the checkpoint inhibitor inhibits one of, or one or more of: PD-1, PD-L1, and CTLA-4. For example, in some embodiments, the checkpoint inhibitor inhibits PD-1. In some embodiments, the checkpoint inhibitor inhibits PD-L1. In some embodiments, the checkpoint inhibitor inhibits CTLA-4. For example, in some embodiments, the checkpoint inhibitor includes at least one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab. In some embodiments, pembrolizumab is dosed at about 200 mg every three weeks or about 400 mg every six weeks. In some embodiments, pembrolizumab is administered as an injection (about 25 mg/mL) via infusion.

Also provided is a method of treating a subject in need thereof. In some embodiments, the method includes providing the subject. In some embodiments, the subject has at least one tissue in need of therapy. In some embodiments, the at least one tissue is characterized by at least one value that is elevated compared to a healthy value in a healthy state of the tissue. In some embodiments, the tissue has an elevated value of $\alpha_V\beta_1$ integrin activity and/or expression. In some embodiments, the tissue has an elevated value of $\alpha_V\beta_6$ integrin activity and/or expression. In some embodiments, the tissue has an elevated value of $\alpha_V\beta_8$ integrin activity and/or expression. In some embodiments, the tissue has an elevated value of a pSMAD/SMAD ratio. In some embodiments, the tissue has an elevated value of new collagen formation or accumulation. In some embodiments, the tissue has an elevated value of total collagen. In some embodiments, the tissue has an elevated value of Type I Collagen gene Col1a1 expression. In some embodiments, the tissue has an elevated value of perforin. In some embodiments, the tissue has an elevated value of Granzyme B. In some embodiments, the tissue has an elevated value of interferon $\gamma$. In some embodiments, the method comprises administering to the subject a therapeutically effective amount of a compound of formula (A) or formula (I), or any variation thereof detailed herein, or a pharmaceutically acceptable salt thereof, or a pharmaceutical composition thereof. In some embodiments, the method comprises administering the therapeutically effective amount of the compound decreasing the at least one value.

In several embodiments, the administering the therapeutically effective amount of the compound decreases the at least one value. For example, in some embodiments, the at least one value is measured after at least one administration of the compound to the subject to determine a post-administration value. In some embodiments, the at least one administration of the compound is therapeutically effective if the post-administration value is decreased compared to the at least one value. In some embodiments, the at least one administration of the compound is therapeutically effective if the post-administration value is about the same as the healthy value.

In some embodiments, the method comprises reducing the activity and/or expression, e.g., activity, of certain integrins. For example, in some embodiments, the method comprises reducing the activity and/or expression of $\alpha_V\beta_1$. In some embodiments, the method comprises reducing the activity and/or expression of $\alpha_V\beta_8$. In some embodiments, the method comprises reducing the activity and/or expression of $\alpha_V\beta_1$ and $\alpha_V\beta_8$. In some embodiments, the method comprises reducing the activity and/or expression of $\alpha_V\beta_6$ and $\alpha_V\beta_8$. In some embodiments, the method comprises reducing the activity and/or expression of $\alpha_V\beta_1$, $\alpha_V\beta_6$, and $\alpha_V\beta_8$. In some embodiments, the reducing the activity and/or expression of each integrin is selective compared to at least one other $\alpha_V$-containing integrin in the subject.

In several embodiments, the activity of $\alpha_V\beta_1$ integrin is reduced in one or more fibroblasts in the subject. In some embodiments, the activity of $\alpha_V\beta_6$ integrin is reduced in one or more epithelial cells in the subject. In some embodiments, the activity of $\alpha_V\beta_8$ integrin is reduced in one or more epithelial cells or cancer cells in the subject.

In various embodiments, the at least one tissue in the subject comprises lung tissue. In some embodiments, the at least one tissue in the subject comprises liver tissue. In some embodiments, the at least one tissue in the subject comprises skin tissue. In some embodiments, the at least one tissue in the subject comprises heart tissue. In some embodiments, the at least one tissue in the subject comprises kidney tissue. In some embodiments, the at least one tissue in the subject comprises gastrointestinal tissue. In some embodiments, the at least one tissue in the subject comprises gall bladder tissue. In some embodiments, the at least one tissue in the subject comprises bile duct tissue. In some embodiments, the at least one tissue in the subject comprises intrahepatic biliary system tissue. In some embodiments, the at least one tissue in the subject comprises extrahepatic biliary system tissue. In some embodiments, the at least one tissue in the subject comprises intrahepatic biliary system tissue and extrahepatic biliary system tissue.

In some embodiments, the at least one tissue in the subject comprises brain tissue. In some embodiments, the at least one tissue in the subject comprises lymph node tissue. In some embodiments, the at least one tissue in the subject comprises stomach tissue. In some embodiments, the at least one tissue in the subject comprises urethra tissue. In some embodiments, the at least one tissue in the subject comprises bladder tissue. In some embodiments, the at least one tissue in the subject comprises prostate tissue. In some embodiments, the at least one tissue in the subject comprises pancreas tissue. In some embodiments, the at least one tissue in the subject comprises mesothelium tissue. In some embodiments, the at least one tissue in the subject comprises breast tissue.

In various embodiments, the tissue has an elevated pSMAD2/SMAD2 value compared to the healthy state of the tissue. In some embodiments, the tissue has an elevated pSMAD3/SMAD3 value compared to the healthy state of the tissue.

In various embodiments, the tissue comprises the tissue of the eye. In some embodiments, the tissue of the eye expresses one, two, or three integrins selected from $\alpha_V\beta_1$, $\alpha_V\beta_6$, and $\alpha_V\beta_8$.

In some embodiments, the subject has cancer. In some embodiments, the subject has a cancer selected from the group consisting of melanoma, colon cancer, breast cancer, prostate cancer, non-small cell lung cancer, head and neck squamous cell carcinoma, squamous cell lung cancer, renal cell carcinoma, lymphoma (such as Hodgkin's lymphoma), cutaneous squamous cell carcinoma (CSCC), urothelial carcinoma, metastatic Merkel cell carcinoma, gastric cancer, lung cancer, pancreatic cancer, and mesothelioma. In some embodiments, the subject has Hodgkin's lymphoma. In some embodiments, the subject has a solid tumor. In some embodiments, the subject has melanoma. In some embodiments, the subject has colon cancer. In some embodiments, the subject has breast cancer. In some embodiments, the subject has prostate cancer. In some embodiments, the subject has non-small cell lung cancer. In some embodiments, the subject has head and neck squamous cell carcinoma. In some embodiments, the subject has squamous cell lung cancer. In some embodiments, the subject has renal cell carcinoma. In some embodiments, the subject has lymphoma, such as Hodgkin's lymphoma. In some embodiments, the subject has cutaneous squamous cell carcinoma (CSCC). In some embodiments, the subject has urothelial carcinoma. In some embodiments, the subject has metastatic Merkel cell carcinoma. In some embodiments, the subject has gastric cancer. In some embodiments, the subject has lung cancer. In some embodiments, the subject has pancreatic cancer. In some embodiments, the subject has pancreatic ductal adenocarcinoma (PDAC). In some embodiments, the subject has mesothelioma.

In some embodiments, the subject has a solid tumor. In some embodiments, the subject has a cancer selected from the group consisting of: breast cancer, non-small cell lung cancer, head and neck squamous cell carcinoma, squamous cell lung cancer, renal cell carcinoma, CSCC, urothelial carcinoma, metastatic Merkel cell carcinoma, gastric cancer, lung cancer, pancreatic cancer, and mesothelioma. In some embodiments, the subject has pancreatic cancer. In some embodiments, the subject has pancreatic ductal adenocarcinoma (PDAC).

In some embodiments, the subject has pulmonary fibrosis. In some embodiments, the subject has liver fibrosis. In some embodiments, the subject has skin fibrosis. In some embodiments, the subject has cardiac fibrosis. In some embodiments, the subject has kidney fibrosis. In some embodiments, the subject has gastrointestinal fibrosis. In some embodiments, the subject has primary sclerosing cholangitis. In some embodiments, the subject has biliary fibrosis. In some embodiments, the subject has biliary atresia.

Also provided is a method of characterizing anticancer activity of a small molecule inhibitor in a subject. In some embodiments, the method comprises providing a first live cell sample from the subject. In some embodiments, the first live cell sample is characterized by the presence of at least one integrin capable of activating transforming growth factor β (TGF-β) from latency associated peptide-TGF-β. In some embodiments, the method comprises determining a first value in the first live cell sample. In some embodiments, the first value is a pSMAD2/SMAD2 ratio. In some embodiments, the first value is a pSMAD3/SMAD3 ratio. In some embodiments, the first value is a perforin level. In some embodiments, the first value is a granzyme B level. In some embodiments, the first value is an interferon γ level. In some embodiments, the method comprises administering the small molecule to the subject. In some embodiments, the method comprises providing a second live cell sample from the subject. In some embodiments, the second live cell sample is drawn from the same tissue in the subject as the first live cell sample. In some embodiments, the method comprises determining a second value in the second live cell sample. In some embodiments, the second value corresponds to the pSMAD2/SMAD2 ratio, pSMAD3/SMAD3 ratio, perforin level, granzyme B level, or interferon γ level of the first value. In some embodiments, the method comprises characterizing the anticancer activity of the small molecule in the subject by comparing the second value to the first value.

In some embodiments, each live cell sample comprises a plurality of cancer cells derived from a tissue of the subject. In some embodiments, each live cell sample comprises a plurality of cancer cells derived from a hematocyte of the subject. In some embodiments, the at least one tissue in the subject comprises skin. In some embodiments, the at least one tissue in the subject comprises lung. In some embodiments, the at least one tissue in the subject comprises brain. In some embodiments, the at least one tissue in the subject comprises lymph node. In some embodiments, the at least one tissue in the subject comprises stomach. In some embodiments, the at least one tissue in the subject comprises urethra. In some embodiments, the at least one tissue in the subject comprises kidney. In some embodiments, the at least one tissue in the subject comprises bladder. In some embodiments, the at least one tissue in the subject comprises prostate. In some embodiments, the at least one tissue in the subject comprises liver. In some embodiments, the at least one tissue in the subject comprises pancreas. In some embodiments, the at least one tissue in the subject comprises mesothelium. In some embodiments, the at least one tissue in the subject comprises breast.

In several embodiments, the at least one integrin includes $\alpha_V$. In some embodiments, the at least one integrin is $\alpha_V\beta_1$. In some embodiments, the at least one integrin is $\alpha_V\beta_6$. In some embodiments, the at least one integrin is $\alpha_V\beta_8$. In some embodiments, the at least one integrin includes $\alpha_V\beta_1$ and $\alpha_V\beta_6$. In some embodiments, the at least one integrin includes $\alpha_V\beta_6$ and $\alpha_V\beta_8$. In some embodiments, the at least one integrin includes $\alpha_V\beta_1$, $\alpha_V\beta_6$, and $\alpha_V\beta_8$. In some embodiments, the first and second values are pSMAD2/SMAD2 ratios or pSMAD3/SMAD3 ratios.

In various embodiments, the administering the small molecule to the subject comprises administering any aspect of the compound of formula (A) or formula (I) or a salt thereof, or a pharmaceutical composition thereof, as described herein. In some embodiments, the method further comprise administering a checkpoint inhibitor to the subject. In some embodiments, the characterizing the anticancer activity of the small molecule in the subject comprise comparing the second value to a first value. In some embodiments, the method comprises characterizing the anticancer activity of the small molecule together with the checkpoint inhibitor.

In some embodiments, the subject has breast cancer. In some embodiments, an effective amount of Compound 39 is administered to the subject. In some embodiments, the effective amount of Compound 39 is administered to the subject in a solution. In some embodiments, the solution comprises ethanol, propylene glycol, and PBS. In some embodiments, the solution comprises about 5% to about 15% v/v ethanol, about 65% to about 75% w/v propylene glycol, and about 15% to about 25% v/v PBS. In some embodiments, the solution comprises about 10% v/v ethanol, about 70% w/v propylene glycol, and about 20% v/v PBS. In some embodiments, the effective amount of the Compound 39 is administered to the subject at a dose over a duration. In some embodiments, the dose is about 135 to about 150 mg/kg body weight of the subject. In some embodiments, the dose is about 144 mg/kg body weight of the subject. In some embodiments, the duration is about 20 days, about 25 days, or about 30 days. In some embodiments, the duration is about 28 days. In some embodiments, at least one of mAbs, anti-mPD-1 and anti-$\alpha_V\beta_8$ is administered to the subject. In some embodiments, at least one of mAbs, anti-mPD-1 and anti-$\alpha_V\beta_8$ is administered to the subject in PBS by intraperitoneal injection. In some embodiments, at least one of mAbs, anti-mPD-1 and anti-$\alpha_V\beta_8$ is administered to the subject in PBS by intraperitoneal injection at a dose of about 10 mg/kg body weight of the subject for a frequency during a time period. In some embodiments, at least one of mAbs, anti-mPD-1 and anti-$\alpha_V\beta_8$ is administered to the subject in PBS by intraperitoneal injection at a dose of about 10 mg/kg body weight of the subject twice a week during the time period of two weeks. In some embodiments, administering Compound 39+anti-mPD-1 to the subject reduces tumor volume in the subject having breast cancer. In some embodiments, administering Compound 39+anti-$\alpha_V\beta_8$+anti-mPD-1 to the subject having breast cancer reduces growth and volume of the tumor. In some embodiments, administering Compound 39 to the subject having breast cancer reduces tumor growth.

In some embodiments, the subject has pancreatic cancer. In some embodiments, an effective amount of Compound 39 is administered to the subject. In some embodiments, the effective amount of Compound 39 is administered to the subject in a solution. In some embodiments, the solution comprises ethanol, propylene glycol, and PBS. In some embodiments, the solution comprises about 5% to about 15% v/v ethanol, about 65% to about 75% w/v propylene glycol, and about 15% to about 25% v/v PBS. In some embodiments, the solution comprises about 10% v/v ethanol, about 70% w/v propylene glycol, and about 20% v/v PBS. In some embodiments, the effective amount of the Compound 39 is administered to the subject at a dose over a duration. In some embodiments, the dose is about 135 to about 150 mg/kg body weight of the subject. In some embodiments, the dose is about 144 mg/kg body weight of the subject. In some embodiments, the duration is about 20 days, about 25 days, or about 30 days. In some embodiments, the duration is about 28 days. In some embodiments, at least one of mAbs, anti-mPD-1 and anti-$\alpha_v\beta_8$ is administered to the subject. In some embodiments, at least one of mAbs, anti-mPD-1 and anti-$\alpha_v\beta_8$ is administered to the subject in PBS by intraperitoneal injection. In some embodiments, at least one of mAbs, anti-mPD-1 and anti-$\alpha_v\beta_8$ is administered to the subject in PBS by intraperitoneal injection at a dose of about 10 mg/kg body weight of the subject for a frequency during a time period. In some embodiments, at least one of mAbs, anti-mPD-1 and anti-$\alpha_v\beta_8$ is administered to the subject in PBS by intraperitoneal injection at a dose of about 10 mg/kg body weight of the subject twice a week during the time period of two weeks. In some embodiments, administering Compound 39 to the subject having pancreatic cancer reduces tumor growth.

In some embodiments, the subject has colon cancer. In some embodiments, an effective amount of Compound 39 is administered to the subject. In some embodiments, the effective amount of Compound 39 is administered to the subject in a solution. In some embodiments, the solution comprises ethanol, propylene glycol, and PBS. In some embodiments, the solution comprises about 5% to about 15% v/v ethanol, about 65% to about 75% w/v propylene glycol, and about 15% to about 25% v/v PBS. In some embodiments, the solution comprises about 10% v/v ethanol, about 70% w/v propylene glycol, and about 20% v/v PBS. In some embodiments, the effective amount of the Compound 39 is administered to the subject at a dose over a duration. In some embodiments, the dose is about 135 to about 150 mg/kg body weight of the subject. In some embodiments, the dose is about 144 mg/kg body weight of the subject. In some embodiments, the duration is about 20 days, about 25 days, or about 30 days. In some embodiments, the duration is about 28 days. In some embodiments, at least one of mAbs, anti-mPD-1 and anti-$\alpha_v\beta_8$ is administered to the subject. In some embodiments, at least one of mAbs, anti-mPD-1 and anti-$\alpha_v\beta_8$ is administered to the subject in PBS by intraperitoneal injection. In some embodiments, at least one of mAbs, anti-mPD-1 and anti-$\alpha_v\beta_8$ is administered to the subject in PBS by intraperitoneal injection at a dose of about 10 mg/kg body weight of the subject for a frequency during a time period. In some embodiments, at least one of mAbs, anti-mPD-1 and anti-$\alpha_v\beta_8$ is administered to the subject in PBS by intraperitoneal injection at a dose of about 10 mg/kg body weight of the subject twice a week during the time period of two weeks. In some embodiments, administering Compound 39 to the subject having colon cancer reduces tumor growth.

In some embodiments, the subject has pancreatic ductal adenocarcinoma (PDAC). In some embodiments, a compound of formula (A) or formula (I) is administered to the subject that has PDAC via a dosing route for a dosing frequency. In some embodiments, the compound of formula (A) or formula (I) is Compound 39. In some embodiments, the dosing route is an oral gavage dosing route. In some embodiments, the dosing route is the oral gavage dosing route at a dosing level and a dosing volume. In some embodiments, the dosing level is about 300 mg/kg BID and the dosing volume is between about 5 to about 10 mL/kg. In some embodiments, the dosing frequency is a daily dosing frequency for a time period. In some embodiments, the time period is a week, two weeks, three weeks, a month, two months, or three months. In some embodiments, the compound of formula (A) or formula (I) is administered in a solution. In some embodiments, the solution comprises at least one alcohol and a buffer. In some embodiments, the solution comprises ethanol, propylene glycol, and PBS. In some embodiments, the solution comprises between about 5 to about 15% v/v ethanol, between about 65 to about 75% w/v propylene glycol, and between about 15 to about 25% v/v PBS. In some embodiments, the solution comprises about 10% v/v ethanol, about 70% w/v propylene glycol, and about 20% v/v PBS. In some embodiments, the compound of formula (A) or formula (I) is administered to the subject via oral gavage at a dose of about 300 mg/kg body weight over the duration of the time period, where the time period is between about 20 to about 25 days or between about 75 to about 85 days. In some embodiments, the compound of formula (A) or formula (I) is administered to the subject via oral gavage at a dose of about 300 mg/kg body weight over the duration of the time period, where the time period is about 22 days or is about 80 days.

In some embodiments, the compound of formula (A) or formula (I) is co-administered with an antibody during the time period. In some embodiments, the compound of formula (A) or formula (I) is administered prior to administration of the antibody. In some embodiments, the compound of formula (A) or formula (I) is administered subsequent administration of the antibody. In some embodiments, the antibody is anti-PD-1. In some embodiments, the subject is administered the anti-PD-1 in a buffer by intraperitoneal injection. In some embodiments, the subject is administered the anti-PD-1 in PBS by intraperitoneal injection at a dose of 10 mg/kg body weight twice a week for a time period. In some embodiments, the subject is administered the anti-PD-1 in PBS by intraperitoneal injection at the dose of about 10 mg/kg body weight twice a week for the time period of two weeks. In some embodiments, administration of Compound 39 with the anti-PD-1 reduces a weight of a KPC tumor in the subject. In some embodiments, administration of Compound 39 with the anti-PD-1 increases at least one of: $CD8^+$ T cell infiltration in a KPC tumor in the subject, $CD4^+$ T cell infiltration in the KPC tumor in the subject, and survival of the subject having the KPC tumor.

In some embodiments, a compound of formula (A) or formula (I) is administered to the subject that has PDAC via a dosing route for a dosing frequency. In some embodiments, the compound of formula (A) or formula (I) is Compound 39. In some embodiments, the dosing route is an oral gavage dosing route. In some embodiments, the dosing route is an oral gavage dosing route at a dosing level. In some embodiments, the dosing level is about 300 mg/kg BID. In some embodiments, the dosing frequency is once a month.

In some embodiments, the compound of formula (A) or formula (I) is co-administered with a chemotherapy agent. In some embodiments, the compound of formula (A) or formula (I) is administered prior to administration of the chemotherapy agent. In some embodiments, the compound of formula (A) or formula (I) is administered subsequent administration of the chemotherapy agent. In some embodiments, the chemotherapy agent is gemcitabine or abraxane. In some embodiments, administering the chemotherapy agent in combination with the compound of formula (A) or formula (I) reduces at least one of a weight of the tumor in the subject and lung metastases in the subject. In some embodiments, administering the compound of formula (A) or formula (I) reduces lung metastases in the subject.

In some embodiments, the compound of formula (A) or formula (I) is co-administered with a chemotherapy regimen. In some embodiments, the chemotherapy regimen comprises at least two chemotherapy agents. In some embodiments, the chemotherapy regimen comprises folfirinox (FNX). In some embodiments, the compound of formula (A) or formula (I) is administered prior to administration of the chemotherapy regimen. In some embodiments, the compound of formula (A) or formula (I) is administered subsequent administration of the chemotherapy regimen. In some embodiments, administering the chemotherapy regimen in combination with the compound of formula (A) or formula (I) reduces a weight of the tumor in the subject. In some embodiments, administering the chemotherapy regimen in combination with the compound of formula (A) or formula (I) reduces a weight of the tumor in the subject, where the tumor is FNX-resistant.

In some embodiments, the subject has cancer. In some embodiments, the subject has a solid tumor. In some embodiments, the subject has an advanced solid tumor. In some embodiments, the subject has a metastatic solid tumor. In some embodiments, the cancer is treatment-resistant. In some embodiments, the subject is a human subject that is at least 18 years of age. In some embodiments, the subject has received more than one dose of an immunotherapy. In some embodiments, the subject has received at least three doses of the immunotherapy. In some embodiments, the subject has received the at least three doses (200 mg Q3W) of the immunotherapy. In some embodiments, the immunotherapy is pembrolizumab. In some embodiments, the subject has evidence of disease progression at least one month after initiation of the immunotherapy. In some embodiments, the subject has evidence of disease progression at least two months after initiation of the immunotherapy. In some embodiments, subject has evidence of disease progression at least three months after initiation of the immunotherapy. In some embodiments, the subject has no other available treatment options. In some embodiments, the subject has an Eastern Cooperative Oncology Group (ECOG) performance status of 0 or 1. In some embodiments, the subject has adequate bone marrow and organ function. "Adequate bone marrow and organ function" includes hemoglobin ≥10.0 g/dL with no blood transfusions (packed red blood cells and platelet transfusions) in the past 28 days prior to the start of treatment, absolute neutrophil count (ANC) ≥1.5×109/L, no features suggestive of myelodysplastic syndrome (MDS)/acute myeloid leukemia (AML) on a peripheral blood smear, platelet count ≥100×109/L, white blood cells (WBC) >3×109/L, total bilirubin ≤1.5× institutional upper limit of normal, and aspartate transaminase (AST) (SGOT)/alanine transaminase (ALT) (SGPT) ≤2.5× institutional upper limit of normal. In some embodiments, Compound 39 is administered to the subject as a monotherapy for a time period. In some embodiments, the time period is at least 1 day, at least 2 days, at least 3 days, at least 4 days, at least 5 days, at least 6 days, or at least 7 days. In some embodiments, the time period is at least 8 days, at least 9 days, at least 10 days, at least 11 days, at least 12 days, at least 13 days, at least 14 days, at least three weeks, or at least a month. In some embodiments, the immunotherapy is administered in combination with Compound 39 to the subject for a frequency beginning on Day 15. In some embodiments, the frequency is every day, every week, every two weeks, every three weeks, or every month. In some embodiments, pembrolizumab (200 mg Q3W) is administered in combination with Compound 39 to the subject on Day 15 every three weeks. In some embodiments, dose-escalation is determined by a Bayesian optimal interval (BOIN) dose escalation design. In some embodiments, the dose levels comprise multiple levels. In some embodiments, a starting dose of Compound 39 is administered to the target number of subjects in a treatment cohort. In some embodiments, if the stopping rules are met, administration of Compound 39 is stopped. In some embodiments, if the stopping rules have not been met, an assumed dose-limiting toxicity (DLT) rate is calculated. The assumed DLT rate is calculated as (number of subjects experiencing at least one DLT at the current dose during the DLT assessment period)/(total number of subjects being exposed to the current dose). In some embodiments, the target DLT rate is 30%, indicating that less than one out of three subjects is experiencing at least one DLT at the current dose during the DLT assessment period). In some embodiments, if zero out of the three subjects has the DLT and the DLT rate is ≤23.7%, dose-escalation occurs. In some embodiments, if one out of three subjects has the DLT and the DLT rate is between 23.7% and 35.9% (e.g., a 95% confidence interval), the current dose is maintained and the cohort is expanded. In some embodiments, if two out of the three subjects have the DLT and the DLT rate is >35.9%, dose de-escalation occurs. In some embodiments, following the dose-escalation and dose-expansion cohorts, a Simon's 2-stage design is used. In some embodiments, biomarkers are collected from the subject during a time period. In some embodiments, the time period is at Day 28. In some embodiments, the biomarkers include circulating immune cells, circulating markers, circulating tumor DNA, and archival tissue. In some embodiments, the circulating immune cells are retrieved using a CyTOF human immune panel. In some embodiments, the circulating markers include Pro-C3, C4G, GzmB, IFN γ, IL-10, PD-1, PD-L1, TNFα, CXCL9, CCXL12, VEGFα, and $\alpha_V\beta_8$. In some embodiments, the archival tissue is retrieved using the RNA-Seq technique. In some embodiments, the treatment is concluded if one or more endpoints are reached.

Compounds described herein include inhibitors of at least one or more of $\alpha_V\beta_8$, $\alpha_V\beta_1$, and $\alpha_V\beta_6$ integrins. For example, in some embodiments, the compound inhibits $\alpha_V\beta_8$ integrin. In some embodiments, the compound inhibits $\alpha_V\beta_1$ integrin. In some instances, it is desirable for the compound to inhibit two or more integrins. For example, in some embodiments, the compound inhibits $\alpha_V\beta_8$ integrin and $\alpha_V\beta_1$ integrin. In some embodiments, the compound inhibits $\alpha_V\beta_8$ integrin and $\alpha_V\beta_6$ integrin. In some embodiments, the compound inhibits $\alpha_V\beta_8$ integrin, $\alpha_V\beta_1$ integrin, and $\alpha_V\beta_6$ integrin.

In some instances, it is desirable to avoid inhibition of other integrins. In some embodiments, the compound is a selective $\alpha_V\beta_8$ integrin inhibitor. For example, in some embodiments, the compound is a selective $\alpha_V\beta_8$ integrin inhibitor that does not substantially inhibit one or more integrins such as $\alpha_V\beta_1$, $\alpha_V\beta_6$, $\alpha_V\beta_3$, $\alpha_V\beta_5$, $\alpha_4\beta_1$, or $\alpha_5\beta_1$. In some embodiments, the compound is a selective $\alpha_V\beta_8$ integrin inhibitor that does not substantially inhibit $\alpha_V\beta_1$ integrin. In some embodiments, the compound is a selective $\alpha_V\beta_8$ integrin inhibitor that does not substantially inhibit $\alpha_V\beta_6$ integrin. In some embodiments, the compound is a selective $\alpha_V\beta_8$ integrin inhibitor that does not substantially inhibit $\alpha_V\beta_1$ integrin or $\alpha_V\beta_6$ integrin. In some embodiments, the compound is a selective $\alpha_V\beta_8$ integrin inhibitor that does not substantially inhibit $\alpha_V\beta_3$ integrin. In some embodiments, the compound is a selective $\alpha_V\beta_8$ integrin inhibitor that does not substantially inhibit $\alpha_V\beta_5$ integrin. In some embodiments, the compound is a selective $\alpha_V\beta_8$ integrin inhibitor that does not substantially inhibit $\alpha_V\beta_3$ integrin or $\alpha_V\beta_5$ integrin. In some embodiments, the compound is a selective $\alpha_v\beta_8$ integrin inhibitor that does not substantially inhibit $\alpha_4\beta_1$ integrin. In some embodiments, the compound is a selective $\alpha_v\beta_8$ integrin inhibitor that does not substantially inhibit $\alpha_5\beta_1$ integrin. In some embodiments, the compound is a selective $\alpha_v\beta_8$ integrin inhibitor that does not substantially inhibit $\alpha_4\beta_1$ integrin or $\alpha_5\beta_1$ integrin. In some embodiments, the compound is a selective $\alpha_v\beta_8$ integrin inhibitor that does not substantially inhibit $\alpha_v\beta_3$ integrin, $\alpha_v\beta_5$ integrin, $\alpha_4\beta_1$ integrin, or $\alpha_5\beta_1$ integrin. In some embodiments, the compound is a selective $\alpha_v\beta_8$ integrin inhibitor that does not substantially inhibit $\alpha_v\beta_6$ integrin, $\alpha_v\beta_3$ integrin, $\alpha_v\beta_5$ integrin, $\alpha_4\beta_1$ integrin, or $\alpha_5\beta_1$ integrin. In some embodiments, the compound is a selective $\alpha_v\beta_8$ integrin inhibitor that does not substantially inhibit $\alpha_v\beta_1$ integrin, $\alpha_v\beta_3$ integrin, $\alpha_v\beta_5$ integrin, $\alpha_4\beta_1$ integrin, or $\alpha_5\beta_1$ integrin. In some embodiments, the compound is a selective $\alpha_v\beta_8$ integrin inhibitor that does not substantially inhibit $\alpha_v\beta_1$ integrin, $\alpha_v\beta_6$ integrin, $\alpha_v\beta_3$ integrin, $\alpha_v\beta_5$ integrin, $\alpha_4\beta_1$ integrin, or $\alpha_5\beta_1$ integrin.

In some embodiments, isotopically-labeled and/or isotopically-enriched forms of compounds of formula (A) or formula (I) are included. The compounds herein may contain unnatural proportions of atomic isotopes at one or more of the atoms that constitute such compounds. In some embodiments, the compound is isotopically-labeled, such as an isotopically-labeled compound of the formula (A) or formula (I) or variations thereof described herein, where one or more atoms are replaced by an isotope of the same element. Exemplary isotopes that can be incorporated into compounds of formula (A) or formula (I) include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Incorporation of heavier isotopes such as deuterium ($^{2}H$ or D) can afford certain therapeutic advantages resulting from greater metabolic stability, for example, increased in vivo half-life, or reduced dosage requirements and, hence may be preferred in some instances. In some embodiments, provided herein is an isotopically enriched form of any of the formulae described herein, wherein the compound comprises one or more deuterium atoms. In some embodiments, the compounds of formula (A) or formula (I) have one or more of the hydrogen atoms replaced by deuterium. Specific groups may be labeled preferentially with deuterium; for example, a cyclopropyl group can have its attached hydrogen atoms replaced by one or more deuterium atoms, or may be perdeuterated.

Isotopically-labeled compounds of formula (A) or formula (I) can generally be prepared by standard methods and techniques known to those skilled in the art or by procedures similar to those described in the accompanying Examples substituting appropriate isotopically-labeled reagents in place of the corresponding non-labeled reagent.

In some embodiments, any or all metabolites of any of the compounds described. In some embodiments, the metabolites include any chemical species generated by a biotransformation of any of the compounds described, such as intermediates and products of metabolism of the compound.

Articles of manufacture comprising a compound of formula (A) or formula (I), or a salt or solvate thereof, in a suitable container are provided. In some embodiments, the container is a vial, jar, ampoule, preloaded syringe, IV bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms.

General Synthetic Methods

The compounds of formula (A) or formula (I) may be prepared by a number of processes as generally described below and more specifically in the Examples hereinafter (such as the schemes provided below). In the following process descriptions, the symbols when used in the formulae depicted are to be understood to represent those groups described above in relation to the formulae herein.

Where it is desired to obtain a particular stereoisomer of a compound, this may be accomplished from a corresponding mixture of stereoisomers using any suitable conventional procedure for separating stereoisomers or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular stereoisomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds provided herein may be prepared according to Schemes A, B, C, D, E, F, G, H, I, J, K, L, and M; General Procedures B, C, D, E, F, G, H, I, J, K, L, M, N, O, P, Q, R, S, T, U, and V; Examples 1-82 (i.e., Compounds 1-82), and Examples 83-104 (i.e., Compounds 83-104).

Scheme A

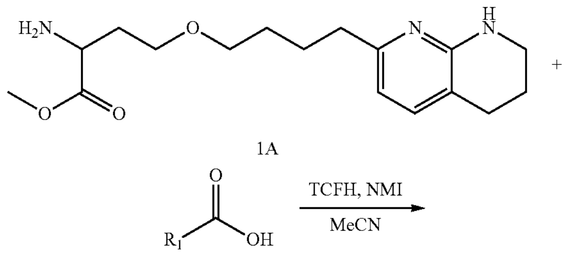

1A

-continued
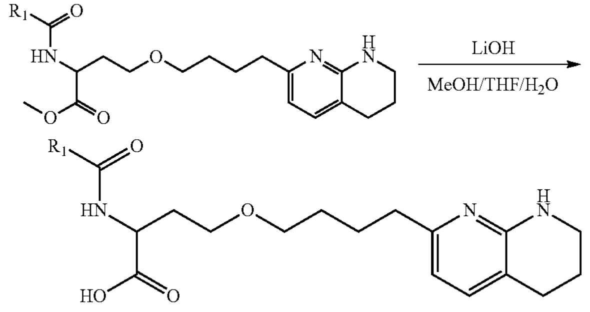
Intermediate 1A was prepared according to US20200109141A1, herein incorporated by reference in its entirety.
Scheme B
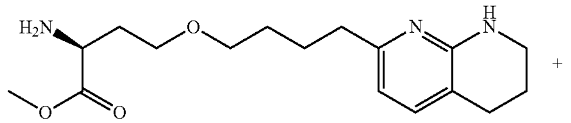
1B
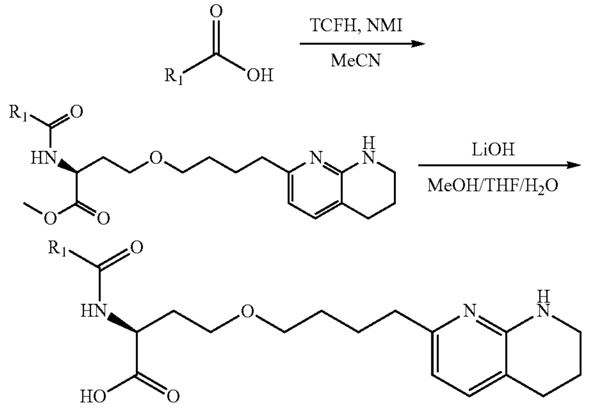
Intermediate 1B was prepared according to US20200109141A1, herein incorporated by reference in its entirety.
Scheme C
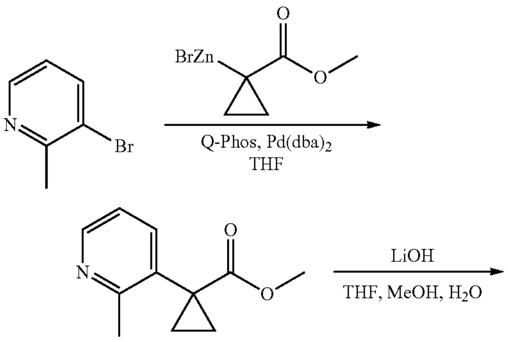
-continued
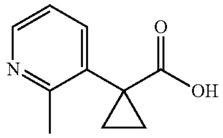
Procedures were adapted from Greszler et al. *Org. Lett.* 2017, 19, 2490-2493, herein incorporated by reference in its entirety.
Scheme D
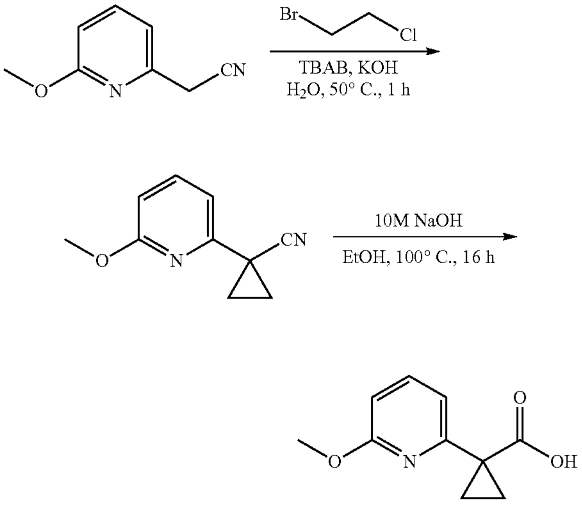
Scheme E
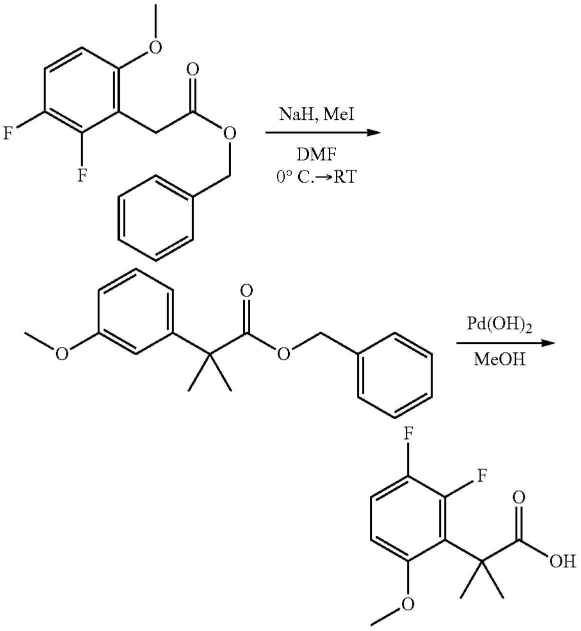

Scheme F
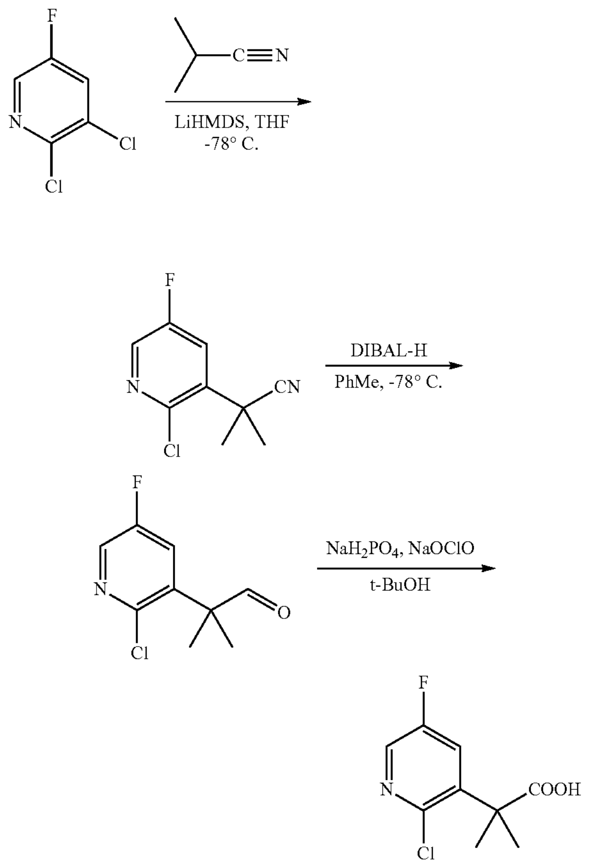
Scheme G
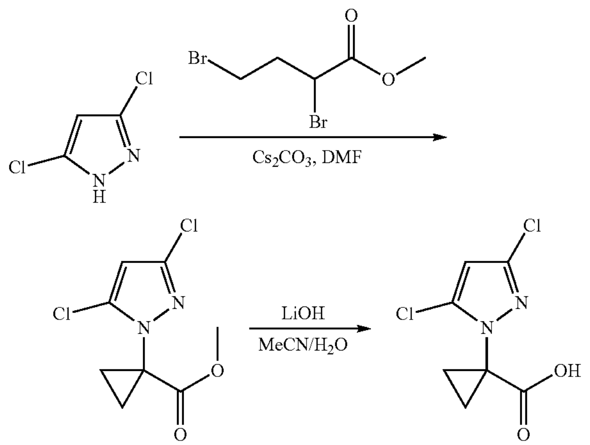
Scheme H
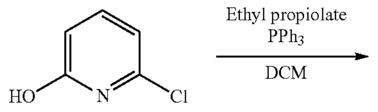
-continued
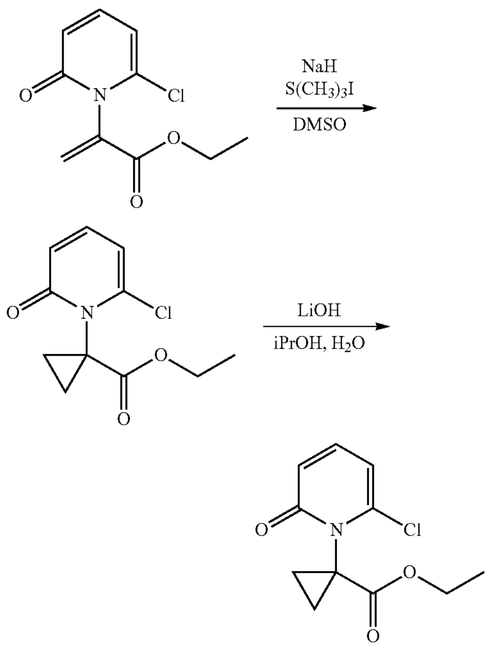
Scheme I
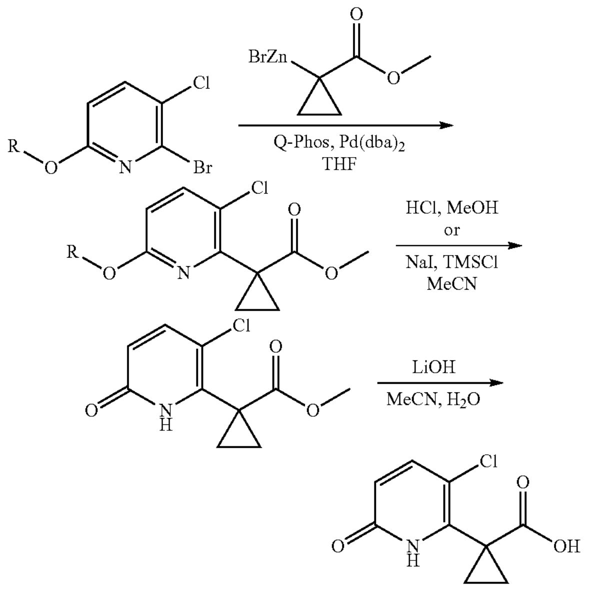
R = Me, Bn
Scheme J
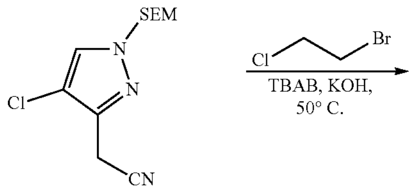

-continued

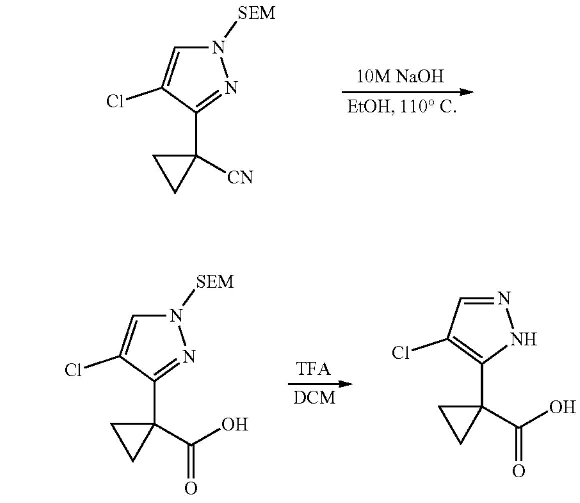

Scheme K

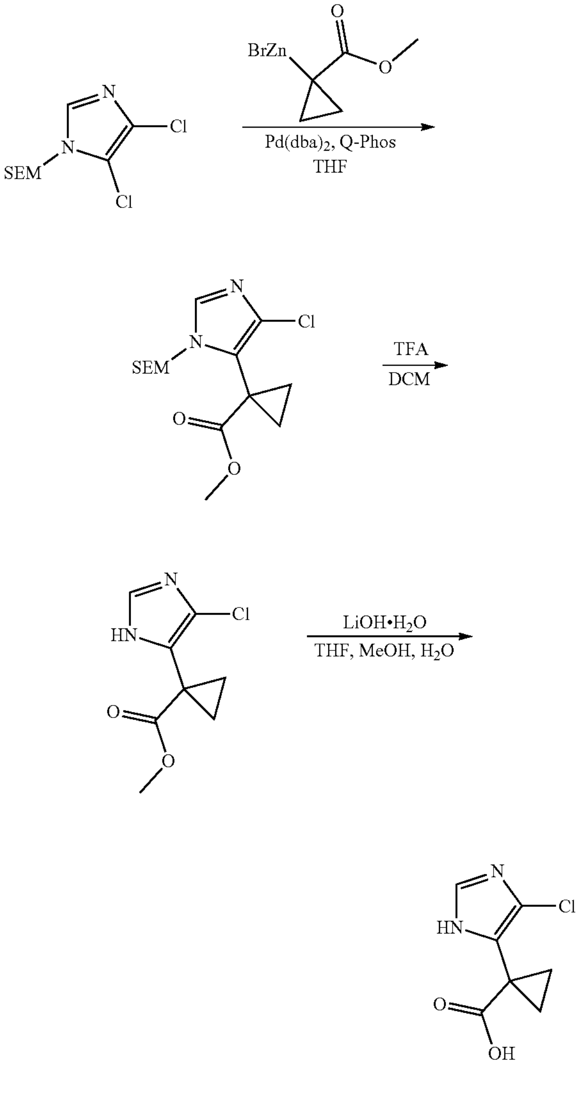

Scheme L

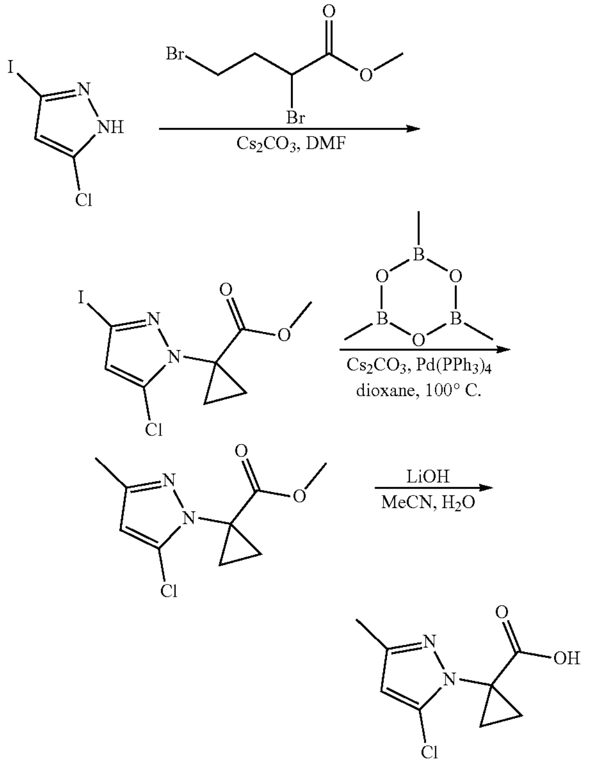

It is understood that the schemes above may be modified to arrive at various compounds of formula (A) or formula (I) by selection of appropriate reagents and starting materials. For a general description of protecting groups and their use, see P. G. M. Wuts and T. W. Greene, *Greene's Protective Groups in Organic Synthesis* 4th edition, Wiley-Interscience, New York, 2006, herein incorporated by reference in its entirety.

Additional methods of preparing compounds according to formula (A) or formula (I), and salts thereof, are provided in the Examples. As a skilled artisan would recognize, the methods of preparation taught herein may be adapted to provide additional compounds within the scope of formula (A) or formula (I), for example, by selecting starting materials which would provide a desired compound.

Pharmaceutical Compositions and Formulations

Pharmaceutical compositions of any of the compounds detailed herein, including compounds of the formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), and (IV), or a pharmaceutically acceptable salt thereof, or compounds 1-82 depicted in Table 1, or compounds 83-104 depicted in Table 1, or a stereoisomer thereof, or a pharmaceutically acceptable salt thereof, or mixtures thereof, are also provided. Thus, in some embodiments, pharmaceutical compositions comprising a compound or a pharmaceutically acceptable salt thereof and a pharmaceutically acceptable carrier or excipient are provided. In one aspect, the pharmaceutically acceptable salt is an acid addition salt, such as a salt formed with an inorganic or organic acid. Pharmaceutical compositions according to the instant disclosure may take a form suitable for oral, buccal, parenteral, nasal, topical or rectal administration or a form suitable for administration by inhalation. In some embodiments, the pharmaceutical composition is prepared from mixtures of any of the compounds detailed herein, or salts thereof. In some embodiments, the pharmaceutical composition is a composition for controlled release of any of the compounds detailed herein.

Pharmaceutical compositions of any of the compounds detailed herein, including compounds of the formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), and (IV), a compound of Table 1, or any one of compounds 1-82 or a stereoisomer thereof, or any one of compounds 83-104 depicted in Table 1 or a stereoisomer thereof, or a pharmaceutically acceptable salt thereof, or mixtures thereof, are also provided.

A compound as detailed herein may in one aspect be in a purified form and compositions comprising a compound in purified forms are detailed herein. In some embodiments, compositions have no more than about 35% impurity, wherein the impurity denotes a compound other than the compound comprising the majority of the composition or a pharmaceutically acceptable salt thereof, for example, in some embodiments, a composition of a compound selected from a compound of Table 1 contains no more than about 35% impurity, wherein the impurity denotes a compound other than the compound of Table 1 or a pharmaceutically acceptable salt thereof. In some embodiments, compositions contain no more than about 25% impurity. In some embodiments, compositions contain no more than about 20% impurity. In still further embodiments, compositions comprising a compound as detailed herein or a pharmaceutically acceptable salt thereof are provided as compositions of substantially pure compounds. "Substantially pure" compositions comprise no more than about 10% impurity, such as a composition comprising less than about 9%, about 7%, about 5%, about 3%, about 1%, or about 0.5% impurity. In some embodiments, a composition containing a compound as detailed herein or a pharmaceutically acceptable salt thereof is in substantially pure form. In still another variation, a composition of substantially pure compound or a pharmaceutically acceptable salt thereof is provided wherein the composition contains or no more than about 10% impurity. In a further variation, a composition of substantially pure compound or a pharmaceutically acceptable salt thereof is provided wherein the composition contains or no more than about 9% impurity. In a further variation, a composition of substantially pure compound or a pharmaceutically acceptable salt thereof is provided wherein the composition contains or no more than about 7% impurity. In a further variation, a composition of substantially pure compound or a pharmaceutically acceptable salt thereof is provided wherein the composition contains or no more than about 5% impurity. In another variation, a composition of substantially pure compound or a pharmaceutically acceptable salt thereof is provided wherein the composition contains or no more than about 3% impurity. In still another variation, a composition of substantially pure compound or a pharmaceutically acceptable salt thereof is provided wherein the composition contains or no more than about 1% impurity. In a further variation, a composition of substantially pure compound or a pharmaceutically acceptable salt thereof is provided wherein the composition contains or no more than about 0.5% impurity. In yet other variations, a composition of substantially pure compound means that the composition contains no more than about 10% or preferably no more than about 5% or more preferably no more than about 3% or even more preferably no more than about 1% impurity or most preferably no more than about 0.5% impurity, which impurity may be the compound in a different stereochemical form. For instance, a composition of substantially pure (S) compound means that the composition contains no more than about 10% or no more than about 5% or no more than about 3% or no more than about 1% or no more than about 0.5% of the I form of the compound.

In further embodiments, the purified forms and substantially pure forms of the compounds apply to any compounds of the formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), and (IV), a compound of Table 1, or any one of compounds 1-82, compounds 83-104, or a stereoisomer thereof.

In one variation, the compounds herein are synthetic compounds prepared for administration to an individual such as a human. In another variation, compositions are provided containing a compound in substantially pure form. In another variation, pharmaceutical compositions comprising a compound detailed herein and a pharmaceutically acceptable carrier or excipient are provided. In another variation, methods of administering a compound are provided. The purified forms, pharmaceutical compositions and methods of administering the compounds are suitable for any compound or form thereof detailed herein.

The compounds detailed herein or pharmaceutically acceptable salts thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or pharmaceutically acceptable salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a pharmaceutically acceptable salt thereof can be used in the preparation of a formulation, such as a pharmaceutical formulation, by combining the compound or compounds, or a pharmaceutically acceptable salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, $21^{st}$ ed. (2005), which is incorporated herein by reference in its entirety.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a tablet of about 10 mg.

Compositions comprising a compound provided herein are also described. In one variation, the composition comprises a compound and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use

Compounds and compositions of, such as a pharmaceutical composition containing a compound of any formula provided herein or a pharmaceutically acceptable salt thereof and a pharmaceutically acceptable carrier or excipient, may be used in methods of administration and treatment as provided herein. In some embodiments, the compounds and compositions are used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (A) or formula (I), or any variation thereof, e.g., a compound of formulae (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof. In one aspect, the individual is a human. In some embodiments, the individual, such as a human, is in need of treatment, such as a human who has or is suspected of having a fibrotic disease. In some embodiments, a variation of the compounds includes any stereoisomer thereof.

In a further aspect, provided is a method of treating a fibrotic disease in an individual in need thereof comprising administering to the individual a therapeutically effective amount of a compound of formula (A), formula (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof. In one aspect, the individual is a human. In some embodiments, the individual, such as a human, is in need of treatment, such as a human who has or is suspected of having a fibrotic disease. In some embodiments, a variation of the compounds includes any stereoisomer thereof.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease. In some embodiments, the individual at risk for developing a fibrotic disease is an individual who has or is suspected of having NAFLD, NASH, CKD, scleroderma, Crohn's Disease, NSIP, PSC, PBC, biliary atresia, or is an individual who has had or is suspected of having had a myocardial infarction.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In some embodiments, the fibrotic disease is a pulmonary fibrosis, e.g., idiopathic pulmonary fibrosis (IPF), interstitial lung disease, systemic sclerosis-associated interstitial lung disease, or radiation-induced pulmonary fibrosis. In some embodiments, the individual at risk for developing a fibrotic disease is an individual who has or is suspected of having a history of viral lung infections.

In some embodiments, the fibrotic disease is a primary sclerosing cholangitis, or biliary fibrosis. In some embodiments, the fibrotic disease is primary biliary cholangitis (also known as primary biliary cirrhosis). In some embodiments, the fibrotic disease is biliary atresia.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic liver disease induced fibrosis, alcoholic steatosis induced liver fibrosis, nonalcoholic fatty liver disease, biliary atresia and cirrhosis.

In some embodiments, the fibrotic disease is biliary tract fibrosis.

In some embodiments, the fibrotic disease is renal fibrosis, e.g., diabetic kidney disease, diabetic nephrosclerosis, hypertensive nephrosclerosis, diabetic nephropathy, focal segmental glomerulosclerosis ("FSGS"), Alport syndrome, chronic kidney disease, and acute kidney injury from contrast induced nephropathy.

In some embodiments, the fibrotic disease is systemic and local sclerosis or scleroderma, keloids and hypertrophic scars, or post-surgical adhesions.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In one aspect, provided is a compound of formula (A) or formula (I), or any variation thereof, e.g., a compound of formulae (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof, for use in the treatment of a fibrotic disease.

Also provided is use of a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof, in the manufacture of a medicament for the treatment of a fibrotic disease.

In another aspect, provided is a method of inhibiting $\alpha_V\beta_8$ integrin in an individual comprising administering a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a stereoisomer thereof, or a compound selected from the compounds depicted in Table 1, or a pharmaceutically acceptable salt thereof.

Also provided is a method of inhibiting TGFβ activation in a cell comprising administering to the cell a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof. In some embodiments, the cell expresses one of, or one or more of: $\alpha_V\beta_1$; $\alpha_V\beta_6$; and $\alpha_V\beta_8$. In some embodiments, the cell expresses $\alpha_V\beta_1$. In some embodiments, the cell expresses $\alpha_V\beta_6$. In some embodiments, the cell expresses $\alpha_V\beta_8$. In some embodiments, the cell expresses $\alpha_V\beta_1$ and $\alpha_V\beta_6$. In some embodiments, the cell expresses $\alpha_V\beta_1$ and $\alpha_V\beta_8$. In some embodiments, the cell expresses $\alpha_V\beta_6$ and $\alpha_V\beta_8$. In some embodiments, the cell expresses $\alpha_V\beta_1$, $\alpha_V\beta_6$, and $\alpha_V\beta_8$. In some embodiments, the cell or cells are associated with the eye.

In some embodiments, the method includes administering to the cell a checkpoint inhibitor. In some embodiments, the checkpoint inhibitor inhibits PD-1. In some embodiments, the checkpoint inhibitor inhibits PD-L1. In some embodiments, the checkpoint inhibitor inhibits CTLA-4. In some embodiments, the checkpoint inhibitor inhibits one or more of: PD-1, PD-L1, and CTLA-4. In some embodiments, the checkpoint inhibitor includes one of, or one or more of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab. In some embodiments, the checkpoint inhibitor is pembrolizumab, which is marketed as Keytruda® (www.keytrudahcp.com, U.S. Pat. Nos. 8,354,509 and 8,900,587, each of which is hereby incorporated by reference in its entirety). In some embodiments, pembrolizumab is dosed at about 200 mg every three weeks or about 400 mg every six weeks. In some embodiments, pembrolizumab is administered as an injection (about 25 mg/mL) via infusion.

In some embodiments, the cells comprise cells associated with a solid tumor. In various embodiments, the cells comprise cells associated with one of, or one or more of: melanoma, colon cancer, non-small cell lung cancer, head and neck squamous cell carcinoma, squamous cell lung cancer, renal cell carcinoma, lymphoma (e.g., Hodgkin's lymphoma), cutaneous squamous cell carcinoma (CSCC), urothelial carcinoma, metastatic Merkel cell carcinoma, gastric cancer, lung cancer, pancreatic cancer, or mesothelioma. In some embodiments, the subject can have pancreatic cancer. In some embodiments, the subject has pancreatic ductal adenocarcinoma (PDAC). In some embodiments, the cells are associated with breast cancer. In some embodiments, the cells are associated with a disease mediated by one or more of $\alpha_V\beta_1$ integrin, $\alpha_V\beta_6$ integrin, and/or $\alpha_V\beta_8$ integrin, e.g., a fibrotic disease, or cancer. For example, in some embodiments, the cells are associated with one of, or one or more of: pulmonary fibrosis, liver fibrosis, skin fibrosis, cardiac fibrosis, kidney fibrosis, gastrointestinal fibrosis, primary sclerosing cholangitis, or biliary fibrosis. In some embodiments, the cells are human cells. In some embodiments, the cell or cells are associated with the eye. In some embodiments, the cell or cells express one, two, or three integrins selected from $\alpha_V\beta_1$, $\alpha_V\beta_6$, and $\alpha_V\beta_8$.

Also provided is a method of inhibiting at least one integrin in an individual in need thereof, comprising administering to the individual a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof. In various embodiments of the method, compounds described herein inhibit at least one or more of $\alpha_V\beta_8$, $\alpha_V\beta_1$, and $\alpha_V\beta_6$ integrins. For example, in some embodiments, the compound inhibits $\alpha_V\beta_8$ integrin. In some embodiments, the compound inhibits $\alpha_V\beta_1$ integrin. In some instances, it is desirable for the compound to inhibit two or more integrins. For example, in some embodiments, the compound inhibits $\alpha_V\beta_8$ integrin and $\alpha_V\beta_1$ integrin. In some embodiments, the compound inhibits $\alpha_V\beta_8$ integrin and $\alpha_V\beta_6$ integrin. In some embodiments, the compound inhibits $\alpha_V\beta_8$ integrin, $\alpha_V\beta_1$ integrin, and $\alpha_V\beta_6$ integrin. In some instances of the method, it is desirable to avoid inhibition of other integrins. In some embodiments, the compound is a selective $\alpha_V\beta_8$ integrin inhibitor. For example, in some embodiments, the compound is a selective $\alpha_V\beta_8$ integrin inhibitor that does not substantially inhibit one or more integrins such as $\alpha_V\beta_1$, $\alpha_V\beta_6$, $\alpha_V\beta_3$, $\alpha_V\beta_5$, $\alpha_4\beta_1$, or $\alpha_5\beta_1$. In some embodiments, the compound is a selective $\alpha_V\beta_8$ integrin inhibitor that does not substantially inhibit $\alpha_V\beta_1$ integrin. In some embodiments, the compound is a selective $\alpha_V\beta_8$ integrin inhibitor that does not substantially inhibit $\alpha_V\beta_6$ integrin. In some embodiments, the compound is a selective $\alpha_V\beta_8$ integrin inhibitor that does not substantially inhibit $\alpha_V\beta_1$ integrin or $\alpha_V\beta_6$ integrin. In some embodiments, the compound is a selective $\alpha_V\beta_8$ integrin inhibitor that does not substantially inhibit $\alpha_V\beta_3$ integrin. In some embodiments, the compound is a selective $\alpha_V\beta_8$ integrin inhibitor that does not substantially inhibit $\alpha_V\beta_5$ integrin. In some embodiments, the compound is a selective $\alpha_V\beta_8$ integrin inhibitor that does not substantially inhibit $\alpha_V\beta_3$ integrin or $\alpha_V\beta_5$ integrin. In some embodiments, the compound is a selective $\alpha_V\beta_8$ integrin inhibitor that does not substantially inhibit $\alpha_4\beta_1$ integrin. In some embodiments, the compound is a selective $\alpha_V\beta_8$ integrin inhibitor that does not substantially inhibit $\alpha_5\beta_1$ integrin. In some embodiments, the compound is a selective $\alpha_V\beta_8$ integrin inhibitor that does not substantially inhibit $\alpha_4\beta_1$ integrin or $\alpha_5\beta_1$ integrin. In some embodiments, the compound is a selective $\alpha_V\beta_8$ integrin inhibitor that does not substantially inhibit $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_6$ integrin, $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_1$ integrin, $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_1$ integrin, $\alpha_V\beta_6$ integrin, $\alpha_V\beta_3$ integrin, $\alpha_V\beta_5$ integrin, $\alpha_4\beta_1$ integrin, or $\alpha_5\beta_1$ integrin. In various embodiments of the method, compounds described herein inhibit at least one or more integrins, and/or selectively inhibit one or more integrins in any combination as described herein.

In all such embodiments, in one aspect the method of inhibition is for an individual in need thereof, such as an individual who has or is suspected of having a fibrotic disease, and wherein the method comprises administering to the individual a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or a stereoisomer thereof, or a pharmaceutically acceptable salt thereof.

Also provided is a method of modulating TGFβ activation in a cell, comprising contacting the cell with the compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a stereoisomer thereof, or a compound selected from the compounds depicted in Table 1, or a pharmaceutically acceptable salt thereof. In another aspect, the modulating comprises inhibiting TGFβ activation in the cell. In another aspect, the TGFβ activation being mediated in the cell by at least one or more of $\alpha_V\beta_8$, $\alpha_V\beta_1$, and $\alpha_V\beta_6$ integrins.

Also provided is a method of treating a subject in need thereof, comprising: administering to the subject a therapeutically effective amount of the compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a stereoisomer thereof, or a compound selected from the compounds depicted in Table 1, or a pharmaceutically acceptable salt thereof, wherein the subject has at least one tissue in need of therapy and the tissue has at least one elevated level of: TGFβ activation and/or expression; $\alpha_V\beta_8$ integrin activity and/or expression; $\alpha_V\beta_1$ integrin activity and/or expression; or $\alpha_V\beta_6$ integrin activity and/or expression; wherein the at least one elevated level is elevated compared to a healthy state of the tissue. In some aspects, the method selectively inhibits at least one integrin as described herein for the compounds, for example, with respect to at least one other integrin such as an $\alpha_V$-containing integrin as described herein for the compounds. For example, in some embodiments, the method selectively inhibits $\alpha_V\beta_8$ integrin compared to $\alpha_V\beta_6$ integrin in the subject. In some embodiments, the method selectively inhibits $\alpha_V\beta_8$ integrin compared to $\alpha_V\beta_1$ integrin in the subject. In some embodiments, the method selectively inhibits $\alpha_V\beta_8$ integrin compared to $\alpha_V\beta_1$ integrin and $\alpha_V\beta_6$ integrin in the subject. In some embodiments, the method inhibits, e.g., selectively with respect to one or more other integrins as described herein such as an $\alpha_V$-containing integrin, $\alpha_V\beta_8$ and $\alpha_V\beta_6$ integrin in the subject. In some embodiments, the method inhibits, e.g., selectively with respect to one or more other integrins as described herein such as an $\alpha_V$-containing integrin, $\alpha_V\beta_8$ and $\alpha_V\beta_1$ integrin in the subject. In some embodiments, the method inhibits, e.g., selectively with respect to one or more other integrins as described herein such as an $\alpha_V$-containing integrin, $\alpha_V\beta_8$, $\alpha_V\beta_1$, and $\alpha_V\beta_6$ integrin in the subject. In some aspects, the $\alpha_V\beta_1$ integrin is inhibited in one or more fibroblasts in the subject. In some aspects, the $\alpha_V\beta_6$ integrin is inhibited in one or more epithelial cells in the subject. In some aspects, the at least one tissue in the subject comprises one or more of: lung tissue, liver tissue, skin tissue, cardiac tissue, kidney tissue, gastrointestinal tissue, gall bladder tissue, and bile duct tissue.

In some embodiments, the method comprises administering to the individual a checkpoint inhibitor. In some embodiments, the checkpoint inhibitor inhibits PD-1. In some embodiments, the checkpoint inhibitor inhibits PD-L1. In some embodiments, the checkpoint inhibitor inhibits CTLA-4. In some embodiments, the checkpoint inhibitor inhibits one or more of: PD-1, PD-L1, and CTLA-4. In some embodiments, the checkpoint inhibitor includes one of, or one or more of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab. In some embodiments, the checkpoint inhibitor is pembrolizumab, which is marketed as Keytruda® (www.keytrudahcp.com, U.S. Pat. Nos. 8,354,509 and 8,900,587, each of which is hereby incorporated by reference in its entirety). In some embodiments, pembrolizumab is dosed at about 200 mg every three weeks or about 400 mg every six weeks. In some embodiments, pembrolizumab is administered as an injection (about 25 mg/mL) via infusion.

In various embodiments, the individual in need of treatment thereof has a solid tumor. In various embodiments, the individual in need of treatment thereof has at least one of: melanoma, colon cancer, non-small cell lung cancer, head and neck squamous cell carcinoma, squamous cell lung cancer, renal cell carcinoma, lymphoma (e.g., Hodgkin's lymphoma), cutaneous squamous cell carcinoma (CSCC), urothelial carcinoma, metastatic Merkel cell carcinoma, gastric cancer, lung cancer, pancreatic cancer, or mesothelioma. In some embodiments, the subject has pancreatic cancer. In some embodiments, the subject has pancreatic ductal adenocarcinoma (PDAC). In some embodiments, the individual in need of treatment thereof has breast cancer. In some embodiments, the individual in need of treatment thereof has a disease mediated by one or more of $\alpha_V\beta_1$ integrin, $\alpha_V\beta_6$ integrin, and/or $\alpha_V\beta_8$ integrin, e.g., a fibrotic disease, or cancer. For example, in some embodiments, the individual has at least one of: pulmonary fibrosis, liver fibrosis, skin fibrosis, cardiac fibrosis, kidney fibrosis, gastrointestinal fibrosis, primary sclerosing cholangitis, or biliary fibrosis.

Also provided is a method of treating cancer in an individual in need thereof, comprising: administering to the subject a therapeutically effective amount of the compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a stereoisomer thereof, or a compound selected from the compounds depicted in Table 1, or a pharmaceutically acceptable salt thereof, or a pharmaceutical composition thereof.

In some embodiments, the cancer comprises a solid tumor. In some embodiments, the cancer is selected from the group consisting of: melanoma, colon cancer, non-small cell lung cancer, head and neck squamous cell carcinoma, squamous cell lung cancer, renal cell carcinoma, lymphoma (e.g., Hodgkin's lymphoma), cutaneous squamous cell carcinoma (CSCC), urothelial carcinoma, prostate cancer, metastatic Merkel cell carcinoma, gastric cancer, lung cancer, pancreatic cancer, and mesothelioma. In some embodiments, the cancer is breast cancer. In some embodiments, the subject has pancreatic cancer. In some embodiments, the subject has pancreatic ductal adenocarcinoma (PDAC).

In some embodiments, the method further comprise administering to the individual a checkpoint inhibitor. In some embodiments, the checkpoint inhibitor inhibits PD-1. In some embodiments, the checkpoint inhibitor inhibits PD-L1. In some embodiments, the checkpoint inhibitor inhibits CTLA-4. In some embodiments, the checkpoint inhibitor inhibits one or more of: PD-1, PD-L1, and CTLA-4. In some embodiments, the checkpoint inhibitor includes one of, or one or more of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab. In some embodiments, the checkpoint inhibitor is pembrolizumab, which is marketed as Keytruda® (www.keytrudahcp.com, U.S. Pat. Nos. 8,354,509 and 8,900,587, each of which is hereby incorporated by reference in its entirety). In some embodiments, pembrolizumab is dosed at about 200 mg every three weeks or about 400 mg every six weeks. In some embodiments, pembrolizumab is administered as an injection (about 25 mg/mL) via infusion.

In one aspect, provided is a compound of formula (A) or formula (I), or any variation thereof, e.g., a compound of formula (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof, for use in the treatment of a fibrotic disease.

Also provided is use of a compound of formula (A), formula (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof, in the manufacture of a medicament for the treatment of a fibrotic disease.

In another aspect, provided is a method of inhibiting at least one integrin in an individual comprising administering a compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof. In various embodiments of the method, compounds described herein inhibit at least one or more of $\alpha_V\beta_8$, $\alpha_V\beta_1$, and $\alpha_V\beta_6$ integrins, as described herein.

Also provided is a method of inhibiting TGFβ activation in a cell comprising administering to the cell a compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV) a compound selected from the compounds depicted in Table 1, or any one of compounds 1-82, or any one of compounds 83-104, or a stereoisomer thereof, or a pharmaceutically acceptable salt thereof.

Also provided is a method of inhibiting at least one integrin in an individual in need thereof, comprising administering to the individual a compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV) a compound selected from the compounds depicted in Table 1, or any one of compounds 1-82, or any one of compounds 83-104, or a stereoisomer thereof, or a pharmaceutically acceptable salt thereof. In various embodiments of the method, compounds described herein inhibit at least one or more of $\alpha_V\beta_8$, $\alpha_V\beta_1$, and $\alpha_V\beta_6$ integrins. For example, in some embodiments, the compound inhibits $\alpha_V\beta_8$ integrin. In some embodiments, the compound inhibits $\alpha_V\beta_1$ integrin. In some instances, it is desirable for the compound to inhibit two or more integrins. For example, in some embodiments, the compound inhibits $\alpha_V\beta_8$ integrin and $\alpha_V\beta_1$ integrin. In some embodiments, the compound inhibits $\alpha_V\beta_8$ integrin and $\alpha_V\beta_6$ integrin. In some embodiments, the compound inhibits $\alpha_V\beta_8$ integrin, $\alpha_V\beta_1$ integrin, and $\alpha_V\beta_6$ integrin. In some instances of the method, it is desirable to avoid inhibition of other integrins. In some embodiments, the compound is a selective $\alpha_V\beta_8$ integrin inhibitor. For example, in some embodiments, the compound is a selective $\alpha_V\beta_8$ integrin inhibitor that does not substantially inhibit one or more integrins such as $\alpha_V\beta_1$, $\alpha_V\beta_6$, $\alpha_V\beta_3$, $\alpha_V\beta_5$, $\alpha_4\beta_1$, or $\alpha_5\beta_1$. In some embodiments, the compound is a selective $\alpha_V\beta_8$ integrin inhibitor that does not substantially inhibit $\alpha_V\beta_1$ integrin. In some embodiments, the compound is a selective $\alpha_V\beta_8$ integrin inhibitor that does not substantially inhibit $\alpha_V\beta_6$ integrin. In some embodiments, the compound is a selective $\alpha_V\beta_8$ integrin inhibitor that does not substantially inhibit $\alpha_V\beta_1$ integrin or $\alpha_V\beta_6$ integrin. In some embodiments, the compound is a selective $\alpha_V\beta_8$ integrin inhibitor that does not substantially inhibit $\alpha_V\beta_3$ integrin. In some embodiments, the compound is a selective $\alpha_V\beta_8$ integrin inhibitor that does not substantially inhibit $\alpha_V\beta_5$ integrin. In some embodiments, the compound is a selective $\alpha_V\beta_8$ integrin inhibitor that does not substantially inhibit $\alpha_V\beta_3$ integrin or $\alpha_V\beta_5$ integrin. In some embodiments, the compound is a selective $\alpha_V\beta_8$ integrin inhibitor that does not substantially inhibit $\alpha_4\beta_1$ integrin. In some embodiments, the compound is a selective $\alpha_V\beta_8$ integrin inhibitor that does not substantially inhibit $\alpha_5\beta_1$ integrin. In some embodiments, the compound is a selective $\alpha_V\beta_8$ integrin inhibitor that does not substantially inhibit $\alpha_4\beta_1$ integrin or $\alpha_5\beta_1$ integrin. In some embodiments, the compound is a selective $\alpha_V\beta_8$ integrin inhibitor that does not substantially inhibit $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_6$ integrin, $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_1$ integrin, $\alpha_V\beta_3$ integrin, $\alpha_V\beta_5$ integrin, $\alpha_4\beta_1$ integrin, or $\alpha_5\beta_1$ integrin. In some embodiments, the compound is a selective $\alpha_V\beta_8$ integrin inhibitor that does not substantially inhibit $\alpha_V\beta_1$ integrin, $\alpha_V\beta_6$ integrin, $\alpha_V\beta_3$ integrin, $\alpha_V\beta_5$ integrin, $\alpha_4\beta_1$ integrin, or $\alpha_5\beta_1$ integrin. In various embodiments of the method, compounds described herein inhibit at least one or more integrins, and/or selectively inhibit one or more integrins in any combination as described herein.

In all such embodiments, in one aspect the method of inhibition is for an individual in need thereof, such as an individual who has or is suspected of having a fibrotic disease, and wherein the method comprises administering to the individual a compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV) a compound selected from the compounds depicted in Table 1, or any one of compounds 1-82, or any one of compounds 83-104, or a stereoisomer thereof, or a pharmaceutically acceptable salt thereof.

Also provided is a method of modulating at least one integrin in a subject, the at least one integrin comprising an $\alpha_V$ subunit, the method comprising administering to the subject an effective amount of the compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof. In another aspect, the modulating comprises inhibiting the at least one integrin in the subject. In another aspect, the at least one integrin comprises at least one or more of $\alpha_V\beta_8$, $\alpha_V\beta_1$, and $\alpha_V\beta_6$ integrins. In another aspect, the subject has or is at risk of a fibrotic disease selected from the group consisting of: pulmonary fibrosis, skin fibrosis, liver fibrosis, cardiac fibrosis, kidney fibrosis, gastrointestinal fibrosis, primary sclerosing cholangitis, or biliary fibrosis. In another aspect, the subject has or is at risk of a fibrotic disease selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease; and the method comprises inhibiting at least one or more of $\alpha_V\beta_8$, $\alpha_V\beta_1$, and $\alpha_V\beta_6$ integrins, as described herein in the subject, thereby treating the fibrotic disease in the subject. In another aspect, the subject being in need of treatment for NASH, the effective amount administered to the subject being effective to inhibit, in the subject, at least one or more of $\alpha_V\beta_8$, $\alpha_V\beta_1$, and $\alpha_V\beta_6$ integrins, as described for the compounds herein, e.g., at least $\alpha_V\beta_1$ integrin, thereby treating the subject for NASH. In another aspect, the subject being in need of treatment for IPF, the effective amount administered to the subject being effective to inhibit, in the subject, at least one or more of $\alpha_V\beta_8$, $\alpha_V\beta_1$, and $\alpha_V\beta_6$ integrins, as described for the compounds herein, e.g., at least $\alpha_V\beta_6$ integrin, thereby treating the subject for IPF. In another aspect, the subject being in need of treatment for PSC, the effective amount administered to the subject being effective to inhibit, in the subject, at least one or more of $\alpha_V\beta_8$, $\alpha_V\beta_1$, and $\alpha_V\beta_6$ integrins, as described for the compounds herein, e.g., at least one of $\alpha_V\beta_1$ integrin and $\alpha_V\beta_6$ integrin, thereby treating the subject for PSC.

Also provided is a method of modulating TGFβ activation in a cell, comprising contacting the cell with the compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof. In another aspect, the modulating comprises inhibiting TGFβ activation in the cell. In another aspect, the TGFβ activation is mediated in the cell by at least one or more of $\alpha_V\beta_8$, $\alpha_V\beta_1$, and $\alpha_V\beta_6$ integrins, as described herein.

Also provided is a method of treating a subject in need thereof, comprising: administering to the subject a therapeutically effective amount of the compound of formula (A) or formula (I), or any variation thereof, e.g., a compound of formulae (A), (I), (II-a), (II-b), (II-c), (II-d), (II-e), (II-f), (II-g), (III-a), (III-b-1), (III-b-2), (III-b-3), (III-b-4), (III-b-5), (III-b-6), (III-b-7), (III-b-8), (III-b-9), or (IV), a compound selected from the compounds depicted in Table 1, or any one of compounds 1-82, or any one of compounds 83-104, or a stereoisomer thereof, or a pharmaceutically acceptable salt thereof, wherein the subject has at least one tissue in need of therapy and the tissue has at least one elevated level of: TGFβ activation and/or expression; $\alpha_V\beta_8$ integrin activity and/or expression; $\alpha_V\beta_1$ integrin activity and/or expression; or $\alpha_V\beta_6$ integrin activity and/or expression; wherein the at least one elevated level is elevated compared to a healthy state of the tissue. In some aspects, the method selectively inhibits $\alpha_V\beta_8$ integrin compared to $\alpha_V\beta_6$ integrin in the subject. In some aspects, the method selectively inhibits $\alpha_V\beta_8$ integrin compared to $\alpha_V\beta_1$ integrin in the subject. In some aspects, the method inhibits both of $\alpha_V\beta_1$ integrin and $\alpha_V\beta_8$ integrin in the subject. In some aspects, the method inhibits $\alpha_V\beta_1$ integrin, $\alpha_V\beta_6$ integrin, and $\alpha_V\beta_8$ integrin in the subject. In some aspects, the method selectively inhibits both $\alpha_V\beta_1$ integrin and $\alpha_V\beta_8$ integrin compared to at least one other $\alpha_V$-containing integrin in the subject. In some aspects, the method selectively inhibits $\alpha_V\beta_1$ integrin, $\alpha_V\beta_6$ integrin, and $\alpha_V\beta_8$ integrin compared to at least one other $\alpha_V$-containing integrin in the subject. In some aspects, the $\alpha_V\beta_1$ integrin is inhibited in one or more fibroblasts in the subject. In some aspects, the $\alpha_V\beta_6$ integrin is inhibited in one or more epithelial cells in the subject. In some aspects, the at least one tissue in the subject comprises one or more of: lung tissue, liver tissue, skin tissue, cardiac tissue, kidney tissue, gastrointestinal tissue, gall bladder tissue, and bile duct tissue.

In some embodiments, provided is a method of treating ocular fibrosis in an individual in need thereof comprising administering a compound of formula (A) or formula (I), or any variation thereof detailed herein, or a pharmaceutically acceptable salt thereof, or a pharmaceutical composition thereof.

In some embodiments, provided is a method of treating anterior subcapsular cataracts or posterior capsule opacification in an individual in need thereof comprising administering a compound of formula (A) or formula (I), or any variation thereof detailed herein, or a pharmaceutically acceptable salt thereof, or a pharmaceutical composition thereof.

In some embodiments, provided is use of a compound of formula (A) or formula (I), or any variation thereof detailed herein, or a pharmaceutically acceptable salt thereof, or a pharmaceutical composition thereof, in the manufacture of a medicament for the treatment of ocular fibrosis. In some embodiments, provided is the use of a compound of formula (A) or formula (I), or any variation thereof detailed herein, or a pharmaceutically acceptable salt thereof, or a pharmaceutical composition thereof, in the manufacture of a medicament for the treatment of anterior subcapsular cataracts or posterior capsule opacification.

In any of the described methods, in one aspect the individual is a human, such as a human in need of the method. In some embodiments, the individual is a human who has been diagnosed with or is suspected of having a fibrotic disease. In some embodiments, the individual is a human who does not have detectable disease but who has one or more risk factors for developing a fibrotic disease.

Kits

Also provided are kits for carrying out the methods, which comprises one or more compounds described herein, or a pharmaceutically acceptable salt thereof, or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease.

For example, provided is a kit comprising a compound of formula (A) or formula (I), or any variation thereof detailed herein, or a pharmaceutically acceptable salt thereof. In some embodiments, the kit comprises instructions for use according to a method described herein, such as a method of treating a disease in an individual mediated by one or more of $\alpha_V\beta_1$ integrin, $\alpha_V\beta_6$ integrin, and/or $\alpha_V\beta_8$ integrin, e.g., a fibrotic disease, or cancer. In some embodiments, the kit comprises instructions for use according to a method described herein, such as a method of treating a cancer in an individual. In some embodiments, the kit includes instructions for use according to a method described herein, such as directing a user to administer the compound of the kit and a checkpoint inhibitor in a method of treating a cancer in an individual.

Also provided is a kit comprising a compound of formula (A) or formula (I), or any variation thereof detailed herein, or a pharmaceutically acceptable salt thereof, and a checkpoint inhibitor. In some embodiments, the kit comprises instructions for use according to a method described herein, such as a method of treating a disease in an individual that is mediated by one or more of $\alpha_V\beta_1$ integrin, $\alpha_V\beta_6$ integrin, and/or $\alpha_V\beta_8$ integrin, e.g., a fibrotic disease, or cancer. In some embodiments, the kit comprises instructions for use according to a method described herein, such as a method of treating a cancer in an individual. For example, the instructions may direct the user to administer to the subject: the checkpoint inhibitor; and the compound or the pharmaceutically acceptable salt thereof.

In various embodiments, the kit may include any checkpoint inhibitor as described herein. For example, in some embodiments, the checkpoint inhibitor inhibits PD-1. In some embodiments, the checkpoint inhibitor inhibits PD-L1. In some embodiments, the checkpoint inhibitor inhibits CTLA-4. In some embodiments, the checkpoint inhibitor inhibits one of, or one or more of PD-1, PD-L1, and CTLA-4. Further, for example, in some embodiments, the checkpoint inhibitor is selected from at least one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab. In some embodiments, the checkpoint inhibitor is pembrolizumab, which is marketed as Keytruda® (www.keytrudahcp.com, U.S. Pat. Nos. 8,354,509 and 8,900,587, each of which is hereby incorporated by reference in its entirety). In some embodiments, pembrolizumab is dosed at about 200 mg every three weeks or about 400 mg every six weeks. In some embodiments, pembrolizumab is administered as an injection (about 25 mg/mL) via infusion.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

ENUMERATED EMBODIMENTS

Embodiment 1. A compound of formula (I):

(I)

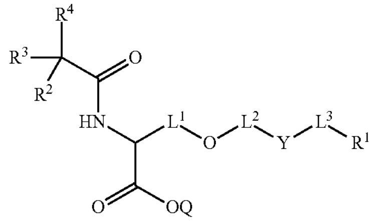

or a salt thereof, wherein:

$R^1$ is 5,6,7,8-tetrahydro-1,8-naphthyridin-2-yl optionally substituted by $R^{1a}$, 1,2,3,4-tetrahydro-1,8-naphthyridin-2-yl optionally substituted by $R^{1b}$, 6-aminopyridin-2-yl optionally substituted by $R^{1c}$, or (pyridin-2-yl) amino optionally substituted by $R^{1d}$;

$R^2$ is H or $C_1$-$C_6$ alkyl;

$R^3$ is H or $C_1$-$C_6$ alkyl;

or $R^2$ and $R^3$ are taken together with the carbon atom to which they are attached to form a $C_3$-$C_6$ cycloalkyl or a 3-to-6-membered heterocyclyl;

$R^4$ is phenyl, 5-to-6-membered heteroaryl, or 6-membered heterocyclyl, wherein the 5-to-6-membered heteroaryl contains at least one nitrogen atom and is optionally fused to a phenyl group;

wherein the 6-membered heterocyclyl contains at least one nitrogen atom and is optionally fused to a phenyl group;

wherein the phenyl and 5-to-6-membered heteroaryl are optionally substituted by $R^{4a}$; and wherein the 6-membered heterocyclyl is optionally substituted by one or more groups selected from the group consisting of $R^{4a}$ and oxo;

each $R^{4a}$ is independently halo, CN, $C_1$-$C_6$ alkyl, $C_1$-$C_6$ haloalkyl, —($C_1$-$C_6$ alkylene)-O—($C_1$-$C_6$ alkyl), $C_3$-$C_6$ cycloalkyl, —O—($C_1$-$C_6$ alkyl), —O—($C_1$-$C_6$ haloalkyl), or —$S(O)_2$($C_1$-$C_6$ alkyl);

or $R^{4a}$ and $R^2$ are taken together with the atoms to which they are attached to form a 6-membered heterocyclyl, wherein the heterocyclyl contains one oxygen atom;

Q is H or $C_1$-$C_8$ alkyl;

$L^1$ is $C_2$-$C_4$ alkylene optionally substituted by $L^{1a}$;

$L^2$ is a bond or $C_1$-$C_3$ alkylene optionally substituted by $L^{2a}$;

$L^3$ is $C_2$-$C_4$ alkylene optionally substituted by $L^{3a}$;

Y is a bond;

$R^{1a}$, $R^{1b}$, $R^{1c}$, $R^{1d}$, $L^{1a}$, $L^{2a}$, and $L^{3a}$ are each independently selected from $R^A$;

two $R^{1a}$ groups on the same carbon atom are optionally taken together with the carbon atom to which they are attached to form a $C_3$-$C_6$ cycloalkyl;

two $R^{1b}$ groups on the same carbon atom are optionally taken together with the carbon atom to which they are attached to form a $C_3$-$C_6$ cycloalkyl;

each $R^A$ is independently deuterium, halogen, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, 5- to 10-membered heteroaryl, —CN, —$OR^5$, —$SR^5$, —$NR^6R^7$, —$NO_2$, —C═NH($OR^5$), —C(O)$R^5$, —OC(O)$R^5$, —C(O)O$R^5$, —C(O)N$R^6R^7$, —N$R^5$C(O)$R^6$, —N$R^5$C(O)O$R^6$, —N$R^5$C(O)N$R^6R^7$, —S(O)$R^5$, —$S(O)_2R^5$, —N$R^5$S(O)$R^6$, —N$R^5S(O)_2R^6$, —S(O)N$R^6R^7$, —$S(O)_2NR^6R^7$, or —P(O)($OR^5$)($OR^6$), wherein the $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, and 5- to 10-membered heteroaryl of $R^A$ are independently optionally substituted by $R^{Aa}$;

each $R^{Aa}$ is independently deuterium, halogen, oxo, —$OR^8$, —$NR^8R^9$, —C(O)$R^8$, —C(O)O$R^8$, —N$R^8$C(O)O$R^{10}$, —CN, —S(O)$R^8$, —$S(O)_2R^8$, —P(O)($OR^8$)($OR^9$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl, wherein the 3- to 12-membered heterocyclyl, 5- to 10-membered heteroaryl, $C_6$-$C_{14}$ aryl, and $C_1$-$C_6$ alkyl of $R^{Aa}$ are independently optionally substituted by $R^{Ab}$;

each $R^{Ab}$ is independently deuterium, oxo, —OH, —O($^2$H), halogen, or $C_1$-$C_6$ alkyl optionally substituted by deuterium, halogen, —OH, —O($^2$H), or oxo;

each $R^5$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 10-membered heterocyclyl of $R^5$ are each independently optionally substituted by $R^{5a}$;

each $R^{5a}$ is independently halogen, deuterium, oxo, —CN, —$OR^{10}$, —$NR^{11}R^{12}$, —P(O)($OR^{11}$)($OR^{12}$), 3- to 12-membered heterocyclyl, or $C_1$-$C_6$ alkyl optionally substituted by deuterium, halogen, —OH, —O($^2$H), or oxo;

each $R^6$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^6$ are independently optionally substituted by deuterium, halogen, oxo, —CN, —$OR^{10}$, —$NR^{11}R^{12}$, or $C_1$-$C_6$ alkyl optionally substituted by deuterium, halogen, —OH, —O($^2$H), or oxo;

each $R^7$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^7$ are independently optionally substituted by deuterium, halogen, oxo, —CN, —$OR^{10}$, —$NR^{11}R^{12}$, or $C_1$-$C_6$ alkyl optionally substituted by deuterium, halogen, —OH, —O($^2$H), or oxo;

or $R^6$ and $R^7$ are taken together with the atom to which they are attached to form a 3- to 10-membered heterocyclyl optionally substituted by deuterium, halogen, oxo, —$OR^{10}$, —$NR^{11}R^{12}$, or $C_1$-$C_6$ alkyl optionally substituted by deuterium, halogen, oxo, —OH, or —O($^2$H);

each $R^8$ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each $R^9$ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each $R^{10}$ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each $R^{11}$ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo; and each $R^{12}$ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

or $R^{11}$ and $R^{12}$ are taken together with the atom to which they are attached to form a 3-6 membered heterocyclyl optionally substituted by deuterium, halogen, oxo or $C_1$-$C_6$ alkyl optionally substituted by deuterium, oxo, or halogen.

Embodiment 2. The compound of Embodiment 1, or a salt thereof, wherein $L^1$ is —$CH_2CH_2$—.

Embodiment 3. The compound of Embodiment 1, or a salt thereof, wherein -$L^1$-O-$L^2$-Y-$L^3$- are taken together to form

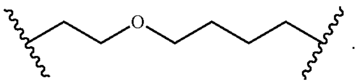 [SMILES: *CCCCOCC*]

Embodiment 4. The compound of any one of Embodiments 1-3, or a salt thereof, wherein $R^2$ and $R^3$ are independently $C_1$-$C_6$ alkyl.

Embodiment 5. The compound of Embodiment 4, or a salt thereof, wherein $R^2$ and $R^3$ are the same.

Embodiment 6. The compound of Embodiment 5, or a salt thereof, wherein $R^2$ and $R^3$ are —$CH_3$.

Embodiment 7. The compound of any one of Embodiments 1-3, or a salt thereof, wherein $R^2$ and $R^3$ are taken together with the carbon atom to which they are attached to form cyclopropyl.

Embodiment 8. The compound of any one of Embodiments 1-7, or a salt thereof, wherein $R^4$ is phenyl optionally substituted by $R^{4a}$.

Embodiment 9. The compound of Embodiment 8, or a salt thereof, wherein $R^4$ is unsubstituted phenyl.

Embodiment 10. The compound of Embodiment 8, or a salt thereof, wherein $R^4$ is phenyl substituted by 1-5 $R^{4a}$ groups, wherein at least one $R^{4a}$ group is F or Cl.

Embodiment 11. The compound of Embodiment 8, or a salt thereof, wherein $R^4$ is phenyl substituted by 1-5 $R^{4a}$ groups, wherein at least one $R^{4a}$ group is CN.

Embodiment 12. The compound of Embodiment 8, or a salt thereof, wherein $R^4$ is phenyl substituted by 1-5 $R^{4a}$ groups, wherein at least one $R^{4a}$ group is $C_1$-$C_3$ alkyl.

Embodiment 13. The compound of Embodiment 8, or a salt thereof, wherein $R^4$ is phenyl substituted by 1-5 $R^{4a}$ groups, wherein at least one $R^{4a}$ group is —O—($C_1$-$C_3$ alkyl).

Embodiment 14. The compound of Embodiment 8, or a salt thereof, wherein $R^4$ is phenyl substituted by 1-5 $R^{4a}$ groups, wherein at least one $R^{4a}$ group is —$S(O)_2$($C_1$-$C_3$ alkyl).

Embodiment 15. The compound of any one of Embodiments 1-7, or a salt thereof, wherein $R^4$ is 5-to-6-membered heteroaryl, wherein the 5-to-6-membered heteroaryl contains at least one nitrogen atom and is optionally substituted by $R^{4a}$.

Embodiment 16. The compound of Embodiment 15, or a salt thereof, wherein $R^4$ is 5-membered heteroaryl, wherein the 5-membered heteroaryl contains two nitrogen atoms and is optionally substituted by $R^{4a}$.

Embodiment 17. The compound of Embodiment 15, or a salt thereof, wherein $R^4$ is 6-membered heteroaryl, wherein the 6-membered heteroaryl contains one nitrogen atom and is optionally substituted by $R^{4a}$.

Embodiment 18. The compound of Embodiment 15, or a salt thereof, wherein $R^4$ is 6-membered heteroaryl, wherein the 6-membered heteroaryl contains two nitrogen atoms and is optionally substituted by $R^{4a}$.

Embodiment 19. The compound of any one of Embodiments 15-18, or a salt thereof, wherein $R^4$ is substituted by 1-4 $R^{4a}$ groups, wherein at least one $R^{4a}$ group is F or Cl.

Embodiment 20. The compound of any one of Embodiments 15-18, or a salt thereof, wherein $R^4$ is substituted by 1-4 $R^{4a}$ groups, wherein at least one $R^{4a}$ group is CN.

Embodiment 21. The compound of any one of Embodiments 15-18, or a salt thereof, wherein $R^4$ is substituted by 1-4 $R^{4a}$ groups, wherein at least one $R^{4a}$ group is $C_1$-$C_3$ alkyl.

Embodiment 22. The compound of any one of Embodiments 15-18, or a salt thereof, wherein $R^4$ is substituted by 1-4 $R^{4a}$ groups, wherein at least one $R^{4a}$ group is $C_1$-$C_3$ haloalkyl.

Embodiment 23. The compound of any one of Embodiments 15-18, or a salt thereof, wherein $R^4$ is substituted by 1-4 $R^{4a}$ groups, wherein at least one $R^{4a}$ group-is —($C_1$-$C_3$ alkylene)-O—($C_1$-$C_3$ alkyl).

Embodiment 24. The compound of any one of Embodiments 15-18, or a salt thereof, wherein $R^4$ is substituted by 1-4 $R^{4a}$ groups, wherein at least one $R^{4a}$ group is cyclopropyl.

Embodiment 25. The compound of any one of Embodiments 15-18, or a salt thereof, wherein $R^4$ is substituted by 1-4 $R^{4a}$ groups, wherein at least one $R^{4a}$ group is —O—($C_1$-$C_3$ alkyl).

Embodiment 26. The compound of any one of Embodiments 15-18, or a salt thereof, wherein $R^4$ is substituted by 1-4 $R^{4a}$ groups, wherein at least one $R^{4a}$ group is —O—($C_1$-$C_3$ haloalkyl).

Embodiment 27. The compound of any one of Embodiments 15-18, or a salt thereof, wherein $R^4$ is substituted by 2-4 $R^{4a}$ groups, wherein at least one $R^{4a}$ group is F, and wherein at least one $R^{4a}$ group is Cl.

Embodiment 28. The compound of any one of Embodiments 15-18, or a salt thereof, wherein $R^4$ is substituted by 2-4 $R^{4a}$ groups, wherein at least one $R^{4a}$ group is F, and wherein at least one $R^{4a}$ group is $C_1$-$C_3$ alkyl.

Embodiment 29. The compound of any one of Embodiments 15-18, or a salt thereof, wherein $R^4$ is substituted by 2-4 $R^{4a}$ groups, wherein at least one $R^{4a}$ group is Cl, and wherein at least one $R^{4a}$ group is $C_1$-$C_3$ alkyl.

Embodiment 30. The compound of any one of Embodiments 15-18, or a salt thereof, wherein $R^4$ is substituted by 2-4 $R^{4a}$ groups, wherein at least one $R^{4a}$ group is Cl, and wherein at least one $R^{4a}$ group is —O—($C_1$-$C_3$ alkyl).

Embodiment 31. The compound of any one of Embodiments 15-18, or a salt thereof, wherein $R^4$ is substituted by 2-4 $R^{4a}$ groups, wherein at least two $R^{4a}$ groups are Cl.

Embodiment 32. The compound of any one of Embodiments 1-7, or a salt thereof, wherein $R^4$ is 6-membered heterocyclyl, wherein the 6-membered heterocyclyl contains at least one nitrogen atom and is optionally substituted by one or more groups selected from the group consisting of $R^{4a}$ and oxo.

Embodiment 33. The compound of Embodiment 32, or a salt thereof, wherein $R^4$ is 6-membered heterocyclyl, wherein the 6-membered heterocyclyl contains one nitrogen atom and is optionally substituted by one or more groups selected from the group consisting of $R^{4a}$ and oxo.

Embodiment 34. The compound of Embodiment 32, or a salt thereof, wherein $R^4$ is 6-membered heterocyclyl, wherein the 6-membered heterocyclyl contains two nitrogen atoms and is optionally substituted by one or more groups selected from the group consisting of $R^{4a}$ and oxo.

Embodiment 35. The compound of any one of Embodiments 32-34, or a salt thereof, wherein $R^4$ is substituted by Cl and oxo.

Embodiment 36. The compound of any one of Embodiments 1-7, or a salt thereof, wherein $R^4$ is selected from the group consisting of:

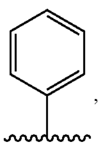 , 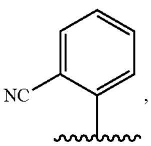 , 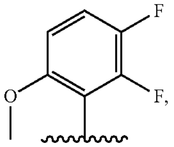

-continued
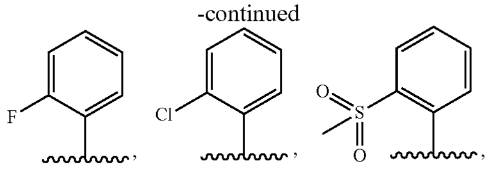
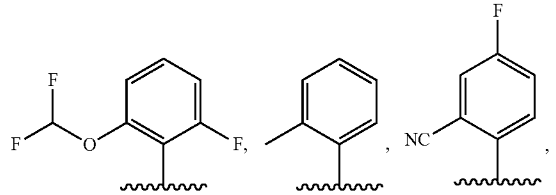
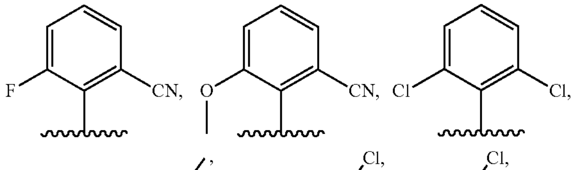
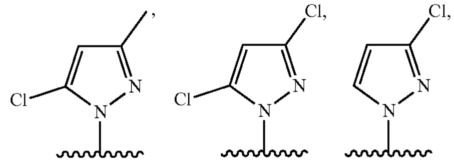
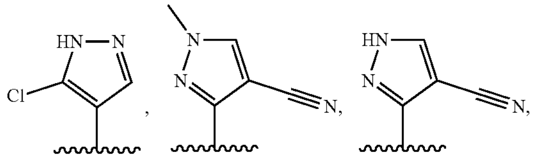
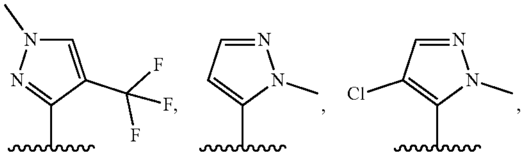
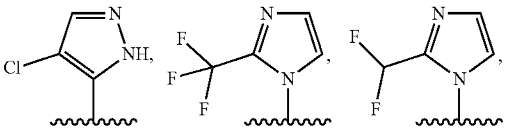
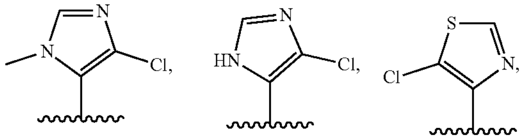
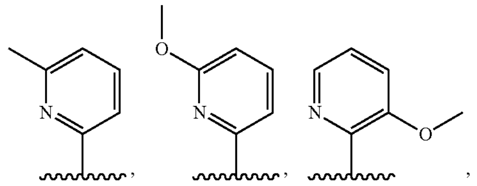
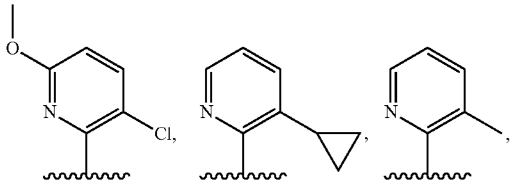
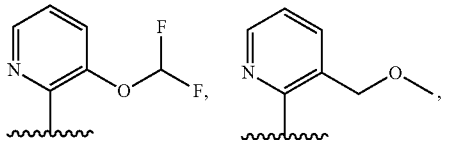
-continued
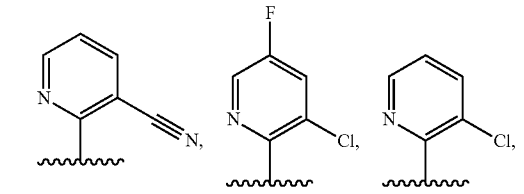
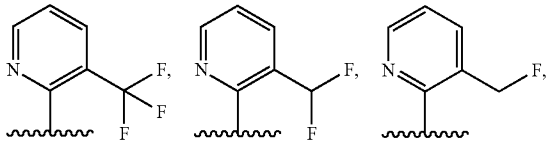
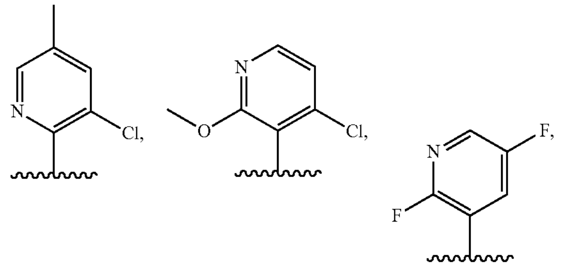
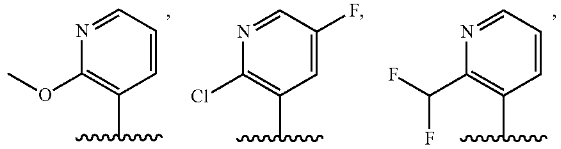
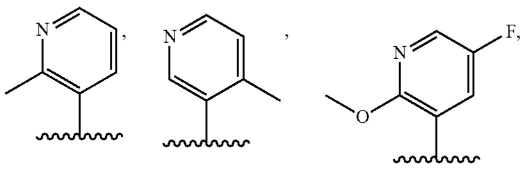
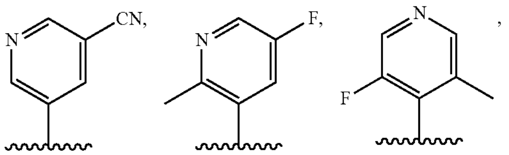
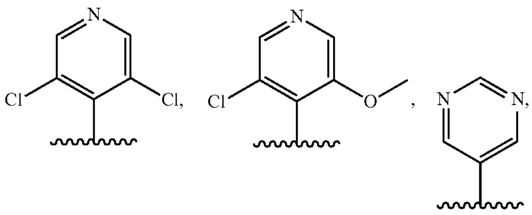
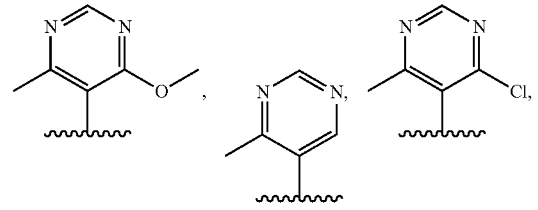
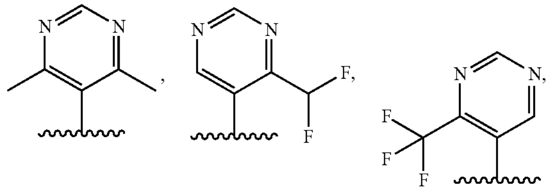

-continued
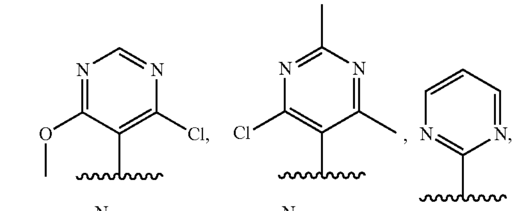
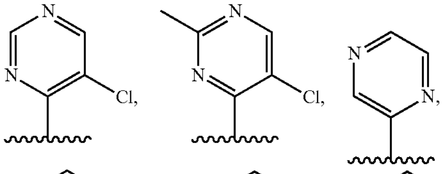
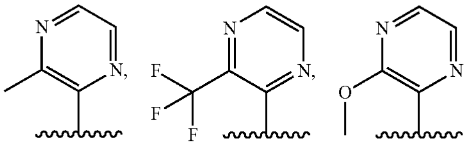
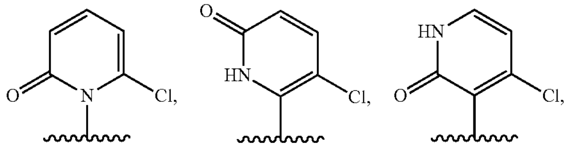
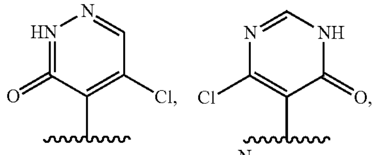
and
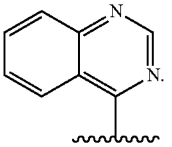
Embodiment 37. The compound of any one of Embodiments 1-7, or a salt thereof, wherein $R^4$ is selected from the group consisting of:
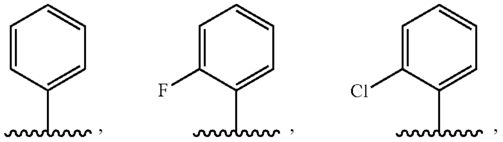
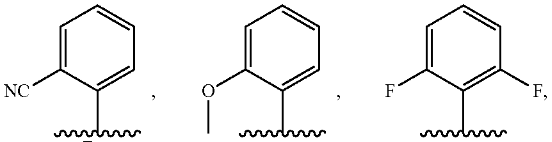
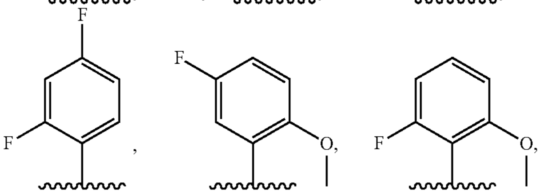
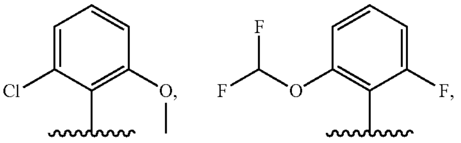
-continued
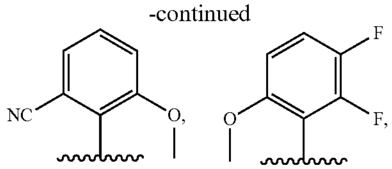
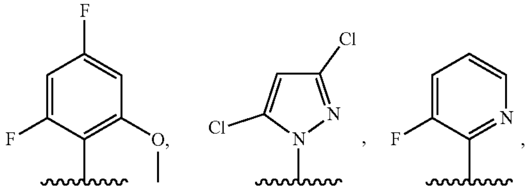
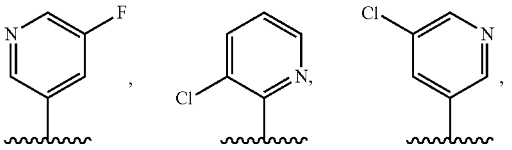
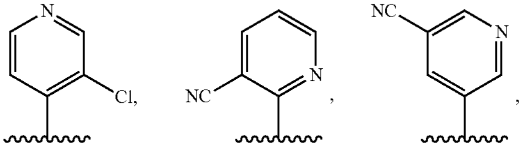
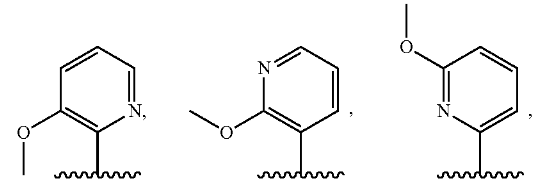
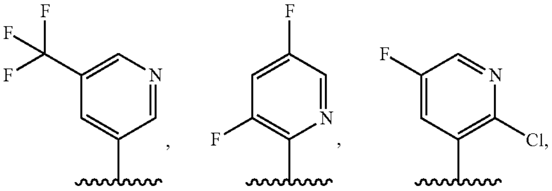
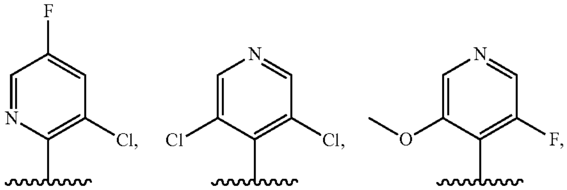
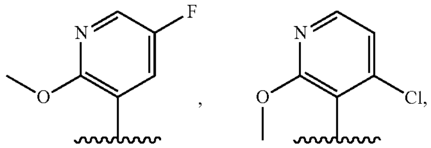
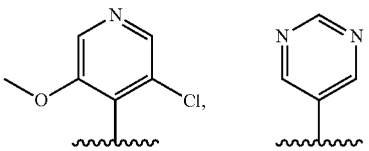
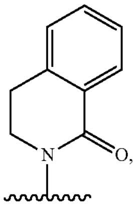
and
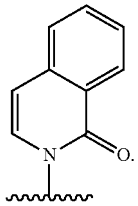

Embodiment 38. The compound of any one of Embodiments 1-37, or a salt thereof, wherein $R^1$ is 5,6,7,8-tetrahydro-1,8-naphthyridin-2-yl optionally substituted by $R^{1a}$.

Embodiment 39. The compound of any one of Embodiments 1-38, or a salt thereof, wherein Q is H.

Embodiment 40. A compound selected from one of Compound Nos. 1-82 in Table 1, or a salt thereof.

Embodiment 41. A pharmaceutical composition comprising a compound of any one of Embodiments 1-40, or a salt thereof, and a pharmaceutically acceptable carrier or excipient.

Embodiment 42. The pharmaceutical composition of Embodiment 41, further comprising a checkpoint inhibitor.

Embodiment 43. The pharmaceutical composition of Embodiment 41, further comprising a checkpoint inhibitor that inhibits one of: PD-1, PD-L1, and CTLA-4.

Embodiment 44. The pharmaceutical composition of Embodiment 41, further comprising at least one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab.

Embodiment 45. A method of treating a fibrotic disease in an individual in need thereof comprising administering a compound of any one of Embodiments 1-40, or a pharmaceutically acceptable salt thereof, or the pharmaceutical composition of Embodiment 41.

Embodiment 46. The method of Embodiment 45, wherein the fibrotic disease is pulmonary fibrosis, liver fibrosis, skin fibrosis, cardiac fibrosis, kidney fibrosis, gastrointestinal fibrosis, primary sclerosing cholangitis, or biliary fibrosis.

Embodiment 47. A kit comprising a compound of any one of Embodiments 1-40, or a pharmaceutically acceptable salt thereof, or the pharmaceutical composition of any one of Embodiments 41-44.

Embodiment 48. The kit of Embodiment 47, further comprising instructions for the treatment of a fibrotic disease.

Embodiment 49. The kit of Embodiment 47, further comprising instructions directing a user to treat cancer in a subject in need thereof, the instructions comprising directing the user to administer to the subject the compound or the pharmaceutically acceptable salt thereof.

Embodiment 50. The kit of Embodiment 47, further comprising:

- a checkpoint inhibitor; and
- instructions directing a user to treat cancer in a subject in need thereof, the instructions comprising directing the user to administer to the subject: the checkpoint inhibitor; and the compound or the pharmaceutically acceptable salt thereof.

Embodiment 51. The kit of Embodiment 47, further comprising:

- a checkpoint inhibitor that inhibits one of: PD-1, PD-L1, and CTLA-4; and
- instructions directing a user to treat cancer in a subject in need thereof, the instructions comprising directing the user to administer to the subject: the checkpoint inhibitor; and the compound or the pharmaceutically acceptable salt thereof.

Embodiment 52. The kit of Embodiment 47, further comprising:

- a checkpoint inhibitor selected from at least one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab; and
- instructions directing a user to treat cancer in a subject in need thereof, the instructions comprising directing the user to administer to the subject: the checkpoint inhibitor; and the compound or the pharmaceutically acceptable salt thereof.

Embodiment 53. A method of inhibiting $\alpha_V\beta_8$ integrin in an individual comprising administering a compound of any one of Embodiments 1-40, or a pharmaceutically acceptable salt thereof, a pharmaceutical composition of any one of Embodiments 41-44.

Embodiment 54. A method of inhibiting one or more of $\alpha_V\beta_1$, $\alpha_V\beta_6$, or $\alpha_V\beta_8$ integrin in an individual in need thereof, comprising administering to the individual a compound of any one of Embodiments 1-40, or a pharmaceutically acceptable salt thereof, or a pharmaceutical composition of any one of Embodiments 41-44.

Embodiment 55. The method of Embodiment 54, comprising inhibiting in the individual one of:

$\alpha_V\beta_1$;
$\alpha_V\beta_8$;
$\alpha_V\beta_1$ and $\alpha_V\beta_8$;
$\alpha_V\beta_6$ and $\alpha_V\beta_8$; or
$\alpha_V\beta_1$, $\alpha_V\beta_6$, and $\alpha_V\beta_8$.

Embodiment 56. The method of Embodiment 54, comprising administering to the individual the compound of any one of Embodiments 1-40, or the pharmaceutically acceptable salt thereof, or the pharmaceutical composition of Embodiment 41, the method further comprising administering to the individual a checkpoint inhibitor.

Embodiment 57. The method of Embodiment 56, wherein the checkpoint inhibitor inhibits one of: PD-1, PD-L1, and CTLA-4.

Embodiment 58. The method of Embodiment 56, wherein the checkpoint inhibitor is one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab.

Embodiment 59. The method of Embodiment 54, wherein the individual is in need of treatment for a disease or condition comprising a solid tumor.

Embodiment 60. The method of Embodiment 54, wherein the individual is in need of treatment for a disease or condition comprising at least one of: melanoma, non-small cell lung cancer, head and neck squamous cell carcinoma, squamous cell lung cancer, renal cell carcinoma, Hodgkin's lymphoma, cutaneous squamous cell carcinoma (CSCC), urothelial carcinoma, metastatic Merkel cell carcinoma, gastric cancer, lung cancer, pancreatic cancer, or mesothelioma.

Embodiment 61. The method of Embodiment 54, wherein the individual is in need of treatment for breast cancer.

Embodiment 62. The method of Embodiment 54, wherein the individual is in need of treatment for a disease or condition comprising at least one of: pulmonary fibrosis, liver fibrosis, skin fibrosis, cardiac fibrosis, kidney fibrosis, gastrointestinal fibrosis, primary sclerosing cholangitis, or biliary fibrosis.

Embodiment 63. A method of inhibiting TGFβ activation in a cell comprising administering to the cell a compound of any one of Embodiments 1-40, or a pharmaceutically acceptable salt thereof, or a pharmaceutical composition of any one of Embodiments 41-44.

Embodiment 64. The method of Embodiment 63, wherein the cell expresses one or more of: $\alpha_V\beta_1$; $\alpha_V\beta_6$; and $\alpha_V\beta_8$.

Embodiment 65. The method of Embodiment 63, wherein the cell expresses one of:

$\alpha_V\beta_1$;
$\alpha_V\beta_6$;
$\alpha_V\beta_8$;
$\alpha_V\beta_1$ and $\alpha_V\beta_8$;
$\alpha_V\beta_1$ and $\alpha_V\beta_6$;
$\alpha_V\beta_6$ and $\alpha_V\beta_8$; or
$\alpha_V\beta_1$, $\alpha_V\beta_6$, and $\alpha_V\beta_8$.

Embodiment 66. The method of Embodiment 63, further comprising administering to the cell a checkpoint inhibitor.

Embodiment 67. The method of Embodiment 66, wherein the checkpoint inhibitor inhibits one of: PD-1, PD-L1, and CTLA-4.

Embodiment 68. The method of Embodiment 66, wherein the checkpoint inhibitor is one of: pembrolizumab, nivolumab, cemiplimab, spartalizumab, camrelizumab, sintilimab, tislelizumab, toripalimab, dostarlimab, INCMGA00012, AMP-224, AMP-514, atezolizumab, avelumab, durvalumab, KN035, CK-301, AUNP12, CA-170, BMS-986189, ipilimumab, and tremelimumab.

Embodiment 69. The method of Embodiment 66, wherein the cells are cancer cells associated with a solid tumor.

Embodiment 70. The method of Embodiment 66, wherein the cells are cancer cells associated with at least one of: melanoma, non-small cell lung cancer, head and neck squamous cell carcinoma, squamous cell lung cancer, renal cell carcinoma, Hodgkin's lymphoma, cutaneous squamous cell carcinoma (CSCC), urothelial carcinoma, metastatic Merkel cell carcinoma, gastric cancer, lung cancer, pancreatic cancer, or mesothelioma.

Embodiment 71. The method of Embodiment 66, wherein the cells are breast cancer cells.

Embodiment 72. The method of Embodiment 63, wherein the cells are human cells.

Embodiment 73. The method of Embodiment 63, wherein the cells are associated with a fibrotic disease that is at least one of: pulmonary fibrosis, liver fibrosis, skin fibrosis, cardiac fibrosis, kidney fibrosis, gastrointestinal fibrosis, primary sclerosing cholangitis, or biliary fibrosis.

Embodiment 74. Use of a compound of any one of Embodiments 1-40, or a pharmaceutically acceptable salt thereof, or a pharmaceutical composition of any one of Embodiments 41-44 in the manufacture of a medicament for the treatment of a fibrotic disease.

Embodiment 75. Use of a compound of any one of Embodiments 1-40, or a pharmaceutically acceptable salt thereof, or a pharmaceutical composition of any one of Embodiments 41-44 in the manufacture of a medicament for the treatment of a disease mediated by cells that express one or more of: $\alpha_V\beta_1$; $\alpha_V\beta_6$; and $\alpha_V\beta_8$.

Embodiment 76. Use of a compound of any one of Embodiments 1-40, or a pharmaceutically acceptable salt thereof, or a pharmaceutical composition of any one of Embodiments 41-44 in the manufacture of a medicament for the treatment of cancer.

Embodiment 77. Use of:

a compound of any one of Embodiments 1-40, or a pharmaceutically acceptable salt thereof, or a pharmaceutical composition of Embodiment 41; and a checkpoint inhibitor, together in the manufacture of a medicament for the treatment of a disease mediated by cells that express one or more of: $\alpha_V\beta_1$; $\alpha_V\beta_6$; and $\alpha_V\beta_8$.

Embodiment 78. Use of:

a compound of any one of Embodiments 1-40, or a pharmaceutically acceptable salt thereof, or a pharmaceutical composition of Embodiment 41; and a checkpoint inhibitor, together in the manufacture of a medicament for the treatment of cancer.

Embodiment 79. A method of therapy for a subject in need thereof, comprising:

providing the subject, the subject comprising at least one tissue in need of therapy, the at least one tissue characterized by at least one value that is elevated compared to a healthy value in a healthy state of the tissue, the at least one value selected from the group consisting of:

$\alpha_V\beta_1$ integrin activity and/or expression;
$\alpha_V\beta_6$ integrin activity and/or expression;
$\alpha_V\beta_8$ integrin activity and/or expression;
a pSMAD/SMAD ratio;
new collagen formation or accumulation;
total collagen;
Type I Collagen gene Col1a1 expression;
perforin;
Granzyme B; and
interferon γ; and administering to the subject a therapeutically effective amount of a compound of any one of Embodiments 1-40, or a pharmaceutical composition of any one of Embodiments 41-44.

Embodiment 80. The method of Embodiment 79, the administering the therapeutically effective amount of the compound decreasing the at least one value.

Embodiment 81. The method of Embodiment 79, comprising reducing the activity and/or expression of one of:

$\alpha_V\beta_1$;
$\alpha_V\beta_8$;
$\alpha_V\beta_1$ and $\alpha_V\beta_8$;
$\alpha_V\beta_6$ and $\alpha_V\beta_8$; or
$\alpha_V\beta_1$, $\alpha_V\beta_6$, and $\alpha_V\beta_8$.

Embodiment 82. The method of Embodiment 79, wherein the reducing the activity and/or expression is selective compared to at least one other $\alpha_V$-containing integrin in the subject.

Embodiment 83. The method of Embodiment 79, wherein one of:

the activity of $\alpha_V\beta_1$ integrin is reduced in one or more fibroblasts in the subject;

the activity of $\alpha_V\beta_6$ integrin is reduced in one or more epithelial cells in the subject; or the activity of $\alpha_V\beta_8$ integrin is reduced in one or more epithelial cells or cancer cells in the subject.

Embodiment 84. The method of any one of Embodiments 79-83, wherein the at least one tissue in the subject comprises one or more of: lung, liver, skin, heart, kidney, gastrointestinal, gall bladder, and bile duct.

Embodiment 85. The method of any one of Embodiments 79-83, wherein the at least one tissue in the subject comprises one or more of: skin, lung, brain, lymph node, stomach, urethra, kidney, bladder, prostate, liver, pancreas carcinoma, mesothelium, or breast.

Embodiment 86. The method of any one of Embodiments 79-83, wherein the tissue has an elevated pSMAD2/SMAD2 value or an elevated pSMAD3/SMAD3 value compared to the healthy state of the tissue.

Embodiment 87. The method of Embodiment 79, wherein the subject comprises a solid tumor.

Embodiment 88. The method of Embodiment 79, wherein the subject comprises at least one of: melanoma, non-small cell lung cancer, head and neck squamous cell carcinoma, squamous cell lung cancer, renal cell carcinoma, Hodgkin's lymphoma, cutaneous squamous cell carcinoma (CSCC), urothelial carcinoma, metastatic Merkel cell carcinoma, gastric cancer, lung cancer, pancreatic cancer, or mesothelioma.

Embodiment 89. The method of Embodiment 79, wherein the subject comprises at least one of: pulmonary fibrosis, liver fibrosis, skin fibrosis, cardiac fibrosis, kidney fibrosis, gastrointestinal fibrosis, primary sclerosing cholangitis, or biliary fibrosis.

Embodiment 90. A method of characterizing anticancer activity of a small molecule inhibitor in a subject, comprising:

providing a first live cell sample from the subject, the first live cell sample characterized by the presence of at least one integrin capable of activating transforming growth factor β (TGF-β) from latency associated peptide-TGF-β;

determining a first value in the first live cell sample, the first value being a pSMAD2/SMAD2 ratio, pSMAD3/SMAD3 ratio, a perforin level, a granzyme B level, or an interferon γ level;

administering the small molecule to the subject;

providing a second live cell sample from the subject, the second live cell sample being drawn from the same tissue in the subject as the first live cell sample;

determining a second value in the second live cell sample, the second value corresponding to the pSMAD2/SMAD2 ratio, the pSMAD3/SMAD3 ratio, the perforin level, the granzyme B level, or the interferon γ level of the first value; and characterizing the anticancer activity of the small molecule in the subject by comparing the second value to the first value.

Embodiment 91. The method of Embodiment 90, wherein each live cell sample comprises a plurality of cancer cells derived from a tissue of the subject or a hematocyte of the subject.

Embodiment 92. The method of Embodiment 90, wherein the at least one tissue in the subject comprises one or more of: skin, lung, brain, lymph node, stomach, urethra, kidney, bladder, prostate, liver, pancreas, mesothelium, or breast.

Embodiment 93. The method of Embodiment 90, wherein the subject comprises a solid tumor.

Embodiment 94. The method of Embodiment 90, wherein the subject comprises melanoma, non-small cell lung cancer, head and neck squamous cell carcinoma, squamous cell lung cancer, renal cell carcinoma, Hodgkin's lymphoma, cutaneous squamous cell carcinoma (CSCC), urothelial carcinoma, metastatic Merkel cell carcinoma, gastric cancer, lung cancer, pancreatic cancer, or mesothelioma.

Embodiment 95. The method of Embodiment 90, wherein the at least one integrin comprises $\alpha_V$.

Embodiment 96. The method of Embodiment 90, wherein the at least one integrin is selected from the group consisting of: $\alpha_V\beta_1$, $\alpha_V\beta_6$, and $\alpha_V\beta_8$.

Embodiment 97. The method of Embodiment 90, wherein the first and second values are pSMAD2/SMAD2 ratios or pSMAD3/SMAD3 ratios.

Embodiment 98. The method of Embodiment 90, the administering the small molecule to the subject comprising administering the compound of any one of Embodiments 1-40 or the pharmaceutical composition of any one of Embodiments 41-44 to the subject.

Embodiment 99. The method of Embodiment 90, further comprising administering a checkpoint inhibitor to the subject, the characterizing the anticancer activity of the small molecule in the subject by comparing the second value to the first value comprising characterizing the anticancer activity of the small molecule together with the checkpoint inhibitor.

Embodiment 100. The method of any one of Embodiments 53-55 or 62 wherein the individual is in need of treatment for biliary atresia.

Embodiment 101. The method of any one of Embodiments 63-65 or 72-73, wherein the cell or cells are associated with the intrahepatic or extrahepatic biliary system.

Embodiment 102. The use of Embodiment 74 or 75, wherein the fibrotic disease or disease is biliary atresia.

Embodiment 103. The method of any one of Embodiments 79-86 or 89, wherein the subject is in need of treatment for biliary atresia.

Embodiment 104. The method of any one of Embodiments 79-86 or 89, wherein the tissue is tissue of the intrahepatic or extrahepatic biliary system.

Embodiment 105. The method of Embodiment 101, wherein the cell or cells express $\alpha_V\beta_1$ and $\alpha_V\beta_8$.

Embodiment 106. The method of Embodiment 104, wherein the tissue expresses $\alpha_V\beta_1$ and $\alpha_V\beta_8$.

Embodiment 107. The method of any one of Embodiments 53-55, wherein the individual is in need of treatment for ocular fibrosis.

Embodiment 108. The method of any one of Embodiments 53-55 or 107, wherein the individual is in need of treatment for anterior subcapsular cataracts or posterior capsule opacification.

Embodiment 109. The method of any one of Embodiments 63-65 or 72, wherein the cell or cells are associated with the eye.

Embodiment 110. The use of Embodiment 74 or 75, wherein the fibrotic disease or disease is ocular fibrosis.

Embodiment 111. The use of any one of Embodiments 74, 75, or 110, wherein the fibrotic disease or disease is anterior subcapsular cataracts or posterior capsule opacification.

Embodiment 112. The method of any one of Embodiments 79-83, or 86, wherein the tissue is the tissue of the eye.

Embodiment 113. The method of Embodiment 109, wherein the cell or cells express one, two, or three integrins selected from $\alpha_V\beta_1$, $\alpha_V\beta_6$, and $\alpha_V\beta_8$.

Embodiment 114. The method of Embodiment 112, wherein the tissue expresses one, two, or three integrins selected from $\alpha_V\beta_1$, $\alpha_V\beta_6$, and $\alpha_V\beta_8$.

General Procedures

Compounds provided herein may be prepared according to General Schemes, as exemplified by the General Procedures and Examples.

When a specific stereoisomer, or an unspecified stereoisomer, or a mixture of stereoisomers is shown in the following general procedures, it is understood that similar chemical transformations can be performed on other specific stereoisomers, or an unspecified stereoisomer, or mixtures thereof. For example, a hydrolysis reaction of an L-homoserinate ester to a corresponding free acid L-homoserine can also be performed on a D-homoserinate ester to prepare a corresponding free acid D-homoserine, or on a mixture of an L-homoserinate ester and a D-homoserinate ester to prepare a mixture of a corresponding free acid L-homoserine and a corresponding free acid D-homoserine.

Some of the following general procedures use specific compounds to illustrate a general reaction (e.g., deprotection of a compound having a Boc-protected amine to a compound having a deprotected amine using acid). The general reaction can be carried out on other specific compounds having the same functional group (e.g., a different compound having a protected amine where the Boc-protecting group can be removed using acid in the same manner) as long as such other specific compounds do not contain additional functional groups affected by the general reaction (i.e., such other specific compounds do not contain acid-sensitive functional groups), or if the effect of the general reaction on those additional functional groups is desired (e.g., such other specific compounds have another group that is affected by acid, and the effect of the acid on that other group is a desirable reaction).

Where specific reagents or solvents are specified for reactions in the general procedures, the skilled artisan will recognize that other reagents or solvents can be substituted as desired. For example, acetylation is performed in the general examples with acetic anhydride, but an active ester of acetic acid can also be used. As another example, where hydrochloric acid is used to remove a Boc group, trifluoroacetic acid can be used instead. As another example, where HATU is used as a coupling reagent, BOP or PyBOP can be used instead.

Scheme A

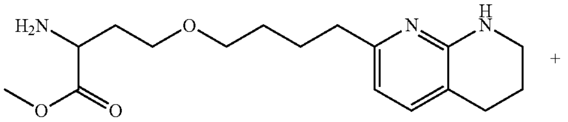

1A

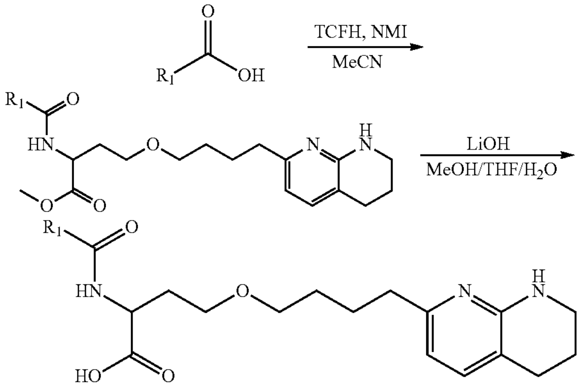

Intermediate 1A was prepared according to US20200109141A1, herein incorporated by reference in its entirety.

General Procedure A

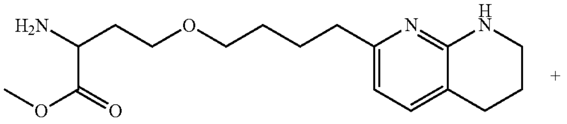

1A

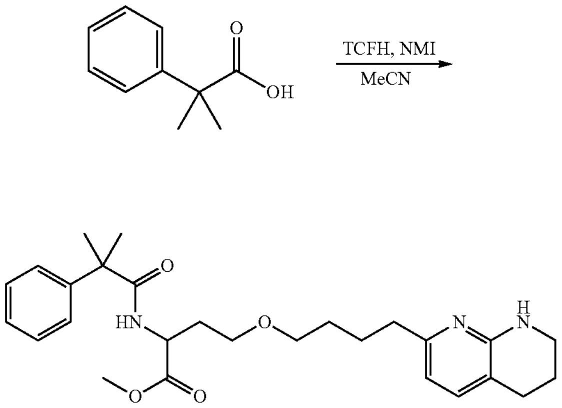

Methyl N-(2-methyl-2-phenylpropanoyl)-O-(4-(5,6,7,8-tetrahydro-1,8-naphthyridin-2-yl)butyl)homoserinate To a solution of methyl 2-amino-4-[4-(5,6,7,8-tetrahydro-1,8-naphthyridin-2-yl)butoxy]butanoate (11.4 mg, 35.47 μmol) in MeCN (70.94 μL) was added 2-methyl-2-phenylpropanoic acid (5.8 mg, 35.47 μmol), 1-methylimidazole (14.56 mg, 177.34 μmol, 14.14 μL), and N,N,N',N'-tetramethylchloroformamidinium hexafluorophosphate (11.94 mg, 42.56 μmol). The mixture was stirred at rt for 30 min then concentrated in vacuo. The crude residue was purified by normal phase chromatography to give the title compound.

General Procedure B

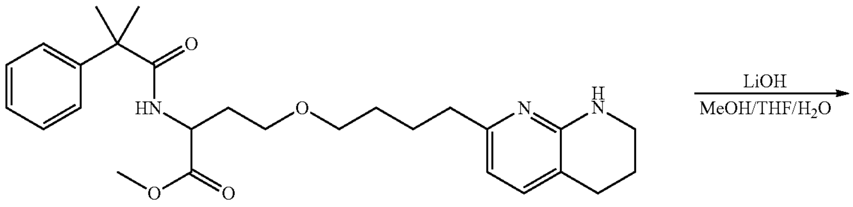

-continued

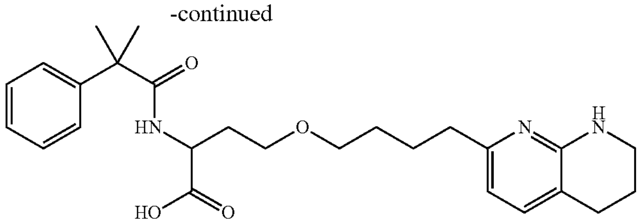

N-(2-methyl-2-phenylpropanoyl)-O-(4-(5,6,7,8-tetrahydro-1,8-naphthyridin-2-yl)butyl)homoserine To a solution of methyl N-(2-methyl-2-phenylpropanoyl)-O-(4-(5,6,7,8-tetrahydro-1,8-naphthyridin-2-yl)butyl)homoserinate (16 mg, 34.2 μmol) in 1:1:1 MeOH/THF/$H_2O$ (1 mL) was added lithium hydroxide (8.2 mg, 342 μmol). The resulting solution was stirred for 1 h and then concentrated in vacuo. The crude residue was purified by reverse phase prep-HPLC to afford the title compound.

Scheme B

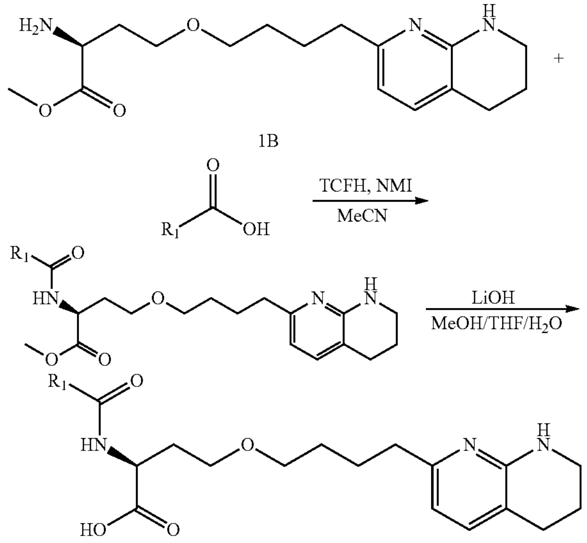

Intermediate 1B was prepared according to US20200109141A1, herein incorporated by reference in its entirety.

General Procedure C

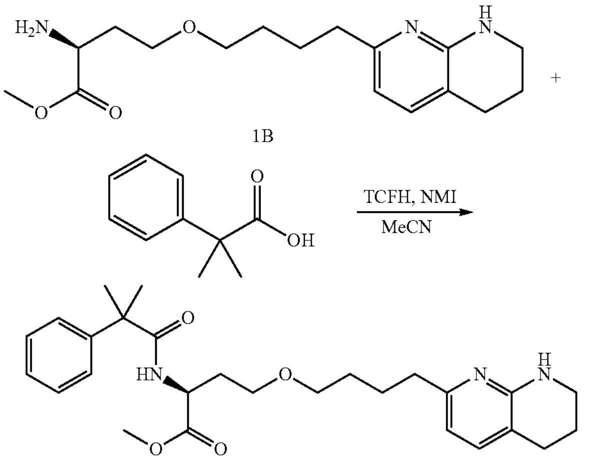

Methyl N-(2-methyl-2-phenylpropanoyl)-O-(4-(5,6,7,8-tetrahydro-1,8-naphthyridin-2-yl)butyl)-L-homoserinate To a solution of methyl (2S)-2-amino-4-[4-(5,6,7,8-tetrahydro-1,8-naphthyridin-2-yl)butoxy]butanoate (45 mg, 114 μmol) in MeCN (70.94 μL) was added 2-methyl-2-phenylpropanoic acid (22.5 mg, 137 μmol), 1-methylimidazole (56.2 mg, 684 μmol, 54.6 μL), and N,N,N',N'-tetramethylchloroformamidinium hexafluorophosphate (38.3 mg, 137 μmol). The mixture was stirred at rt for 30 min then concentrated in vacuo. The crude residue was purified by normal phase chromatography to give the title compound.

General Procedure D

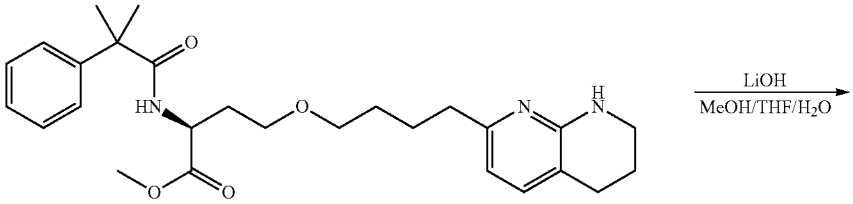

-continued

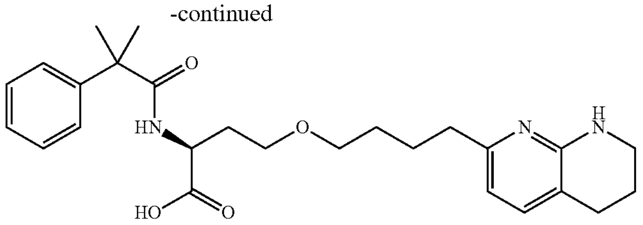

N-(2-methyl-2-phenylpropanoyl)-O-(4-(5,6,7,8-tetrahydro-1,8-naphthyridin-2-yl)butyl)-L-homoserine To a solution of methyl N-(2-methyl-2-phenylpropanoyl)-O-(4-(5,6,7,8-tetrahydro-1,8-naphthyridin-2-yl)butyl)-L-homoserinate (647 mg, 137 μmol) in 1:1:1 MeOH/THF/$H_2O$ (1 mL) was added lithium hydroxide (56 mg, 1.4 mmol). The resulting solution was stirred for 1 h and then concentrated in vacuo. The crude residue was purified by reverse phase prep-HPLC to afford the title compound.

Scheme C

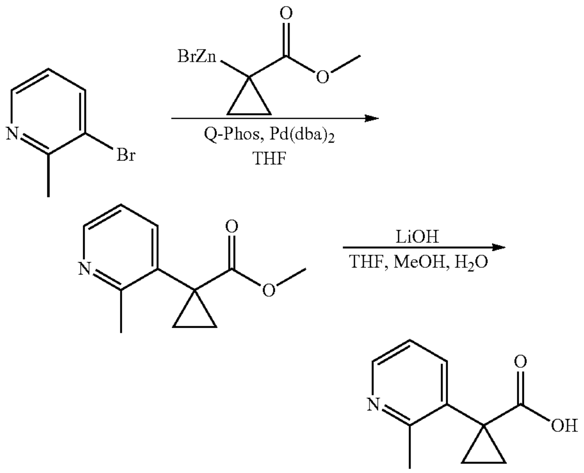

Procedures were adapted from Greszler et al. *Org. Lett.* 2017, 19, 2490-2493, herein incorporated by reference in its entirety.

General Procedure E

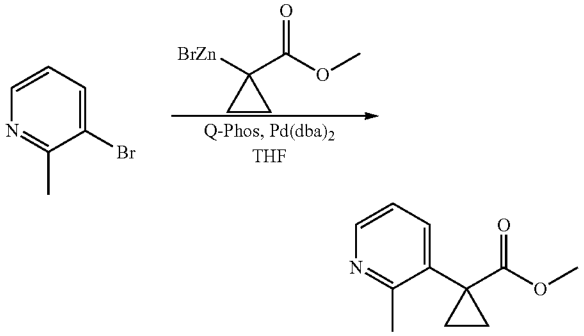

Methyl 1-(2-methylpyridin-3-yl)cyclopropane-1-carboxylate

To a vial containing Q-Phos (16.53 mg, 23.25 μmol) and $Pd(dba)_2$ (13.37 mg, 23.25 μmol) under nitrogen was added THF (0.73 mL) followed by 3-bromo-2-methyl-pyridine (200 mg, 1.16 mmol, 133.78 μL). The red solution was stirred for 5 min, then bromo-(1-methoxycarbonylcyclopropyl)zinc (0.16 M, 10.90 mL) was added and the solution stirred for 20 min. Upon completion, the mixture was diluted with MTBE and washed with saturate aqueous $NH_4Cl$ and brine. The organic layer was dried over sodium sulfate, concentrated, and purified by normal phase chromatography to afford the desired compound.

General Procedure F

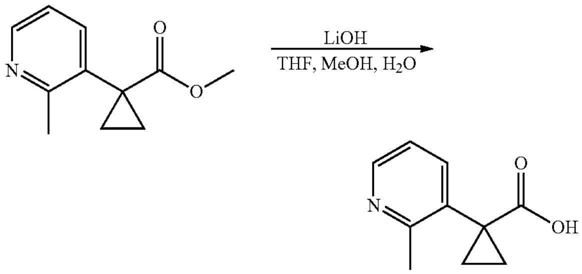

1-(2-methylpyridin-3-yl)cyclopropane-1-carboxylic acid

To a solution of methyl 1-(2-methyl-3-pyridyl)cyclopropanecarboxylate (230 mg, 1.20 mmol) in water (1 mL), MeOH (1 mL) and THF (1 mL) was added lithium hydroxide (144 mg, 6.01 mmol). The mixture was stirred at RT for 2 h and then purified by reverse phase chromatography to afford the desired product.

Scheme D

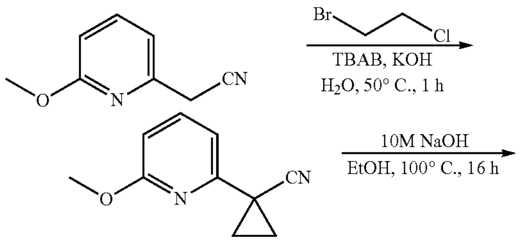

-continued

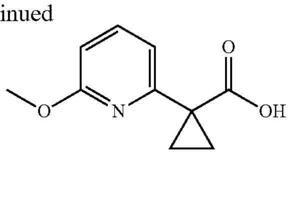

General Procedure G

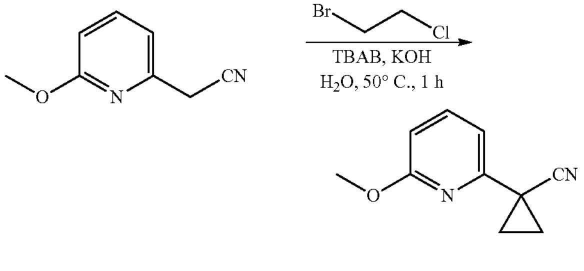

1-(6-methoxypyridin-2-yl)cyclopropanecarbonitrile

To a solution of 2-(6-methoxypyridin-2-yl)acetonitrile (1 g, 6.8 mmol) in KOH (10 mL, 75% purity) was added 1-bromo-2-chloro-ethane (1.94 g, 14 mmol, 1.1 mL) and tetrabutylammonium bromide (2.2 g, 6.8 mmol) and the resulting mixture was stirred at 50° C. for 1 h then was diluted with water and EtOAc. The layers were separated, and the aqueous layer was extracted with EtOAc. The combined organic layers were washed with water and brine, dried over $Na_2SO_4$, filtered, and concentrated in vacuo. The crude residue was purified by normal phase chromatography to give the title compound.

General Procedure H

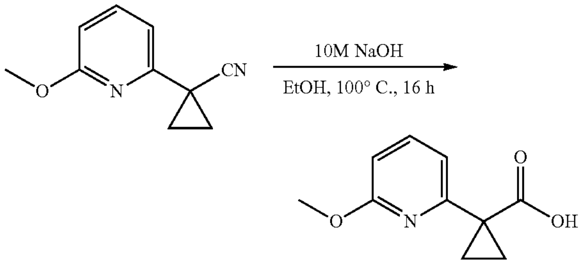

1-(6-methoxypyridin-2-yl)cyclopropanecarboxylic acid

To a solution of 1-(6-methoxypyridin-2-yl)cyclopropanecarbonitrile (0.8 g, 4.6 mmol) in EtOH (8 mL) was added 10 M aqueous NaOH (9.18 mL) and the resulting mixture was stirred at 100° C. for 16 h and then was diluted with water, acidified to pH=4. The layers were separated, and the aqueous layer was extracted with EtOAc. The combined organic layers were washed with water and brine, dried over $Na_2SO_4$, filtered, and concentrated in vacuo. The crude residue was purified by normal phase chromatography to give the title compound.

Scheme E

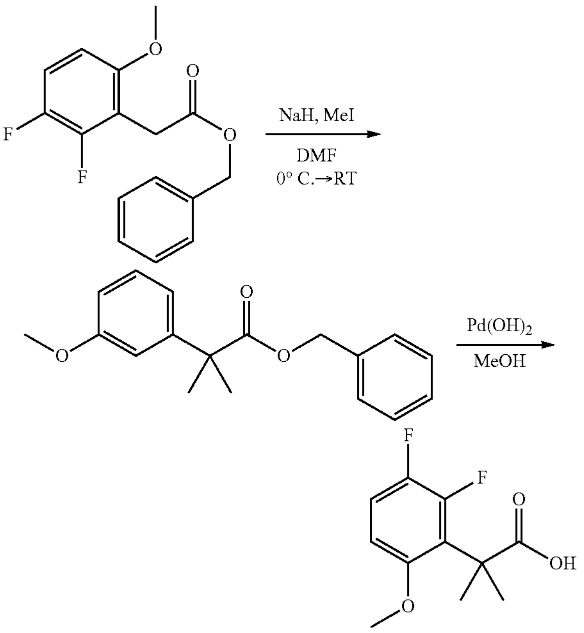

General Procedure I

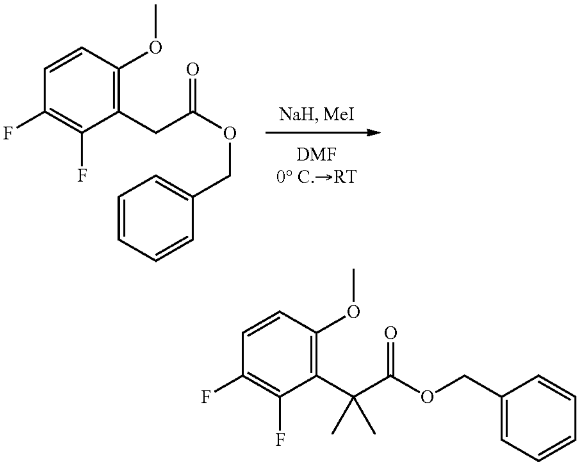

benzyl 2-(2,3-difluoro-6-methoxyphenyl)-2-methyl-propanoate

To an ice-cold solution of benzyl 2-(2,3-difluoro-6-methoxy-phenyl)acetate (400 mg, 1.37 mmol) in DMF (5 mL) was added NaH (164 mg, 4.11 mmol) and the resulting mixture was stirred at 0° C. for 30 min. Methyl iodide (0.51 mL, 8.21 mmol) was added and the mixture was stirred at RT. Upon completion, the reaction was quenched with saturated aqueous $NH_4Cl$ and diluted with EtOAc. The organic layer was washed with water and brine, dried over $Na_2SO_4$, filtered, and concentrated in vacuo. The crude residue was purified by normal phase chromatography to give the title compound.

General Procedure J

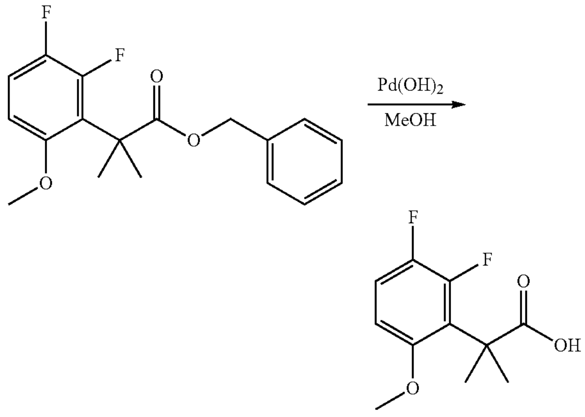

2-(2,3-difluoro-6-methoxyphenyl)-2-methylpropanoic acid

To a solution of benzyl 2-(2,3-difluoro-6-methoxyphenyl)-2-methylpropanoate (304 mg, 0.95 mmol) in MeOH (3 mL) was added palladium hydroxide (66 mg, 0.95 mmol). The reaction mixture stirred under a balloon of hydrogen for 12 h and then filtered through celite. The filtrate was concentrated under vacuum and purified by normal phase chromatography to afford the desired compound.

Scheme F

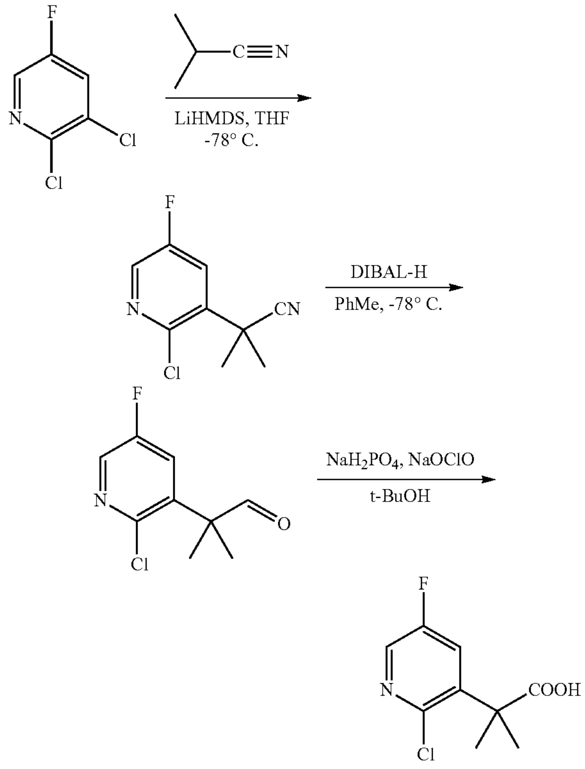

General Procedure K

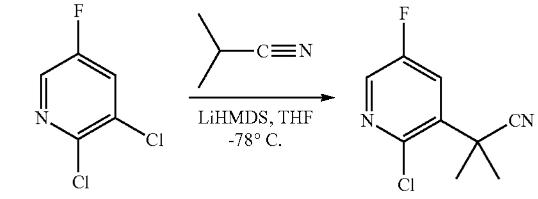

2-(2-chloro-5-fluoropyridin-3-yl)-2-methylpropanenitrile

To a solution of 2,3-dichloro-5-fluoropyridine (2 g, 12.05 mmol) and isobutyronitrile (874.32 mg, 12.65 mmol) in THF (30 mL) was added LiHMDS (1 M, 13.25 mL) dropwise at −78° C. The reaction mixture was stirred at −78° C. for 1 h and then quenched with $NH_4Cl$ (100 ml) and extracted with EtOAc. The combined organic layers were dried over $Na_2SO_4$, filtered and concentrated under reduced pressure. The crude mixture was purified by normal phase chromatography to afford the desired compound.

General Procedure L

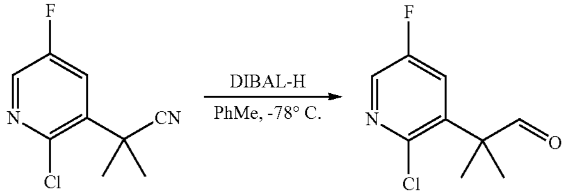

2-(2-chloro-5-fluoropyridin-3-yl)-2-methylpropanal

To a solution of 2-(2-chloro-5-fluoropyridin-3-yl)-2-methylpropanenitrile (900 mg, 4.53 mmol) in toluene (10 mL) was added diisobutylaluminium hydride (1 M in toluene, 6.82 mL) at −78° C. The reaction mixture was stirred at −78° C. for 2 h and then quenched with saturated aqueous solution (8 mL) of Rochelle's salt at 0° C. The mixture was diluted with EtOAc, stirred for 2 h at RT, and then further extracted with EtOAc. The combined organic layers were dried over $Na_2SO_4$, filtered, and concentrated under reduced pressure to afford the desired compound.

General Procedure M

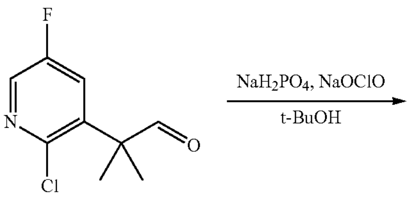

-continued

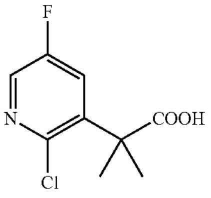

2-(2-chloro-5-fluoropyridin-3-yl)-2-methylpropanoic acid

A solution of $NaH_2PO_4$ (1.61 g, 13.39 mmol) in $H_2O$ (3 mL) was added to 2-(2-chloro-5-fluoropyridin-3-yl)-2-methylpropanal (900 mg, 4.46 mmol in t-BuOH (12 mL) at 20° C. Sodium chlorite (1.21 g, 13.39 mmol) was added in portions and the mixture was stirred overnight. After such time, the mixture was purified by reverse phase chromatography.

Scheme G

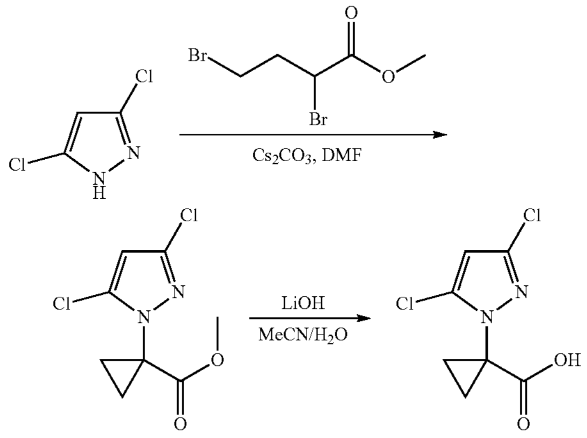

General Procedure N

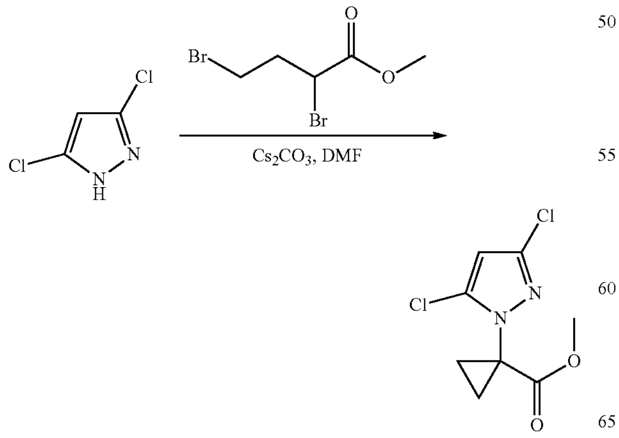

methyl 1-(3,5-dichloro-1H-pyrazol-1-yl)cyclopropanecarboxylate

To a solution of 3,5-dichloro-1H-pyrazole (2.00 g, 10.95 mmol) in DMF (20 mL) was added $Cs_2CO_3$ (14.27 g, 43.81 mmol) and methyl 2,4-dibromobutanoate (3.13 g, 12.05 mmol). The mixture was stirred at 25° C. for 2 h. The reaction mixture diluted with brine and extracted with ethyl acetate. The combined organic layers were washed with brine, dried over $Na_2SO_4$, filtered, and concentrated under reduced pressure. The crude residue was purified by normal phase chromatography to afford the desired compound.

General Procedure O

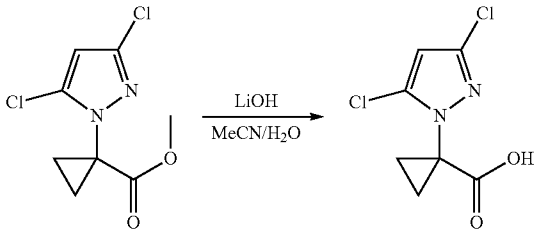

1-(3,5-dichloro-1H-pyrazol-1-yl)cyclopropanecarboxylic acid

To a solution of methyl 1-(3,5-dichloro-1H-pyrazol-1-yl)cyclopropanecarboxylate (1.4 g, 5.96 mmol) in MeCN (7 mL) and $H_2O$ (7 mL) was added $LiOH \cdot H_2O$ (625 mg, 14.89 mmol). The mixture was stirred at 20° C. for 1 h and then concentrated under reduced pressure to half the volume. The reaction mixture was adjusted to pH~6 with 1 M aqueous HCl, and then concentrated under reduced pressure. The crude mixture was purified by reverse phase chromatography to afford the desired compound.

Scheme H

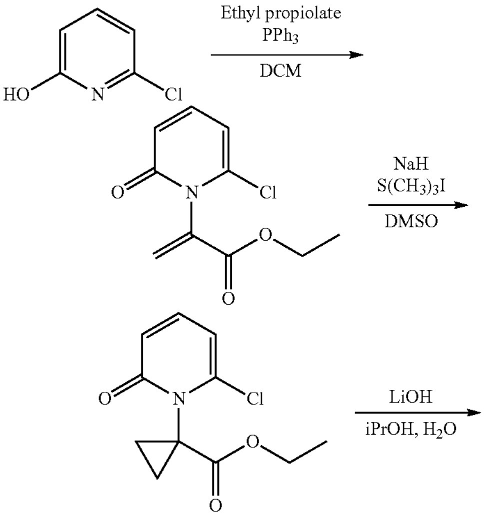

-continued

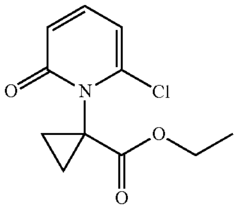

General Procedure P

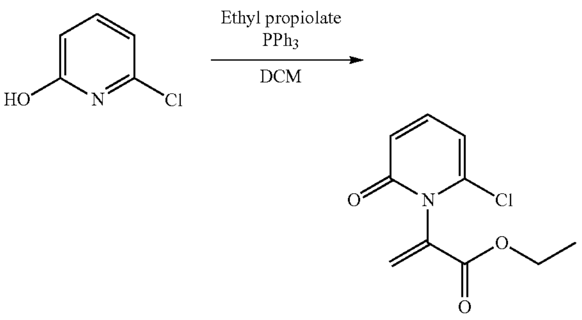

ethyl 2-(6-chloro-2-oxopyridin-1(2H)-yl)acrylate 6-chloropyridin-2-ol (5 g, 38.6 mmol) and triphenylphosphine (1.52 g, 5.79 mmol) were added to a solution of ethyl propiolate (4.7 mL, 46.3 mmol) in dry DCM (190 mL) at 0° C. The resulting solution was warmed to reach room temperature and stirred overnight. The mixture was concentrated under reduced pressure and purified by normal phase chromatography to afford the desired compound.

General Procedure Q

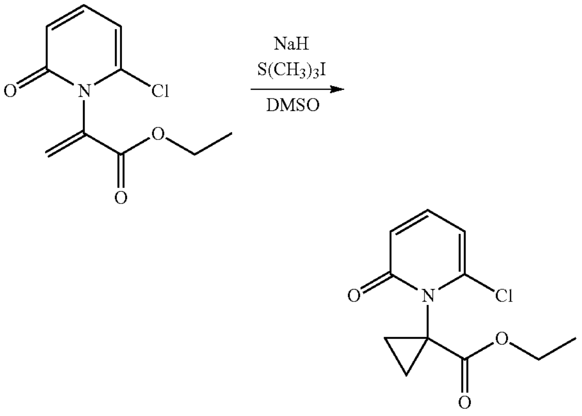

ethyl 1-(6-chloro-2-oxopyridin-1(2H)-yl)cyclopropane-1-carboxylate

NaH (79 mg, 60% in mineral oil, 1.98 mmol) was suspended in dry DMSO (8 mL), under an argon atmosphere. Trimethylsulfonium iodide (538 mg, 2.64 mmol) was added to the suspension in three portions and the mixture was vigorously stirred at room temperature for 30 min. Then, a solution of ethyl 2-(6-chloro-2-oxopyridin-1(2H)-yl)acrylate (300 mg, 1.32 mmol) in dry DMSO (4 mL) was added dropwise and the resulting mixture was stirred for 2 h. Water was slowly added and the aqueous layer was extracted with EtOAc. The combined organics were dried over $MgSO_4$, filtered, concentrated under reduced pressure, and purified by normal phase chromatography to afford the desired compound.

General Procedure R

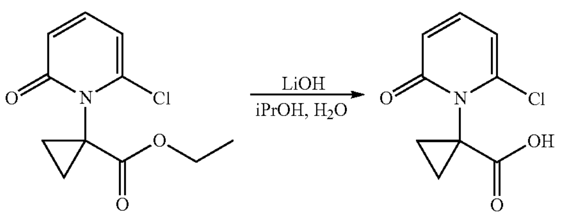 [SMILES: CCOC(=O)C1(n2c(Cl)cccc2=O)CC1 ; "LiOH" ; O=C(O)C1(n2c(Cl)cccc2=O)CC1]

1-(6-chloro-2-oxopyridin-1(2H)-yl)cyclopropane-1-carboxylic acid

A solution of LiOH monohydrate (1.52 g, 36.2 mmol) in water (36 mL) was added to a solution of ethyl 1-(6-chloro-2-oxopyridin-1(2H)-yl)cyclopropane-1-carboxylate (1.75 g, 7.24 mmol) in iPrOH (109 mL). The mixture was refluxed for 1 h, then neutralized to pH=7-8 with the addition of 2 N HCl and concentrated under reduce pressure. The crude mixture was purified by reverse phase chromatography to afford the desired compound.

Scheme I

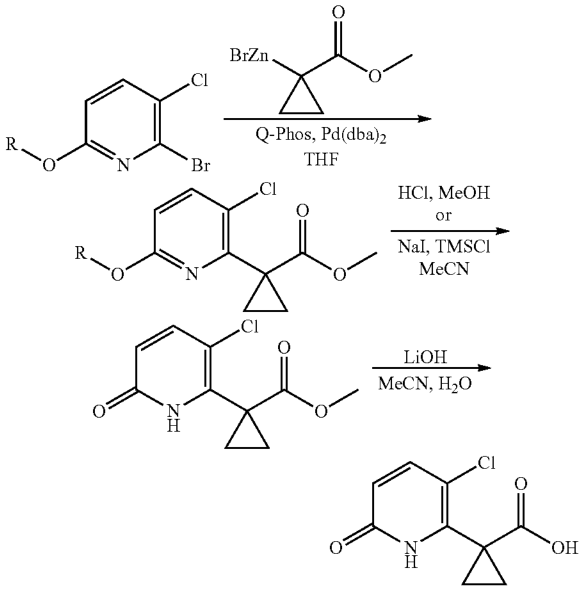

R = Me, Bn

General Procedure S

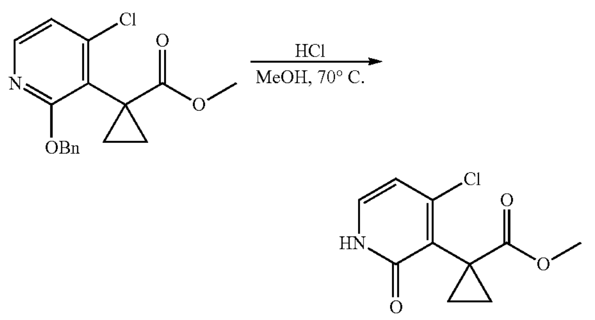

methyl 1-(4-chloro-2-oxo-1,2-dihydropyridin-3-yl) cyclopropanecarboxylate

To a solution of methyl 1-(2-(benzyloxy)-4-chloropyridin-3-yl)cyclopropanecarboxylate (1.7 g, 5.35 mmol) in MeOH (50 mL) was added HCl (12 M, 4.46 mL). The reaction mixture was stirred at 70° C. for 3 h and then concentrated under reduced pressure to afford the desired compound.

General Procedure T

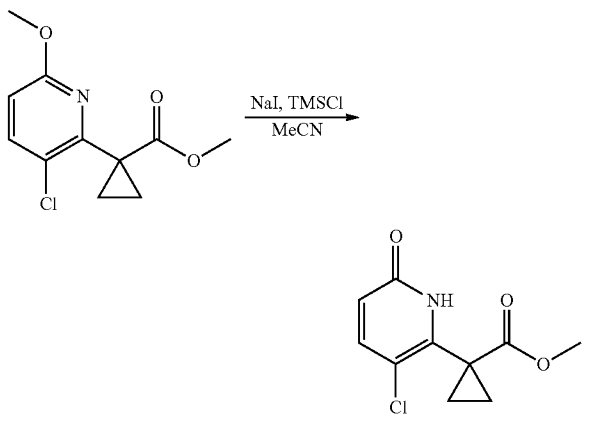

methyl 1-(3-chloro-6-oxo-1,6-dihydropyridin-2-yl) cyclopropanecarboxylate

To a solution of methyl 1-(3-chloro-6-methoxypyridin-2-yl)cyclopropanecarboxylate (1.9 g, 7.86 mmol) in MeCN (20 mL) was added trimethylsilyl chloride (2.99 mL, 23.59 mmol) and sodium iodide (3.54 g, 23.59 mmol). The mixture was stirred at 30° C. for 12 h, then quenched with $H_2O$ at 0° C. and extracted with ethyl acetate. The combined organic layers were dried over $Na_2SO_4$, filtered, and concentrated under reduced pressure. The crude mixture was purified by normal phase chromatography to afford the desired compound.

Scheme J

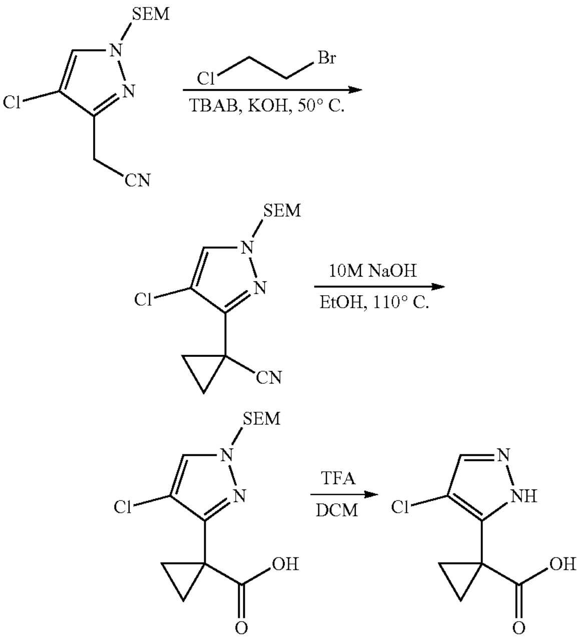

General Procedure U

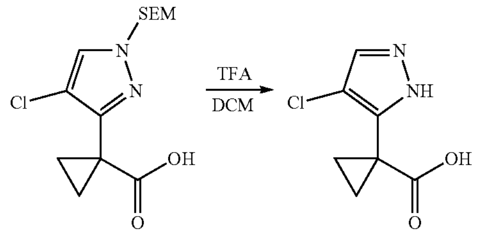 [SMILES: C[Si](C)(C)CCOCn1cc(Cl)c(C2(C(=O)O)CC2)n1 ; O=C(O)C1(c2[nH]ncc2Cl)CC1]

1-(4-chloro-1H-pyrazol-5-yl)cyclopropanecarboxylic acid: To a solution of 1-(4-chloro-1-((2-(trimethylsilyl)ethoxy)methyl)-1H-pyrazol-3-yl)cyclopropanecarboxylic acid (1.26 g, 3.98 mmol) in DCM (10 mL) was added TFA (2 mL, 27.01 mmol). The mixture was stirred at 25° C. for 12 h and then concentrated under reduced pressure. The crude mixture was purified by column chromatography to afford the desired compound.

Scheme K

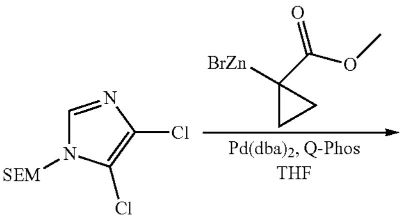

-continued

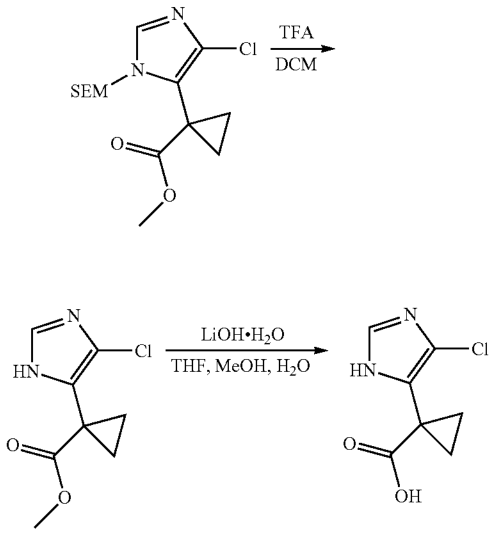

Scheme L

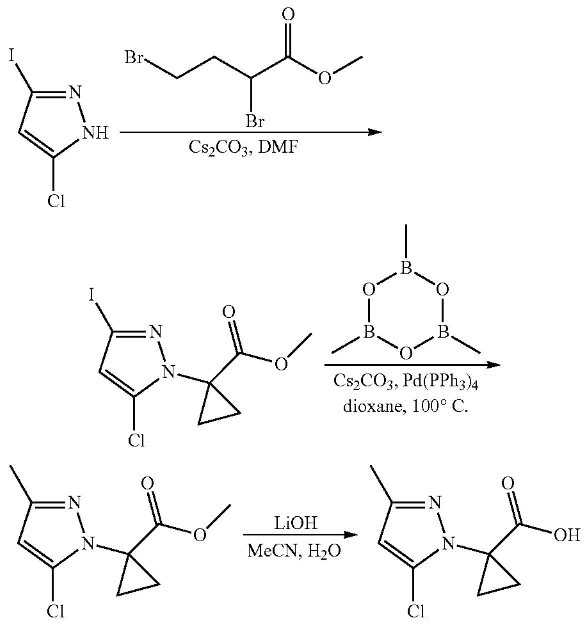

General Procedure V

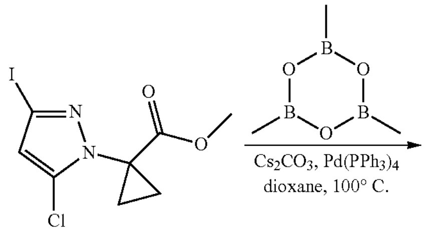

-continued

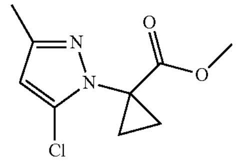

methyl 1-(5-chloro-3-methyl-1H-pyrazol-1-yl)cyclopropanecarboxylate

To a solution of methyl 1-(5-chloro-3-iodo-1H-pyrazol-1-yl)cyclopropanecarboxylate (900 mg, 2.76 mmol) and 2,4,6-trimethyl-1,3,5,2,4,6-trioxatriborinane (269.72 μL, 1.93 mmol) in dioxane (10 mL) was added $Cs_2CO_3$ (1.80 g, 5.51 mmol) and $Pd(PPh_3)_4$ (31.85 mg, 27.56 μmol). The reaction mixture was stirred at 100° C. for 24 h. The reaction mixture was diluted with $H_2O$ and extracted with ethyl acetate. The combined organic layers were dried over $Na_2SO_4$, filtered, and concentrated under reduced pressure. The crude mixture was purified by reverse phase chromatography to afford the desired compound.

Scheme M

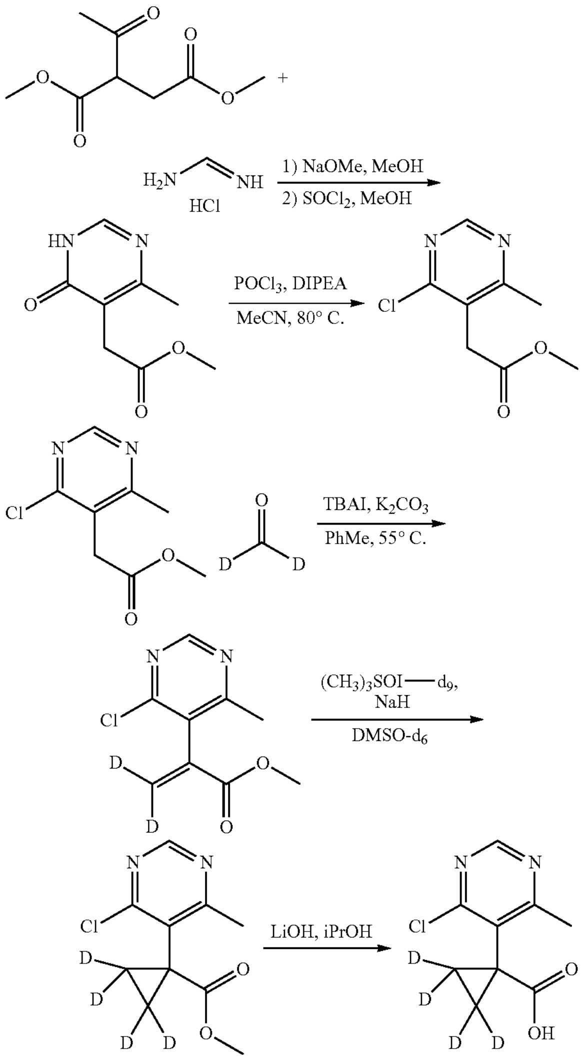

-continued

Representative Procedures for Scheme M

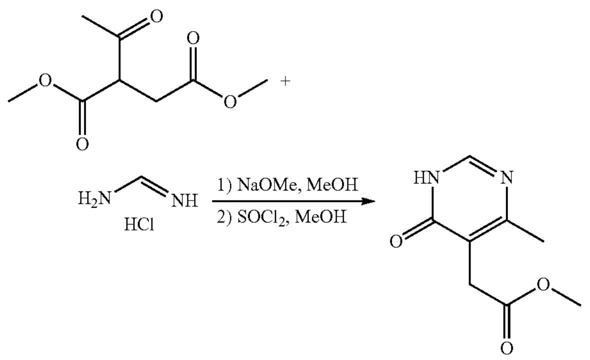

methyl 2-(4-methyl-6-oxo-1,6-dihydropyrimidin-5-yl)acetate

A flame-dried 100 mL round-bottom flask was charged with formamidine hydrochloride (2.25 g, 27.9 mmol, 1.05 eq.) and anhydrous methanol (26.6 mL, 1 M). A separate flame-dried 100 mL round-bottom flask equipped with stir bar was charged with dimethyl acetylsuccinate (5.00 g, 26.6 mmol, 1 eq.) and sodium methoxide (25% in MeOH, 11.5 mL, 53.1 mmol, 2 eq.). The mixture of formamidine hydrochloride and methanol was added to the mixture of dimethyl acetylsuccinate and sodium methoxide, then heated at reflux overnight. After overnight reaction, LC-MS indicated a crude mixture of the desired methyl ester and the corresponding carboxylic acid. The cooled reaction mixture was acidified to pH ~6-7 by dropwise addition of HCl in dioxane (4 M, ~6 mL). The mixture was cooled on ice, followed by dropwise addition of thionyl chloride (3.92 mL, 53.1 mmol, 2 eq.). The resulting mixture was heated at reflux for 90 min, after which LC-MS indicated complete conversion of remaining carboxylic acid to the desired methyl ester product. The reaction was concentrated under reduced pressure. The desired product was isolated by dissolving the residue in minimal amount of methanol, followed by MTBE and hexanes. The resulting precipitate was isolated by filtration, and dried under high vacuum overnight to yield the desired product as a a greyish red solid. $^1H$ NMR ($CH_3OH$-$d_4$, 300 MHz): $\delta_H$ 9.14 (1H, s), 3.74 (3H, s), 3.69 (2H, s), 2.45 (3H, s).

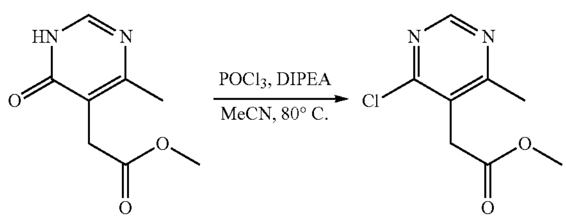

methyl 2-(4-chloro-6-methylpyrimidin-5-yl)acetate

A flame-dried flask equipped with a stir bar was charged with methyl 2-(4-methyl-6-oxo-1,6-dihydropyrimidin-5-yl) acetate (3.61 g, 19.8 mmol, 1 eq.), phosphorus(V) oxychloride (2.22 mL, 23.8 mmol, 1.2 eq), and anhydrous acetonitrile (21.8 mL, 0.91 M). The resulting mixture was cooled on ice, and N,N-diisopropylethylamine (5.23 mL, 29.7 mmol, 1.5 eq.) was added dropwise. After complete addition, the reaction mixture was heated to 80° C. for 3 h. The mixture was cooled to room temperature, then poured directly into saturated aqueous sodium bicarbonate (~100 mL) and stirred vigorously for 10 min. The mixture was extracted three times with DCM. The combined organic phases were dried with sodium sulfate, decanted, and concentrated onto silica gel. Purification by normal phase chromatography afforded the desired product. $^1H$ NMR ($CHCl_3$-d, 300 MHz): $\delta_H$ 8.80 (1H, s), 3.88 (2H, s), 3.77 (3H, s), 2.59 (3H, s).

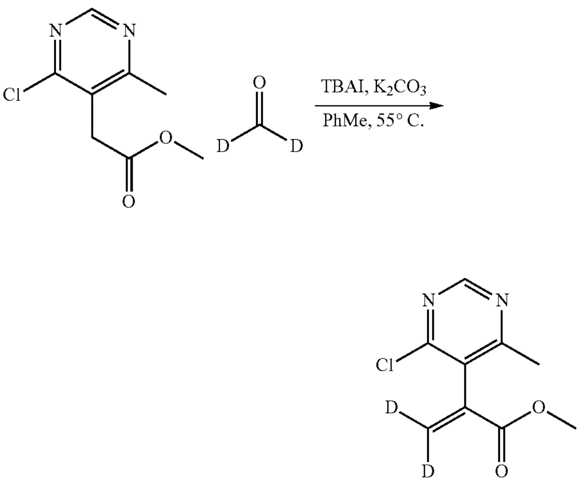

methyl 2-(4-chloro-6-methylpyrimidin-5-yl)acrylate-d2

An oven dried flask equipped with a stir bar was charged with methyl 2-(4-chloro-6-methylpyrimidin-5-yl)acetate (1.63 g, 8.14 mmol), anhydrous toluene (11.2 mL), $K_2CO_3$ (3.38 g, 24.4 mmol), paraformaldehyde-d2 (522 mg, 16.3 mmol) and tetrabutylammonium iodide (3.07 g, 8.14 mmol) in that order. The flask was equipped with an oven dried reflux condenser and heated at 55° C. for 20 h. The reaction mixture was diluted with water (70 mL) and EtOAc (30 mL). The organic layer was separated, and the aqueous phase was extracted with EtOAc (3×20 ml). The combined organic layers were washed with water, brine, dried over $Na_2SO_4$, and filtered under reduced pressure. The filtrate was concentrated in vacuo. The crude material was purified on silica gel afford the desired product. LCMS (ES, m/z) $[M+H]^+$: 215.1; $^1H$ NMR ($CHCl_3$-d, 300 MHz): $\delta_H$ 8.82 (1H, s), 3.80 (3H, s), 2.46 (3H, s).

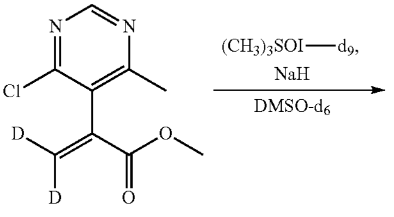

-continued

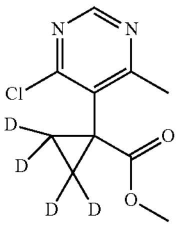

1-(4-chloro-6-methylpyrimidin-5-yl)cyclopropane-1-carboxylate-2,2,3,3-d4

Trimethyl-d9-sulfoxonium iodide (1.93 g, 8.42 mmol) was added portion wise over 1 h to a stirred mixture of sodium hydride (303 mg, 7.58 mmol) in DMSO-d6 (18.1 mL) under argon. This was stirred for 45 min and a solution of methyl 2-(4-chloro-6-methylpyrimidin-5-yl)acrylate-d2 (0.904 g, 4.21 mmol) in DMSO-d6 (12.8 mL) was then added dropwise. The flask containing methyl 2-(4-chloro-6-methylpyrimidin-5-yl)acrylate-d2 (0.904 g, 4.21 mmol) was subsequently rinsed with DMSO-d6 (3×5 mL). The solution was stirred for 1 h. The reaction was quenched with saturated aq. NH4Cl and diluted with water and EtOAc. The organic layer was separated, and the aqueous layer extracted with EtOAc. The combined organic layers were washed with water (2×), brine, then dried over $Na_2SO_4$, filtered under reduced pressure. The filtrate was concentrated in vacuo. The crude material was purified by normal phase chromatography to afford the desired compound as a mixture of d4, d5, d6 and d7. LCMS (ES, m/z) [M+H]+ (d4): 231.1. 1H NMR (CHCl3-d, 300 MHz): δH 8.74 (1H, s), 3.65 (3H, s), 2.52-2.57 (2H, m). Multiplet at 2.52 to 2.57 is an overlap of a CH3 singlet, CDH2 triplet and a CHD2 quintet.

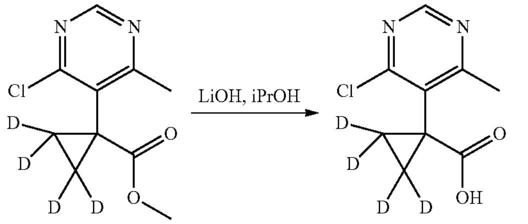 [SMILES: [2H]C1([2H])C([2H])([2H])C1(C(=O)OC)c1c(C)ncnc1Cl ; [2H]C1([2H])C([2H])([2H])C1(C(=O)O)c1c(C)ncnc1Cl]

1-(4-chloro-6-methylpyrimidin-5-yl)cyclopropane-1-carboxylic-2,2,3,3-d4

A solution of lithium hydroxide monohydrate (947 mg, 22.6 mmol) in water (22.3 mL) was added to a solution of methyl 1-(4-chloro-6-methylpyrimidin-5-yl)cyclopropane-1-carboxylate-2,2,3,3-d4 (1.04 g, 4.51 mmol) in isopropanol (22.3 mL) at rt. The reaction was stirred for 16 h. The mixture was acidified by slowly adding HCl 2 N (pH=7-8). The reaction was then concentrated under reduced pressure to remove most of the organic solvent. This was diluted with water and washed with EtOAc. The aqueous layer was then acidified with HCl 2N to pH 2 and extracted with EtOAc. The combined organic layers were washed with brine, dried over $Na_2SO_4$, filtered under reduced pressure, and concentrated in vacuo. The resulting white solid was stirred briefly in pentane (10 mL) and the supernatant removed using a pipette. This was repeated 3 more times and the suspension concentrated to dryness. The solid was placed under vacuum to afford the desired product as a white solid. LCMS (ES, m/z) [M+H]+: 217.1. $^1$H NMR ($CHCl_3$-d, 300 MHz): δH 8.77 (1H, s), 2.58-2.62 (3H, m).

Synthetic Examples

The following Synthetic Examples are set forth for Compounds 1-104 below to enable this disclosure to be more fully understood. It should be understood that these Synthetic Examples are for illustrative purposes only and are not to be construed as limiting this disclosure in any manner.

The chemical reactions in the Synthetic Examples described can be readily adapted to prepare a number of other compounds, and alternative methods for preparing the compounds are deemed to be within the scope of this disclosure. For example, the synthesis of non-exemplified compounds of formula (A) or formula (I) can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of formula (A) or formula (I). In the following Examples, certain compounds are noted as racemic, as separated isomers, or with unassigned absolute stereochemistry at some stereocenters, and the like. For some compounds, further separation of isomers and/or assignment of absolute stereochemistry was performed. The assigned stereochemistry of such compounds is shown in the structures as depicted in Table 1.

Compound 1

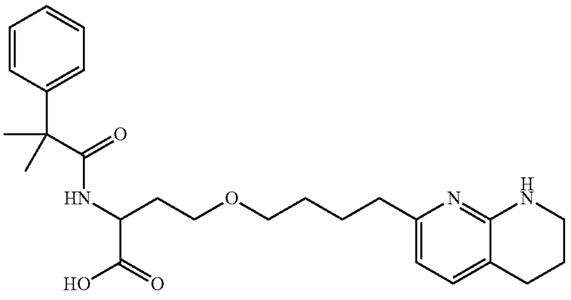 [SMILES: CC(C)(C(=O)NC(CCOCCCCc1ccc2c(n1)NCCC2)C(=O)O)c1ccccc1]

N-(2-methyl-2-phenylpropanoyl)-O-(4-(5,6,7,8-tetrahydro-1,8-naphthyridin-2-yl)butyl)homoserine Prepared according to Scheme A using General Procedure A with 2-methyl-2-phenylpropanoic acid and General Procedure B. LCMS theoretical m/z=453.3. [M+H]+, found 454.3.

Compound 2

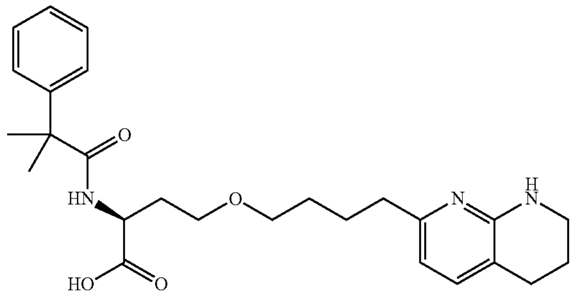 [SMILES: CC(C)(C(=O)N[C@@H](CCOCCCCc1ccc2c(n1)NCCC2)C(=O)O)c1ccccc1]

N-(2-methyl-2-phenylpropanoyl)-O-(4-(5,6,7,8-tetrahydro-1,8-naphthyridin-2-yl)butyl)-L-homoserine Prepared according to Scheme B using General Procedure C with 2-methyl-2-phenylpropanoic acid and General Procedure D. LCMS theoretical m/z=453.3. [M+H]+, found 454.1.

Compound 3

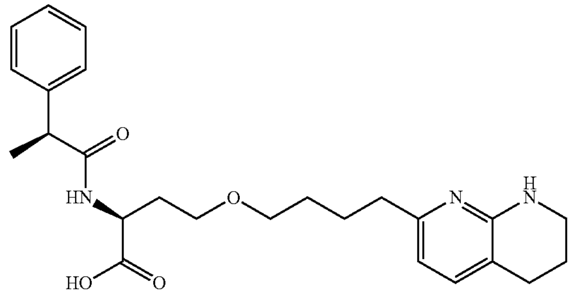 [SMILES: C[C@H](C(=O)N[C@@H](CCOCCCCc1ccc2c(n1)NCCC2)C(=O)O)c1ccccc1]

N-((S)-2-phenylpropanoyl)-O-(4-(5,6,7,8-tetrahydro-1,8-naphthyridin-2-yl)butyl)-L-homoserine Prepared according to Scheme B using General Procedure C with (S)-2-phenylpropanoic acid and General Procedure D. LCMS theoretical m/z=439.2. [M+H]+, found 440.1.

Compound 4

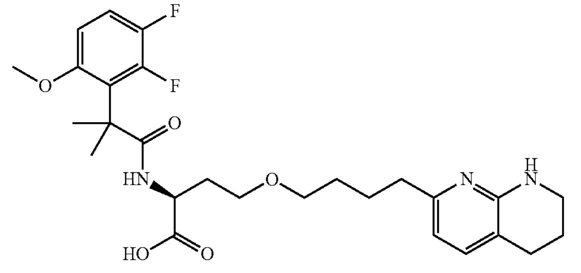 [SMILES: COc1ccc(F)c(F)c1C(C)(C)C(=O)N[C@@H](CCOCCCCc1ccc2c(n1)NCCC2)C(=O)O]

N-(2-(2,3-difluoro-6-methoxyphenyl)-2-methylpropanoyl)-O-(4-(5,6,7,8-tetrahydro-1,8-naphthyridin-2-yl)butyl)-L-homoserine Prepared according to Scheme B using General Procedure C with 2-(2,3-difluoro-6-methoxyphenyl)-2-methylpropanoic acid and General Procedure D, and Scheme E using General Procedure I with benzyl 2-(2,3-difluoro-6-methoxyphenyl)acetate and General Procedure J. LCMS theoretical m/z=439.2. [M+H]+, found 440.1.

Compound 5

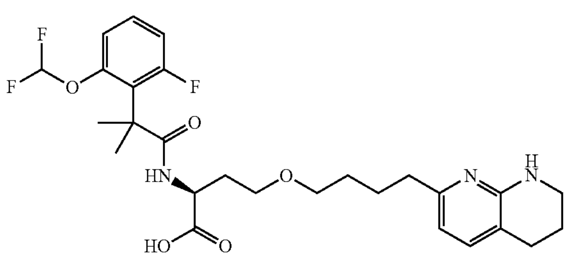 [SMILES: CC(C)(C(=O)N[C@@H](CCOCCCCc1ccc2c(n1)NCCC2)C(=O)O)c1c(F)cccc1OC(F)F]

N-(2-(2-(difluoromethoxy)-6-fluorophenyl)-2-methylpropanoyl)-O-(4-(5,6,7,8-tetrahydro-1,8-naphthyridin-2-yl)butyl)-L-homoserine Prepared according to Scheme B using General Procedure C with 2-[2-(difluoromethoxy)-6-fluoro-phenyl]-2-methylpropanoic acid and General Procedure D, and Scheme E using General Procedure I with benzyl 2-[2-(difluoromethoxy)-6-fluoro-phenyl]acetate and General Procedure J. LCMS theoretical m/z=519.3. [M+H]+, found 520.3.

Compound 6

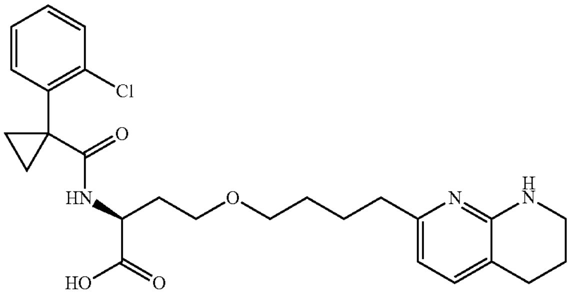 [SMILES: O=C(O)[C@H](CCOCCCCc1ccc2c(n1)NCCC2)NC(=O)C1(c2ccccc2Cl)CC1]

N-(1-(2-chlorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-chlorophenyl)cyclopropane-1-carboxylic acid and General Procedure D. LCMS theoretical m/z=485.2. [M+H]+, found 486.2.

Compound 7

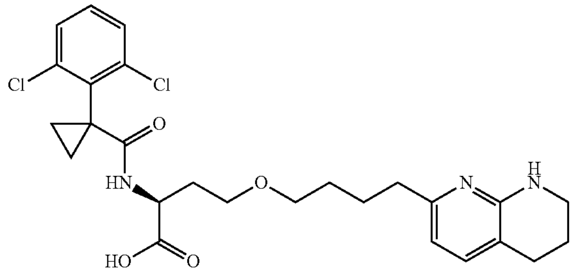 [SMILES: O=C(O)[C@H](CCOCCCCc1ccc2c(n1)NCCC2)NC(=O)C1(c2c(Cl)cccc2Cl)CC1]

N-(1-(2,6-dichlorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2,6-dichlorophenyl)cyclopropane-1-carboxylic acid and General Procedure D. LCMS theoretical m/z=519.2. [M+H]+, found 520.2.

Compound 8

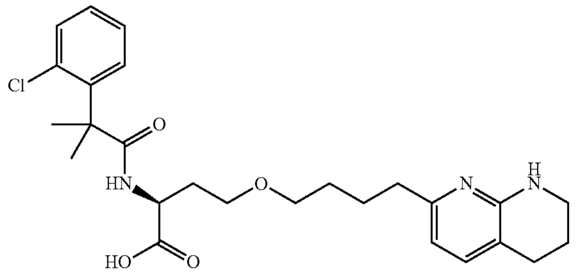 [SMILES: CC(C)(C(=O)N[C@@H](CCOCCCCc1ccc2c(n1)NCCC2)C(=O)O)c1ccccc1Cl]

N-(2-(2-chlorophenyl)-2-methylpropanoyl)-O-(4-(5,6,7,8-tetrahydro-1,8-naphthyridin-2-yl)butyl)-L-homoserine Prepared according to Scheme B using General Procedure C with 2-(2-chlorophenyl)-2-methylpropanoic acid and General Procedure D. LCMS theoretical m/z=487.2. [M+H]+, found 488.3.

Compound 9

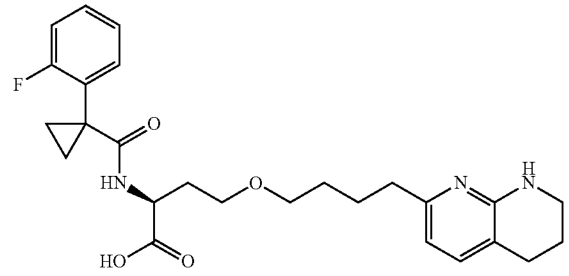 [SMILES: O=C(O)[C@H](CCOCCCCc1ccc2c(n1)NCCC2)NC(=O)C1(c2ccccc2F)CC1]

N-(1-(2-fluorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-fluorophenyl)cyclopropane-1-carboxylic acid and General Procedure D. LCMS theoretical m/z=469.2. [M+H]+, found 470.3.

Compound 10

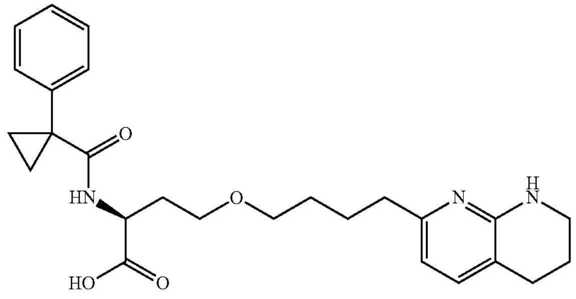 [SMILES: O=C(O)[C@H](CCOCCCCc1ccc2c(n1)NCCC2)NC(=O)C1(c2ccccc2)CC1]

N-(1-phenylcyclopropane-1-carbonyl)-O-(4-(5,6,7,8-tetrahydro-1,8-naphthyridin-2-yl)butyl)-L-homoserine Prepared according to Scheme B using General Procedure C with 1-phenylcyclopropane-1-carboxylic acid and General Procedure D. LCMS theoretical m/z=451.3. [M+H]+, found 452.3.

Compound 11

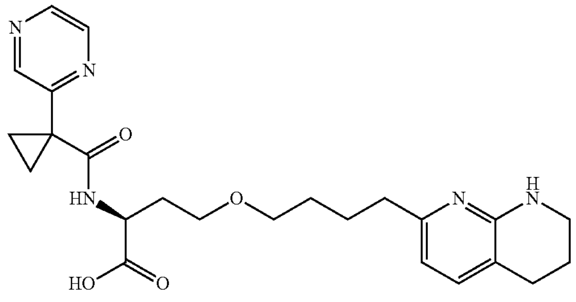 [SMILES: O=C(O)[C@H](CCOCCCCc1ccc2c(n1)NCCC2)NC(=O)C1(c2cnccn2)CC1]

N-(1-(pyrazin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(pyrazin-2-yl)cyclopropane-1-carboxylic acid and General Procedure D. LCMS theoretical m/z=453.2. [M+H]+, found 454.3.

Compound 12

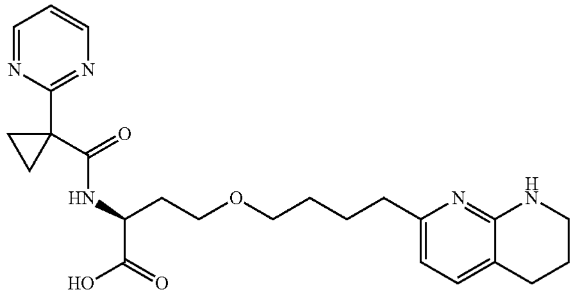 [SMILES: O=C(O)[C@H](CCOCCCCc1ccc2c(n1)NCCC2)NC(=O)C1(c2ncccn2)CC1]

N-(1-(pyrimidin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(pyrimidin-2-yl)cyclopropane-1-carboxylic acid and General Procedure D. LCMS theoretical m/z=453.2. [M+H]+, found 454.3.

Compound 13

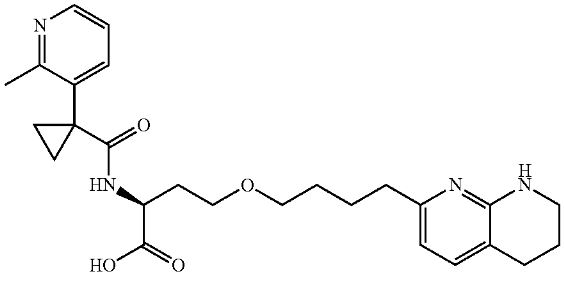

N-(1-(2-methylpyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-methylpyridin-3-yl)cyclopropane-1-carboxylic acid and General Procedure D, and Scheme C using General Procedure E with 3-bromo-2-methylpyridine and General Procedure F. LCMS theoretical m/z=466.3. [M+H]+, found 467.3.

Compound 14

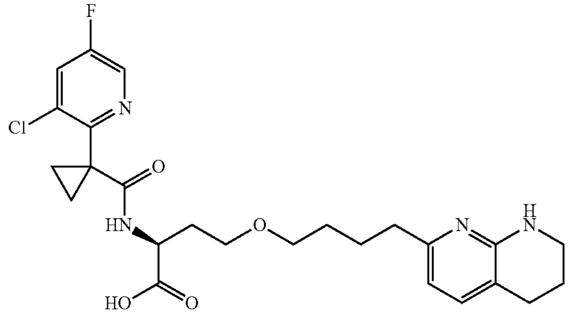 [SMILES: O=C(O)[C@H](CCOCCCCc1ccc2c(n1)NCCC2)NC(=O)C1(c2ncc(F)cc2Cl)CC1]

N-(1-(3-chloro-5-fluoropyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-5-fluoropyridin-2-yl)cyclopropane-1-carboxylic acid and General Procedure D, and Scheme C using General Procedure E with 2-bromo-3-chloro-5-fluoropyridine and General Procedure F. LCMS theoretical m/z=504.2. [M+H]+, found 505.2.

Compound 15

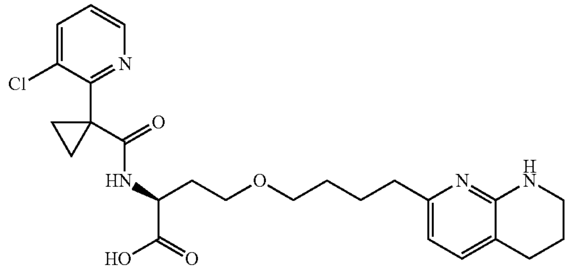 [SMILES: O=C(O)[C@H](CCOCCCCc1ccc2c(n1)NCCC2)NC(=O)C1(c2ncccc2Cl)CC1]

N-(1-(3-chloropyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloropyridin-2-yl)cyclopropane-1-carboxylic acid and General Procedure D, and Scheme C using General Procedure E with 2-bromo-3-chloropyridine and General Procedure F. LCMS theoretical m/z=486.2. [M+H]+, found 487.2.

Compound 16

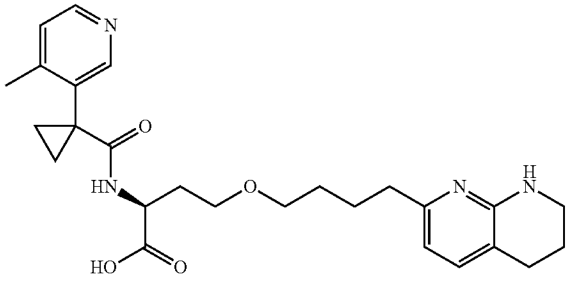 [SMILES: Cc1ccncc1C1(C(=O)N[C@@H](CCOCCCCc2ccc3c(n2)NCCC3)C(=O)O)CC1]

N-(1-(4-methylpyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-methylpyridin-3-yl)cyclopropane-1-carboxylic acid and General Procedure D, and Scheme C using General Procedure E with 3-bromo-4-methylpyridine and General Procedure F. LCMS theoretical m/z=466.3. [M+H]+, found 467.3.

Compound 17

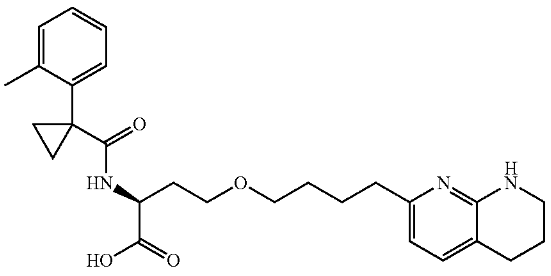 [SMILES: Cc1ccccc1C1(C(=O)N[C@@H](CCOCCCCc2ccc3c(n2)NCCC3)C(=O)O)CC1]

O-(4-(5,6,7,8-tetrahydro-1,8-naphthyridin-2-yl)butyl)-N-(1-(o-tolyl)cyclopropane-1-carbonyl)-L-homoserine Prepared according to Scheme B using General Procedure C with 1-(o-tolyl)cyclopropane-1-carboxylic acid and General Procedure D, and Scheme C using General Procedure E with 1-bromo-2-methylbenzene and General Procedure F. LCMS theoretical m/z=465.3. [M+H]+, found 466.3.

Compound 18

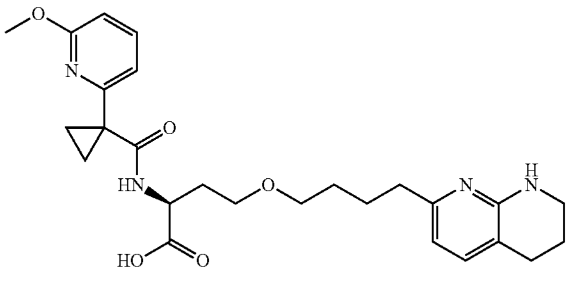 [SMILES: COc1cccc(C2(C(=O)N[C@@H](CCOCCCCc3ccc4c(n3)NCCC4)C(=O)O)CC2)n1]

N-(1-(6-methoxypyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-methoxypyridin-2-yl)cyclopropane-1-carboxylic acid and General Procedure D, and Scheme D using General Procedure G with 2-(6-methoxypyridin-2-yl)acetonitrile and General Procedure H. LCMS theoretical m/z=482.3. [M+H]+, found 483.3.

Compound 19

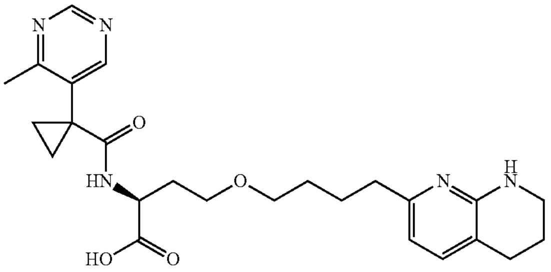 [SMILES: Cc1ncncc1C1(C(=O)N[C@@H](CCOCCCCc2ccc3c(n2)NCCC3)C(=O)O)CC1]

N-(1-(4-methylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-methylpyrimidin-5-yl)cyclopropane-1-carboxylic acid and General Procedure D, and Scheme C using General Procedure E with 5-bromo-4-methylpyrimidine and General Procedure F. LCMS theoretical m/z=467.3. [M+H]+, found 468.3.

Compound 20

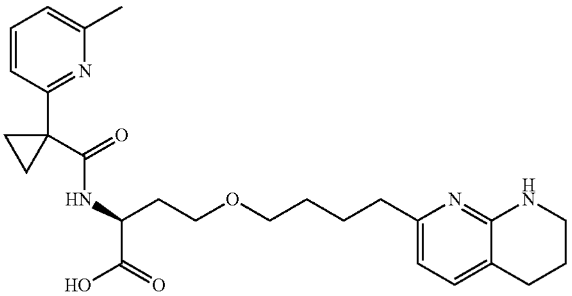 [SMILES: Cc1cccc(C2(C(=O)N[C@@H](CCOCCCCc3ccc4c(n3)NCCC4)C(=O)O)CC2)n1]

N-(1-(6-methylpyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-methylpyridin-2-yl)cyclopropane-1-carboxylic acid and General Procedure D, and Scheme C using General Procedure E with 2-bromo-6-methylpyridine and General Procedure F. LCMS theoretical m/z=466.3. [M+H]+, found 467.3.

Compound 21

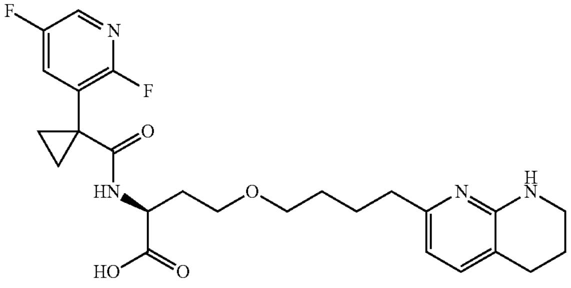 [SMILES: O=C(O)[C@H](CCOCCCCc1ccc2c(n1)NCCC2)NC(=O)C1(c2cc(F)cnc2F)CC1]

N-(1-(2,5-difluoropyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2,5-difluoropyridin-3-yl)cyclopropane-1-carboxylic acid and General Procedure D, and Scheme F using General Procedure K with 3-chloro-2,5-difluoropyridine and cyclopropanecarbonitrile, General Procedure L, and General Procedure M. LCMS theoretical m/z=488.2. [M+H]+, found 489.2.

Compound 22

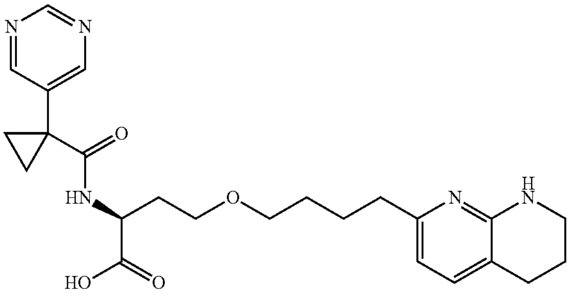 [SMILES: O=C(O)[C@H](CCOCCCCc1ccc2c(n1)NCCC2)NC(=O)C1(c2cncnc2)CC1]

N-(1-(pyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(pyrimidin-5-yl)cyclopropane-1-carboxylic acid and General Procedure D, and Scheme C using General Procedure E with 5-bromopyrimidine and General Procedure F. LCMS theoretical m/z=453.2. [M+H]+, found 454.3.

Compound 23

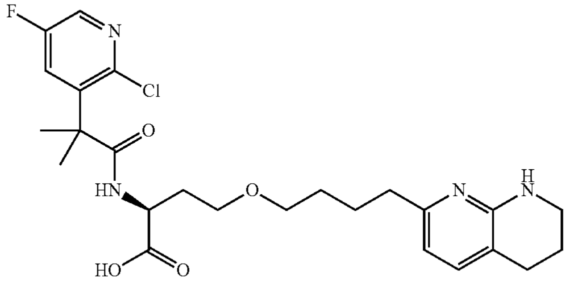 [SMILES: CC(C)(C(=O)N[C@@H](CCOCCCCc1ccc2c(n1)NCCC2)C(=O)O)c1cc(F)cnc1Cl]

N-(2-(2-chloro-5-fluoropyridin-3-yl)-2-methylpropanoyl)-O-(4-(5,6,7,8-tetrahydro-1,8-naphthyridin-2-yl)butyl)-L-homoserine Prepared according to Scheme B using General Procedure C with 2-(2-chloro-5-fluoropyridin-3-yl)-2-methylpropanoic acid and General Procedure D, and Scheme F using General Procedure K with 2,3-dichloro-5-fluoropyridine and isobutyronitrile, General Procedure L, and General Procedure M. LCMS theoretical m/z=506.2. [M+H]+, found 507.3.

Compound 24

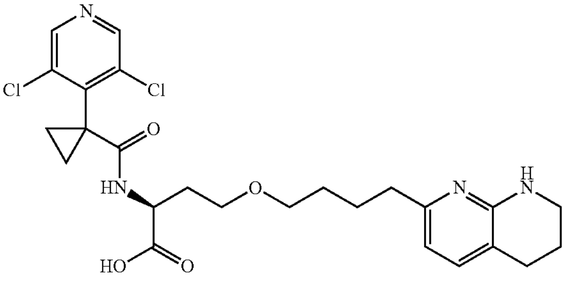 [SMILES: O=C(O)[C@H](CCOCCCCc1ccc2c(n1)NCCC2)NC(=O)C1(c2c(Cl)cncc2Cl)CC1]

N-(1-(3,5-dichloropyridin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3,5-dichloropyridin-4-yl)cyclopropane-1-carboxylic acid and General Procedure D, and Scheme F using General Procedure K with 3,5-dichloroisonicotinonitrile and cyclopropanecarbonitrile, General Procedure L, and General Procedure M. LCMS theoretical m/z=520.2. [M+H]+, found 521.3.

Compound 25

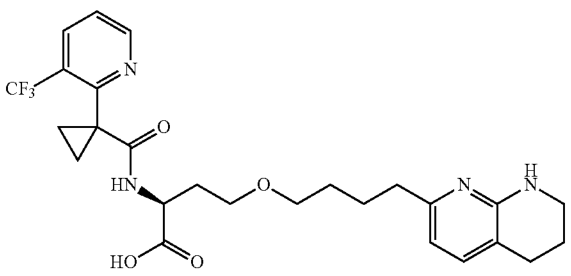 [SMILES: O=C(O)[C@H](CCOCCCCc1ccc2c(n1)NCCC2)NC(=O)C1(c2ncccc2C(F)(F)F)CC1]

O-(4-(5,6,7,8-tetrahydro-1,8-naphthyridin-2-yl) butyl)-N-(1-(3-(trifluoromethyl)pyridin-2-yl)cyclopropane-1-carbonyl)-L-homoserine Prepared according to Scheme B using General Procedure C with 1-(3-(trifluoromethyl)pyridin-2-yl)cyclopropane-1-carboxylic acid and General Procedure D, and Scheme D using General Procedure G with 2-(3-(trifluoromethyl)pyridin-2-yl)acetonitrile and General Procedure H. LCMS theoretical m/z=520.2. [M+H]+, found 521.3.

Compound 26

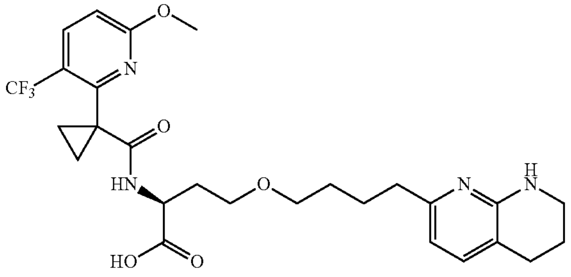 [SMILES: COc1ccc(C(F)(F)F)c(C2(C(=O)N[C@@H](CCOCCCCc3ccc4c(n3)NCCC4)C(=O)O)CC2)n1]

N-(1-(3-chloro-6-methoxypyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-6-methoxypyridin-2-yl)cyclopropane-1-carboxylic acid and General Procedure D, and Scheme D using General Procedure G with 2-(3-chloro-6-methoxypyridin-2-yl)acetonitrile and General Procedure H. LCMS theoretical m/z=516.2. [M+H]+, found 517.3.

Compound 27

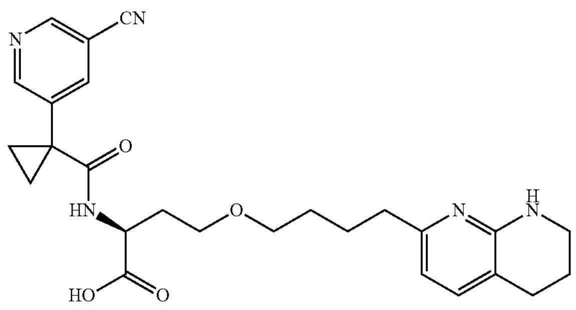 [SMILES: N#Cc1cncc(C2(C(=O)N[C@@H](CCOCCCCc3ccc4c(n3)NCCC4)C(=O)O)CC2)c1]

N-(1-(5-cyanopyridin-3-yl)cyclopropane-1-carbonyl)-O-(4-(5,6,7,8-tetrahydro-1,8-naphthyridin-2-yl) butyl)-L-homoserine Prepared according to Scheme B using General Procedure C with 1-(5-cyanopyridin-3-yl)cyclopropane-1-carboxylic acid and General Procedure D, and Scheme C using General Procedure E with 5-bromonicotinonitrile and General Procedure F. LCMS theoretical m/z=477.2. [M+H]+, found 478.3.

Compound 28

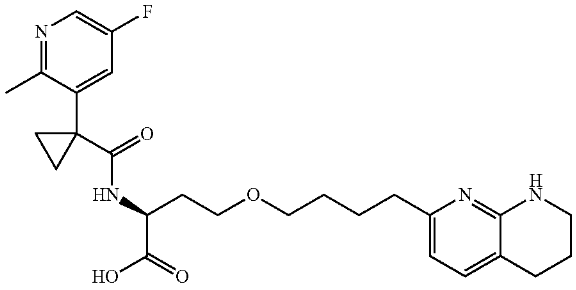 [SMILES: Cc1ncc(F)cc1C1(C(=O)N[C@@H](CCOCCCCc2ccc3c(n2)NCCC3)C(=O)O)CC1]

N-(1-(5-fluoro-2-methylpyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-fluoro-2-methylpyridin-3-yl)cyclopropane-1-carboxylic acid and General Procedure D, and Scheme C using General Procedure E with 3-bromo-5-fluoro-2-methylpyridine and General Procedure F. LCMS theoretical m/z=484.3. [M+H]+, found 485.3.

Compound 29

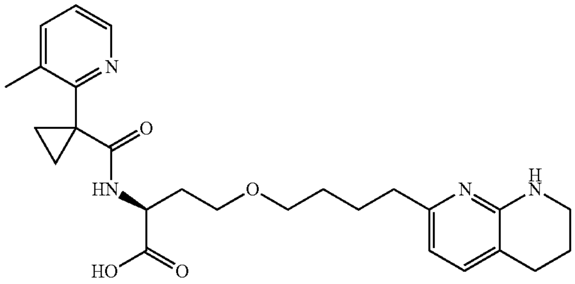

N-(1-(3-methylpyridin-2-yl)cyclopropane-1-carbonyl)-O-(4-(5,6,7,8-tetrahydro-1,8-naphthyridin-2-yl) butyl)-L-homoserine Prepared according to Scheme B using General Procedure C with 1-(3-methylpyridin-2-yl)cyclopropane-1-carboxylic acid and General Procedure D, and Scheme C using General Procedure E with 2-bromo-3-methylpyridine and General Procedure F. LCMS theoretical m/z=466.3. [M+H]+, found 467.3.

Compound 30

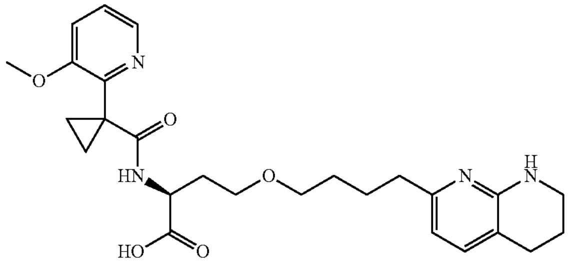 [SMILES: COc1cccnc1C1(C(=O)N[C@@H](CCOCCCCc2ccc3c(n2)NCCC3)C(=O)O)CC1]

N-(1-(3-methoxypyridin-2-yl)cyclopropane-1-carbonyl)-O-(4-(5,6,7,8-tetrahydro-1,8-naphthyridin-2-yl) butyl)-L-homoserine Prepared according to Scheme B using General Procedure C with 1-(3-methoxypyridin-2-yl)cyclopropane-1-carboxylic acid and General Procedure D, and Scheme C using General Procedure E with 2-bromo-3-methoxypyridine and General Procedure F. LCMS theoretical m/z=482.3. [M+H]+, found 482.3.

Compound 31

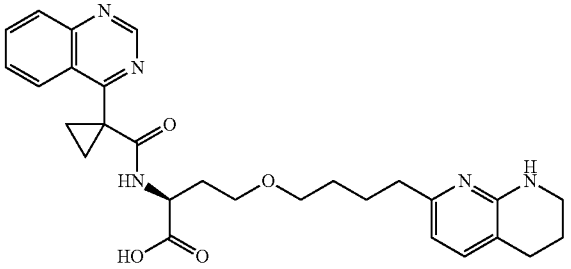 [SMILES: O=C(O)[C@H](CCOCCCCc1ccc2c(n1)NCCC2)NC(=O)C1(c2ncnc3ccccc23)CC1]

N-(1-(quinazolin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(quinazolin-4-yl)cyclopropane-1-carboxylic acid and General Procedure D, and Scheme C using General Procedure E with 4-bromoquinazoline and General Procedure F. LCMS theoretical m/z=503.3. [M+H]+, found 504.3.

Compound 32

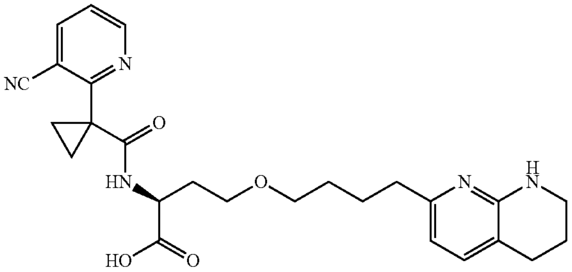 [SMILES: N#Cc1cccnc1C1(C(=O)N[C@@H](CCOCCCCc2ccc3c(n2)NCCC3)C(=O)O)CC1]

N-(1-(3-cyanopyridin-2-yl)cyclopropane-1-carbonyl)-O-(4-(5,6,7,8-tetrahydro-1,8-naphthyridin-2-yl) butyl)-L-homoserine Prepared according to Scheme B using General Procedure C with 1-(3-cyanopyridin-2-yl)cyclopropane-1-carboxylic acid and General Procedure D, and Scheme C using General Procedure E with 2-bromonicotinonitrile and General Procedure F. LCMS theoretical m/z=477.3. [M+H]+, found 478.3.

Compound 33

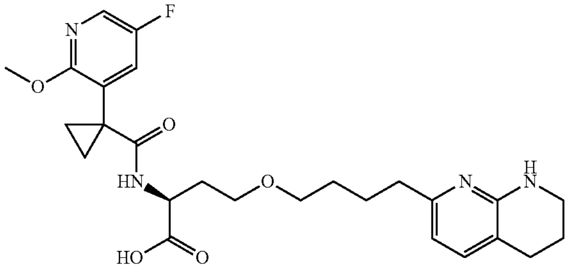 [SMILES: COc1ncc(F)cc1C1(C(=O)N[C@@H](CCOCCCCc2ccc3c(n2)NCCC3)C(=O)O)CC1]

N-(1-(5-fluoro-2-methoxypyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-fluoro-2-methoxypyridin-3-yl)cyclopropane-1-carboxylic acid and General Procedure D, and Scheme D using General Procedure G with 2-(5-fluoro-2-methoxypyridin-3-yl)acetonitrile and General Procedure H. LCMS theoretical m/z=500.3. [M+H]+, found 501.3.

Compound 34

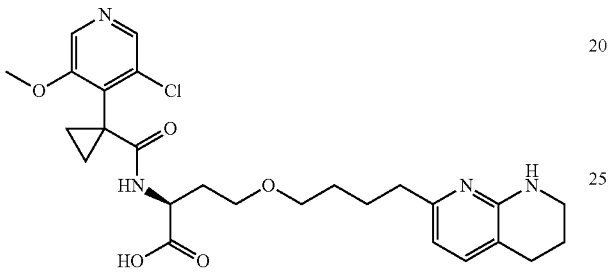

N-(1-(3-chloro-5-methoxypyridin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-5-methoxypyridin-4-yl)cyclopropane-1-carboxylic acid and General Procedure D, and Scheme D using General Procedure G with 2-(3-chloro-5-methoxypyridin-4-yl)acetonitrile and General Procedure H. LCMS theoretical m/z=516.2. [M+H]+, found 517.3.

Compound 35

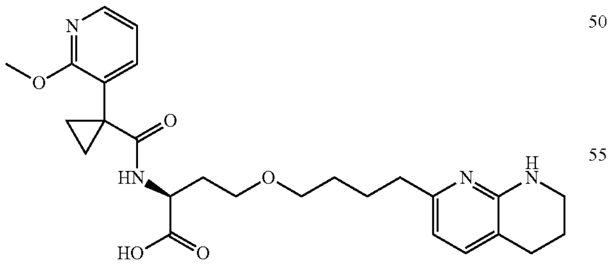

N-(1-(2-methoxypyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-methoxypyridin-3-yl)cyclopropane-1-carboxylic acid and General Procedure D, and Scheme C using General Procedure E with 3-bromo-2-methoxypyridine and General Procedure F. LCMS theoretical m/z=482.3. [M+H]+, found 483.3.

Compound 36

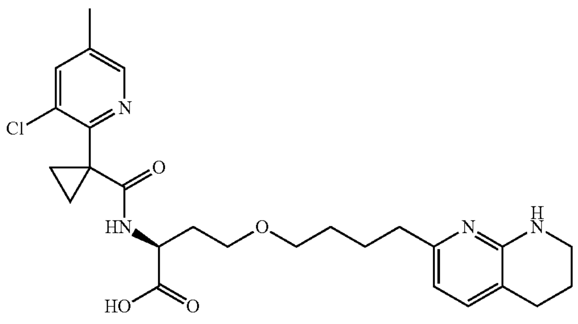 [SMILES: Cc1cnc(C2(C(=O)N[C@@H](CCOCCCCc3ccc4c(n3)NCCC4)C(=O)O)CC2)c(Cl)c1]

N-(1-(3-chloro-5-methylpyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-5-methylpyridin-2-yl)cyclopropane-1-carboxylic acid and General Procedure D, and Scheme C using General Procedure E with 2-bromo-3-chloro-5-methylpyridine and General Procedure F. LCMS theoretical m/z=500.2. [M+H]+, found 501.3.

Compound 37

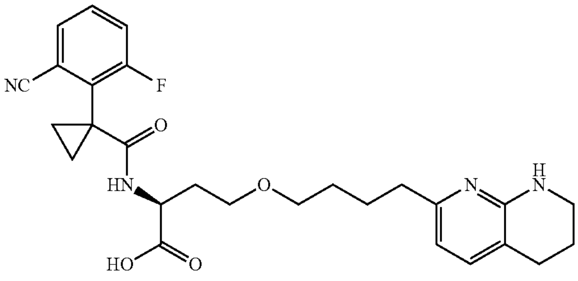 [SMILES: N#Cc1cccc(F)c1C1(C(=O)N[C@@H](CCOCCCCc2ccc3c(n2)NCCC3)C(=O)O)CC1]

N-(1-(2-cyano-6-fluorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-cyano-6-fluorophenyl)cyclopropane-1-carboxylic acid and General Procedure D, and Scheme C using General Procedure E with 2-bromo-3-fluorobenzonitrile and General Procedure F. LCMS theoretical m/z=494.2. [M+H]+, found 495.3.

Compound 38

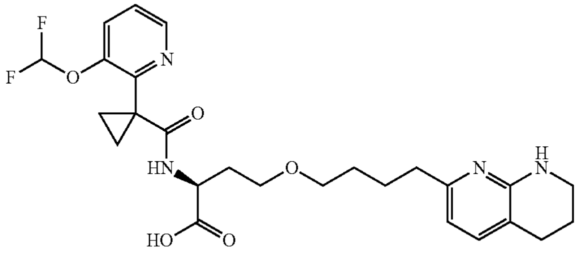 [SMILES: O=C(O)[C@H](CCOCCCCc1ccc2c(n1)NCCC2)NC(=O)C1(c2ncccc2OC(F)F)CC1]

N-(1-(3-(difluoromethoxy)pyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-(difluoromethoxy)pyridin-2-yl)cyclopropane-1-carboxylic acid and General Procedure D, and Scheme C using General Procedure E with 2-bromo-3-(difluoromethoxy)pyridine and General Procedure F. LCMS theoretical m/z=518.2. [M+H]+, found 519.3.

Compound 39

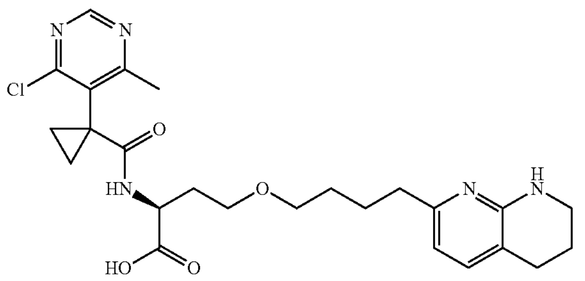 [SMILES: Cc1ncnc(Cl)c1C1(C(=O)N[C@@H](CCOCCCCc2ccc3c(n2)NCCC3)C(=O)O)CC1]

N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-6-methylpyrimidin-5-yl)cyclopropane-1-carboxylic acid and General Procedure D, and Scheme C using General Procedure E with 5-bromo-4-chloro-6-methylpyrimidine and General Procedure F. LCMS theoretical m/z=501.2. [M+H]+, found 502.3.

Compound 40

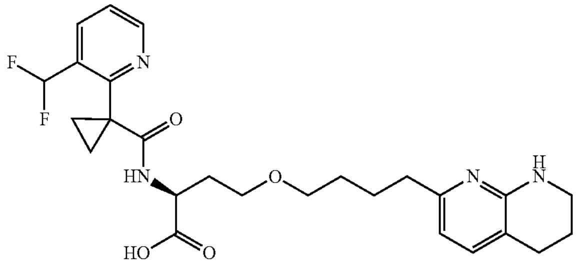 [SMILES: O=C(O)[C@H](CCOCCCCc1ccc2c(n1)NCCC2)NC(=O)C1(c2ncccc2C(F)F)CC1]

N-(1-(3-(difluoromethyl)pyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-(difluoromethyl)pyridin-2-yl)cyclopropane-1-carboxylic acid and General Procedure D, and Scheme C using General Procedure E with 2-bromo-3-(difluoromethyl)pyridine and General Procedure F. LCMS theoretical m/z=502.2. [M+H]+, found 503.3.

Compound 41

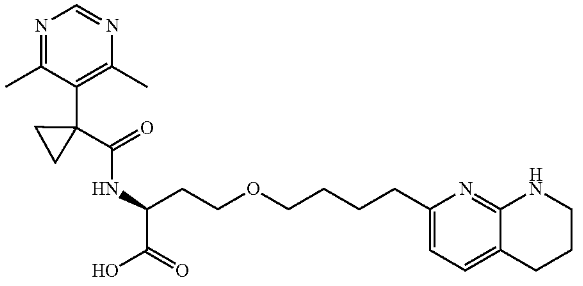 [SMILES: Cc1ncnc(C)c1C1(C(=O)N[C@@H](CCOCCCCc2ccc3c(n2)NCCC3)C(=O)O)CC1]

N-(1-(4,6-dimethylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4,6-dimethylpyrimidin-5-yl)cyclopropane-1-carboxylic acid and General Procedure D, and Scheme C using General Procedure E with 5-bromo-4,6-dimethylpyrimidine and General Procedure F. LCMS theoretical m/z=481.3. [M+H]+, found 482.3.

Compound 42

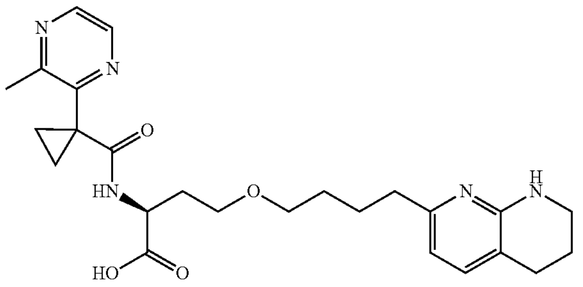

N-(1-(3-methylpyrazin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-methylpyrazin-2-yl)cyclopropane-1-carboxylic acid and General Procedure D, and Scheme C using General Procedure E with 2-bromo-3-methylpyrazine and General Procedure F. LCMS theoretical m/z=467.3. [M+H]+, found 468.3.

Compound 43

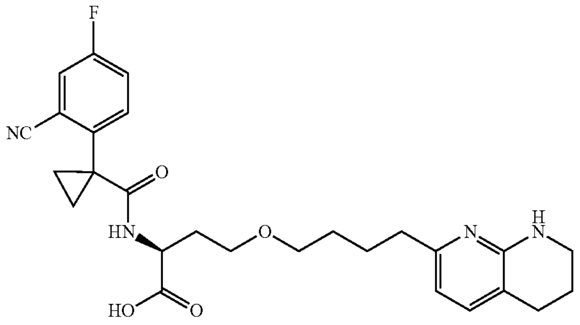 [SMILES: N#Cc1cc(F)ccc1C1(C(=O)N[C@@H](CCOCCCCc2ccc3c(n2)NCCC3)C(=O)O)CC1]

N-(1-(2-cyano-4-fluorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-cyano-4-fluorophenyl)cyclopropane-1-carboxylic acid and General Procedure D, and Scheme C using General Procedure E with 2-bromo-5-fluorobenzonitrile and General Procedure F. LCMS theoretical m/z=494.2. [M+H]+, found 495.2.

Compound 44

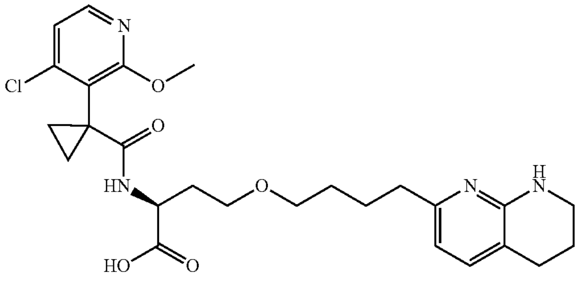 [SMILES: COc1nccc(Cl)c1C1(C(=O)N[C@@H](CCOCCCCc2ccc3c(n2)NCCC3)C(=O)O)CC1]

N-(1-(4-chloro-2-methoxypyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-2-methoxypyridin-3-yl)cyclopropane-1-carboxylic acid and General Procedure D, and Scheme D using General Procedure G with 2-(4-chloro-2-methoxypyridin-3-yl)acetonitrile and General Procedure H. LCMS theoretical m/z=516.2. [M+H]+, found 517.2.

Compound 45

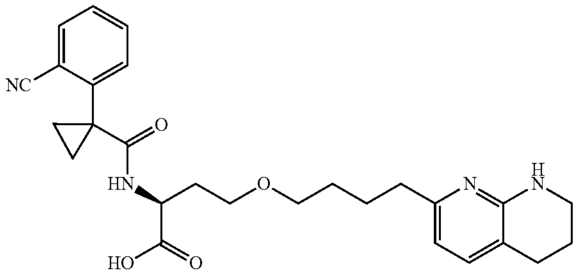 [SMILES: N#Cc1ccccc1C1(C(=O)N[C@@H](CCOCCCCc2ccc3c(n2)NCCC3)C(=O)O)CC1]

N-(1-(2-cyanophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-cyanophenyl)cyclopropane-1-carboxylic acid and General Procedure D, and Scheme C using General Procedure E with 2-bromobenzonitrile and General Procedure F. LCMS theoretical m/z=476.2. [M+H]+, found 477.2.

Compound 46

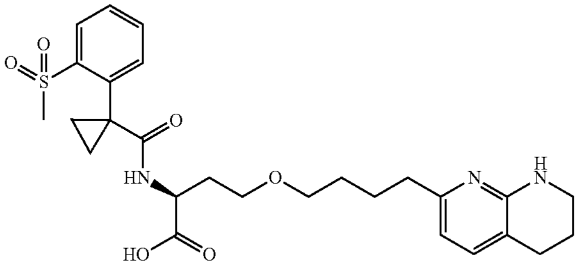 [SMILES: CS(=O)(=O)c1ccccc1C1(C(=O)N[C@@H](CCOCCCCc2ccc3c(n2)NCCC3)C(=O)O)CC1]

N-(1-(2-(methylsulfonyl)phenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-(methylsulfonyl)phenyl)cyclopropane-1-carboxylic acid and General Procedure D, and Scheme C using General Procedure E with 1-bromo-2-(methylsulfonyl)benzene and General Procedure F. LCMS theoretical m/z=529.2. [M+H]+, found 530.2.

Compound 47

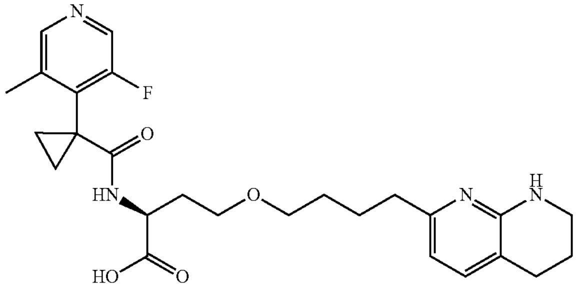 [SMILES: Cc1cncc(F)c1C1(C(=O)N[C@@H](CCOCCCCc2ccc3c(n2)NCCC3)C(=O)O)CC1]

N-(1-(3-fluoro-5-methylpyridin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-fluoro-5-methylpyridin-4-yl)cyclopropane-1-carboxylic acid and General Procedure D, and Scheme D using General Procedure G with 2-(3-fluoro-5-methylpyridin-4-yl)acetonitrile and General Procedure H. LCMS theoretical m/z=484.3. [M+H]+, found 485.3.

Compound 48

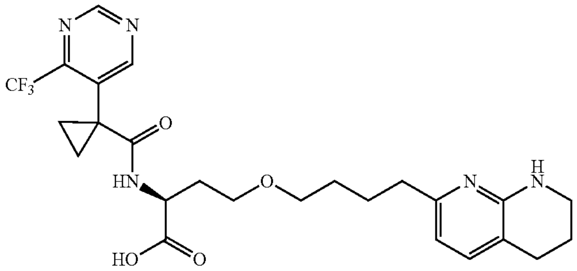 [SMILES: O=C(O)[C@H](CCOCCCCc1ccc2c(n1)NCCC2)NC(=O)C1(c2cncnc2C(F)(F)F)CC1]

O-(4-(5,6,7,8-tetrahydro-1,8-naphthyridin-2-yl)butyl)-N-(1-(4-(trifluoromethyl)pyrimidin-5-yl)cyclopropane-1-carbonyl)-L-homoserine Prepared according to Scheme B using General Procedure C with 1-(4-(trifluoromethyl)pyrimidin-5-yl)cyclopropane-1-carboxylic acid and General Procedure D, and Scheme C using General Procedure E with 5-bromo-4-(trifluoromethyl)pyrimidine and General Procedure F. LCMS theoretical m/z=521.2. [M+H]+, found 522.2.

Compound 49

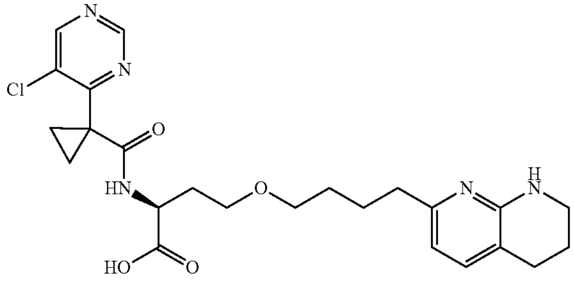 [SMILES: O=C(O)[C@H](CCOCCCCc1ccc2c(n1)NCCC2)NC(=O)C1(c2ncncc2Cl)CC1]

N-(1-(5-chloropyrimidin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chloropyrimidin-4-yl)cyclopropane-1-carboxylic acid and General Procedure D, and Scheme C using General Procedure E with 4-bromo-5-chloropyrimidine and General Procedure F. LCMS theoretical m/z=487.2. [M+H]+, found 488.2.

Compound 50

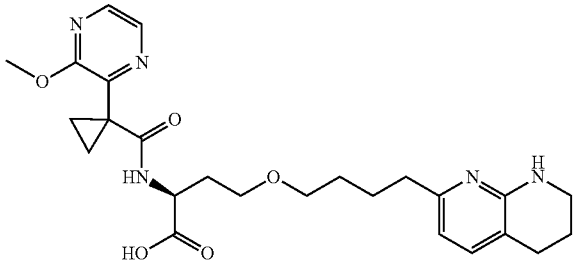 [SMILES: COc1nccnc1C1(C(=O)N[C@@H](CCOCCCCc2ccc3c(n2)NCCC3)C(=O)O)CC1]

N-(1-(3-methoxypyrazin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-methoxypyrazin-2-yl)cyclopropane-1-carboxylic acid and General Procedure D, and Scheme C using General Procedure E with 2-bromo-3-methoxypyrazine and General Procedure F. LCMS theoretical m/z=483.3. [M+H]+, found 484.3.

Compound 51

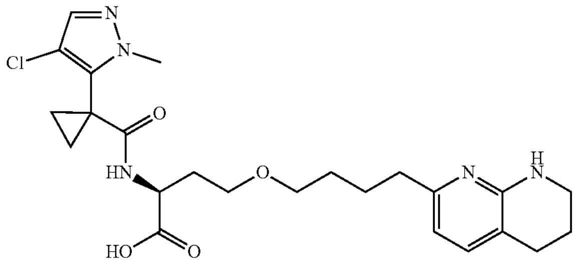 [SMILES: Cn1ncc(Cl)c1C1(C(=O)N[C@@H](CCOCCCCc2ccc3c(n2)NCCC3)C(=O)O)CC1]

N-(1-(4-chloro-1-methyl-1H-pyrazol-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-1-methyl-1H-pyrazol-5-yl)cyclopropane-1-carboxylic acid and General Procedure D, and Scheme D using General Procedure G with 2-(4-chloro-1-methyl-1H-pyrazol-5-yl)acetonitrile and General Procedure H. LCMS theoretical m/z=489.2. [M+H]+, found 490.2.

Compound 52

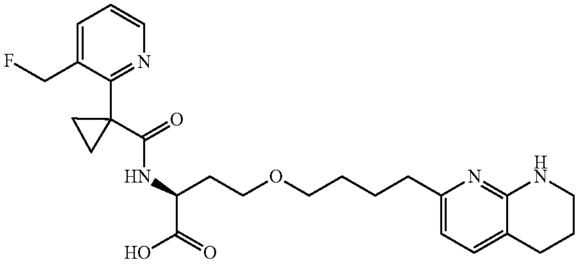 [SMILES: O=C(O)[C@H](CCOCCCCc1ccc2c(n1)NCCC2)NC(=O)C1(c2ncccc2CF)CC1]

N-(1-(3-(fluoromethyl)pyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-(fluoromethyl)pyridin-2-yl)cyclopropane-1-carboxylic acid and General Procedure D, and Scheme C using General Procedure E with 2-bromo-3-(fluoromethyl)pyridine and General Procedure F. LCMS theoretical m/z=484.3. [M+H]+, found 485.3.

Compound 53

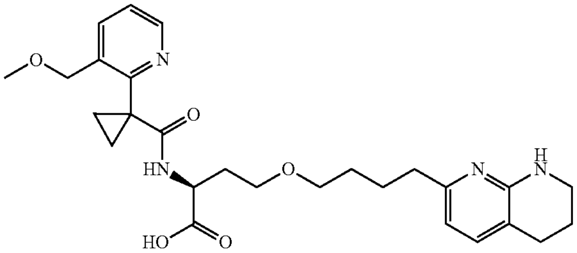 [SMILES: COCc1cccnc1C1(C(=O)N[C@@H](CCOCCCCc2ccc3c(n2)NCCC3)C(=O)O)CC1]

N-(1-(3-(methoxymethyl)pyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-(methoxymethyl)pyridin-2-yl)cyclopropane-1-carboxylic acid and General Procedure D, and Scheme C using General Procedure E with 2-bromo-3-(methoxymethyl)pyridine and General Procedure F. LCMS theoretical m/z=496.3. [M+H]+, found 497.3.

Compound 54

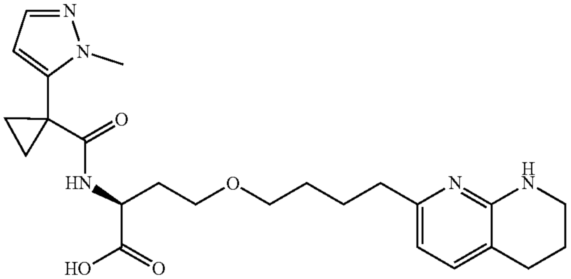 [SMILES: Cn1nccc1C1(C(=O)N[C@@H](CCOCCCCc2ccc3c(n2)NCCC3)C(=O)O)CC1]

N-(1-(1-methyl-1H-pyrazol-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(1-methyl-1H-pyrazol-5-yl)cyclopropane-1-carboxylic acid and General Procedure D, and Scheme C using General Procedure E with 5-iodo-1-methyl-1H-pyrazole and General Procedure F. LCMS theoretical m/z=455.3. [M+H]+, found 456.3.

Compound 55

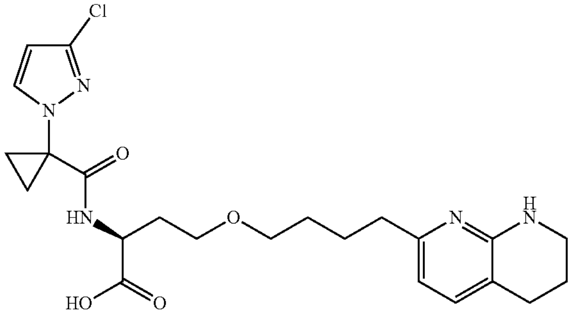 [SMILES: O=C(O)[C@H](CCOCCCCc1ccc2c(n1)NCCC2)NC(=O)C1(n2ccc(Cl)n2)CC1]

N-(1-(3-chloro-1H-pyrazol-1-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-1H-pyrazol-1-yl)cyclopropane-1-carboxylic acid and General Procedure D, and Scheme G using General Procedure N with 5-chloro-1H-pyrazole and General Procedure O. LCMS theoretical m/z=475.2. [M+H]+, found 476.2.

Compound 56

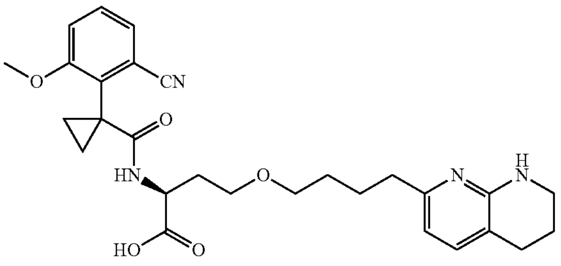 [SMILES: COc1cccc(C#N)c1C1(C(=O)N[C@@H](CCOCCCCc2ccc3c(n2)NCCC3)C(=O)O)CC1]

N-(1-(2-cyano-6-methoxyphenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-cyano-6-methoxyphenyl)cyclopropane-1-carboxylic acid and General Procedure D, and Scheme C using General Procedure E with 2-bromo-3-methoxybenzonitrile and General Procedure F. LCMS theoretical m/z=506.3. [M+H]+, found 507.3.

Compound 57

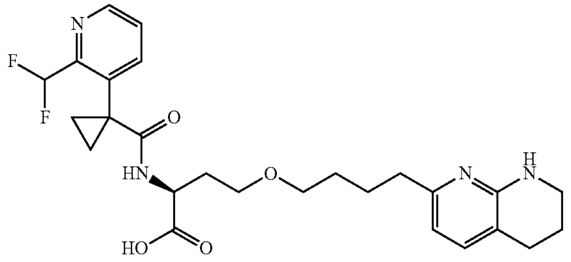 [SMILES: O=C(O)[C@H](CCOCCCCc1ccc2c(n1)NCCC2)NC(=O)C1(c2cccnc2C(F)F)CC1]

N-(1-(2-(difluoromethyl)pyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-(difluoromethyl)pyridin-3-yl)cyclopropane-1-carboxylic acid and General Procedure D, and Scheme C using General Procedure E with 3-bromo-2-(difluoromethyl)pyridine and General Procedure F. LCMS theoretical m/z=502.2. [M+H]+, found 503.2.

Compound 58

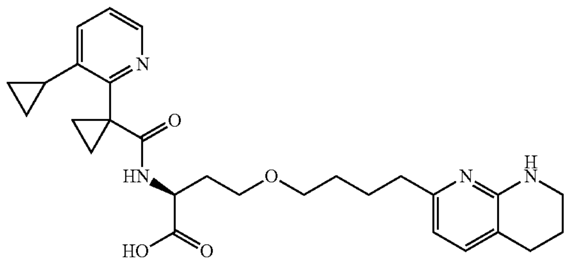 [SMILES: O=C(O)[C@H](CCOCCCCc1ccc2c(n1)NCCC2)NC(=O)C1(c2ncccc2C2CC2)CC1]

N-(1-(3-cyclopropylpyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-cyclopropylpyridin-2-yl)cyclopropane-1-carboxylic acid and General Procedure D, and Scheme C using General Procedure E with 2-bromo-3-cyclopropylpyridine and General Procedure F. LCMS theoretical m/z=492.3. [M+H]+, found 493.3.

Compound 59

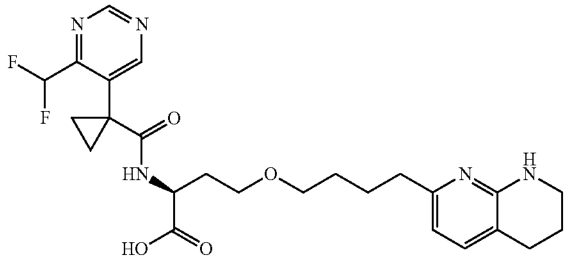 [SMILES: O=C(O)[C@H](CCOCCCCc1ccc2c(n1)NCCC2)NC(=O)C1(c2cncnc2C(F)F)CC1]

N-(1-(4-(difluoromethyl)pyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-(difluoromethyl)pyrimidin-5-yl)cyclopropane-1-carboxylic acid and General Procedure D, and Scheme C using General Procedure E with 5-bromo-4-(difluoromethyl)pyrimidine and General Procedure F. LCMS theoretical m/z=503.2. [M+H]+, found 504.3.

Compound 60

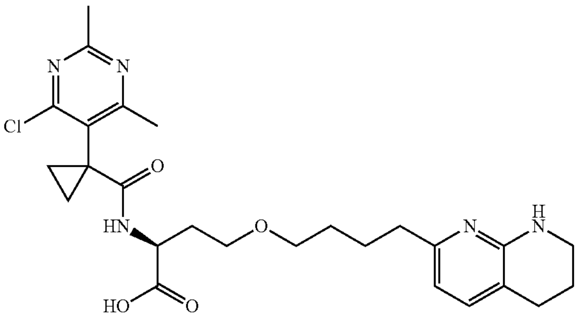 [SMILES: Cc1nc(C)c(C2(C(=O)N[C@@H](CCOCCCCc3ccc4c(n3)NCCC4)C(=O)O)CC2)c(Cl)n1]

N-(1-(4-chloro-2,6-dimethylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-2,6-dimethylpyrimidin-5-yl)cyclopropane-1-carboxylic acid and General Procedure D, and Scheme C using General Procedure E with 5-bromo-4-chloro-2,6-dimethylpyrimidine and General Procedure F. LCMS theoretical m/z=515.2. [M+H]+, found 516.3.

Compound 61

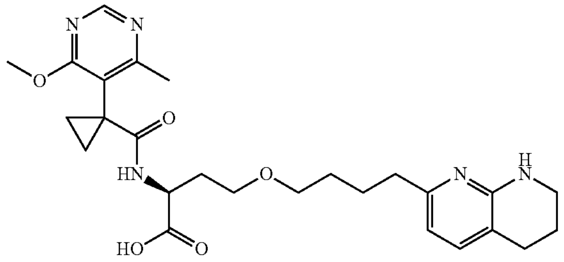 [SMILES: COc1ncnc(C)c1C1(C(=O)N[C@@H](CCOCCCCc2ccc3c(n2)NCCC3)C(=O)O)CC1]

N-(1-(4-methoxy-6-methylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-methoxy-6-methylpyrimidin-5-yl)cyclopropane-1-carboxylic acid and General Procedure D, and Scheme C using General Procedure E with 5-bromo-4-methoxy-6-methylpyrimidine and General Procedure F. LCMS theoretical m/z=497.3. [M+H]+, found 498.3.

Compound 62

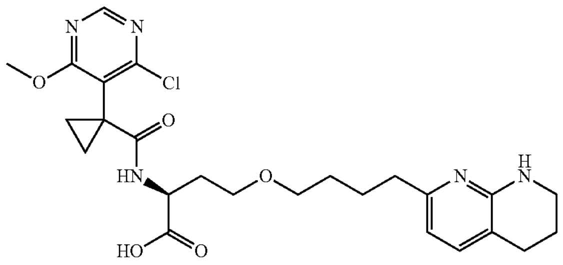 [SMILES: COc1ncnc(Cl)c1C1(C(=O)N[C@@H](CCOCCCCc2ccc3c(n2)NCCC3)C(=O)O)CC1]

N-(1-(4-chloro-6-methoxypyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-6-methoxypyrimidin-5-yl)cyclopropane-1-carboxylic acid and General Procedure D, and Scheme C using General Procedure E with 5-bromo-4-chloro-6-methoxypyrimidine and General Procedure F. LCMS theoretical m/z=517.2. [M+H]+, found 518.3.

Compound 63

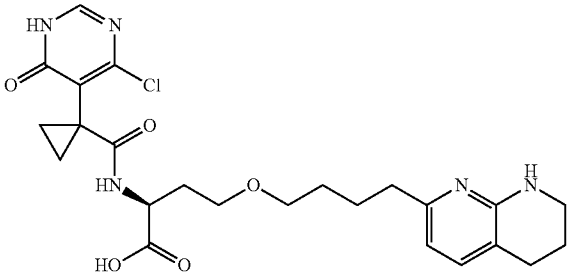 [SMILES: O=C(O)[C@H](CCOCCCCc1ccc2c(n1)NCCC2)NC(=O)C1(c2c(Cl)nc[nH]c2=O)CC1]

N-(1-(4-chloro-6-oxo-1,6-dihydropyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-6-oxo-1,6-dihydropyrimidin-5-yl)cyclopropane-1-carboxylic acid and General Procedure D, and Scheme I using General Procedure E with 5-bromo-4-chloro-6-methoxypyrimidine, General Procedure T, and General Procedure O. LCMS theoretical m/z=503.2. [M+H]+, found 504.2.

Compound 64

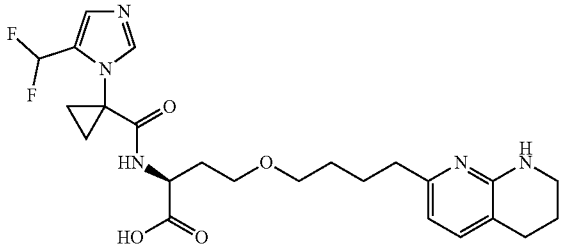 [SMILES: O=C(O)[C@H](CCOCCCCc1ccc2c(n1)NCCC2)NC(=O)C1(n2cncc2C(F)F)CC1]

N-(1-(5-(difluoromethyl)-1H-imidazol-1-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-(difluoromethyl)-1H-imidazol-1-yl)cyclopropane-1-carboxylic acid and General Procedure D, and Scheme G using General Procedure N with 5-(difluoromethyl)-1H-imidazole and General Procedure O. LCMS theoretical m/z=491.2. [M+H]+, found 492.3.

Compound 65

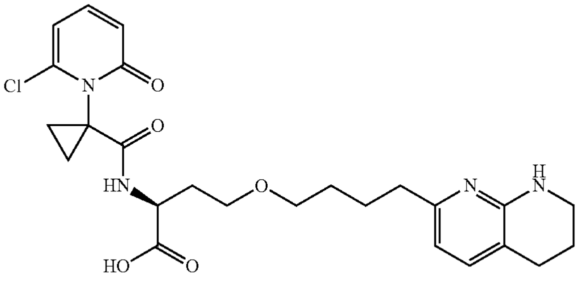 [SMILES: O=C(O)[C@H](CCOCCCCc1ccc2c(n1)NCCC2)NC(=O)C1(n2c(Cl)cccc2=O)CC1]

N-(1-(6-chloro-2-oxopyridin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-chloro-2-oxopyridin-1(2H)-yl)cyclopropane-1-carboxylic acid and General Procedure D, and Scheme H using General Procedure P with 6-chloropyridin-2-ol, General Procedure Q and General Procedure R. LCMS theoretical m/z=502.2. [M+H]+, found 503.2.

Compound 66

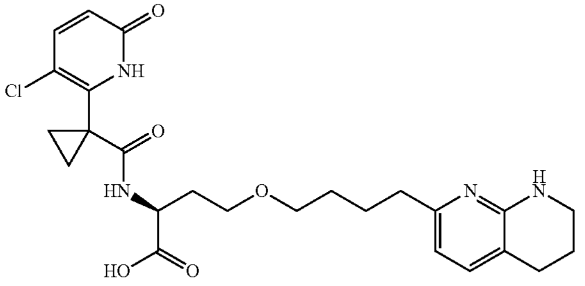 [SMILES: O=C(O)[C@H](CCOCCCCc1ccc2c(n1)NCCC2)NC(=O)C1(c2[nH]c(=O)ccc2Cl)CC1]

N-(1-(3-chloro-6-oxo-1,6-dihydropyridin-2-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3-chloro-6-oxo-1,6-dihydropyridin-2-yl)cyclopropane-1-carboxylic acid and General Procedure D, and Scheme I using General Procedure E with 2-bromo-3-chloro-6-methoxypyridine, General Procedure T, and General Procedure O. LCMS theoretical m/z=502.2. [M+H]+, found 503.3.

Compound 67

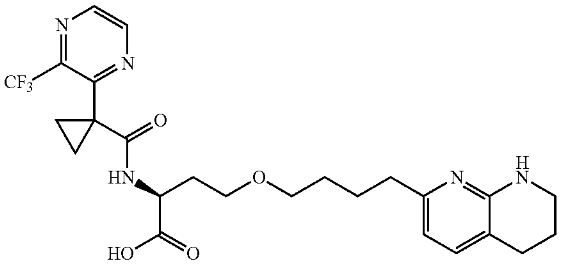 [SMILES: O=C(O)[C@H](CCOCCCCc1ccc2c(n1)NCCC2)NC(=O)C1(c2nccnc2C(F)(F)F)CC1]

O-(4-(5,6,7,8-tetrahydro-1,8-naphthyridin-2-yl)butyl)-N-(1-(3-(trifluoromethyl)pyrazin-2-yl)cyclopropane-1-carbonyl)-L-homoserine Prepared according to Scheme B using General Procedure C with 1-(3-(trifluoromethyl)pyrazin-2-yl)cyclopropane-1-carboxylic acid and General Procedure D, and Scheme C using General Procedure E with 2-bromo-3-(trifluoromethyl)pyrazine and General Procedure F. LCMS theoretical m/z=521.2. [M+H]+, found 522.3.

Compound 68

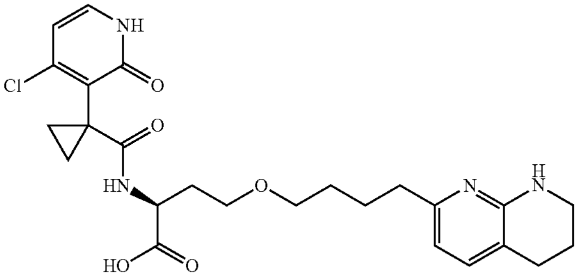 [SMILES: O=C(O)[C@H](CCOCCCCc1ccc2c(n1)NCCC2)NC(=O)C1(c2c(Cl)cc[nH]c2=O)CC1]

N-(1-(4-chloro-2-oxo-1,2-dihydropyridin-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-2-oxo-1,2-dihydropyridin-3-yl)cyclopropane-1-carboxylic acid and General Procedure D, and Scheme I using General Procedure E with 2-(benzyloxy)-3-bromo-4-chloropyridine, General Procedure S, and General Procedure O. LCMS theoretical m/z=502.2. [M+H]+, found 503.3.

Compound 69

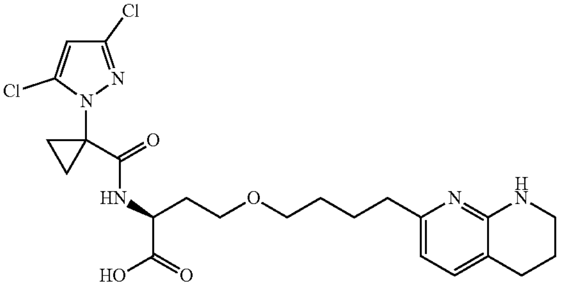 [SMILES: O=C(O)[C@H](CCOCCCCc1ccc2c(n1)NCCC2)NC(=O)C1(n2nc(Cl)cc2Cl)CC1]

N-(1-(3,5-dichloro-1H-pyrazol-1-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(3,5-dichloro-1H-pyrazol-1-yl)cyclopropane-1-carboxylic acid and General Procedure D, and Scheme G using General Procedure N with 3,5-dichloro-1H-pyrazole and General Procedure O. LCMS theoretical m/z=509.2. [M+H]+, found 510.3.

Compound 70

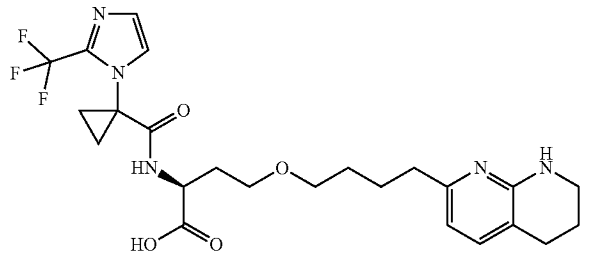 [SMILES: O=C(O)[C@H](CCOCCCCc1ccc2c(n1)NCCC2)NC(=O)C1(n2ccnc2C(F)(F)F)CC1]

O-(4-(5,6,7,8-tetrahydro-1,8-naphthyridin-2-yl)butyl)-N-(1-(2-(trifluoromethyl)-1H-imidazol-1-yl)cyclopropane-1-carbonyl)-L-homoserine Prepared according to Scheme B using General Procedure C with 1-(2-(trifluoromethyl)-1H-imidazol-1-yl)cyclopropane-1-carboxylic acid and General Procedure D, and Scheme G using General Procedure N with 2-(trifluoromethyl)-1H-imidazole and General Procedure O. LCMS theoretical m/z=509.2. [M+H]+, found 510.3.

Compound 71

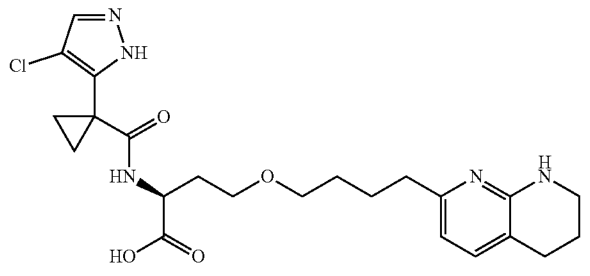 [SMILES: O=C(O)[C@H](CCOCCCCc1ccc2c(n1)NCCC2)NC(=O)C1(c2[nH]ncc2Cl)CC1]

N-(1-(4-chloro-1H-pyrazol-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-1H-pyrazol-5-yl)cyclopropane-1-carboxylic acid and General Procedure D, and Scheme J using General Procedure G with 2-(4-chloro-1-((2-(trimethylsilyl)ethoxy)methyl)-1H-pyrazol-5-yl)acetonitrile, General Procedure H, and General Procedure U. LCMS theoretical m/z=475.2. [M+H]+, found 476.3.

Compound 72

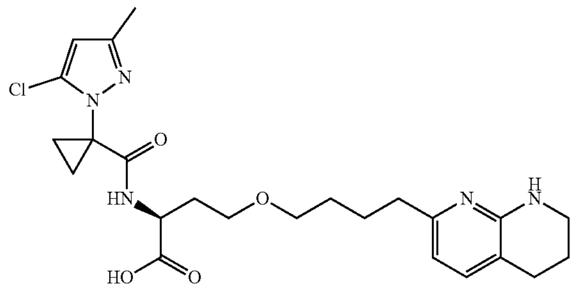 [SMILES: Cc1cc(Cl)n(C2(C(=O)N[C@@H](CCOCCCCc3ccc4c(n3)NCCC4)C(=O)O)CC2)n1]

N-(1-(5-chloro-3-methyl-1H-pyrazol-1-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chloro-3-methyl-1H-pyrazol-1-yl)cyclopropane-1-carboxylic acid and General Procedure D, and Scheme L using General Procedure N with 5-chloro-3-iodo-1H-pyrazole, General Procedure V, and General Procedure O. LCMS theoretical m/z=489.2. [M+H]+, found 490.2

Compound 73

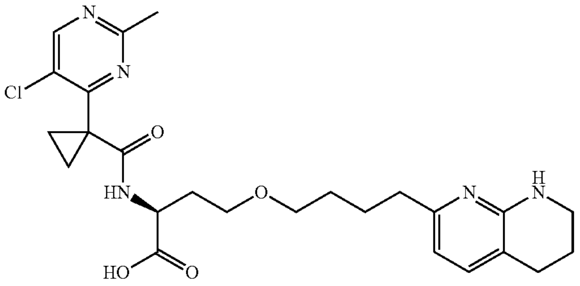 [SMILES: Cc1ncc(Cl)c(C2(C(=O)N[C@@H](CCOCCCCc3ccc4c(n3)NCCC4)C(=O)O)CC2)n1]

N-(1-(5-chloro-2-methylpyrimidin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chloro-2-methylpyrimidin-4-yl)cyclopropane-1-carboxylic acid and General Procedure D, and Scheme C using General Procedure E with 4-bromo-5-chloro-2-methylpyrimidine and General Procedure F. LCMS theoretical m/z=489.2. [M+H]+, found 490.2.

Compound 74

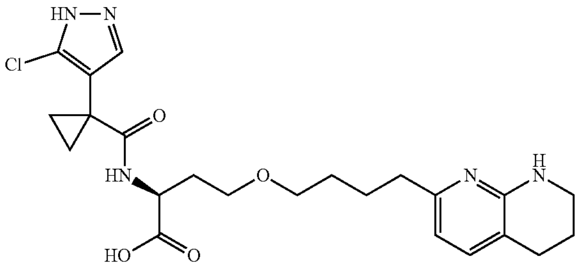 [SMILES: O=C(O)[C@H](CCOCCCCc1ccc2c(n1)NCCC2)NC(=O)C1(c2cn[nH]c2Cl)CC1]

N-(1-(5-chloro-1H-pyrazol-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chloro-1H-pyrazol-4-yl)cyclopropane-1-carboxylic acid and General Procedure D, and Scheme J using General Procedure G with 2-(3-chloro-1-((2-(trimethylsilyl)ethoxy)methyl)-1H-pyrazol-4-yl)acetonitrile, General Procedure H, and General Procedure U. LCMS theoretical m/z=475.2. [M+H]+, found 476.3.

Compound 75

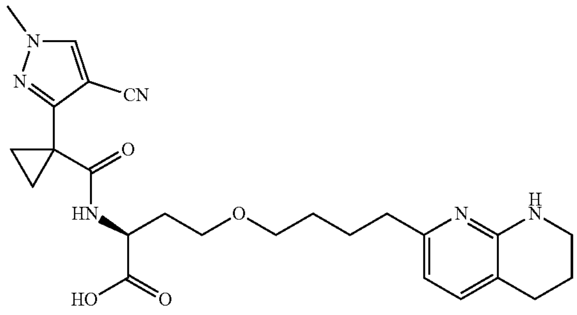 [SMILES: Cn1cc(C#N)c(C2(C(=O)N[C@@H](CCOCCCCc3ccc4c(n3)NCCC4)C(=O)O)CC2)n1]

N-(1-(4-cyano-1-methyl-1H-pyrazol-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-cyano-1-methyl-1H-pyrazol-3-yl)cyclopropane-1-carboxylic acid and General Procedure D, and Scheme C using General Procedure E with 3-bromo-1-methyl-1H-pyrazole-4-carbonitrile and General Procedure F. LCMS theoretical m/z=480.3. [M+H]+, found 481.3.

Compound 76

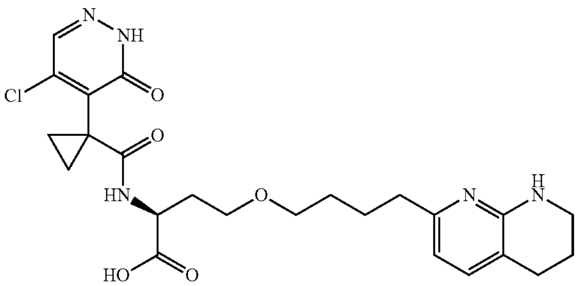 [SMILES: O=C(O)[C@H](CCOCCCCc1ccc2c(n1)NCCC2)NC(=O)C1(c2c(Cl)cn[nH]c2=O)CC1]

N-(1-(5-chloro-3-oxo-2,3-dihydropyridazin-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chloro-3-oxo-2,3-dihydropyridazin-4-yl)cyclopropane-1-carboxylic acid and General Procedure D, and Scheme K using General Procedure E with 4-bromo-5-chloro-2-((2-(trimethylsilyl)ethoxy)methyl)pyridazin-3(2H)-one, General Procedure U, and General Procedure F. LCMS theoretical m/z=503.2. [M+H]+, found 504.2.

Compound 77

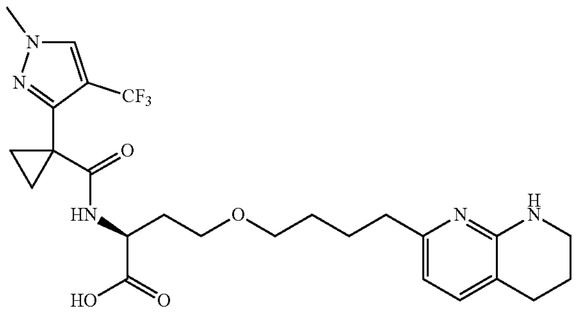

N-(1-(1-methyl-4-(trifluoromethyl)-1H-pyrazol-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(1-methyl-4-(trifluoromethyl)-1H-pyrazol-3-yl)cyclopropane-1-carboxylic acid and General Procedure D, and Scheme D using General Procedure G with 2-(1-methyl-4-(trifluoromethyl)-1H-pyrazol-3-yl)acetonitrile and General Procedure H. LCMS theoretical m/z=523.2. [M+H]+, found 524.2.

Compound 78

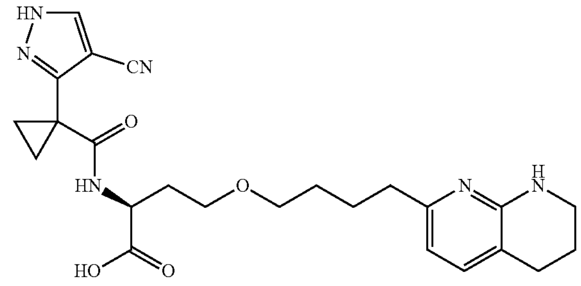 [SMILES: N#Cc1c[nH]nc1C1(C(=O)N[C@@H](CCOCCCCc2ccc3c(n2)NCCC3)C(=O)O)CC1]

N-(1-(4-cyano-1H-pyrazol-3-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-cyano-1H-pyrazol-3-yl)cyclopropane-1-carboxylic acid and General Procedure D, and Scheme C using General Procedure E with 3-bromo-1H-pyrazole-4-carbonitrile and General Procedure F. LCMS theoretical m/z=466.2. [M+H]+, found 467.2.

Compound 79

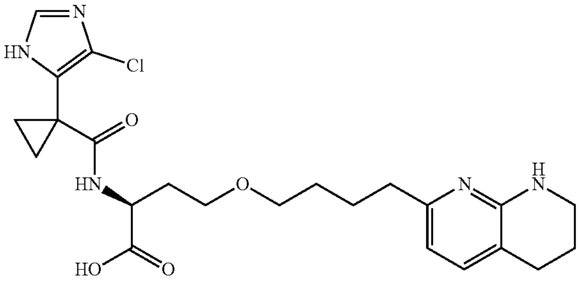 [SMILES: O=C(O)[C@H](CCOCCCCc1ccc2c(n1)NCCC2)NC(=O)C1(c2[nH]cnc2Cl)CC1]

N-(1-(4-chloro-1H-imidazol-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-1H-imidazol-5-yl)cyclopropane-1-carboxylic acid and General Procedure D, and Scheme K using General Procedure E with 4,5-dichloro-1-((2-(trimethylsilyl)ethoxy)methyl)-1H-imidazole, General Procedure U, and General Procedure F. LCMS theoretical m/z=475.2. [M+H]+, found 476.2.

Compound 80

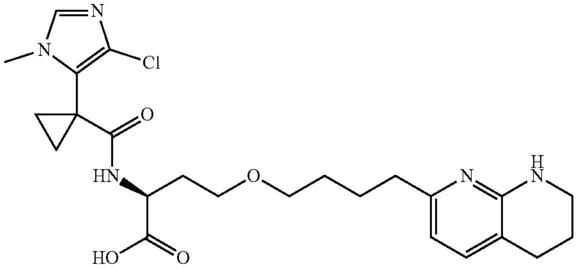 [SMILES: Cn1cnc(Cl)c1C1(C(=O)N[C@@H](CCOCCCCc2ccc3c(n2)NCCC3)C(=O)O)CC1]

N-(1-(4-chloro-1-methyl-1H-imidazol-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-1-methyl-1H-imidazol-5-yl)cyclopropane-1-carboxylic acid and General Procedure D, and Scheme C using General Procedure E with 4,5-dichloro-1-methyl-1H-imidazole and General Procedure F. LCMS theoretical m/z=489.2. [M+H]+, found 490.2.

Compound 81

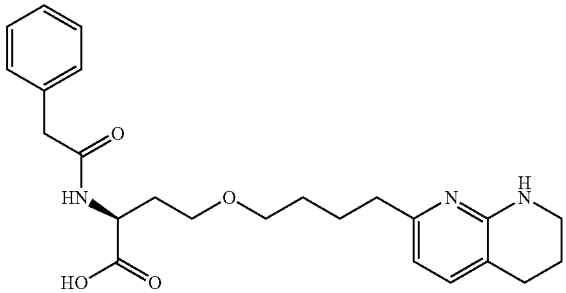 [SMILES: O=C(Cc1ccccc1)N[C@@H](CCOCCCCc1ccc2c(n1)NCCC2)C(=O)O]

N-(2-phenylacetyl)-O-(4-(5,6,7,8-tetrahydro-1,8-naphthyridin-2-yl)butyl)-L-homoserine Prepared according to Scheme B using General Procedure C with 2-phenylacetic acid and General Procedure D. LCMS theoretical m/z=425.2. [M+H]+, found 426.3.

Compound 82

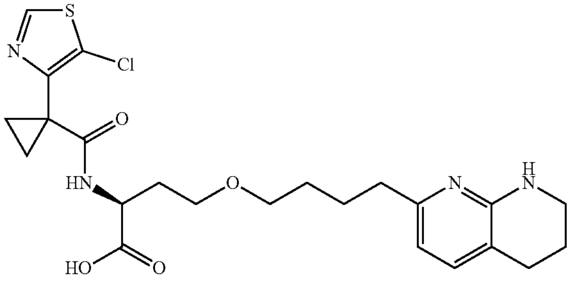 [SMILES: O=C(O)[C@H](CCOCCCCc1ccc2c(n1)NCCC2)NC(=O)C1(c2ncsc2Cl)CC1]

N-(1-(5-chlorothiazol-4-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(5-chlorothiazol-4-yl)cyclopropane-1-carboxylic acid and General Procedure D, and Scheme C using General Procedure E with 4-bromo-5-chlorothiazole and General Procedure F. LCMS theoretical m/z=492.2. [M+H]+, found 493.1.

Compound 83

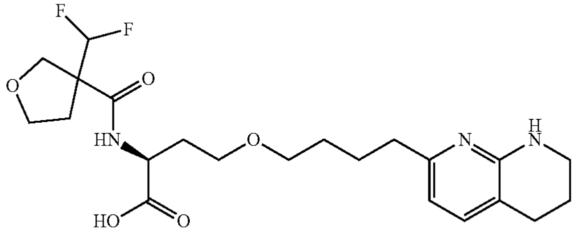 [SMILES: O=C(O)[C@H](CCOCCCCc1ccc2c(n1)NCCC2)NC(=O)C1(C(F)F)CCOC1]

N-(3-(difluoromethyl)tetrahydrofuran-3-carbonyl)-O-(4-(5,6,7,8-tetrahydro-1,8-naphthyridin-2-yl)butyl)-L-homoserine Prepared according to Scheme B using General Procedure C with 3-(difluoromethyl)tetrahydrofuran-3-carboxylic acid and General Procedure D. LCMS theoretical m/z=455.2. [M+H]+, found 456.4.

Compound 84

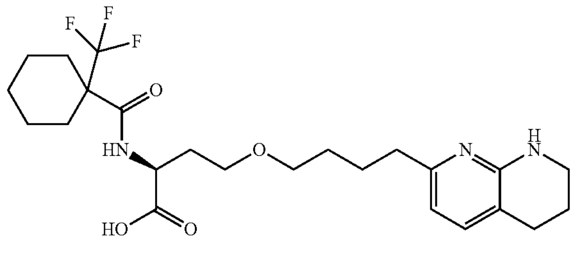 [SMILES: O=C(O)[C@H](CCOCCCCc1ccc2c(n1)NCCC2)NC(=O)C1(C(F)(F)F)CCCCC1]

O-(4-(5,6,7,8-tetrahydro-1,8-naphthyridin-2-yl)butyl)-N-(1-(trifluoromethyl)cyclohexane-1-carbonyl)-L-homoserine Prepared according to Scheme B using General Procedure C with 1-(trifluoromethyl)cyclohexane-1-carboxylic acid and General Procedure D. LCMS theoretical m/z=485.5. [M+H]+, found 486.5.

Compound 85

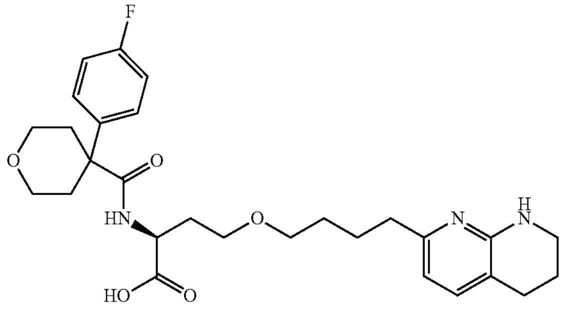 [SMILES: O=C(O)[C@H](CCOCCCCc1ccc2c(n1)NCCC2)NC(=O)C1(c2ccc(F)cc2)CCOCC1]

N-(4-(4-fluorophenyl)tetrahydro-2H-pyran-4-carbonyl)-O-(4-(5,6,7,8-tetrahydro-1,8-naphthyridin-2-yl)butyl)-L-homoserine Prepared according to Scheme B using General Procedure C with 4-(4-fluorophenyl)tetrahydro-2H-pyran-4-carboxylic acid and General Procedure D. LCMS theoretical m/z=513.3. [M+H]+, found 514.3.

Compound 86

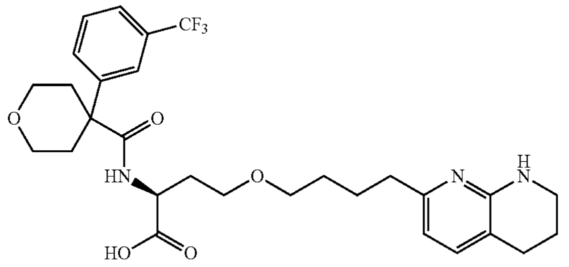

O-(4-(5,6,7,8-tetrahydro-1,8-naphthyridin-2-yl)butyl)-N-(4-(3-(trifluoromethyl)phenyl)tetrahydro-2H-pyran-4-carbonyl)-L-homoserine Prepared according to Scheme B using General Procedure C with 4-(3-(trifluoromethyl)phenyl)tetrahydro-2H-pyran-4-carboxylic acid and General Procedure D. LCMS theoretical m/z=563.3. [M+H]+, found 564.4.

Compound 87

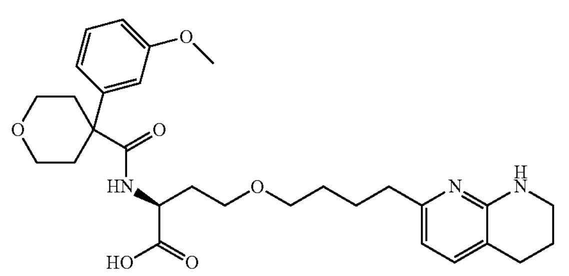 [SMILES: COc1cccc(C2(C(=O)N[C@@H](CCOCCCCc3ccc4c(n3)NCCC4)C(=O)O)CCOCC2)c1]

N-(4-(3-methoxyphenyl)tetrahydro-2H-pyran-4-carbonyl)-O-(4-(5,6,7,8-tetrahydro-1,8-naphthyridin-2-yl)butyl)-L-homoserine Prepared according to Scheme B using General Procedure C with 4-(3-methoxyphenyl)tetrahydro-2H-pyran-4-carboxylic acid and General Procedure D. LCMS theoretical m/z=525.3. [M+H]+, found 526.4.

Compound 88

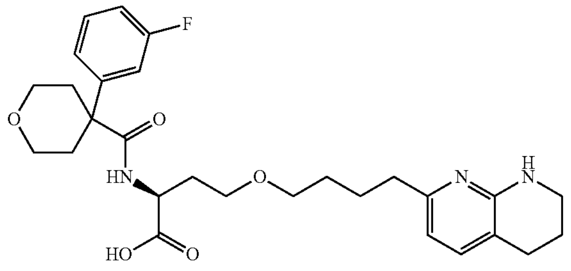 [SMILES: O=C(O)[C@H](CCOCCCCc1ccc2c(n1)NCCC2)NC(=O)C1(c2cccc(F)c2)CCOCC1]

N-(4-(3-fluorophenyl)tetrahydro-2H-pyran-4-carbonyl)-O-(4-(5,6,7,8-tetrahydro-1,8-naphthyridin-2-yl)butyl)-L-homoserine Prepared according to Scheme B using General Procedure C with 4-(3-fluorophenyl)tetrahydro-2H-pyran-4-carboxylic acid and General Procedure D. LCMS theoretical m/z=513.3. [M+H]+, found 514.3.

Compound 89

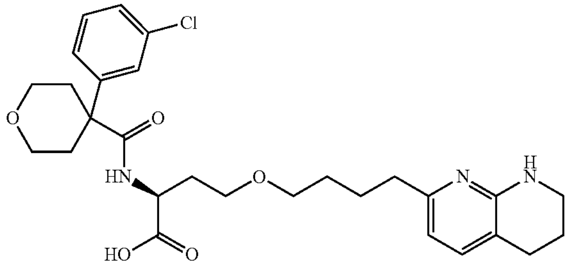 [SMILES: O=C(O)[C@H](CCOCCCCc1ccc2c(n1)NCCC2)NC(=O)C1(c2cccc(Cl)c2)CCOCC1]

N-(4-(3-chlorophenyl)tetrahydro-2H-pyran-4-carbonyl)-O-(4-(5,6,7,8-tetrahydro-1,8-naphthyridin-2-yl)butyl)-L-homoserine Prepared according to Scheme B using General Procedure C with 4-(3-chlorophenyl)tetrahydro-2H-pyran-4-carboxylic acid and General Procedure D. LCMS theoretical m/z=529.2. [M+H]+, found 530.3.

Compound 90

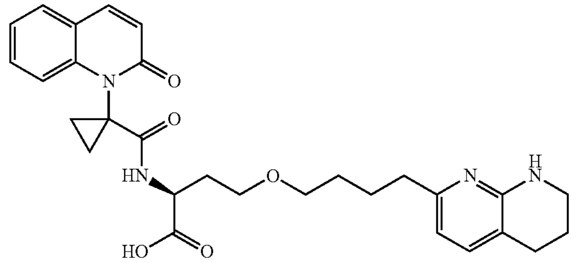 [SMILES: O=C(O)[C@H](CCOCCCCc1ccc2c(n1)NCCC2)NC(=O)C1(n2c(=O)ccc3ccccc32)CC1]

N-(1-(2-oxoquinolin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-oxoquinolin-1(2H)-yl)cyclopropane-1-carboxylic acid and General Procedure D, and Scheme H using General Procedure P with quinolin-2(1H)-one, General Procedure Q and General Procedure R. LCMS theoretical m/z=518.3. [M+H]+, found 519.3.

Compound 91

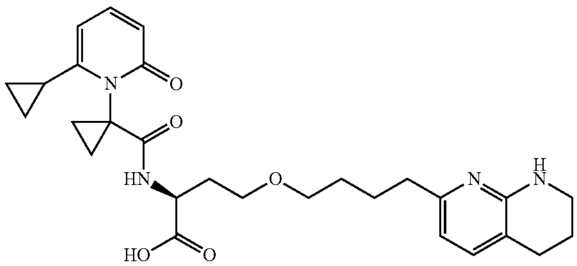 [SMILES: O=C(O)[C@H](CCOCCCCc1ccc2c(n1)NCCC2)NC(=O)C1(n2c(C3CC3)cccc2=O)CC1]

N-(1-(6-cyclopropyl-2-oxopyridin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-cyclopropyl-2-oxopyridin-1(2H)-yl)cyclopropane-1-carboxylic acid and General Procedure D, and Scheme H using General Procedure P with 6-cyclopropylpyridin-2(1H)-one, General Procedure Q and General Procedure R. LCMS theoretical m/z=508.3. [M+H]+, found 509.3.

Compound 92

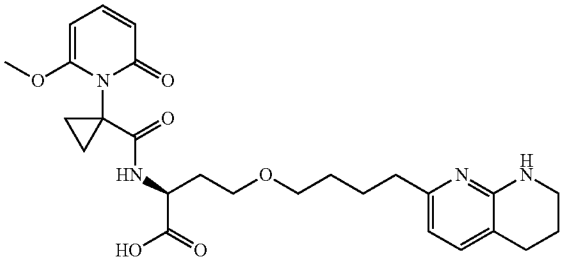 [SMILES: COc1cccc(=O)n1C1(C(=O)N[C@@H](CCOCCCCc2ccc3c(n2)NCCC3)C(=O)O)CC1]

N-(1-(6-methoxy-2-oxopyridin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-methoxy-2-oxopyridin-1(2H)-yl)cyclopropane-1-carboxylic acid and General Procedure D, and Scheme H using General Procedure P with 6-methoxypyridin-2(1H)-one, General Procedure Q and General Procedure R. LCMS theoretical m/z=498.3. [M+H]+, found 499.3.

Compound 93

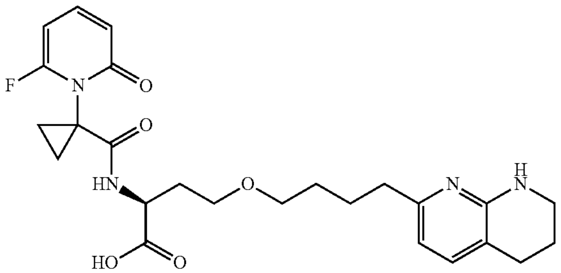 [SMILES: O=C(O)[C@H](CCOCCCCc1ccc2c(n1)NCCC2)NC(=O)C1(n2c(F)cccc2=O)CC1]

N-(1-(6-fluoro-2-oxopyridin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-fluoro-2-oxopyridin-1(2H)-yl)cyclopropane-1-carboxylic acid and General Procedure D, and Scheme H using General Procedure P with 6-fluoropyridin-2(1H)-one, General Procedure Q and General Procedure R. LCMS theoretical m/z=486.2. [M+H]+, found 487.2.

Compound 94

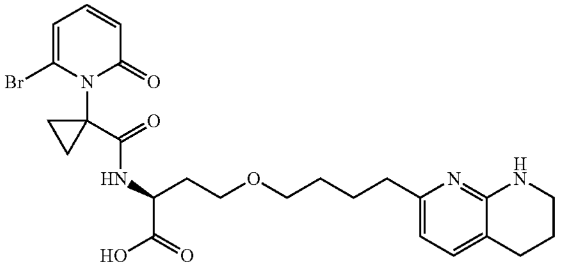 [SMILES: O=C(O)[C@H](CCOCCCCc1ccc2c(n1)NCCC2)NC(=O)C1(n2c(Br)cccc2=O)CC1]

N-(1-(6-bromo-2-oxopyridin-1(2H)-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(6-bromo-2-oxopyridin-1(2H)-yl)cyclopropane-1-carboxylic acid and General Procedure D, and Scheme H using General Procedure P with 6-bromopyridin-2(1H)-one, General Procedure Q and General Procedure R. LCMS theoretical m/z=546.2. [M+H]+, found 547.2.

Compound 95

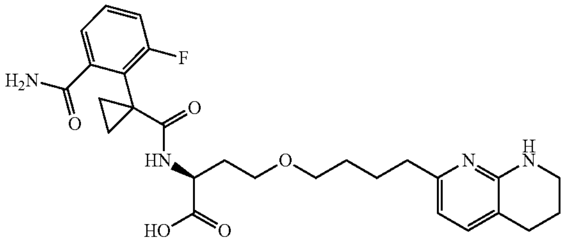 [SMILES: NC(=O)c1cccc(F)c1C1(C(=O)N[C@@H](CCOCCCCc2ccc3c(n2)NCCC3)C(=O)O)CC1]

N-(1-(2-carbamoyl-6-fluorophenyl)cyclopropane-1-carbonyl)-O-(4-(5,6,7,8-tetrahydro-1,8-naphthyridin-2-yl)butyl)-L-homoserine Prepared according to Scheme B using General Procedure C with 1-(2-carbamoyl-6-fluorophenyl)cyclopropane-1-carboxylic acid and General Procedure D, and Scheme C using General Procedure E with 2-bromo-3-fluorobenzamide and General Procedure F. LCMS theoretical m/z=512.2. [M+H]+, found 513.3.

Compound 96

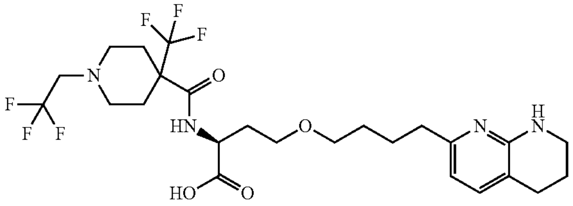 [SMILES: O=C(O)[C@H](CCOCCCCc1ccc2c(n1)NCCC2)NC(=O)C1(C(F)(F)F)CCN(CC(F)(F)F)CC1]

O-(4-(5,6,7,8-tetrahydro-1,8-naphthyridin-2-yl) butyl)-N-(1-(2,2,2-trifluoroethyl)-4-(trifluoromethyl) piperidine-4-carbonyl)-L-homoserine Prepared according to Scheme B using General Procedure C with 1-(2,2,2-trifluoroethyl)-4-(trifluoromethyl)piperidine-4-carboxylic acid and General Procedure D. LCMS theoretical m/z=568.3. [M+H]+, found 569.5.

Compound 97

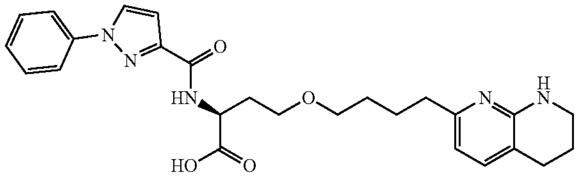 [SMILES: O=C(N[C@@H](CCOCCCCc1ccc2c(n1)NCCC2)C(=O)O)c1ccn(-c2ccccc2)n1]

N-(1-phenyl-1H-pyrazole-3-carbonyl)-O-(4-(5,6,7,8-tetrahydro-1,8-naphthyridin-2-yl)butyl)-L-homoserine Prepared according to Scheme B using General Procedure C with 1-phenyl-1H-pyrazole-3-carboxylic acid and General Procedure D. LCMS theoretical m/z=477.2. [M+H]+, found 478.3.

Compound 98

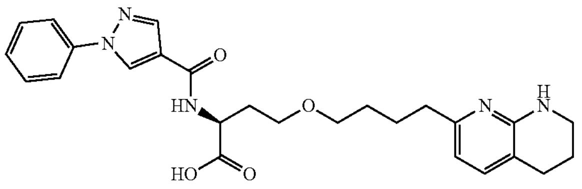 [SMILES: O=C(N[C@@H](CCOCCCCc1ccc2c(n1)NCCC2)C(=O)O)c1cnn(-c2ccccc2)c1]

N-(1-phenyl-1H-pyrazole-4-carbonyl)-O-(4-(5,6,7,8-tetrahydro-1,8-naphthyridin-2-yl)butyl)-L-homoserine Prepared according to Scheme B using General Procedure C with 1-phenyl-1H-pyrazole-4-carboxylic acid and General Procedure D. LCMS theoretical m/z=477.2. [M+H]+, found 478.3.

Compound 99

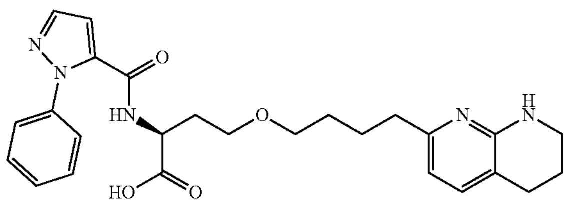 [SMILES: O=C(N[C@@H](CCOCCCCc1ccc2c(n1)NCCC2)C(=O)O)c1ccnn1-c1ccccc1]

N-(1-phenyl-1H-pyrazole-5-carbonyl)-O-(4-(5,6,7,8-tetrahydro-1,8-naphthyridin-2-yl)butyl)-L-homoserine Prepared according to Scheme B using General Procedure C with 1-phenyl-1H-pyrazole-5-carboxylic acid and General Procedure D. LCMS theoretical m/z=477.2. [M+H]+, found 478.3.

Compound 100

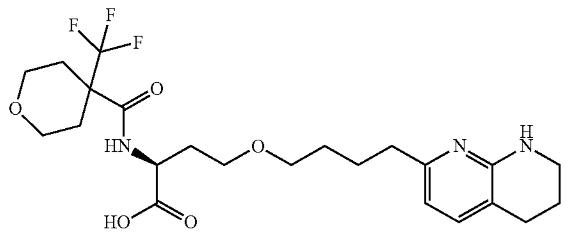 [SMILES: O=C(O)[C@H](CCOCCCCc1ccc2c(n1)NCCC2)NC(=O)C1(C(F)(F)F)CCOCC1]

O-(4-(5,6,7,8-tetrahydro-1,8-naphthyridin-2-yl) butyl)-N-(4-(trifluoromethyl)tetrahydro-2H-pyran-4-carbonyl)-L-homoserine Prepared according to Scheme B using General Procedure C with 4-(trifluoromethyl)tetrahydro-2H-pyran-4-carboxylic acid and General Procedure D. LCMS theoretical m/z=487.2. [M+H]+, found 488.2.

Compound 101

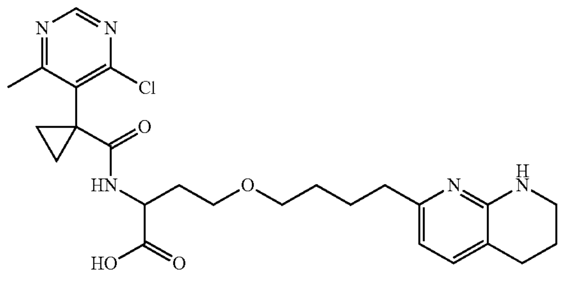 [SMILES: Cc1ncnc(Cl)c1C1(C(=O)NC(CCOCCCCc2ccc3c(n2)NCCC3)C(=O)O)CC1]

N-(1-(4-chloro-6-methylpyrimidin-5-yl)cyclopropane-1-carbonyl)-O-(4-(5,6,7,8-tetrahydro-1,8-naphthyridin-2-yl)butyl)homoserine Prepared according to Scheme A using General Procedure A with 1-(4-chloro-6-methylpyrimidin-5-yl)cyclopropane-1-carboxylic acid and General Procedure B, and Scheme C using General Procedure E with 5-bromo-4-chloro-6-methylpyrimidine and General Procedure F. LCMS theoretical m/z=501.2. [M+H]+, found 502.3.

Compound 102

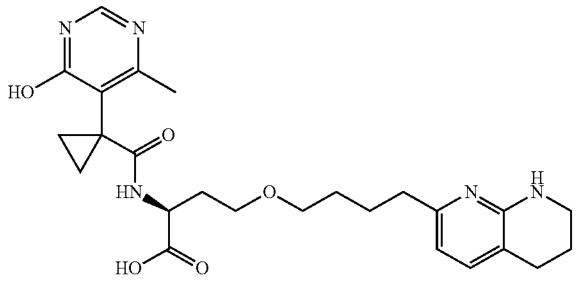 [SMILES: Cc1ncnc(O)c1C1(C(=O)N[C@@H](CCOCCCCc2ccc3c(n2)NCCC3)C(=O)O)CC1]

N-(1-(4-hydroxy-6-methylpyrimidin-5-yl)cyclopropane-1-carbonyl)-O-(4-(5,6,7,8-tetrahydro-1,8-naphthyridin-2-yl)butyl)-L-homoserine Prepared according to Scheme B using General Procedure C with 1-(4-chloro-6-methylpyrimidin-5-yl)cyclopropane-1-carboxylic acid and General Procedure D, and Scheme C using General Procedure E with 5-bromo-4-chloro-6-methylpyrimidine and General Procedure F. LCMS theoretical m/z=483.3. [M+H]+, found 484.3.

Compound 103

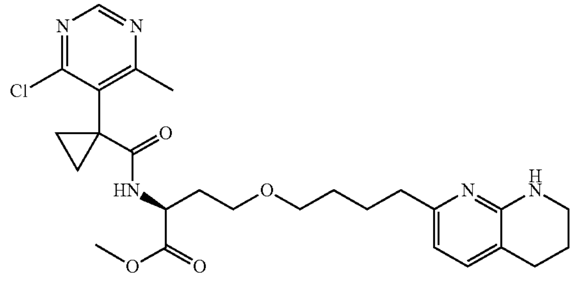 [SMILES: COC(=O)[C@H](CCOCCCCc1ccc2c(n1)NCCC2)NC(=O)C1(c2c(C)ncnc2Cl)CC1]

methyl N-(1-(4-chloro-6-methylpyrimidin-5-yl)cyclopropane-1-carbonyl)-O-(4-(5,6,7,8-tetrahydro-1,8-naphthyridin-2-yl)butyl)-L-homoserinate Prepared according to Scheme B using General Procedure C with 1-(4-chloro-6-methylpyrimidin-5-yl)cyclopropane-1-carboxylic acid, and Scheme C using General Procedure E with 5-bromo-4-chloro-6-methylpyrimidine and General Procedure F. LCMS theoretical m/z=515.2. [M+H]+, found 516.3.

Compound 104

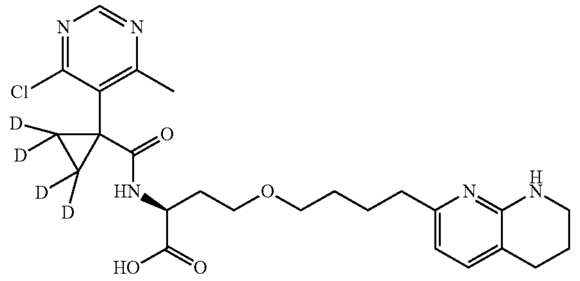 [SMILES: [2H]C1([2H])C([2H])([2H])C1(C(=O)N[C@@H](CCOCCCCc1ccc2c(n1)NCCC2)C(=O)O)c1c(C)ncnc1Cl]

N-(1-(4-chloro-6-methylpyrimidin-5-yl)cyclopropane-1-carbonyl-2,2,3,3-d4)-O-(4-(5,6,7,8-tetrahydro-1,8-naphthyridin-2-yl)butyl)-L-homoserine Prepared according to Scheme B using General Procedure C with 1-(4-chloro-6-methylpyrimidin-5-yl)cyclopropane-1-carboxylic-2,2,3,3-d4 acid (prepared according to Scheme M) and General Procedure D. LCMS theoretical m/z=505.2. [M+H]+, found 506.5.

BIOLOGICAL EXAMPLES

The following Biological Examples are set forth to enable this disclosure to be more fully understood. It should be understood that these Biological Examples are for illustrative purposes only and are not to be construed as limiting this disclosure in any manner.

Example B1—The Disclosed Compounds are Integrin Inhibitors

The biochemical potency of the disclosed compounds was determined using the AlphaScreen® (Perkin Elmer, Waltham, MA) proximity-based assay as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994, herein incorporated by reference in its entirety). To gauge the potency of inhibitors of binding to each of human integrins $\alpha_V\beta_1$, $\alpha_V\beta_6$, and $\alpha_V\beta_8$, inhibitor compounds were independently incubated with one of $\alpha_V\beta_1$, $\alpha_V\beta_6$, or $\alpha_V\beta_8$, together with TGF-b1 LAP and biotinylated anti-LAP antibody plus acceptor and donor beads, following the manufacture's recommendations. The donor beads were coated with streptavidin. The acceptor beads had a nitrilotriacetic acid Ni chelator, for binding to a 6×His Tag on human integrin $\alpha_V\beta_1$, $\alpha_V\beta_6$, or $\alpha_V\beta_8$, respectively. All incubations occurred at room temperatures in 50 mM Tris-HCl, pH 7.5, 0.1% BSA supplemented with 1 mM each $CaCl_2$ and $MgCl_2$.

The order of reagent addition was as follows:

1. $\alpha_V\beta_1$, $\alpha_V\beta_6$, or $\alpha_V\beta_8$ integrin, test inhibitor compound, LAP, biotinylated anti-LAP antibody and acceptor beads were all added together.
2. After 2 hours, donor beads were added. After another 30 minute incubation, samples were then read.

Integrin binding was evaluated by exciting donor beads at 680 nm, and measuring the fluorescent signal produced, between 520-620 nm, using a Biotek Instruments (Winooski, VT, USA) SynergyNeo2 multimode plate reader. Compound potency was assessed by determining inhibitor concentrations required to reduce fluorescent light output by 50%. Data analysis for $IC_{50}$ determinations was carried out by nonlinear four parameter logistic regression analysis using Dotmatics ELN Software (Core Informatics Inc., Branford, Ct). $IC_{50}$ values for the compounds in the Examples are provided below in Table B-1 in ranges: below 50 nM; from above 50 nM to 250 nM; from above 250 nM to 500 nM; and above 500 nM. Comp # in the Table and Examples below refers to the compound of the corresponding Example number as described in the Synthetic Examples.

TABLE B-1

| Comp # | $\alpha_V\beta_8$ | $\alpha_V\beta_1$ | $\alpha_V\beta_6$ |
|---|---|---|---|
| 1 | 50-<150 | <50 | ≥500 |
| 2 | 50-<150 | <50 | ≥500 |
| 3 | <50 | <50 | ≥500 |
| 4 | 150-<250 | 50-<150 | ≥500 |
| 5 | 50-<150 | <50 | ≥500 |
| 6 | <50 | <50 | ≥500 |
| 7 | <50 | <50 | ≥500 |
| 8 | 50-<150 | <50 | ≥500 |
| 9 | <50 | <50 | ≥500 |
| 10 | 50-<150 | <50 | ≥500 |
| 11 | 50-<150 | <50 | ≥500 |
| 12 | ≥500 | 50-<150 | ≥500 |
| 13 | <50 | <50 | ≥500 |
| 14 | <50 | <50 | ≥500 |
| 15 | <50 | <50 | ≥500 |
| 16 | <50 | <50 | ≥500 |
| 17 | <50 | 50-<150 | ≥500 |
| 18 | <50 | 50-<150 | ≥500 |
| 19 | <50 | <50 | ≥500 |
| 20 | ≥500 | 250-<500 | ≥500 |
| 21 | <50 | <50 | 150-<250 |
| 22 | 150-<250 | <50 | ≥500 |
| 23 | 50-<150 | <50 | 250-<500 |
| 24 | <50 | <50 | 50-<150 |
| 25 | <50 | <50 | ≥500 |
| 26 | <50 | <50 | 250-<500 |
| 27 | 150-<250 | <50 | ≥500 |
| 28 | <50 | <50 | ≥500 |
| 29 | <50 | 50-<150 | ≥500 |
| 30 | 50-<150 | 50-<150 | ≥500 |
| 31 | <50 | <50 | ≥500 |
| 32 | <50 | <50 | ≥500 |
| 33 | <50 | <50 | ≥500 |
| 34 | <50 | <50 | ≥500 |
| 35 | 50-<150 | 50-<150 | ≥500 |
| 36 | <50 | <50 | ≥500 |
| 37 | <50 | <50 | 250-<500 |
| 38 | <50 | <50 | ≥500 |
| 39 | <50 | <50 | ≥500 |
| 40 | <50 | <50 | ≥500 |
| 41 | 50-<150 | <50 | ≥500 |
| 42 | <50 | <50 | ≥500 |
| 43 | <50 | <50 | ≥500 |
| 44 | 50-<150 | <50 | ≥500 |
| 45 | 50-<150 | <50 | ≥500 |
| 46 | 250-<500 | 50-<150 | ≥500 |
| 47 | <50 | <50 | 250-<500 |
| 48 | <50 | <50 | ≥500 |
| 49 | <50 | <50 | ≥500 |
| 50 | 50-<150 | <50 | ≥500 |
| 51 | <50 | <50 | ≥500 |
| 52 | <50 | <50 | ≥500 |
| 53 | 50-<150 | 50-<150 | ≥500 |
| 54 | 50-<150 | <50 | ≥500 |
| 55 | 50-<150 | <50 | ≥500 |
| 56 | <50 | 50-<150 | ≥500 |
| 57 | 50-<150 | <50 | ≥500 |
| 58 | 150-<250 | <50 | ≥500 |
| 59 | <50 | <50 | ≥500 |
| 60 | <50 | <50 | ≥500 |
| 61 | <50 | <50 | ≥500 |
| 62 | <50 | <50 | ≥500 |
| 63 | 50-<150 | 150-<250 | ≥500 |
| 64 | 50-<150 | <50 | ≥500 |
| 65 | <50 | <50 | ≥500 |
| 66 | <50 | <50 | ≥500 |
| 67 | <50 | <50 | ≥500 |
| 68 | <50 | <50 | ≥500 |
| 69 | <50 | <50 | 250-<500 |
| 70 | <50 | <50 | ≥500 |
| 71 | <50 | <50 | ≥500 |
| 72 | <50 | <50 | ≥500 |
| 73 | <50 | <50 | ≥500 |
| 74 | <50 | <50 | ≥500 |
| 75 | <50 | <50 | ≥500 |
| 76 | <50 | <50 | ≥500 |
| 77 | <50 | <50 | ≥500 |

TABLE B-1-continued

| Comp # | $\alpha_V\beta_8$ | $\alpha_V\beta_1$ | $\alpha_V\beta_6$ |
|---|---|---|---|
| 78 | <50 | <50 | ≥500 |
| 79 | <50 | <50 | ≥500 |
| 80 | <50 | <50 | ≥500 |
| 81 | 50-<150 | <50 | ≥500 |
| 82 | <50 | <50 | ≥500 |
| 83 | 50-<150 | <50 | 250-<500 |
| 84 | <50 | <50 | 250-<500 |
| 85 | 50-<150 | <50 | >500 |
| 86 | <50 | <50 | >500 |
| 87 | <50 | <50 | >500 |
| 88 | <50 | <50 | >500 |
| 89 | <50 | <50 | >500 |
| 90 | <50 | 50-<150 | >500 |
| 91 | 50-<150 | <50 | >500 |
| 92 | 50-<150 | 50-<150 | >500 |
| 93 | <50 | <50 | >500 |
| 94 | <50 | <50 | >500 |
| 95 | 50-<150 | 50-<150 | >500 |
| 96 | <50 | <50 | >500 |
| 97 | 250-<500 | 50-<150 | 250-<500 |
| 98 | 250-<500 | 50-<150 | >500 |
| 99 | 50-<150 | <50 | <50 |
| 100 | <50 | <50 | 50-<150 |
| 101 | <50 | <50 | >500 |
| 102 | 50-<150 | 50-<150 | >500 |
| 104 | <50 | <50 | >500 |

Figure 1:
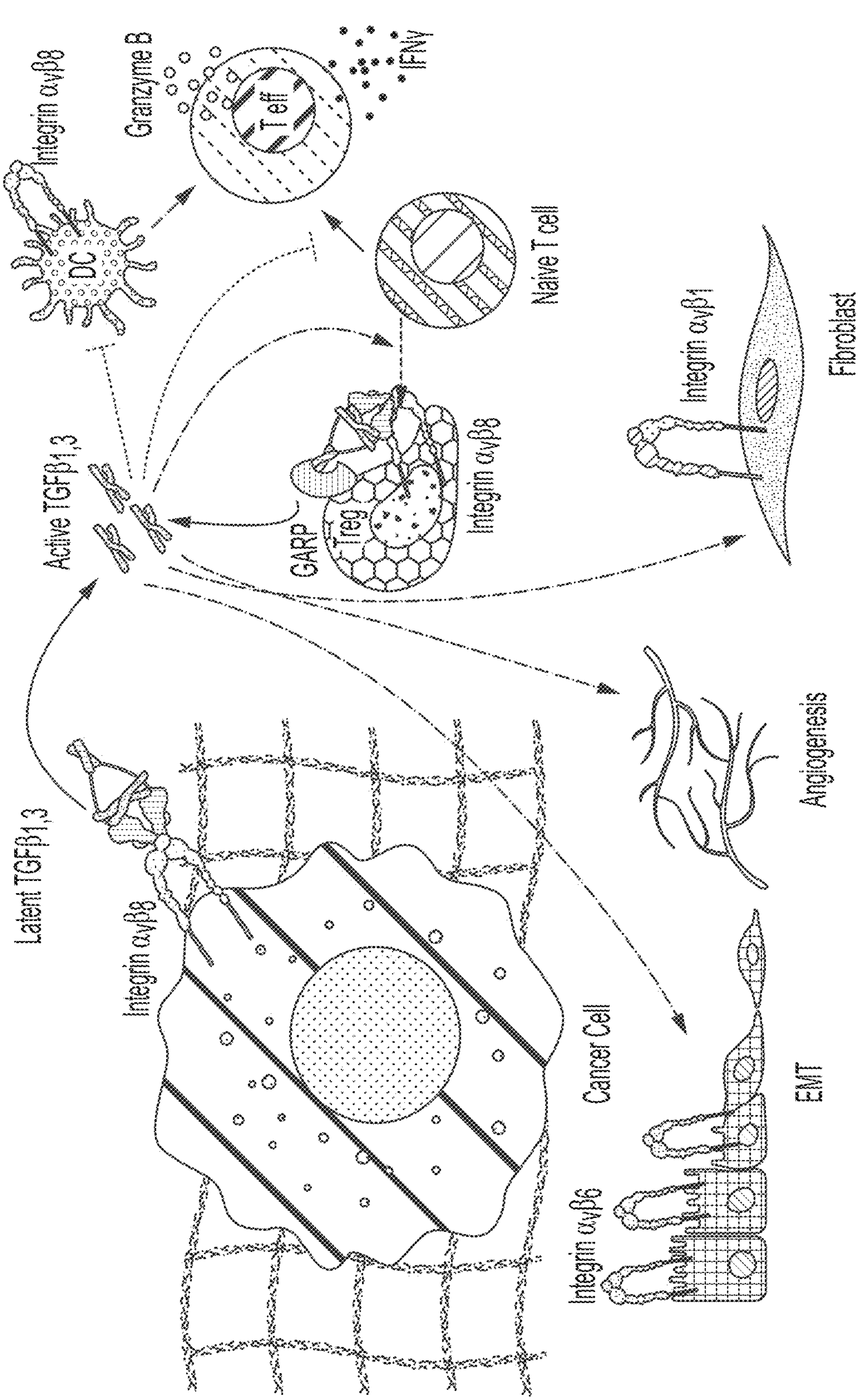
FIG. 1 is a diagram illustrating aspects of integrin-mediated TGF-β activation in tumor adaptive immunity.

Example B2—Anti-$\alpha_V\beta_8$ Antibody and PD-1 Inhibitor Block Cancer Growth FIG. 1 is a diagram illustrating aspects of integrin-mediated TGF-b activation in tumor adaptive immunity. Integrin expression on different cell types may contribute to TGF-b activation. For example, $\alpha_V\beta_8$ integrins on tumor cells and Treg cells may bind and activate latent TGF-b. Elevated TGF-b levels may block naive T cell differentiation toward a Th1 effector phenotype, may promote naive T cell conversion toward the Treg subset, and may dampen antigen-presenting functions of dendritic cells. Elevated TGF-b levels may induce fibroblast activation, endothelial mesenchymal transition (EMT), promote angiogenesis and facilitate further cancer cell growth.

Figure 2A:
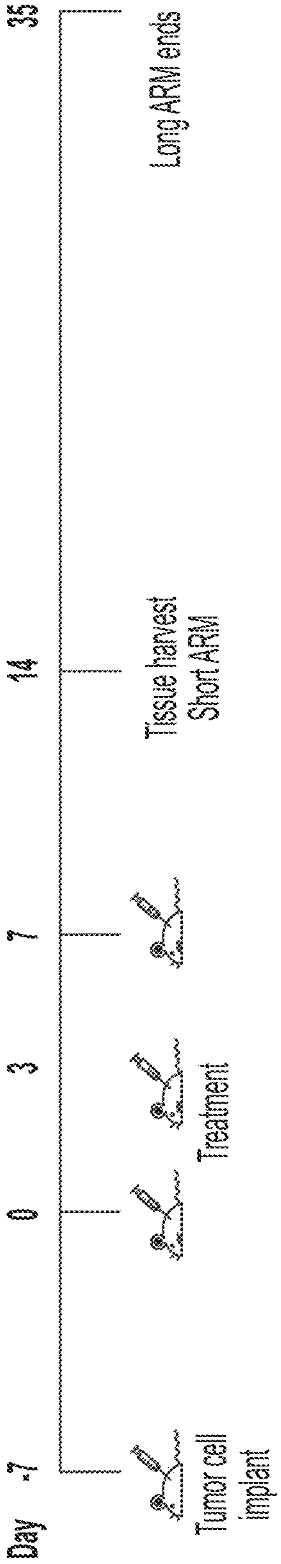
FIG. 2A is a diagram illustrating an initial experiment in mice.

FIG. 2A is a diagram illustrating an initial experiment in mice. A cancer cell line (EMT6 (ATCC® CRL-2755™) was obtained and $30\times10^3$ cells were implanted into the fourth mammary fat pad in Balb/c mice. Tumors were measured in two dimensions to monitor growth. Mice were randomized into 5 groups when tumors reached size around 50 $mm^3$ at day 7 before treatment, which occurred on days 0, 3, and 7. Group 1, the control group, was administered a mIgG1 antibody. Group 2 was administered an anti-PD1 antibody and the mIgG1 control. Group 3 was administered an anti-$\alpha_V\beta_8$ antibody (ADWA11). Group 4 was administered the anti-PD1 and anti-$\alpha_V\beta_8$ antibodies. Group 5 was administered the anti-PD1 antibody and an anti-TGF$\beta_{1-2}$ antibody (XOMA089) to compare against general inhibition of TGF$\beta_{1-2}$.

Figure 2B:
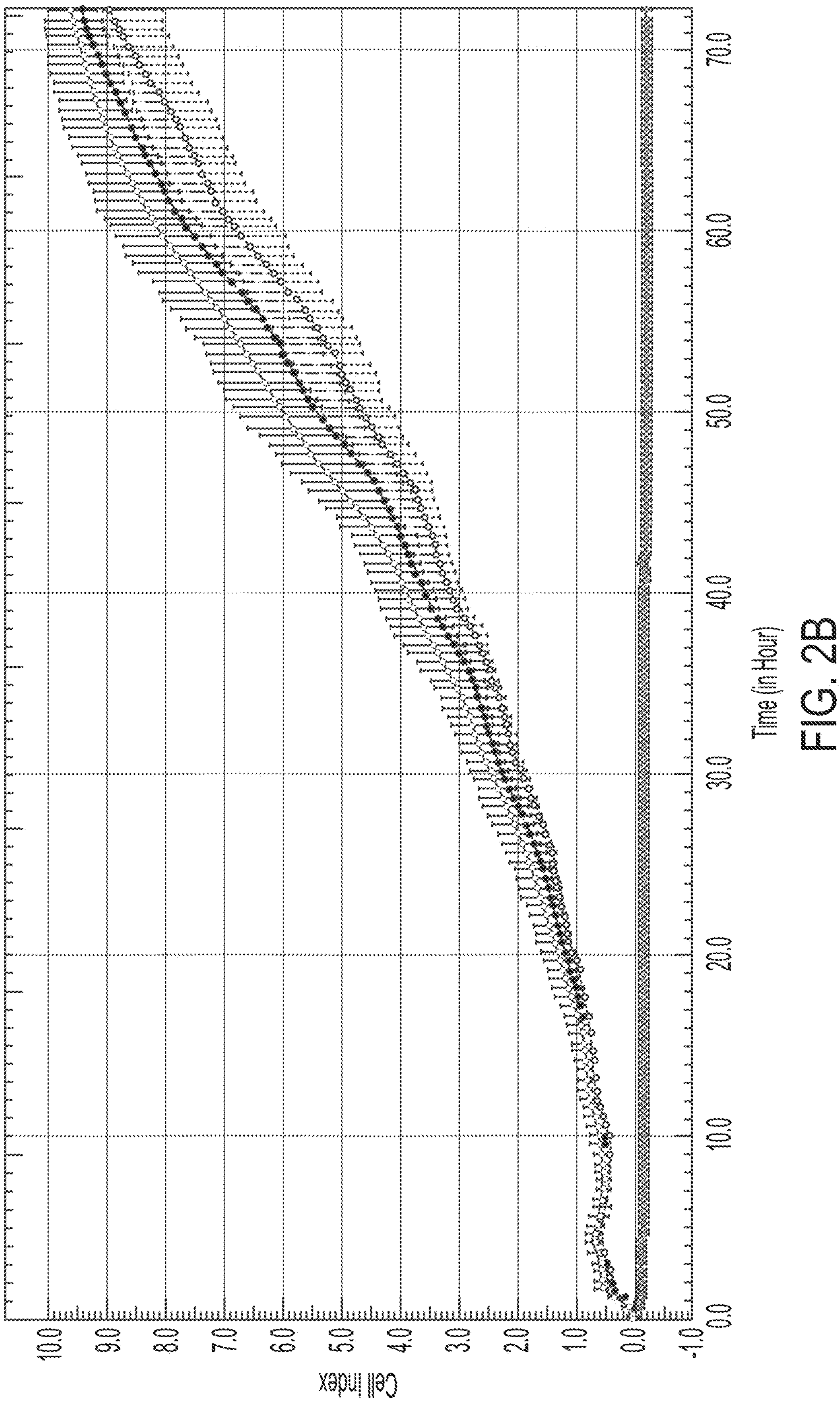
FIG. 2B is a graph showing that EMT6 cell proliferation was not affected by anti-$\alpha_V\beta_8$ or IgG control in vitro.

FIG. 2B is a graph of EMT6 cell proliferation with xCELLigence RTCA (real time cell analysis) showing that EMT6 cell proliferation was not affected by anti-$\alpha_V\beta_8$ or IgG control in vitro.

Figure 3A:
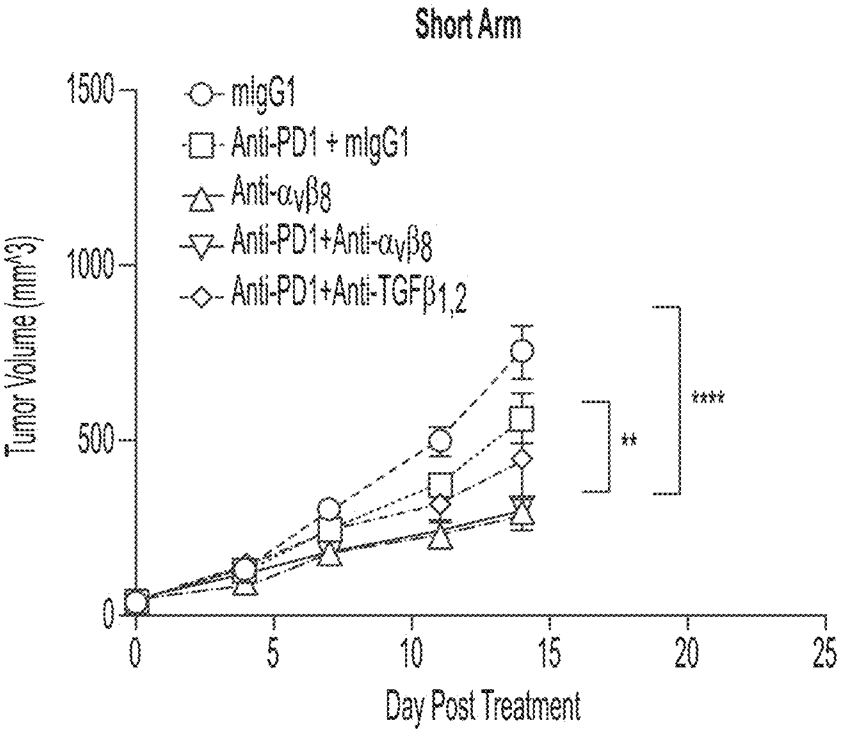
FIG. 3A is a graph showing tumor volume as a function of time for the short arm of the study of Example B3.
Figure 3B:
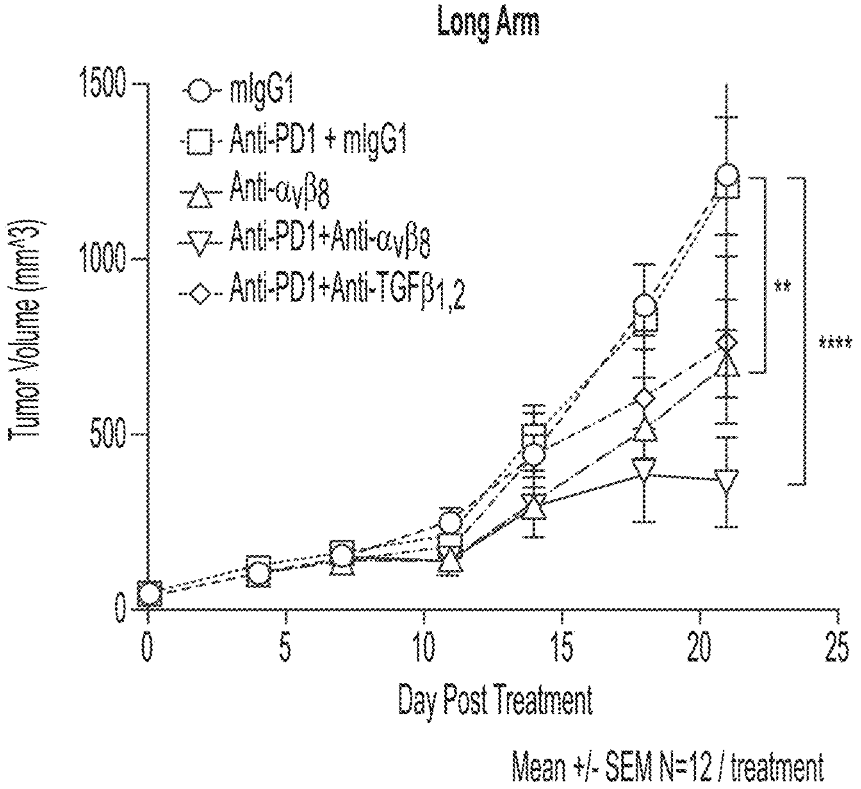
FIG. 3B is a graph showing tumor volume as a function of time for the long arm of the study of Example B3.
Figure 4A:
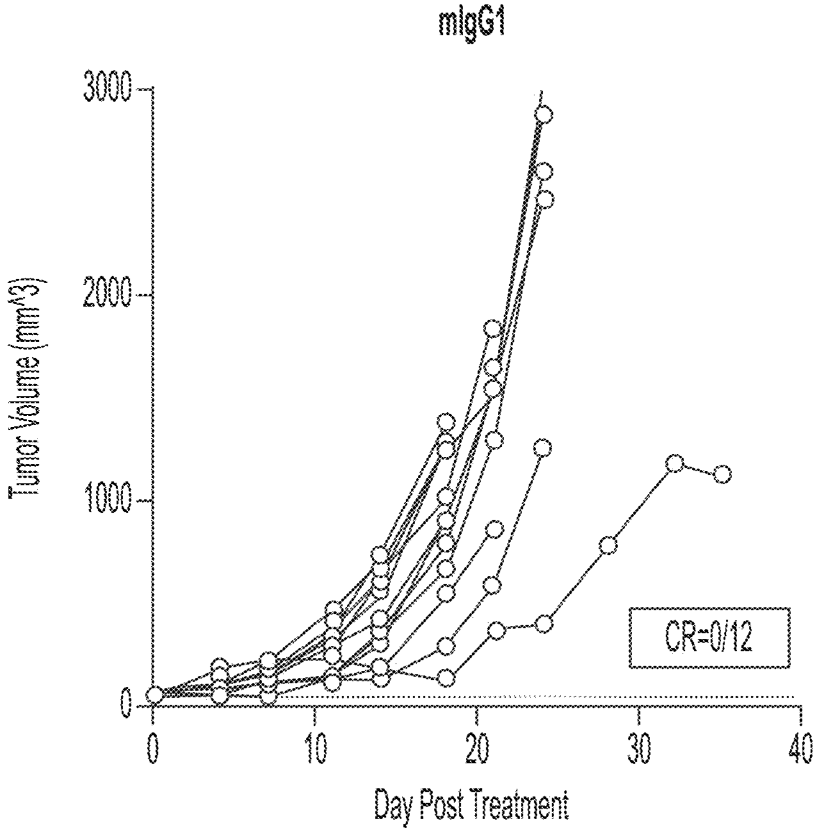
FIG. 4A is a graph showing tumor volume versus time for mice in Group 1.
Figure 4B:
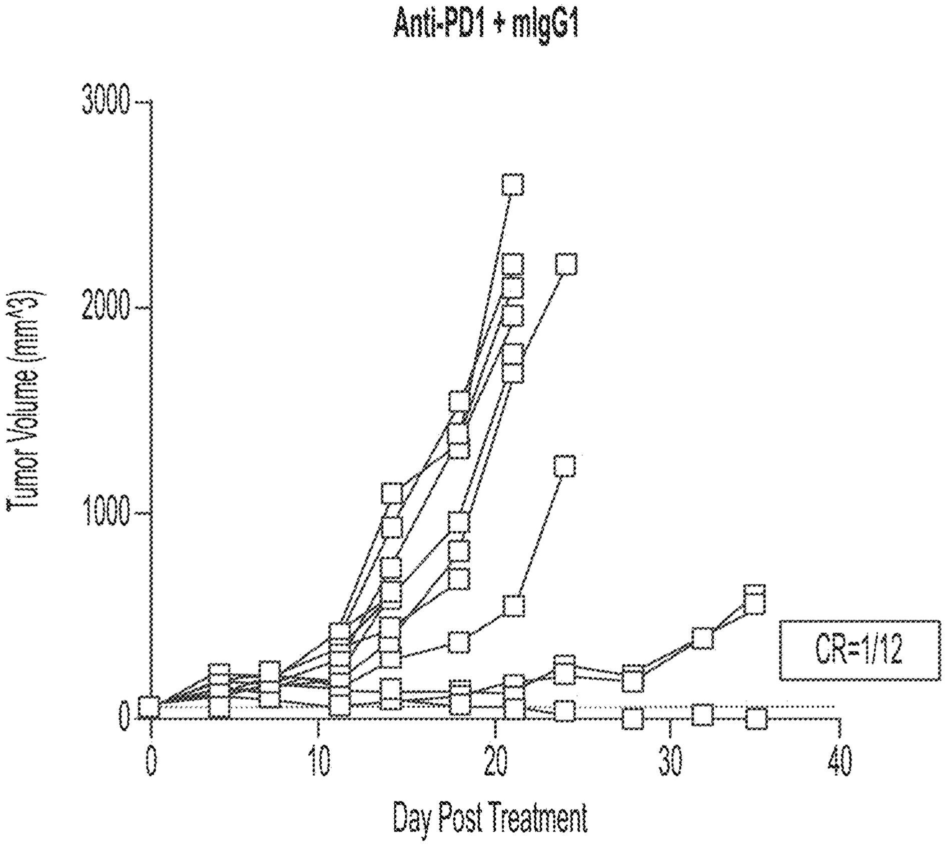
FIG. 4B is a graph showing tumor volume versus time for mice in Group 2.
Figure 4C:
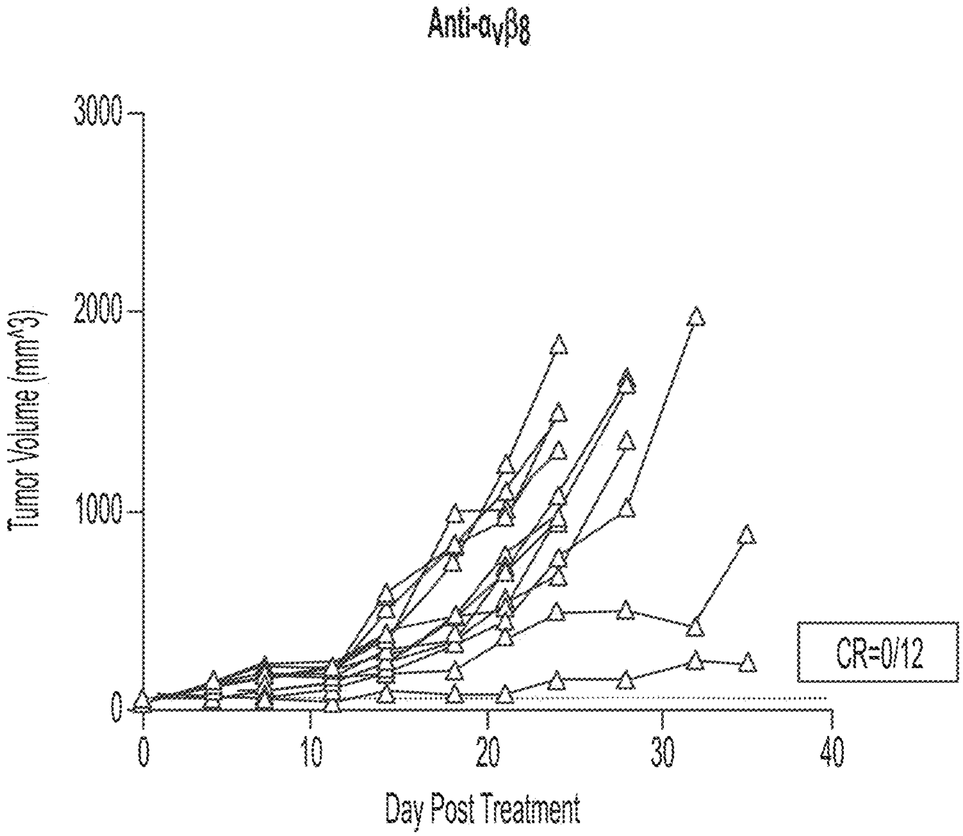
FIG. 4C is a graph showing tumor volume versus time for mice in Group 3.
Figure 4D:
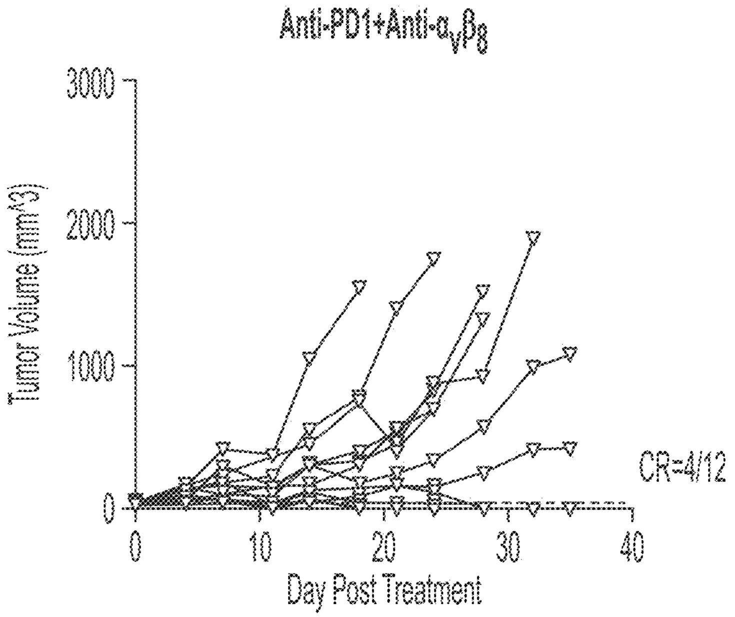
FIG. 4D is a graph showing tumor volume versus time for mice in Group 4.
Figure 4E:
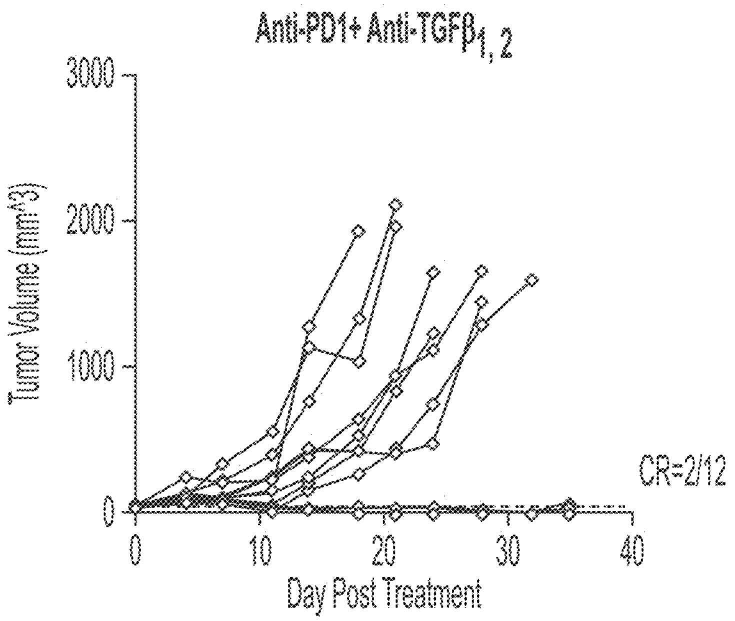
FIG. 4E is a graph showing tumor volume versus time for mice in Group 5.

FIGS. 3A and 3B are graphs showing tumor volume as a function of time, post-treatment. FIG. 3A shows results of the short arm of the study in which tumor growth was attenuated compared to control in treatment Groups 2-5, and particularly in treatment Groups 3 and 4, containing the anti-$\alpha_v\beta_8$ antibody. FIG. 3B shows results of the long arm of the study, indicating that group 2, containing anti-PD1 and mIgG1, was similar to the mIgG1 control. Group 3, containing the anti-$\alpha_v\beta_8$ antibody, and Group 5, containing the anti-PD1 and anti-TGF$\beta_{1-2}$ antibodies were similar. Group 4, containing the anti-PD1 and anti-$\alpha_v\beta_8$ antibodies, reduced the growth of tumor volume the most. These results demonstrate that anti-$\alpha_v\beta_8$ antibody consistently reduced EMT6 tumor growth, and anti-$\alpha_v\beta_8$ antibody showed better anti-tumor potency than the TGFβ blocking antibody.

FIGS. 4A, 4B, 4C, 4D, and 4E are a series of graphs of tumor volume versus time for individual mice in Groups 1-5. Compared to control, some growth inhibition was seen in all treatment groups. In Group 4, simultaneous inhibition of $\alpha_v\beta_8$ and PD-1 pathways dramatically inhibited EMT6 breast carcinoma growth, as well as improving complete response (CR) rate to 30%.

Figure 5:
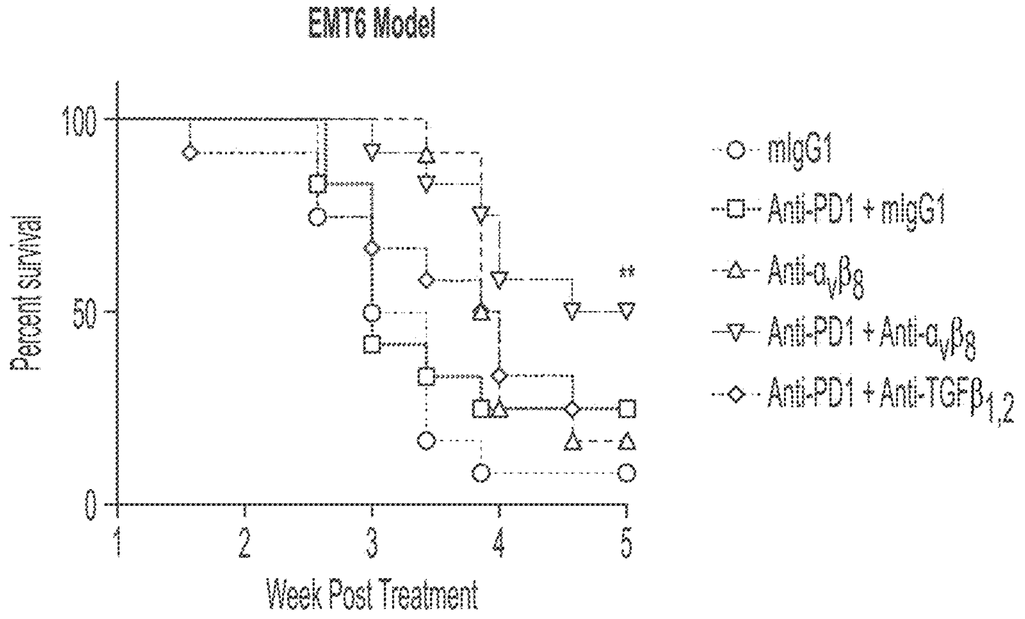
FIG. 5 is a graph of percent survival versus time over 5 weeks, showing that long term survival was significantly improved by the combination of the anti-PD1 and anti-$\alpha_V\beta_8$ antibodies in Group 4.

FIG. 5 is a graph of percent survival versus time over 5 weeks, showing that long term survival was significantly improved by the combination of the anti-PD1 and anti-$\alpha_v\beta_8$ antibodies in Group 4. Moreover, in combination with PD1 inhibition, selective TGFβ inhibition via the anti-$\alpha_v\beta_8$ antibody in Group 4 was superior to general TGF$\beta_{1-2}$ inhibition in Group 5.

Figure 6A:
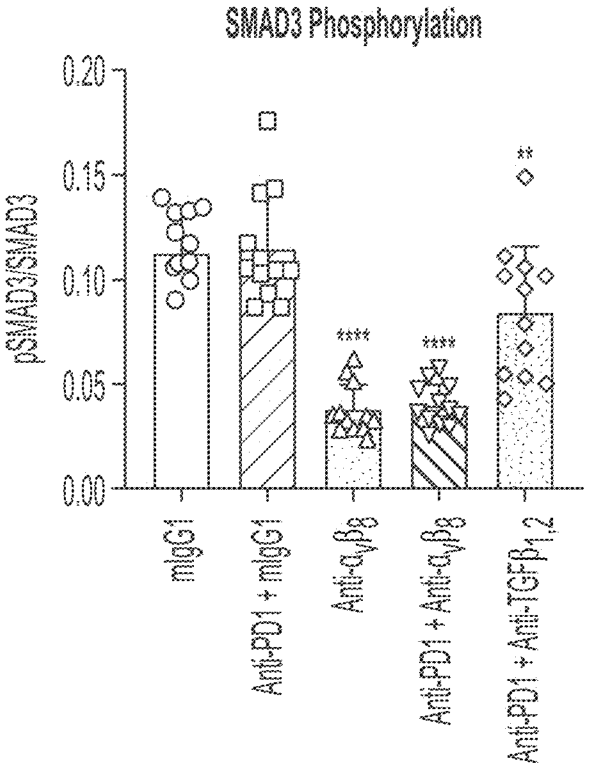
FIG. 6A is a graph showing that inhibiting $\alpha_V\beta_8$ significantly reduced SMAD3 phosphorylation in Groups 3 and 4, consistent with significantly reduced TGFβ signaling inside the tumor cells.
Figure 6B:
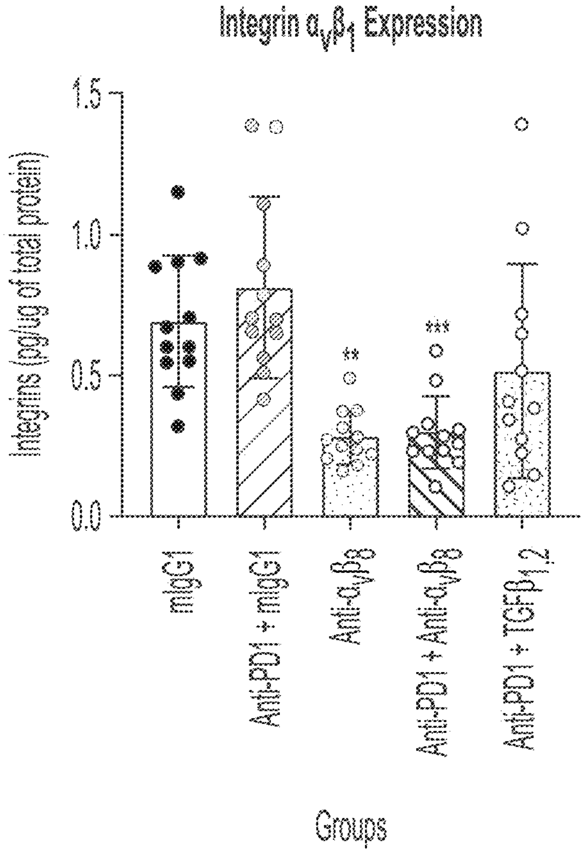
FIG. 6B is a graph showing that inhibiting $\alpha_V\beta_8$ significantly reduced integrin $\alpha_V\beta_1$ expression in myofibroblasts.

FIGS. 6A and 6B are graphs showing that $\alpha_v\beta_8$ inhibition reduced TGFβ signaling inside tumor tissues. FIG. 6A shows that inhibiting $\alpha_v\beta_8$ significantly reduced SMAD3 phosphorylation in Groups 3 and 4, consistent with significantly reduced TGFβ signaling inside the tumor cells. FIG. 6B shows that inhibiting $\alpha_v\beta_8$ significantly reduced integrin $\alpha_v\beta_1$ expression in myofibroblasts. Expression of $\alpha_v\beta_3$ and $\alpha_v\beta_5$ integrins was not affected (data not shown). These data also demonstrated that inhibition of $\alpha_v\beta_8$ and TGFβ each had significant impact on tumor micro-environment signaling.

Figure 7A:
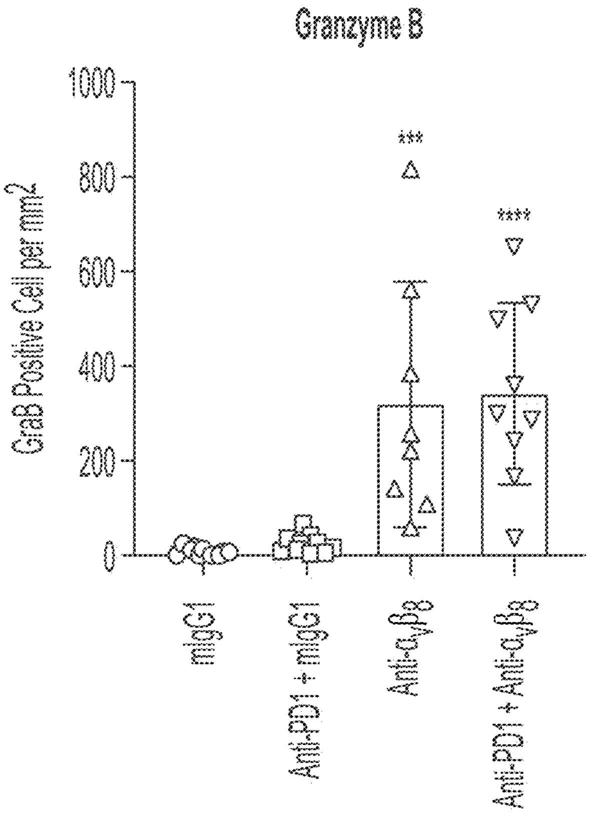
FIG. 7A is a bar graph showing that Granzyme B expression, assessed by immunohistochemistry staining with an anti-granzyme B antibody was significantly enhanced in Groups 3 and 4 with the anti-$\alpha_V\beta_8$ antibody.
Figure 7B:
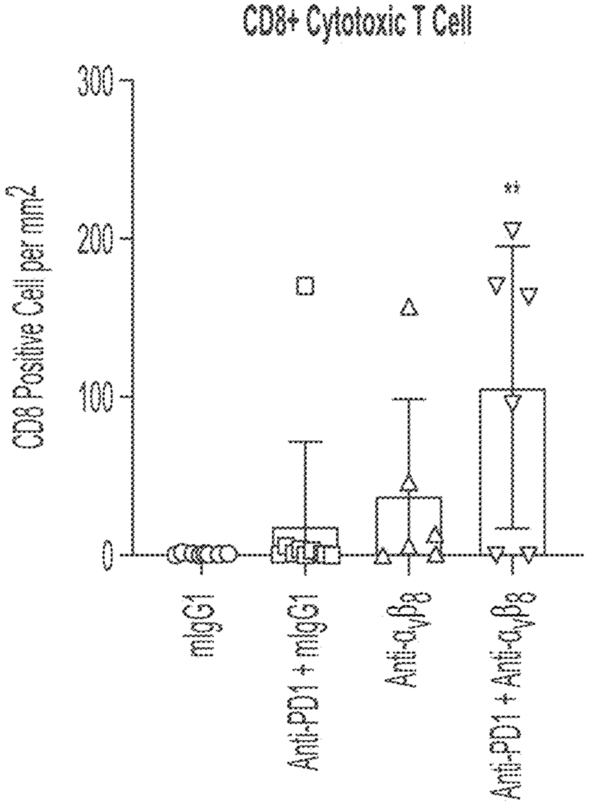
FIG. 7B is a graph showing that CD8+ cytotoxic T cells were increased in Group 3, containing the anti $\alpha_V\beta_8$ antibody alone, and significantly increased in Group 4, containing the anti PD-1 and anti $\alpha_V\beta_8$ antibodies together.
Figure 8A:
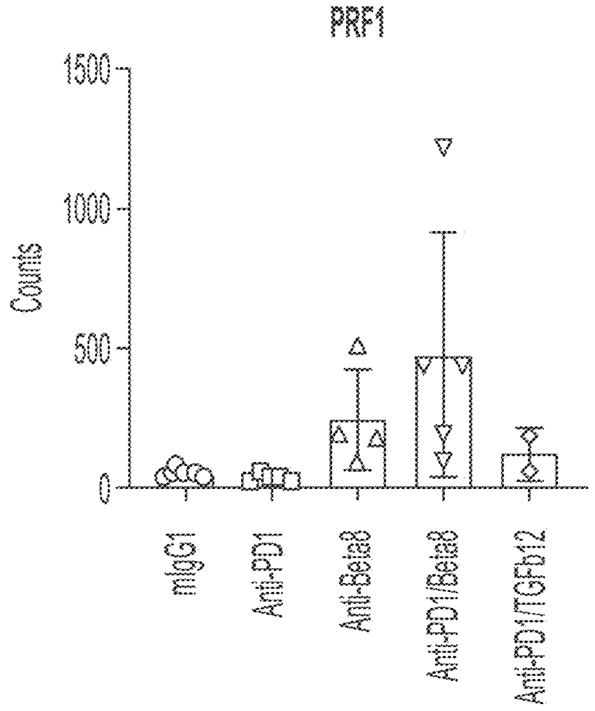
FIG. 8A is a graph showing that $\alpha_V\beta_8$ inhibition results in cytotoxic T cell activation 14 days post treatment for perforin (PRF1).
Figure 8B:
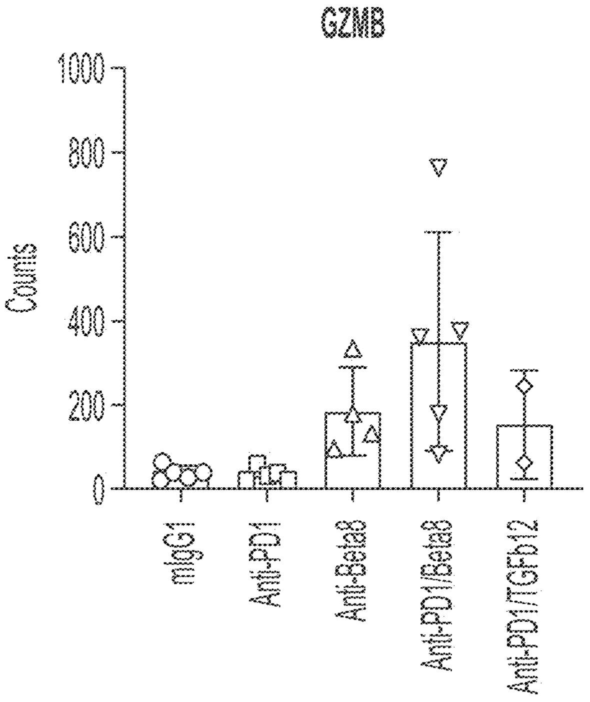
FIG. 8B is a graph showing that $\alpha_V\beta_8$ inhibition results in cytotoxic T cell activation 14 days post treatment for granzyme B (GZMB).
Figure 8C:
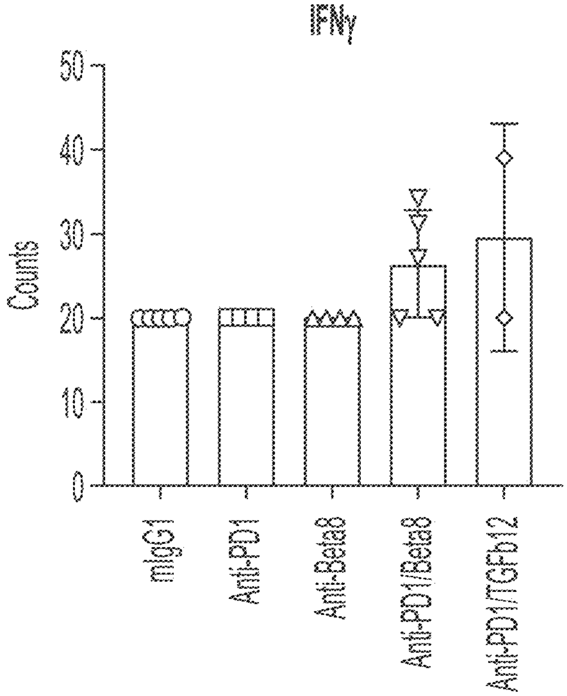
FIG. 8C is a graph showing that $\alpha_V\beta_8$ inhibition results in cytotoxic T cell activation 14 days post treatment for interferon γ (IFNg).
Figure 8D:
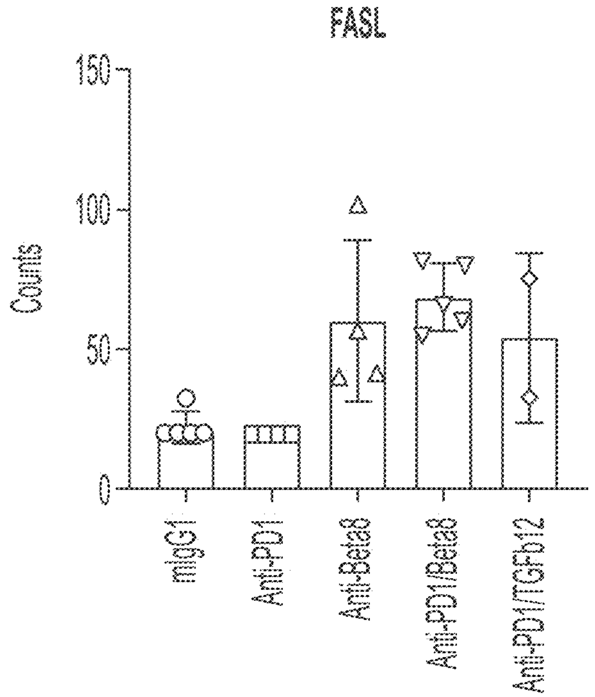
FIG. 8D is a graph showing that $\alpha_V\beta_8$ inhibition results in cytotoxic T cell activation 14 days post treatment for Fas ligand (FASL).

FIG. 7A is a bar graph showing that Granzyme B expression, assessed by immunohistochemistry staining with an anti-granzyme B antibody was significantly enhanced in Groups 3 and 4 with the anti-$\alpha_v\beta_8$ antibody. FIG. 7B is a graph showing that CD8+ cytotoxic T cells were increased in Group 3, containing the anti $\alpha_v\beta_8$ antibody alone, and significantly increased in Group 4, containing the anti PD-1 and anti $\alpha_v\beta_8$ antibodies together.

FIGS. 8A, 8B, 8C, and 8D are a series of graphs showing that $\alpha_v\beta_8$ inhibition results in cytotoxic T cell activation 14 days post treatment. TGF-b activation plays an important role in cytotoxic T cell proliferation by PRF1, granzyme B, IFNg and FAS1 inhibition. $\alpha_v\beta_8$ inhibition increased each of these important cytotoxic T cell activation markers: perforin (PRF1, FIG. 8A), increased granzyme B (GZMB, FIG. 8B), interferon γ (IFNg, FIG. 8C), and Fas ligand (FASL, FIG. 8D).

Figure 9A:
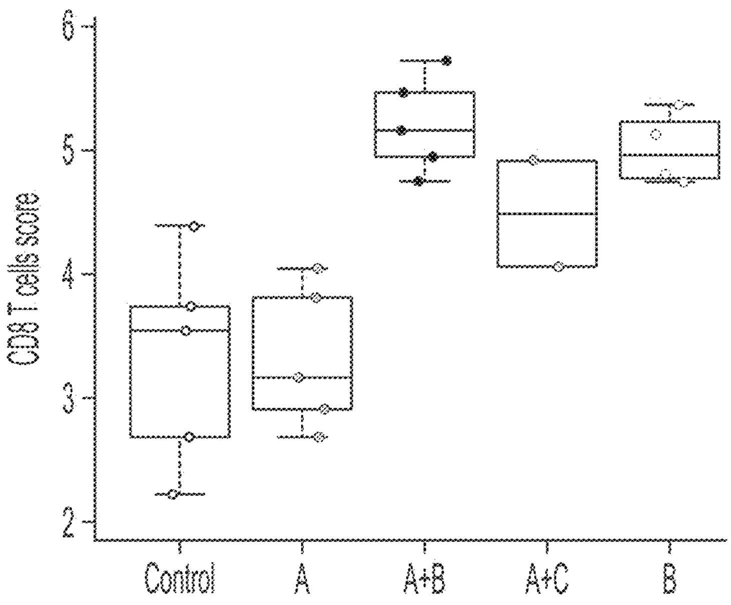
FIG. 9A is a graph of cell profiling analysis showing that CD8 T cells were upregulated by $\alpha_V\beta_8$ inhibition.
Figure 9B:
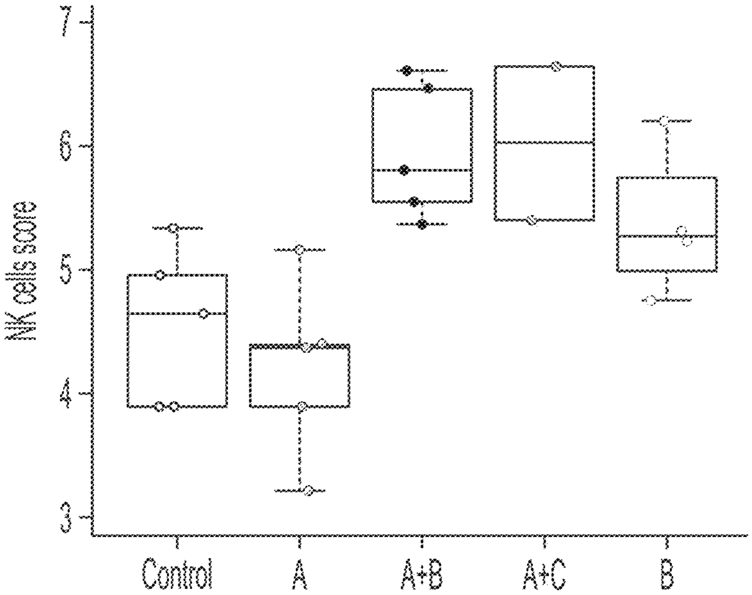
FIG. 9B is a graph of cell profiling analysis showing that NK cells were upregulated by $\alpha_V\beta_8$ inhibition.
Figure 9C:
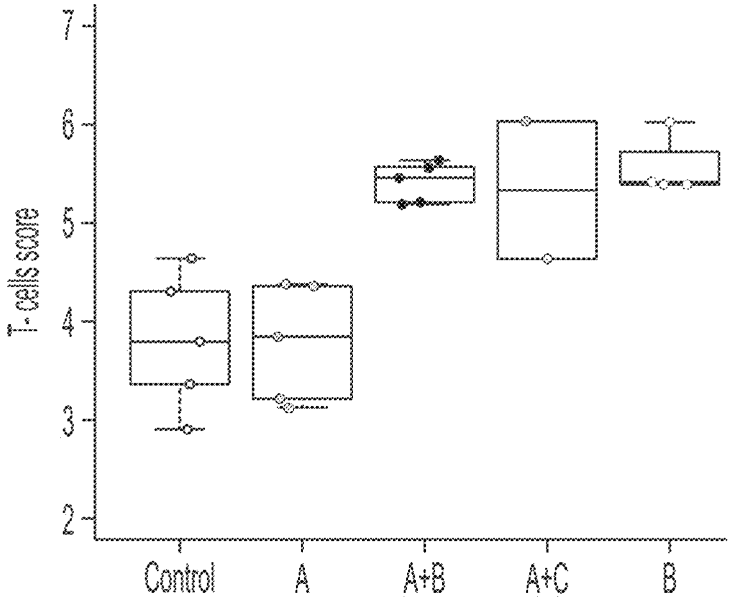
FIG. 9C is a graph of cell profiling analysis showing that cytotoxic T cells were upregulated by $\alpha_V\beta_8$ inhibition.

FIGS. 9A, 9B, and 9C show that $\alpha_v\beta_8$ inhibition had a significant impact on immune cell profiling. Gene expression was analyzed using a Nanostring mouse IO Pan cancer panel. Immune cell profiling analysis showed that CD8 T (FIG. 9A), NK (FIG. 9B), and cytotoxic T cells (FIG. 9C) were upregulated by $\alpha_v\beta_8$ inhibition.

Figure 10A:
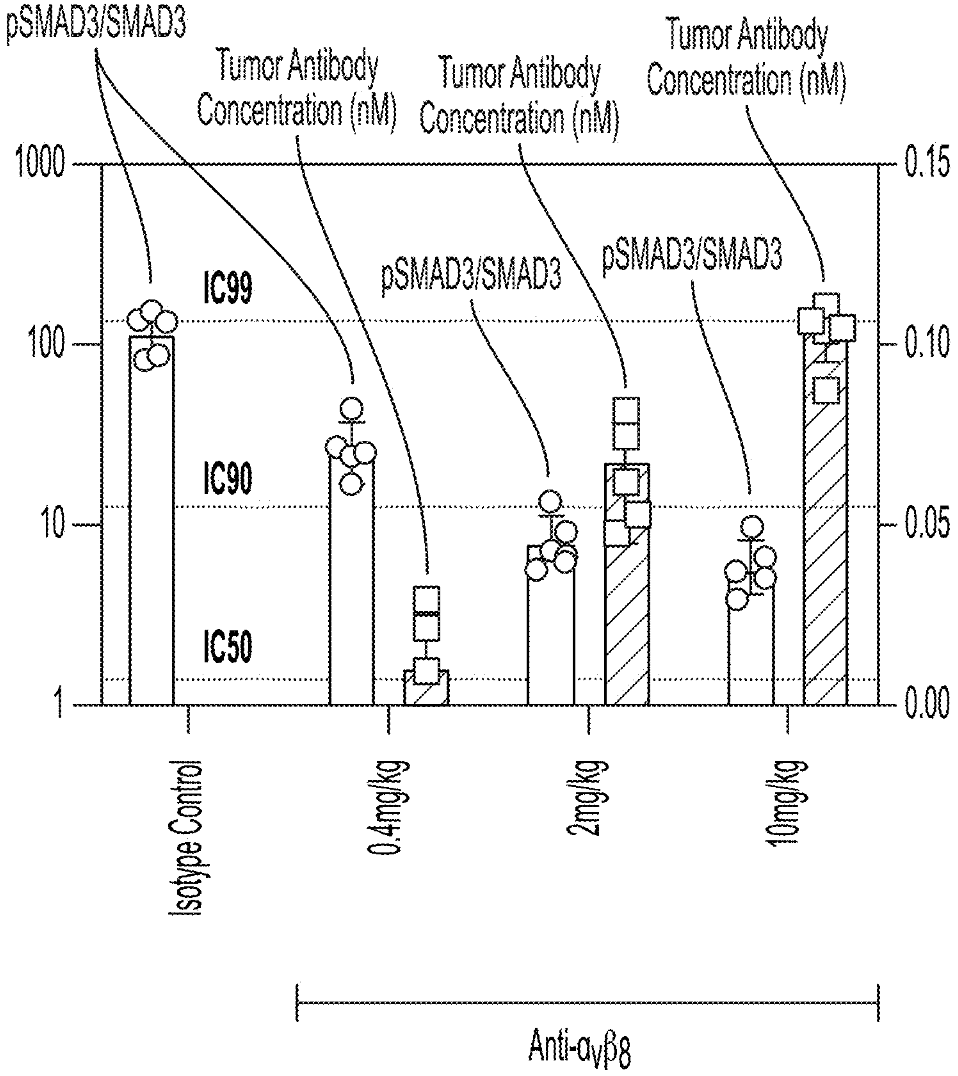
FIG. 10A shows tumor antibody concentration (left axis) and pSMAD3/SMAD3 ratio (right axis), indicating a clear, dose-responsive relationship for treatment with the anti-$\alpha_V\beta_8$ antibody at 0.4, 2, and 10 mg/kg in combination with the anti-PD-1 antibody.
Figure 10B:
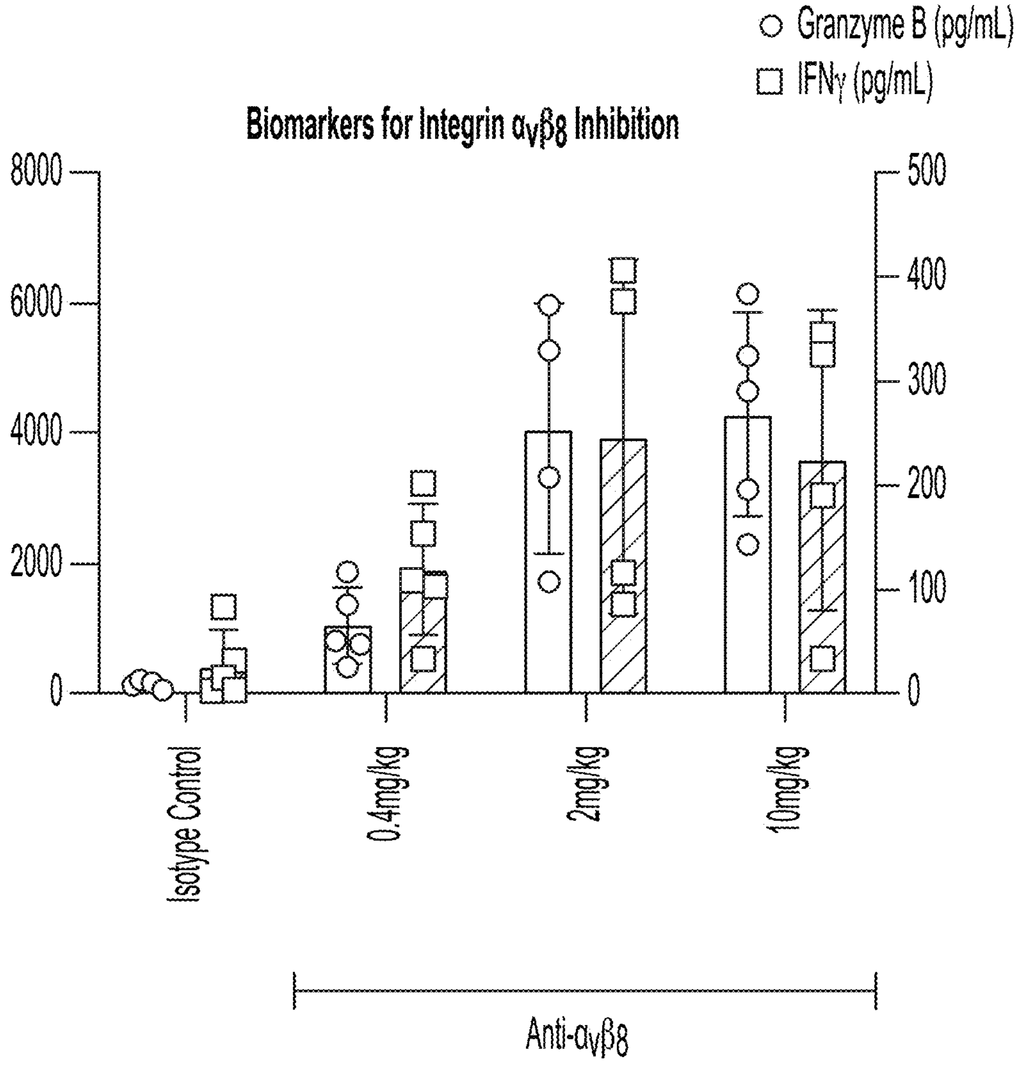
FIG. 10B shows a clear, dose-responsive relationship for the anti-$\alpha_V\beta_8$ antibody at 0.4, 2, and 10 mg/kg in combination with the anti-PD-1 antibody versus Granzyme B (pg/mL, left axis) and interferon γ (IFNγ, pg/mL, right axis).
Figure 33:
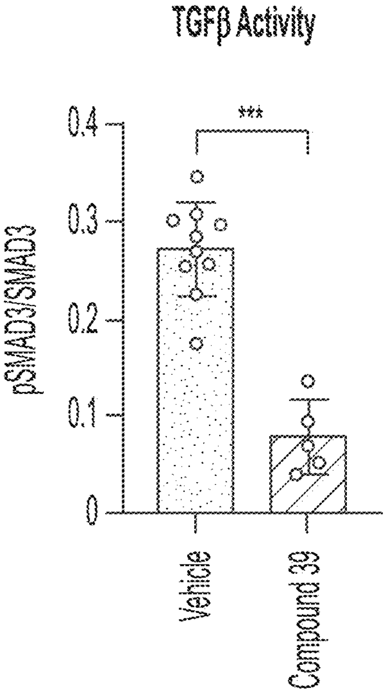
FIG. 33 depicts a graph showing reduced TGFβ activity for Compound 39 as compared to a vehicle.
Figures 34A, 34B, 34C, 34D:
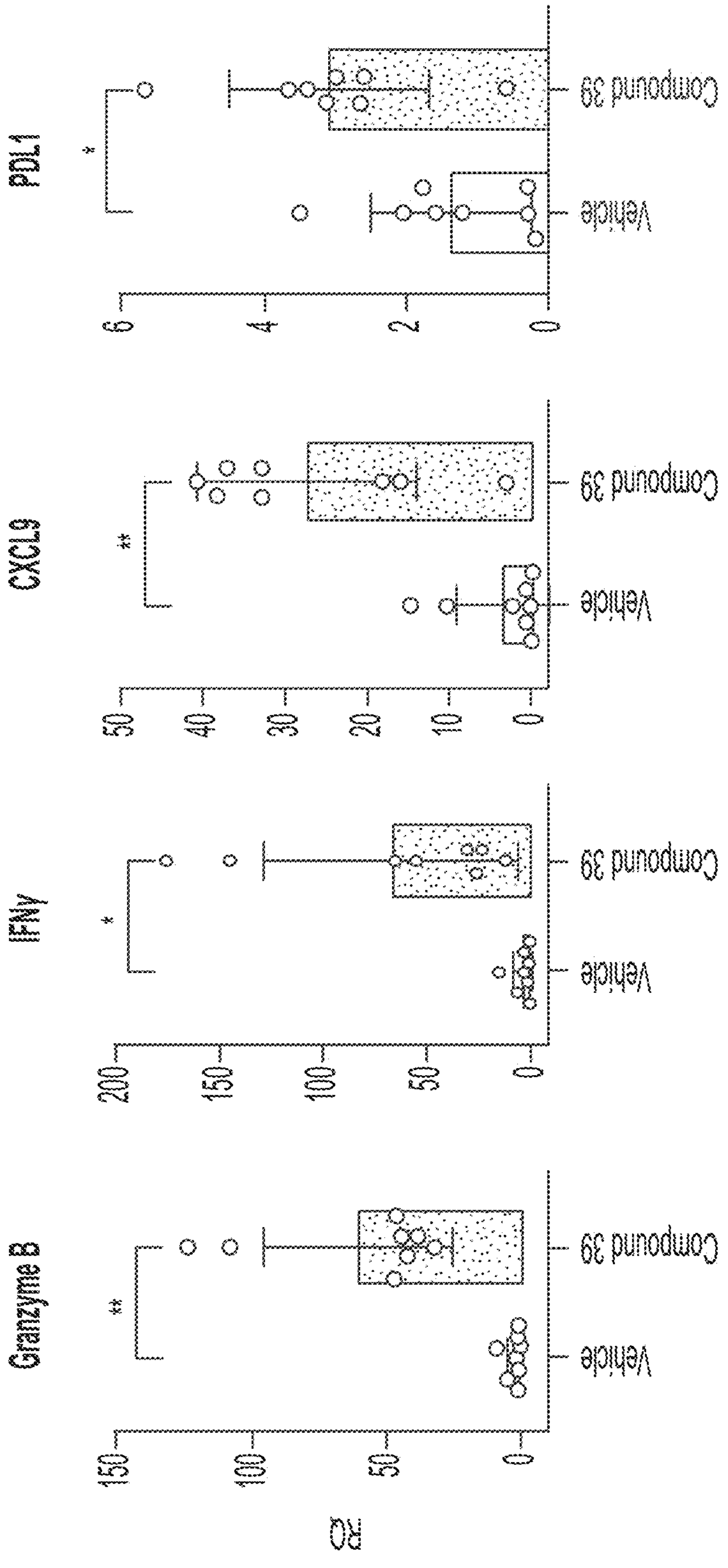
FIG. 34A depicts a graph showing increased expression of IFNγ-regulated gene, Granzyme B, for Compound 39 as compared to a vehicle.
FIG. 34B depicts a graph showing increased expression of IFNγ-regulated gene, IFNγ, for Compound 39 as compared to a vehicle.
FIG. 34C depicts a graph showing increased expression of IFNγ-regulated gene, CXCL9, for Compound 39 as compared to a vehicle.
FIG. 34D depicts a graph showing increased expression of IFNγ-regulated gene, PDL1, for Compound 39 as compared to a vehicle.

FIGS. 10A and 10B show the results of a dose range study for the anti-$\alpha_v\beta_8$ antibody in the EMT6 cells, in which tumor cells were harvested 6 days after treatment. FIG. 10A shows tumor antibody concentration (left axis) and pSMAD3/SMAD3 ratio (right axis), indicating a clear, dose-responsive relationship for treatment with the anti-$\alpha_v\beta_8$ antibody at 0.4, 2, and 10 mg/kg in combination with the anti-PD-1 antibody at 10 mg/kg. FIG. 10B shows a clear, dose-responsive relationship for the anti-$\alpha_v\beta_8$ antibody at 0.4, 2, and 10 mg/kg in combination with the anti-PD-1 antibody at 10 mg/kg versus Granzyme B (pg/mL, left axis) and interferon γ (IFNγ, pg/mL, right axis). FIG. 33 depicts a graph showing reduced TGFβ activity for Compound 39 as compared to a vehicle. FIG. 34A depicts a graph showing increased expression of IFNγ-regulated gene, Granzyme B, for Compound 39 as compared to a vehicle. FIG. 34B depicts a graph showing increased expression of IFN7-regulated gene, IFNγ, for Compound 39 as compared to a vehicle. FIG. 34C depicts a graph showing increased expression of IFNγ-regulated gene, CXCL9, for Compound 39 as compared to a vehicle. FIG. 34D depicts a graph showing increased expression of IFNγ-regulated gene, PDL1, for Compound 39 as compared to a vehicle. These results also demonstrate that pSMAD3/SMAD3 ratio, Granzyme B, and interferon γ can be effective biomarkers for $\alpha_v\beta_8$ inhibition.

Figure 11:
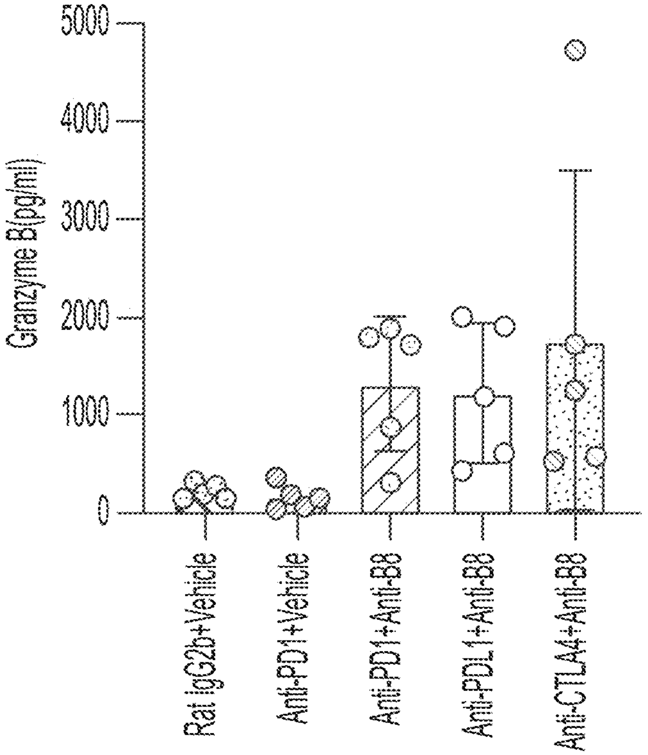
FIG. 11 shows the results of combinations of the anti-$\alpha_V\beta_8$ antibody with anti-PD1, anti-PDL1 or anti-CTLA-4 resulted in similar T cell activation.

FIG. 11 shows the results of combinations of the anti-$\alpha_v\beta_8$ antibody with anti-PD1, anti-PDL1 or anti-CTLA-4 resulted in similar T cell activation. Granzyme B was used as cytotoxic T cell activation.

Compound 39 increases IFNγ Signature & Reduces TGFβ Gene Signatures. FIG. 48 depicts an IFN-γ gene signature (top) and a TGFβ gene signature (bottom) for vehicle+αPD1 and Compound 39+α-PD1. FIG. 49 depicts a schematic diagram associated with Compound 39 promoting ICI responsiveness.

Figure 39:
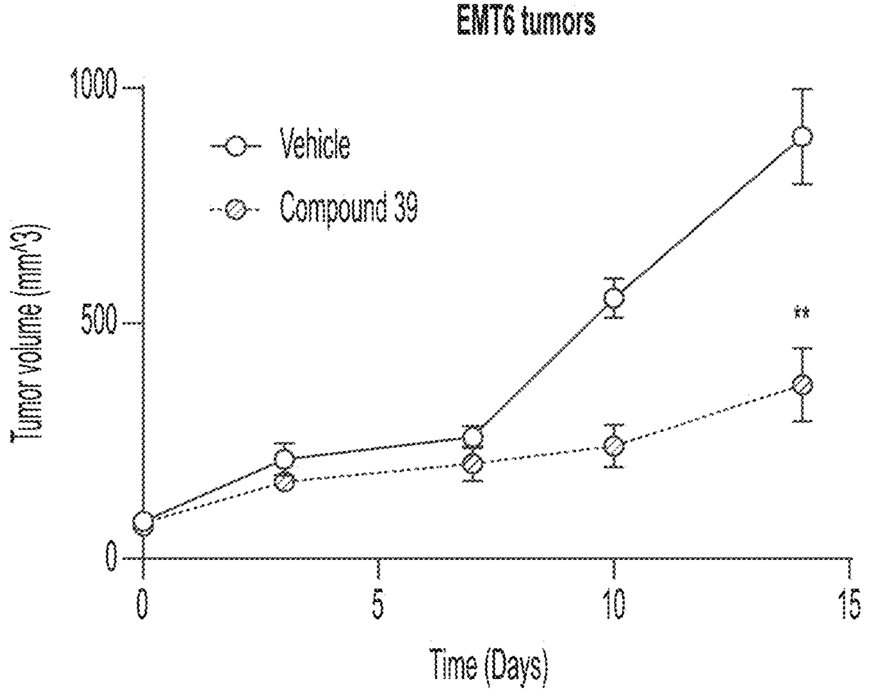
Figure 40B:
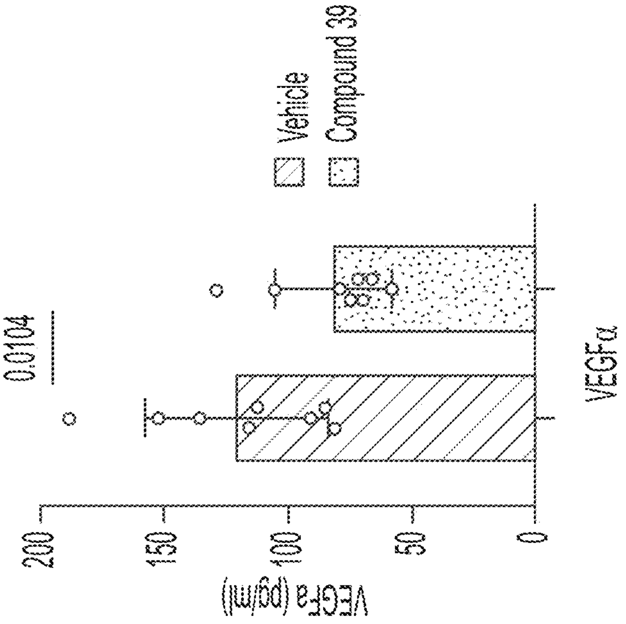
Figure 40A:
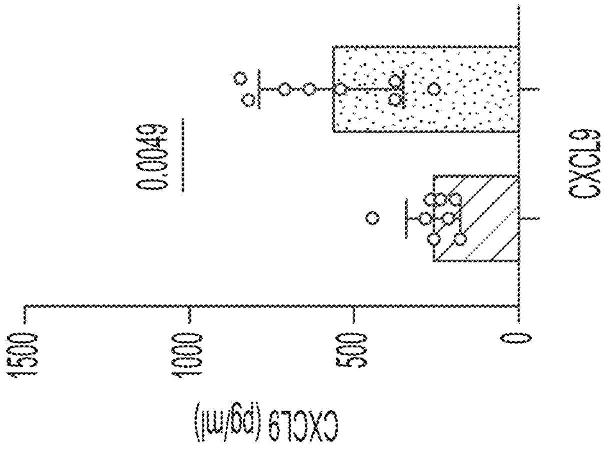

Putative Circulating Biomarkers of Response to Compound 39. FIG. 39 depicts a graph showing tumor volume in EMT6 tumors for vehicle and Compound 39 over a 15 day time period. FIG. 40A depicts a graph showing plasma biomarker response for CXCL9 after 14 days of monotherapy with Compound 39. FIG. 40B depicts a graph showing plasma biomarker response for VEGFα after 14 days of monotherapy with Compound 39.

Figure 44:
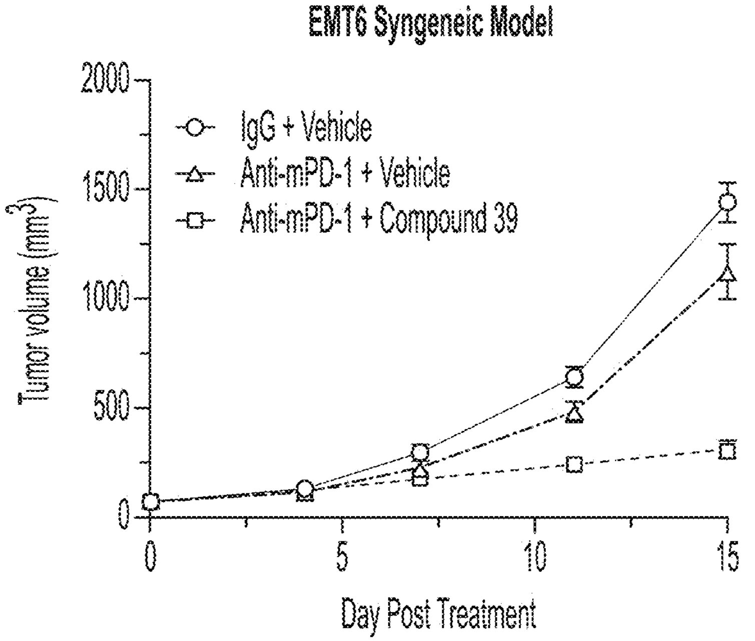

Putative Circulating Biomarkers of Response to Compound 39+PD-1. FIG. 44 depicts a graph showing tumor volume in an EMT6 syngeneic model for IgG+vehicle, anti-mPD-1+vehicle, and Compound 39+anti-mPD-1 up to 15 days post-treatment. FIG. 45A depicts a percent of total non-granulocytes associated with a healthy group, a vehicle+IgG group, a vehicle+α-mPD-1 group, and an α-mPD-1+Compound 39 group. FIG. 45B depicts a percent of total T cells associated with a healthy group, a vehicle+IgG group, a vehicle+α-mPD-1 group, and an α-mPD-1+Compound 39 group. FIG. 45C depicts a percent of total $CD8^+$ T cells associated with a healthy group, a vehicle+IgG group, a vehicle+α-mPD-1 group, and an α-mPD-1+Compound 39 group. FIG. 45D depicts a percent of non-granulocytes associated with a healthy group, a vehicle+IgG group, a vehicle+α-mPD-1 group, and an α-mPD-1+Compound 39 group. FIG. 45E depicts a percent of $CD4^+$ T cells associated with a healthy group, a vehicle+IgG group, a vehicle+α-mPD-1 group, and an α-mPD-1+Compound 39 group. FIG. 45F depicts a percent of tissue homing Treg cells associated with a healthy group, a vehicle+IgG group, a vehicle+α-mPD-1 group, and an α-mPD-1+Compound 39 group.

Figure 12A:
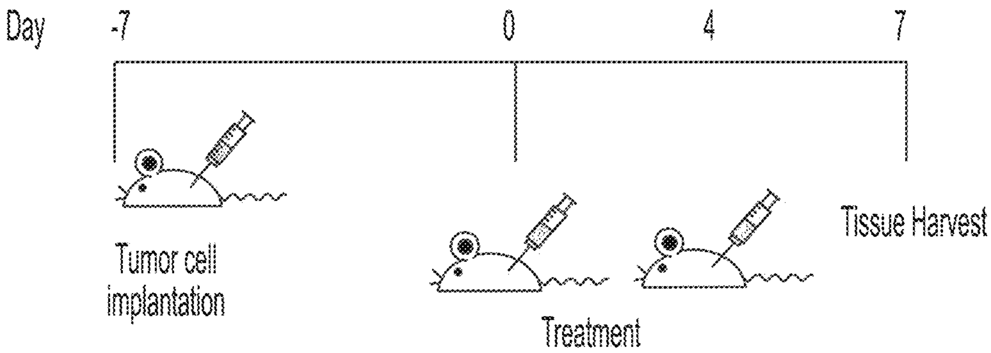
FIG. 12A is a diagram illustrating an experiment in mice.

Example B3—Small Molecule $\alpha_v\beta_8$ Inhibitor and PD-1 Inhibitor Block Cancer Growth FIG. 12A is a diagram illustrating an experiment in mice. A breast cancer cell line (EMT6 (ATCC® CRL-2755™) is obtained and $30\times10^3$ cells are implanted into the fourth mammary fat pad in Balb/c mice. Tumors are measured in two dimensions to monitor growth. Mice are randomized into 8 groups when tumors reach size around 50 $mm^3$ at day 7 before treatment, which occurs on days 0, 3, and 7.

FIG. 12B is a table showing the compounds and dosages used for each group. Group 1, the control group, is administered a rat IgG1 antibody. Group 2 is administered 10 mg/kg of an anti-PD1 antibody (RMP1-14). RMP1-14 is a monoclonal antibody that targets the murine PD-1 protein. Group 3 is administered 10 mg/kg of an anti-PD1 antibody (RMP1-14) and an anti-$\alpha_V\beta_8$ antibody (ADWA11/PF-06940434). Group 4 is administered 10 mg/kg of an anti-PD1 antibody (RMP1-14) and a high dose of 500 mg/kg of a small molecule $\alpha_V\beta_8$ inhibitor test compound. Group 5 is administered the high dose of a test compound. Group 6 is administered 10 mg/kg of an anti-PD1 antibody (RMP1-14) and a medium dose of 150 mg/kg of a test compound. Group 7 is administered 10 mg/kg of an anti-PD1 antibody (RMP1-14) and a low dose of 50 mg/kg of a test compound. Group 8 is administered 10 mg/kg of an anti-PD1 antibody (RMP1-14) and 1 mg/kg of 6-(2-(tert-butyl)-4-(6-methylpyridin-2-yl)-1H-imidazol-5-yl)quinoxaline (SB 525334, CAS Reg. 356559-20-1), a 14.3 nM ALK5 inhibitor.

Individual subjects of various treatment Groups are assessed at 0, 3, and 7 days post-treatment.

The change in tumor volume for individual mice subjects and the median change in tumor volume among all subjects in each Group is assessed and shown.

pSMAD3/SMAD3 ratios for the corresponding Groups, a marker of TGFβ signaling, are assessed and shown.

Scores for interferon γ signaling for various treatment Groups as range and median are assessed and shown.

Scores for Granzyme B concentration for various treatment Groups as range and median are assessed and shown.

Scores for T cell activation for various treatment Groups as range and median are assessed and shown.

Example B4—Testing the Anti-Fibrotic Efficacy of Dual $\alpha_V\beta_6/\alpha_V\beta_1$ Inhibition in a Mouse Model of Biliary Atresia Genetically modified rotavirus strains will be injected into BALB/c pups to induce fibrosis, and the mice are monitored and studied, in procedures similar to those described in Mohanty et al., Hepatology 71:1316 (2020), herein incorporated by reference in its entirety. Starting at 2 weeks post injection of virus (21 days of life) pups will be administered one of the following: a testing compound, a known integrin inhibitor, a positive control, or vehicle as a negative control, by either subcutaneous or intraperitoneal injections. Mice will be tracked for symptoms of fibrosis with tissue/blood harvested at 4 weeks after viral injection (35 days of life). Samples will be analyzed by histology, serum chemistry, and gene expression. Sample type and respective aliquots and location will be taken as shown in Table B-2.

TABLE B-2

| Sample Type | Aliquots |
|---|---|
| Serum | 2 |
| Plasma (EDTA) for PK | 1 |
| Formalin-fixed liver tissue | 2 |
| Optional: Formalin-fixed extrahepatic bile ducts | 1 |
| Snap frozen tissue for hydroxyproline | 1 tube (consistent lobe) |
| Snap frozen tissue for gene expression/protein analysis | 1 tube with multiple pieces |

Example B5—Testing the Anti-Fibrotic Efficacy of One or More of $\alpha_V\beta_1$, $\alpha_V\beta_6$, or $\alpha_V\beta_8$ Inhibition in a Mouse Model of Ocular Fibrosis The effect of cataract surgery on lens cells is modelled in living mice by surgical removal of lens fiber cells as previously described (Mamuya et al., *J Cell Mol Med* 2014; 18:656-670; Desai et al., *Differentiation* 2010; 79: 111-9.29; Call et al., *Exp Eye Res.* 2004; 78:297-9; each of which is herein incorporated by reference in its entirety). Briefly, 3-month-old mice are anesthetized, a central corneal incision is made and the entire lens fiber cell mass is removed by a sharp forceps, leaving behind an intact lens capsule. The corneal incision is closed with a single 10-0 nylon corneal suture and normal saline is injected to inflate the eye back to its normal shape.

Mice are then randomized into a vehicle control group, three positive control groups, and two test groups per compound to be tested, with at least n=3 mice in each group.

Vehicle (e.g., phosphate buffered saline) is administered to the mice in the control group on day 0 post surgery.

Mice in the three positive control groups are administered a dose of an antibody on day 0 post surgery. The antibody is of one of $\alpha_V\beta_1$, $\alpha_V\beta_6$, and $\alpha_V\beta_8$, respectively, in vehicle, in an amount to deliver the antibody at an effective concentration in the lens capsule equivalent to the $IC_{90}$ concentration of the antibody for that integrin.

Mice in the two test groups are administered a dose in vehicle of each compound of the Examples to be tested on day 0 post surgery. Any compound of the examples can be tested, e.g., the compound of Example 1. The dose is in an amount to deliver an effective concentration of the compound in the lens capsule equivalent to the $IC_{50}$ or $IC_{90}$ concentration for the compound's most potent integrin binding among $\alpha_V\beta_1$, $\alpha_V\beta_6$, and $\alpha_V\beta_8$. For example, when testing a compound such as that of Example 1, the mice are administered doses of the compound of Example 1 in vehicle to deliver a concentration in the lens capsule equivalent to the $IC_{50}$ or $IC_{90}$ concentration of $\alpha_V\beta_6$, the integrin to which the compound of Example 1 has the most potent binding. This is repeated for each desired compound of the Examples.

Mice are killed at a time after surgery effective to provide observable fibrosis in untreated mice, e.g., 5 days. The eyes are isolated, sliced under cryogenic conditions, and subjected to quantitative confocal immunofluorescence analysis of fibrotic marker expression performed. The efficacy of each tested compound of the Examples is compared to the vehicle control and the positive $\alpha_V\beta_1$, $\alpha_V\beta_6$, and $\alpha_V\beta_8$ antibody controls.

Example B5-1—Characterizing the Dose Dependent Effect of Reference Compound A in Posterior Capsular Opacification in a Mouse Cataract Surgery Model Experimental Method Each group included 6 mice (3 male and 3 female). A first group was associated with a 0-hour post-cataract surgery (PCS) control. A second group received the control and the buffer and Compound A (3 mg/mL, 30 mg/mL, and 300 mg/mL) for a time period of 6 days via osmotic pump. Osmotic pump implantation occurred on Day 1, cataract surgery occurred on Day 2 and samples were harvested on Day 6. A third group received, via tail vain injection, the control and Compound C for a time period of 5 days PCS. The samples were then harvested. A fourth group received, via tail injection, a control, Compound D, for a time period of 5 days PCS. The samples were then harvested.

Figures 28A, 28B, 28C, 28D:
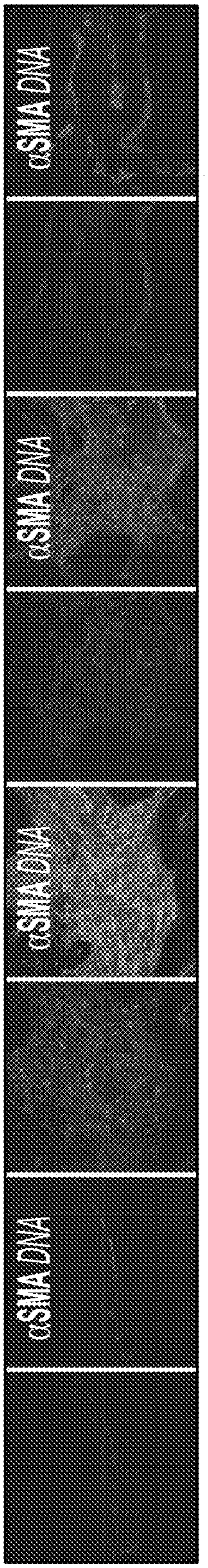
FIG. 28A depicts a first image (left) of pSMAD3 and a second image (right) of a fibrotic/EMT marker αSMA 0 hours post-cataract surgery (PCS) for Example B5-1.
FIG. 28B depicts a first image (left) of pSMAD3 and a second image (right) of a fibrotic/EMT marker αSMA associated with a control for Reference Compound A 5 days post-cataract surgery (PCS) for Example B5-1.
FIG. 28C depicts a first image (left) of pSMAD3 and a second image (right) of a fibrotic/EMT marker αSMA associated with 3 mg/mL of Reference Compound A 5 days post-cataract surgery (PCS) for Example B5-1.
FIG. 28D depicts a first image (left) of pSMAD3 and a second image (right) of a fibrotic/EMT marker αSMA associated with 30 mg/mL of Reference Compound A 5 days post-cataract surgery (PCS) for Example B5-1.
Figure 28E:
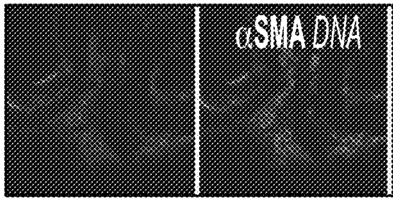
FIG. 28E depicts a first image (left) of pSMAD3 and a second image (right) of a fibrotic/EMT marker αSMA associated with 300 mg/mL of Reference Compound A 5 days post-cataract surgery (PCS) for Example B5-1.
Figure 28F:
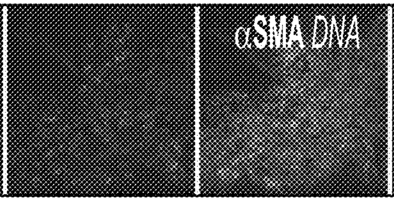
FIG. 28F depicts a first image (left) of pSMAD3 and a second image (right) of a fibrotic/EMT marker αSMA associated with a control for Compound C 5 days post-cataract surgery (PCS) of Example B5-1.
Figure 28G:
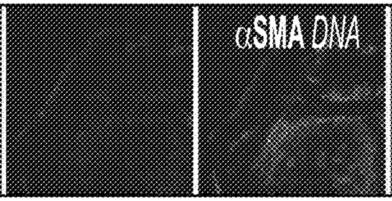
FIG. 28G depicts a first image (left) of pSMAD3 and a second image (right) of a fibrotic/EMT marker αSMA associated with Compound C 5 days post-cataract surgery (PCS) of Example B5-1.
Figure 28H:
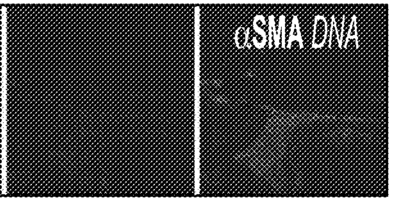
FIG. 28H depicts a first image (left) of pSMAD3 and a second image (right) of a fibrotic/EMT marker αSMA associated with Compound D 5 days post-cataract surgery (PCS) of Example B5-1.

FIG. 28A depicts a first image (left) of pSMAD3 and a second image (right) of a fibrotic/EMT marker αSMA 0 hours post-cataract surgery (PCS) for Example B5-1. FIG. 28B depicts a first image (left) of pSMAD3 and a second image (right) of a fibrotic/EMT marker αSMA associated with a control for Reference Compound A 5 days post-cataract surgery (PCS) for Example B5-1. FIG. 28C depicts a first image (left) of pSMAD3 and a second image (right) of a fibrotic/EMT marker αSMA associated with 3 mg/mL of Reference Compound A 5 days post-cataract surgery (PCS) for Example B5-1. FIG. 28D depicts a first image (left) of pSMAD3 and a second image (right) of a fibrotic/EMT marker αSMA associated with 30 mg/mL of Reference Compound A 5 days post-cataract surgery (PCS) for Example B5-1. FIG. 28E depicts a first image (left) of pSMAD3 and a second image (right) of a fibrotic/EMT marker αSMA associated with 300 mg/mL of Reference Compound A 5 days post-cataract surgery (PCS) for Example B5-1. FIG. 28F depicts a first image (left) of pSMAD3 and a second image (right) of a fibrotic/EMT marker αSMA associated with a control for Compound C 5 days post-cataract surgery (PCS) of Example B5-1. FIG. 28G depicts a first image (left) of pSMAD3 and a second image (right) of a fibrotic/EMT marker αSMA associated with Compound C 5 days post-cataract surgery (PCS) of Example B5-1. FIG. 28H depicts a first image (left) of pSMAD3 and a second image (right) of a fibrotic/EMT marker αSMA associated with Compound D 5 days post-cataract surgery (PCS) of Example B5-1.

Figure 28I:
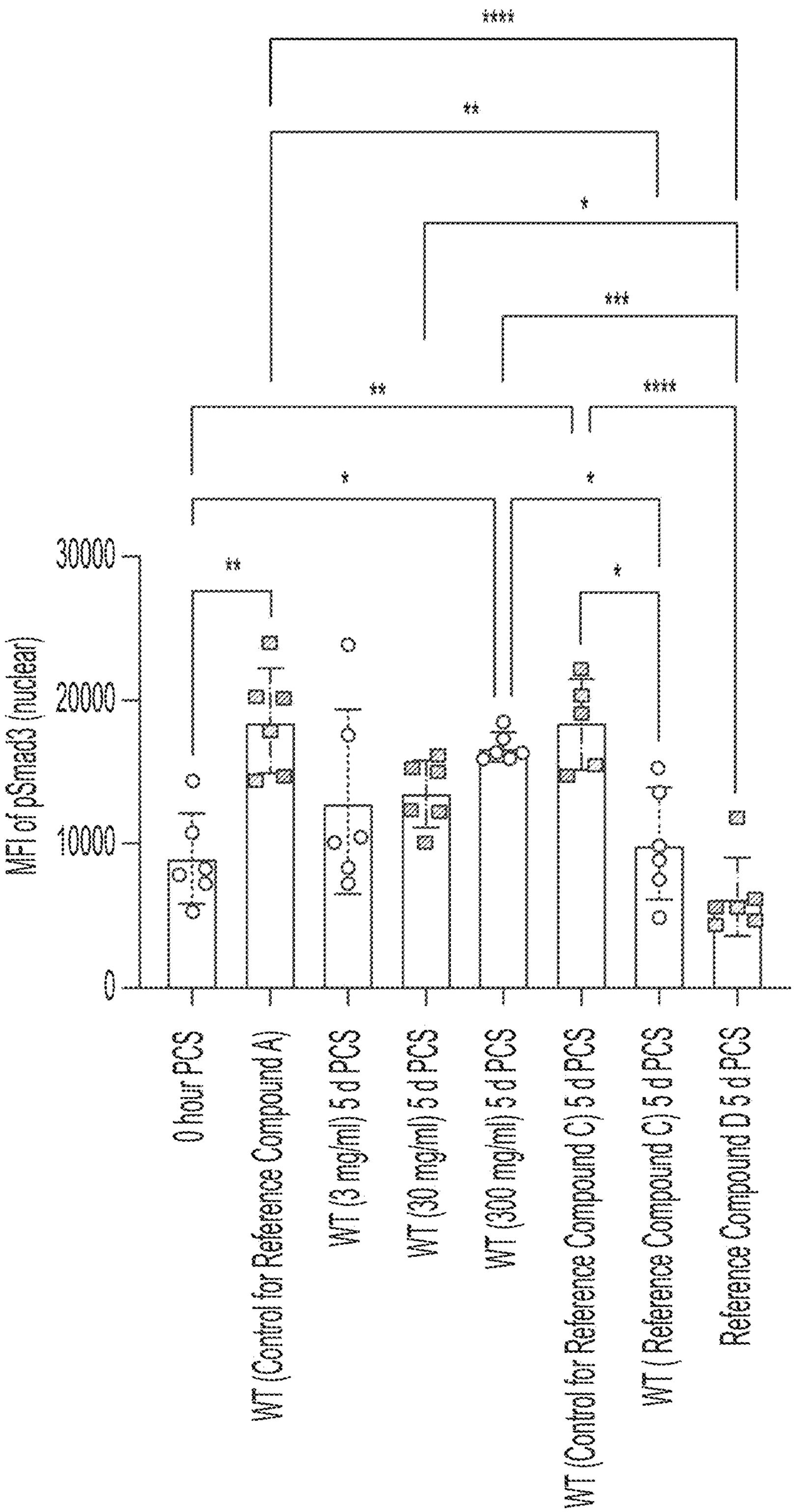
FIG. 28I depicts a graph measuring mean fluorescence intensity (MFI) of pSMAD3 for various amounts of Compound A, Compound C, and Compound D 5 days post-cataract surgery (PCS) in Example B5-1.
Figure 28J:
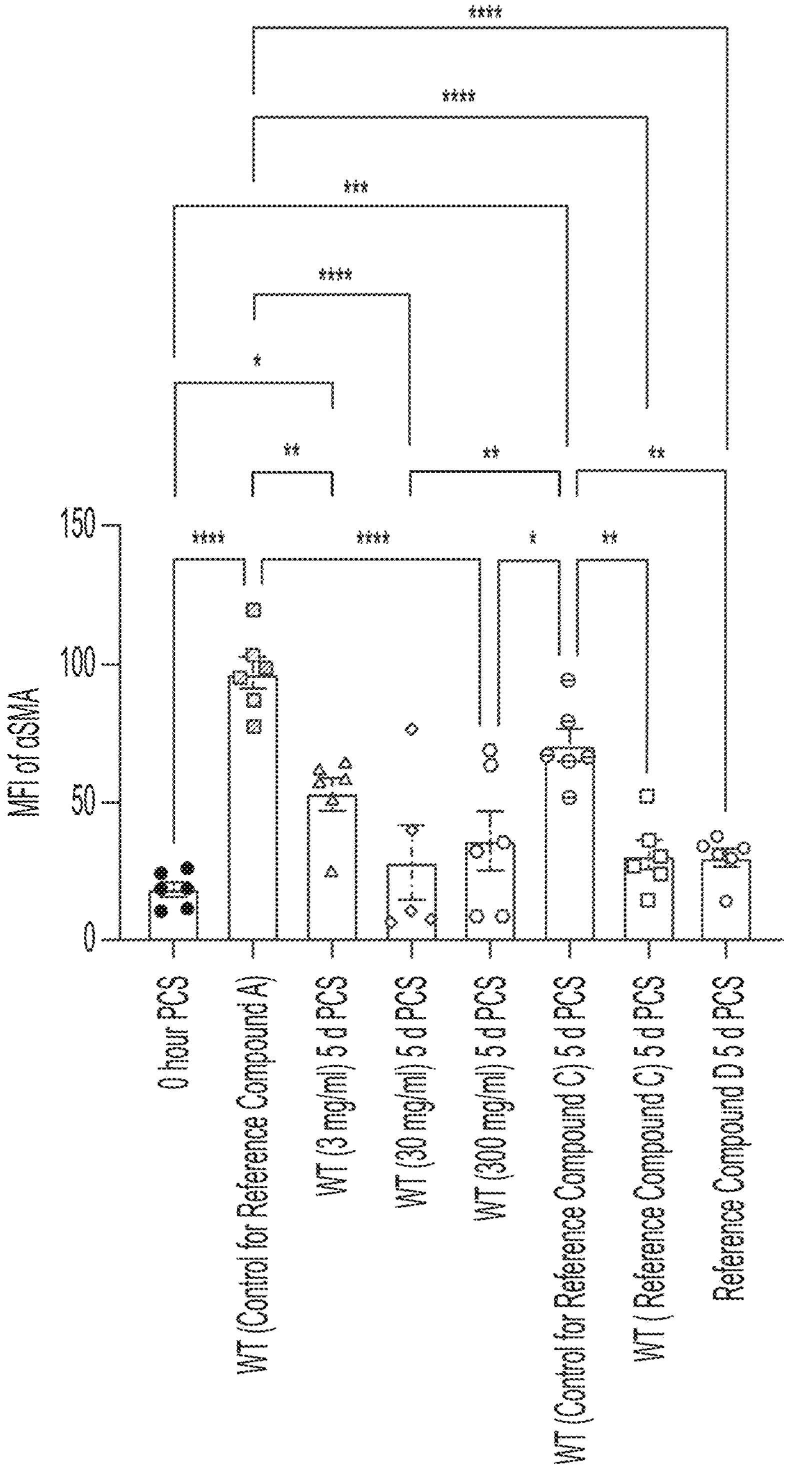
FIG. 28J depicts a graph measuring mean fluorescence intensity (MFI) of αSMA for various amounts of Compound A, Compound C, and Compound D 5 days post-cataract surgery (PCS) in Example B5-1.

FIG. 28I depicts a graph measuring mean fluorescence intensity (MFI) of pSMAD3 for various amounts of Compound A, Compound C, and Compound D 5 days post-cataract surgery (PCS) in Example B5-1. FIG. 28J depicts a graph measuring mean fluorescence intensity (MFI) of αSMA for various amounts of Compound A, Compound C, and Compound D 5 days post-cataract surgery (PCS) in Example B5-1.

Figures 29A, 29B, 29C, 29D:
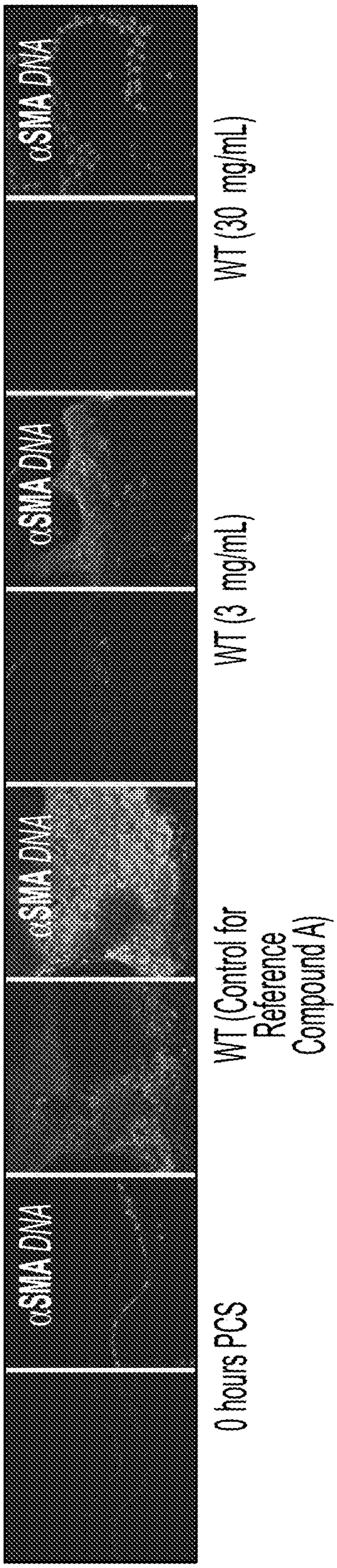
FIG. 29A depicts a first image (left) of a fibrotic marker Tenascin C and a second image (right) of a fibrotic/EMT marker αSMA 0 hours post-cataract surgery (PCS) for Example B5-1.
FIG. 29B depicts a first image (left) of a fibrotic marker Tenascin C and a second image (right) of a fibrotic/EMT marker αSMA associated with a control for Reference Compound A 5 days post-cataract surgery (PCS) for Example B5-1.
FIG. 29C depicts a first image (left) of a fibrotic marker Tenascin C and a second image (right) of a fibrotic/EMT marker αSMA associated with 3 mg/mL of Reference Compound A 5 days post-cataract surgery (PCS) for Example B5-1.
FIG. 29D depicts a first image (left) of a fibrotic marker Tenascin C and a second image (right) of a fibrotic/EMT marker αSMA associated with 30 mg/mL of Reference Compound A 5 days post-cataract surgery (PCS) for Example B5-1.
Figures 29E, 29F, 29G, 29H:
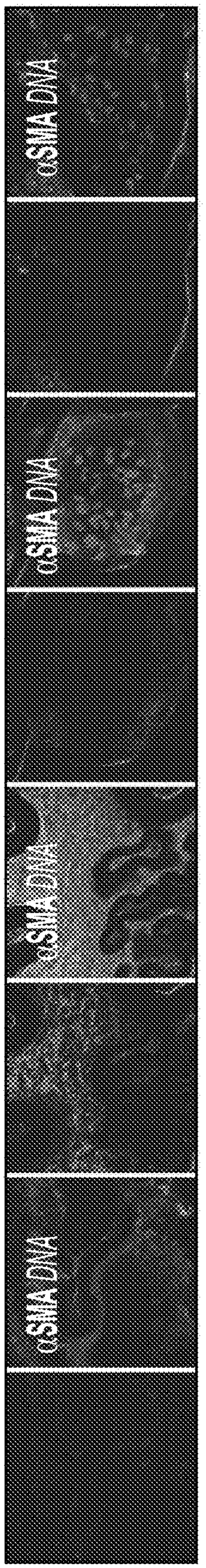
FIG. 29E depicts a first image (left) of a fibrotic marker Tenascin C and a second image (right) of a fibrotic/EMT marker αSMA associated with 300 mg/mL of Reference Compound A 5 days post-cataract surgery (PCS) for Example B5-1.
FIG. 29F depicts a first image (left) of a fibrotic marker Tenascin C and a second image (right) of a fibrotic/EMT marker αSMA associated with a control for Compound C 5 days post-cataract surgery (PCS) of Example B5-1.
FIG. 29G depicts a first image (left) of a fibrotic marker Tenascin C and a second image (right) of a fibrotic/EMT marker αSMA associated with Compound C 5 days post-cataract surgery (PCS) of Example B5-1.
FIG. 29H depicts a first image (left) of a fibrotic marker Tenascin C and a second image (right) of a fibrotic/EMT marker αSMA associated with Compound D 5 days post-cataract surgery (PCS) of Example B5-1.
Figure 29I:
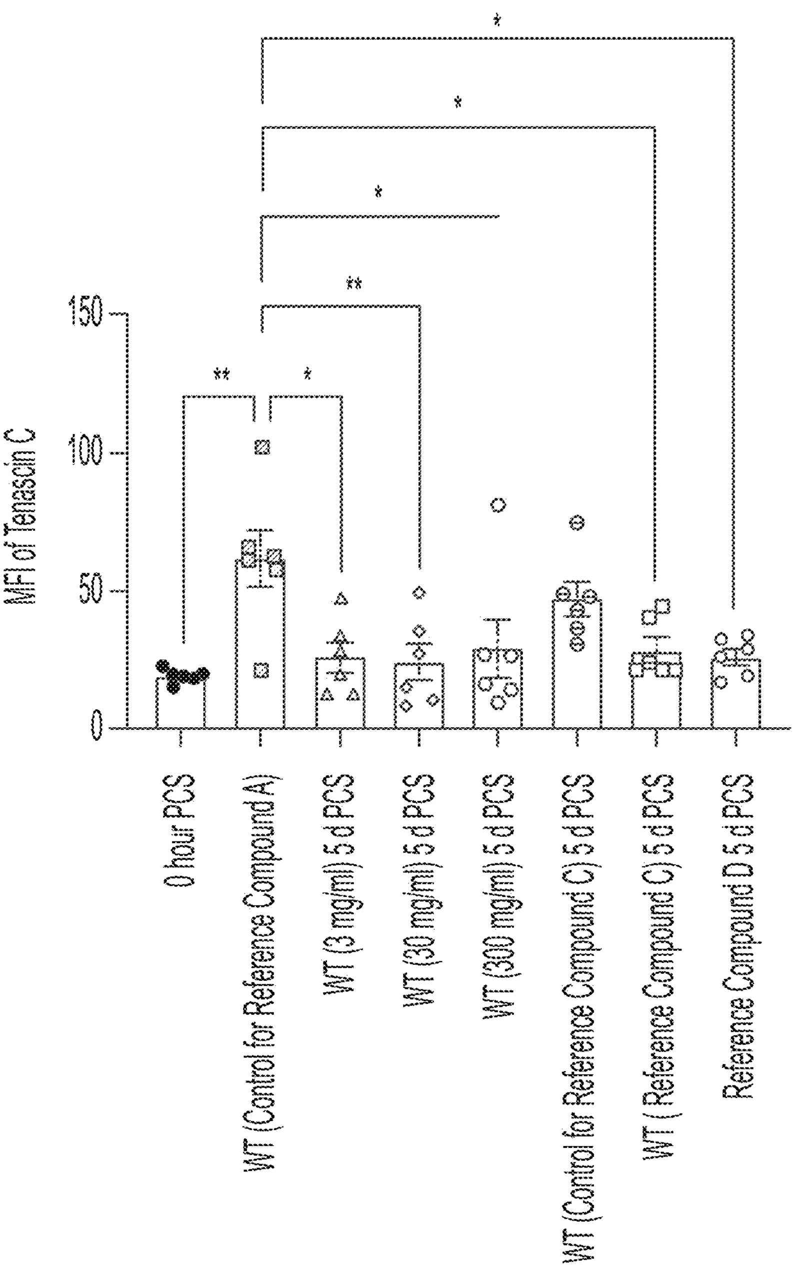
FIG. 29I depicts a graph measuring mean fluorescence intensity (MFI) of Tenascin C for various amounts of Compound A, Compound C, and Compound D 5 days post-cataract surgery (PCS) in Example B5-1.

FIG. 29A depicts a first image (left) of a fibrotic marker Tenascin C and a second image (right) of a fibrotic/EMT marker αSMA 0 hours post-cataract surgery (PCS) for Example B5-1. FIG. 29B depicts a first image (left) of a fibrotic marker Tenascin C and a second image (right) of a fibrotic/EMT marker αSMA associated with a control for Reference Compound A 5 days post-cataract surgery (PCS) for Example B5-1. FIG. 29C depicts a first image (left) of a fibrotic marker Tenascin C and a second image (right) of a fibrotic/EMT marker αSMA associated with 3 mg/mL of Reference Compound A 5 days post-cataract surgery (PCS) for Example B5-1. FIG. 29D depicts a first image (left) of a fibrotic marker Tenascin C and a second image (right) of a fibrotic/EMT marker αSMA associated with 30 mg/mL of Reference Compound A 5 days post-cataract surgery (PCS) for Example B5-1. FIG. 29E depicts a first image (left) of a fibrotic marker Tenascin C and a second image (right) of a fibrotic/EMT marker αSMA associated with 300 mg/mL of Reference Compound A 5 days post-cataract surgery (PCS) for Example B5-1. FIG. 29F depicts a first image (left) of a fibrotic marker Tenascin C and a second image (right) of a fibrotic/EMT marker αSMA associated with a control for Compound C 5 days post-cataract surgery (PCS) of Example B5-1. FIG. 29G depicts a first image (left) of a fibrotic marker Tenascin C and a second image (right) of a fibrotic/EMT marker αSMA associated with Compound C 5 days post-cataract surgery (PCS) of Example B5-1. FIG. 29H depicts a first image (left) of a fibrotic marker Tenascin C and a second image (right) of a fibrotic/EMT marker αSMA associated with Compound D 5 days post-cataract surgery (PCS) of Example B5-1. FIG. 29I depicts a graph measuring mean fluorescence intensity (MFI) of Tenascin C for various amounts of Compound A, Compound C, and Compound D 5 days post-cataract surgery (PCS) in Example B5-1.

Figure 30A:
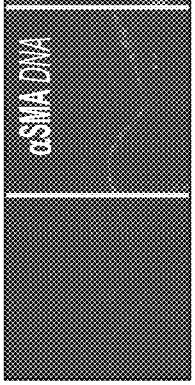
FIG. 30A depicts a first image (left) of a fibrotic marker fibronectin and a second image (right) of a fibrotic/EMT marker αSMA 0 hours post-cataract surgery (PCS) for Example B5-1.
Figure 30B:
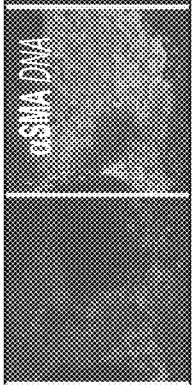
FIG. 30B depicts a first image (left) of a fibrotic marker fibronectin and a second image (right) of a fibrotic/EMT marker αSMA associated with a control for Reference Compound A 5 days post-cataract surgery (PCS) for Example B5-1.
Figure 30C:
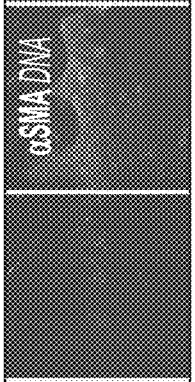
FIG. 30C depicts a first image (left) of a fibrotic marker fibronectin and a second image (right) of a fibrotic/EMT marker αSMA associated with 3 mg/mL of Reference Compound A 5 days post-cataract surgery (PCS) for Example B5-1.
Figure 30D:
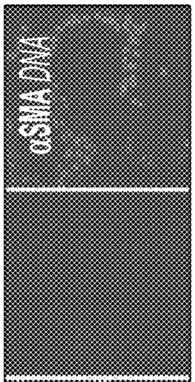
FIG. 30D depicts a first image (left) of a fibrotic marker fibronectin and a second image (right) of a fibrotic/EMT marker αSMA associated with 30 mg/mL of Reference Compound A 5 days post-cataract surgery (PCS) for Example B5-1.
Figure 30E:
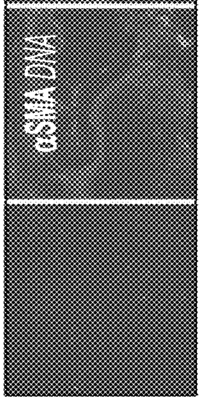
FIG. 30E depicts a first image (left) of a fibrotic marker fibronectin and a second image (right) of a fibrotic/EMT marker αSMA associated with 300 mg/mL of Reference Compound A 5 days post-cataract surgery (PCS) for Example B5-1.
Figure 30F:
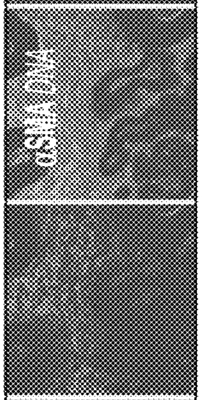
FIG. 30F depicts a first image (left) of a fibrotic marker fibronectin and a second image (right) of a fibrotic/EMT marker αSMA associated with a control for Compound C 5 days post-cataract surgery (PCS) of Example B5-1.
Figure 30G:
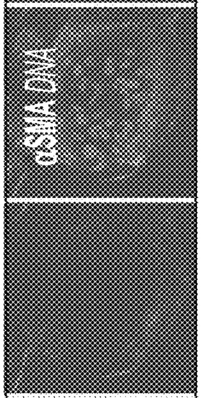
FIG. 30G depicts a first image (left) of a fibrotic marker fibronectin and a second image (right) of a fibrotic/EMT marker αSMA associated with Compound C 5 days post-cataract surgery (PCS) of Example B5-1.
Figure 30H:
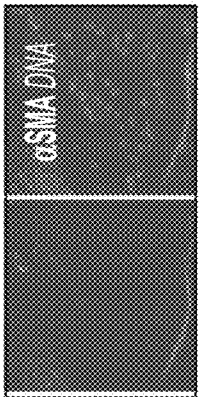
FIG. 30H depicts a first image (left) of a fibrotic marker fibronectin and a second image (right) of a fibrotic/EMT marker αSMA associated with Compound D 5 days post-cataract surgery (PCS) of Example B5-1.

FIG. 30A depicts a first image (left) of a fibrotic marker fibronectin and a second image (right) of a fibrotic/EMT marker αSMA 0 hours post-cataract surgery (PCS) for Example B5-1. FIG. 30B depicts a first image (left) of a fibrotic marker fibronectin and a second image (right) of a fibrotic/EMT marker αSMA associated with a control for Reference Compound A 5 days post-cataract surgery (PCS) for Example B5-1. FIG. 30C depicts a first image (left) of a fibrotic marker fibronectin and a second image (right) of a fibrotic/EMT marker αSMA associated with 3 mg/mL of Reference Compound A 5 days post-cataract surgery (PCS) for Example B5-1. FIG. 30D depicts a first image (left) of a fibrotic marker fibronectin and a second image (right) of a fibrotic/EMT marker αSMA associated with 30 mg/mL of Reference Compound A 5 days post-cataract surgery (PCS) for Example B5-1. FIG. 30E depicts a first image (left) of a fibrotic marker fibronectin and a second image (right) of a fibrotic/EMT marker αSMA associated with 300 mg/mL of Reference Compound A 5 days post-cataract surgery (PCS) for Example B5-1. FIG. 30F depicts a first image (left) of a fibrotic marker fibronectin and a second image (right) of a fibrotic/EMT marker αSMA associated with a control for Compound C 5 days post-cataract surgery (PCS) of Example B5-1. FIG. 30G depicts a first image (left) of a fibrotic marker fibronectin and a second image (right) of a fibrotic/EMT marker αSMA associated with Compound C 5 days post-cataract surgery (PCS) of Example B5-1. FIG. 30H depicts a first image (left) of a fibrotic marker fibronectin and a second image (right) of a fibrotic/EMT marker αSMA associated with Compound D 5 days post-cataract surgery (PCS) of Example B5-1.

Figure 30I:
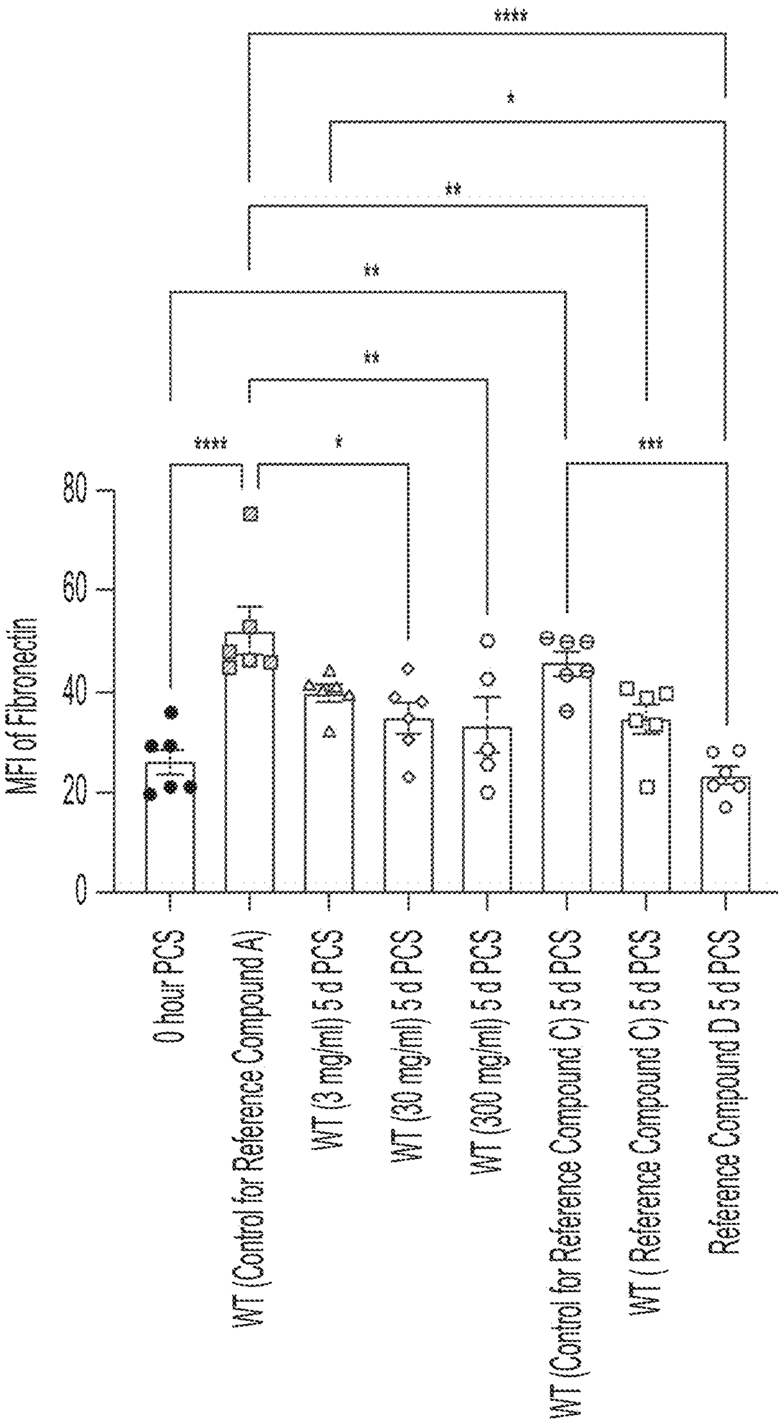
FIG. 30I depicts a graph measuring mean fluorescence intensity (MFI) of fibronectin for various amounts of Compound A, Compound C, and Compound D 5 days post-cataract surgery (PCS) in Example B5-1.
Figure 30J:
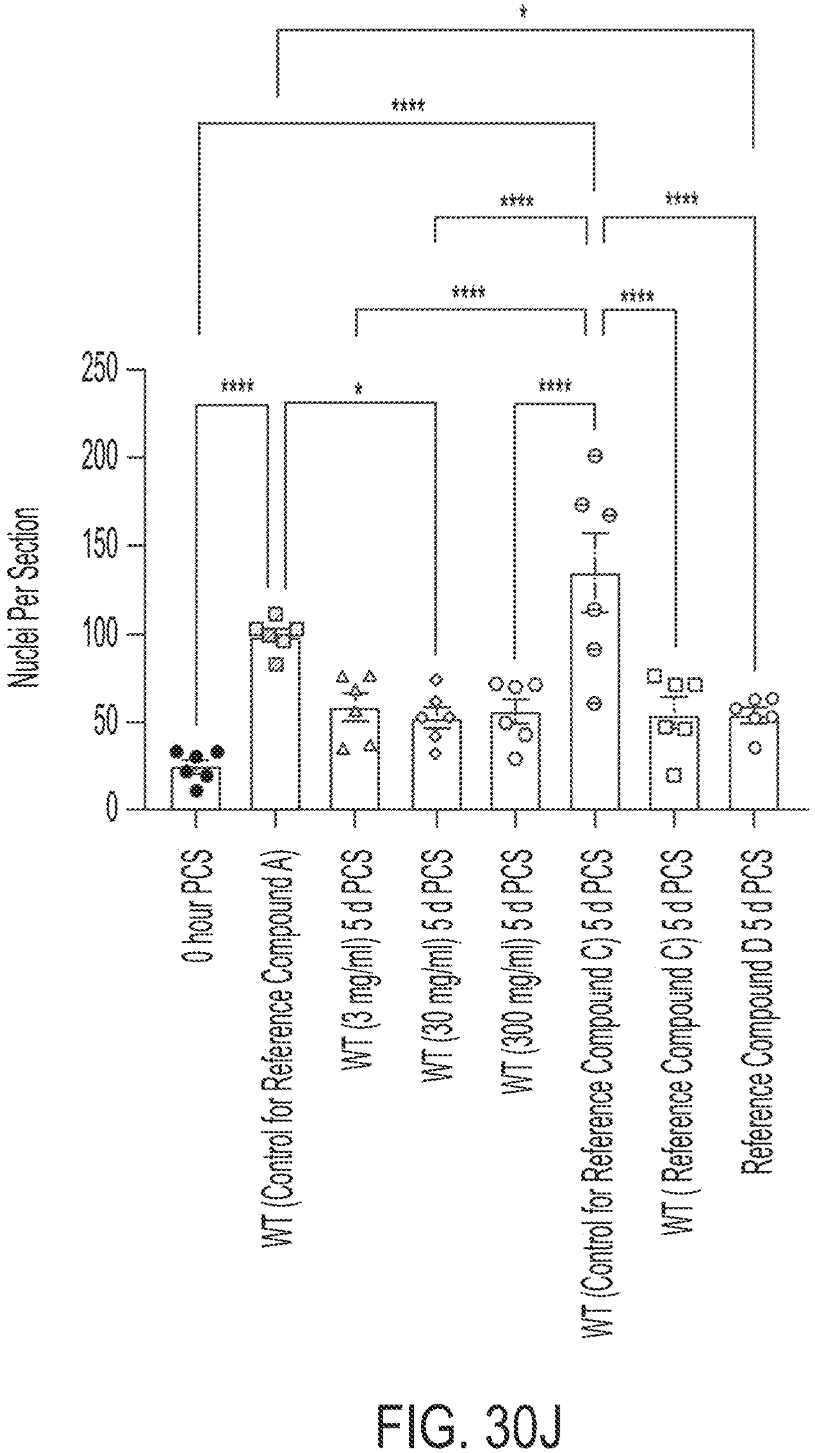
FIG. 30J depicts a graph measuring nuclei per section for various amounts of Compound A, Compound C, and Compound D 5 days post-cataract surgery (PCS) in Example B5-1.

FIG. 30I depicts a graph measuring mean fluorescence intensity (MFI) of fibronectin for various amounts of Compound A, Compound C, and Compound D 5 days post-cataract surgery (PCS) in Example B5-1. FIG. 30J depicts a graph measuring nuclei per section for various amounts of Compound A, Compound C, and Compound D 5 days post-cataract surgery (PCS) in Example B5-1.

Example B6—Characterization of the Therapeutic Impact of Compound 39 in Combination with Anti PD-1 in Syngeneic Cancer Models Experimental Methods The therapeutic impact of Compound 39 of the examples in combination with anti PD-1 was studied for several xenograft mouse models, as shown in Table B-3. For each model, four dosing regimens were studied, using a group size of 10 mice per dosing regimen per model, and a total of 40 mice per model.

Animals were prepared for injection using standard approved anesthesia. Mice were shaved and tumor cells as indicated in Table B-3 were subcutaneously implanted in a 100 μl cell suspension that was subcutaneously injected into the front/rear flank of each mouse (as indicated in Table B-3).

TABLE B-3

| Murine Models | | | | | |
|---|---|---|---|---|---|
| Model | Cancer Type | Inoculum size (cells) | Inoculation site | Gender | Strain |
| A20 | Lymphoma | 500,000 | Rear flank | Female | Balb/c |
| CT26 | Colon | 500,000 | Rear flank | Female | Balb/c |
| EMT6 | Breast | 500,000 | Front flank | Female | Balb/c |
| B16F10 | Melanoma | 200,000 | Rear flank | Female | C57BL/6 |
| Pan02 | Pancreatic | 3 million | Front flank | Female | C57BL/6 |
| RM-1 | Prostate | 1 million | Rear flank | Male | C57BL/6 |

Palpable tumors (ranging from 50-100 $mm^3$) were randomized into groups and treated with indicated compounds according to schema outlined in Table B-4. Compound 39 was administered in a solution containing 10% v/v ethanol, 70% w/v propylene glycol, and 20% v/v PBS and administered to mice via osmotic Alzet-2002 minipumps at a dose of 144 mg/kg body weight over the duration of 28 days (at a rate of 0.5 μL/h; charge replaced on Day 14). The mAbs, anti-mPD-1 and anti-$\alpha_v\beta_8$, were each administered in PBS by intraperitoneal injection at a dose of 10 mg/kg body weight twice a week (for 2 weeks). There was no dosing holiday. Dietary supplements were uniform for all animals in the same group. The mPD-1 (CD279) Ab was purchased from Bio X Cell Inc. (West Lebanon, NH). The anti-$\alpha_v\beta_8$ antibody was synthesized and manufactured by GenScript Biotech Corporation (Piscataway, NJ). The rat immunoglobulin G2a (IgG2A) antibody was purchased by Crown Bio Inc.

TABLE B-4

| Study Groups and Dosing Regimen | | | | | | |
|---|---|---|---|---|---|---|
| Group | N | Treatment | Dose Route | Dosing Frequency & Duration | Dose Level (mg/kg) | Dose Volume (mL/kg) |
| 1 | 10 | Rat IgG2a | IP | BIW x 21 days | 10 | 10 |
| | | Vehicle | SC via pump | 0.5 μL/hr x 28 days | — | 0.48 |
| 2 | 10 | Anti-mPD1 | IP | BIW x 21 days | 10 | 10 |
| | | Vehicle | SC via pump | 0.5 μL/hr x 28 days | — | 0.48 |
| 3 | 10 | Anti-mPD1 | IP | BIW x 21 days | 10 | 10 |
| | | Compound 39 | SC via pump | 0.5 μL/hr x 28 days | 144 | 0.48 |
| 4 | 10 | Anti-mPD1 | IP | BIW x 21 days | 10 | 10 |
| | | Anti-integrin mAb (ADWA11) | IP | BIW x 21 days | 10 | 10 |

Animals were monitored weekly for changes in tumor volume. Tumors were measured at least once a week using calipers. Tumor volume was calculated using the equation: (longest diameter*shortest diameter$^2$)/2. Additionally, body weight of mice and any change in behavior/appearance were monitored twice a week for any signs of discomfort/toxicity.

The study was terminated four weeks after the first dose or when the tumor sizes reached greater than 3000 $mm^3$, whichever was first. Mice were euthanized and tumors were collected. Half of the tumor was snap frozen in liquid nitrogen, and the other half was fixed in formalin.

Tumor tissues (50 to 80 mg) were homogenized using metal beads in pre-chilled RINO screw cap tubes, using lysis matrix (MP Lysing Matrix S [⅛"], 2 mL Tube MP Biomedical Cat #116925100) on MP Fast Prep 24 instrument. Tumor RNA extraction from the tumor homogenate used the Ambion Purelink, RNA kit (Cat #12183018A) according to the manufacturers' protocol. A total of 100 ng RNA was used for the Nanostring analysis of the immuno-oncology and fibrosis panel, and 300 ng RNA was used for the analysis of the integrin panel. RNA was hybridized to gene expression Plexset according to the manufacturers' protocol. Hybridized reactions were read on nCounter MAX (Nanostring), and data were analyzed using nCounter software.

Formalin (10%) fixed tissues were sent to Histowiz for paraffin embedding and sectioning. Tissue sections were stained for hematoxylin and eosin and immunostained for CD8, CD4, and FoxP3, which are specific membrane markers for cytotoxic, helper, and regulator T cells, respectively, and immunostained for granzyme B (a marker for activated cytotoxic T cells and program death-ligand 1 [PD-L1]). Table B-5 lists the catalog numbers of the antibodies used in the immunohistochemical (IHC) studies. Quantification of staining was done using the HALO software package (Indica Labs, Albaquerque, NM).

TABLE B-5

| Antibody | Catalogue number | Manufacturer |
|---|---|---|
| CD8 | CST98941 | Cell-signaling Technology |
| CD4 | ab183685 | AbCam |
| FoxP3 | CST12653 | Cell-signaling Technology |
| Granzyme B | ab4059 | AbCam |
| PD-L1 | CST64988 | Cell-signaling Technology |

Results

Compound 39+Anti-mPD-1 Reduces EMT6 Tumor Growth.

Figure 13:
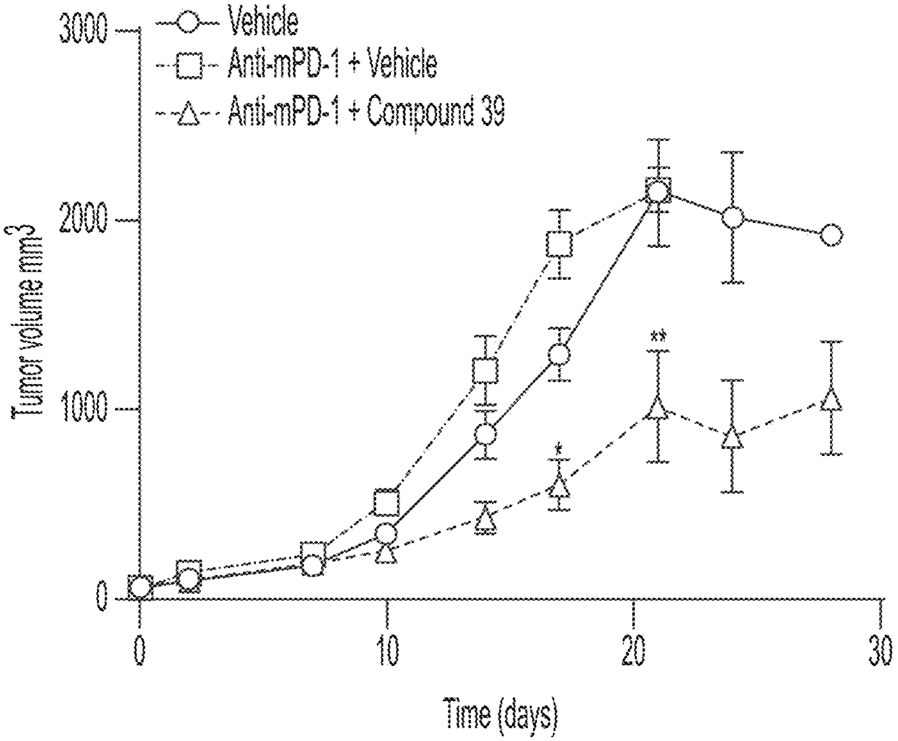
FIG. 13 is a graph showing tumor volume as a function of time for mice with EMT6 tumors in the study of Example B6. Compared to vehicle, treatment with Compound 39+anti-mPD-1 significantly (*$p<0.05$, one-way ANOVA) reduces tumor growth of EMT6 tumors by Day 21 of treatment. Tumors were monitored for an additional 7 days, up to 28 days. Bars: standard error of mean.
Figure 31:
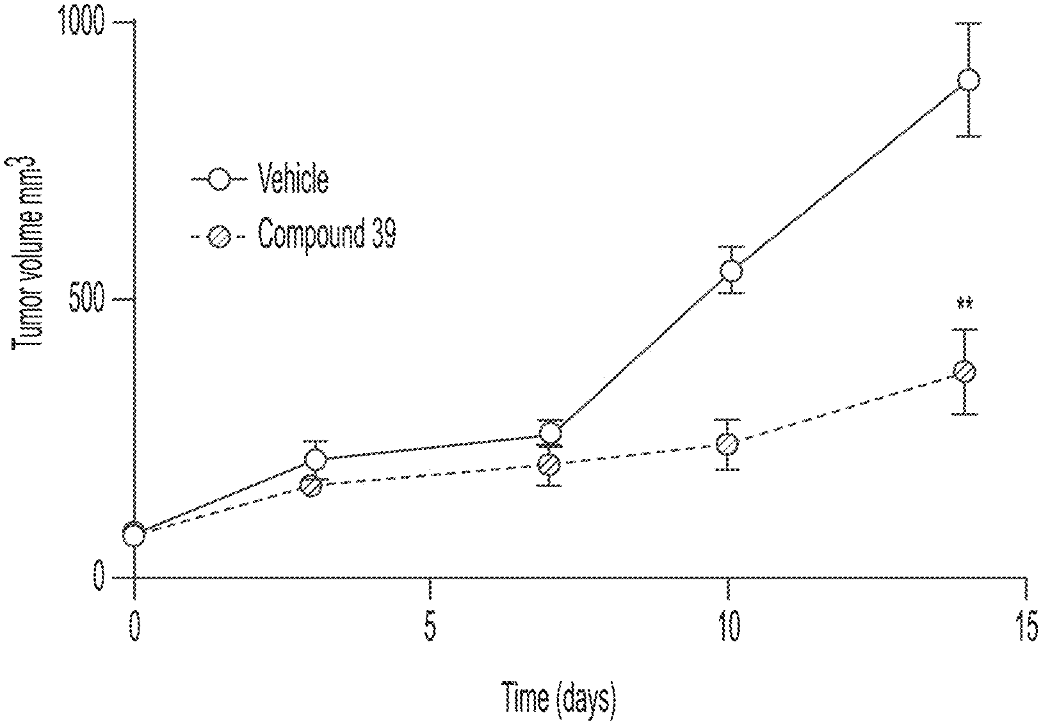
FIG. 31 depicts a graph depicting tumor growth inhibition in EMT6 tumors for a vehicle and Compound 39, associated with Example B6.
Figure 35:
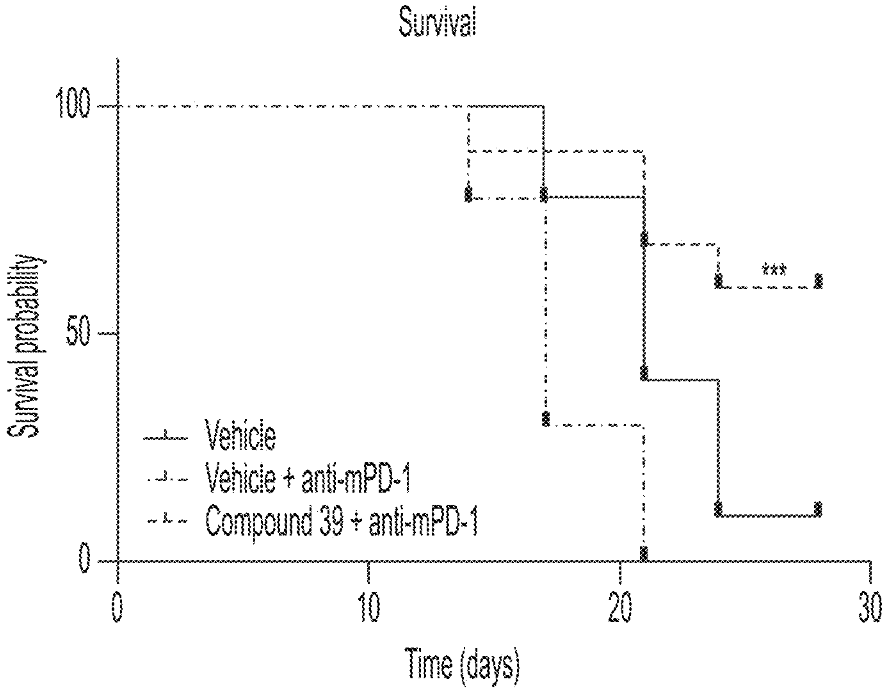

In mice with EMT6 tumors, the mean tumor volumes of mice treated with Compound 39+anti-mPD-1 were significantly lower (mean tumor volume 1017.96±293.26 $mm^3$) than the tumor volumes of mice treated with vehicle (mean tumor volume 2145.39±287.13 $mm^3$) or vehicle+anti-PD1 (mean tumor volume 2162.10±117.49 $mm^3$) (FIG. 13) after day 21 of treatment. Tumors were further monitored until day 28, and tumor volumes of the Compound 39+anti-mPD-1 treated group remained lower until end of study (for doses, see Methods). FIG. 31 depicts a graph depicting tumor growth inhibition in EMT6 tumors for a vehicle and Compound 39, associated with Example B6. FIG. 35 depicts a survival curve displaying the survival probability over a time period of 30 days for vehicle, vehicle+anti-mPD-1, and Compound 39+anti-mPD-1.

Compound 39+Anti-mPD-1 Treatment Results in Increased $CD8^+$ T Cells Recruitment in EMT6 Tumors.

Figure 14A:
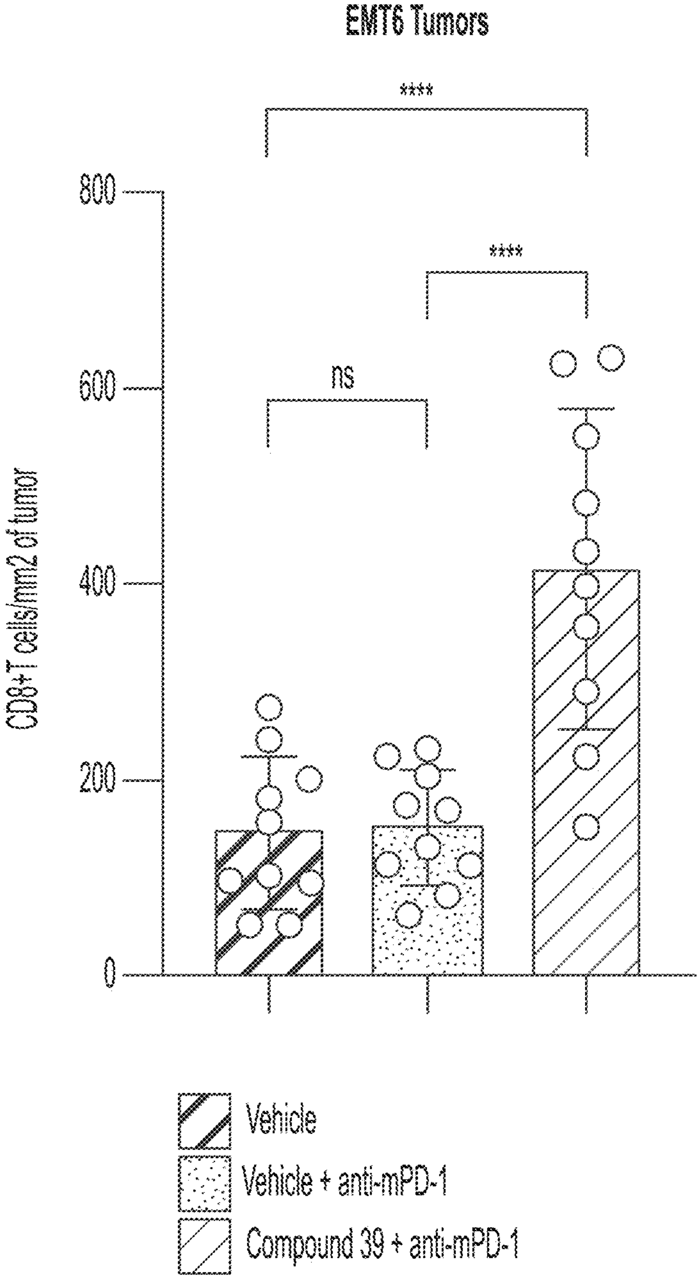
FIG. 14A is a bar graph comparing $CD8^+$ T cell density in EMT6 tumors for different dosing regimens in the study of Example B6. Treatment with Compound 39+anti-mPD-1 significantly increases the number of $CD8^+$ T cells in tumors. Bars: ±standard deviation; n=10 in each group; ns: not significant. ****=$p<0.0001$ (by one-way ANOVA)
Figure 14B:
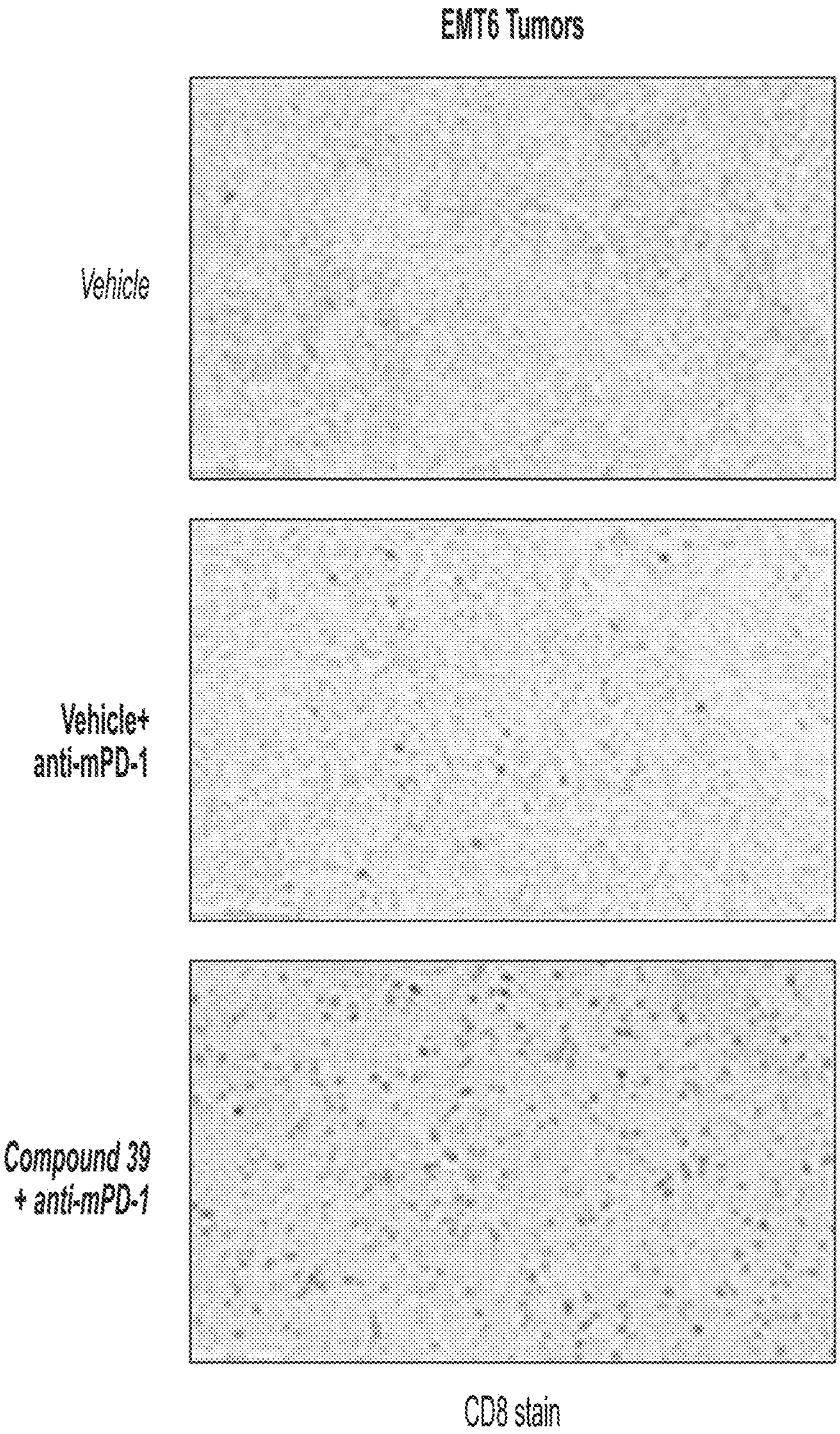
FIG. 14B shows CD8 stains of EMT6 tumors subjected to different dosing regimens in the study of Example B6. Treatment with Compound 39+anti-mPD-1 significantly increases the number of $CD8^+$ T cells in tumors.
Figure 14C:
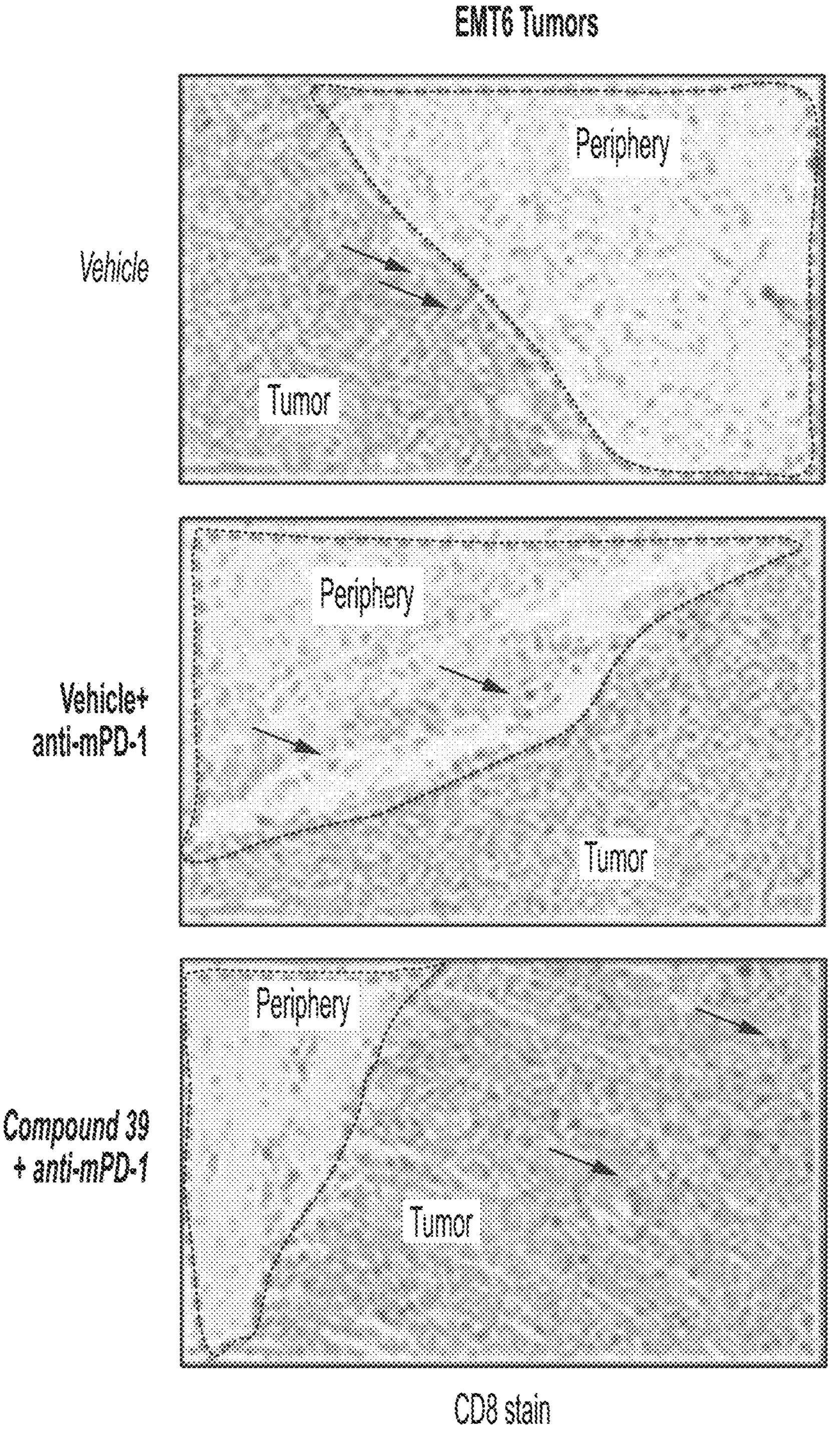
FIG. 14C shows CD8 stains of EMT6 tumors subjected to different dosing regimens in the study of Example B6. $CD8^+$ T cells are aligned on the periphery of tumors treated with vehicle or vehicle+anti-mPD-1 but are within tumors treated with Compound 39+anti-mPD-1 and in high numbers.
Figure 32A:
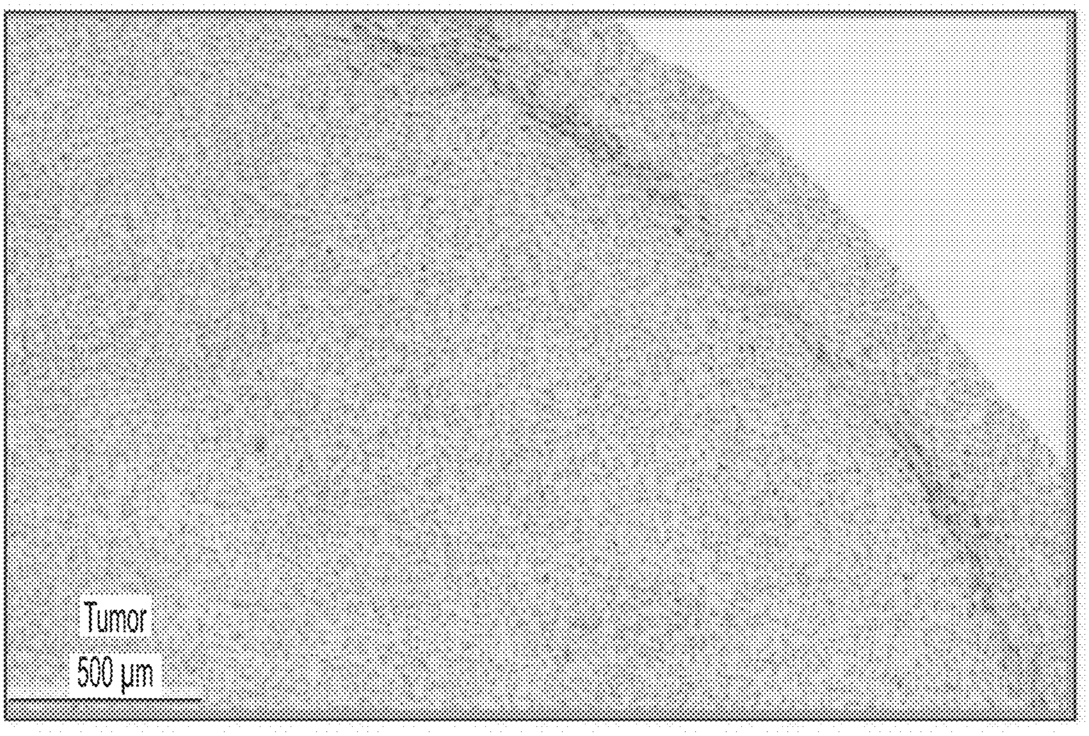
FIG. 32A depicts an image of $CD8^+$ T cells associated with a tumor for a vehicle, associated with Example B6.
Figure 32B:
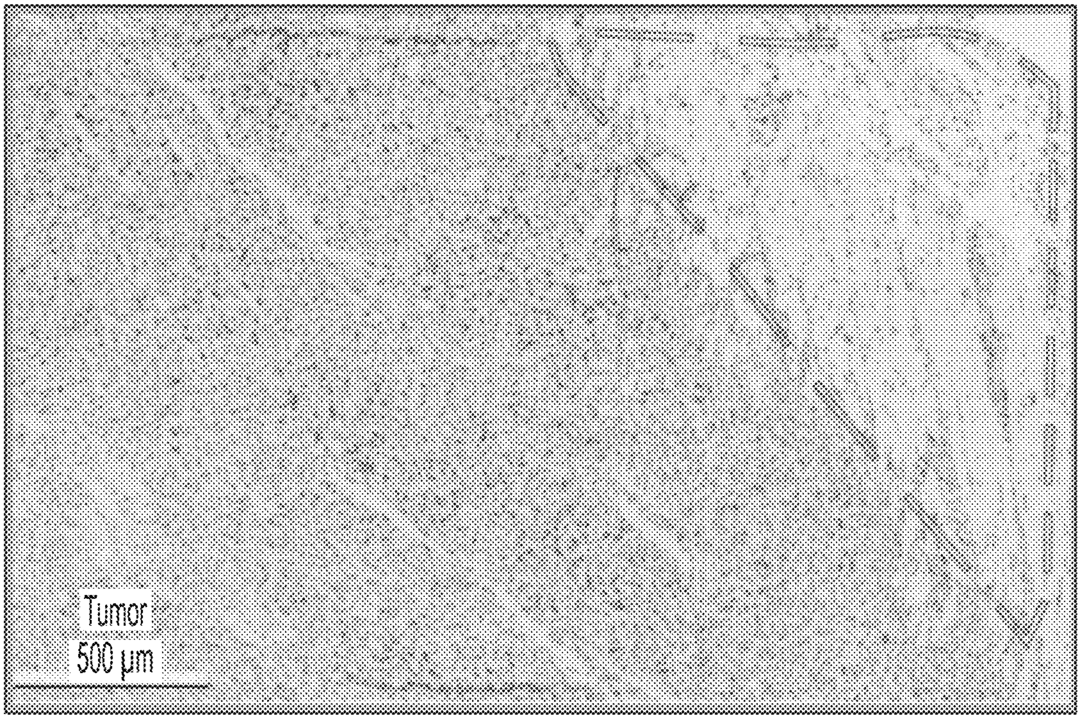
FIG. 32B depicts an image of $CD8^+$ T cells associated with a tumor for Compound 39, associated with Example B6.
Figure 32C:
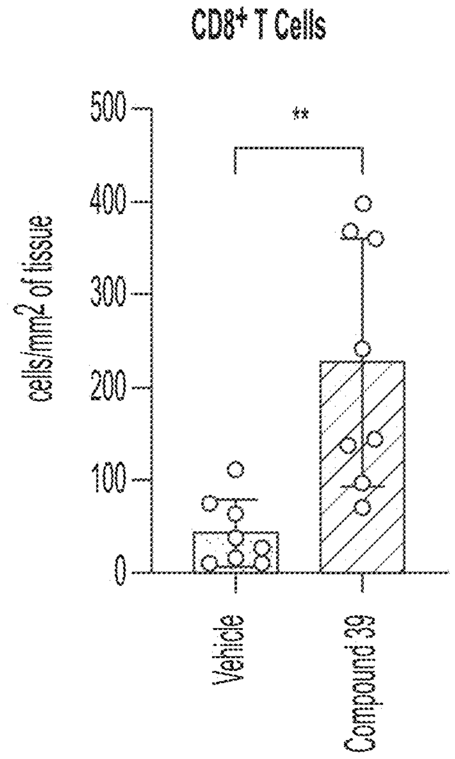
FIG. 32C depicts a graph showing $CD8^+$ T cells/$mm^2$ of tissue for a vehicle and for Compound 39, associated with Example B6.

In mice with EMT6 tumors, those treated with Compound 39+anti-mPD-1 showed higher infiltration and numbers of $CD8^+$ T cells within the tumors (mean $CD8^+$ T cell count 414.86±163.27/mm$^2$ of tumor tissue) than those treated with vehicle (mean $CD8^+$ T cell count 145.79±77.70/mm$^2$ of tumor tissue) or vehicle+anti-mPD-1 (mean $CD8^+$ T cell count 151.82±59.27/mm$^2$ of tumor tissue) (FIG. 14A, 14B; $CD8^+$ T cells are seen as brown stained cells). The $CD8^+$ T cells lined the periphery of the tumors of mice treated with vehicle or vehicle+anti-mPD-1 and were few (FIG. 14C, upper and middle panel, red dotted line shows the demarcation of tumor and periphery), indicating an immune excluded phenotype of EMT6 tumors. In contrast, $CD8^+$ T cells were observed to have migrated into the tumors of mice treated with Compound 39+anti-mPD-1 (FIG. 14C, bottom panel) and to be greater in number. These observations indicate that addition of Compound 39 to anti-mPD-1 treatment converts an immune excluding tumor into a tumor with increased infiltration of cytotoxic $CD8^+$ T cells. FIG. 32A depicts an image of $CD8^+$ T cells associated with a tumor for a vehicle, FIG. 32B depicts an image of $CD8^+$ T cells associated with a tumor for Compound 39, and FIG. 32C depicts a graph showing $CD8^+$ T cells/mm$^2$ of tissue for a vehicle and for Compound 39.

Compound 39+Anti-mPD-1 Treatment has Similar Anti-Tumor Effect as Treatment with Anti-$\alpha_V\beta_8$+Anti-mPD-1 Treatment in EMT6 Tumors.

Figure 15A:
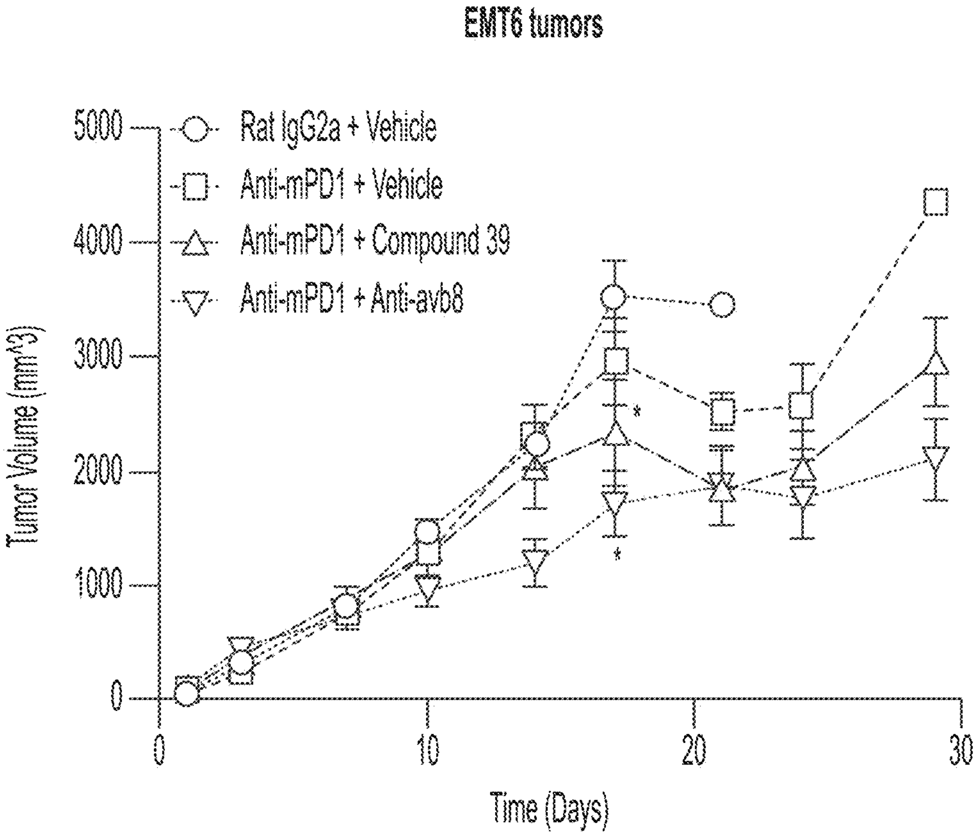
FIG. 15A is a graph showing tumor volume as a function of time for mice with EMT6 tumors in the study of Example B6. Compound 39+anti-mPD-1 treatment significantly impairs EMT6 tumor growth (*$p<0.05$ by two-way ANOVA compared to vehicle+Rat IgG2A). Bars in growth curves: ±standard error of mean. N (number of mice)=9 in vehicle+anti-mPD-1, and n=10 mice in Compound 39+anti-mPD-1 group.

The efficacy of Compound 39 in tumor growth reduction was compared with that of a mAb targeting $\alpha_V\beta_8$ (anti-$\alpha_V\beta_8$). Like the Compound 39+anti-mPD-1 treatment, anti-$\alpha_V\beta_8$+anti-mPD-1 treatment of mice with EMT6 tumors reduced growth and volumes of tumors comparted with EMT6 tumors from mice treated with vehicle or vehicle+anti-mPD-1 treatment (FIG. 15A).

Compound 39+Anti-mPD-1 Treatment was Similar in Reducing the Tumor Growth Compared to Anti-$\alpha_V\beta_8$ Treatment+Anti-mPD-1.

Figure 15B:
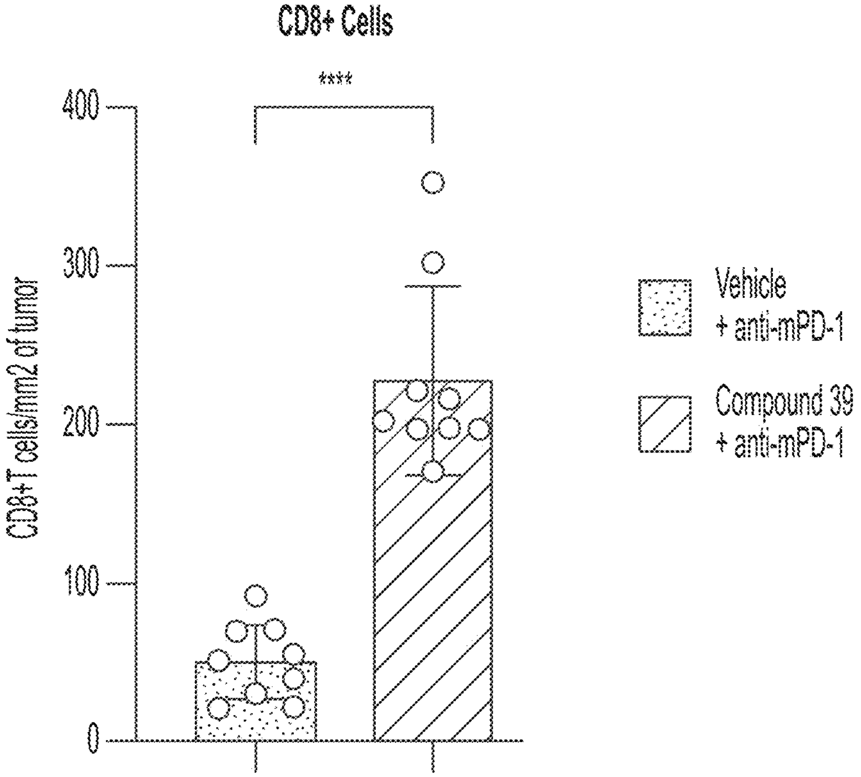
FIG. 15B is a bar graph comparing $CD8^+$ T cell density in EMT6 tumors between different dosing regimens in the study of Example B6. Compound 39+anti-mPD-1 treatment causes a significantly more $CD8^+$ T cell infiltration. Bars on histograms: ±standard deviation; ****=$p<0.0001$ by student's t test (unpaired, two tailed). N (number of mice)=9 in vehicle+anti-mPD-1, and n=10 mice in Compound 39+anti-mPD-1 group.
Figure 15C:
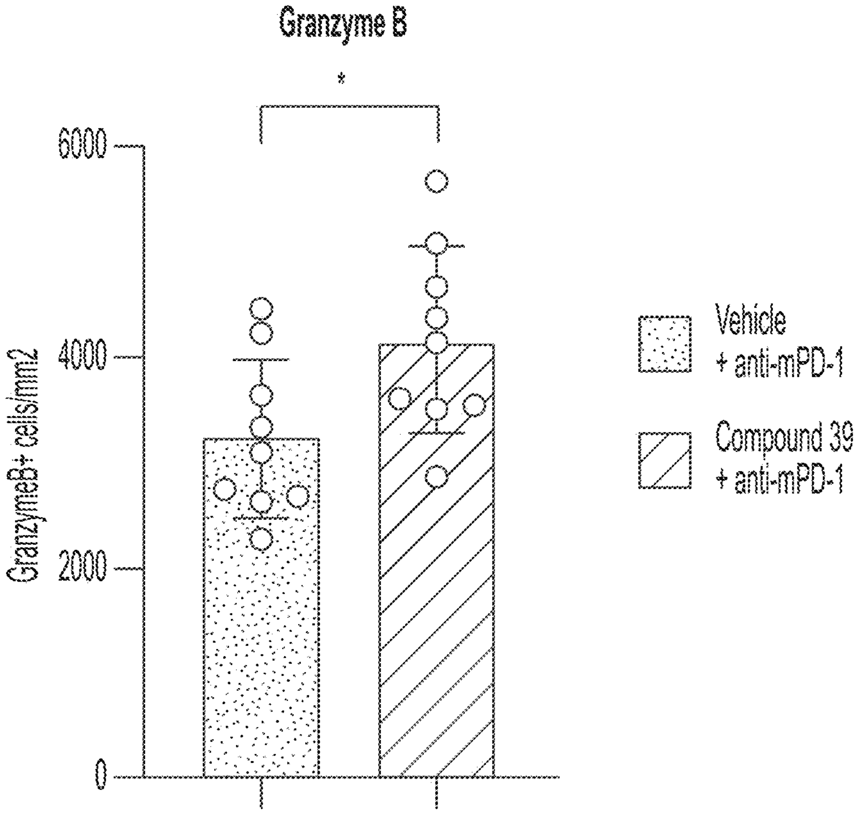
FIG. 15C is a bar graph comparing granzyme $B^+$ cell density in EMT6 tumors between different dosing regimens in the study of Example B6. Compound 39+anti-mPD-1 treatment causes an increased number of granzyme B positive cells. Bars on histograms: ±standard deviation; *$p=0.0291$ for Granzyme B by student's t test (unpaired, two tailed). N (number of mice)=9 in vehicle+anti-mPD-1, and n=10 mice in Compound 39+anti-mPD-1 group.

As observed by comparison of immune-staining shown in FIG. 14, the mean $CD8^+$ T cell count was significantly greater in EMT6 tumors from mice treated with Compound 39+anti-mPD-1 (mean $CD8^+$ T cell count 228.6±59.3/mm$^2$ of tumor tissue) than the mean count in EMT6 tumors from mice treated with vehicle+anti-mPD1 (mean $CD8^+$ T cell count 50.28±24.21/mm$^2$ of tumor tissue) (FIG. 15B). This correlated with significantly greater mean count of cells positively immunostained for the cytolytic enzyme, granzyme B, which is responsible for tumor cell lysis and killing (mean cell count 4158±884.56/mm$^2$ of tumor tissue in the Compound 39+anti-mPD-1 treatment arm, compared to 3230±752.22/mm$^2$ of tumor tissue in vehicle+anti-mPD-1 treatment arm) (FIG. 15C).

Figure 15D:
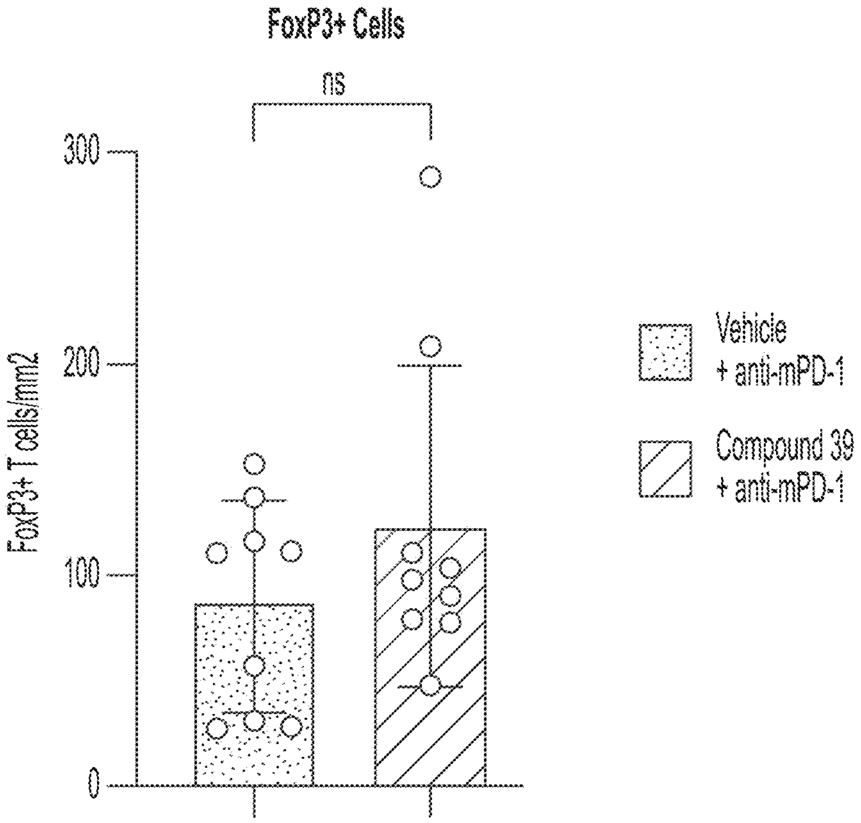
FIG. 15D is a bar graph comparing $FoxP3^+$ cell density in EMT6 tumors between different dosing regimens in the study of Example B6. Compound 39+anti-mPD-1 treatment causes no difference in infiltration of Treg cells (=$FoxP3^+$ cells). Bars on histograms: ±standard deviation; ns: not significant (by student's t test). N (number of mice)=9 in vehicle+anti-mPD-1, and n=10 mice in Compound 39+anti-mPD-1 group.
Figure 15E:
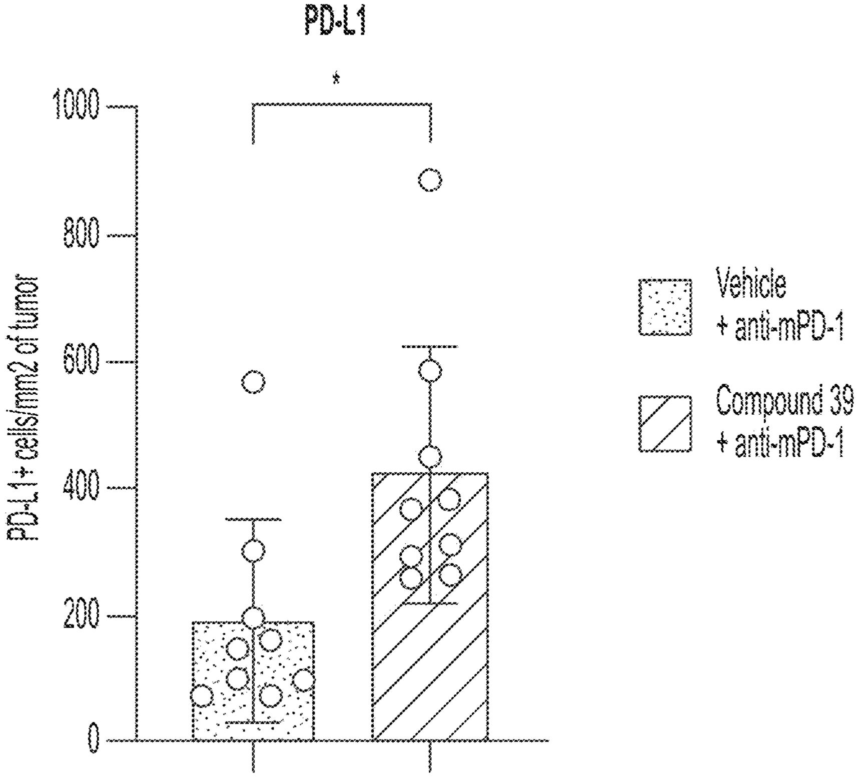
FIG. 15E is a bar graph comparing PD-$L1^+$ cell density in EMT6 tumors between different dosing regimens in the study of Example B6. Compound 39+anti-mPD-1 treatment causes an increased PD-L1 expression than vehicle+anti-mPD-1 treatment. Bars on histograms: ±standard deviation; *$p=0.0169$ for PD-L1 by student's t test (unpaired, two tailed). N (number of mice)=9 in vehicle+anti-mPD-1, and n=10 mice in Compound 39+anti-mPD-1 group.

There was greater expression of PD-L1 in EMT6 tumors cells of mice treated with Compound 39+anti-mPD-1 (Mean cell count 397.18±202.09/mm$^2$ of tumor tissue) compared to EMT6 tumors cells of mice treated with vehicle+anti-mPD-1 (mean cell count 190.12±158.94/mm$^2$ of tumor tissue) (FIG. 15E), which may explain an enhanced response of EMT6 tumors to anti-mPD-1 when combined with the Compound 39.

To investigate whether the Compound 39+anti-mPD-1 treatment causes activation of immunosuppressive mechanisms via increased infiltration of regulatory T cells ($T_{reg}$) cells, EMT6 tumor sections were immunostained for FoxP3, a marker of $T_{reg}$ cells. This analysis did not show any significant difference between the mean cell counts of $FoxP3^+$ cells between mice treated with Compound 39+anti-mPD-1 (mean cell count 122.92±75.88/mm$^2$ of tumor tissue) and mice treated with vehicle+anti-mPD-1 (mean cell count 86.02±49.62/mm$^2$ of tumor tissue) (FIG. 15D), indicating that the Compound 39 treatment is not associated with increased infiltration of $T_{reg}$ cells.

$\alpha_V\beta_8$ and $\alpha_V\beta_1$ Inhibition Reduces Fibrosis and TGFβ Regulated Genes More than $\alpha_V\beta_8$ Alone in EMT6 Model.

FIG. 53A depicts two picrosirius red stains for vehicle+anti-mPD-1 (top) and Compound 39+anti-mPD-1 (bottom). FIG. 53B depicts a graph showing the fibrosis composite score for vehicle+anti-PD-1, anti-$\alpha_V\beta_8$+anti-PD-1, and Compound 39+anti-mPD-1. FIG. 54A depicts a graph associated with changes in ACTA2 for vehicle+anti-PD-1, anti-$\alpha_V\beta_8$+anti-PD-1, and Compound 39+anti-mPD-1. FIG. 54B depicts a graph associated with changes in SERPINE1 for vehicle+anti-PD-1, anti-$\alpha_V\beta_8$+anti-PD-1, and Compound 39+anti-mPD-1. FIG. 54C depicts a graph associated with changes in CTHRC1 for vehicle+anti-PD-1, anti-$\alpha_V\beta_8$+anti-PD-1, and Compound 39+anti-mPD-1. FIG. 54D depicts a graph associated with changes in SMAD7 for vehicle+anti-PD-1, anti-$\alpha_V\beta_8$+anti-PD-1, and Compound 39+anti-mPD-1.

Integrin $\alpha_V\beta_1$ is Expressed in Multiple Solid Tumors and Drives the Adhesion of Cancer-Associated Fibroblasts (CAFs) to Latent TGFβ.

In human tumor tissues and in CAFs, $\alpha_V\beta_1$ protein expression was evaluated via immunohistochemistry (IHC) and custom electroluminescence assay, respectively. CAF adhesion to the TGFβ latency-associated peptide (LAP) was quantified in the presence or absence of Compound 39 in vitro by high-content microscopy imaging. The activity of Compound 39 in combination with anti-mPD-1 on fibrotic markers was evaluated in the EMT6 tumor model in vivo by gene expression analysis using the Nanostring® nCounter analysis system. Compound 39-treated human breast tumor tissue was analyzed for fibrotic marker α-smooth muscle actin (αSMA) using immunofluorescence.

FIG. 99 depicts a schematic diagram of Compound 39 (top) and a molecular rendering bound to $\alpha_V\beta_8$ (bottom). FIG. 100 depicts a heatmap showing the relative $IC_{50}$ potencies of Compound 39 compared to indicated integrin indications.

FIG. 101 depicts images of OCT-embedded human tissue cores showing the expression of $\alpha_V\beta_1$ by IHC. The overall expression of $\alpha_V\beta_1$ increased in tumor tissues compared to corresponding healthy tissues. IHC was performed using a specific $\alpha_V\beta_1$ antibody. Isotype control is shown in FIG. 101 to indicate antibody specificity. Moreover, in FIG. 101, percent positive cells showing $\alpha_V\beta_1$ staining are indicated.

Inhibition of $\alpha_V\beta_1$ prevents cell adhesion to LAP. FIG. 102 depicts a chart showing protein expression of $\alpha_V\beta_1$ on CAFs isolated from indicated carcinomas compared to normal human lung fibroblasts (NHLF) determined by electroluminescence meso scale discovery assay. Integrin $\alpha_V\beta_8$ was undetected in CAFs and NHLFs. The black dotted line in the graph represents the lower limit of detection.

FIG. 103 depicts a graph associated with a cell adhesion assay depicting a percentage of adherent cells associated with lung adenocarcinoma (LUAD) CAFs for various concentrations of Compound 39 (log nM). FIG. 104A depicts a graph associated with a cell adhesion assay depicting a percentage of adherent cells associated with lung squamous cell carcinoma (LUSC) CAFs for various concentrations of Compound 39 (log nM). FIG. 104B depicts a graph associated with a cell adhesion assay depicting a percentage of adherent cells associated with pancreatic stellate CAFs for various concentrations of Compound 39 (log nM). These dose-response curves show that Compound 39 inhibits the adhesion of LUAD, LUSC, and PSC CAFs to TGFβ latency-associated peptide in a dose-dependent manner. FIG. 105 depicts images showing the adhesion of CAFs on LAP-coated plates in the presence or absence of Compound 39. Cell membranes are stained with cell mask green dye and nuclei are stained with DAPI.

Compound 39 decreases fibroblast activation marker αSMA. FIG. 106 depicts a schematic diagram of a process (left) associated with freshly collected human breast tumor tissue being treated with Compound 39 ex vivo for a time period, a graph showing an immune-fluorescence analysis of αSMA+ cells (middle), and representative images of αSMA and DAPI-stained tissues (right).

Compound 39 reduces fibrotic markers in EMT6 tumors. FIG. 107 depicts Compound 39 in combination with anti-mPD-1 reducing the expression of fibrotic markers in EMT6 tumors.

Compound 39 in combination with anti-mPD-1 reduces the expression of fibrotic markers and tissue fibrosis in the tumor microenvironment compared to anti-$\alpha_V\beta_8$ in combination with anti-mPD-1. FIG. 108 depicts a graph showing the expression of connective tissue growth factor (CTGF) for vehicle+anti-mPD-1, anti-$\alpha_V\beta_8$+anti-mPD-1, and Compound 39+anti-mPD-1. FIG. 109 depicts a graph showing the expression of periostin (POSTN) for vehicle+anti-mPD-1, anti-$\alpha_V\beta_8$+anti-mPD-1, and Compound 39+anti-mPD-1. FIG. 110 depicts a graph showing the expression of plasminogen activator inhibitor-1 (SERPINE1) gene for vehicle+anti-mPD-1, anti-$\alpha_V\beta_8$+anti-mPD-1, and Compound 39+anti-mPD-1—In FIG. 109-FIG. 110, error bars show ±S.D. *p=0.05, p=0.01, *p=0.001, and ****p=0.0001 calculated by one-way Anova.

FIG. 111 depicts images associated with a Pico Sirius red stain for Vehicle+anti-mPD-1 (top) and vehicle+Compound 39 (bottom). FIG. 112 depicts a graph associated with a fibrosis score for vehicle+anti-mPD-1, anti-$\alpha_V\beta_8$+anti-mPD-1, and Compound 39+anti-mPD-1. Error bars show S.D. *p=0.05, p=0.01, *p=0.001, and ****p=0.0001 calculated by one-way Anova.

Compound 39 in combination with anti-mPD-1 inhibits tumor growth compared to anti-mPD-1 and increases the survival of animals. $\alpha_V\beta_1$ protein expression was detected by IHC analysis in both tumor regions and stromal-rich areas of human tumors. Compared to normal human lung fibroblasts, $\alpha_V\beta_1$ protein was elevated in primary human CAFs, with pancreatic stellate CAFs showing the highest protein expression (2.8-fold). Inhibition of $\alpha_V\beta_1$ with Compound 39 blocked the binding of CAFs to LAP; the integrin RGD binding region of latent TGFβ, in a dose-dependent manner, demonstrating an $\alpha_V\beta_1$-specific interaction with latent TGFβ. EMT6 tumors treated with Compound 39 and anti-mPD-1 showed a significant reduction in fibrotic markers compared to anti-$\alpha_V\beta_8$ and anti-mPD-1. Human breast tumor tissues treated with Compound 39 ex vivo showed reduced expression of the fibroblast activation marker αSMA (2.9-fold) compared to vehicle-treated tissues, indicating a decreased TGFβ activity within the stromal regions of the TME. The TGFβ activating integrin $\alpha_V\beta_1$ is expressed in multiple human tumors, is present on primary human CAFs, mediates CAF interaction with latent TGFβ, and has a functional role in mediating fibrotic gene expression in murine and human tumors.

Compound 39 Treatment is Effective in Reducing Tumor Growth of EMT6, Pan02 and CT26 Tumors.

To ascertain whether the effects of the Compound 39 observed in EMT6 tumors (breast cancer model), applies to other tumor types, mice bearing Pan02 tumors (murine pancreatic cancer model) and CT26 (murine colon cancer model) were treated with (i) vehicle+rat IgG2A (control group), (ii) vehicle+anti-mPD-1, (iii) Compound 39+anti-mPD-1, and (iv) anti-$\alpha_V\beta_8$ antibody+anti-mPD-1 (as described in Methods).

Figure 16A:
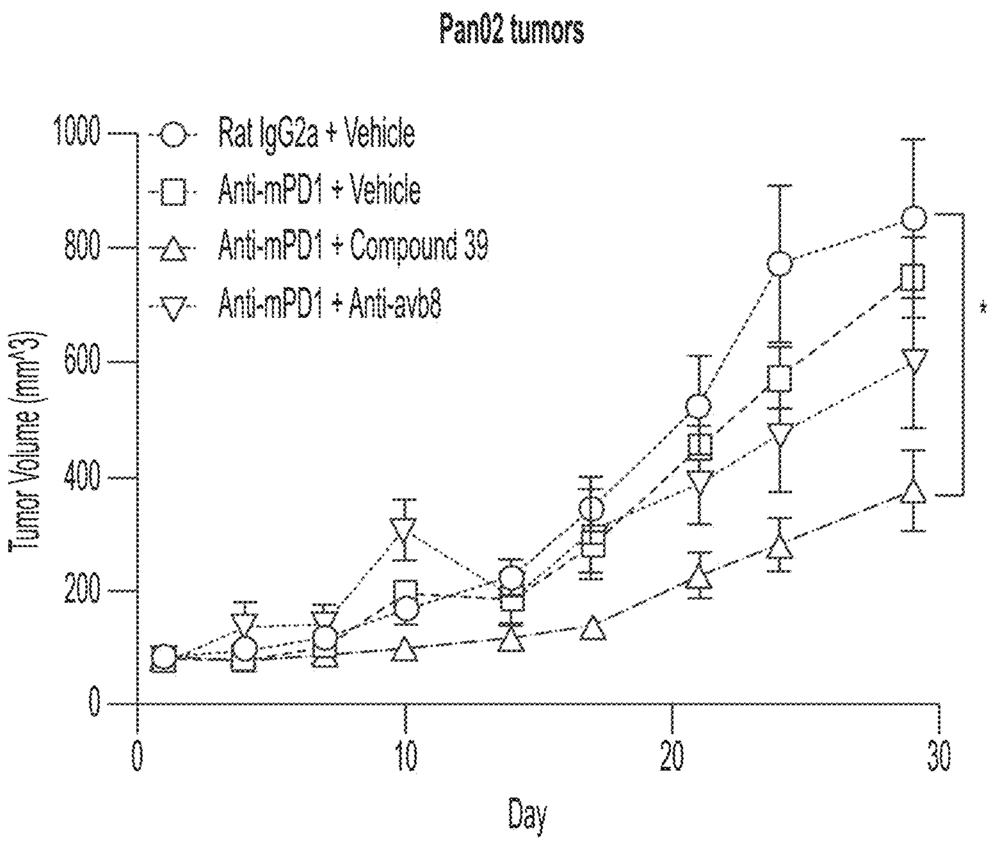
FIG. 16A is a graph showing tumor volume as a function of time for mice with Pan02 tumors in the study of Example B6. A combined treatment of Compound 39+anti-mPD-1 is more effective in reducing tumor growth and volume, compared to anti-$\alpha_v\beta_8$ treatment+anti-mPD-1. Error bars in growth curves: ±standard error of mean, n=10 mice in each group, ****=$p<0.0001$ (one way ANOVA), and ns: not significant.
Figure 16B:
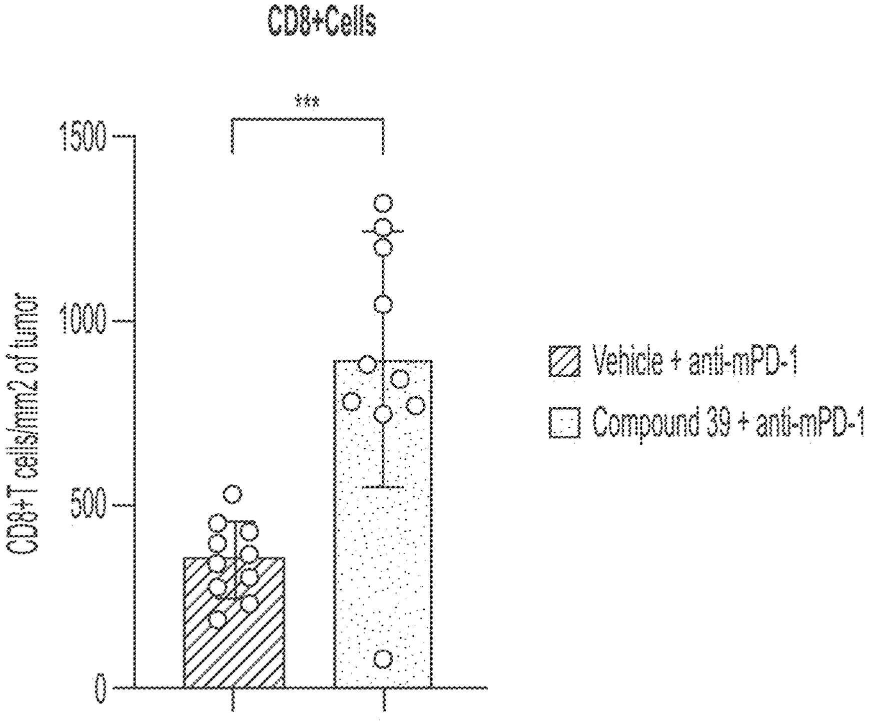
FIG. 16B is a bar graph comparing $CD8^+$ T cell density in Pan02 tumors between different dosing regimens in the study of Example B6. Compound 39+anti-mPD-1 treatment (bar on right) causes a significantly increased $CD8^+$ T cell infiltration as compared to vehicle+anti mPD-1 treatment (bar on left). N=10 mice in each group, bars on histograms: ±standard deviation, ****=$p<0.0001$ (student's t-test), and ns: not significant.
Figure 16C:
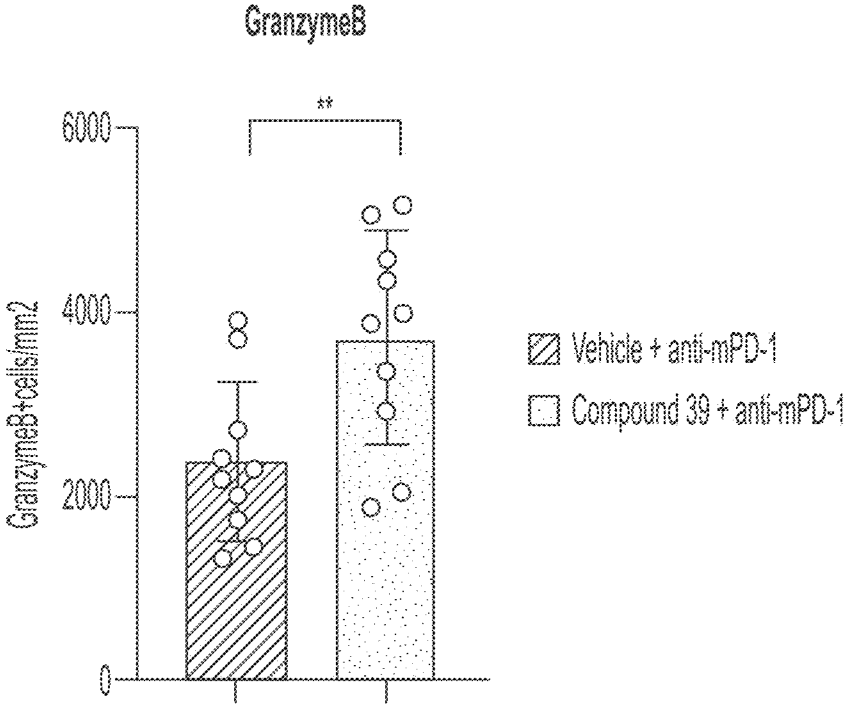
FIG. 16C is a bar graph comparing granzyme $B^+$ cell density in Pan02 tumors between different dosing regimens in the study of Example B6. Compound 39+anti-mPD-1 treatment (bar on right) causes a significantly increased release of granzyme B as compared to vehicle+anti mPD-1 treatment (bar on left). N=10 mice in each group, bars on histograms: standard deviation, ****=$p<0.0001$ (student's t-test), and ns: not significant.
Figure 16D:
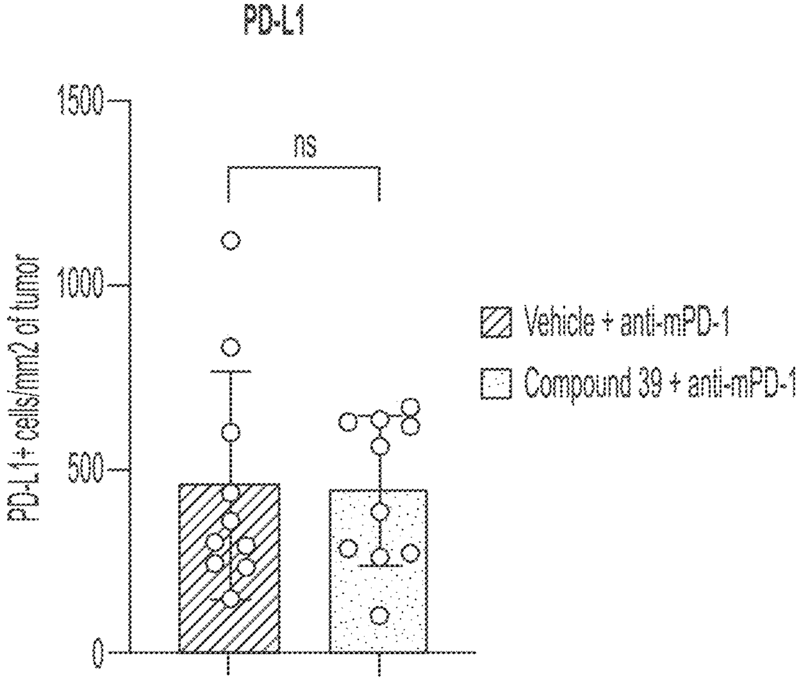
FIG. 16D is a bar graph comparing PD-$L1^+$ cell density in Pan02 tumors between different dosing regimens in the study of Example B6. Compound 39+anti-mPD-1 treatment (bar on right) causes a significantly increased and PD-L1 expression as compared to vehicle+anti mPD-1 treatment (bar on left). N=10 mice in each group, bars on histograms: ±standard deviation, ****=$p<0.0001$ (one way ANOVA), and ns: not significant.
Figure 16E:
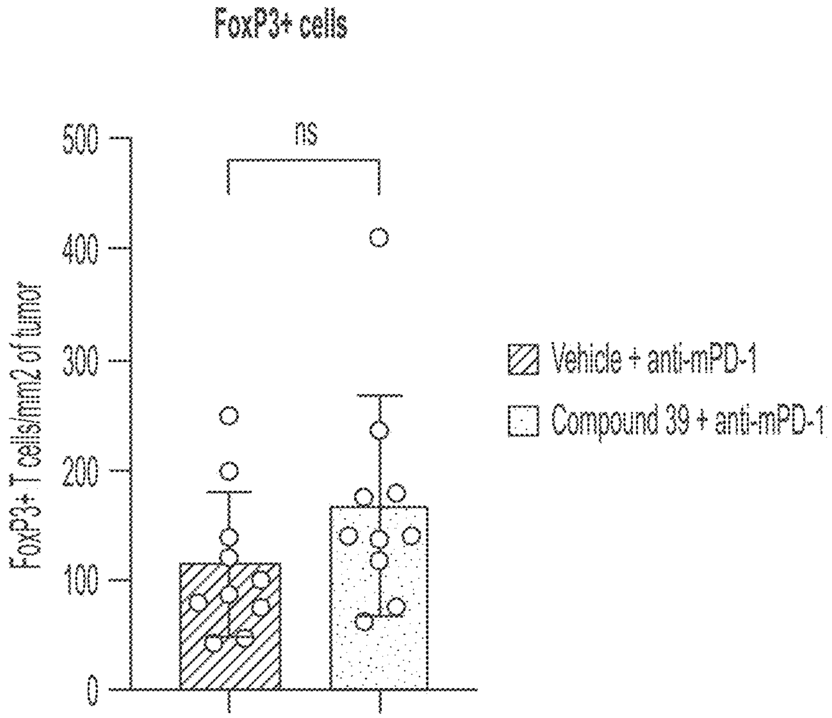
FIG. 16E is a bar graph comparing $FoxP3^+$ cell density in Pan02 tumors between different dosing regimens in the study of Example B6. Compound 39+anti-mPD-1 treatment (bar on right) causes no difference in $T_{reg}$ cells (marked by $FoxP3^+$ cells) as compared to vehicle+anti mPD-1 treatment (bar on left). N=10 mice in each group, bars on histograms: ±standard deviation, ****=$p<0.0001$ (one way ANOVA), and ns: not significant.

As in the EMT6 model, Pan02 tumors in mice treated with Compound 39+anti-mPD-1 or anti-$\alpha_V\beta_8$+anti-mPD-1 showed markedly lower growth rates compared to Pan02 tumors in mice of the other treatment groups. FIG. 16A shows mean tumor growth curves. Similar to EMT6 tumors, a significant ($p<0.05$) increase in $CD8^+$ T cell infiltration (mean cell count 351.67±103.63/$mm^2$ of tumor tissue in vehicle+anti PD-1 treated group vs 897.17±346.5/$mm^2$ of tumor tissue in anti mPD-1+Compound 39 treated group) and granzyme $B^+$ cells (mean cell count 2384.17±873.72/$mm^2$ of tumor tissue in vehicle+anti mPD-1 treated group vs 3734±1163.29/$mm^2$ of tumor tissue in anti-mPD-1+Compound 39 treated group) was observed, while no significant difference in PD-L1 and $FoxP3^+$ cells was observed between Pan02 tumors of mice treated with Compound 39+anti-mPD-1 compared to mice treated with control or vehicle+anti mPD-1 group (FIG. 16B, FIG. 16C, FIG. 16D, and FIG. 16E, respectively).

Figure 41:
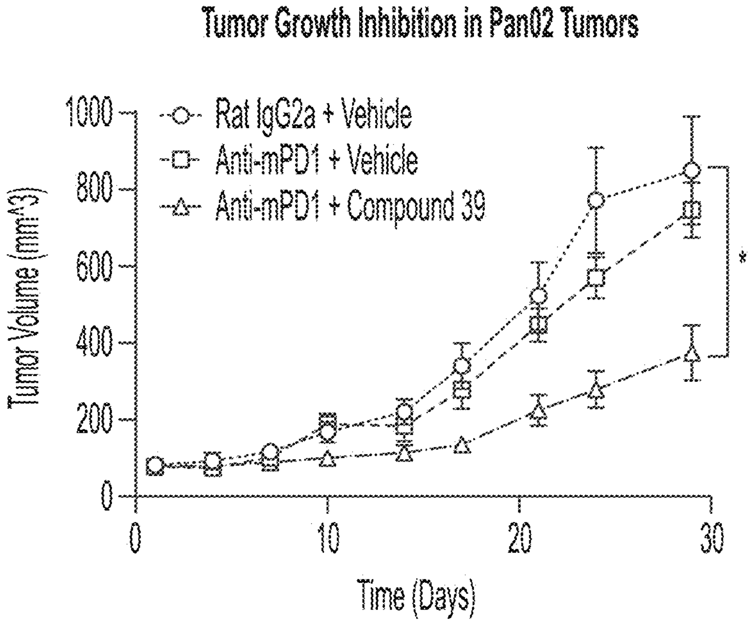
Figure 42:
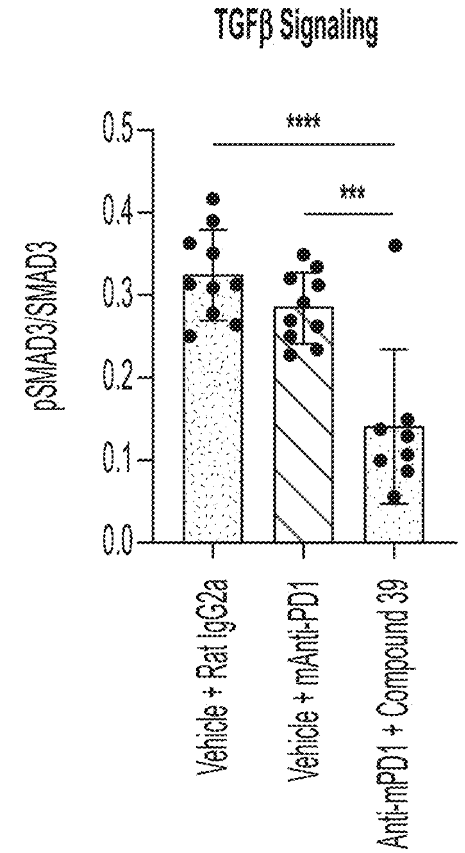
Figure 43:
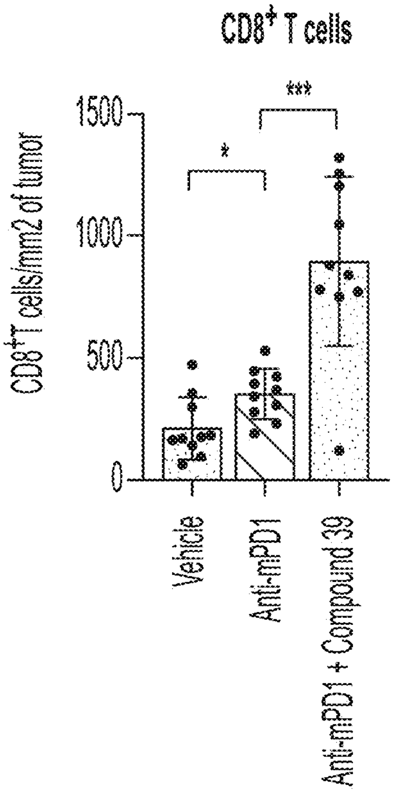

FIG. 41 depicts a graph showing tumor growth inhibition in Pan02 tumors for Rat IgG2a+vehicle, anti-mPD-1+vehicle, and anti-mPD-1+Compound 39 over a 30 day time period. FIG. 42 depicts a graph comparing pSMAD3/SMAD3 between vehicle+Rat IgG2a, anti-mPD-1+vehicle, and anti-mPD-1+Compound 39. FIG. 43 depicts a graph comparing size of $CD8^+$ T cells/$mm^2$ of tumor between vehicle, anti-mPD-1, and anti-mPD-1+Compound 39. As shown in FIG. 41-FIG. 43, Compound 39 inhibited Pan02 tumor growth and increased T-cell infiltration.

Figure 17A:
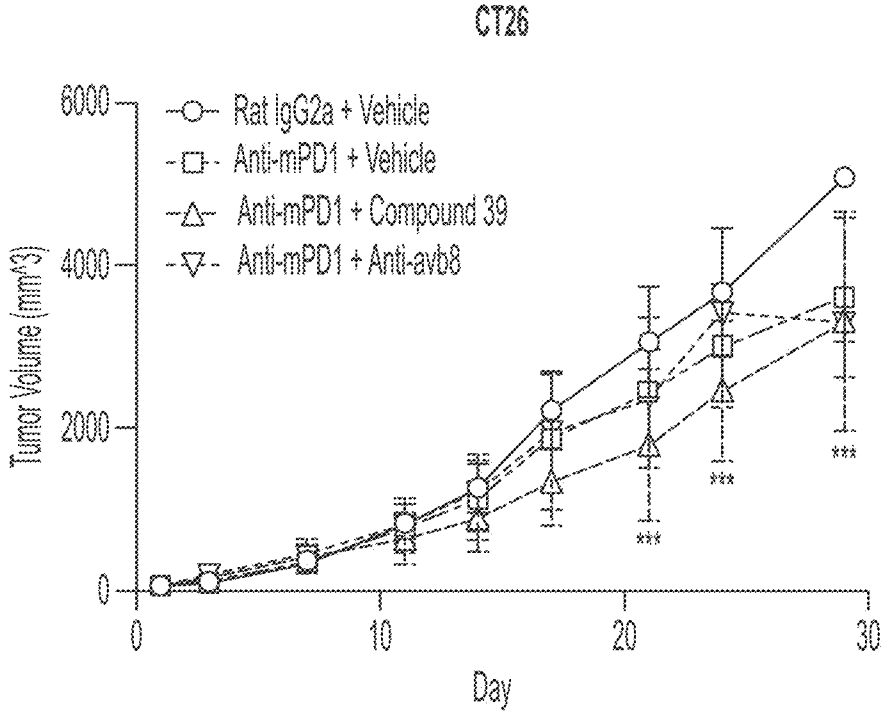
FIG. 17A is a graph showing tumor volume as a function of time for mice with CT26 tumors in the study of Example B6. A combined treatment of Compound 39+anti-mPD-1 significantly reduces tumor growth and volume, compared to anti-mPD-1+ vehicle treatment in CT26 tumor bearing mice. Error bars in growth curves: ±standard error of mean. ***=$p<0.001$ (Two-way ANOVA). N=10 mice in each group.
Figure 17B:
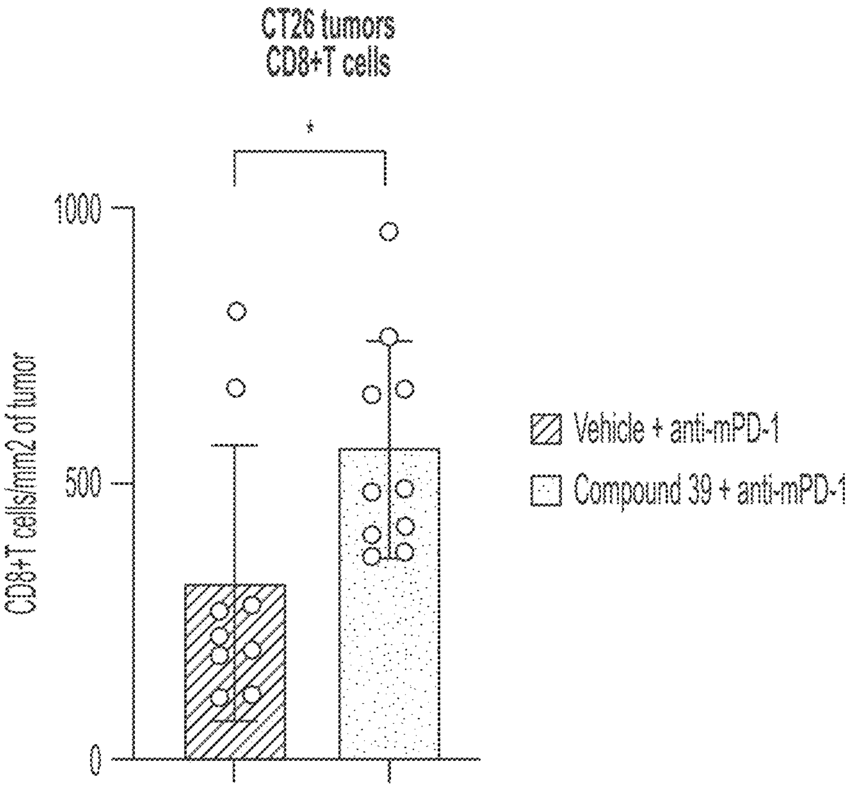
FIG. 17B shows a bar graph comparing $CD8^+$ T cell density in CT26 tumors for different dosing regimens in the study of Example B6. Compound 39+anti-mPD-1 treatment (bar on right) causes a significantly increased $CD8^+$ T cell infiltration compared to vehicle+anti mPD-1 treatment (bar on left). Bars on histograms: ±standard deviation. *=$p<0.05$ (student's t test). N=10 mice in each group.
Figure 17C:
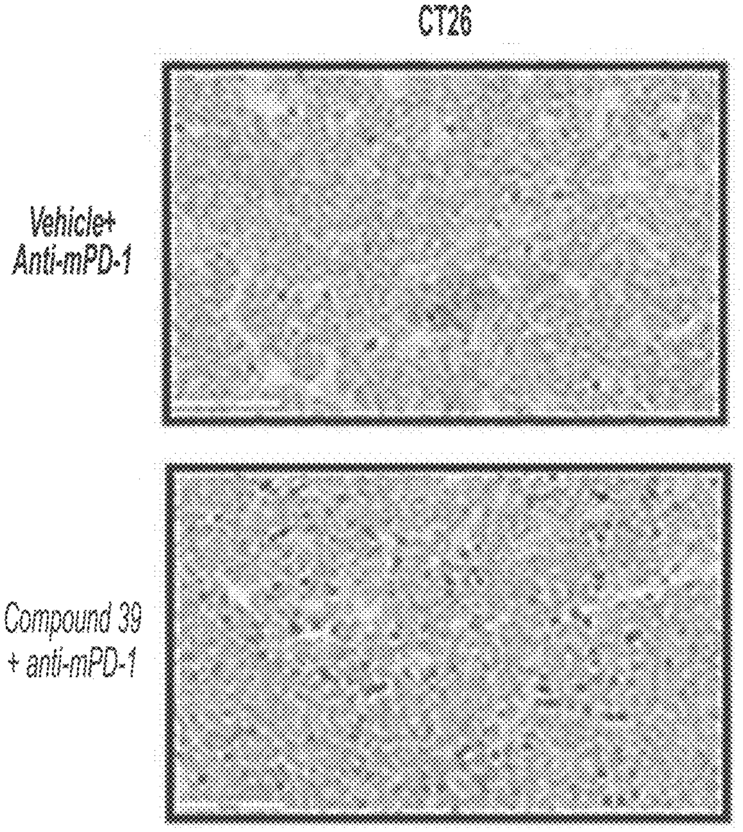
FIG. 17C shows representative immunohistochemistry (IHC) images of $CD8^+$ cells in CT26 tumors subjected to different dosing regimens in the study of Example B6.
Figure 18A:
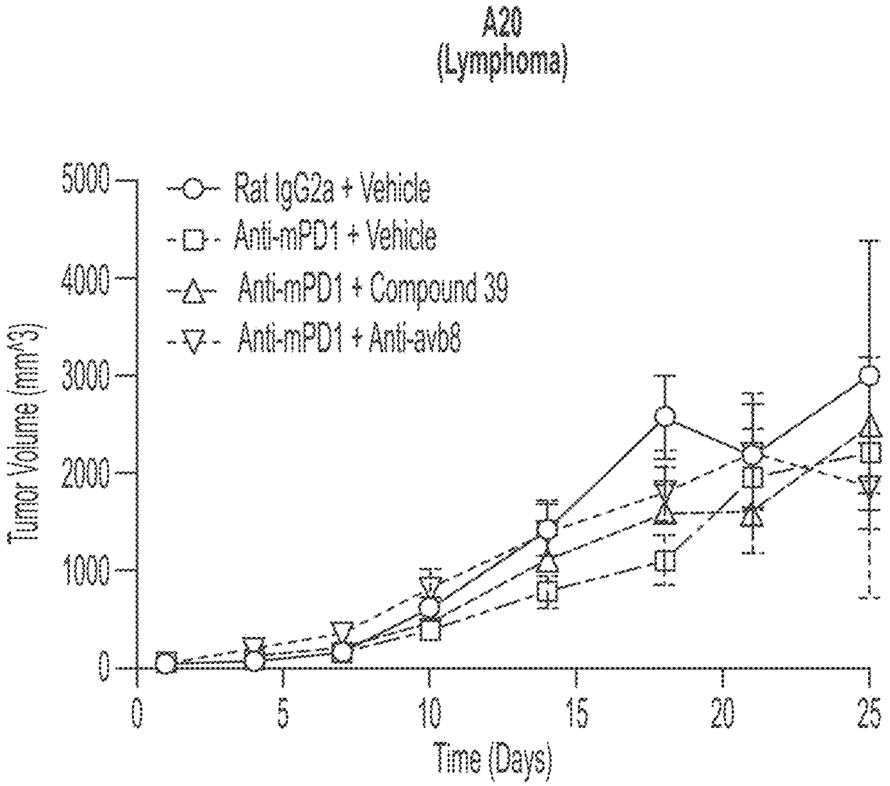
FIG. 18A is a graph showing tumor volume as a function of time for mice with A20 tumors in the study of Example B6.
Figure 18B:
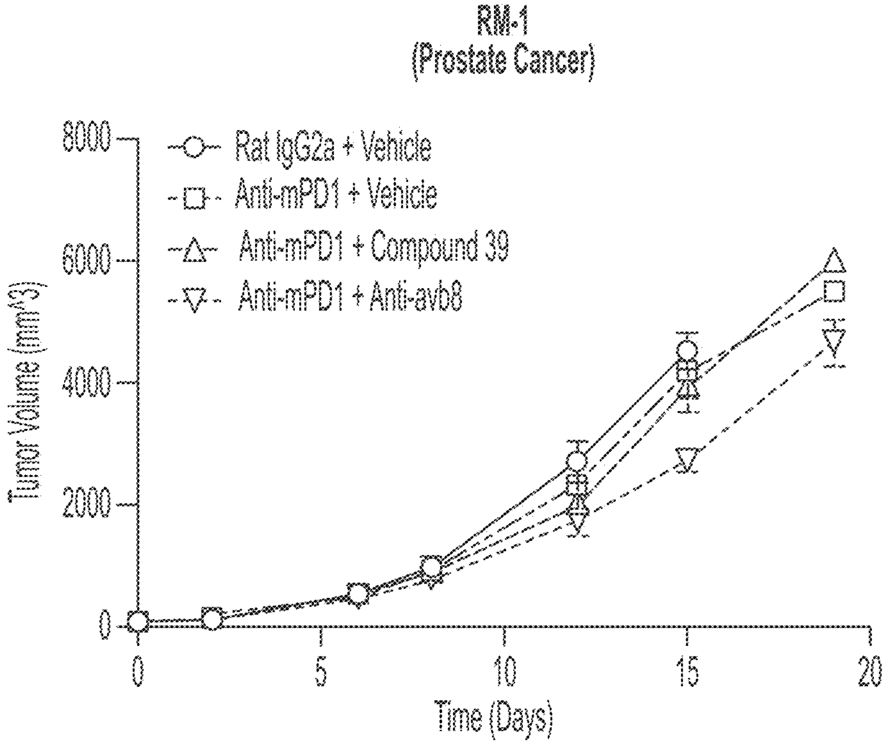
FIG. 18B is a graph showing tumor volume as a function of time for mice with RM-1 tumors in the study of Example B6.
Figure 18C:
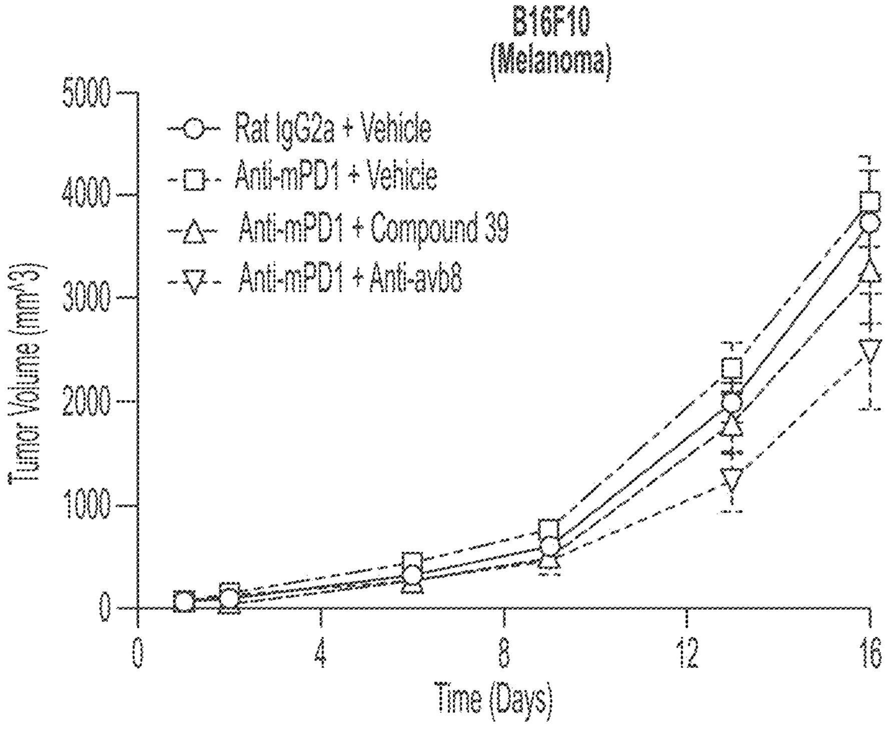
FIG. 18C is a graph showing tumor volume as a function of time for mice with B16F10 tumors in the study of Example B6.
Figure 18D:
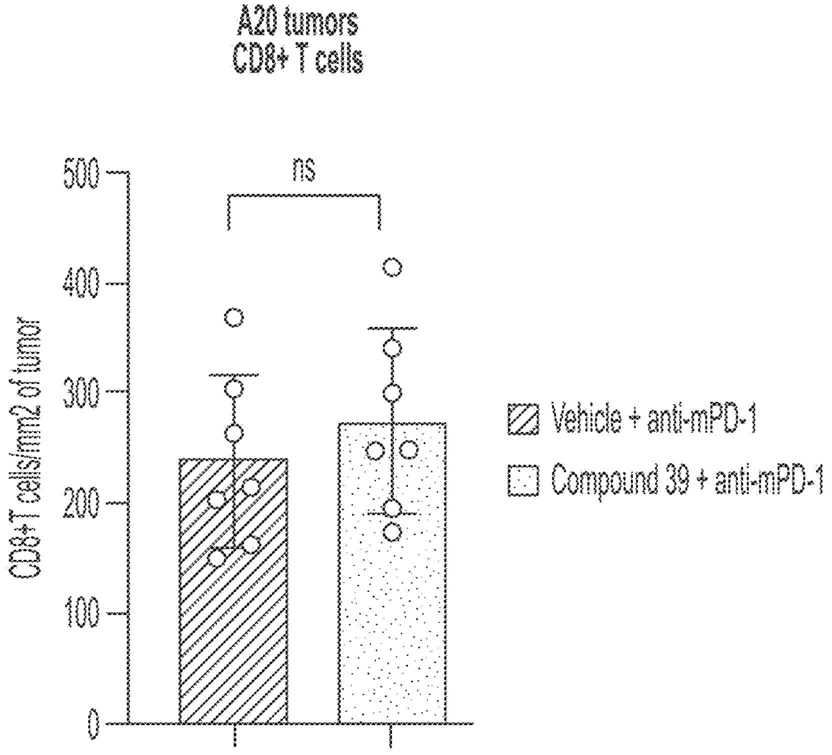
FIG. 18D is a bar graph comparing $CD8^+$ T cell densities in A20 tumors in the study of Example B6. N=10 mice in each group. Ns=not significant (using student's t test).
Figure 18E:
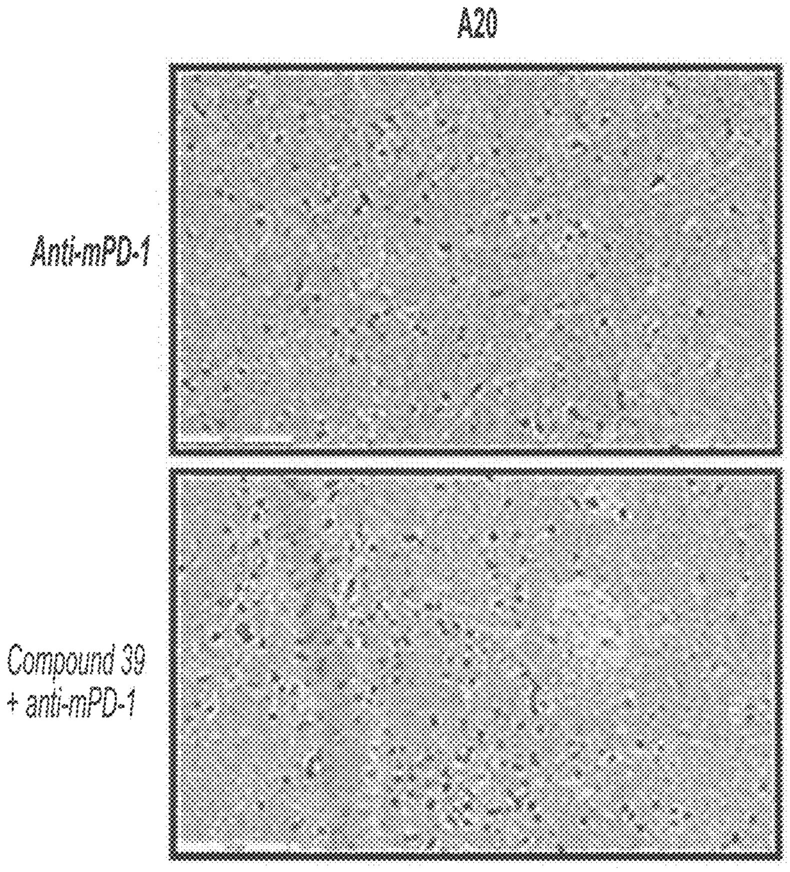
FIG. 18E shows CD8 stains of A20 tumors subjected to different dosing regimens in the study of Example B6.
Figure 18F:
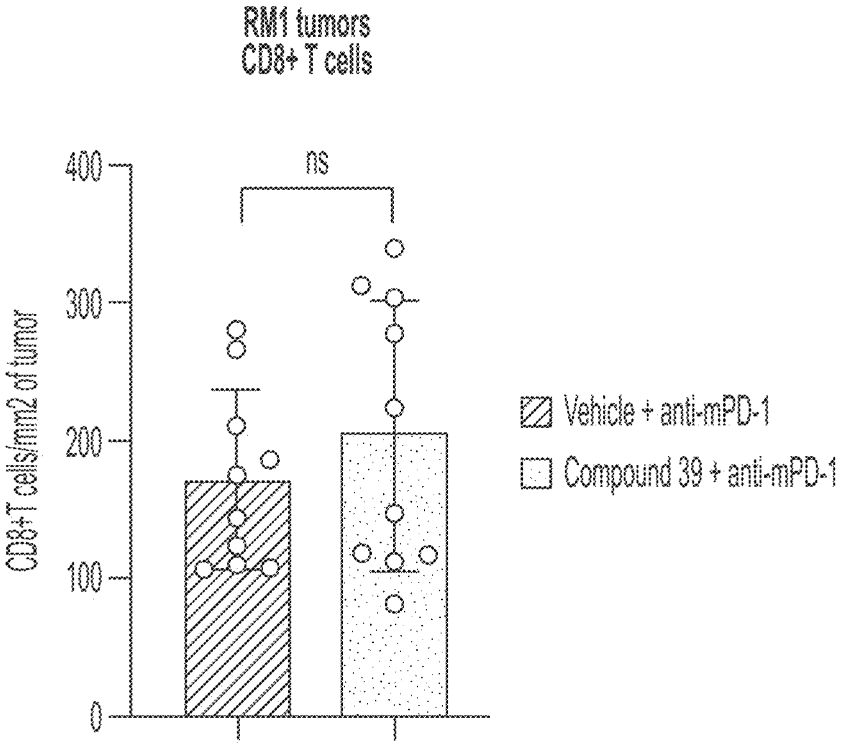
FIG. 18F is a bar graph comparing $CD8^+$ T cell densities in RM-1 tumors in the study of Example B6. N=10 mice in each group. Ns=not significant (using student's t test).
Figure 18G:
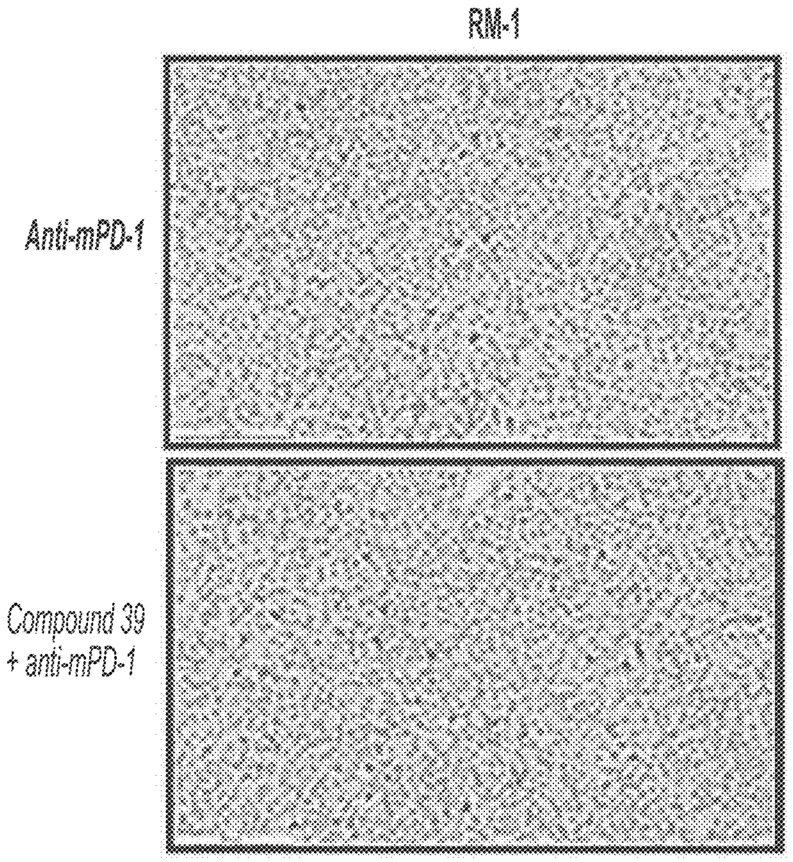
FIG. 18G shows CD8 stains of RM-1 tumors subjected to different dosing regimens in the study of Example B6.
Figure 18H:
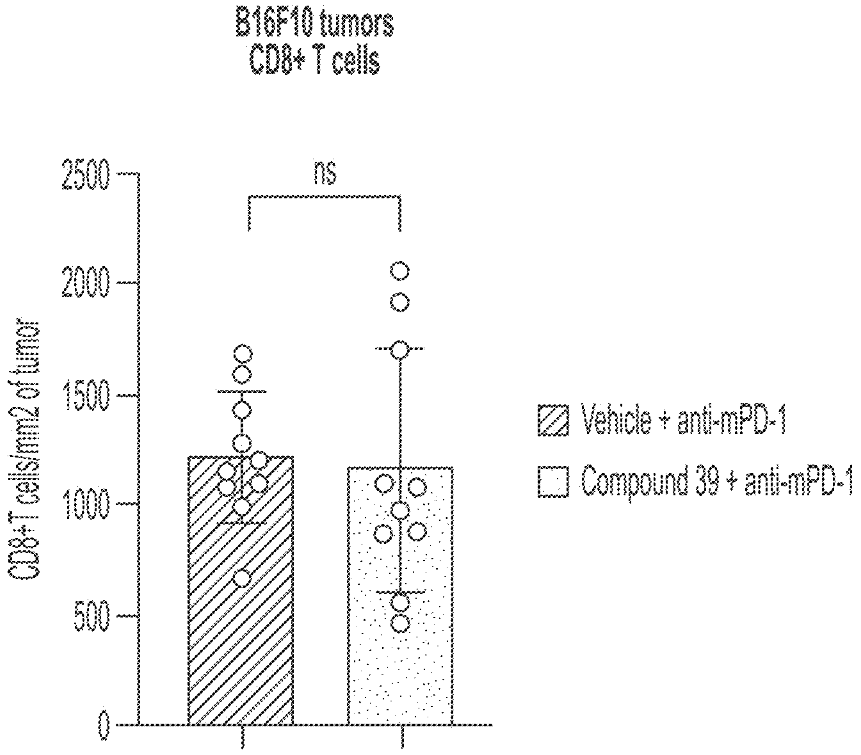
FIG. 18H is a bar graph comparing $CD8^+$ T cell densities in B16F10 tumors in the study of Example B6. N=10 mice in each group. Ns=not significant (using student's t test).
Figure 18I:
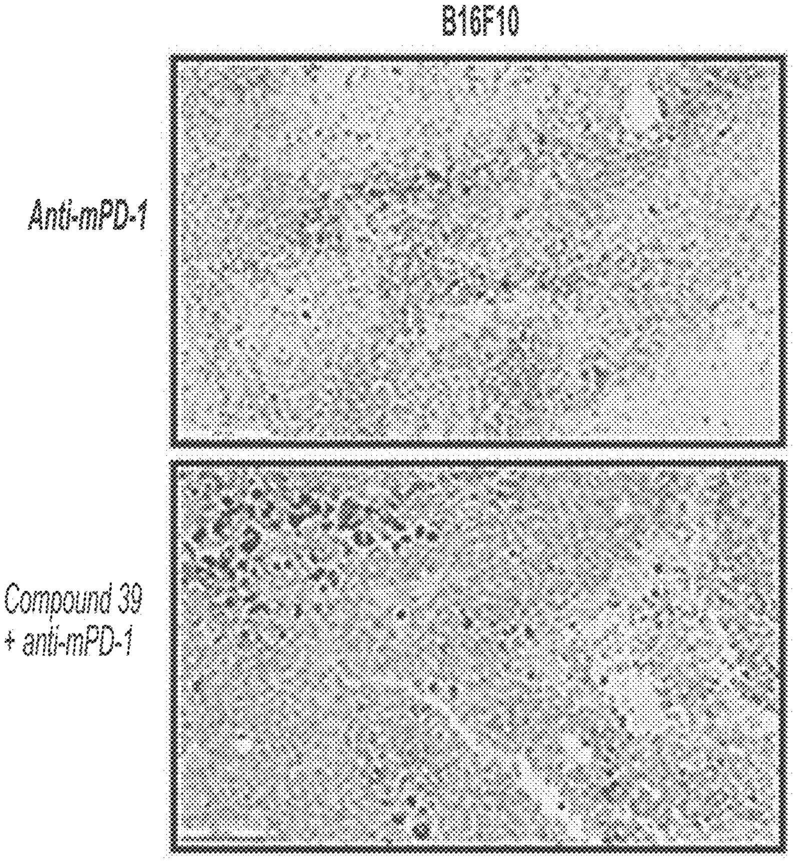
FIG. 18I shows CD8 stains of B16F10 tumors subjected to different dosing regimens in the study of Example B6.

CT26 tumors in mice treated with Compound 39+anti-mPD-1 showed markedly lower growth rates compared to CT26 tumors in mice of the Rat IgG2A+vehicle treated group (FIG. 17A). Similar to EMT6 tumors, a significant ($p<0.05$) increase in $CD8^+$ T cell infiltration (mean cell count 320.7±249.39/$mm^2$ of tumor tissue in vehicle+anti-mPD-1 treated group vs 561.05±195.94/$mm^2$ of tumor tissue in anti PD-1+Compound 39 treated group) was observed in CT26 tumors treated with Compound 39+anti-mPD-1 (FIG. 17B and FIG. 17C).

$\alpha_V\beta_1$ IHC Detects Expression Across Human Cancers.

FIG. 50A depicts images associated with IHC detection of $\alpha_V\beta_1$ in lung adenocarcinoma. FIG. 50B depicts images associated with IHC detection of $\alpha_V\beta_1$ in prostate cancer. FIG. 50C depicts images associated with IHC detection of $\alpha_V\beta_1$ in pancreatic adenocarcinoma.

Compound 39+Anti-mPD-1 Treatment does not Impair Tumor Growth of A20, RM-1, and B16F10 Tumors.

RM-1 (murine prostate cancer model), A20 (murine lymphoma model) and B16F10 (murine melanoma model) treated with Compound 39+anti-mPD-1 did not show a significant growth impairment compared to corresponding Rat IgG2A+vehicle treated groups. There were no significant differences in $CD8^+$ cell infiltration in these tumors (FIG. 18A-18I).

Compound 39 Increases IFNγ Signature & Reduces TGFβ Gene Signatures.

FIG. 48 depicts an IFN-γ gene signature (top) and a TGFβ gene signature (bottom) for vehicle+αPD1 and Compound 39+α-PD1. FIG. 49 depicts a schematic diagram associated with Compound 39 promoting ICI responsiveness.

Summary

In models of three separate mouse tumor types (breast, pancreas, and colon), Compound 39+anti-mPD-1 was significantly more effective than vehicle+anti-mPD-1 in reducing tumor growth. With this treatment, there was increased infiltration of cytotoxic T cells (marked by the expression of CD8) and granzyme $B^+$ cells (mainly secreted by activated cytotoxic T cells). Additionally, there was a significant increase in anti-tumor cytokines, such as IFNγ, CXCL9, CXCL10, and CCL4, as well as MHC class II molecules, such as h2-Ab1 and H2DMa as tested in EMT6 model. The Compound 39+anti-mPD-1 treatment evokes a greater anti-tumor immunological response by blocking immunosuppressive processes.

Example B7—Selective Targeting of Integrins $\alpha_V\beta_8$ and $\alpha_V\beta_{11}$ within the Dynamic Ecosystem of Pancreatic Cancer to Improve the Overall Anti-Tumor Response TGF-β promotes stromal cell reprogramming, immunosuppression, and fibrinogenesis in cancers, including pancreatic ductal adenocarcinoma (PDA). See A. T. Krishnamurty, et al. (2022) Nature 611(7934):148 and G. Biffi, et al. (2019) Cancer Discovery 9(2):282, each of which are incorporated herein by reference in their entirety. Integrins $\alpha_V\beta_8$ and $\alpha_V\beta_1$ are important activators of TGF-β signaling. Selective integrin blockade is therapeutic approach to address TGF-β-mediated immunotherapy and chemotherapy resistance and improve anti-tumor response across cancer models. See E. Dodagatta-Marri, et al. (2021) Cell Reports 36(1):109309 and N. Takasaka, et al. (2018) JCI Insight 3(20):e122591, each of which are incorporated herein by reference in their entirety.

Methods

The preclinical efficacy of Compound 39 of the examples was determined in genetically-defined (LSL-KrasG12D/+; LSL-Trp53R172H/+; Pdx1-Cre (KPC), and Pan02) and genomically diverse patient-derived PDA xenograft models. Clinically relevant combinations with standard of care (SoC) chemotherapy and anti-programmed death receptor-1 antibody (anti mPD-1) were tested by monitoring tumor growth, metastasis, and animal survival. Mechanistic assessment of alterations in the tumor microenvironment (TME) was performed using transcriptomic, immunohistochemical, and immunofluorescence approaches.

Results

FIG. 81 depicts a ductal Uniform Manifold Approximation and Projection (UMAP) plot showing various tumors. FIG. 82 depicts a graph showing a generic epithelial-mesenchymal transition (EMT) signature for various tumors (Tumor A, Tumor C, Tumor E, Tumor B, Tumor G, Tumor F, and Tumor D) subjected to a vehicle and to Compound 39. FIG. 83 depicts a graph showing a differential expression for Tumor A. FIG. 84 depicts a graph showing a differential expression for Tumor C. FIG. 85 depicts a graph showing a differential expression for Tumor E. FIG. 86 depicts a graph showing a differential expression for Tumor F.

Single cell analysis of KPC pancreatic tumors revealed restricted expression of integrin $\alpha_V\beta_8$ (ITGB8) within the T-reg and NK cell subsets, while components of TGF-β signaling were more widely represented across cancer and stromal cell subsets. Dual targeting of $\alpha_V\beta_8$ and $\alpha_V\beta_1$ with Compound 39 in this setting effectively reduced tumor growth (45% reduction in tumor weight compared with Vehicle; P=0.003) and significantly delayed disease progression in vivo (median OS Vehicle 29.5 days vs Compound 39 45 days, P<0.0001). Combining Compound 39 with anti mPD-1 antibody further improved survival in this aggressive model of metastatic PDA (median OS anti mPD-1 33 days vs Compound 39+anti mPD-1 51 days, 22% CR; P<0.0001).

Figure 36:
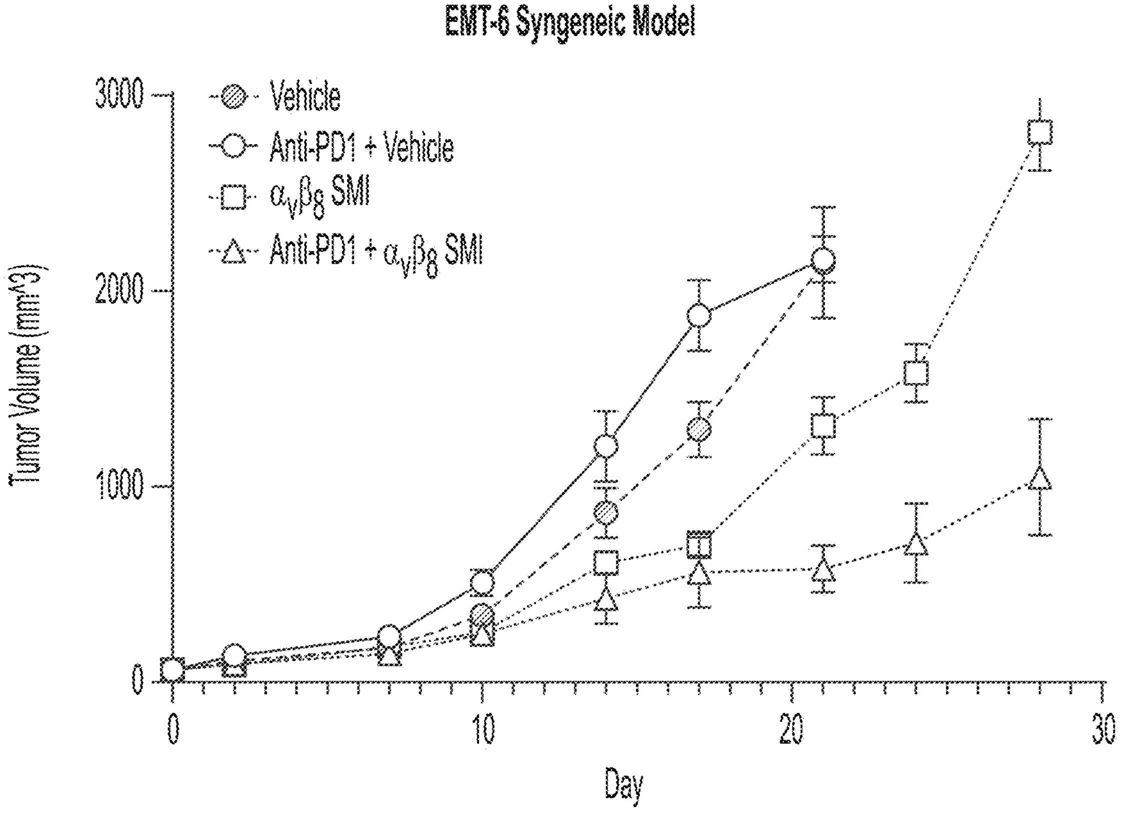
Figure 37:
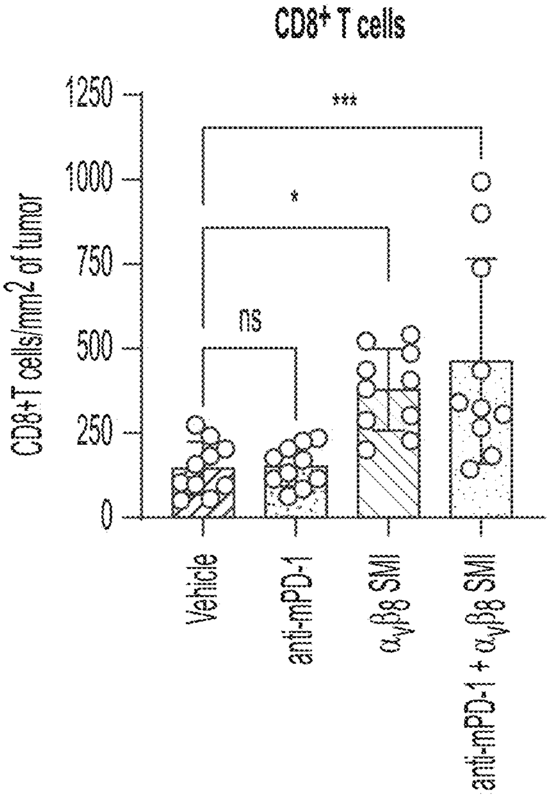
Figure 38:
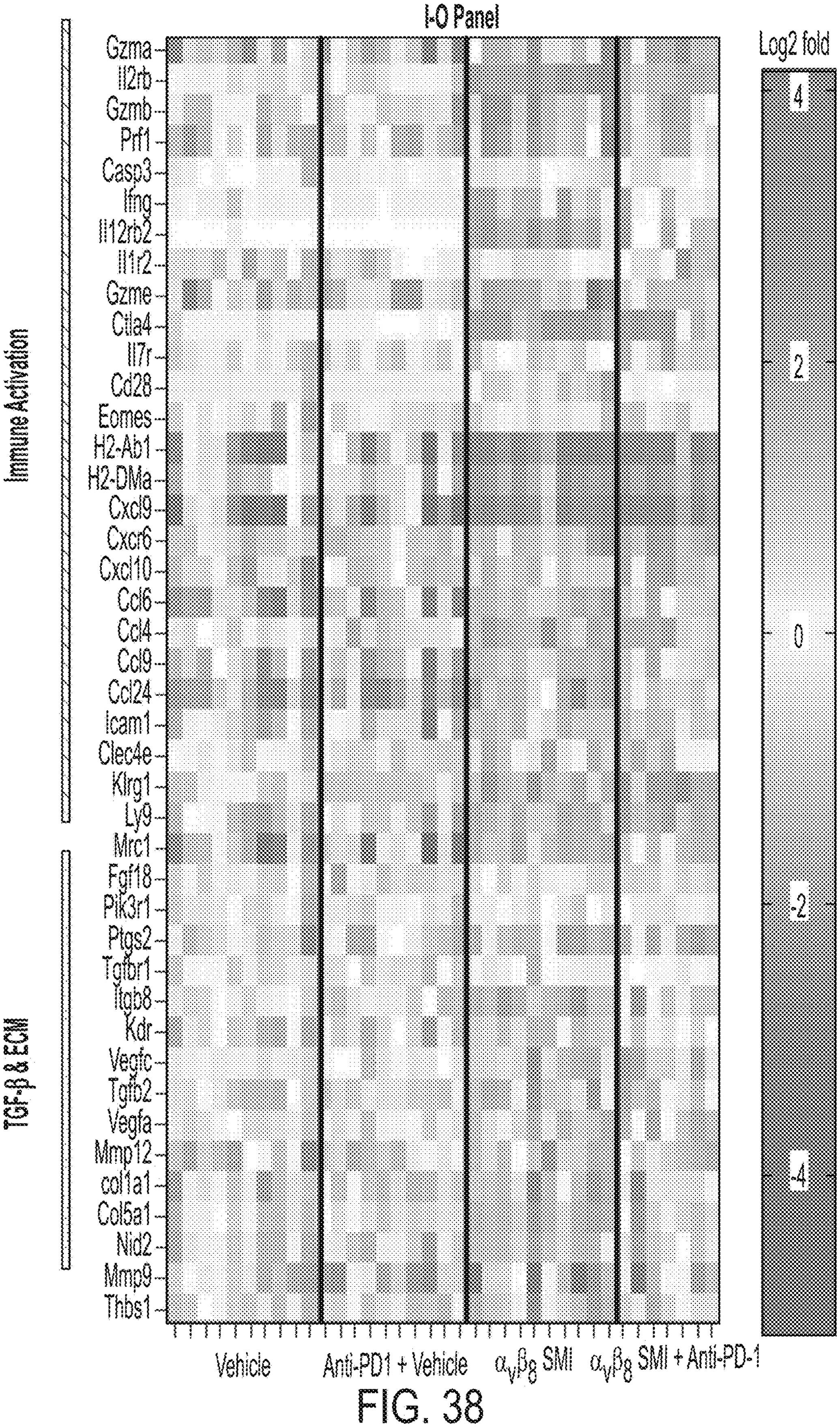

In a second syngeneic model of PDA (Pan02), Compound 39 in combination with immune checkpoint blockade (ICB) significantly reduced tumor growth TGF-β signaling, and fibrosis, while increasing CD8+lymphocyte infiltration. FIG. 36 depicts a graph for an EMT-6 syngeneic model showing tumor volume over a thirty day period for vehicle, anti-PD1+vehicle, $\alpha_V\beta_8$ small molecule inhibitor (SMI), and anti-PD1+$\alpha_V\beta_8$ SMI. FIG. 37 depicts a graph showing $CD8^+$ T cells/$mm^2$ of tumor for vehicle, anti-mPD-1, $\alpha_V\beta_8$ small molecule inhibitor (SMI), and anti-mPD-1+$\alpha_V\beta_8$ SMI. p<0.01 by one way ANOVA and p<0.0001 by one way ANOVA. FIG. 38** depicts an I-O for various enzymes for vehicle, anti-mPD-1+vehicle, $\alpha_V\beta_8$ small molecule inhibitor (SMI), and anti-mPD-1+Compound 39.

Compound 39 in combination with ICB significantly reduces tumor growth and metastases, while increasing CD8+ lymphocyte infiltration. Compound 39 combined with ICB significantly increases major histocompatibility complex (MHC) and type-I interferon (IFN) gene expression. FIG. 78A depicts a schematic diagram showing various major histocompatibility complex (MHC) gene expression associated with anti-PD1 and Compound 39+anti-PD1 in a syngeneic model of PDA (Pan02). FIG. 78B depicts a schematic diagram showing various type-I interferon (IFN) gene expression associated with anti-PD1 and Compound 39+anti-PD1 in a syngeneic model of PDA (Pan02).

Utilizing patient-derived models of metastatic PDA revealed that Compound 39 significantly blocked tumor growth, improved the response to SoC chemotherapy Gemcitabine/Abraxane, and reduced the number and size of lung metastases.

Summary

These data demonstrate that Compound 39 significantly enhances ICB or SoC chemotherapy response in advanced PDA models and provide scientific rationale for future combination studies testing Compound 39 in pancreatic cancer.

Example B8—Integrin $\alpha_v\beta_1$ is Expressed in Multiple Solid Tumor Types and Drives the Adhesion of Cancer Associated Fibroblast to Latent TGF-β

Inhibition of transforming growth factor-β (TGF-β) activity is an attractive strategy to augment the response of human tumors to immune checkpoint blockade (ICB). It has been demonstrated that dual inhibition of integrins $\alpha_v\beta_8$ and $\alpha_v\beta_1$, two cell-surface proteins that activate latent TGF-β, significantly improves response to ICB in multiple preclinical tumor models. Integrin $\alpha_v\beta_8$ is known to be expressed by tumor infiltrating lymphocytes (TILs) along with some tumor cell types and has previously been associated with poor patient outcomes. However, integrin $\alpha_v\beta_1$, thought to be primarily expressed by mesenchymal cells and previously demonstrated to drive TGF-β activity in several fibrotic diseases, has not been well characterized in solid tumors. Here, $\alpha_v\beta_1$ protein expression in diverse human tumor tissues is evaluated; and the role of integrin $\alpha_v\beta_1$ in primary human cancer associated fibroblasts (CAFs) and tumor tissues is investigated using Compound 39 (a dual inhibitor of $\alpha_v\beta_8$/$\alpha_v\beta_1$), or a small molecule selective inhibitor of $\alpha_v\beta_1$.

Methods $\alpha_v\beta_1$ protein expression was evaluated in human tumor tissues via immunohistochemistry. $\alpha_v\beta_1$ protein levels in primary human CAFs isolated from pancreatic carcinoma, lung adenocarcinoma, and lung squamous cell carcinoma were quantified via custom electrochemiluminescence assay. CAF adhesion to latency associated peptide (LAP), the integrin-binding region of latent TGF-β, was quantified in the presence or absence of Compound 39 of the examples and a small molecule selective inhibitor of $\alpha_v\beta_1$ by high-content imaging in vitro. Anti-fibrotic activity of Compound 39 on ex vivo cultured human breast tumor tissue slices was assessed via immunofluorescence of fibrotic markers α smooth muscle actin (αSMA) and fibroblast activating protein (FAP).

Results

Human Cancer-Associated Fibroblasts (CAFs) Express Integrin $\alpha_v\beta_1$ by MSD.

FIG. 51 depicts a chart associated with $\alpha_v\beta_1$ protein expression in various cancer-associated fibroblasts (CAF). FIG. 52 depicts a graph associated with percent adherent cells (fraction) for Compound 39 in lung adenocarcinoma cancer-associated fibroblasts (CAF) from FIG. 51.

$\alpha_v\beta_1$ protein expression was confirmed in both tumor cell and CAF-rich areas of several human cancer types including breast and pancreatic tumors. Expression of $\alpha_v\beta_1$ protein by primary human CAFs was confirmed in vitro. Inhibition of $\alpha_v\beta_1$ with either Compound 39 or a small molecule selective inhibitor of $\alpha_v\beta_1$ was also shown to significantly block in vitro binding of primary human CAFs to LAP, demonstrating an $\alpha_v\beta_1$-specific interaction with latent TGF-β. Furthermore, human breast tumor tissues treated with Compound 39 ex vivo showed reduced expression of fibrotic markers αSMA and FAP, indicating a reduced TGF-β activity within the stromal regions of the tumor microenvironment.

Summary

Here it is demonstrated that the TGF-β activating integrin $\alpha_v\beta_1$ is expressed by multiple human cancer types, is present on primary human CAFs, and mediates CAF interaction with latent TGF-β.

Example B9—Compound 39 Activates Tumor Immune Responses and Reduces Stromal Fibrogenesis Alone and in Combination with Anti PD-1

Inhibition of transforming growth factor-β (TGF-β) activity is an attractive strategy to augment the response to immune checkpoint blockade (ICB) therapies for the treatment of human cancers. Integrins $\alpha_v\beta_8$ and $\alpha_v\beta_1$ activate TGF-β in a disease and tissue-specific manner. Thus, unlike systemic inhibition of TGF-β, inhibition of $\alpha_v\beta_8/\alpha_v\beta_1$ offers an innocuous approach to enhance ICB efficacy. Integrin $\alpha_v\beta_8$, upregulated on tumor cells and expressed on tumor infiltrating lymphocytes (TILs), is associated with poor cancer patient survival. Integrin $\alpha_v\beta_1$ is expressed on cancer associated fibroblasts (CAFs), but its role in cancer is not understood. The pro-inflammatory, anti-fibrotic activity, and anti-tumor efficacy of Compound 39 alone, or in combination with ICB, is evaluated using murine and human tumor models.

Methods

Inhibition of αvβ1 and TGF-β mediated by Compound 39 of the examples was monitored via cell adhesion assays and transcriptomic analyses. $\alpha_v\beta_1$ protein expression was evaluated on human tumor tissues via immunohistochemistry using an indigenously developed anti-$\alpha_v\beta_1$ antibody. Efficacy of Compound 39 monotherapy and in combination with ICB was evaluated in syngeneic mouse models bearing EMT6 and Pan02 tumors. Animal survival, tumor growth, transcriptomic analyses, tissue fibrosis, and TILs were monitored along with circulating lymphocytes and cytokines. Tissue and circulating biomarkers of response to Compound 39 were identified. Human breast and melanoma tumor tissues were cultured ex vivo and Compound 39 activity was assessed by measuring CD8+ cytotoxic T cells and tumor apoptosis.

Results $\alpha_v\beta_1$ protein expression was detected on tumor cells and CAFs in several tumor types. Compound 39 prevented the binding of latency associated peptide (LAP) to $\alpha_v\beta_1$—an essential step of $\alpha_v\beta_1$-mediated TGF-β activation. Compound 39 alone, and in combination with ICB significantly reduced TGF-β signaling, tumor growth, and significantly increased $CD8^+$ TILs and pro-inflammatory cytokines in pre-clinical models. The changes in $CD8^+$ T cells and cytokines (e.g. CXCL9) were also detected in blood. Compared to treatment with an $\alpha_v\beta_8$-specific antibody, the Compound 39 significantly reduced fibrosis within the tumor micro-environment (TME) attributable to an added inhibition of integrin $\alpha_v\beta_1$-mediated TGF-β activation. Human breast and melanoma tumor tissues treated with Compound 39 showed a significant increase in cytotoxic $CD8^+$T cells and a reduction in fibrotic markers.

Summary

Compound 39 has distinct activities on tumor-immune and stromal compartments within the TME. These activities synergize to promote immune activation and reduce the fibrosis leading to augmented ICB efficacy.

Example B10—Phase 1a Trial of Compound 39, an Integrin $\alpha_v\beta_8$ and $\alpha_v\beta_1$ Inhibitor, as Monotherapy and in Combination with Pembrolizumab, in Treatment-Resistant Patients with Advanced or Metastatic Solid Tumors Analyses of transforming growth factor-β (TGF-β) expression in tumors treated with immune checkpoint inhibitors (ICIs) suggest that increased expression of TGF-β in the tumor microenvironment may play a role in poor response to ICIs. Compound 39 is an orally bioavailable small molecule that inhibits integrin $\alpha_v\beta_8$ and $\alpha_v\beta_1$ binding to the latency-associated peptide of TGF-β, prevents its activation, and enhances the anti-tumor activity of ICIs including CD8+ T-cell infiltration in preclinical models.

Study Design

Figure 19:
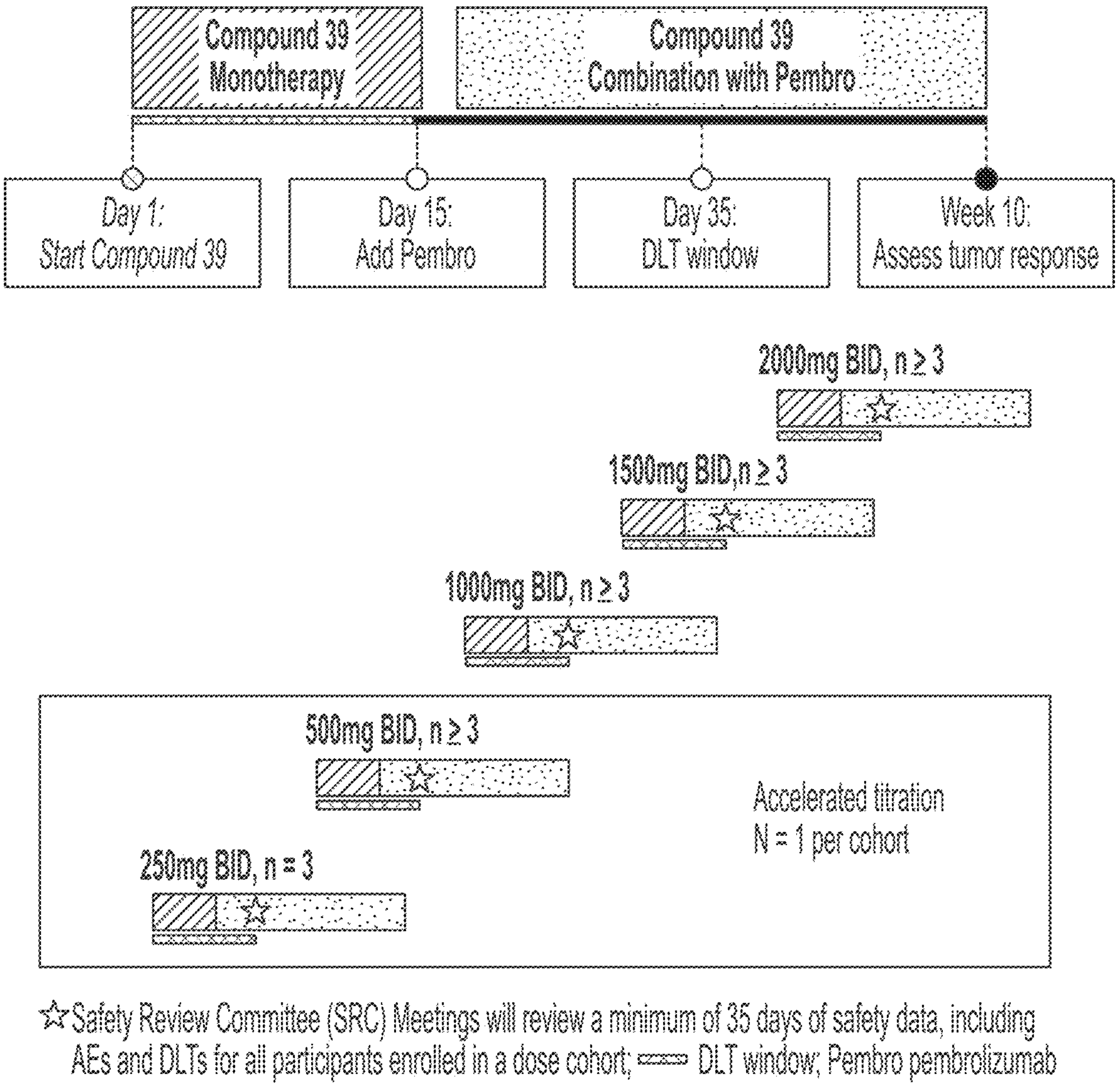
FIG. 19 shows a summary of the study design for the study of Example B10.

A Phase 1a, first-in-human, dose-escalation, consecutive-cohort, open-label study is designed to evaluate the safety, tolerability and pharmacokinetics of Compound 39 of the examples as monotherapy and in combination with pembrolizumab in patients with advanced or metastatic solid tumors progressing on treatment with pembrolizumab. Eligible subjects will be ≥18 years, have received at least 3 doses (200 mg Q3W) of pembrolizumab, have evidence of disease progression at least 3 months after initiation of pembrolizumab, have no other available effective treatment options, have an Eastern Cooperative Oncology Group (ECOG) performance status of 0 or 1, and have adequate bone marrow and organ function. The ECOG performance scale is used to assess how a subjects disease is progressing, to assess how the disease affects the daily living abilities of the subject, and to determine an appropriate treatment and prognosis for the subject. Compound 39 will be administered as a lead-in monotherapy for 14 days, followed by Compound 39 in combination with pembrolizumab Q3W every three weeks, starting on Day 15. The five dose levels will be as follows:

Level 1: 250 mg, administered twice daily (BID)
Level 2: 500 mg BID
Level 3: 1000 mg BID
Level 4: 1500 mg BID
Level 5: 2000 mg BID Dose-escalation will be determined by a Bayesian optimal interval (BOIN) dose escalation design with accelerated titration (n=1) permitted for dose levels 1 and 2 (FIG. 19). FIG. 66 depicts a schematic diagram of the BOIN dose escalation and decision criteria for Example B10. As shown in FIG. 66, the BOIN dose escalation and decision criteria begins with administering a starting dose of Compound 39 to the target number of subjects in a treatment cohort. If the stopping rules have been met, administration of Compound 39 will be stopped. If the stopping rules have not been met, a dose-limiting toxicity (DLT) rate will be calculated. The DLT rate is calculated as (number of subjects experiencing at least one DLT at the current dose during the DLT assessment period)/(total number of subjects being exposed to the current dose).

Table B-6 is associated with FIG. 66.

TABLE B-6

Actions associated with the BOIN dose escalation and decision criteria

| Action[a] | Number of Evaluable Subjects in Current Dose Cohort | | | | | | | | |
|---|---|---|---|---|---|---|---|---|---|
| | 1 | 2 | 3 | 4 | 5 | 6 | 7 | 8 | 9 |
| Escalate if the number of DLTs[d] ≤ | 0 | 0 | 0 | 0 | 1 | 1 | 1 | 1 | 2 |
| De-escalate if the number of DLTs ≥ | 1[b] | 1 | 2 | 2 | 2 | 3 | 3 | 3 | 4 |
| Eliminate Dose | N/A[c] | N/A | 3 | 3 | 4 | 4 | 5 | 5 | 5 |

[a]When none of the actions (escalate, de-escalate, or eliminate) are triggered, the current dose will be maintained and the cohort will be expanded to treat additional subjects.
[b]In a dose level with accelerated titration, if one DLT is observed in the first subject, the cohort will be expanded with two additional subjects.
[c]"N/A" refers to "not applicable."
[d]"DLT" refers to "dose-limiting toxicity."

A minimum of 3 participants are accrued to dose levels 3 to 5. Following the dose-escalation cohorts, dose-expansion cohorts using a Simon's 2-stage design are planned.

FIG. 64 depicts a schematic diagram of the Phase 1 clinical overview: two-part study to assess safety, tolerability, pharmacokinetics and preliminary evidence of antitumor activity. FIG. 65 depicts a schematic diagram of the clinical biomarker plan. As shown in FIG. 65, biomarkers will be collected from the subject on Day 28. The biomarkers may include circulating immune cells, circulating markers, circulating tumor DNA, and archival tissue. In some embodiments, the circulating immune cells are retrieved using a CyTOF human immune panel. In some embodiments, the circulating markers include Pro-C3, C4G, GzmB, IFN γ, IL-10, PD-1, PD-L1, TNFα, CXCL9, CCXL12, VEGFα, and $\alpha_v\beta_8$. In some embodiments, the archival tissue is retrieved using the RNA-Seq technique.

Primary Endpoints

The primary endpoint is safety and tolerability following administration of escalating doses of Compound 39 as the monotherapy for 14 days, followed by Compound 39 in combination with pembrolizumab starting on Day 15 for 21 days. The subjects will be regularly monitored for treatment-emergent adverse events (AEs) and serious AEs. The number of subjects with DLTs (e.g., treatment-emergent AEs within the first 35 days of dosing) will be summarized by Compound 39 dose cohort for the DLT population and for the number of subjects with the DLTs leading to treatment discontinuation. An additional safety follow-up visit for evaluation of any latent serious AEs will be conducted at 16 weeks after completion of dosing with Compound 39 and pembrolizumab.

Secondary Endpoint

The secondary endpoint includes the pharmacokinetics of Compound 39 given as a monotherapy and in combination with pembrolizumab.

Exploratory Endpoints

The exploratory endpoints include the following:

Change from baseline in blood-based biomarkers (e.g., cytokines, circulating tumor DNA, and blood cell profile), Relationship between pharmacokinetic parameters, biomarkers, and clinical outcomes, Objective response rate per Immunological Response Evaluation Criteria in Solid Tumors (iRECIST) at Week 10 (Day 70) and as assessed every 8 weeks thereafter, Disease control rate (DCR) per iRECIST at Week 10 (Day 70) and as assessed every 8 weeks thereafter, Proportion of participants with stable disease per iRECIST at Week 10 (Day 70) and as assessed every 8 weeks thereafter, Proportion of participants with unconfirmed progression at Week 10 (Day 70) and as assessed every 8 weeks thereafter, and Proportion of participants with confirmed progression at Week 10 (Day 70) or Week 14 (Day 98, if applicable).

Summary

This first-in-human trial will evaluate the safety and tolerability of Compound 39, administered first as monotherapy to re-sensitize participants' tumors to pembrolizumab, and subsequently in combination with pembrolizumab. Enrolled patients have demonstrated primary or acquired resistance to pembrolizumab and therefore serve as their own control for assessing anti-tumor activity and pharmacodynamic effects. This trial design allows for the efficient conduct of dose escalation trials involving ICI-sensitizing drugs in patients with resistance to ICIs.

Example B11—Characterization of the Therapeutic Impact of Compound 39 Alone and in Combination with Anti-PD-1 or Chemotherapy in Murine Syngeneic or Patient-Derived Xenograft (PDX) Models of Pancreatic Ductal Adenocarcinoma (PDAC)

Table B-7 depicts the KPC model details associated with Example B11. Table B-8 depicts the KPC study groups and dosing regimen, which included a twenty-two-day timepoint (6-9 subjects in each group) and up to 80 days survival (8-9 subjects in each group).

TABLE B-7

KPC Model Details

| | |
|---|---|
| Model | KPC model with Luciferase-eGFP |
| Strain | C57BL/6 |
| Number of mice on study | 60 |
| Number of groups | 6 |
| N per group | 6-9 |
| Inoculation | 500 KPC cells Intra-Pancreatic Transplantation |
| Dosing regimen | See below |
| Dosing route | Oral Gavage/IP |

TABLE B-7-continued

| KPC Model Details | |
|---|---|
| Dosing duration | 22 days for timepoint and 80 days for survival |
| BW and TV measurement frequency | Twice a week (TV estimate via IVIS once per week) |
| Randomization range | Confirmation of single positive signal via IVIS imaging (day 7 post-transplant) |
| Dietary supplements | N/A |
| Dosing holiday | None |
| Tissue collections | Tumors, Serum. |
| Maximal tumor volume (MTV) | Sign of ascites, large palpable tumor mass |

TABLE B-8

KPC Study Groups and Dosing Regimen

| Group | N | Treatment | Dose Route | Dosing Frequency & Duration | Dose Level (mg/kg) | Dose Volume (mL/kg) |
|---|---|---|---|---|---|---|
| 1 | 13-16 | Vehicle | Oral Gavage | Daily | — | 5-10 |
| 2 | 13-16 | Anti-PD-1 | i.p. | BIW x till study end. Start at D 12 | 10 | 10 |
| 3 | 13-16 | Rat IgG2A | i.p. | BIW x till study end. Start at D 12 | 10 | 10 |
| 4 | 13-16 | Compound 39 | Oral Gavage | daily Start at D 12 | 300 BID | 5-10 |
| 5 | 13-16 | Anti-PD-1 | i.p. | BIW x till study end Start at D 12 | 10 | 10 |
| | | Compound 39 | Oral Gavage | daily Start at D 12 | 300 BID | 5-10 |
| 6 | 13-16 | ADWA11 | i.p. | BIW x till study ends. Start at D 12 | 10 | 10 |

Experimental Methods

Tumor Implantation

Animals were prepared for injection using standard approved anesthesia. Mice were shaved and tumor cells 500 KPC cells were orthotopically implanted (in pancreas) in a 100 μL cell suspension.

Randomization and Drug Treatment

Tumor cells were allowed to form pancreatic tumors for one week. Mice were randomized into groups and treated with indicated compounds and dose regimens according to the schema outlined in Table B-7.

Compound 39 was administered in a solution containing 10% v/v ethanol, 70% w/v propylene glycol, and 20% v/v PBS and administered to mice via oral gavage at a dose of 300 mg/kg body weight over the duration of 22 days (for timepoint study) or 80 days (survival study). The mAbs, anti-mPD-1 and anti-$\alpha_v\beta_8$, were each administered in PBS by intraperitoneal injection at a dose of 10 mg/kg body weight twice a week (for 2 weeks). The mPD-1 (CD279) Ab was purchased from Bio X Cell Inc. (West Lebanon, NH). The anti-$\alpha_v\beta_8$ antibody ADWA11 was synthesized and manufactured by GenScript Biotech Corporation (Piscataway, NJ). The rat immunoglobulin G2a (IgG2A) antibody was purchased by Crown Bio Inc.

Tumor Monitoring and Measurements

Since these were orthotopic tumors, tumor volume measurement was not possible. Tumor weights were determined at the end of the study. Additionally, body weight of mice and any change in behavior/appearance were monitored twice a week for any signs of discomfort/toxicity.

Study Termination

The study was terminated either at 22 days after the first dose, or at 80 days for the survival study. Mice were euthanized and tumors were collected. Half of the tumor was snap frozen in liquid nitrogen and the other half was fixed in formalin.

Immunohistochemical Analysis

Formalin (10%) fixed tissues were sent to Histowiz (a clinical research organization providing complete histology services) for paraffin embedding and sectioning. Using standard protocols optimized by Histowiz, tissue sections were stained for hematoxylin and eosin and immunostained for CD8, CD4, Cleaved caspase-3, and FoxP3, which are specific membrane markers for cytotoxic, helper, and regulator T cells, respectively. Additionally, tissues were stained with Pico Sirius Red (PSR) and second harmonic imaging (SHG) analysis was performed to evaluate stromal collagen density.

Results

Figure 20A:
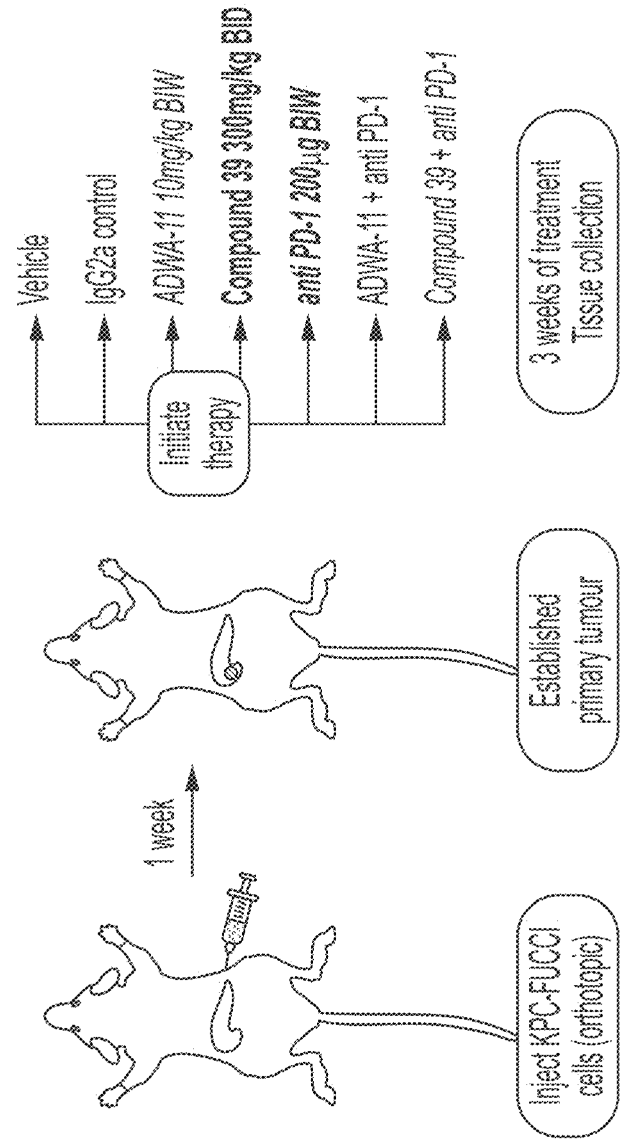
FIG. 20A shows a schematic diagram of the treatment regimen for the study of Example B11.

Compound 39 Alone and in Combination with Anti PD-1 Significantly Reduced KPC Tumor Weight FIG. 20A shows a schematic diagram of the treatment regimen for the study of Example B11. The mean tumor volumes of KPC tumor bearing mice treated with Compound 39 were significantly lower (mean tumor weight 0.44±0.9 g) than the tumor volumes of mice treated with vehicle (mean tumor weight 0.77±0.22).

Figure 20B:
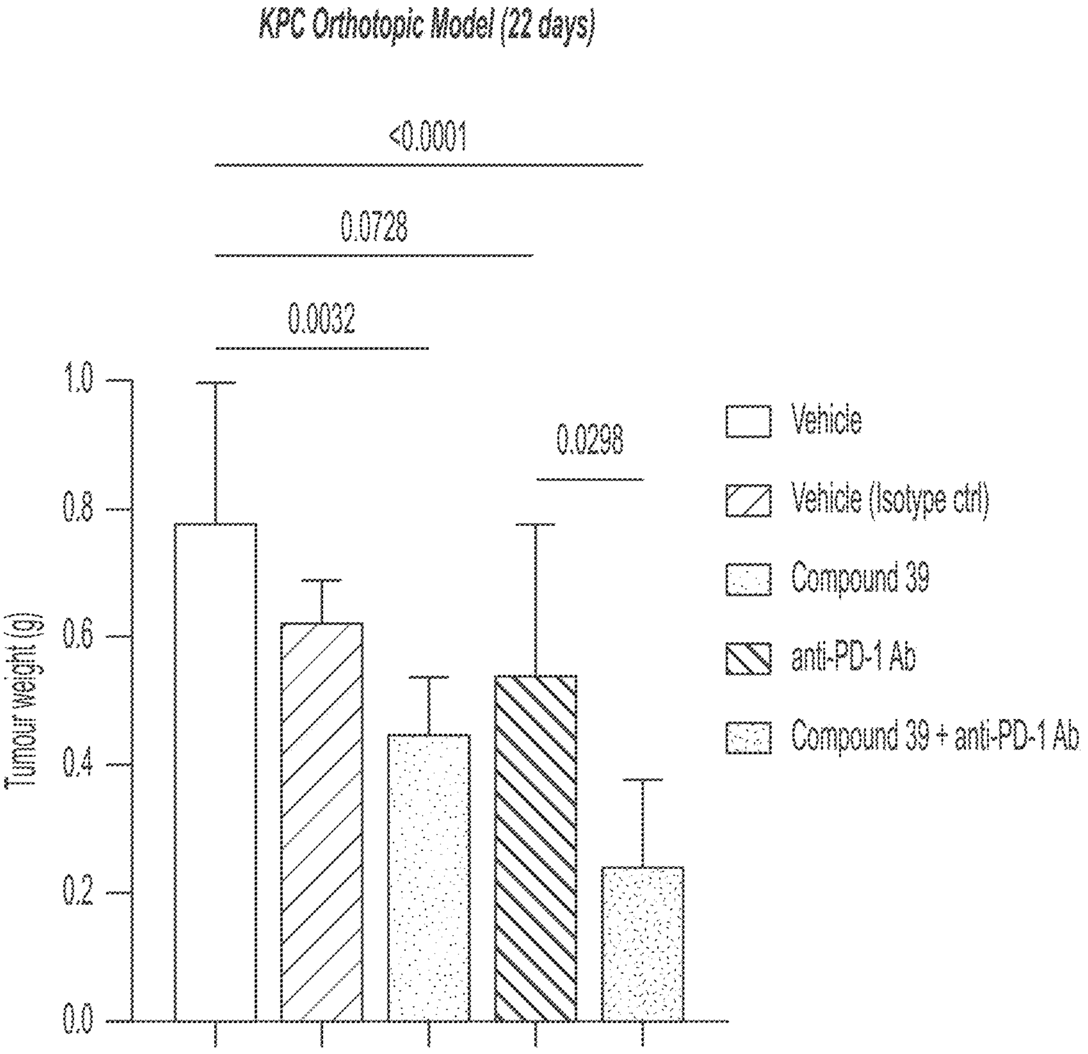
FIG. 20B shows tumor weights of KPC tumors in mice treated with Compound 39 alone or in combination with anti PD-1 Ab. Error bars ±S.D. and p values by one-way ANOVA.
Figure 20C:
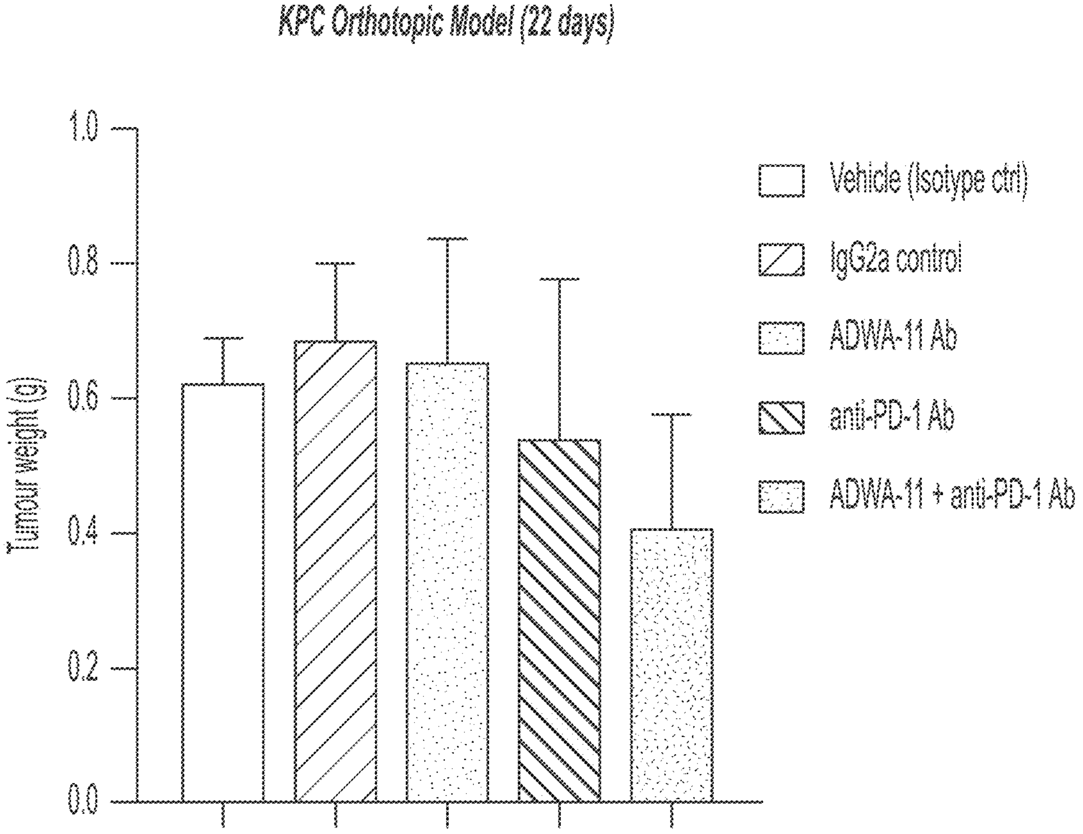
FIG. 20C shows tumor weights of KPC tumors in mice treated with ADWA-11 alone or in combination with anti PD-1. Error bars ±S.D. and p values by one-way ANOVA.

FIG. 20B shows tumor weights (in g) of KPC tumors in mice treated with Compound 39 alone or in combination with anti PD-1 Ab and FIG. 20C shows tumor weights (in g) of KPC tumors in mice treated with ADWA-11 alone or in combination with anti PD-1. As shown in FIG. 20B, a combination of Compound 39+anti PD-1 significantly reduced the tumor weight (mean tumor weight 0.24±0.13 g) compared to tumors treated with anti PD-1 alone (mean tumor weight 0.3±0.23 g). Notably, neither ADWA-11 not ADWA11+anti PD-1 had any significant effect on tumor weights, as shown in FIG. 20C.

Figure 21A:
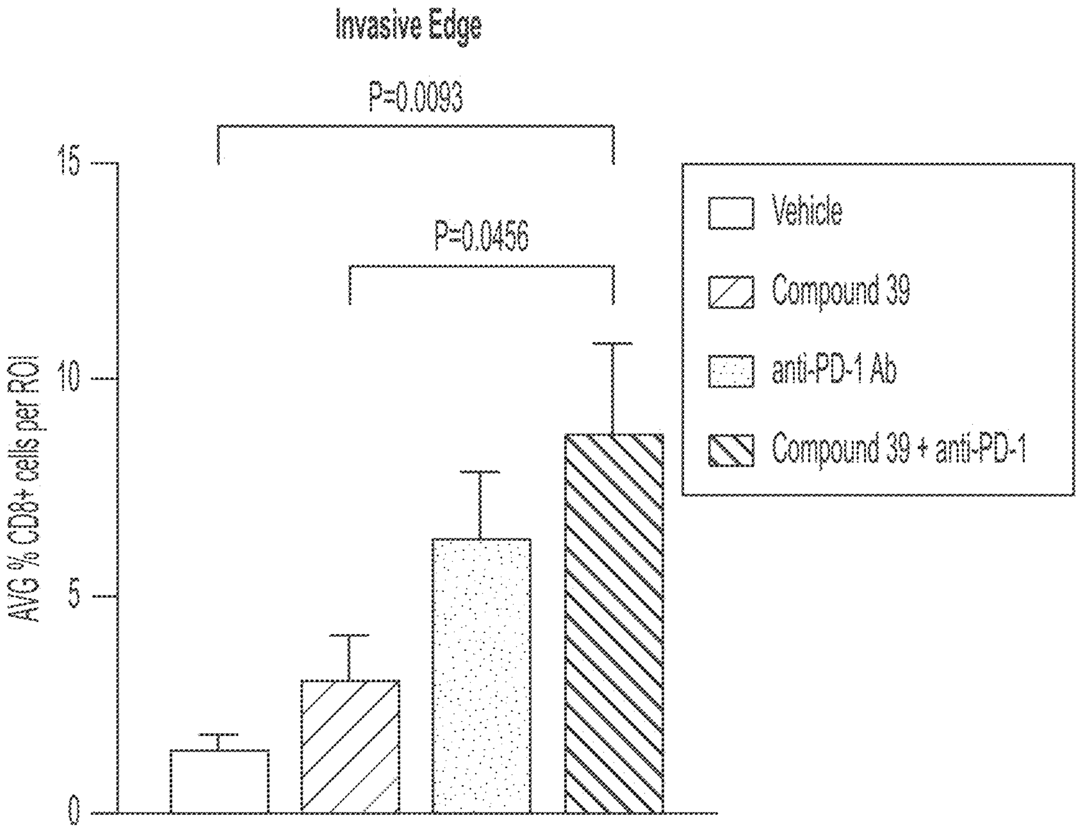
FIG. 21A shows a graph measuring the average percentage of CD8+ cells per ROI in the invasive edge treated with Compound 39 alone or in combination with anti PD-1 Ab. Bars ±SEM and p values by one-way ANOVA.
Figure 21B:
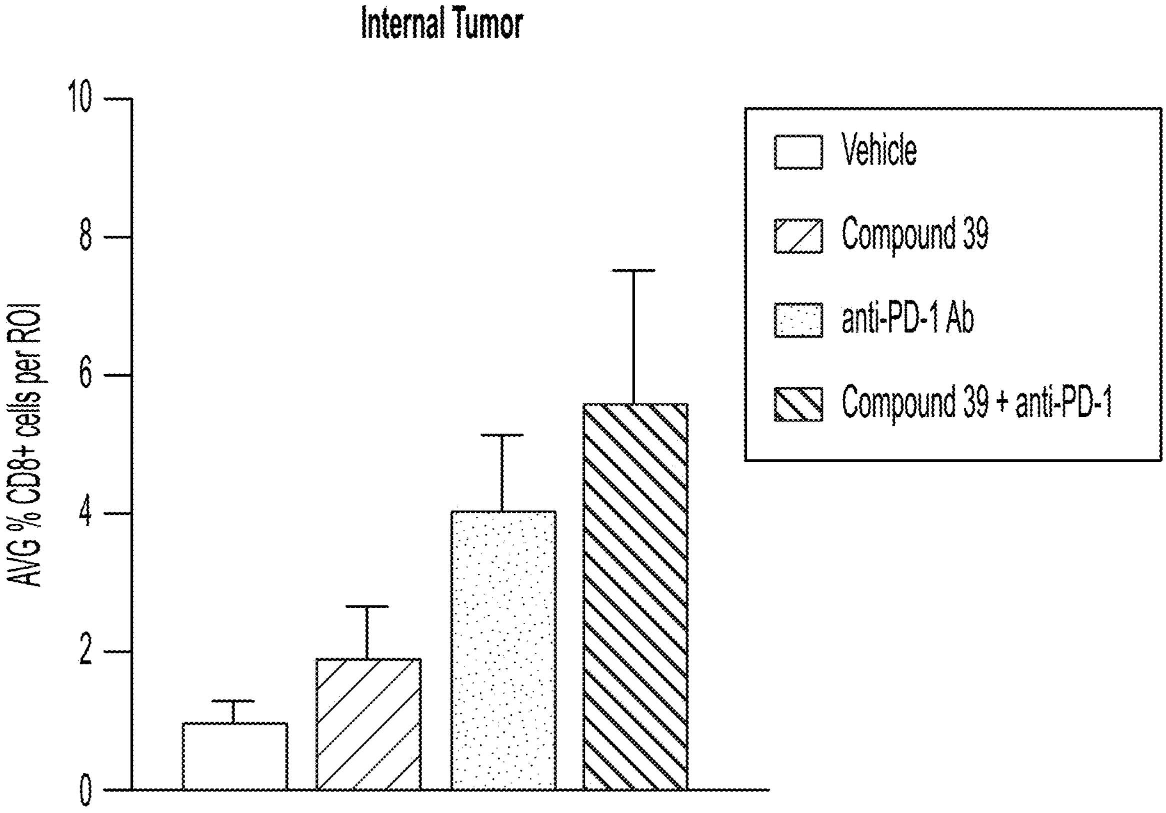
FIG. 21B shows a graph measuring the average percentage of CD8+ cells per ROI in the internal KPC tumor treated with Compound 39 alone or in combination with anti PD-1 Ab. Bars ±SEM and p values by one-way ANOVA.
Figure 21C:
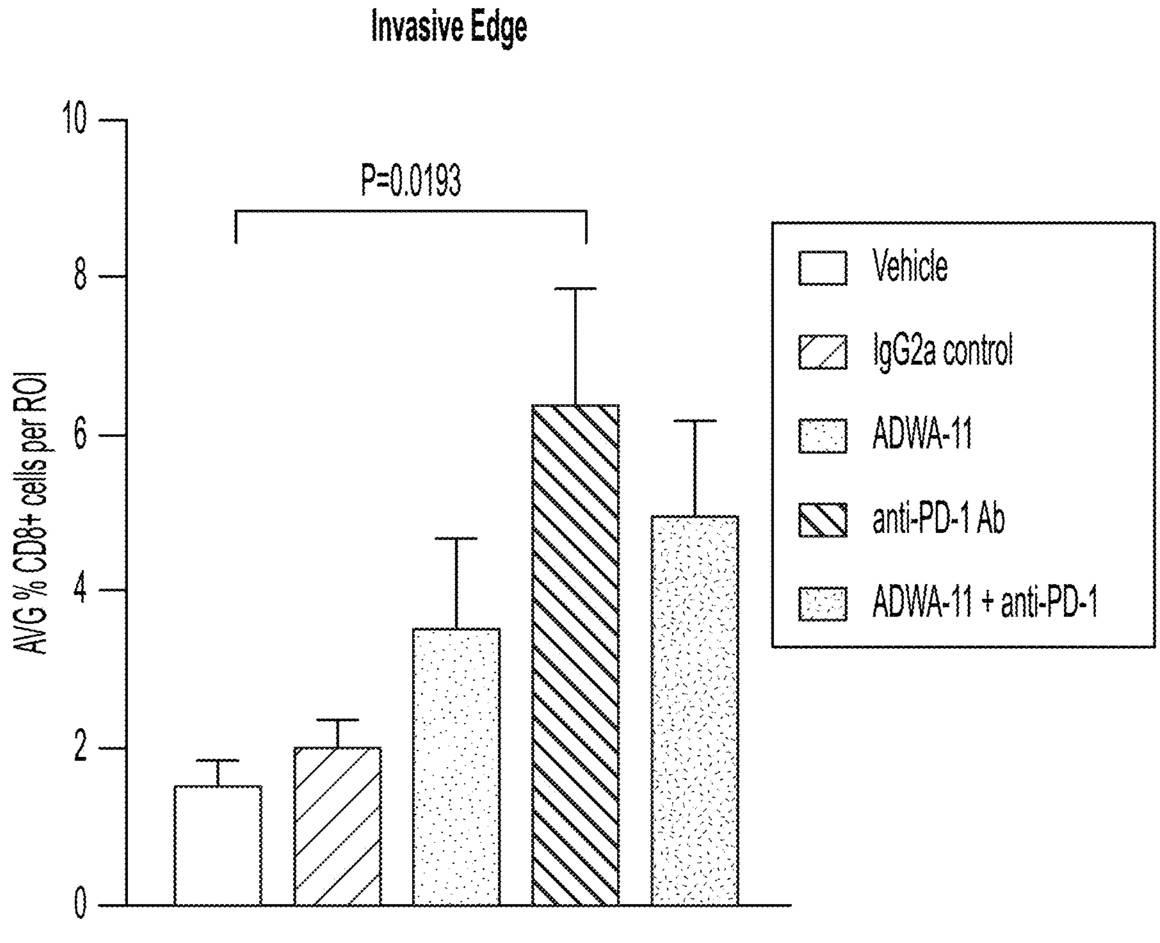
FIG. 21C shows a graph measuring the average percentage of CD8+ cells per ROI in the invasive edge treated with ADWA-11 alone or in combination with anti PD-1. Bars ±SEM and p values by one-way ANOVA.
Figure 21D:
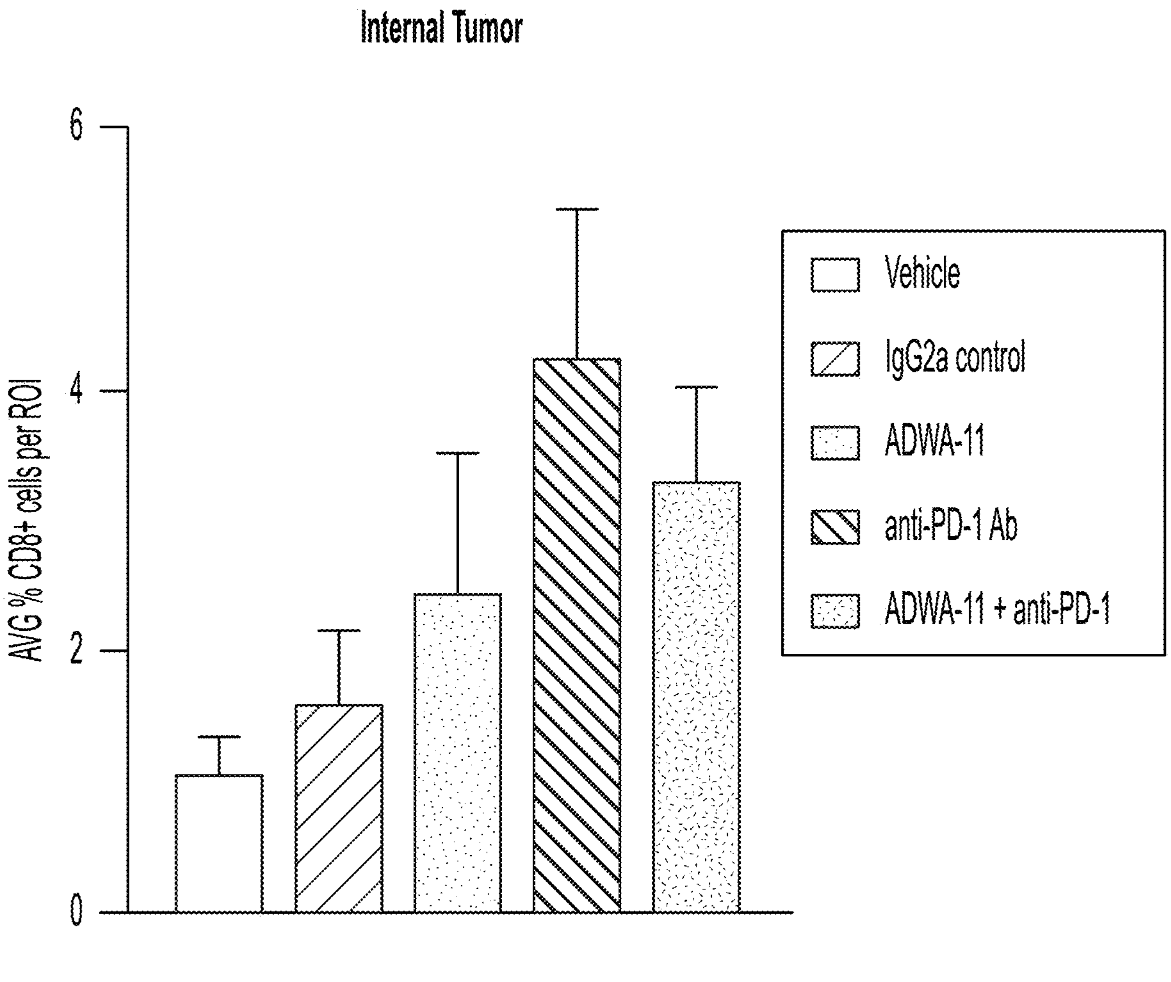
FIG. 21D shows a graph measuring the average percentage of CD8+ cells per ROI in the internal KPC tumor treated with ADWA-11 alone or in combination with anti PD-1. Bars ±SEM and p values by one-way ANOVA.

Compound 39 in Combination with Anti PD-1 Significantly Increased $CD8^+$ T Cell Infiltration in KPC Tumors Paraffin-fixed KPC tumor slices were stained for CD8 antigen to identify cytotoxic T cells. FIG. 21A shows a graph measuring the average percentage of CD8+ cells per ROI in the invasive edge treated with Compound 39 alone or in combination with anti PD-1 Ab. FIG. 21B shows a graph measuring the average percentage of CD8+ cells per ROI in the internal KPC tumor treated with Compound 39 alone or in combination with anti PD-1 Ab. FIG. 21C shows a graph measuring the average percentage of CD8+ cells per ROI in the invasive edge treated with ADWA-11 alone or in combination with anti PD-1. FIG. 21D shows a graph measuring the average percentage of CD8+ cells per ROI in the internal KPC tumor treated with ADWA-11 alone or in combination with anti PD-1.

As shown in FIG. 21A and FIG. 21B, treatment of Compound 39 alone and in combination with anti PD-1 increased $CD8^+$ T cells in KPC tumors. Specifically, as shown in FIG. 21A and FIG. 21B, KPC tumors treated with Compound 39 alone had increased $CD8^+$ cells both in the leading edge (avg % $CD8^+$ T cells/ROI 3.06±1.05 in the Compound 39 arm compared to 1.5±0.32 in the vehicle arm) and in the internal tumor (avg % $CD8^+$ T cells/ROI 2.02±0.77 in the Compound 39 arm compared to 1.04±0.31 in the vehicle arm). Treatment of KPC tumors with Compound 50+anti PD-1 further increased the number of $CD8^+$ T cells both in the invasive edge (avg % $CD8^+$ T cells/ROI 8.77±2.05 in the Compound 39 arm compared to 1.5±0.32 in the vehicle arm) and in the internal tumor (avg % $CD8^+$ T cells/ROI 5.9±1.98 in the Compound 39 arm compared to 1.04±0.31 in the vehicle arm). Interestingly, as shown in FIG. 21C and FIG. 21D, ADWA11 had a similar effect in increasing the $CD8^+$ T cells when used as a single agent. However, the effect was reduced when ADWA11 was combined with anti PD-1.

Figure 21E:
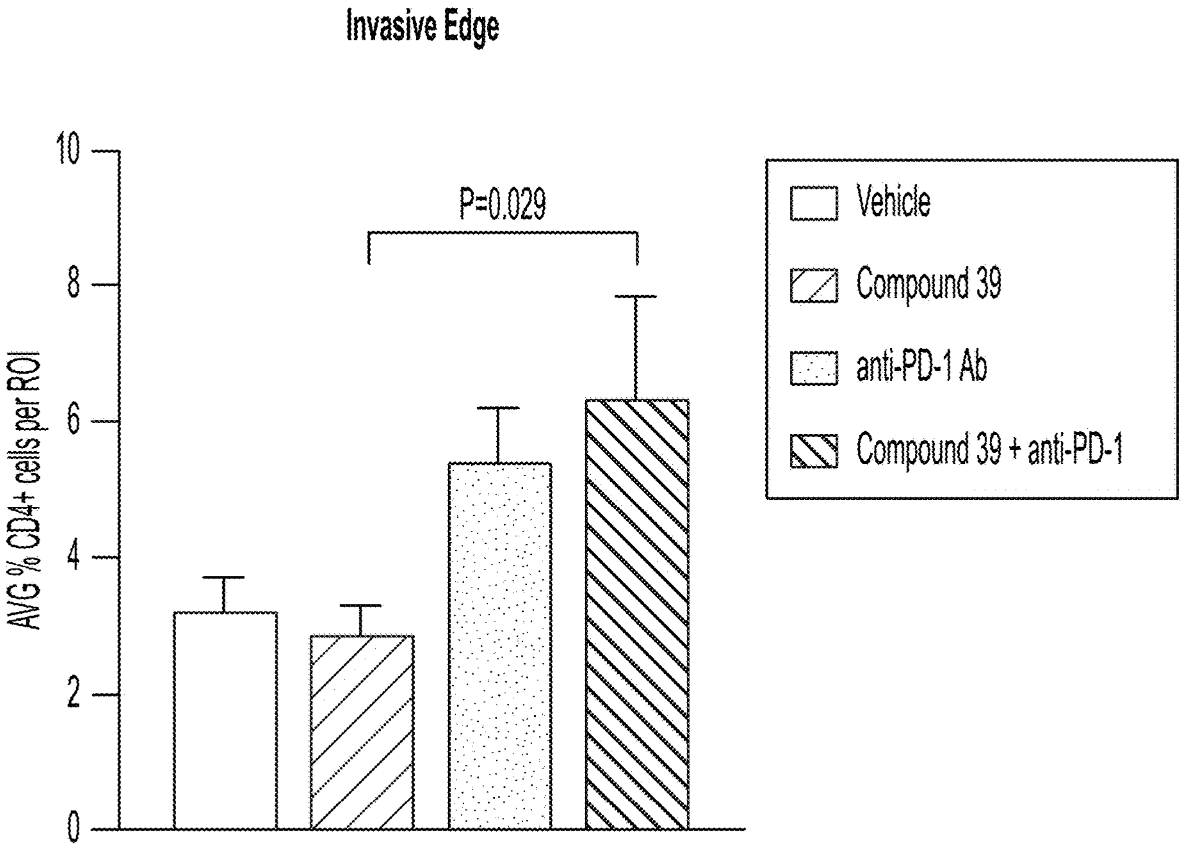
FIG. 21E shows graphs measuring the average percentage of CD4+ cells per ROI in the invasive edge treated with Compound 39 alone or in combination with anti PD-1 Ab. Bars ±SEM and p values by one-way ANOVA.
Figure 21F:
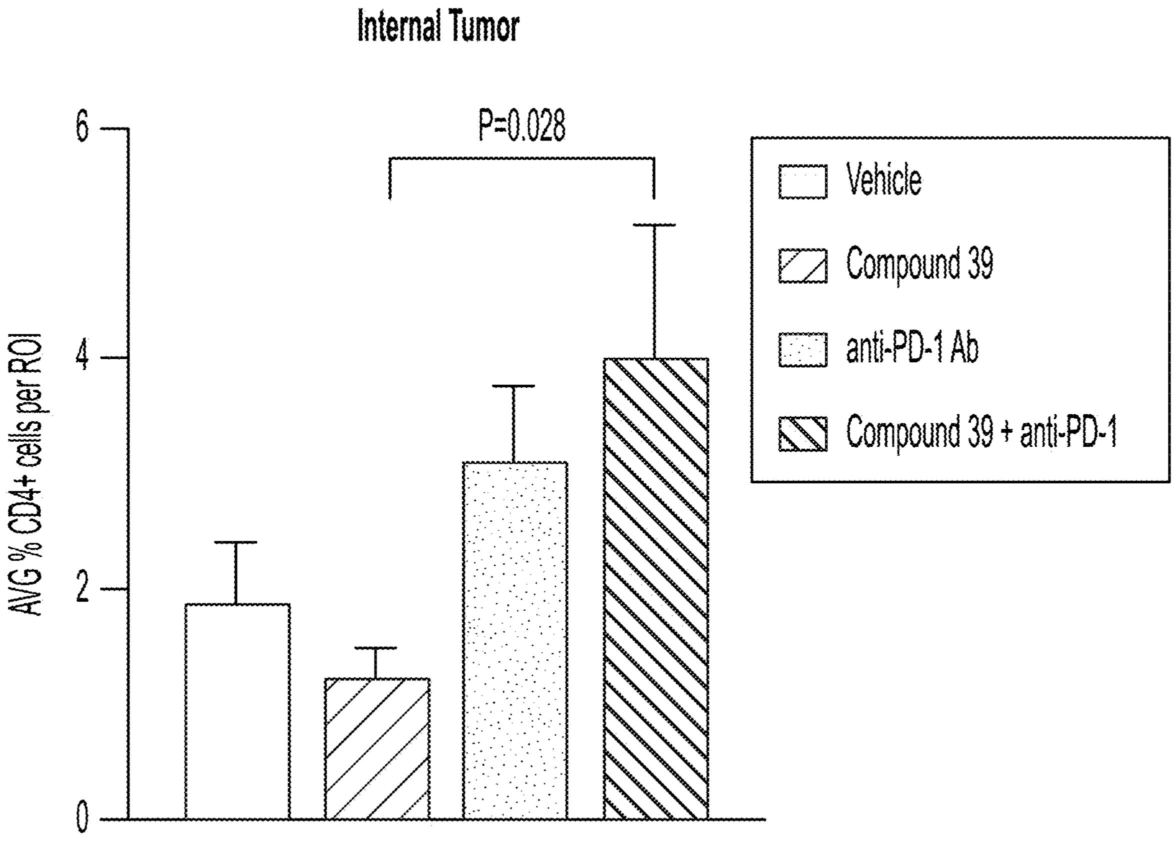
FIG. 21F shows graphs measuring the average percentage of CD4+ cells per ROI in the internal KPC tumor treated with Compound 39 alone or in combination with anti PD-1 Ab. Bars ±SEM and p values by one-way ANOVA.

Compound 39 in Combination with Anti PD-1 Increased $CD4^+$ T Cell Infiltration in KPC Tumors Paraffin-fixed KPC tumor slices were stained for CD4 antigen to identify helper T cells. FIG. 21E shows graphs measuring the average percentage of CD4+ cells per ROI in the invasive edge treated with Compound 39 alone or in combination with anti PD-1 Ab. FIG. 21F shows graphs measuring the average percentage of CD4+ cells per ROI in the internal KPC tumor treated with Compound 39 alone or in combination with anti PD-1 Ab. FIG. 21E and FIG. 21F shows graphs measuring the average percentage of CD4+ cells per ROI in the invasive edge and the internal KPC tumor treated with Compound 39 alone or in combination with anti PD-1 Ab. KPC tumors treated with Compound 39 alone did not show any significant difference in $CD4^+$ T cells compared to the vehicle. However, treatment of KPC tumors with Compound 39+anti PD-1 increased the number of $CD8^+$ T cells compared to the vehicle treated arm in the invasive edge and in the internal tumor (see FIG. 21A, FIG. 21B, FIG. 21C, and FIG. 21D).

Compound 39 Reduced the Collagen Content in KPC Tumors

Figure 22A:
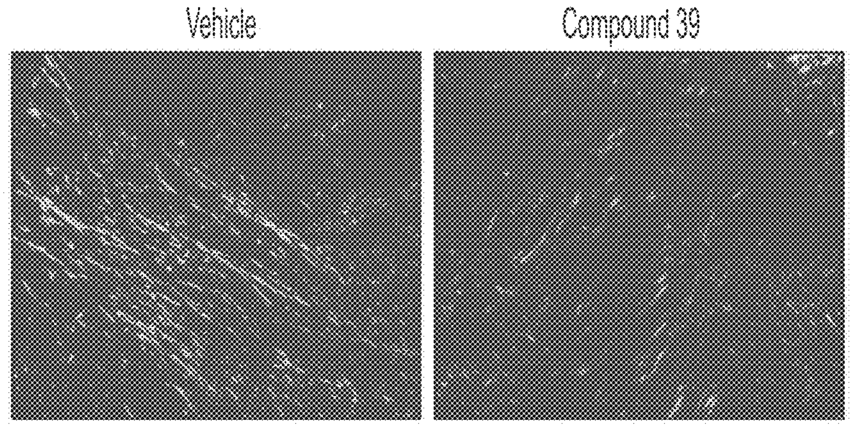
FIG. 22A shows paraffin-fixed KPC tumor slices stained with Pico Sirius Red (PSR) for a vehicle (left) and for KPC tumors treated with Compound 39 (right).
Figure 22B:
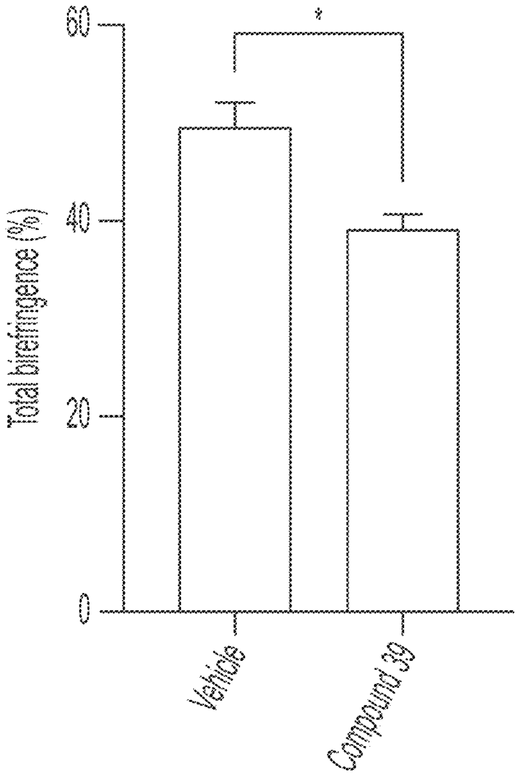
FIG. 22B shows a bar graph depicting a total birefringence for the vehicle and the KPC tumors treated with Compound 39 of FIG. 22A. Bars ±SEM and *=0.05 p value by student's t test.

Paraffin-fixed KPC tumor slices were stained with Pico Sirius Red (PSR) and were evaluated for changes in stromal collagen content (indicative of fibrosis) using SHG imaging. Specifically, FIG. 22A shows paraffin-fixed KPC tumor slices stained with PSR for a vehicle (left) and for KPC tumors treated with Compound 39 (right). As shown in FIG. 22A (right), treatment with Compound 39 significantly reduced the collagen content in the KPC tumors, indicative of reduced fibrotic stroma. FIG. 22B shows a bar graph depicting a total birefringence for the vehicle and the KPC tumors treated with Compound 39 of FIG. 22A. FIG. 55A depicts a graph associated with high birefringence (percentage) for vehicle and Compound 39. Statistical assessment by one-way ANOVA with Tukey. FIG. 55B depicts a graph associated with low birefringence (percentage) for vehicle and Compound 39. Statistical assessment by one-way ANOVA with Tukey. FIG. 55C depicts a graph associated with medium birefringence (percentage) for vehicle and Compound 39. Statistical assessment by one-way ANOVA with Tukey.

Compound 39 in Combination with Anti PD-1 Significantly Increased Survival of KPC Tumor Bearing Mice.

Figure 23A:
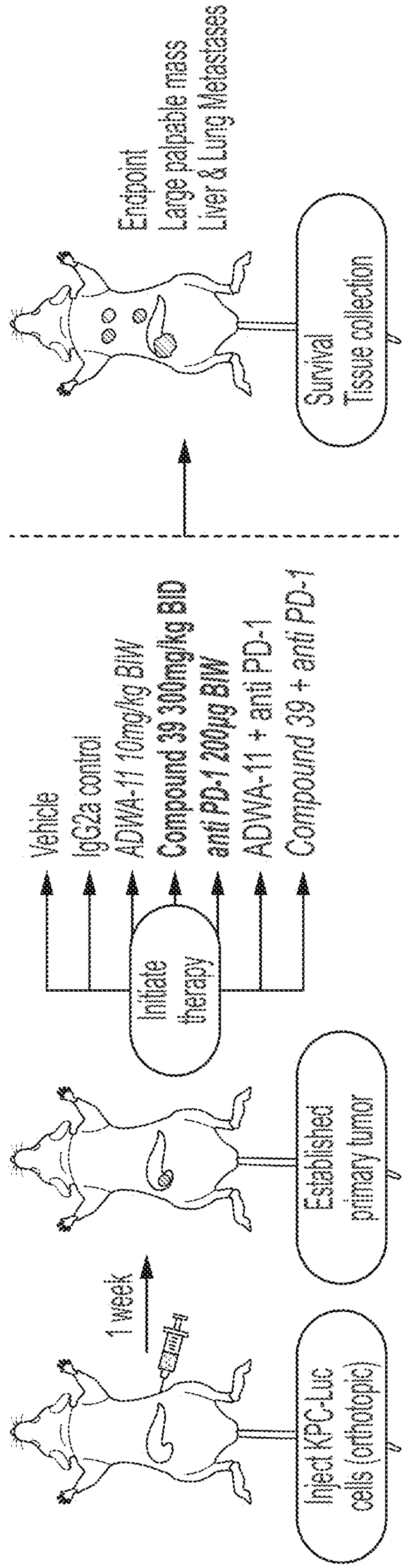
FIG. 23A depicts a schematic diagram of the treatment regimen for the study of KPC tumor mice for the survival study associated with Example B11.
Figure 23B:
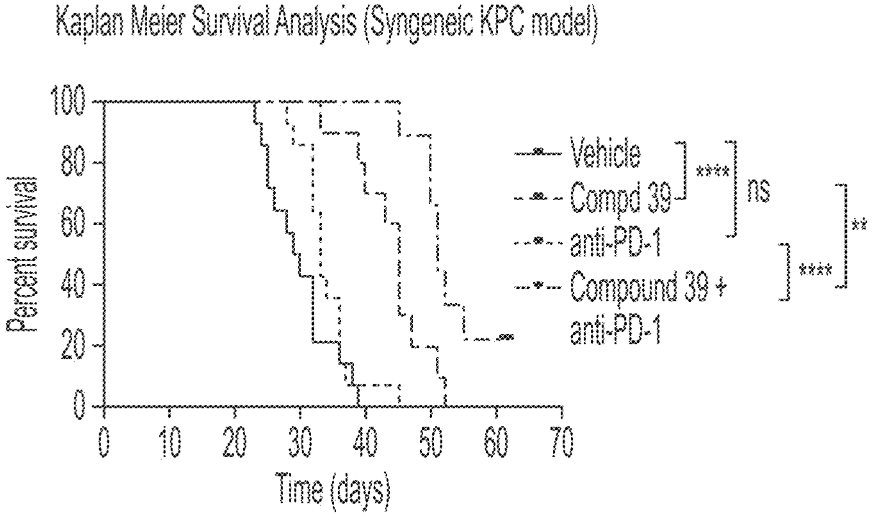
FIG. 23B depicts a first Kaplan Meier survival curve of an indicated treatment in KPC tumor bearing mice. P values by log rank analysis, *p=0.015, p=0.0059, and *p=<0.0001.
Figure 23C:
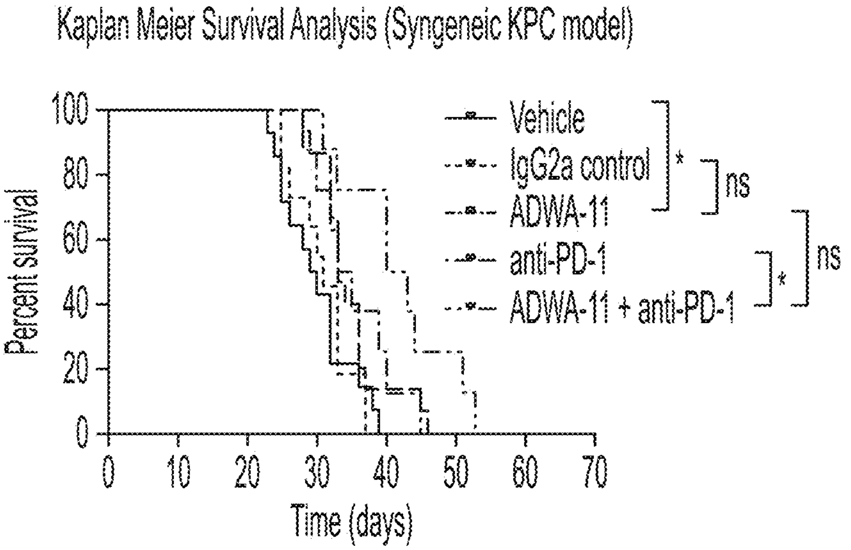
FIG. 23C depicts a second Kaplan Meier survival curve of an indicated treatment in KPC tumor bearing mice. P values by log rank analysis, *p=0.015, p=0.0059, and *p=<0.0001.

To assess if Compound 39 treatment increased the survival of the KPC tumor bearing mice, the KPC tumor bearing mice were treated with Compound 39 or ADWA-11 alone and in combination with anti PD-1 for 80 days according to the schematic diagram of the treatment regimen depicted in FIG. 23A. Compound 39 delayed disease progression in vivo, which was further delayed with the addition of an anti-PD-1 antibody. FIG. 23B depicts a first Kaplan Meier survival curve of an indicated treatment in KPC tumor bearing mice and FIG. 23C depicts a second Kaplan Meier survival curve of an indicated treatment in KPC tumor bearing mice. Specifically, in FIG. 23B, a first Kaplan Meier survival curve measures percent survival for subjects having internal KPC tumor treated with Compound 39 alone or in combination with anti PD-1 Ab. FIG. 23C depicts a second Kaplan Meier survival curve that measures percent survival for subjects having internal KPC tumor treated with ADWA-11 alone or in combination with anti PD-1 Ab.

FIG. 79 depicts a chart showing tumor weight (g) for a vehicle 128, Compound 39 130, anti-PD-1 Ab 132, and Compound 39+anti-PD-1 Ab 134. FIG. 80 depicts a chart showing tumor weight (g) for an IgG2a control 136, ADWA-11 Ab 138, anti-PD-1 Ab 140, and ADWA-11+anti-PD-1 Ab 142. As shown in FIG. 79, Compound 39 treatment effectively reduced tumor growth by 45% compared with vehicle. Combination ADWA-11+anti-PD1 did not significantly reduce tumor growth, as shown in FIG. 80.

Compound 39 treatment significantly increased the survival of animals compared to vehicle treated animals (median survival 45 days compared to 29.5 days in the vehicle treated animals), and compared to ADWA11 treated animals (median survival 34 days in ADWA11 treated animals compared to 45 days in the Compound 39 treated animals). Compound 39+anti PD-1 treatment further increased the survival as compared to anti PD-1 treatment (median survival 51 days in the Compound 39+anti PD-1 arm as compared to 33 days in the anti PD-1 arm) or compared to the ADWA-11+anti PD-1 arm (median survival of 41.5 days in the ADWA11+anti PD-1 arm compared to 51 days in the Compound 39+anti PD-1 arm). Two out of nine mice responded completely (22% complete response) with the Compound 39+anti PD-1 treatment.

Compound 39 Alone has Single Agent Activity and Potentiates α-PD-1 Therapy in the KPC Pancreatic Cancer Model FIG. 46 depicts a graph associated with tumor weight in an immunocompetent KPC model for various groups. Statistical assessment by one-way ANOVA. FIG. 47 depicts a survival curve in in an immunocompetent KPC model for various groups over 70 days. $^{}p<0.01$ by one-way ANOVA with Tukey and $^{}p<0.0001$ by one-way ANOVA with Tukey. As shown in FIG. 46-FIG. 47**, Compound 39 improved overall survival compared to α-PD-1.

Example B12—Assessment of Compound 39 Alone and in Combination with Gemcitabine/Abraxane (G/A) or Folfirinox in Patient-Derived Xenograft (PDX) Models of PDAC Table B-9 depicts the study design to determine the efficacy of selective $\alpha_v\beta_1/\alpha_v\beta_8$ SMI in the orthotopic ECM-high PDX models of PDAC. Table B-10 depicts the study design for the TKCC-10 PDX model.

TABLE B-9

Study design to determine the efficacy of selective $\alpha_v\beta_1/\alpha_v\beta_8$ SMI in the orthotopic ECM-high PDX models of PDAC

| | |
|---|---|
| Model(s) | PDAC-TKCC-10 PDAC-TKCC-05 ortho, PDAC-TKCC-08 (folfirinox resistant) |
| Strain(s) | NSG (NOD/SCIDIL2r gamma null) |
| Number of mice on study | 119 |
| Number of groups | 4-7 |
| N per group | 5-9 |
| Inoculation | Intra-pancreatic (TKCC-05, 10) and subcutaneous (TKCC-08) injection of primary PDCLs |
| Dosing regimen | See below |
| Dosing route | Oral Gavage/IP |
| Dosing duration | 30-60-day timepoint study |
| BW and TV measurement frequency | Twice a week, TV measurement via IVIS weekly |
| Randomization range | Optimized for the above models as 6 weeks post-implantation (IVIS signal confirmation) |

TABLE B-9-continued

| Study design to determine the efficacy of selective $\alpha_v\beta_1/\alpha_v\beta_8$ SMI in the orthotopic ECM-high PDX models of PDAC | |
|---|---|
| Dietary supplements | N/A |
| Dosing holiday | 1 week post completion of each 4-weekly treatment cycle |
| Tissue collections | Tumors, Serum. |
| Maximal tumor volume (MTV) | Endpoint (timepoint study-30 days) |

TABLE B-10

Study design for the TKCC-10 PDX model

| Group | N | Treatment | Dose Route | Dosing Frequency and Duration | Dose Level (mg/kg) | Dose Volume (mL/kg) |
|---|---|---|---|---|---|---|
| 1 | 5 | Vehicle | Oral | 30 days daily | — | |
| 2 | 6 | Compound 39 | Oral | 30 days | 300 mg/kg BID | |
| 3 | 6 | Gemcitabine/ Abraxane | i.p. | Once per week | G: 100 mg/kg/ A: 30 mg/kg | 10 |
| 4 | 6 | Compound 39 + G/A | Oral gavage; i.p. | As above | As above (per mono) | |
| 5 | 5 | ADWA11 | i.p. | BIW for 30 days | 10 mg/kg | |
| 6 | 6 | ADWA11 + Gemcitabine/ abraxane | i.p. | As above for 30 days | ADWA--- 10 mg/kg. Gem as above | |
| 7 | 6 | Rat IgG2A | i.p. | BIW for 30 days | — | |

Results

Figure 24A:
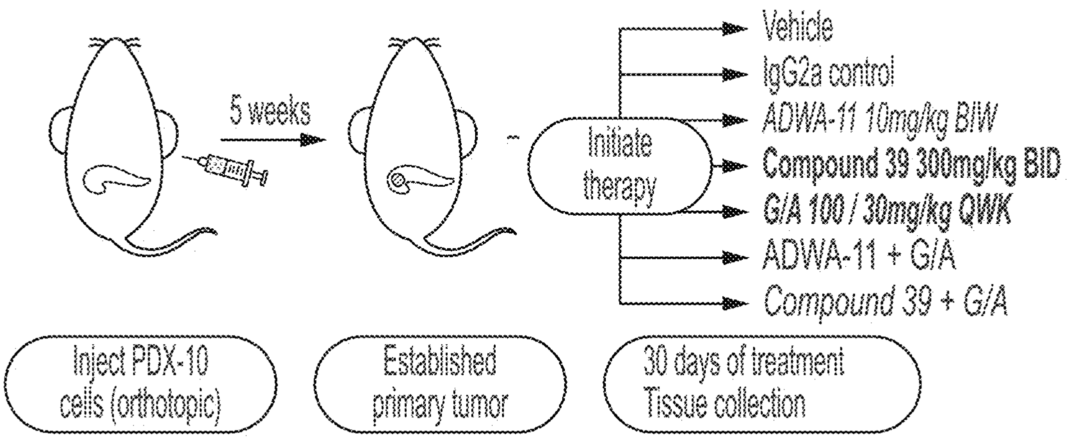
FIG. 24A depicts a schematic diagram of the treatment regimen in TKCC-10 mice for the study associated with Example B12.
Figure 24B:
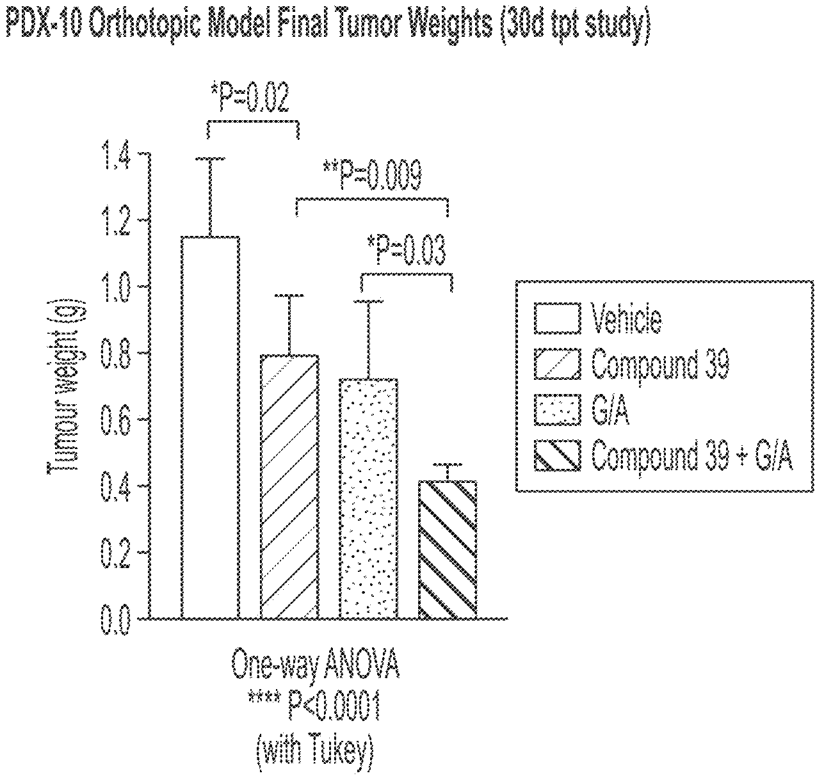
FIG. 24B depicts a graph showing final tumor weight for TKCC-10 PDX bearing mice after treatment with Gemcitabine/Abraxane (G/A), Compound 39, and Compound 39+G/A. P values by one-way ANOVA.
Figure 24C:
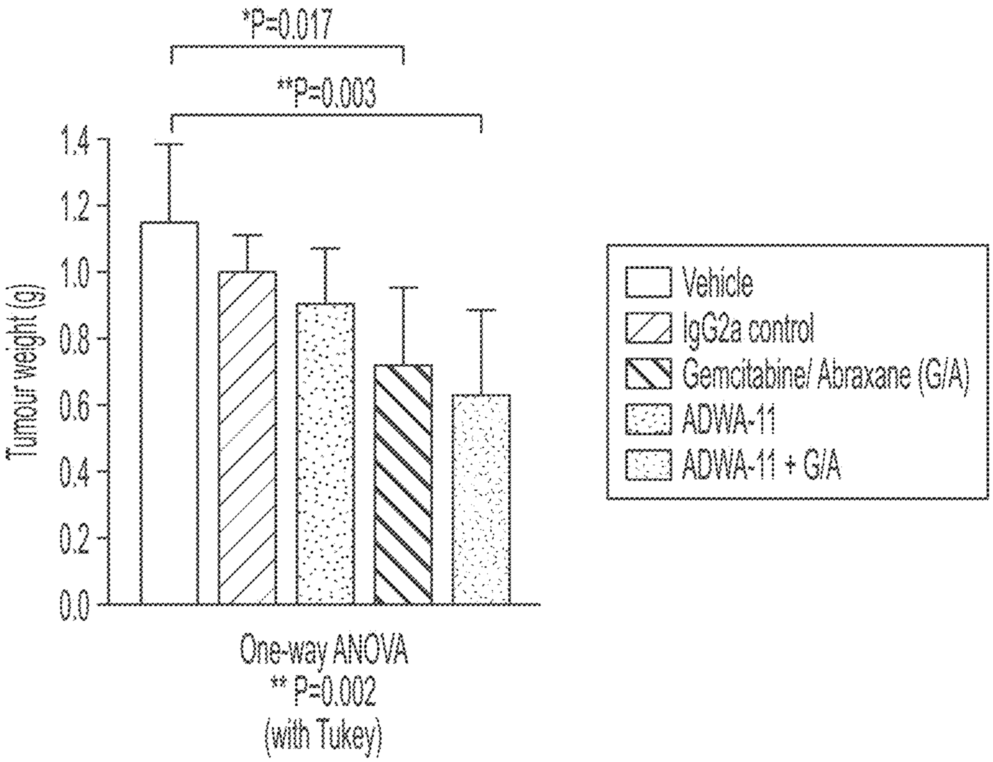
FIG. 24C depicts a graph showing final tumor weight for TKCC-10 PDX bearing mice after treatment with Gemcitabine/Abraxane (G/A), ADWA-11, and ADWA-11+G/A. P values by one-way ANOVA.

Compound 39 Treatment Significantly Reduced Tumor Weight in Mice Bearing TKCC-10 PDX TKCC-10 PDX bearing mice were treated with dose regimen according to the schematic in Table B-9 and FIG. 24A depicts a schematic diagram of the treatment regimen in the TKCC-10 mice. FIG. 24B depicts a graph showing final tumor weight for TKCC-10 PDX bearing mice after treatment with G/A, Compound 39, and Compound 39+G/A. FIG. 24C depicts a graph showing final tumor weight for TKCC-10 PDX bearing mice after treatment with G/A, ADWA-11, and ADWA-11+G/A.

Compound 39 significantly reduced the tumor weight of the TKCC-10 PDX bearing mice (mean tumor weight 0.798±0.17 g in the Compound 39 treated animals compared to 1.152±0.23 g in the vehicle treated animals) compared to the vehicle treated arm (see FIG. 24B). This decrease was similar to the G/A arm (mean tumor weight 0.73±0.22 g in the G/A treated animals) (see FIG. 24B). Compound 39 in combination with G/A further reduced the tumor weight significantly both compared to vehicle (mean tumor weight 0.41±0.04 g in the Compound 39+G/A arm as compared to 1.15±0.23 g in the vehicle) and compared to the G/A arm alone (mean tumor weight 0.73±0.22 g in the G/A arm as compared to 0.41±0.04 g in the Compound 39+G/A arm) (see FIG. 24B). ADWA-11 alone did not have any significant reduction in the tumor weights. ADWA-11 in combination with G/A was as effective as treatment with G/A alone, as shown in FIG. 24C.

Compound 39 Alone and in Combination with G/A Reduced the Lung Metastases in the TKCC-10 PDX Model.

Figure 25A:
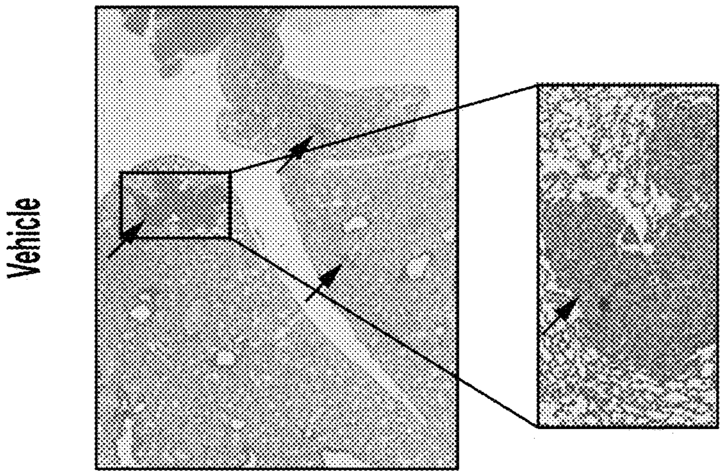
FIG. 25A depicts an image of lung metastases in vehicle treated TKCC-10 PDX bearing mice.
Figure 25B:
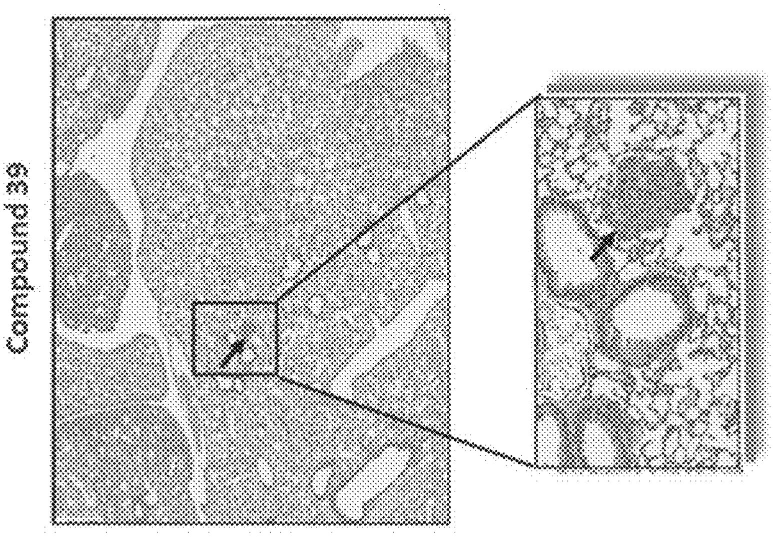
FIG. 25B depicts an image of lung metastases in Compound 39 treated TKCC-10 PDX bearing mice.
Figure 25C:
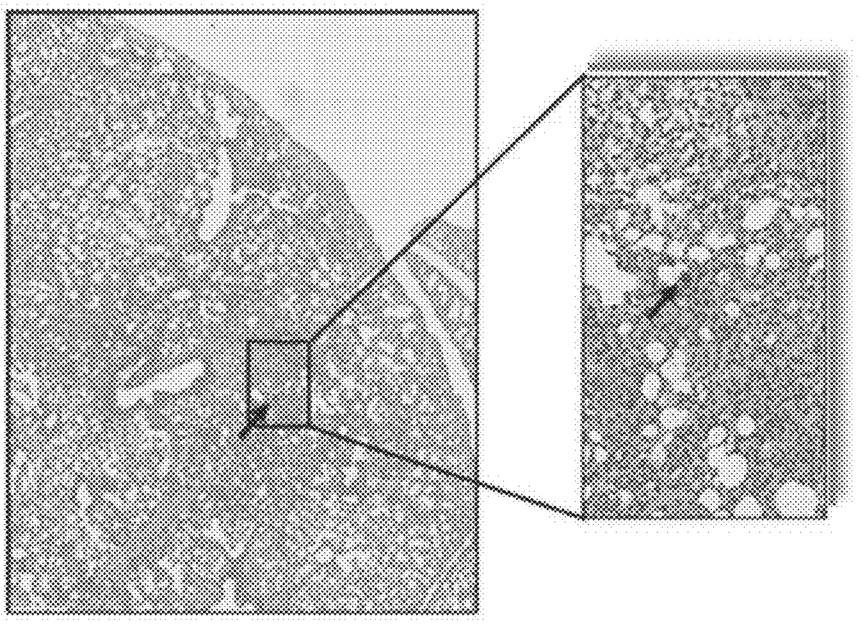
FIG. 25C depicts an image of lung metastases in Compound 39+Gemcitabine/Abraxane (G/A) treated TKCC-10 PDX bearing mice.

FIG. 25A depicts an image of lung metastases in vehicle treated TKCC-10 PDX bearing mice. FIG. 25B depicts an image of lung metastases in Compound 39 treated TKCC-10 PDX bearing mice. FIG. 25C depicts an image of lung metastases in Compound 39+G/A treated TKCC-10 PDX bearing mice.

Figure 25D:
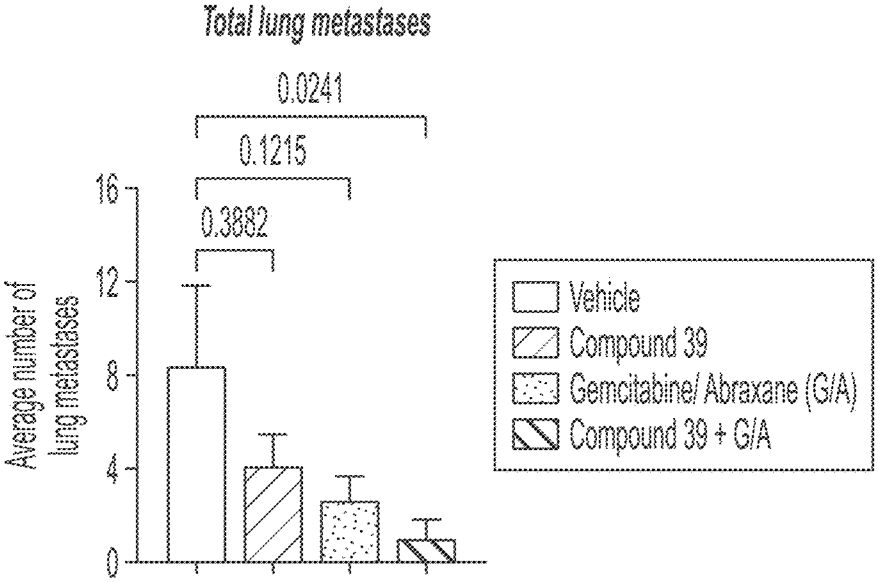
FIG. 25D depicts a graph associated with quantification of total lung metastases in TKCC-10 tumor bearing mice treated with Gemcitabine/Abraxane (G/A), Compound 39, and Compound 39+G/A for the study associated with Example B12. P values by one-way ANOVA.
Figure 25E:
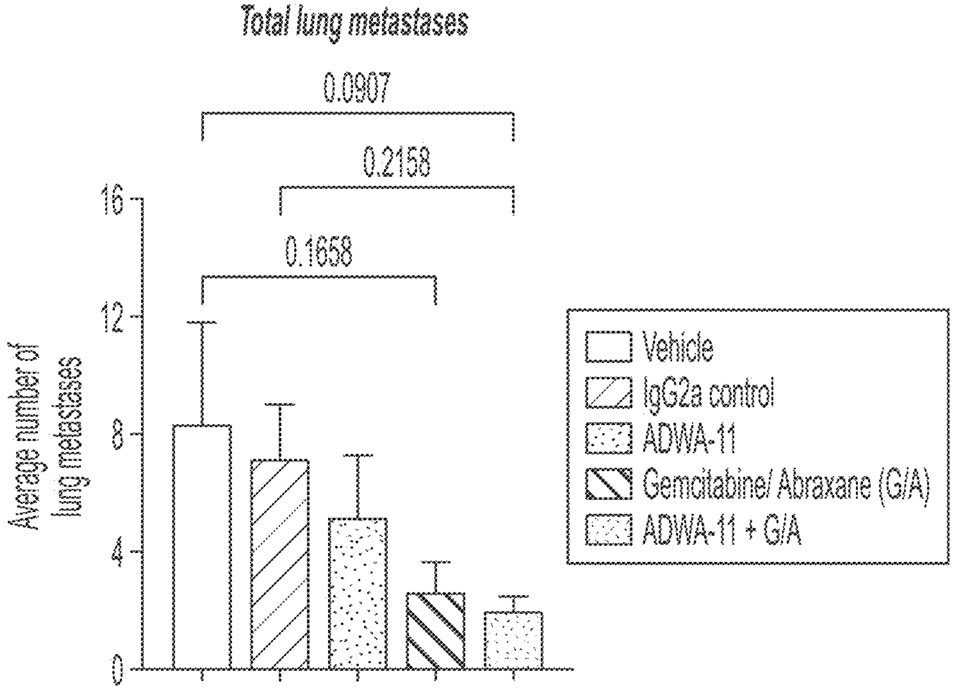
FIG. 25E depicts a graph associated with quantification of total lung metastases in TKCC-10 tumor bearing mice treated with Gemcitabine/Abraxane (G/A), ADWA-11, and ADWA-11+G/A for the study associated with Example B12. P values by one-way ANOVA.

FIG. 25D depicts a graph associated with quantification of total lung metastases in TKCC-10 tumor bearing mice treated with G/A, Compound 39, and Compound 39+G/A for the study associated with Example B12. FIG. 25E depicts a graph associated with quantification of total lung metastases in TKCC-10 tumor bearing mice treated with G/A, ADWA-11, and ADWA-11+G/A for the study associated with Example B12. P values by one-way ANOVA.

Treatment of TKCC-10 PDX bearing ice with Compound 39 alone reduced the number of lung metastases as compared to the vehicle (see FIG. 25A, FIG. 25B, FIG. 25C, and FIG. 25D) (mean number of metastases in the Compound 39 treated animals 4.1±3.2 as compared to 8.4±7.7 in the vehicle treated animals). Animals treated with G/A showed a similar reduction in total lung metastases (mean number of metastases 2.7±2.42). Compound 39+G/A significantly reduced the number of total metastases compared to the vehicle in the TKCC-10 tumor bearing mice (total number of metastases 1±2 in the Compound 39+G/A treated animals as compared to 8.4±7.7 in the vehicle treated animals). As shown in FIG. 25E, ADWA-11 in combination with G/A did not significantly reduce the total metastases.

Compound 39 has Single Agent Activity & Potentiates SOC in a High ECM PDX Model of Pancreatic Cancer FIG. 56 depicts a graph associated with tumor weight in an orthotopic immunodeficient PDX-10 model for vehicle, G/A, Compound 39, and Compound 39+G/A, where *$p<0.05$ by one-way ANOVA with Tukey, $p<0.01$ by one-way ANOVA with Tukey, and $p<0.0001$ by one-way ANOVA with Tukey. FIG. 57** depicts a graph associated with the average number of lung metastases in an orthotopic immunodeficient PDX-10 model for vehicle, G/A, Compound 39, and Compound 39+G/A, where *$p<0.05$ by one-way ANOVA with Tukey. As shown in FIG. 57, 66% of Compound 39+G/A treated mice were lung metastasis free compared to 0% with vehicle.

Compound 39 in Combination with Gemcitabine/Abraxane (G/A) Significantly Reduces Tumor Growth and Metastases in a PDX-10 Orthotopic Model FIG. 71 depicts a schematic diagram of a generic epithelial-mesenchymal transition (EMT) signature of PDX-10. FIG. 72 depicts a chart showing an amount of protein (ng/mg) for $\alpha_V\beta_1$ and $\alpha_V\beta_8$ in a PDX-10 orthotopic model.

FIG. 73 depicts a chart showing a tumor weight (g) for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model. FIG. 74 depicts a chart showing a number of mice with lung metastasis (percentage) for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model. FIG. 75 depicts a chart showing an average number of lung macro-metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model. FIG. 76 depicts a chart showing an average number of lung micro-metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model. FIG. 77 depicts a chart showing an average number of lung metastases for a vehicle 114, Compound 39 116, Gemcitabine/Abraxane (G/A) 118, Compound 39+G/A 120, IgG2a control 122, ADWA-11 Ab 124, and ADWA-11+G/A 126 in a PDX-10 orthotopic model.

Utilizing subject-derived models of metastatic PDA showed that Compound 39 significantly blocked tumor growth and improved the response to the standard of care (SOC) chemotherapy G/A. Significantly less mice had lung metastasis when treated with Compound 39 in combination with G/A. However, this effect was not observed with ADWA-11. ADWA-11 in combination with G/A decreased tumor weight, but not number and size of lung metastases (FIG. 74-FIG. 77).

Assessment of Compound 39 Alone and in Combination with G/A to Reduce Tumor Weight in TKCC-05 Tumor Bearing Mice.

Table B-11 depicts the study design for the TKCC-05 model.

TABLE B-11

Study design for TKCC-05 model

| Group | N | Treatment | Dose Route | Dosing Frequency & Duration | Dose Level (mg/kg) | Dose Volume (mL/kg) |
|---|---|---|---|---|---|---|
| 1 | 5 | Vehicle | Oral gavage | 30 days daily | — | |
| 2 | 8 | Reference compound B* | Oral gavage | 30 days daily | 100 BID | |
| 3 | 8 | Compound 39 | Oral | 30 days | 300 BID | |
| 4 | 6 | ADWA11 | i.p. | BIW for 30 days | 10 | |
| 3 | 7 | Gemcitabine/ Abraxane | i.p. | Once per week for 60 days | G: 100 A: 30 | 10 |
| 4 | 9 | Reference compound B* + G/A | Oral gavage; i.p. | 60 days as above | As above (per mono) | |
| 6 | 8 | Compound 39 + G/A | Oral gavage; i.p. | 60 days as above | As above (per mono) | |
| 8 | 8 | ADWA11+ Gemcitabine/ abraxane | i.p. | As above for 60 days | ADWA--- 10. Gem as above | |

*Reference compound B is N-(3-chloro-5-fluoroisonicotinoyl)-O-(cis-3-(2-(5,6,7,8-tetrahydro-1,8-naphthyridin-2-yl)ethyl)cyclobutyl)homoserine.

Results

Figure 26A:
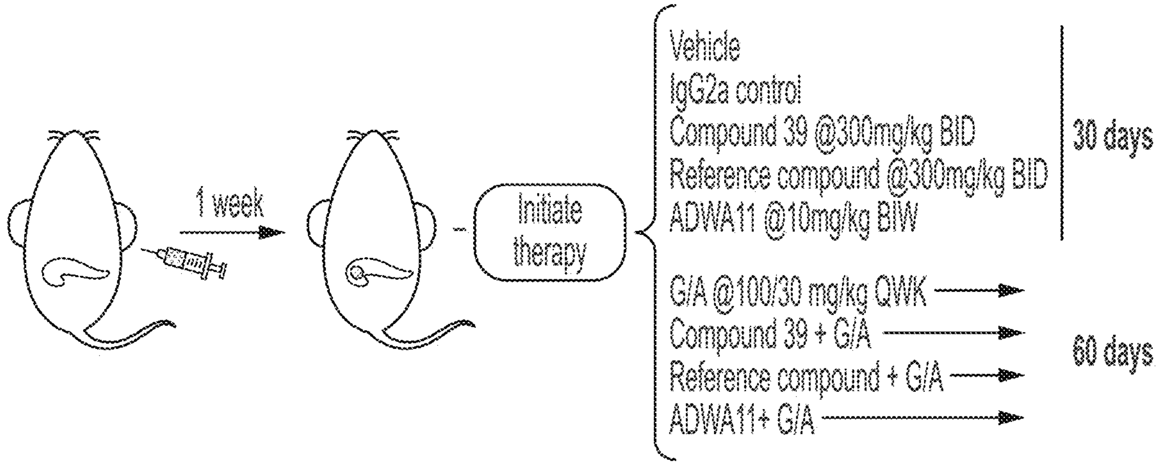
FIG. 26A depicts a schematic diagram of the treatment regimen in the TKCC-05 PDAC PDX model for the study associated with Example B12.
Figure 26B:
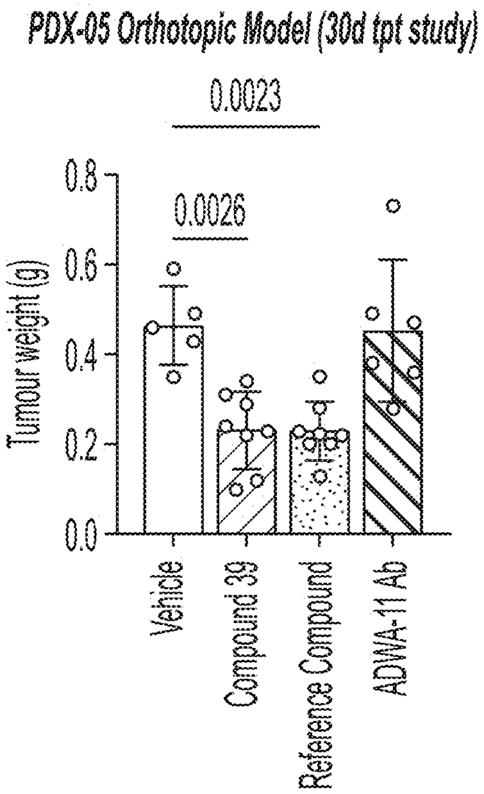
FIG. 26B depicts a graph associated with the quantification of tumor weights in mice treated with Compound 39, Reference compound B, and ADWA-11 Ab for the study associated with Example B12. P values by one-way ANOVA.
Figure 26C:
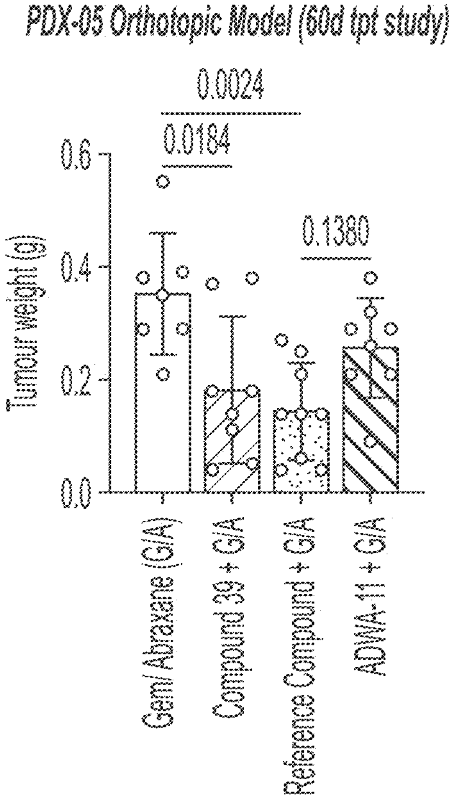
FIG. 26C depicts a graph associated with the quantification of tumor weights in mice treated with Gemcitabine/Abraxane (G/A), Compound 39+G/A, Reference compound B+G/A, and ADWA-11+G/A for the study associated with Example B12. P values by one-way ANOVA.

Compound 39 Alone and in Combination with G/A Significantly Reduced the Tumor Weight in the TKCC-05 Tumor Bearing Mice TKCC-05 cells were inoculated in the pancreas of MSG mice and were allowed to grow into tumors for 1 week. The mice were then treated according to schema outlined in Table B-10, and FIG. 26A, which depicts a schematic diagram of the treatment regimen in the TKCC-05 PDAC PDX model for this study. FIG. 26B depicts a graph associated with the quantification of tumor weights in mice treated with Compound 39, Reference compound B, and ADWA-11 Ab for the study associated with Example B12. FIG. 26C depicts a graph associated with the quantification of tumor weights in mice treated with G/A, Compound 39+G/A, Reference compound B+G/A, and ADWA-11+G/A for the study associated with Example B12. P values by one-way ANOVA.

Treatment of TKCC-05 tumor bearing mice with Compound 39 significantly reduced the tumor weight of the TKCC-05 tumors (mean tumor weight 0.23±0.08 g in the Compound 39 treated group, and 0.228±0.06 g in the Compound 39 group as compared to 0.464±0.09 in the vehicle treated animals) (see FIG. 26B). The TKCC-05 model is responsive to G/A, and as such, the G/A treatment allowed the tumor bearing animals to be treated for 60 days. While the tumors in the G/A treated animals reached the maximum bearable tumor size despite the G/A treatment in 60 days, the tumors treated with Compound 39+G/A remained significantly smaller as compared to the G/A treated tumors (mean tumor weight in the Compound 39+G/A treated animals 0.18±0.13 g) (see FIG. 26C). ADWA-11 alone or in combination with G/A did not significantly reduce the tumor weights (see FIG. 26B and FIG. 26C).

FIG. 58 depicts a graph associated with an average number of lung metastases in an PDX-05 orthotopic model for various groups in a 30 day study. FIG. 59 depicts a graph associated with an average number of liver metastases in an PDX-05 orthotopic model for various groups in a 30 day study. FIG. 60 depicts a graph associated with an average number of lung metastases in an PDX-05 orthotopic model for various groups in a 60 day study. FIG. 61 depicts a graph associated with an average number of liver metastases in an PDX-05 orthotopic model for various groups in a 60 day study. FIG. 62 depicts a graph associated with the number of mice having lung metastasis for various groups. FIG. 63 depicts a graph associated with the number of mice having hepatic metastasis for various groups.

Compound 39 in Combination with G/A Reduces Tumor Growth and Metastases In Vivo

FIG. 87 depicts a schematic diagram associated with a PDX-05 orthotopic model. A patient-derived model of metastatic PDA revealed that Compound 39 significantly blocks tumor growth, improves the response to standard of care (SOC) chemotherapy Gemcitabine/Abraxane (G/A) and reduces the number and size of lung metastases.

FIG. 88 depicts a chart showing an amount of protein (ng/mg) for $\alpha_V\beta_1$ and $\alpha_V\beta_8$ in a PDX-05 orthotopic model. FIG. 89 depicts a chart showing tumor weight (g) for a vehicle 144, Compound 39 146, a Reference Compound 148, ADWA-11 Ab 150, Gemcitabine/Abraxane (G/A) 152, Compound 39+G/A 154, a Reference Compound+G/A 156, and ADWA-11+G/A 158 in a PDX-05 orthotopic model. FIG. 90 depicts a chart showing a number of mice with lung metastasis (percentage) for a vehicle 144, Compound 39 146, a Reference Compound 148, ADWA-11 Ab 150, Gemcitabine/Abraxane (G/A) 152, Compound 39+G/A 154, a Reference Compound+G/A 156, and ADWA-11+G/A 158 in a PDX-05 orthotopic model. FIG. 91 depicts a schematic diagram of a generic epithelial-mesenchymal transition (EMT) signature of PDX-05. FIG. 92 depicts a chart showing a ratio of pSMDA3/SMAD3 for IgG, ADWA-11, Gemcitabine/Abraxane (G/A), Compound 39+G/A, a Reference Compound+G/A, and ADWA-11+G/A in a PDX-05 orthotopic model. FIG. 93 depicts a chart showing an average number of liver metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model. FIG. 94 depicts a chart showing an average number of liver micro-metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model. FIG. 95 depicts a chart showing an average number of lung metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model. FIG. 96 depicts a chart showing an average number of lung micro-metastases for a vehicle 160, Compound 39 162, a Reference compound 164, ADWA-11 Ab 166, Gemcitabine/Abraxane (G/A) 168, Compound 39+G/A 170, a Reference compound+G/A 172, and ADWA-11+G/A 174 in a PDX-05 orthotopic model. FIG. 97 depicts various images of Pico Sirius Red (PSR) stained liver metastases for a vehicle, Compound 39, Gemcitabine/Abraxane (G/A), Compound 39+G/A, a Reference compound, ADWA-11, a Reference compound+G/A and ADWA-11+G/A in an PDX-05 orthotopic model. FIG. 98 depicts various images of Pico Sirius Red (PSR) stained lung metastases for a vehicle, Compound 39, Gemcitabine/Abraxane (G/A), Compound 39+G/A, a Reference compound, ADWA-11, a Reference compound+G/A and ADWA-11+G/A in an PDX-05 orthotopic model.

Assessment of Compound 39 Alone and in Combination with Folfirinox (FNX) to Reduce Tumor Weight in TKCC-08 Tumor Bearing Mice Table B-12 depicts the study design for the TKCC-08 model.

TABLE B-12

Study Design for the TKCC-08 Model

| Group | N | Treatment | Dose route | Dosing frequency & duration | Dose level (mg/kg) | Dose volume (mL/kg) |
|---|---|---|---|---|---|---|
| 1 | 5 | Vehicle | oral gavage | daily | — | 5-10 |
| 2 | 4 | Compound 39 | oral gavage | daily | 300 BID | 5-10 |
| 3 | 5 | FNX | i.v. | weekly x till study end. start at d 5 | 10 | 10 |
| 4 | 6 | FNX | i.v. | weekly x till study end start at d 5 | 10 | 10 |
| | | Compound 39 | oral gavage | daily | 300 BID | 5-10 |

Results

Compound 39 Alone and in Combination with FNX Significantly Reduced the Tumor Weight in the FNX-Resistant TKCC-08 PDX Model of PDAC FNX is a standard of care chemotherapy regimen for pancreatic ductal adenocarcinoma. However, the clinical response to FNX remains bleak. To assess if Compound 39 augmented the therapeutic benefit of FNX, Compound 39 was tested alone and in combination with FNX in the TKCC-08 model, which is made FNX-resistant by continuous exposure to the FNX.

Figure 27A:
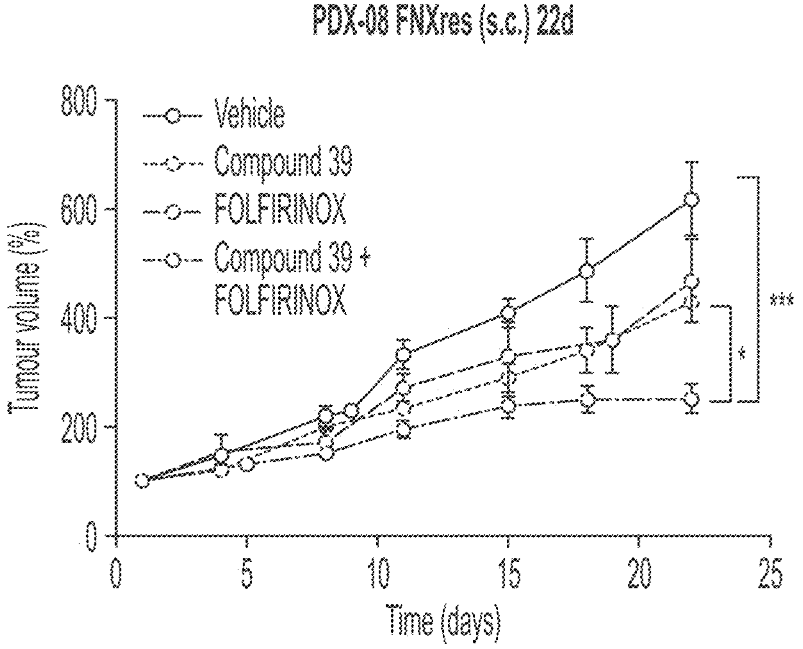
FIG. 27A depicts a graph associated with tumor growth curves of the TKCC-08 PDAC PDX (subcutaneous) model with indicated treatments for the study associated with Example B12.
Figure 27B:
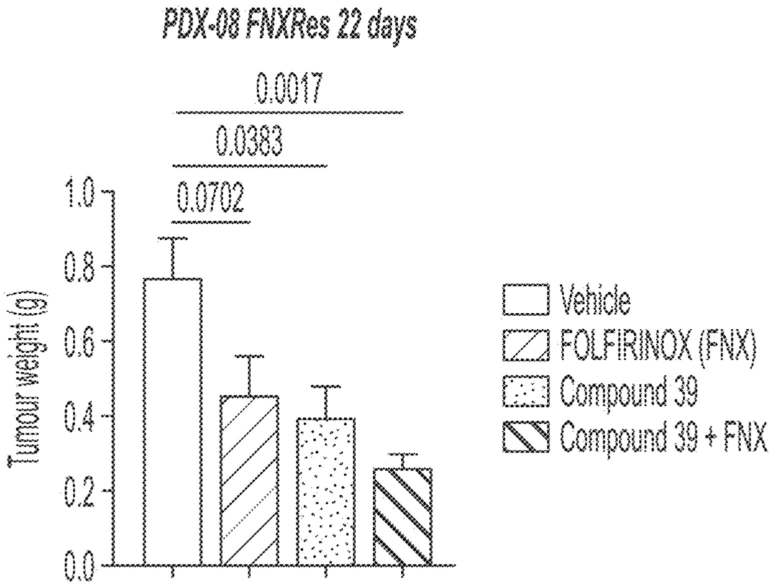
FIG. 27B depicts a graph associated with the quantification of tumor weights in mice treated with indicated treatments for the study associated with Example B12. P values by one-way ANOVA, *p=0.05, and ***p=0.001.

FIG. 27A depicts a graph associated with tumor growth curves of the TKCC-08 PDAC PDX (subcutaneous) model with indicated treatments for this study and FIG. 27B depicts a graph associated with the quantification of tumor weights in mice treated with indicated treatments for this study. Treatment of FNX-resistant subcutaneous TKCC-08 tumors with Compound 39 alone significantly reduced the tumor growth and the tumor weight (mean tumor weight of the Compound 39 treated animals 0.4±0.15 g as compared to 0.77±0.23 g of the vehicle treated animals), which were further reduced upon Compound 39+FNX treatment (mean tumor weight of the Compound 39+FNX treated animals 0.4±0.15 g as compared to 0.77±0.23 g of the vehicle treated animals), as shown in FIG. 27A and FIG. 27B.

Discussion

In the syngeneic KPC model of PDAC, Compound 39 had single agent efficacy and Compound 39+anti PD-1 significantly reduced the tumor weights, compared to the vehicle control. Compound 39 alone and in combination with anti PD-1 also significantly increased the survival of KPC tumor bearing mice. Similarly, in three different PDX models of PDAC in Example B12, Compound 39 had single agent efficacy, and it augmented the response to G/A and FNX. Compound 39+G/A treatment significantly reduced the metastasis of TKCC-10 cells to lung. As such, in some embodiments described herein, Compound 39 is combined with immune checkpoint blockade therapy, as well as with standard of care chemotherapy.

Assessment of Compound 39 in Combination with Folfirinox (FNX) to Reduce Tumor Volume and Weight in an FNX Resistance Model FIG. 67 depicts a schematic diagram of a PDA model of FOLFIRINOX resistance.

Compound 39 in combination with FNX treatment delayed disease progression and reduced tumor growth by 66% compared with vehicle (p=0.003) in vivo in a RNF43 mutant PDA model of FNX resistance.

FIG. 68A depicts a graph showing tumor volume (percentage) for a vehicle 102 and for FOLFIRINOX 104 over a time period of 120 days for the PDA model. FIG. 68B depicts a graph showing tumor volume (percentage) for a vehicle 102 and for FOLFIRINOX 104 over a time period of 40 days for the PDA model. FIG. 69A depicts a graph showing tumor volume (percentage) for a vehicle 106, FOLFIRINOX (FNX) 108, Compound 39 110, and Compound 39+FX 112 over a time period of 25 days for the PDA model. FIG. 69B depicts a chart showing the tumor volume (grams) for a vehicle 106, FOLFIRINOX (FNX) 108, Compound 39 110, and Compound 39+FX 112 associated with FIG. 69A. FIG. 70 depicts a schematic diagram of a generic epithelial-mesenchymal transition (EMT) signature of PDX-08.

This application refers to various published patent applications, journal articles, and other publications, each of which is incorporated herein by reference.

The foregoing has been described of certain non-limiting embodiments of the present disclosure. Those of ordinary skill in the art will appreciate that various changes and modifications to this description may be made without departing from the spirit or scope of the present disclosure, as defined in the following claims.

What is claimed is:

1. A compound of formula (A):

(A)

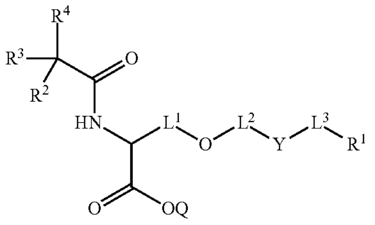

or a pharmaceutically acceptable salt thereof, wherein:

$R^1$ is 5,6,7,8-tetrahydro-1,8-naphthyridin-2-yl;

$R^2$ and $R^3$ are taken together with the carbon atom to which they are attached to form a $C_3$-$C_6$ cycloalkyl;

$R^4$ is 5-to-6-membered heteroaryl, wherein the 5-to-6-membered heteroaryl contains at least one nitrogen atom and is optionally substituted by 1-4 $R^{4a}$ groups;

each $R^{4a}$ is independently selected from the group consisting of halo, —CN, $C_1$-$C_6$ alkyl, $C_1$-$C_6$ haloalkyl, —($C_1$-$C_6$ alkylene)-O-($C_1$-$C_6$ alkyl), $C_3$-$C_6$ cycloalkyl, —OH, —O—($C_1$-$C_6$ alkyl), —O-($C_1$-$C_6$ haloalkyl), —S(O)$_2$($C_1$-$C_6$ alkyl), and —C(=O)—NH$_2$;

Q is H or $C_1$-$C_8$ alkyl; and

-$L^1$-O-$L^2$-Y-$L^3$- are taken together to form

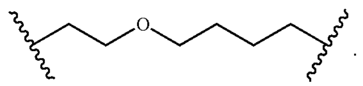 [SMILES: *CCCCOCC*]

2. The compound of claim 1, or a pharmaceutically acceptable salt thereof, wherein $R^2$ and $R^3$ are taken together with the carbon atom to which they are attached to form cyclopropyl.

3. The compound of claim 1, or a pharmaceutically acceptable salt thereof, wherein $R^4$ is 5-membered heteroaryl, wherein the 5-membered heteroaryl contains two nitrogen atoms.

4. The compound of claim 1, or a pharmaceutically acceptable salt thereof, wherein $R^4$ is 6-membered heteroaryl, wherein the 6-membered heteroaryl contains one nitrogen atom.

5. The compound of claim 1, or a pharmaceutically acceptable salt thereof, wherein $R^4$ is 6-membered heteroaryl, wherein the 6-membered heteroaryl contains two nitrogen atoms.

6. The compound of claim 1, or a pharmaceutically acceptable salt thereof, wherein $R^4$ is substituted by 1-4 $R^{4a}$ groups, wherein at least one $R^{4a}$ group is F or Cl.

7. The compound of claim 1, or a pharmaceutically acceptable salt thereof, wherein $R^4$ is substituted by 1-4 $R^{4a}$ groups, wherein at least one $R^{4a}$ group is —CN.

8. The compound of claim 1, or a pharmaceutically acceptable salt thereof, wherein $R^4$ is substituted by 1-4 $R^{4a}$ groups, wherein at least one $R^{4a}$ group is $C_1$-$C_3$ alkyl or $C_1$-$C_3$ haloalkyl.

9. The compound of claim 1, or a pharmaceutically acceptable salt thereof, wherein $R^4$ is substituted by 1-4 $R^{4a}$ groups, wherein at least one $R^{4a}$ group is —($C_1$-$C_3$ alkylene)-O-($C_1$-$C_3$ alkyl).

10. The compound of claim 1, or a pharmaceutically acceptable salt thereof, wherein $R^4$ is substituted by 1-4 $R^{4a}$ groups, wherein at least one $R^{4a}$ group is cyclopropyl.

11. The compound of claim 1, or a pharmaceutically acceptable salt thereof, wherein $R^4$ is substituted by 1-4 $R^{4a}$ groups, wherein at least one $R^{4a}$ group is —O—($C_1$-$C_3$ alkyl) or —O—($C_1$-$C_3$ haloalkyl).

12. The compound of claim 1, or a pharmaceutically acceptable salt thereof, wherein $R^4$ is selected from the group consisting of

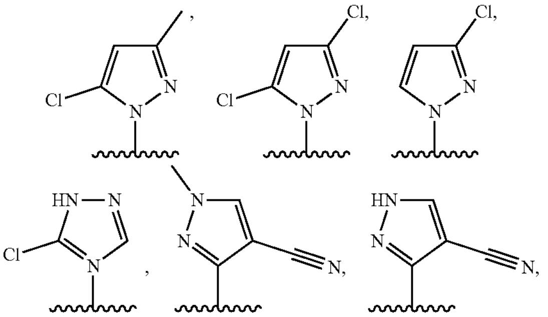

-continued
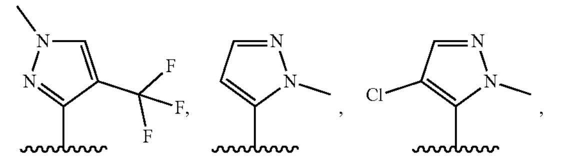
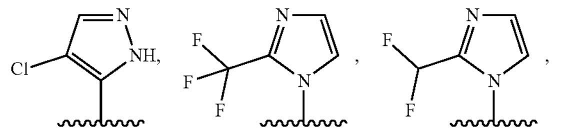
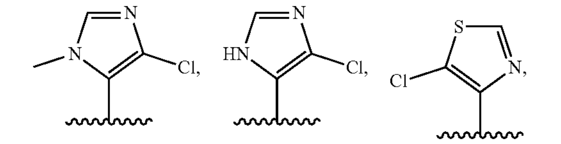
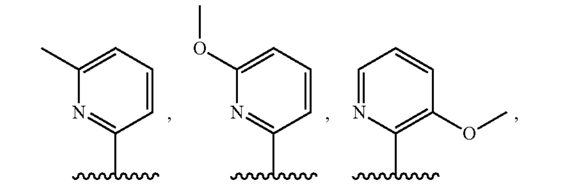
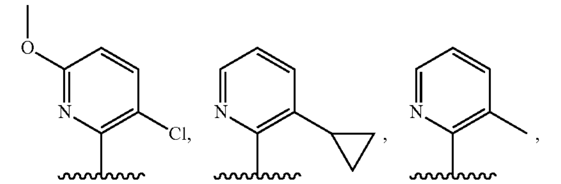
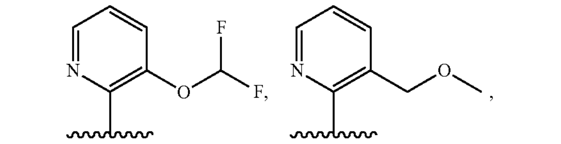
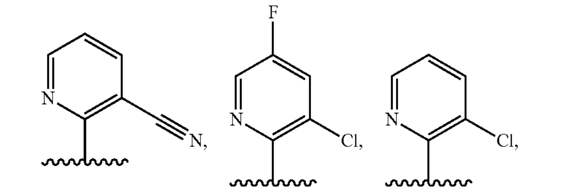
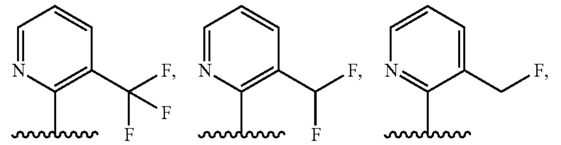
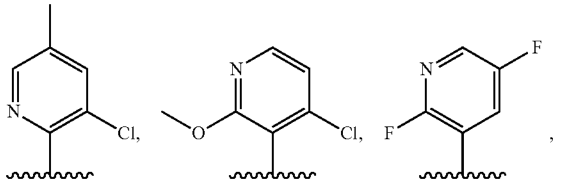
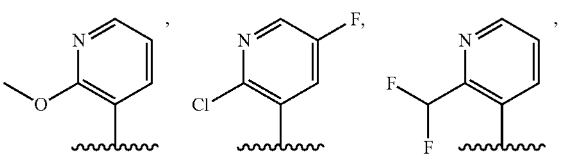
-continued
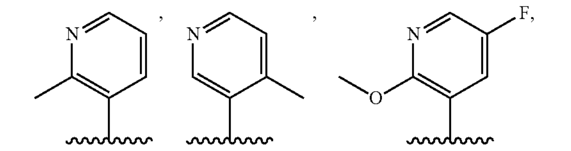
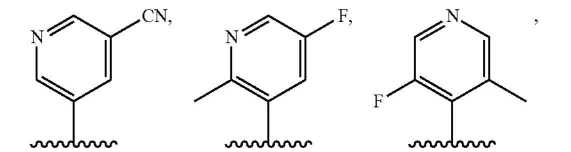
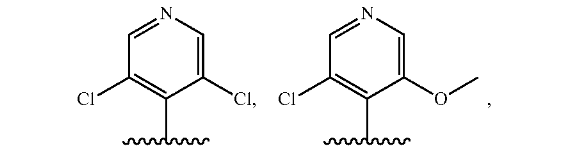
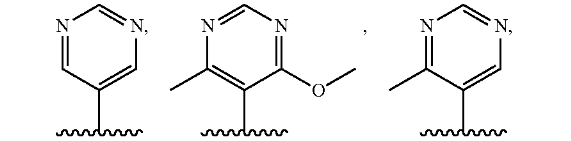
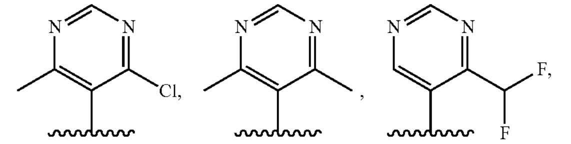
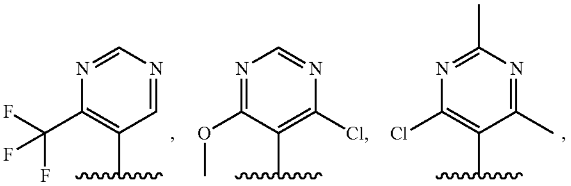
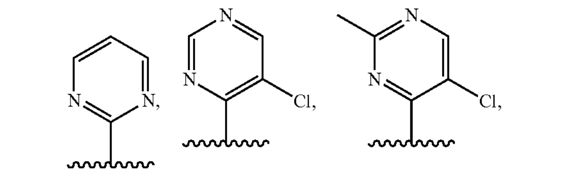
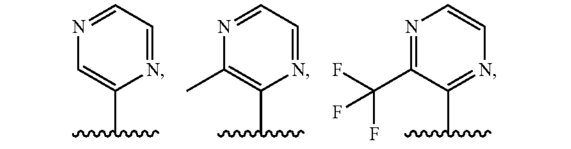
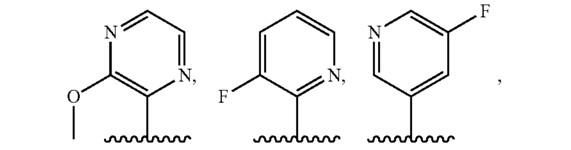
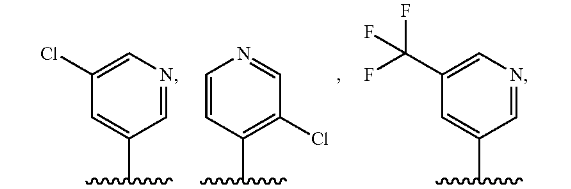

-continued
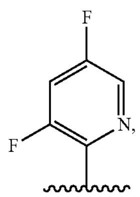
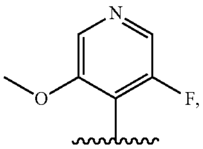
and
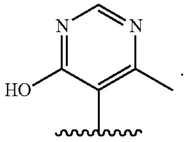
13. A compound selected from the group consisting of:
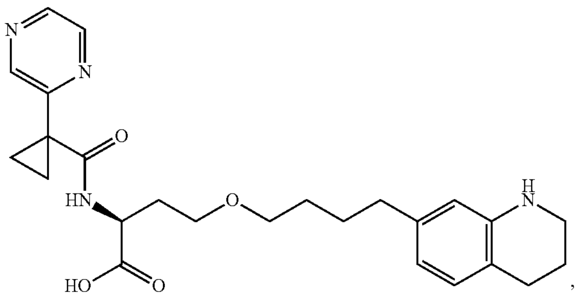
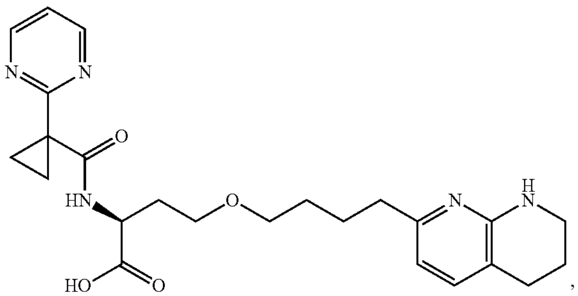
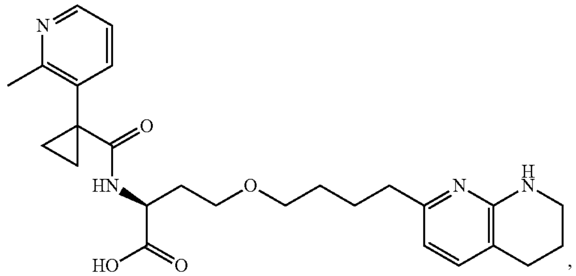
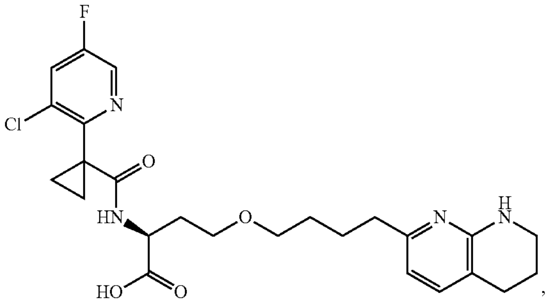
-continued
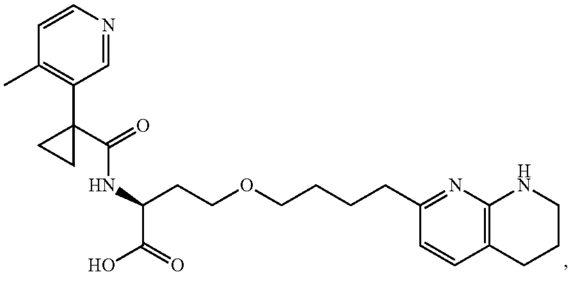
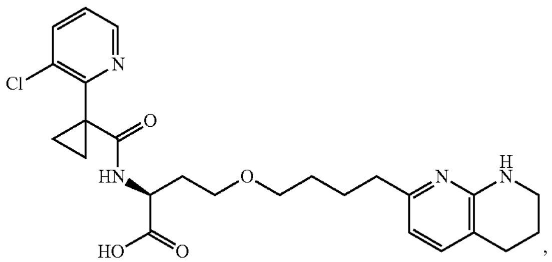
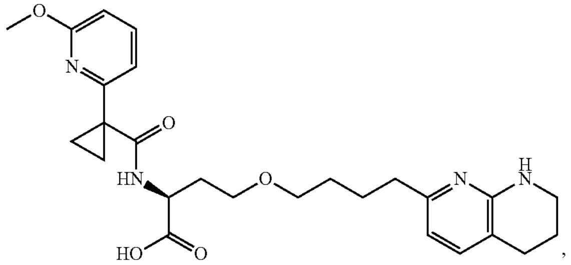
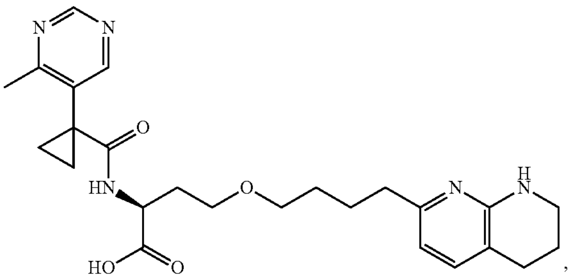
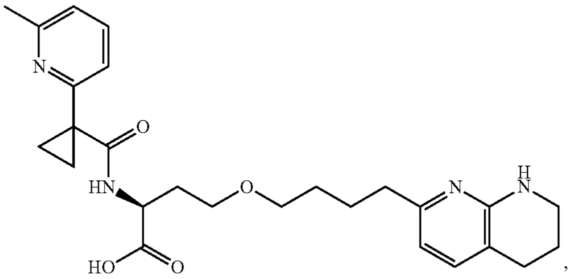
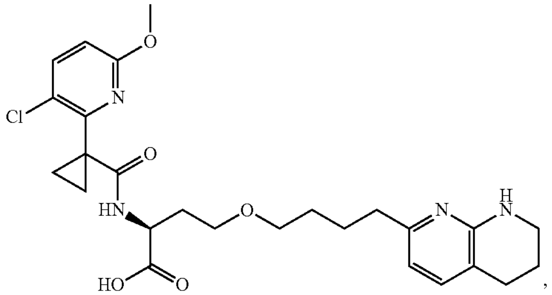

-continued
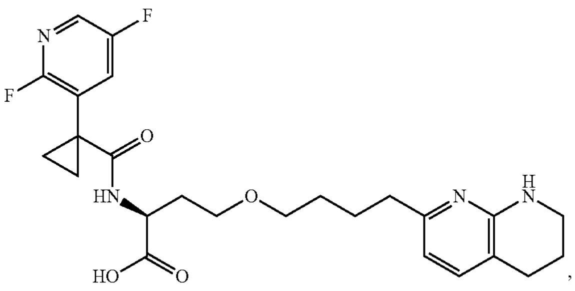
,
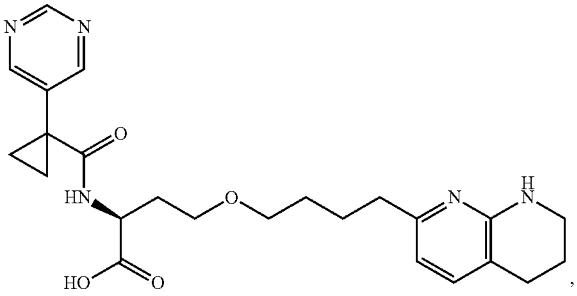
,
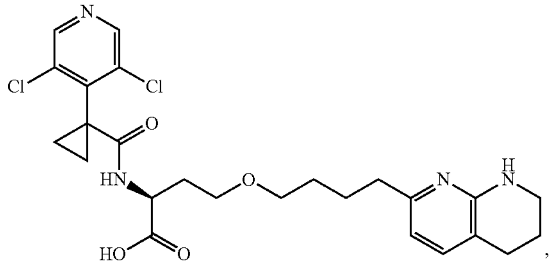
,
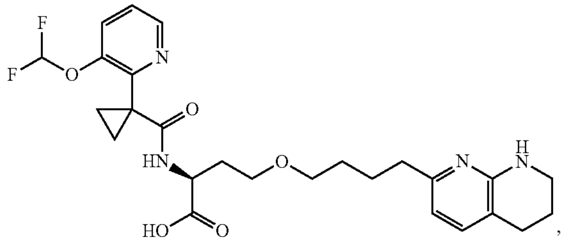
,
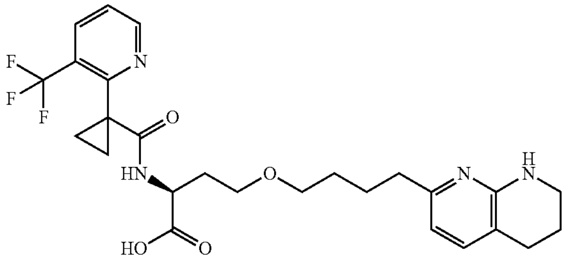
,
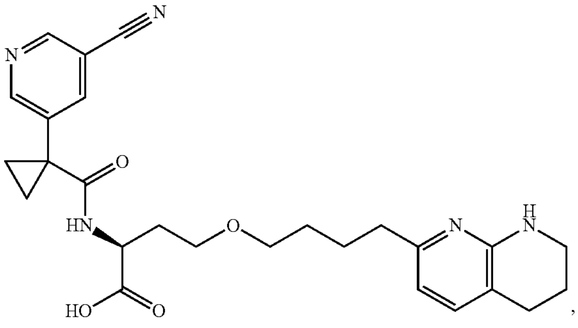
,
-continued
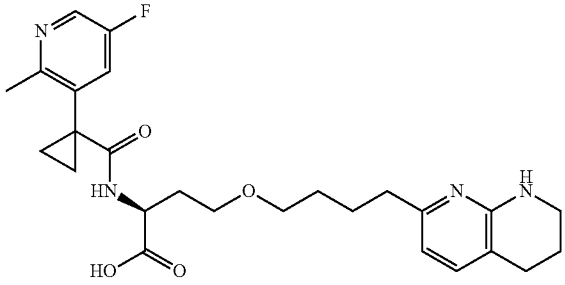
,
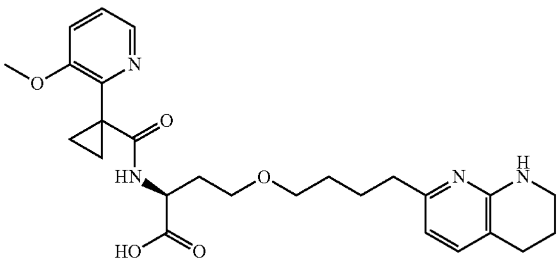
,
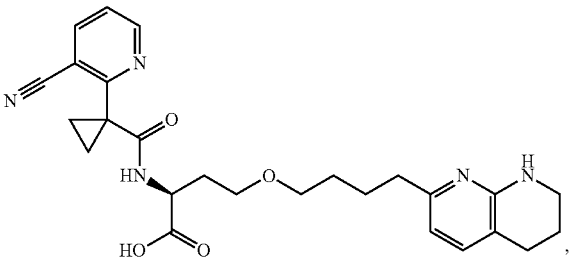
,
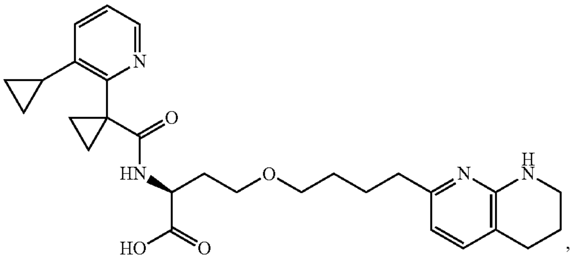
,
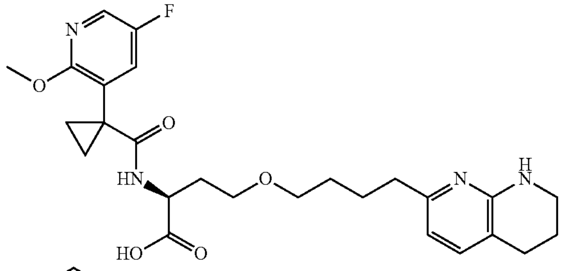
,
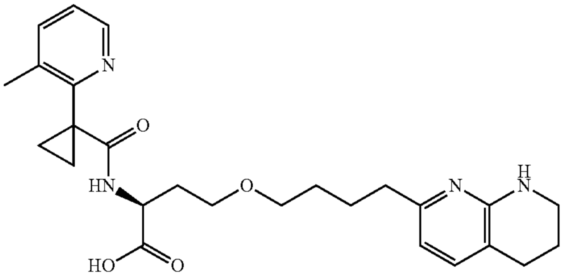
, -continued
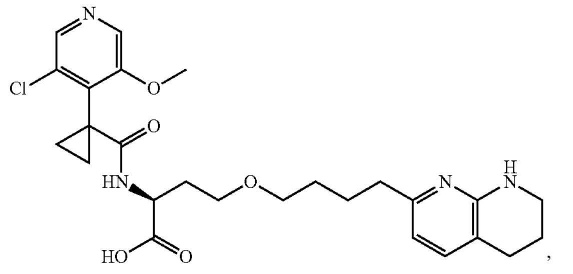
,
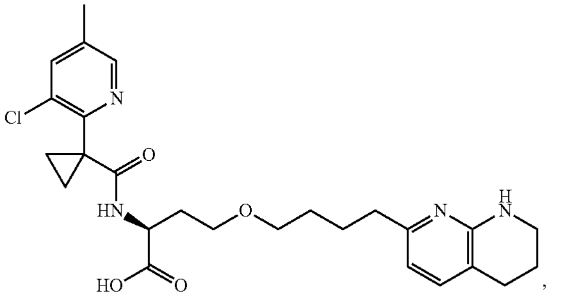
,
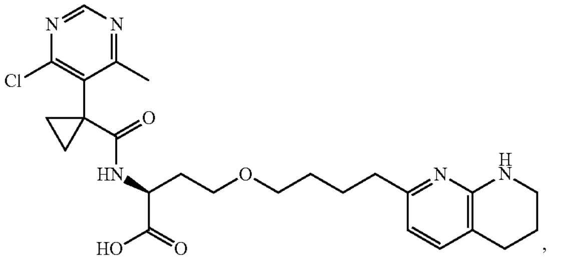
,
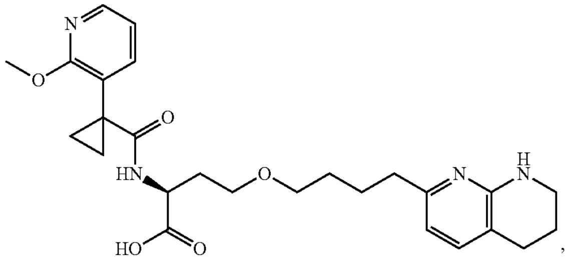
,
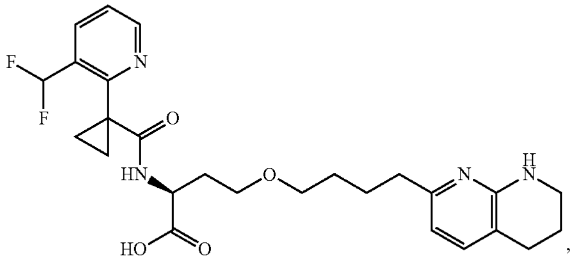
,
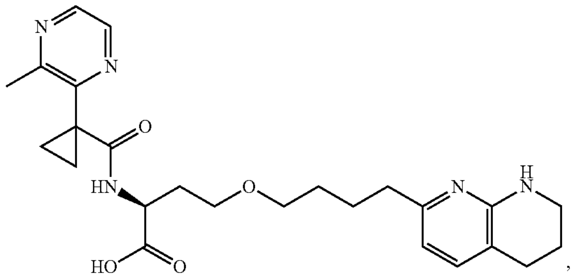
,
-continued
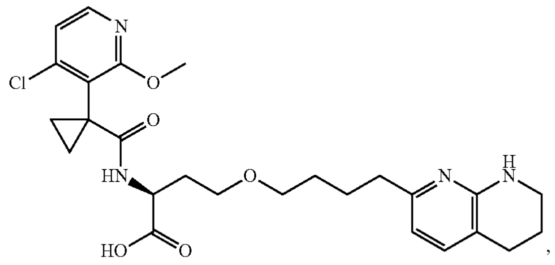
,
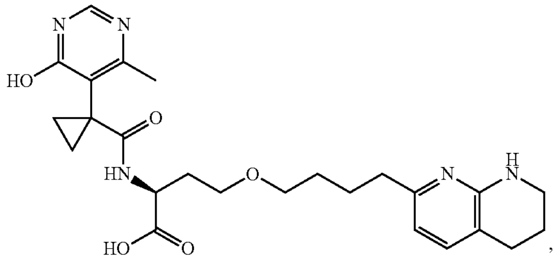
,
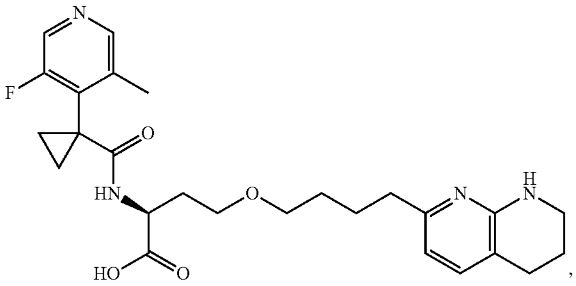
,
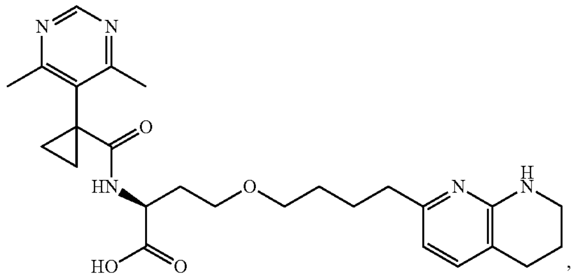
,
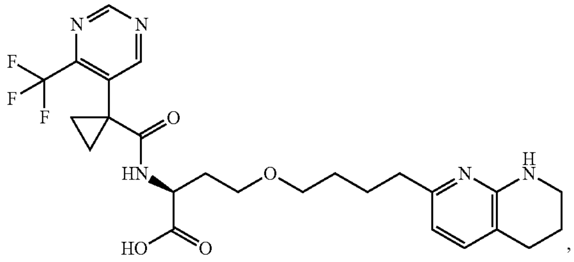
,
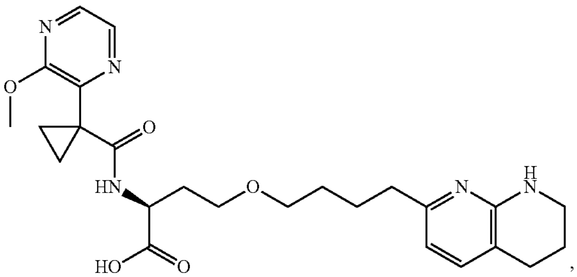
, -continued
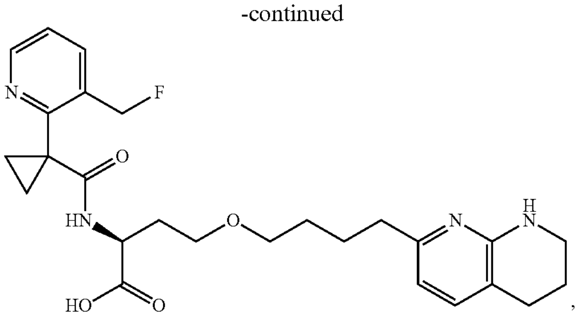
,
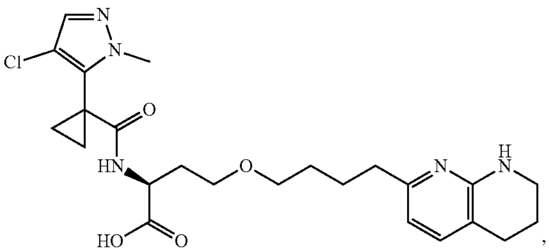
,
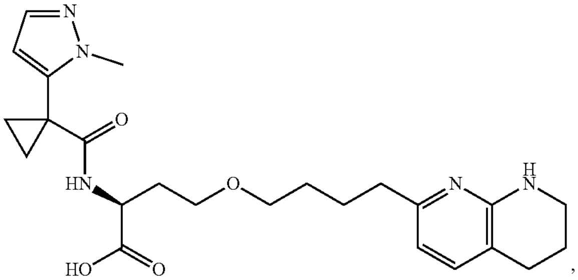
,
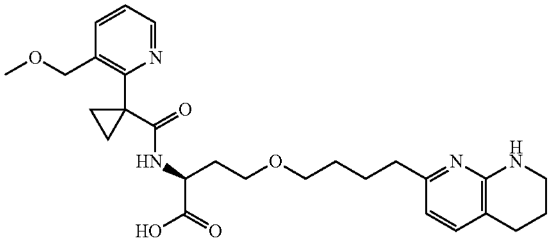
,
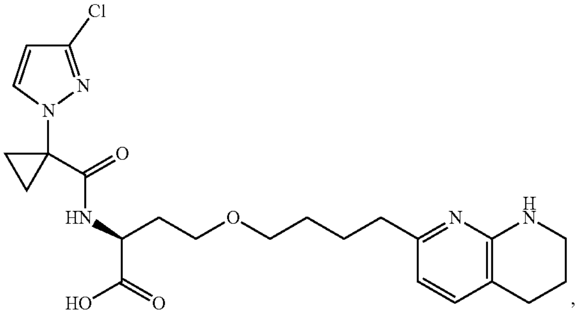
,
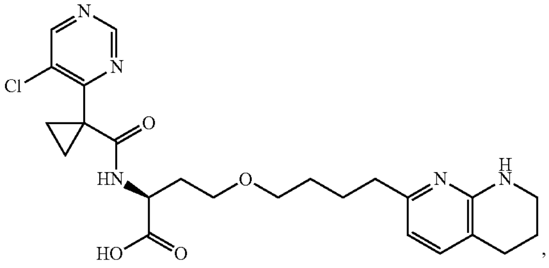
,
-continued
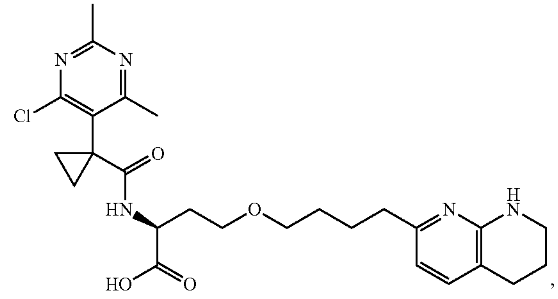
,
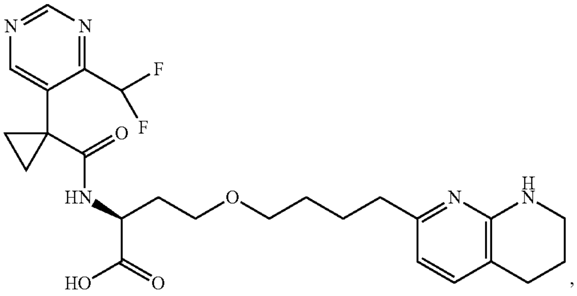
,
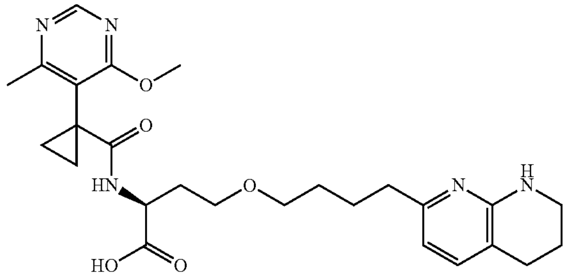
,
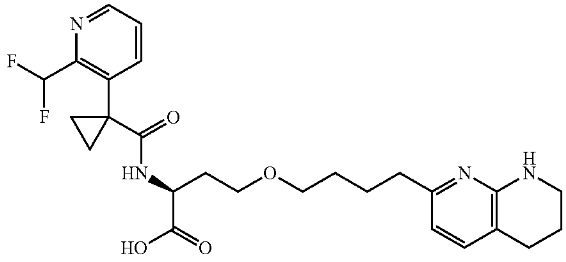
,
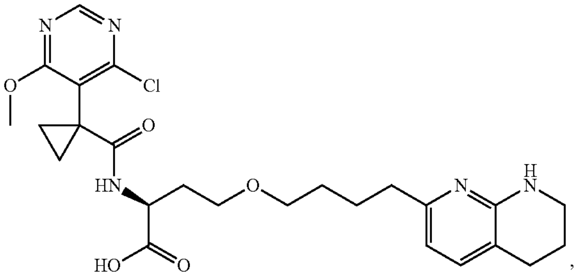
,
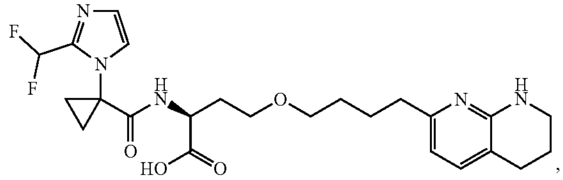
, -continued
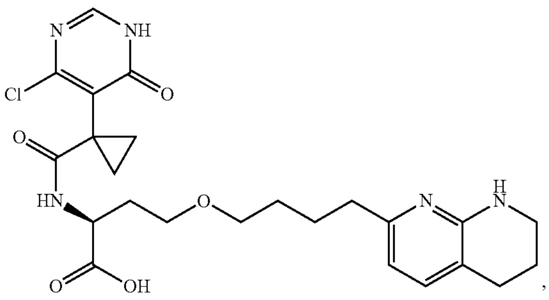
,
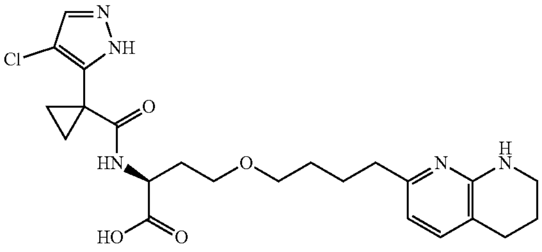
,
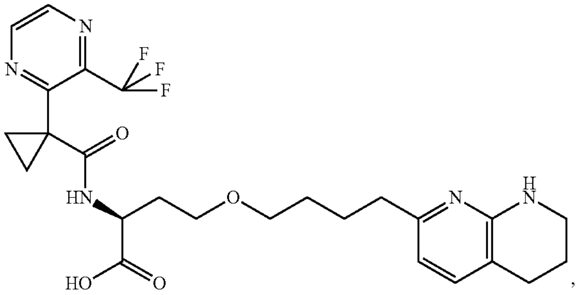
,
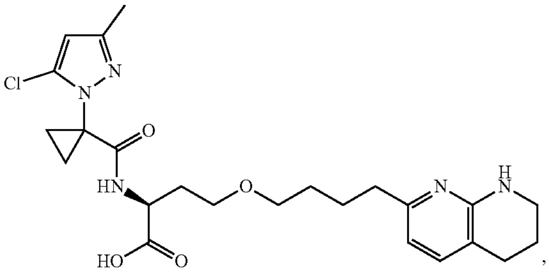
,
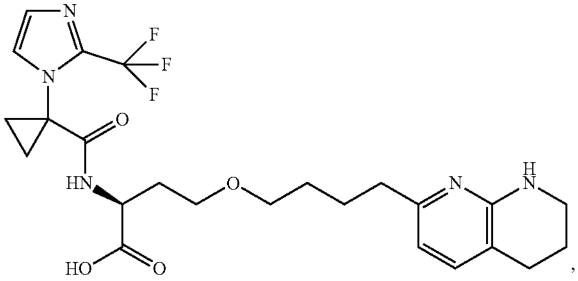
,
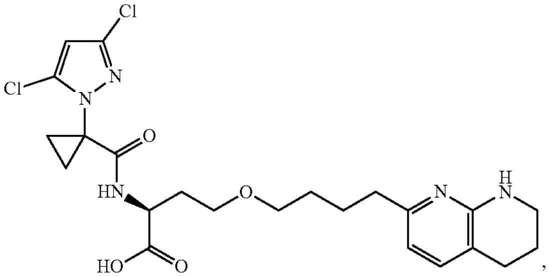
,
-continued
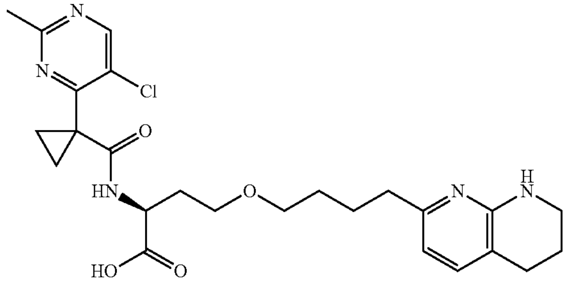
,
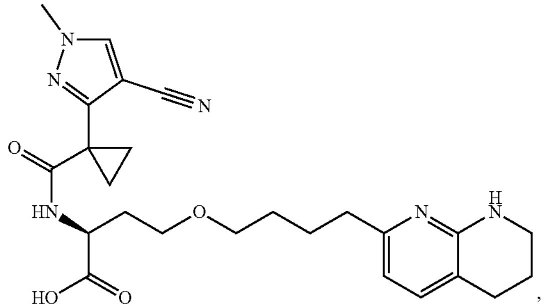
,
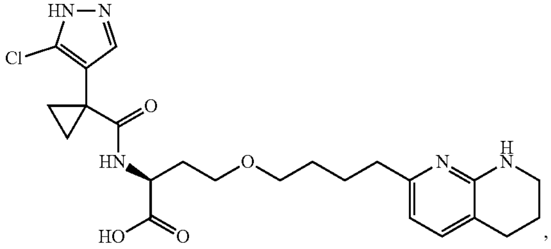
,
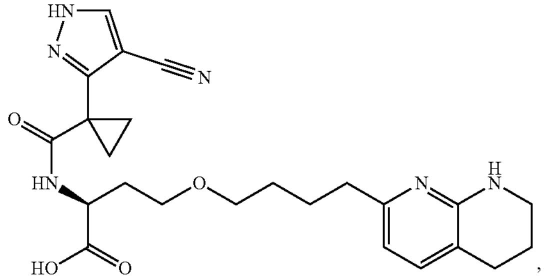
,
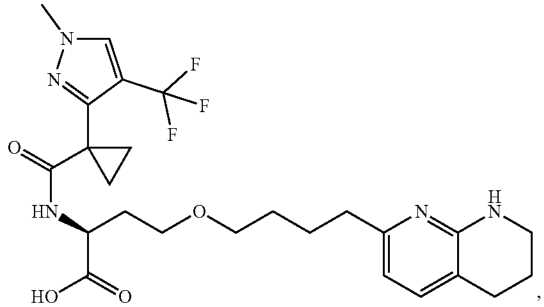
,
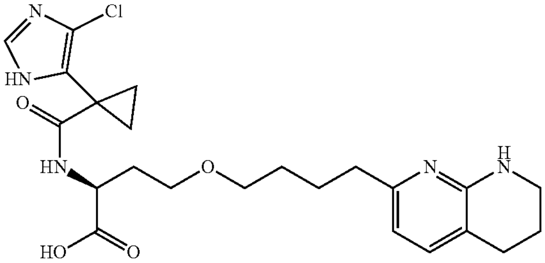
,

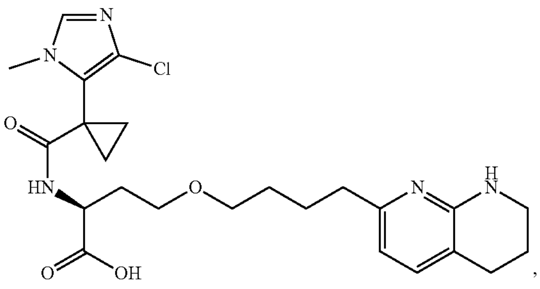
,

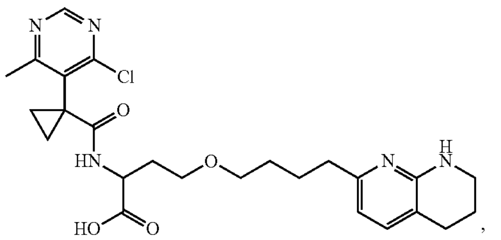
, and

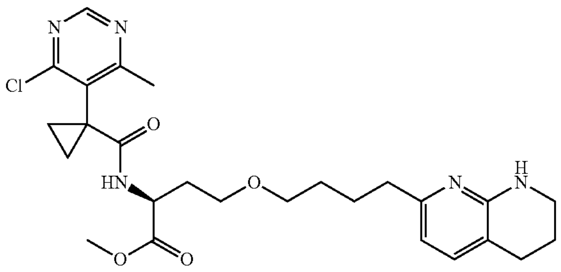
, or a pharmaceutically acceptable salt thereof.

14. The compound, wherein the compound is:

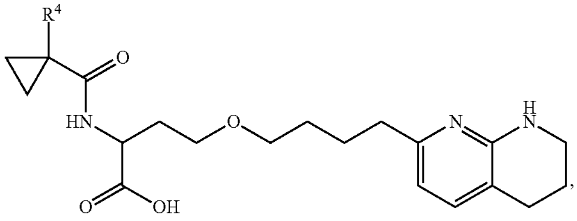
, or a pharmaceutically acceptable salt thereof.

15. The compound, wherein the compound is

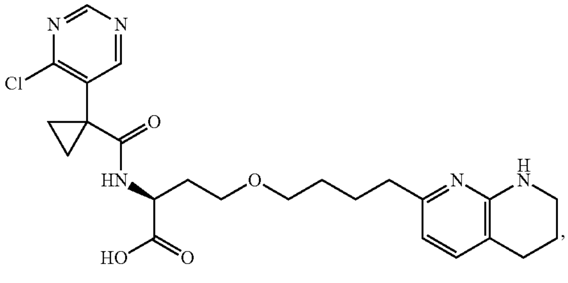 [SMILES: O=C(O)[C@H](CCOCCCCc1ccc2c(n1)NCCC2)NC(=O)C1(c2cncnc2Cl)CC1]
, or a pharmaceutically acceptable salt thereof.

16. The compound of claim 15, wherein the compound is

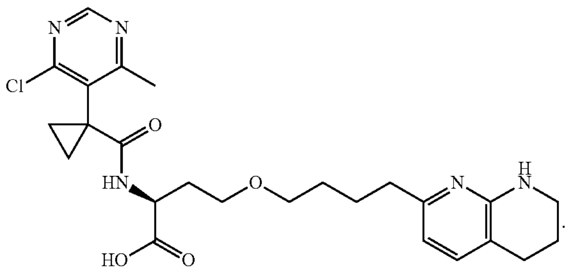 [SMILES: Cc1ncnc(Cl)c1C1(C(=O)N[C@@H](CCOCCCCc2ccc3c(n2)NCCC3)C(=O)O)CC1]
.

17. A pharmaceutical composition comprising a compound of claim 1, or a pharmaceutically acceptable salt thereof, and a pharmaceutically acceptable carrier or excipient.

18. A kit comprising a compound of claim 1, or a pharmaceutically acceptable salt thereof, and:

(a) instructions for the treatment of a fibrotic disease, or (b) instructions directing a user to administer to a subject in need thereof the compound or the pharmaceutically acceptable salt thereof, to treat cancer in the subject.

19. A method of treating a fibrotic disease in an individual in need thereof, comprising administering to the individual a compound of claim 1, or a pharmaceutically acceptable salt thereof, wherein the fibrotic disease is selected from the group consisting of pulmonary fibrosis, liver fibrosis, skin fibrosis, cardiac fibrosis, kidney fibrosis, gastrointestinal fibrosis, primary sclerosing cholangitis, and biliary fibrosis.

20. A method of inhibiting one or more of $\alpha_v\beta_1$, $\alpha_v\beta_6$, or $\alpha_v\beta_8$ integrin in an individual in need thereof, comprising administering to the individual a compound of claim 1, or a pharmaceutically acceptable salt thereof.

21. The method of claim 20, wherein:

(a) the method further comprises inhibiting in the individual one of:

$\alpha_v\beta_1$;

$\alpha_v\beta_8$;

$\alpha_v\beta_1$ and $\alpha_v\beta_8$;

$\alpha_v\beta_6$ and $\alpha_v\beta_8$; or $\alpha_v\beta_1$, $\alpha_v\beta_6$, and $\alpha_v\beta_8$; and (b) the individual is in need of treatment for a disease or a condition, and:

(i) the condition comprises a solid tumor;

(ii) the disease or the condition is selected from the group consisting of breast cancer, melanoma, colon cancer, non-small cell lung cancer, head and neck squamous cell carcinoma, squamous cell lung cancer, renal cell carcinoma, cutaneous squamous cell carcinoma (CSCC), urothelial carcinoma, metastatic Merkel cell carcinoma, gastric cancer, lung cancer, pancreatic cancer, pancreatic ductal adenocarcinoma (PDAC), and mesothelioma; or (iii) the disease or the condition is selected from the group consisting of pulmonary fibrosis, liver fibrosis, skin fibrosis, cardiac fibrosis, kidney fibrosis, gastrointestinal fibrosis, primary sclerosing cholangitis, biliary atresia, ocular fibrosis, and biliary fibrosis.

22. A method of inhibiting TGFβ activation in a cell, comprising administering to the cell a compound of claim 1, or a pharmaceutically acceptable salt thereof.

23. The method of claim 22, wherein the cell expresses one or more of: $\alpha_v\beta_1$; $\alpha_v\beta_6$; and $\alpha_v\beta_8$; and (a) the cells are cancer cells associated with a solid tumor;

(b) the cells are cancer cells associated with at least one of melanoma, colon cancer, non-small cell lung cancer, head and neck squamous cell carcinoma, squamous cell lung cancer, renal cell carcinoma, cutaneous squamous cell carcinoma (CSCC), urothelial carcinoma, metastatic Merkel cell carcinoma, gastric cancer, lung cancer, pancreatic cancer, pancreatic ductal adenocarcinoma (PDAC), breast cancer, and mesothelioma;

(c) the cells are associated with a fibrotic disease, and the fibrotic disease is selected from the group consisting of pulmonary fibrosis, liver fibrosis, skin fibrosis, cardiac fibrosis, kidney fibrosis, gastrointestinal fibrosis, primary sclerosing cholangitis, and biliary fibrosis;

(d) the cells are associated with the eye; or (e) the cells are associated with the intrahepatic or extra-hepatic biliary system.

24. A method of therapy for a subject in need thereof, comprising administering to the subject having at least one tissue in need of therapy, a therapeutically effective amount of a compound of claim 1, wherein:

the at least one tissue is characterized by a value that is elevated as compared to a healthy value in a healthy state of the at least one tissue, the value is selected from the group consisting of $\alpha_v\beta_1$ integrin activity and/or expression;

$\alpha_v\beta_6$ integrin activity and/or expression;

$\alpha_v\beta_8$ integrin activity and/or expression;

a pSMAD/SMAD ratio;

new collagen formation or accumulation;

total collagen;

Type I Collagen gene Col1a1 expression;

perforin;

Granzyme B; and interferon γ, and administering the therapeutically effective amount of the compound decreases the elevated value of in the at least one tissue.

25. The method of claim 24, wherein administering the therapeutically effective amount of the compound reduces the activity of $\alpha_v\beta_1$ integrin in one or more fibroblasts in the subject, reduces the activity of $\alpha_v\beta_6$ integrin in one or more epithelial cells in the subject, or reduces the activity of $\alpha_v\beta_8$ integrin in one or more epithelial cells or cancer cells in the subject.

26. The method of claim 24, wherein at least one of:

(a) each tissue of the at least one tissue is selected from the group consisting of lung, liver, skin, heart, kidney, gastrointestinal, gall bladder, bile duct, brain, lymph node, stomach, urethra, bladder, prostate, pancreas carcinoma, eye, mesothelium, and breast; and (b) each tissue of the at least one tissue has an elevated pSMAD2/SMAD2 value or an elevated pSMAD3/SMAD3 value as compared to the healthy value in the healthy state of the at least one tissue.

27. The method of claim 24, wherein:

(a) the subject has a solid tumor;

(b) the subject has at least one of: melanoma, colon cancer, non-small cell lung cancer, head and neck squamous cell carcinoma, squamous cell lung cancer, renal cell carcinoma, cutaneous squamous cell carcinoma (CSCC), urothelial carcinoma, metastatic Merkel cell carcinoma, gastric cancer, pancreatic ductal adenocarcinoma (PDAC), lung cancer, pancreatic cancer, and mesothelioma; or (c) the subject has at least one of: pulmonary fibrosis, liver fibrosis, skin fibrosis, cardiac fibrosis, kidney fibrosis, gastrointestinal fibrosis, primary sclerosing cholangitis, biliary atresia, and biliary fibrosis.

28. A method of characterizing anticancer activity of the compound of claim 1 in a subject, comprising providing a first live cell sample from the subject, wherein:

the first live cell sample is characterized by a presence of at least one integrin capable of activating transforming growth factor β (TGF-β) from latency associated peptide-TGF-β, and each integrin of the at least one integrin is selected from the group consisting of $\alpha_v\beta_1$; $\alpha_v\beta_6$, and $\alpha_v\beta_8$;

determining a first value in the first live cell sample, wherein the first value is selected from the group consisting of: pSMAD2/SMAD2 ratio, pSMAD3/SMAD3 ratio, a perforin level, a granzyme B level, and an interferon γ level;

administering the compound of claim 1 to the subject;

providing a second live cell sample from the subject, wherein the second live cell sample is drawn from the same tissue in the subject as the first live cell sample;

determining a second value in the second live cell sample, wherein the second value corresponds to the pSMAD2/SMAD2 ratio, the pSMAD3/SMAD3 ratio, the perforin level, the granzyme B level, or the interferon γ level of the first value; and characterizing an anticancer activity of the compound of claim 1 in the subject by comparing the second value to the first value.

29. The method of claim 28, wherein at least one of:

(a) the tissue in the subject is selected from the group consisting of skin, lung, brain, lymph node, stomach, urethra, kidney, bladder, prostate, liver, pancreas, mesothelium, and breast; and (b) the subject has at least one of melanoma, colon cancer, non-small cell lung cancer, head and neck squamous cell carcinoma, squamous cell lung cancer, renal cell carcinoma, cutaneous squamous cell carcinoma (CSCC), pancreatic ductal adenocarcinoma (PDAC), urothelial carcinoma, metastatic Merkel cell carcinoma, gastric cancer, lung cancer, pancreatic cancer, or mesothelioma.

30. A method of treating cancer in a subject in need thereof, comprising administering to the subject an effective amount of a compound of claim 1, or a pharmaceutically acceptable salt thereof.

31. The method of claim 30, wherein:

(a) the cancer comprises a solid tumor; or (b) the cancer is selected from the group consisting of breast cancer, melanoma, colon cancer, non-small cell lung cancer, head and neck squamous cell carcinoma, pancreatic ductal adenocarcinoma (PDAC), squamous cell lung cancer, renal cell carcinoma, cutaneous squamous cell carcinoma (CSCC), urothelial carcinoma, metastatic Merkel cell carcinoma, gastric cancer, lung cancer, pancreatic cancer, and mesothelioma.

32. The method of claim 30, further comprising:

administering a chemotherapy agent or a chemotherapy regimen prior to, concurrently with, or subsequent to the compound, wherein:

the chemotherapy agent is selected from the group consisting of gemcitabine and abraxane;

the chemotherapy regimen comprises folfirinox; and administering the chemotherapy agent or the chemotherapy regimen prior to, concurrently with, or subsequent to the compound reduces at least a weight of a tumor in the subject.

33. The method of claim 32, wherein the tumor is resistant to the chemotherapy regimen.

34. The method of claim 30, wherein the effective amount of the compound, or a pharmaceutically acceptable salt thereof, is a therapeutically effective amount.

35. The method of claim 30, wherein the compound, or a pharmaceutically acceptable salt thereof, is

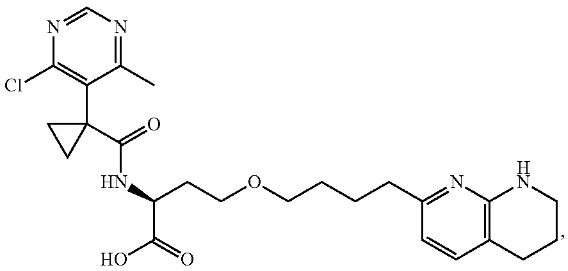 [SMILES: Cc1ncnc(Cl)c1C1(C(=O)N[C@@H](CCOCCCCc2ccc3c(n2)NCCC3)C(=O)O)CC1]

or a pharmaceutically acceptable salt thereof.

36. The method of claim 35, wherein the compound, or a pharmaceutically acceptable salt thereof, is

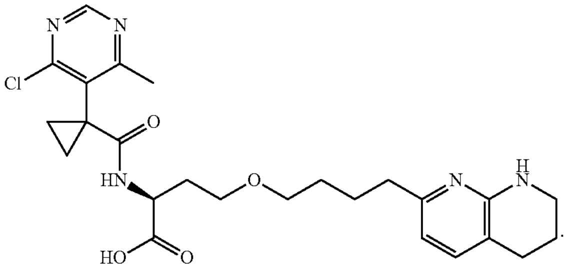 [SMILES: Cc1ncnc(Cl)c1C1(C(=O)N[C@@H](CCOCCCCc2ccc3c(n2)NCCC3)C(=O)O)CC1]

37. The method of claim 36, wherein the method further comprises administering to the subject a checkpoint inhibitor.

38. The method of claim 36, wherein the cancer is melanoma.

39. The method of claim 36, wherein the cancer is head and neck squamous cell carcinoma.

40. The method of claim 36, wherein the cancer is non-small cell lung cancer.

41. The method of claim 37, wherein the checkpoint inhibitor inhibits PD-$L^1$.

42. The method of claim 37, wherein the checkpoint inhibitor is pembrolizumab.

* * * * *